United States Patent
Pendri et al.

(10) Patent No.: US 10,035,760 B2
(45) Date of Patent: Jul. 31, 2018

(54) INHIBITORS OF HUMAN IMMUNODEFICIENCY VIRUS REPLICATION

(71) Applicant: VIIV HEALTHCARE UK (NO. 5) LIMITED, Brentford, Middlesex (GB)

(72) Inventors: Annapurna Pendri, South Glastonbury, CT (US); Guo Li, Wallingford, CT (US); John A. Bender, Middletown, CT (US); Zhong Yang, Southington, CT (US); Alan Xiangdong Wang, Wallingford, CT (US); Brett R. Beno, Cromwell, CT (US); Robert A. Fridell, Guilford, CT (US); Makonen Belema, North Haven, CT (US); Nicholas A. Meanwell, East Hampton, CT (US); Robert G. Gentles, Killingworth, CT (US)

(73) Assignee: ViiV HEALTHCARE UK (NO. 5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/031,352

(22) PCT Filed: Oct. 23, 2014

(86) PCT No.: PCT/US2014/061870
§ 371 (c)(1),
(2) Date: Apr. 22, 2016

(87) PCT Pub. No.: WO2015/061518
PCT Pub. Date: Apr. 30, 2015

(65) Prior Publication Data
US 2016/0257645 A1 Sep. 8, 2016

Related U.S. Application Data

(60) Provisional application No. 61/895,102, filed on Oct. 24, 2013.

(51) Int. Cl.
A61K 31/36 (2006.01)
A61K 31/357 (2006.01)
A61K 31/64 (2006.01)
A61K 31/17 (2006.01)
A61K 31/18 (2006.01)
C07C 275/28 (2006.01)
C07C 275/26 (2006.01)
C07C 275/18 (2006.01)
C07C 275/24 (2006.01)
C07C 275/22 (2006.01)
C07C 311/62 (2006.01)
(Continued)

(52) U.S. Cl.
CPC .......... C07C 311/58 (2013.01); C07D 205/04 (2013.01); C07D 209/08 (2013.01); C07D 209/10 (2013.01); C07D 213/56 (2013.01); C07D 215/08 (2013.01); C07D 231/12 (2013.01); C07D 249/08 (2013.01); C07D 261/08 (2013.01); C07D 265/36 (2013.01); C07D 271/06 (2013.01); C07D 277/82 (2013.01); C07D 307/38 (2013.01); C07D 317/46 (2013.01); C07D 317/66 (2013.01); C07D 333/18 (2013.01); C07D 333/28 (2013.01); C07D 333/54 (2013.01); C07D 401/04 (2013.01); C07D 405/12 (2013.01); C07D 407/12 (2013.01); C07D 409/12 (2013.01); C07D 491/08 (2013.01); C07D 495/04 (2013.01); C07C 2601/08 (2017.05); C07C 2601/14 (2017.05); C07C 2602/08 (2017.05)

(58) Field of Classification Search
CPC .... C07D 317/66; C07D 317/62; A61K 31/36; A61K 31/463; A61K 31/64; A61K 31/17; A61K 31/18; C07C 275/28; C07C 275/26; C07C 275/18; C07C 275/24; C07C 275/22; C07C 311/62; C07C 311/59; C07C 311/58; C07C 311/56; C07C 311/55
USPC ........ 549/439, 446; 514/464, 463, 595, 592, 514/605, 602; 564/84, 85, 86, 94, 99, 56, 564/39
See application file for complete search history.

(56) References Cited

FOREIGN PATENT DOCUMENTS

WO   WO 95/09614   4/1995

OTHER PUBLICATIONS

STN Registry database entry: CAS RN 1322299-39-7 (Entered STN: Aug. 24, 2011). (Year: 2011).*
(Continued)

Primary Examiner — Matthew P Coughlin
Assistant Examiner — Sagar Patel
(74) Attorney, Agent, or Firm — Robert H. Brink; Edward R. Gimmi; William R. Majarian

(57) ABSTRACT

Compounds of Formula I with activity against HIV, including pharmaceutical compositions and methods for using these compounds in treating human immunodeficiency virus (HIV) infection, are set forth:

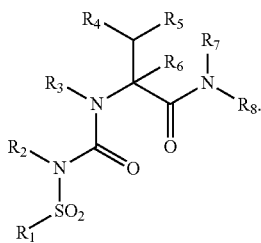

16 Claims, No Drawings

(51) Int. Cl.

| | | |
|---|---|---|
| *C07C 311/59* | (2006.01) | |
| *C07C 311/58* | (2006.01) | |
| *C07C 311/56* | (2006.01) | |
| *C07C 311/55* | (2006.01) | |
| *C07D 317/66* | (2006.01) | |
| *C07D 317/62* | (2006.01) | |
| *C07D 205/04* | (2006.01) | |
| *C07D 209/08* | (2006.01) | |
| *C07D 209/10* | (2006.01) | |
| *C07D 213/56* | (2006.01) | |
| *C07D 215/08* | (2006.01) | |
| *C07D 231/12* | (2006.01) | |
| *C07D 249/08* | (2006.01) | |
| *C07D 261/08* | (2006.01) | |
| *C07D 265/36* | (2006.01) | |
| *C07D 271/06* | (2006.01) | |
| *C07D 277/82* | (2006.01) | |
| *C07D 307/38* | (2006.01) | |
| *C07D 317/46* | (2006.01) | |
| *C07D 333/18* | (2006.01) | |
| *C07D 333/28* | (2006.01) | |
| *C07D 333/54* | (2006.01) | |
| *C07D 401/04* | (2006.01) | |
| *C07D 405/12* | (2006.01) | |
| *C07D 407/12* | (2006.01) | |
| *C07D 409/12* | (2006.01) | |
| *C07D 491/08* | (2006.01) | |
| *C07D 495/04* | (2006.01) | |

(56) References Cited

OTHER PUBLICATIONS

STN Registry database entry: CAS RN 1322021-53-3 (Entered STN: Aug. 23, 2011). (Year: 2011).*
STN Registry database entry: CAS RN 1321895-85-5 (Entered STN: Aug. 23, 2011). (Year: 2011).*
STN Registry database entry: CAS RN 1321806-34-1 (Entered STN: Aug. 23, 2011). (Year: 2011).*
Clare, B. and C. Supuran, "Predictive Flip Regression: A Technique for QSAR of Derivatives of Symmetric Molecules", J. Chem. Inf. Model. (2005), 45, pp. 1385-1391. (Year: 2005).*
Scozzafava, et al., "Carbonic anhydrase activators," European Journal of Pharmaceutical Sciences, vol. 10, No. 1, Mar. 1, 2000, pp. 29-41.
Scozzafava, et al., "Carbonic anhydrase activators: synthesis of high affinity isozymes I, II and IV activators, derivatives of 4-(4-tosylureido-amino acyl)ethyl-1H-imidazole (histamine derivatives)," J. Enzyme Inhibition, vol. 15, 2000, pp. 139-161.
Oette, et al., "Primary HIV Drug Resistance and Efficacy of First-Line Antiretroviral Therapy Guided by Resistance Testing," J. Acquired Immune Deficiency Syndrome, vol. 41, No. 5, Apr. 15, 2006, pp. 573-581.

* cited by examiner

INHIBITORS OF HUMAN IMMUNODEFICIENCY VIRUS REPLICATION

CROSS REFERENCE TO RELATED APPLICATION

This application claims the priority of U.S. Provisional Application Ser. No. 61/895,102 filed Oct. 24, 2013 which is herein incorporated by reference in its entirety.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection.

BACKGROUND OF THE INVENTION

HIV (human immunodeficiency virus) infection/acquired immunodeficiency syndrome (HIV/AIDS) is the result of infection by HIV. It remains a major medical problem, with an estimated 34 million people infected worldwide at the end of 2011, 3.3 million of them under the age of 15. In 2011, there were 2.5 million new infections, with, 1.7 million people dying from complications due to HIV/AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus life cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity (cobicistat) has recently been approved for use in combinations with anti-retroviral agents (ARVs) that require boosting.

Despite the armamentarium of agents and drug combinations, there remains a medical need for new anti-retroviral agents, due in part to the need for chronic dosing to combat infection. Significant problems related to long-term toxicities are documented, creating a need to address and prevent these co-morbidities (e.g. CNS, CV/metabolic, renal disease). Also, increasing failure rates on current therapies continue to be a problem, due either to the presence or emergence of resistant strains or to non-compliance attributed to drug holidays or adverse side effects. For example, despite therapy, it has been estimated that 63% of subjects receiving combination therapy remained viremic, as they had viral loads >500 copies/ml (Oette, M, Kaiser, R, Daiumer, M, et al. Primary HIV Drug Resistance and Efficacy of First-Line Antiretroviral Therapy Guided by Resistance Testing. J Acq Imm Def Synd 2006; 41(5):573-581). Among these patients, 76% had viruses that were resistant to one or more classes of antiretroviral agents.

As a result, new drugs are needed that are easier to take, have high genetic barriers to the development of resistance and have improved safety over current agents. In this panoply of choices, novel MOAs that can be used as part of the preferred HAART regimen can still have a major role to play since they should be effective against viruses resistant to current agents.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

SUMMARY OF THE INVENTION

The invention encompasses compounds of Formula I, including pharmaceutically acceptable salts, their pharmaceutical compositions, and their use in inhibiting HIV and treating those infected with HIV or AIDS.

One aspect of the invention is a compound of Formula I, including pharmaceutically acceptable salts thereof:

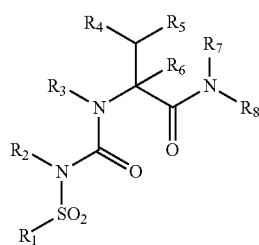

wherein:
$R^1$ is alkyl, aryl, arylalkyl, cycloalkyl or heteroaryl; wherein said aryl, arylalkyl or heteroaryl moieties are linked to the parent molecule through their respective carbon atoms, and further wherein said $R^1$ groups are substituted with 0-4 groups independently selected from the group of alkenyl, alkoxy, alkoxycarbonyl, alkoxycarbonylamino, alkyl, alkylsulphonyl, alkylthioxy, aminocarbonyl, alkynyl, carboxylic acid, cyano, halo, haloalkyl, haloalkoxy, hydroxy, hydroxyalkyl, thioxy, —SO₂alkyl, heteroaryl, and nitro;
$R^2$ is —H, $C_1$-$C_4$ alkyl or $C_3$-$C_4$ cycloalkyl;
or $R^1$ and $R^2$ together with the atoms to which they are attached form a heterocyclic ring optionally substituted with 0-2 alkyl groups;
$R^3$ is —H, $C_1$-$C_4$ alkyl or $C_3$-$C_4$ cycloalkyl;
$R^4$ is —H, alkyl, aryl, $C_5$-$C_{10}$ bicycloalkyl, cycloalkyl or heteroaryl which is substituted with 0-3 groups independently selected from the group of alkenoxy, alkenyl, alkoxy, alkoxycarbonyl, alkyl, benzyloxy, carboamide, cyano, halo, haloalkyl, haloalkoxy, —NHCO(alkyl), —SO₂N-heterocycle, —OH, nitro, and —CH₂OH;
$R^5$ and $R^6$ are independently selected from H or alkyl, or $R^5$ and $R^4$ together with the atom to which they are attached form an aryl group; or $R^5$ and $R^6$ together with the atoms to which they are attached form a $C_3$-$C_4$ cycloalkyl;
$R^7$ is —H, alkyl, aryl, heteroaryl, heteroarylalkyl, $C_3$-$C_7$ cycloalkyl or dialkylaminoalkyl, wherein said aryl or heteroaryl is substituted with 0-3 groups independently selected from the group of —OH, —NHCOalkyl, —NHCON(alkyl)₂, —NHCO₂-alkyl, —CONH₂, —CN, —SO₂N(alkyl)₂, alkoxy, alkyl, halo, haloalkoxy, and haloalkyl; and
$R^8$ is —H, alkyl, arylalkyl, cycloalkyl, haloalkyl or heteroarylalkyl;

or R$^7$ and R$^8$ together with the nitrogen atom to which they are attached form a heterocycle which is substituted with 0-3 groups independently selected from the group of alkyl, alkoxy, halo, —OH, —CN, and —SO$_2$N(alkyl)$_2$.

For a compound of Formula I, the scope of any instance of a variable substituent can be used independently with the scope of any other instance of a variable substituent. As such, the invention includes combinations of the different aspects.

The invention also relates to pharmaceutical compositions comprising a compound of Formula I, including pharmaceutically acceptable salts thereof, and a pharmaceutically acceptable carrier, excipient, and/or diluent.

In addition, the invention provides one or more methods of treating HIV infection comprising administering a therapeutically effective amount of a compound of Formula I to a patient.

Also provided as part of the invention are one or more methods for making the compounds of Formula I.

The present invention is directed to these, as well as other important ends, hereinafter described.

DETAILED DESCRIPTION OF THE EMBODIMENTS

The singular forms "a", "an", and "the" include plural reference unless the context dictates otherwise.

Unless otherwise expressly set forth elsewhere in the application, the following terms shall have the following meanings:

"Alkenyl" means a straight or branched alkyl group comprised of 2 to 10 carbons with at least one double bond and optionally substituted with 0-3 halo or alkoxy group.

"Alkenyloxy" means an alkenyl group attached to the parent structure by an oxygen atom.

"Alkoxy" means an alkyl group attached to the parent structure by an oxygen atom.

"Alkoxycarbonyl" means an alkoxy group attached to the parent structure by a carbonyl moiety.

"Alkoxycarbonylamino" means alkoxycabonyl group attached to the parent structure by nitrogen where the nitrogen is optionally substituted with an alkyl group.

"Alkyl" means a straight or branched saturated hydrocarbon comprised of 1 to 10 carbons, and preferably 1 to 6 carbons.

"Alkylsulphonyl" means an alkyl group attached to the parent structure through —SO$_2$— moiety.

"Alkylthioxy" means an alkyl group attached to the parent structure through a sulfur atom.

"Alkynyl" means an optionally substituted straight or branched alkyl group comprised of 2 to 10 carbons and containing at least one triple bond.

"Aminocabonyl" means an amine group attached to the parent structure through a carbonyl moiety where the amine is optionally substituted with one or two alkyl groups.

"Aryl" mean a carbocyclic group comprised of 1-3 rings that are fused and/or bonded and at least one or a combination of which is aromatic. The non-aromatic carbocyclic portion, where present, will be comprised of C$_3$ to C$_7$ alkyl group. Examples of an aromatic group include phenyl, biphenyl, dihydroindene, naphthalene, and tetrahydronaphthalene. The aryl group can be attached to the parent structure through any substitutable carbon atom in the group.

"Arylalkyl" is a C$_1$-C$_5$ alkyl group attached to 1 to 2 aryl groups and linked to the parent structure through the alkyl moiety and where the aryl component is further substituted with 0-4 groups selected from halo, alkyl, alkoxy, haloalkyl, haloalkoxy or cyano. Examples include, but are not limited to, —(CH$_2$)$_n$Ph and —CH(CH$_3$)Ph with n=1-5.

"Benzyloxy" means a benzyl group attached to the parent structure through an oxygen atom. The phenyl group of the benzyl moiety could be optionally substituted by 1-3 moieties independently selected from the group of alkyl, alkoxy, halo, haloalkyl, haloalkoxy and cyano.

"C$_5$-C$_{10}$ bicycloalkyl" means a bicyclic ring system comprised of 5 to 10 carbons. Examples include bicyclo[2.2.2]octane.

"C$_3$-C$_4$ cycloalkyl" means a monocyclic ring system comprised of 3 to 4 carbons.

"Cycloalkyl" means carbocycle with 1-2 rings optionally substituted with an alkyl or benzyl group.

"Cyano" refers to —CN.

"Dialkylaminoalkyl" means a dialkylamino group attached to the parent structure through a C$_2$ to C$_3$ alkyl moiety.

"Halo" or "halogen" refers to —F, —Cl, —Br, or —I.

"Haloalkyl" means an alkyl group substituted by any combination of one to six halogen atoms.

"Haloalkoxy" means a haloalkyl group attached to the parent structure through an oxygen atom.

"Hydroxy" refers to —OH.

"Heteroaryl" is a subset of heterocyclic group as defined below and is comprised of 1-3 rings where at least one or a combination of which is aromatic and that the aromatic group contains at least one atom chosen from a group of oxygen, nitrogen or sulfur.

"Heteroarylalkyl" is a heteroaryl moiety attached to the parent structure through C$_1$-C$_5$ alkyl group and where the aryl moiety is further substituted with halo, alkyl, alkoxy, haloalkyl, haloalkoxy or cyano. Examples include, but are not limited to, —(CH$_2$)$_n$-pyridine, —(CH$_2$)$_n$-thiazole, —(CH$_2$)$_n$-quinoline, —(CH$_2$)$_n$-phenyl-pyrazole, —(CH$_2$)$_n$-(2-methylbenzimidazole), —(CH$_2$)$_n$—(N-methylimidazole), —(CH$_2$)$_n$-(methyloxadiazole), —CH(CH$_3$)-(pyridine) with n=1-5.

"Heterocyclic" means a cyclic group of 1-3 rings comprised of carbon and at least one other atom selected independently from the group of oxygen, nitrogen and sulfur. The rings could be fused and/or bonded, through a direct or spiro attachment, with the option to have one or a combination thereof be aromatic. Examples include, but are not limited to, azaindole, azaindoline, azetidine, benzimidazole, bezodioxolyl, benzoxazole, benzothiophene, benzothiazole, chroman, dihydro-benzo[1,4]oxazine, dihalobezodioxolyl, dihydrobenzofuran, furanylphenyl, imidazo[1,2-a]pyridine, indazole, indole, indoline, isoquinoline, isoquinolinone, isothiazolidine 1,1-dioxide, morpholine, 2-oxa-5-azabicyclo[2.2.1]heptanes, oxadiazole-phenyl, pyrazole-phenyl, pyridine-phenyl, pyridinylpyrrolidine, pyrimidine-phenyl, quinazoline, quinoxaline, quinoline, tetrahydroisoquinoline, tetrahydrothieno[3,2-c]pyridine, thiophene, thiophene-phenyl, triazole. Unless otherwise specifically set forth, the heterocyclic group can be attached to the parent structure through any suitable atom in the group that results in a stable compound.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

As set forth above, the invention is directed to a compound of Formula I, including pharmaceutically acceptable salts thereof:

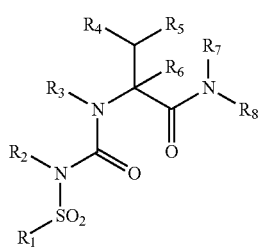

I wherein:
$R^1$ is alkyl, aryl, arylalkyl, cycloalkyl or heteroaryl; wherein said aryl, arylalkyl or heteroaryl moieties are linked to the parent molecule through their respective carbon atoms, and further wherein said $R^1$ groups are substituted with 0-4 groups independently selected from the group of alkenyl, alkoxy, alkoxycarbonyl, alkoxycarbonylamino, alkyl, alkylsulphonyl, alkylthioxy, aminocarbonyl, alkynyl, carboxylic acid, cyano, halo, haloalkyl, haloalkoxy, hydroxy, hydroxyalkyl, thioxy, —SO$_2$alkyl, heteroaryl, and nitro;

$R^2$ is —H, $C_1$-$C_4$ alkyl or $C_3$-$C_4$ cycloalkyl;

or $R^1$ and $R^2$ together with the atoms to which they are attached form a heterocyclic ring optionally substituted with 0-2 alkyl groups;

$R^3$ is —H, $C_1$-$C_4$ alkyl or $C_3$-$C_4$ cycloalkyl;

$R^4$ is —H, alkyl, aryl, $C_5$-$C_{10}$ bicycloalkyl, cycloalkyl or heteroaryl which is substituted with 0-3 groups independently selected from the group of alkenoxy, alkenyl, alkoxy, alkoxycarbonyl, alkyl, benzyloxy, carboamide, cyano, halo, haloalkyl, haloalkoxy, —NHCO(alkyl), —SO$_2$N-heterocycle, —OH, nitro, and —CH$_2$OH;

$R^5$ and $R^6$ are independently selected from H or alkyl, or $R^5$ and $R^4$ together with the atom to which they are attached form an aryl group; or $R^5$ and $R^6$ together with the atoms to which they are attached form a $C_3$-$C_4$ cycloalkyl;

$R^7$ is —H, alkyl, aryl, heteroaryl, heteroarylalkyl, $C_3$-$C_7$ cycloalkyl or dialkylaminoalkyl, wherein said aryl or heteroaryl is substituted with 0-3 groups independently selected from the group of —OH, —NHCOalkyl, —NHCON(alkyl)$_2$, —NHCO$_2$-alkyl, —CONH$_2$, —CN, —SO$_2$N(alkyl)$_2$, alkoxy, alkyl, halo, haloalkoxy, and haloalkyl; and $R^8$ is —H, alkyl, arylalkyl, cycloalkyl, haloalkyl or heteroarylalkyl;

or $R^7$ and $R^8$ together with the nitrogen atom to which they are attached form a heterocycle which is substituted with 0-3 groups independently selected from the group of alkyl, alkoxy, halo, —OH, —CN, and —SO$_2$N(alkyl)$_2$.

In a preferred embodiment of the invention, $R^1$ is aryl. More preferably, $R^1$ is aryl which is selected from the group of phenyl, biphenyl, and naphthalenyl.

In a further embodiment, $R^1$ is heteroaryl. More preferably, $R^1$ is selected from the group of thiophene, pyrrazolophenyl, furanylphenyl, pyridinylphenyl, pyrimidinylphenyl, thiophenylphenyl, benzothiophene, oxadiazolephenyl, indole, and andazaindole.

In a further preferred embodiment, $R^1$ and $R^2$ form a heteroaryl ring. More preferably, the heteroaryl ring is isothiazolidine 1,1-dioxide.

It is also preferred that $R^4$ is aryl. More preferably, $R^4$ is phenyl, naphthalenyl, or biaryl.

In another embodiment it is preferred that $R^4$ is heteroaryl. More preferably, $R^4$ is triazole or thiophene.

It is further preferred that $R^7$ is aryl. More preferably, $R^7$ is phenyl or naphthalenyl.

In another embodiment it is preferred that $R^7$ is heteroaryl. More preferably $R^7$ is selected from the group of bezodioxolyl, dihalobezodioxolyl, benzothiazole, quinoline, benzothiazole, benzimidazole, quinazoline, quinoxaline, dihydrobenzofuran, chroman, benzoxazole, isoquinoline, and isoquinolinone.

In a further embodiment of the invention, $R^7$ and $R^8$ form a heterocycle. More preferably, the heterocycle is selected from the group of tetrahydroisoquinoline, dihydro-benzo[1,4]oxazine, dihydroindole, tetrahydrothieno[3,2-c]pyridine, 2-oxa-5-azabicyclo[2.2.1]heptanes, azetidine, and pyridinylpyrrolidine.

Preferred compounds of the invention, including pharmaceutically acceptable salts thereof, are selected from the group of:

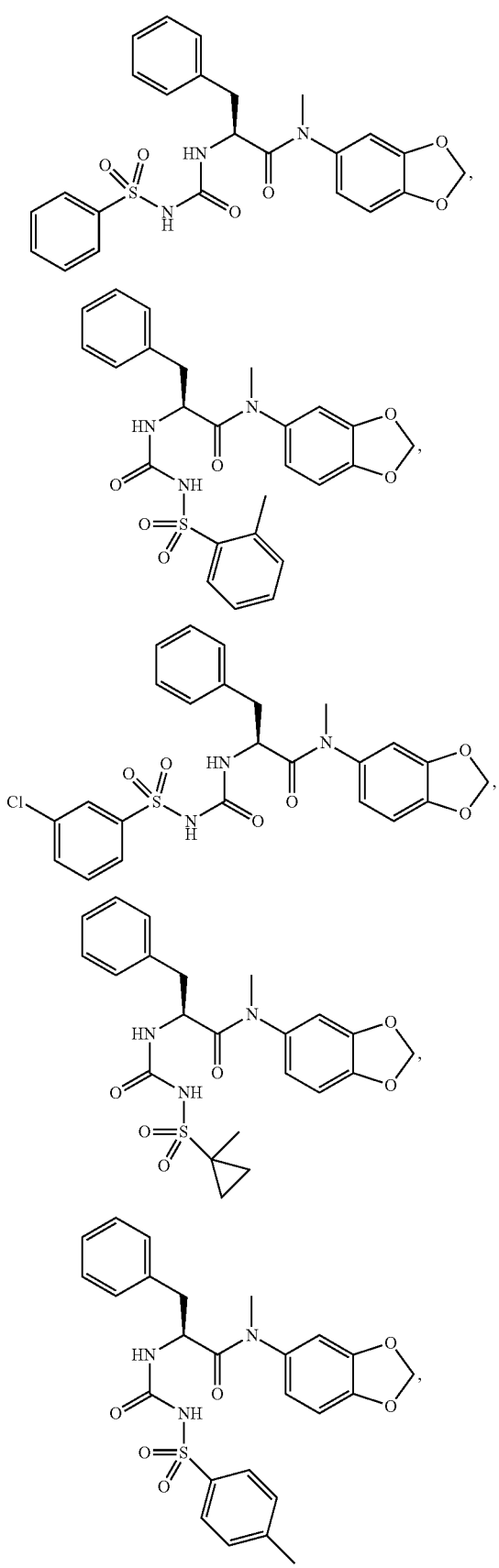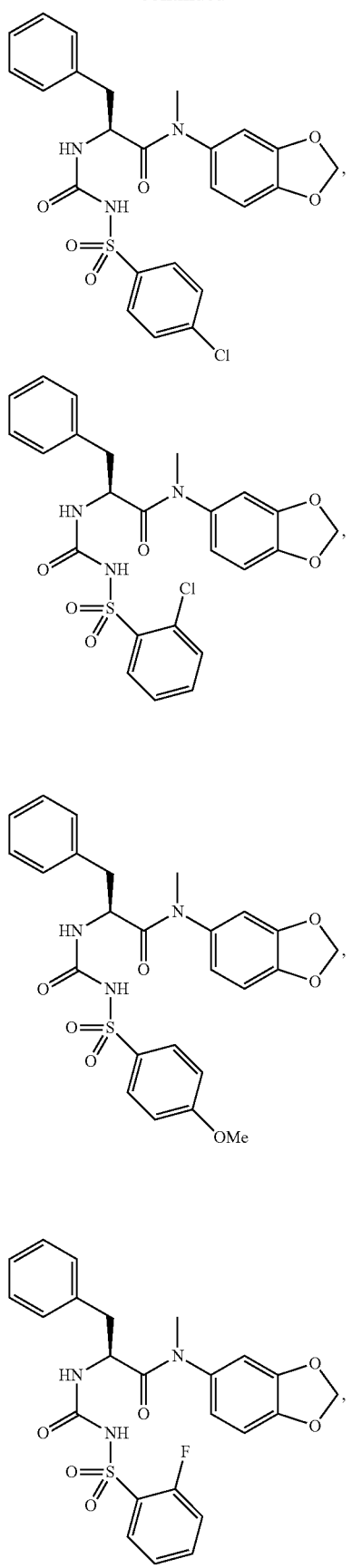

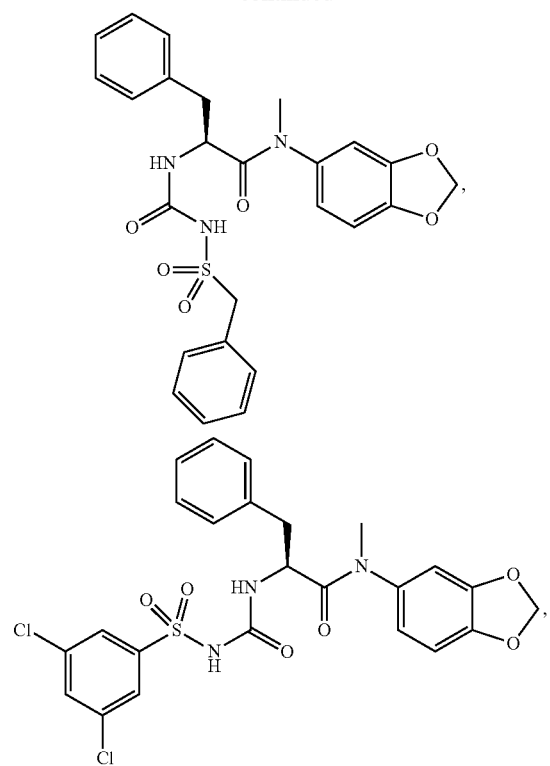
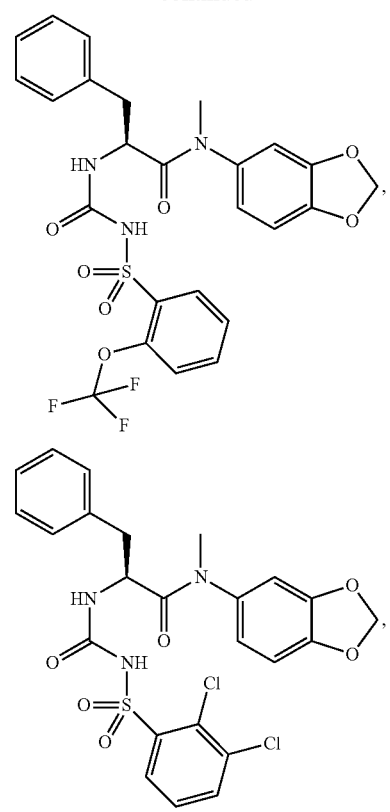
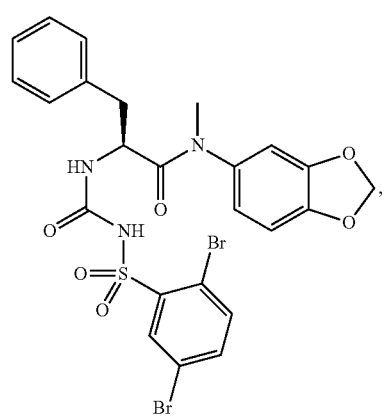
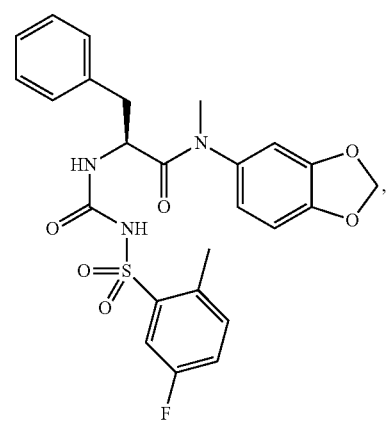
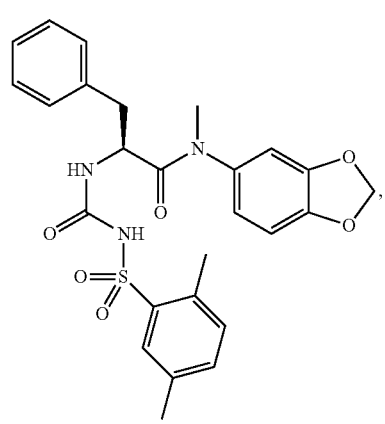
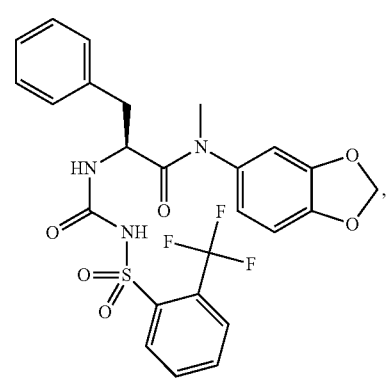

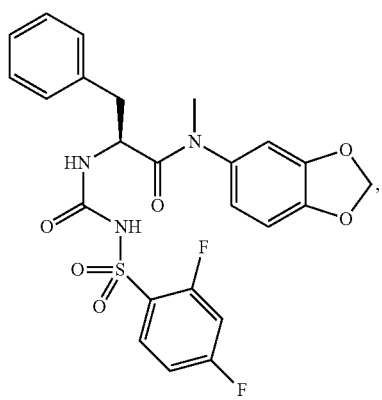
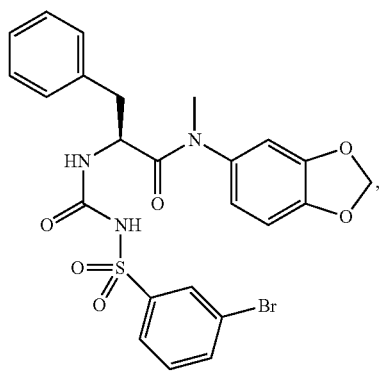
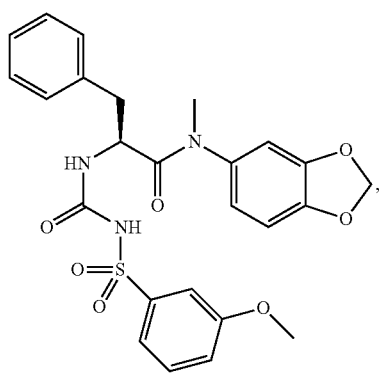
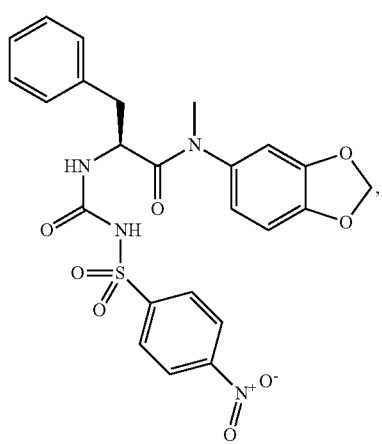
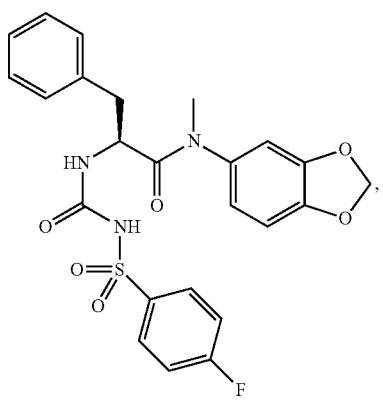
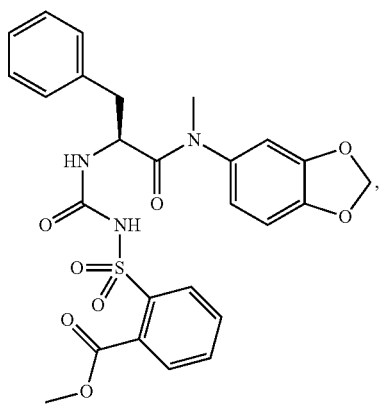
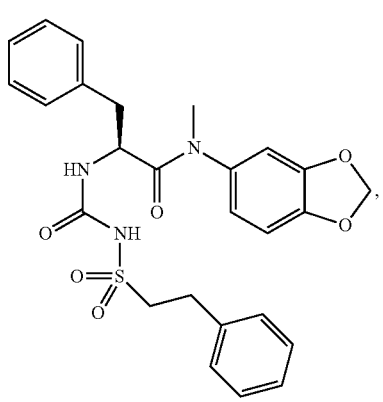
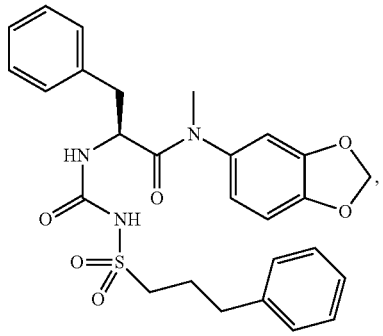

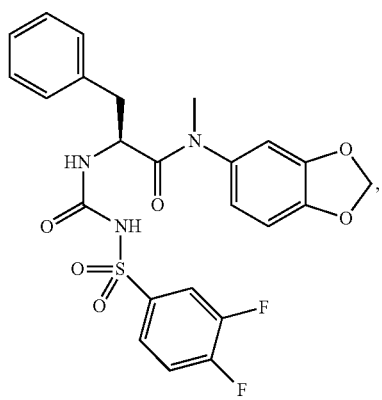
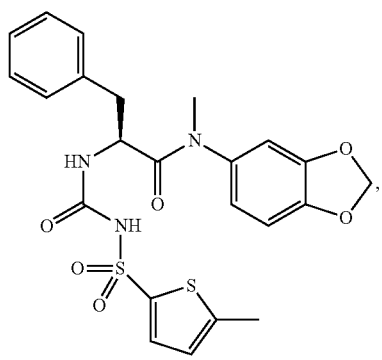
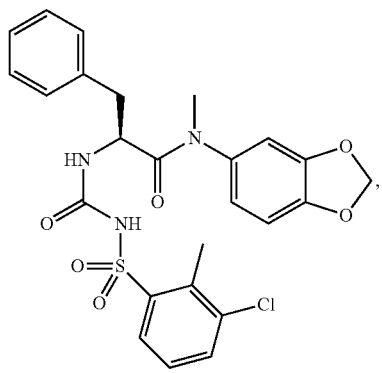
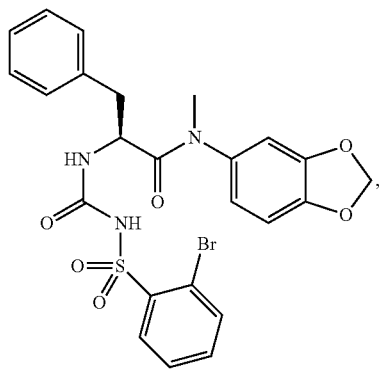
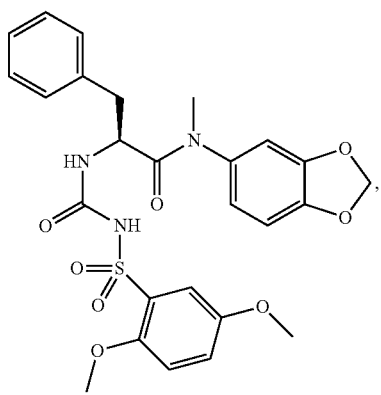
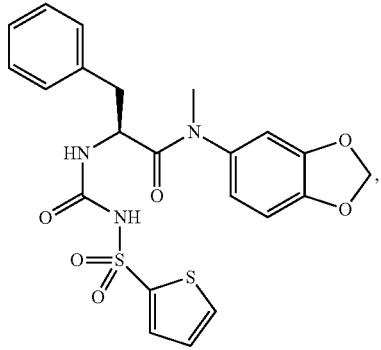
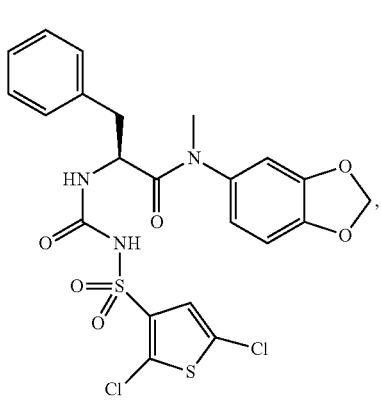
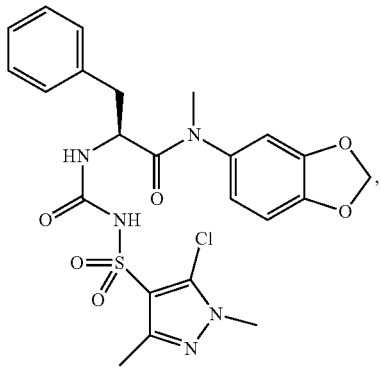

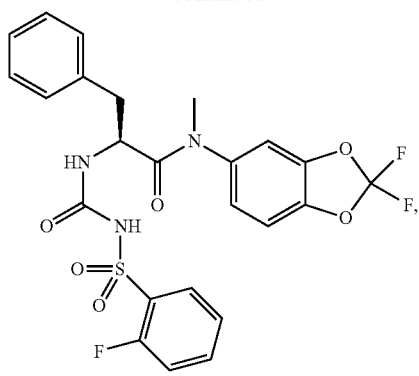
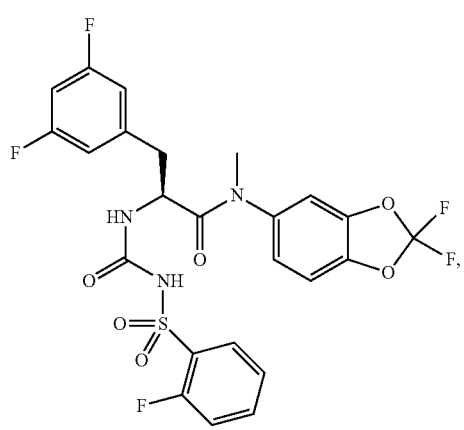
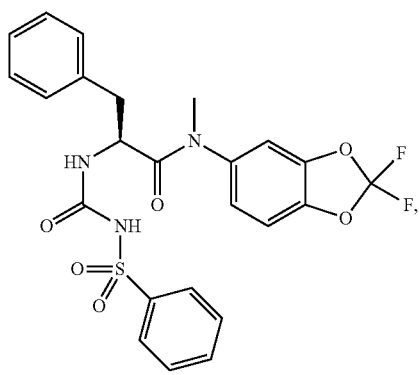
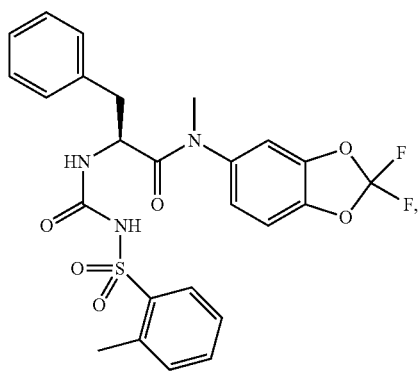
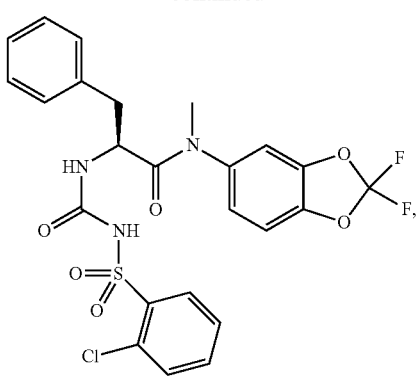
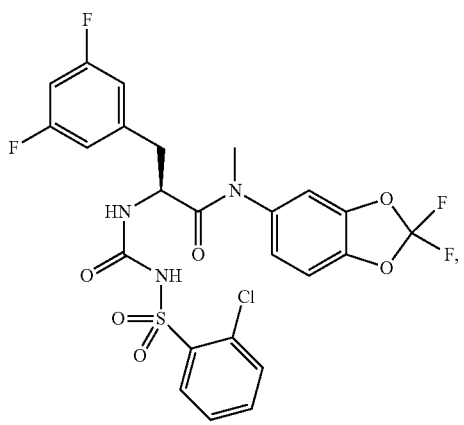
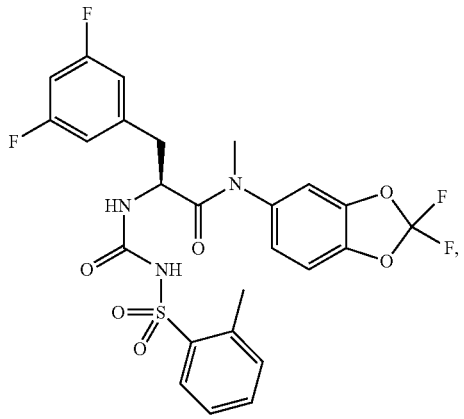
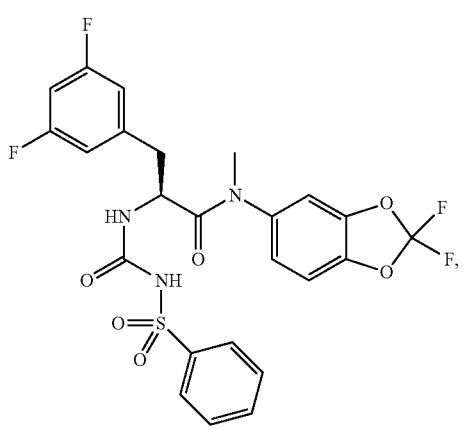

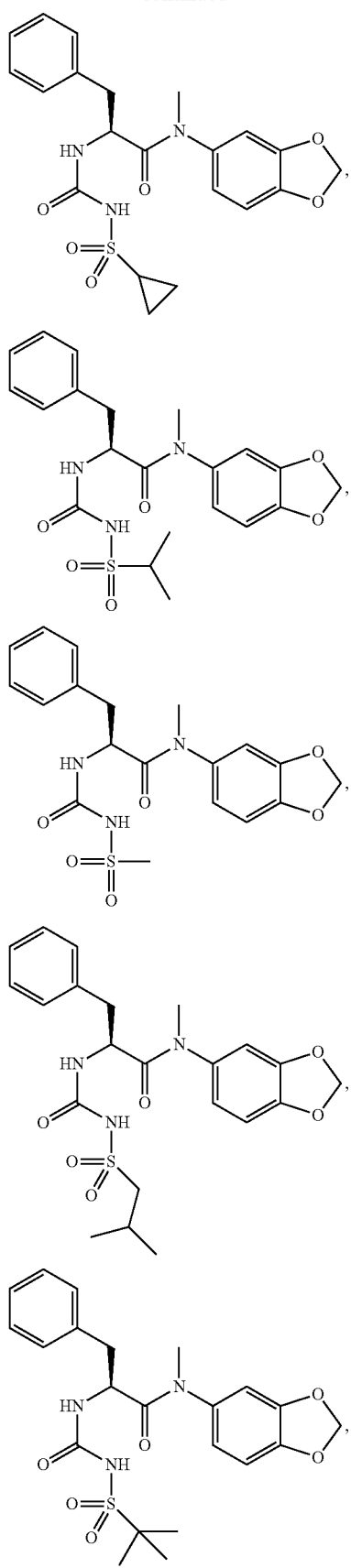
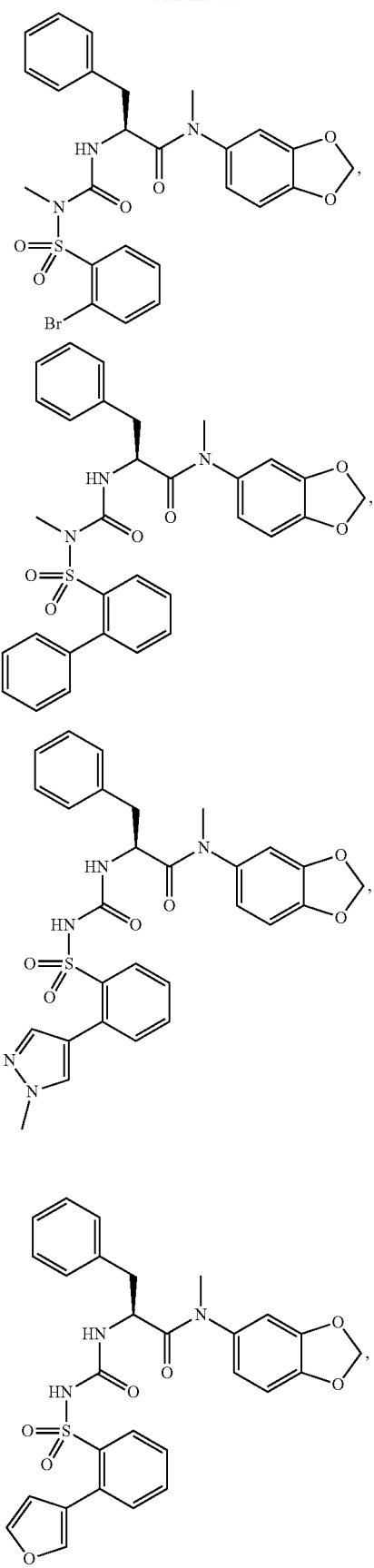

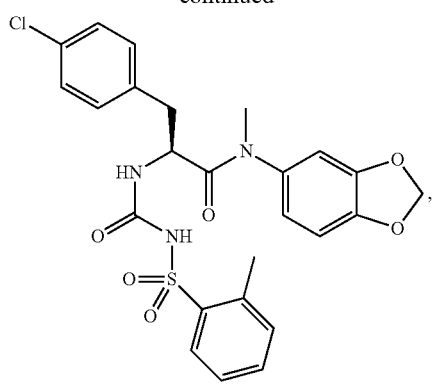
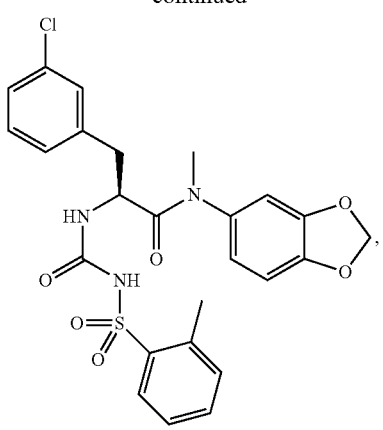
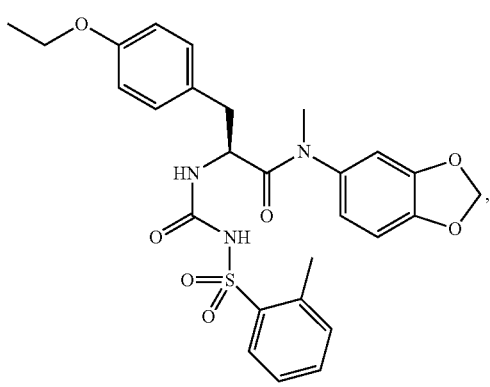
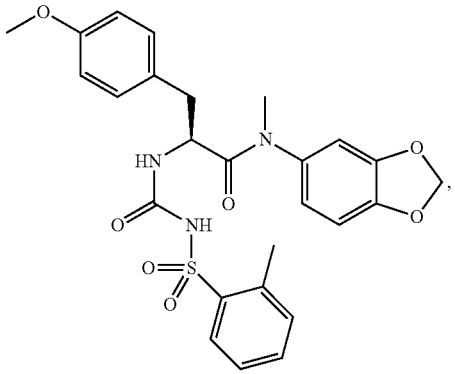
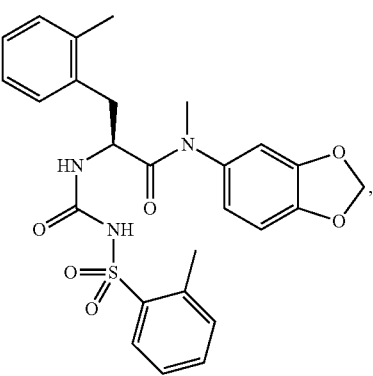
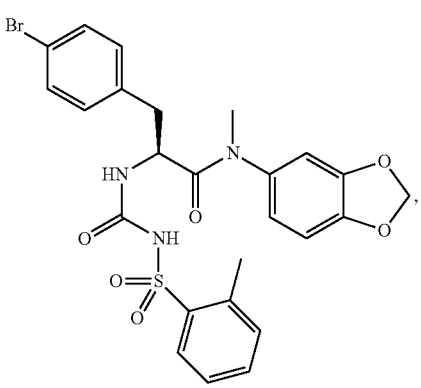
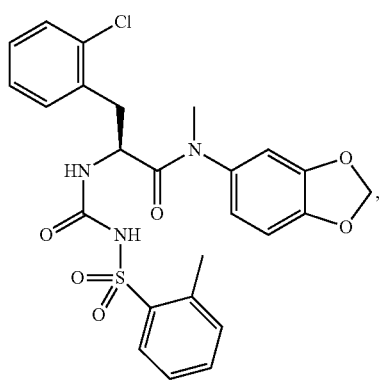
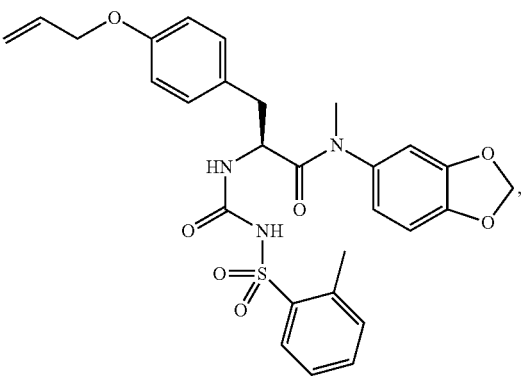

-continued
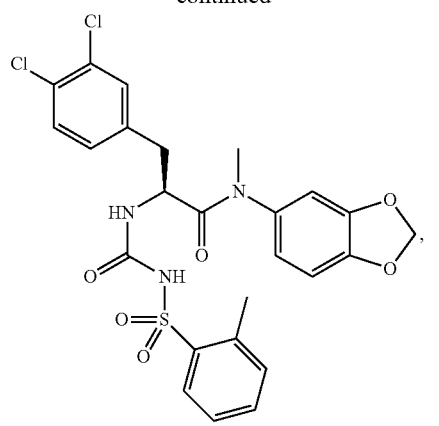
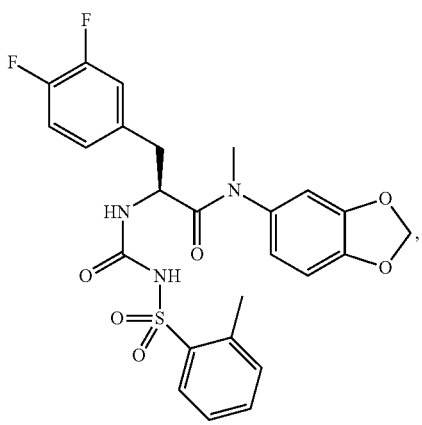
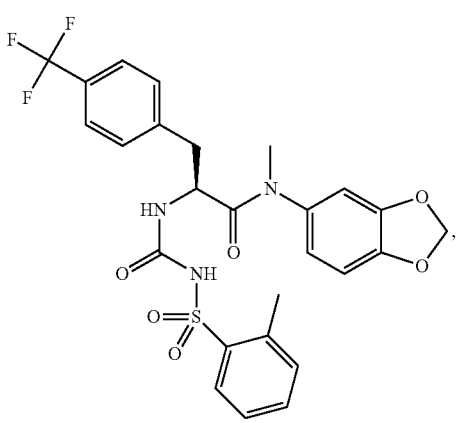
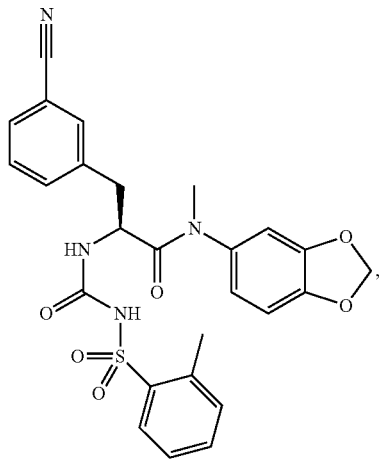
-continued
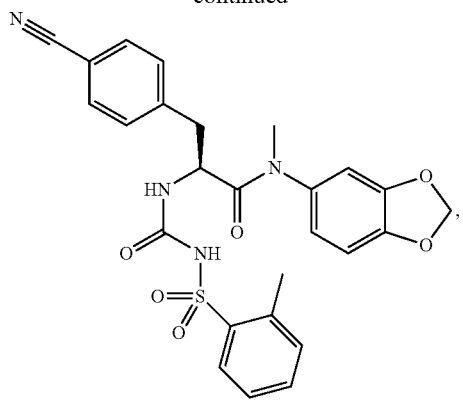
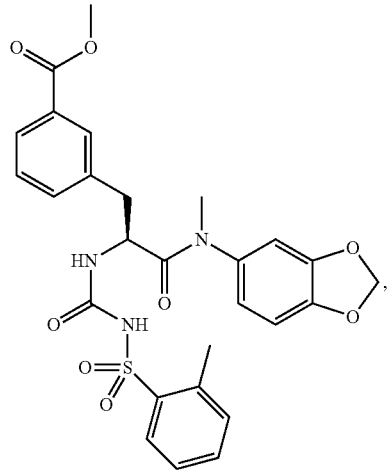
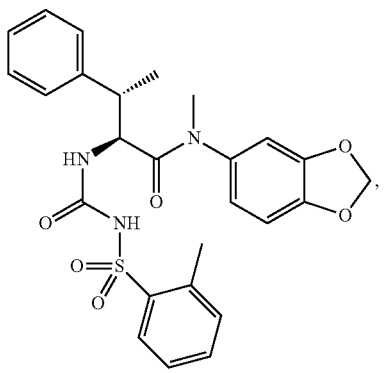
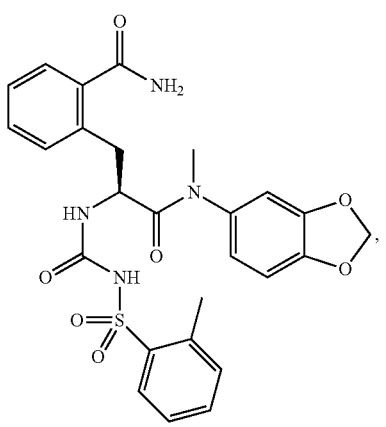

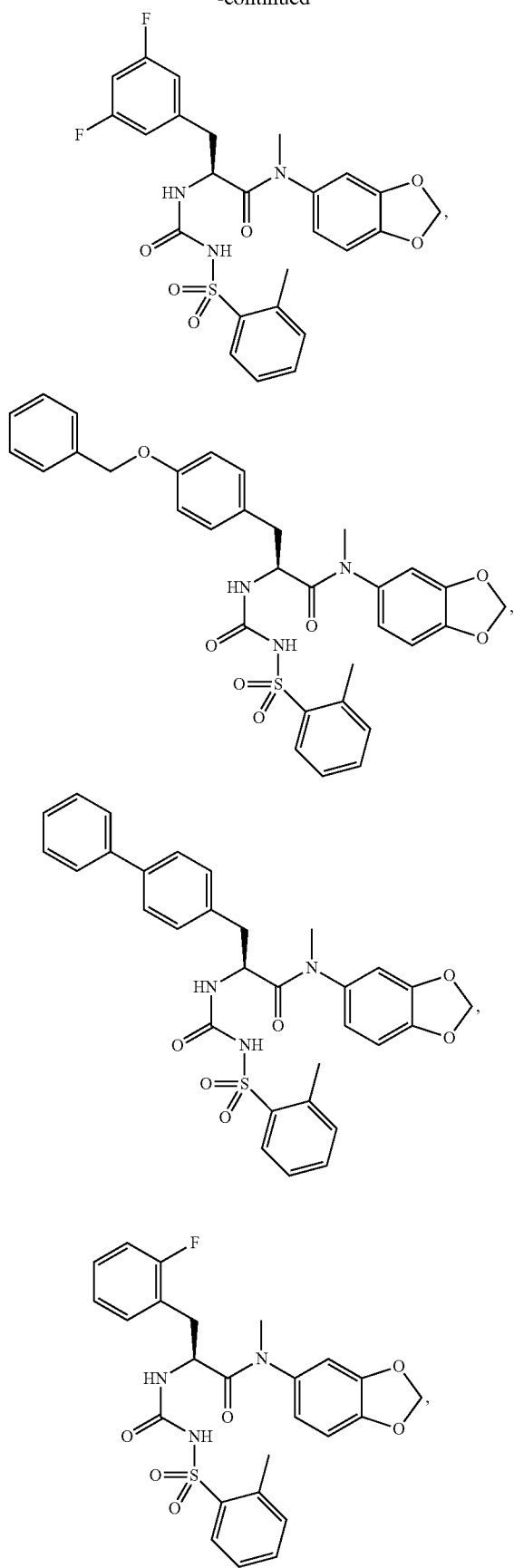
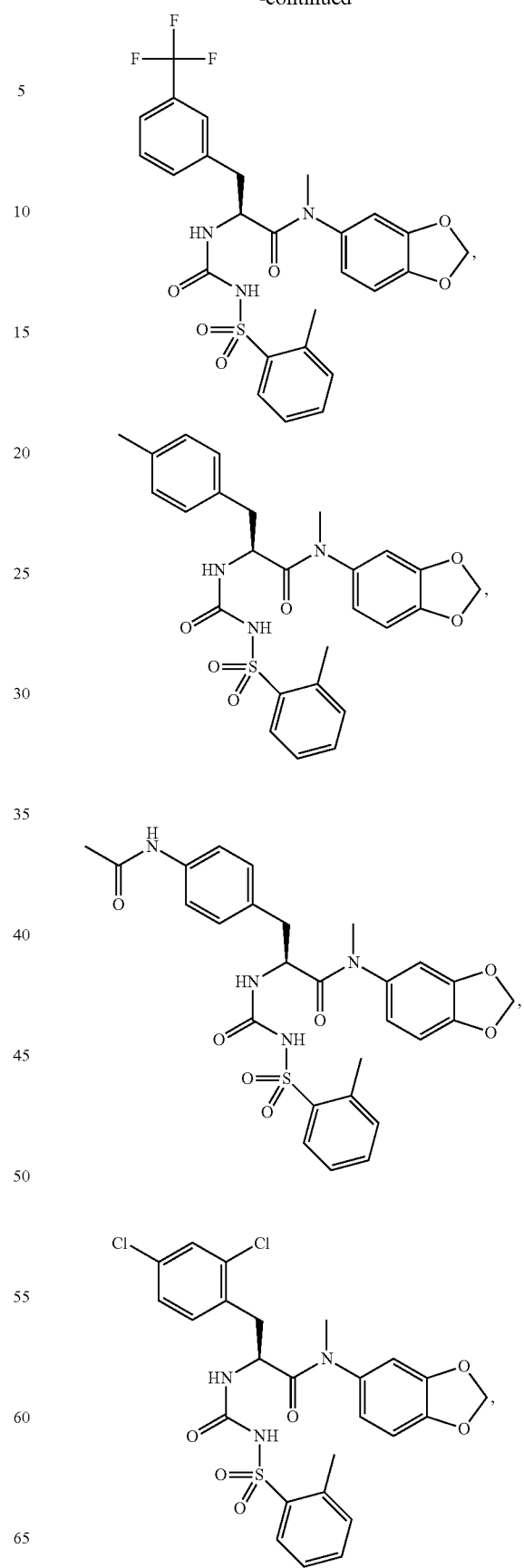

25
-continued
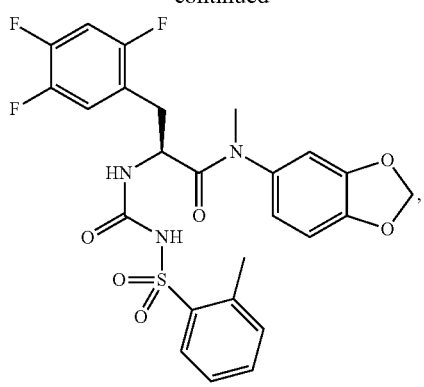
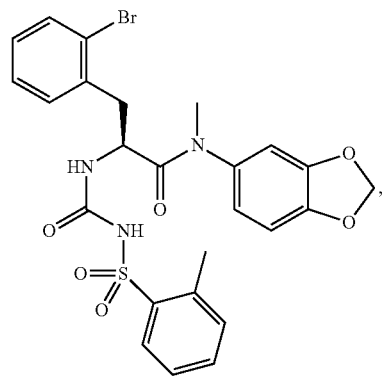
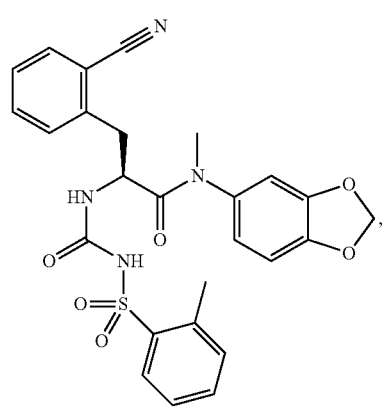
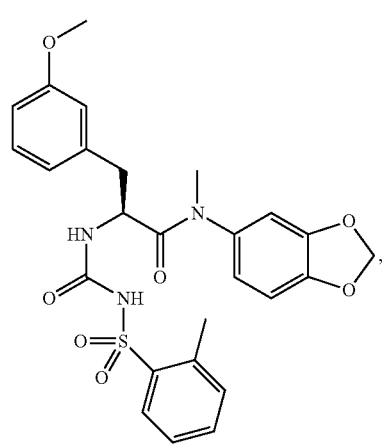
26
-continued
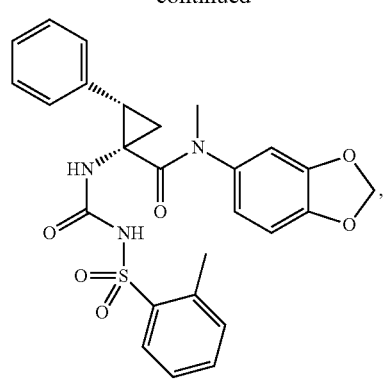
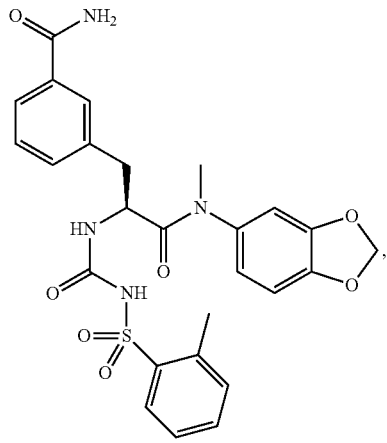
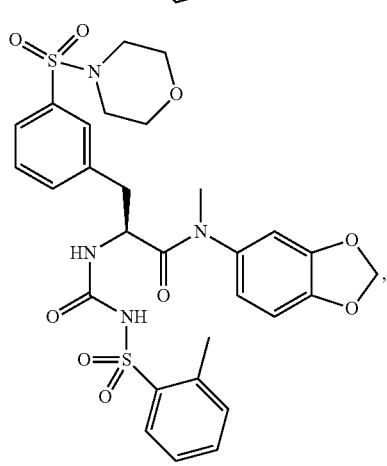
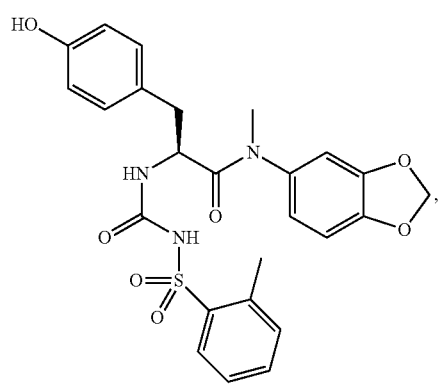

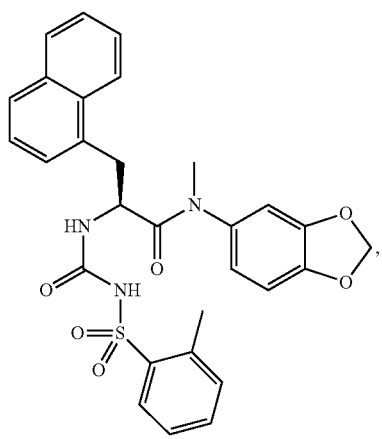
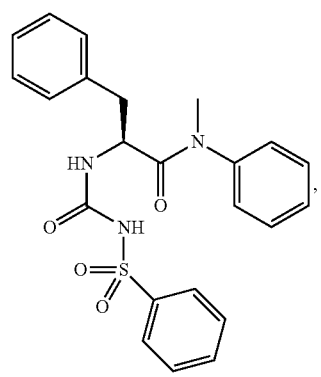
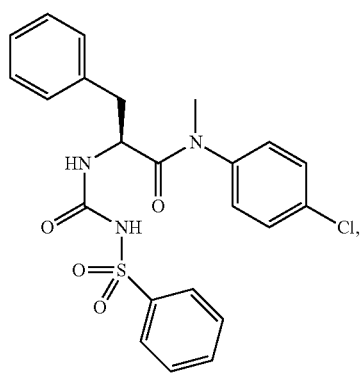
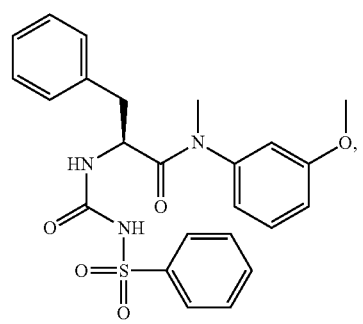
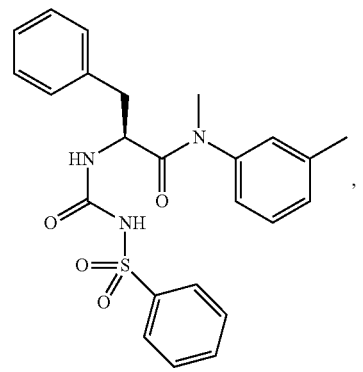

29
-continued
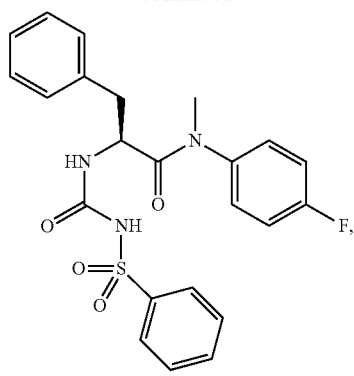
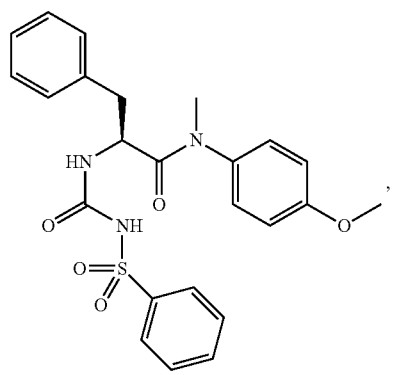
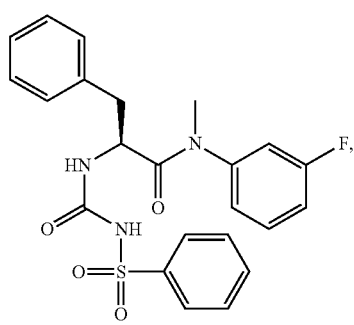
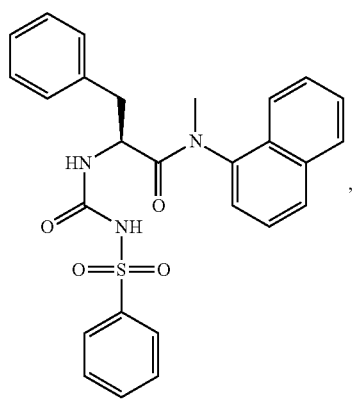
30
-continued
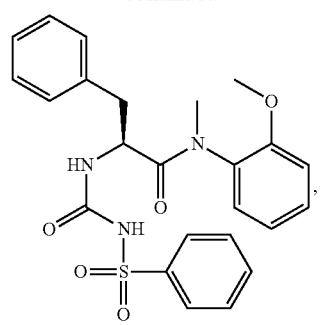
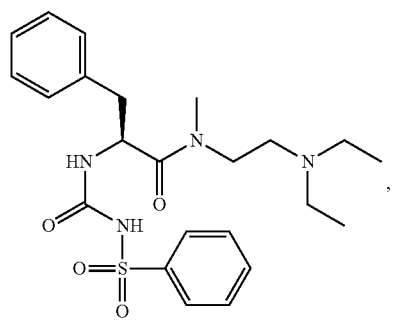
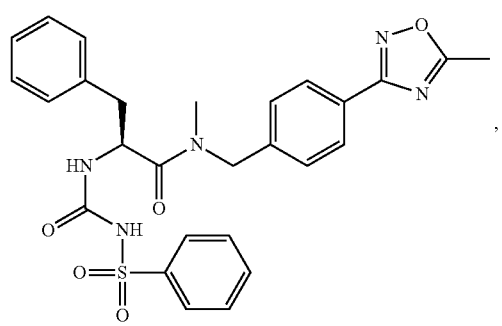
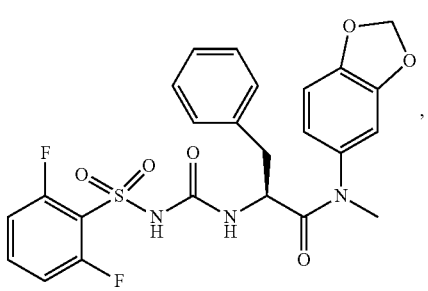
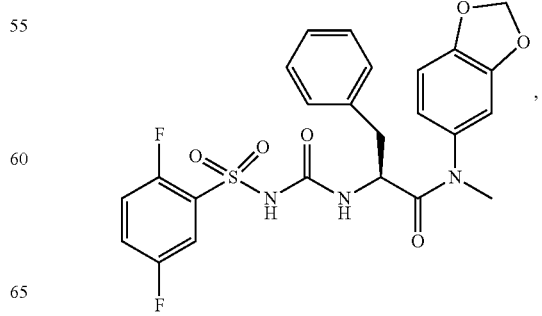

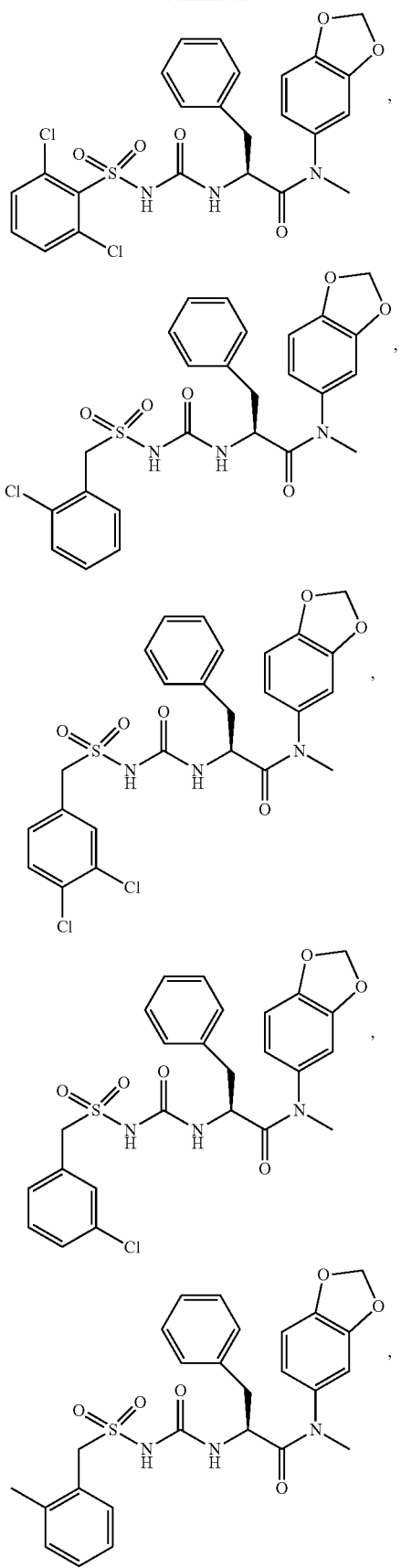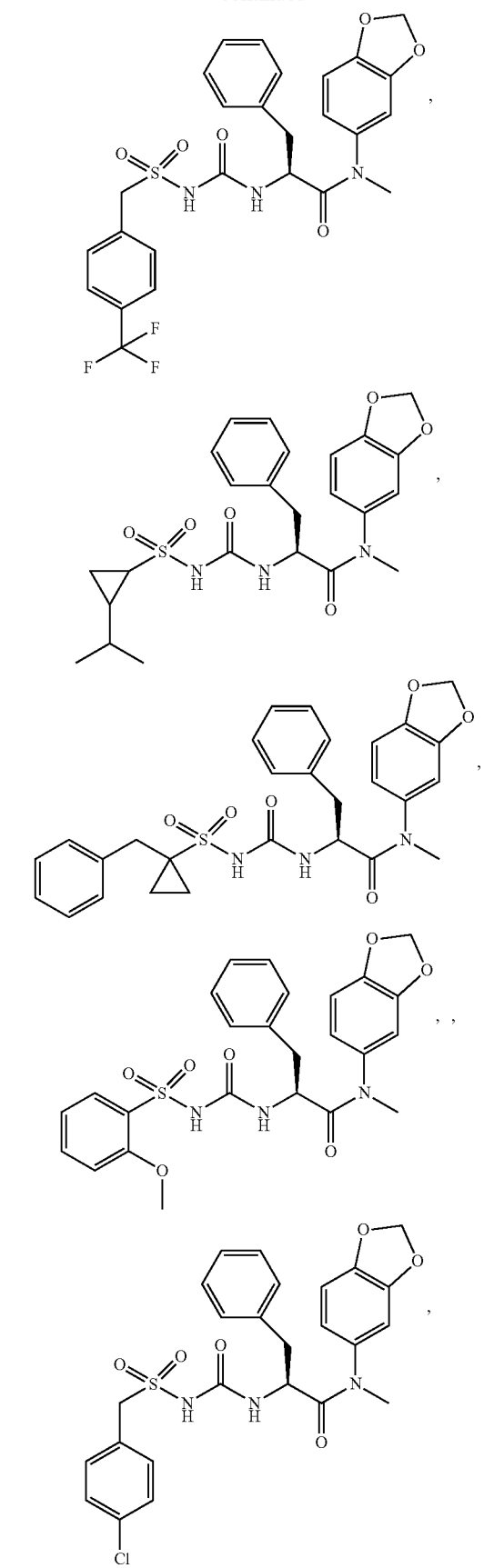

-continued
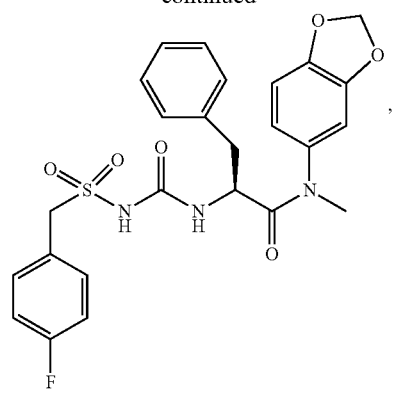
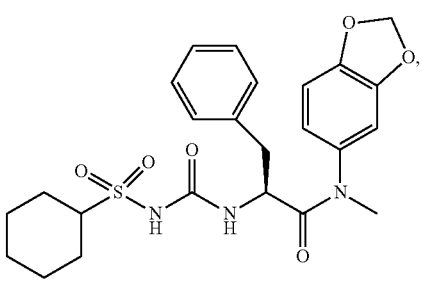
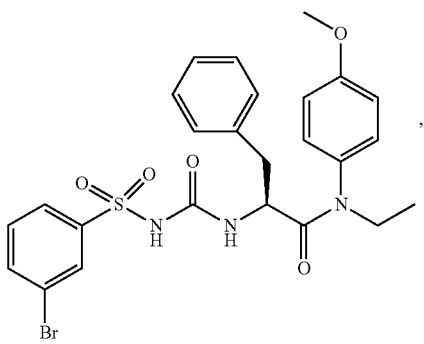
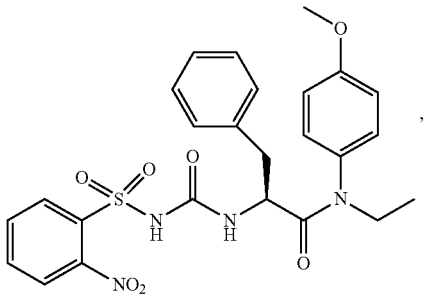
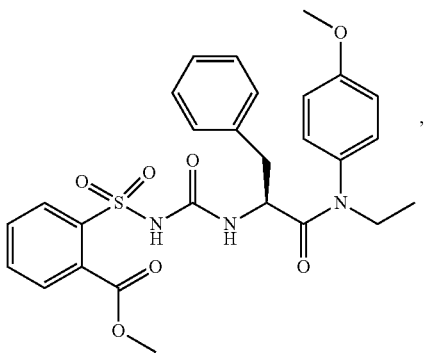
-continued
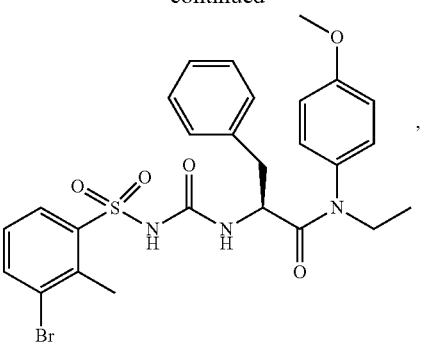
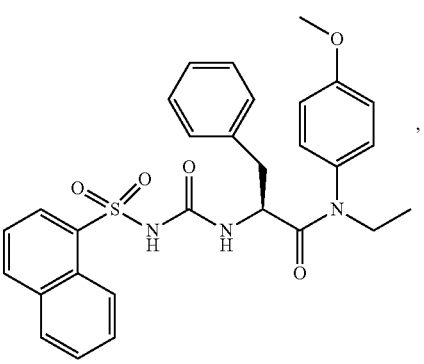
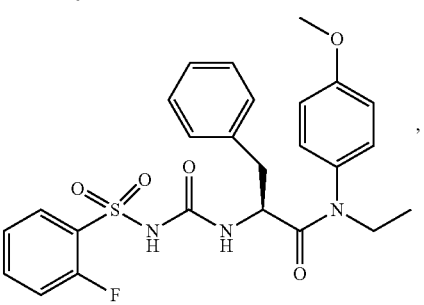
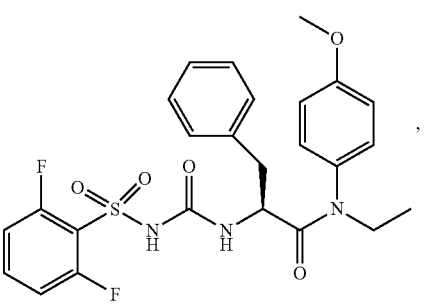
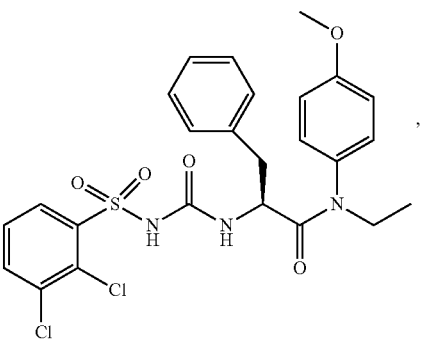

35
-continued
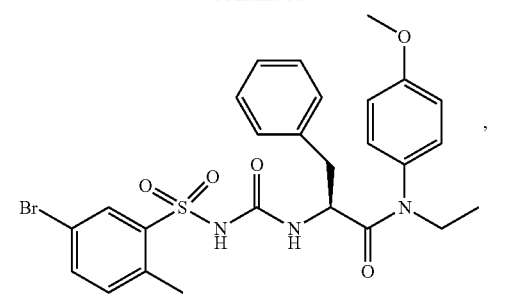
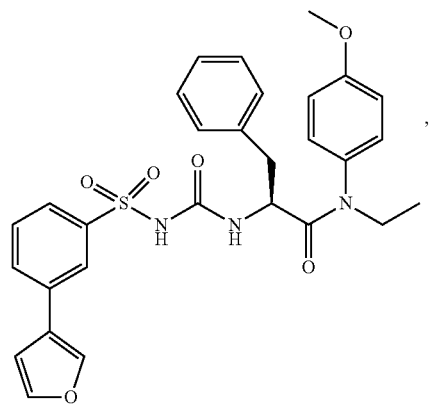
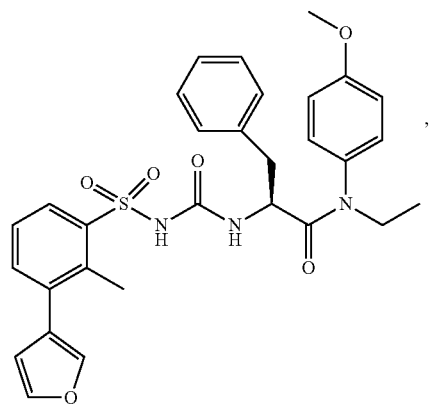
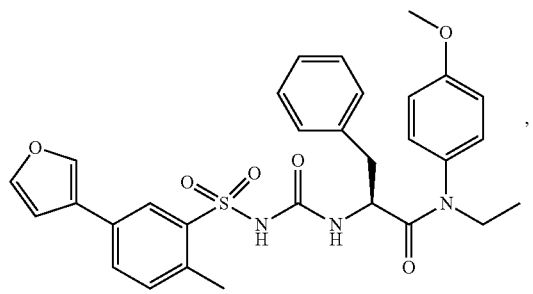
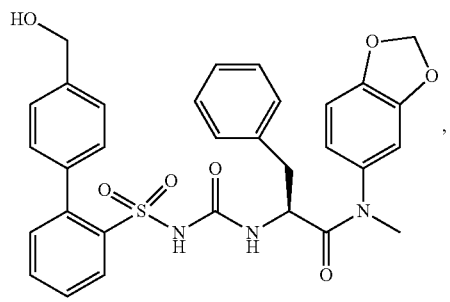
36
-continued
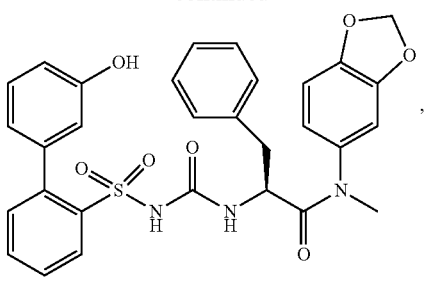
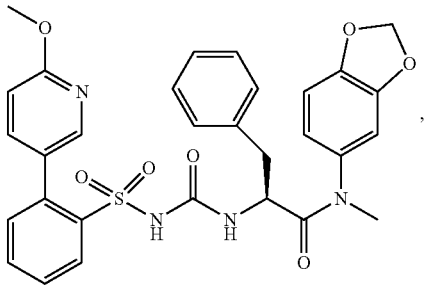
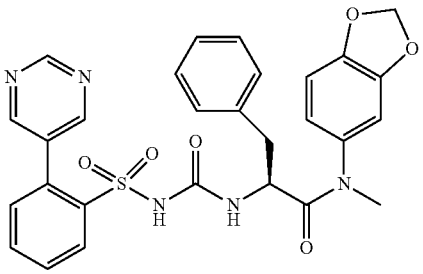
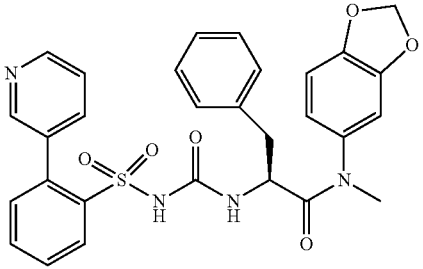
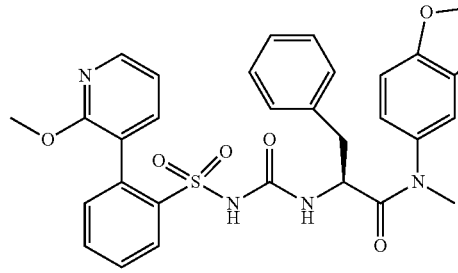
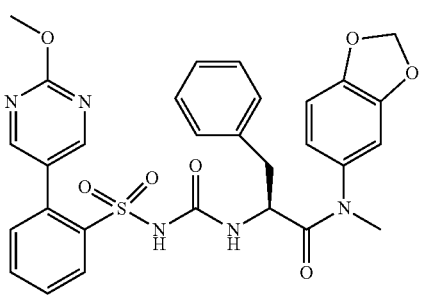

37
-continued
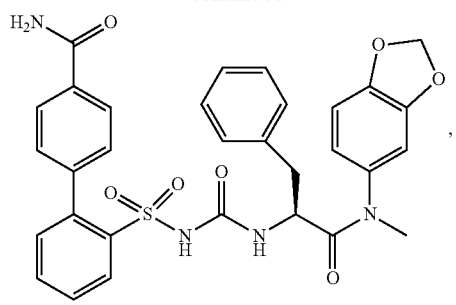
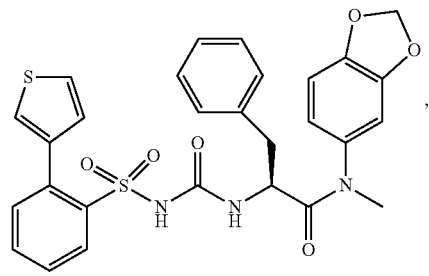
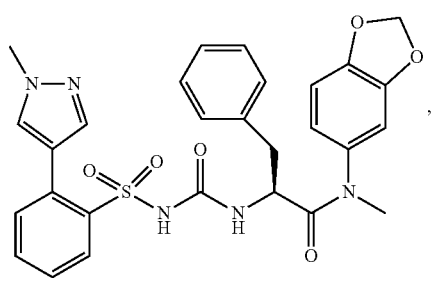
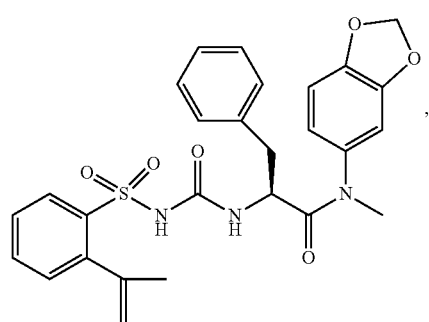
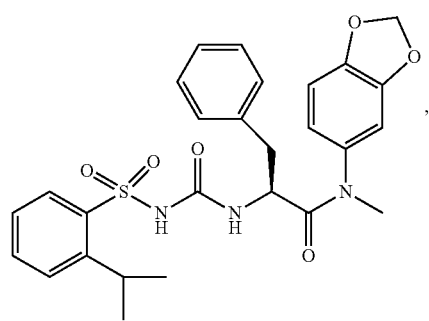
38
-continued
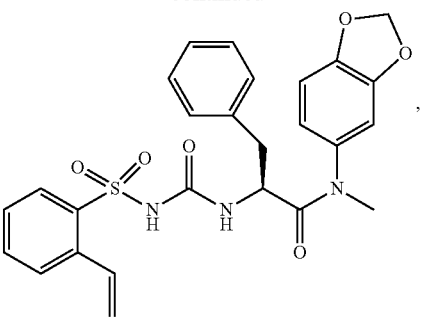
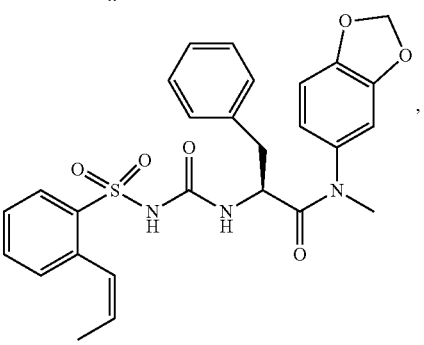
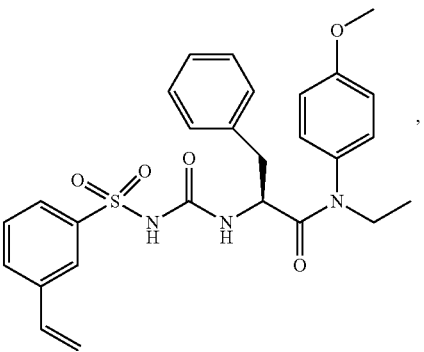
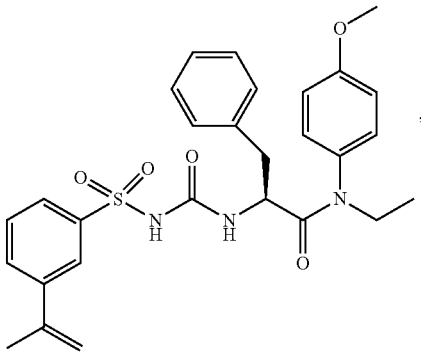
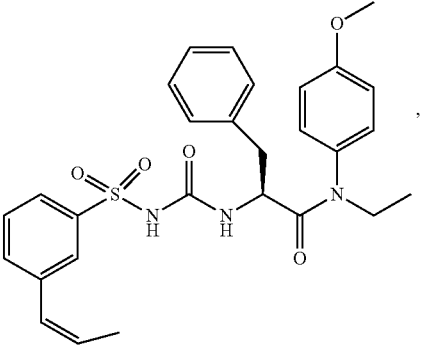

39
-continued
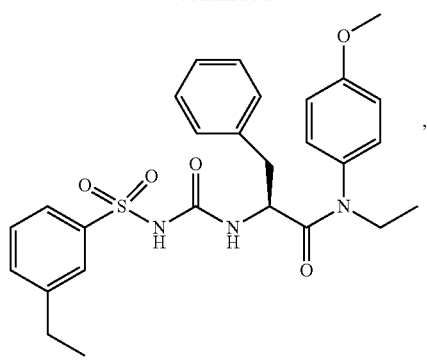
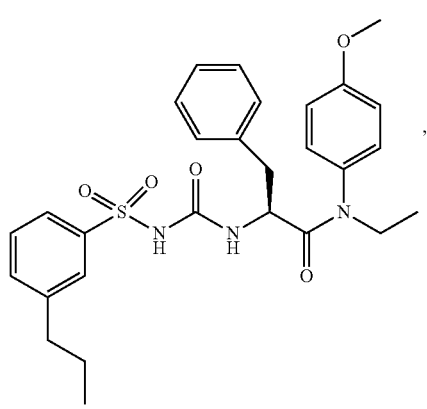
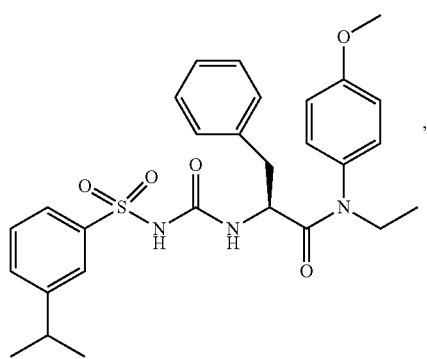
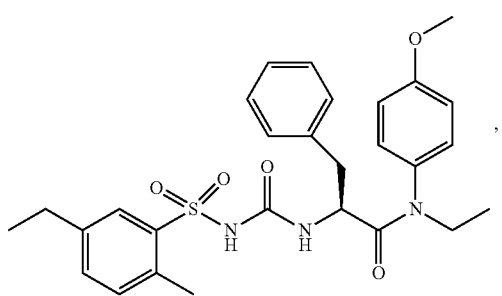
40
-continued
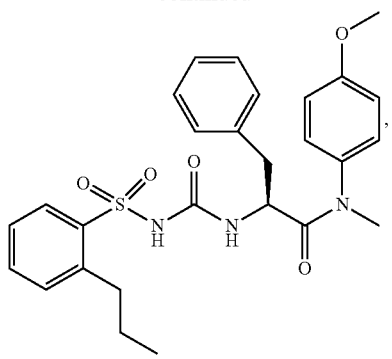
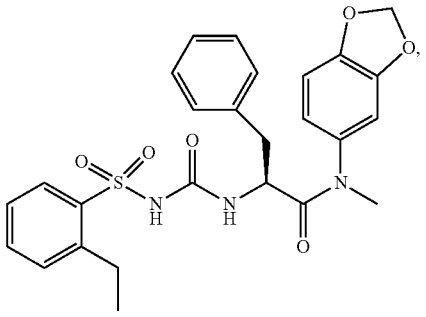
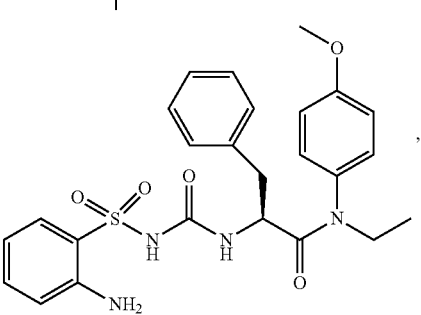
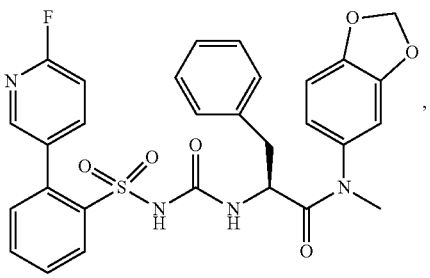
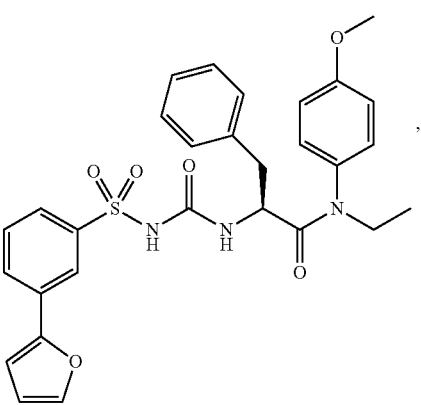

41
-continued
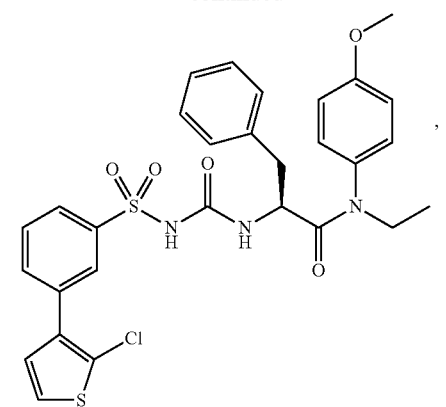
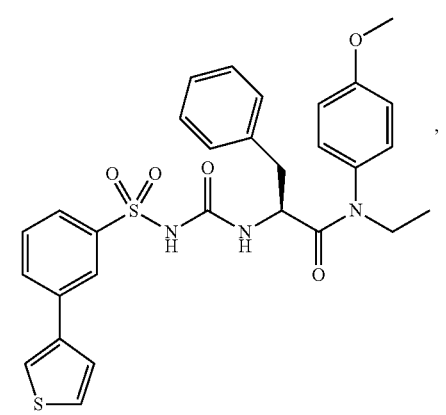
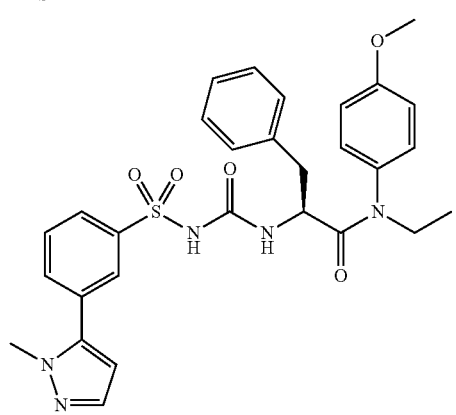
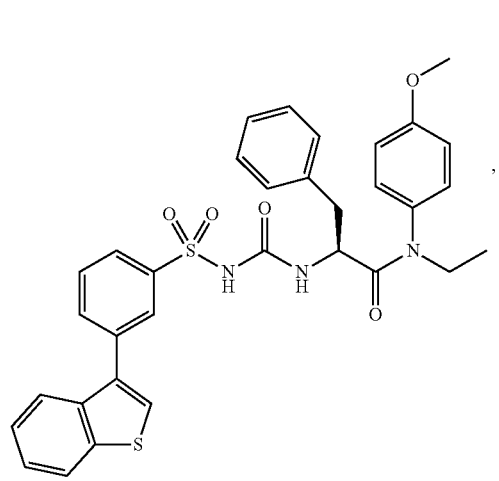
42
-continued
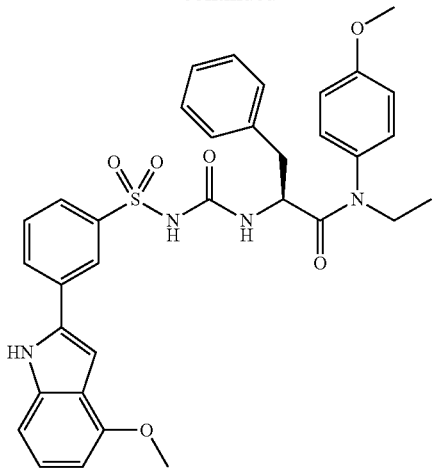
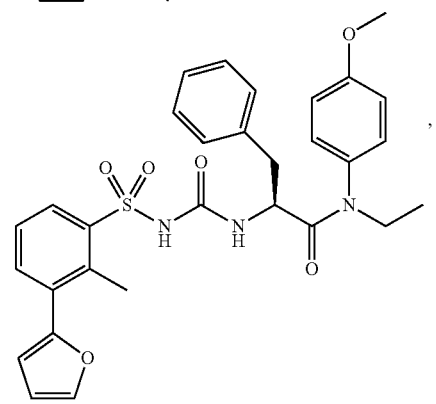
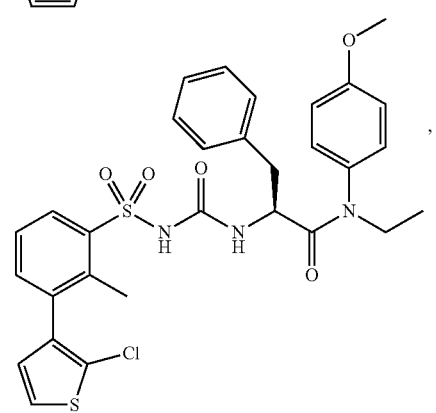
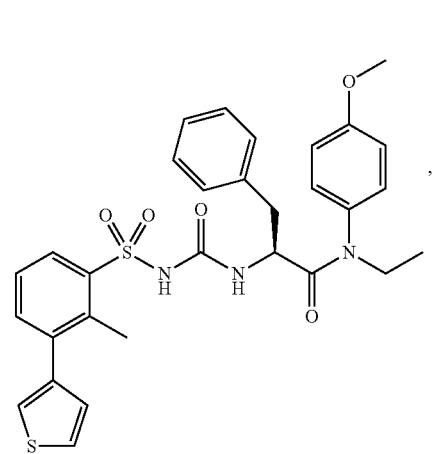

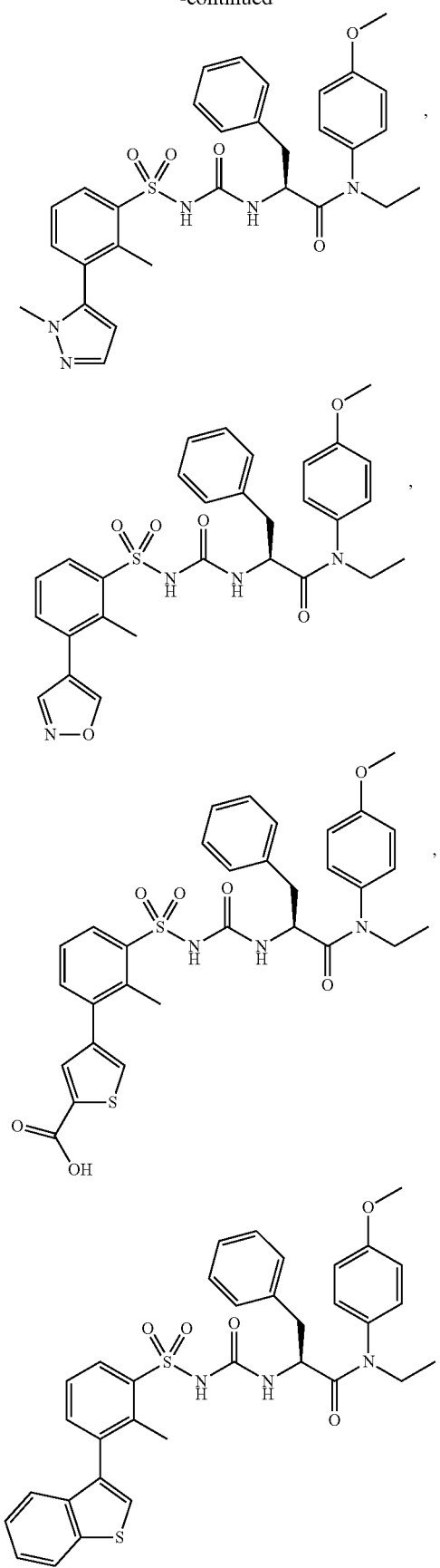
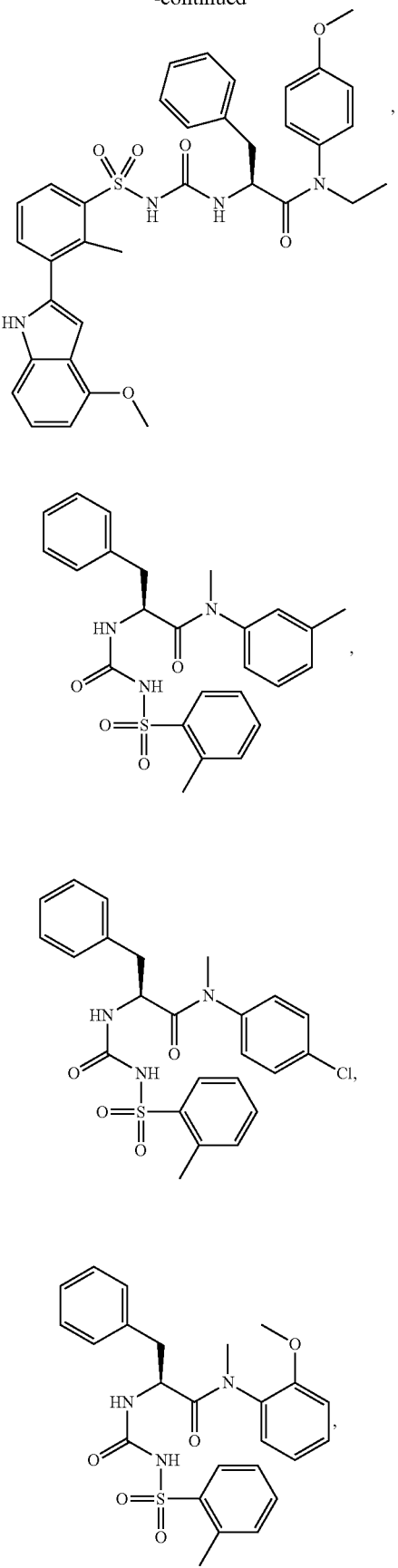

45
-continued
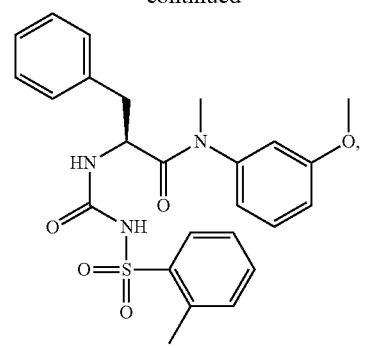
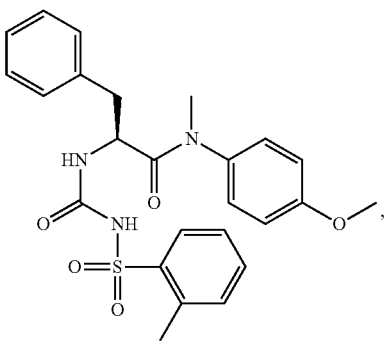
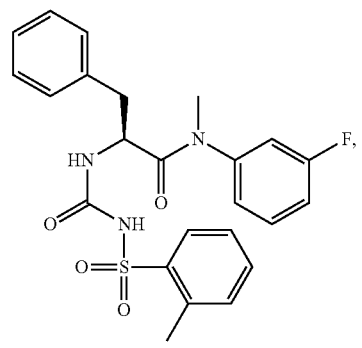
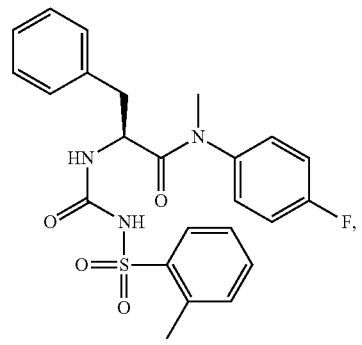
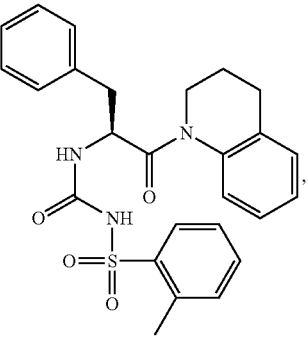
46
-continued
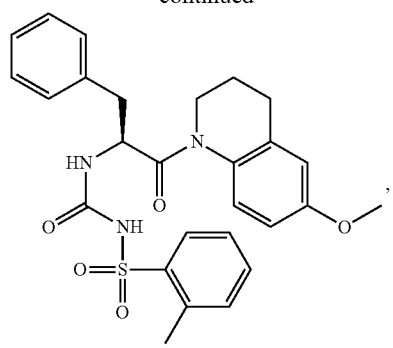
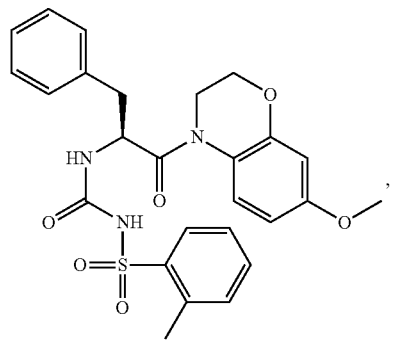
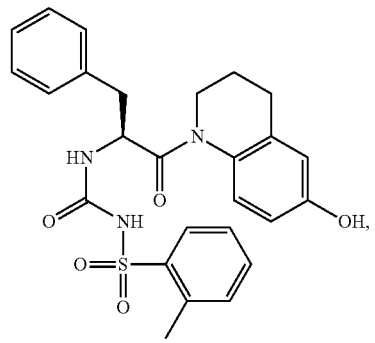
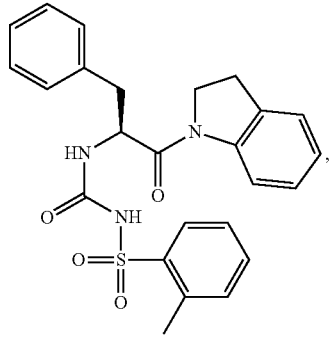
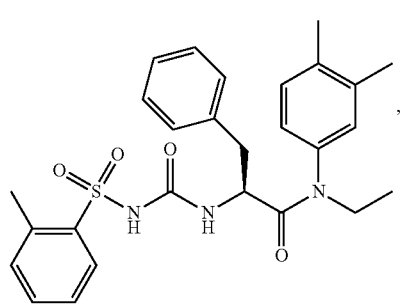

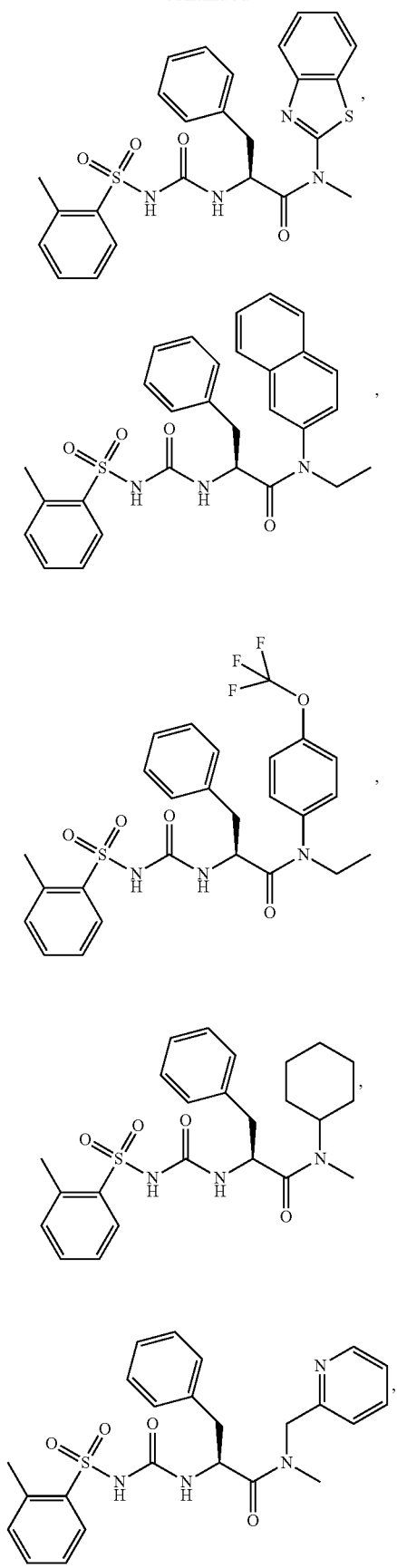
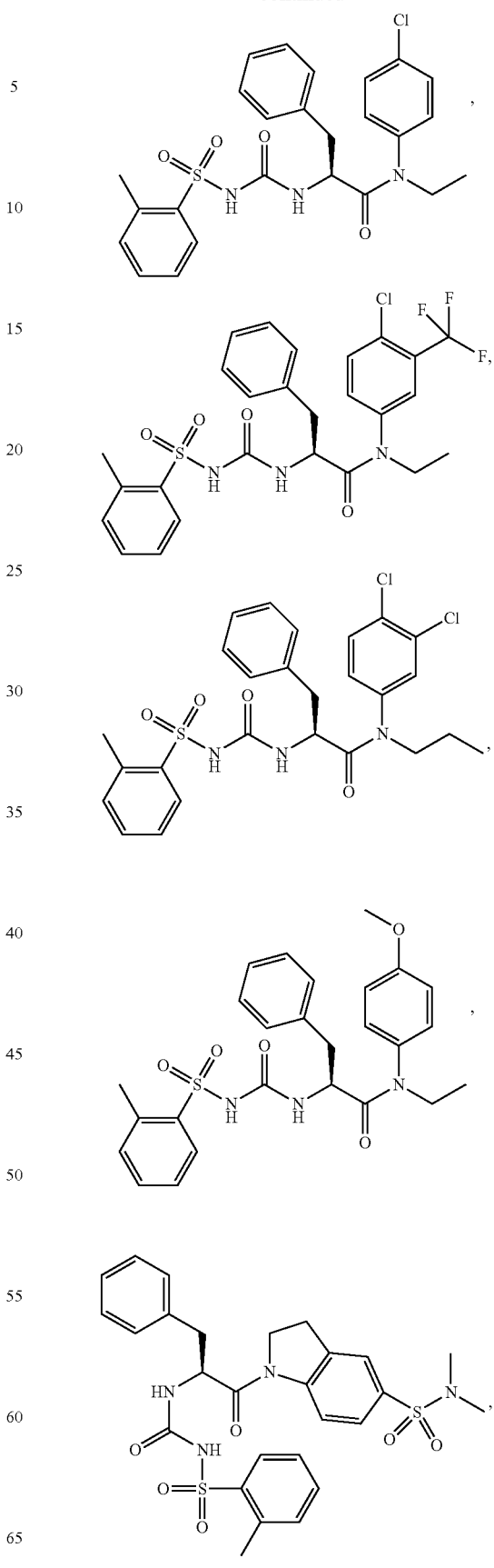

49
-continued
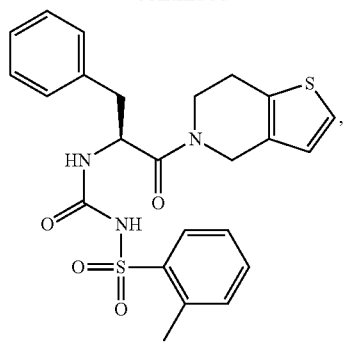
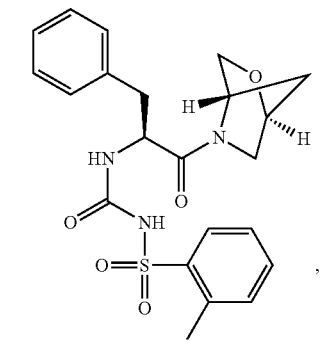
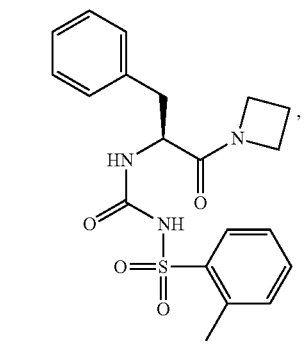
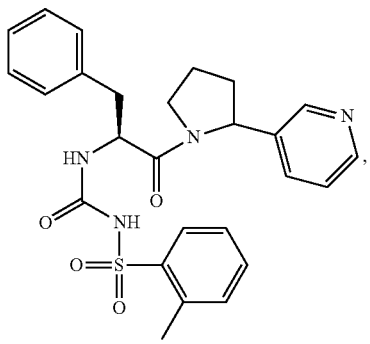
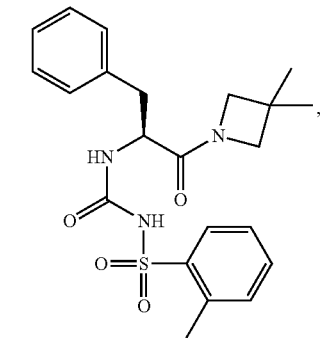
50
-continued
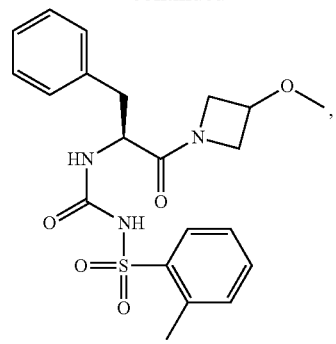
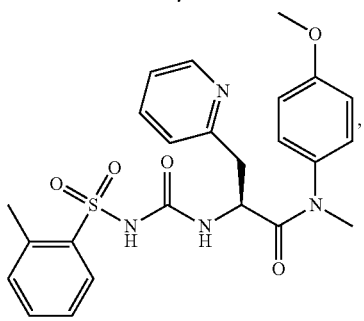
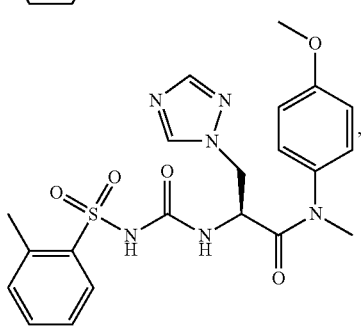
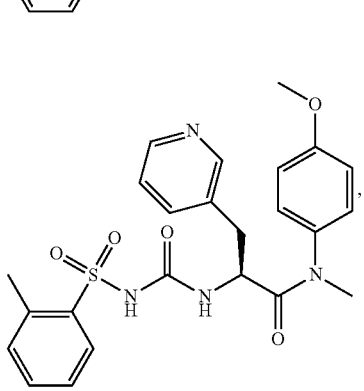
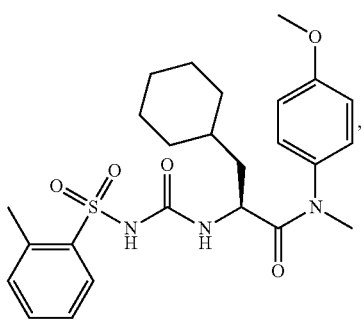

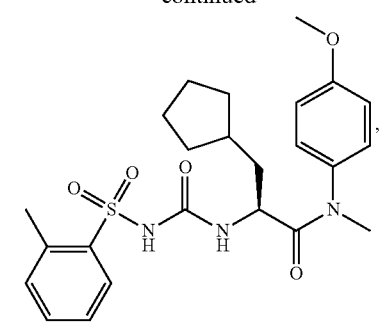
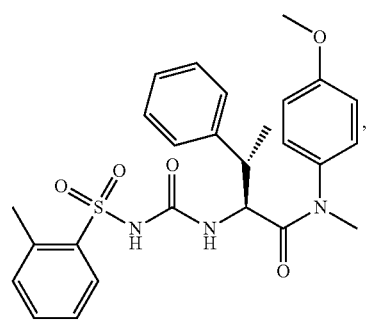
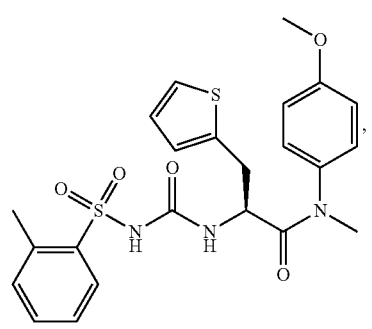
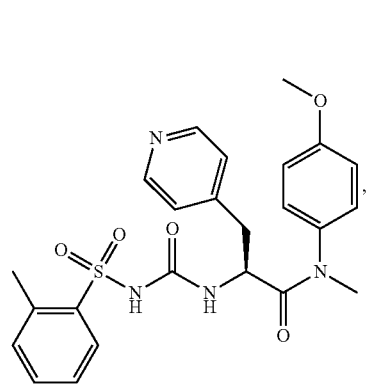
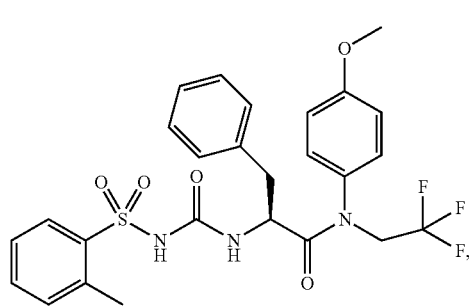
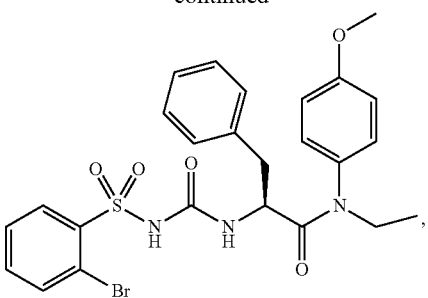
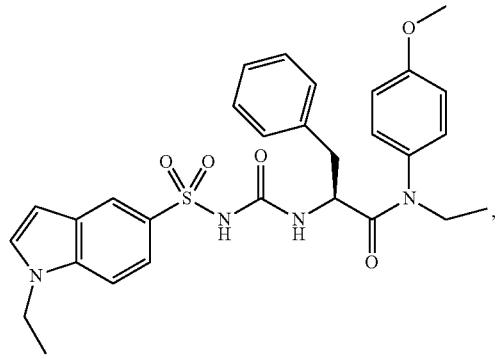
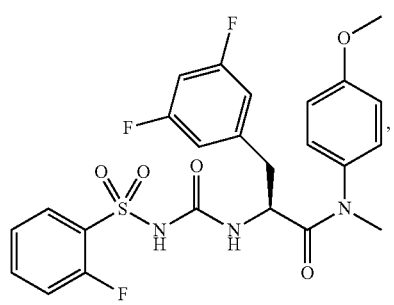
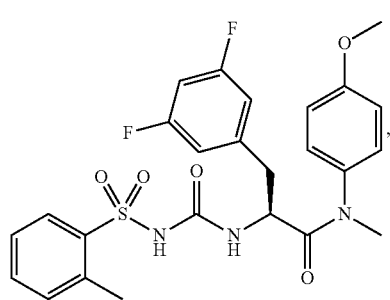
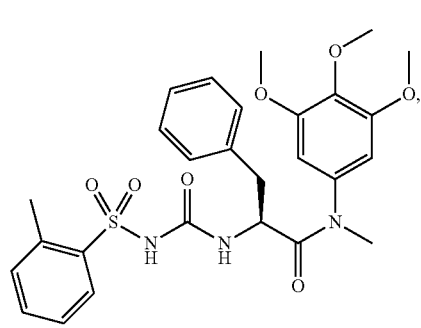

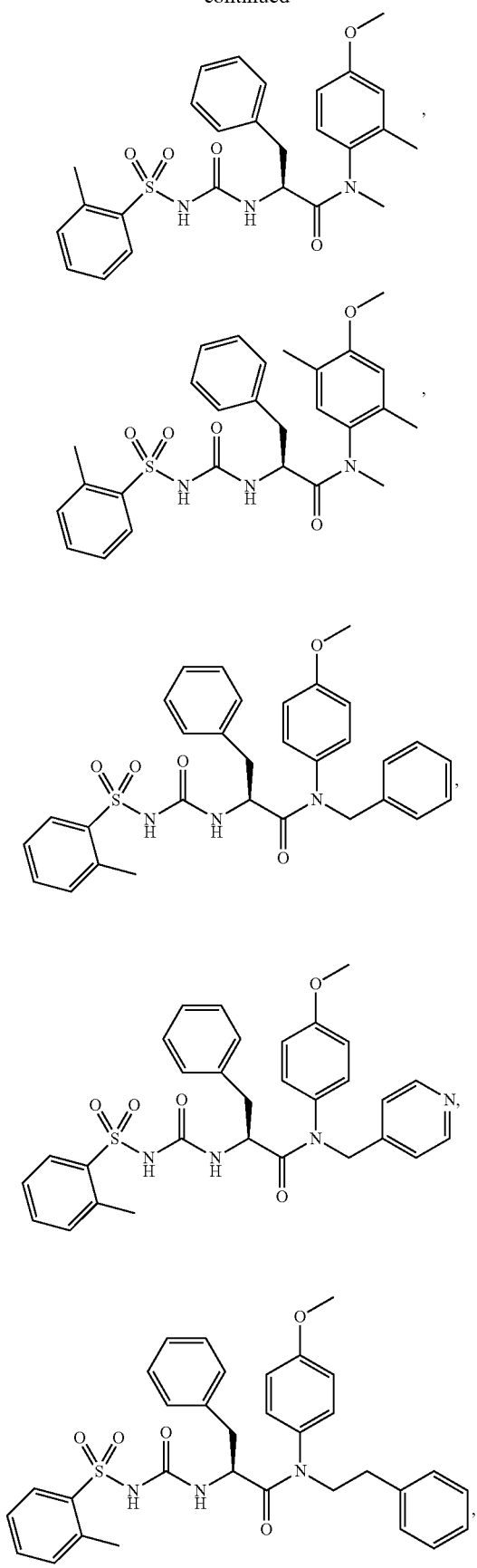
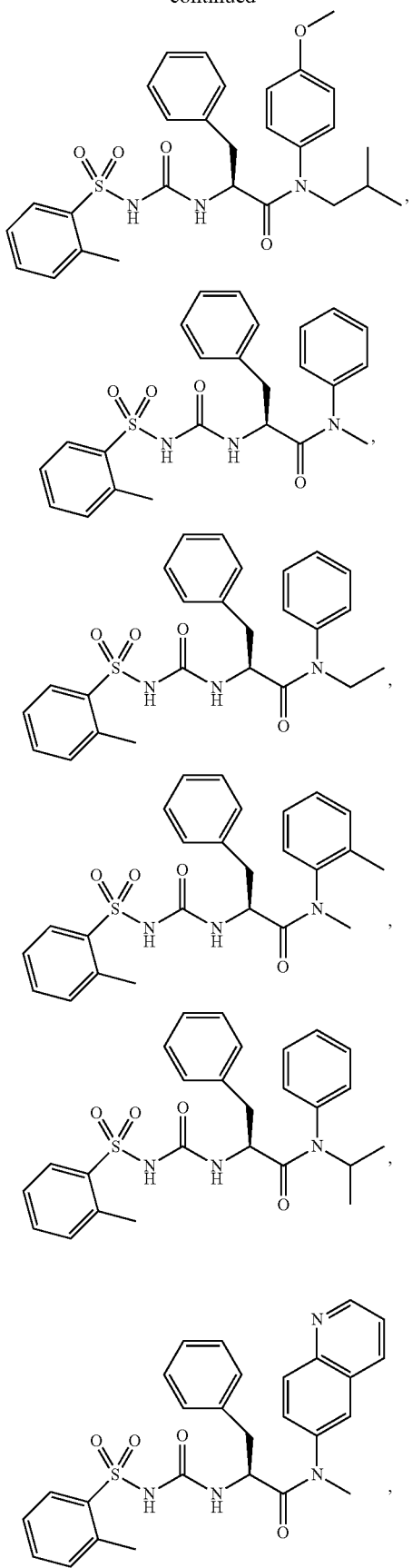

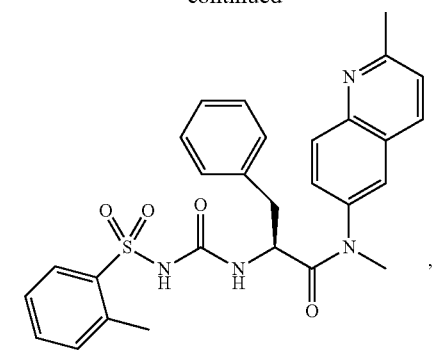
,
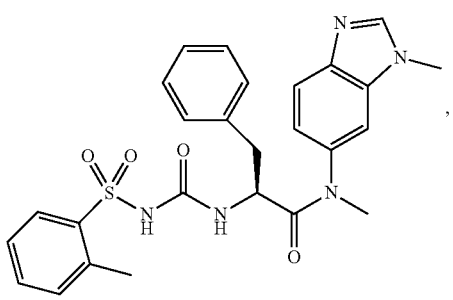
,
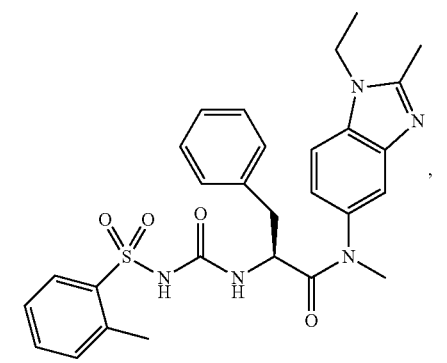
,
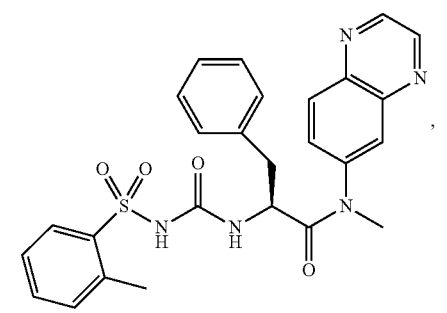
,
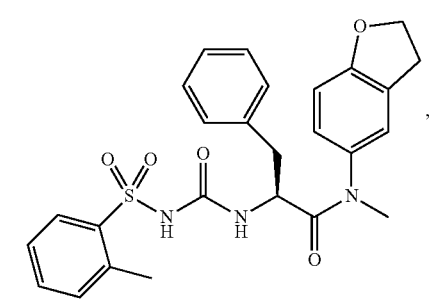
,
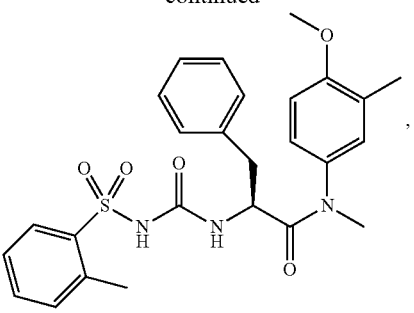
,
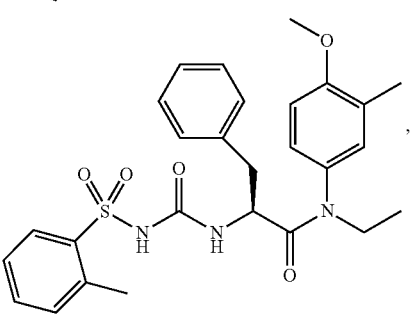
,
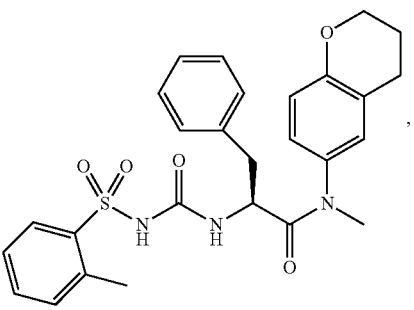
,
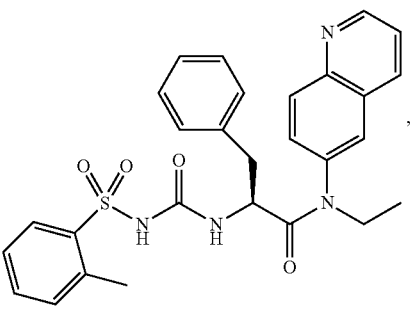
,
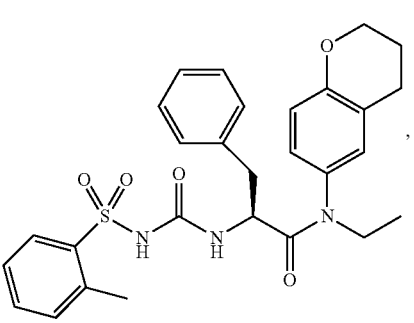
, 57
-continued
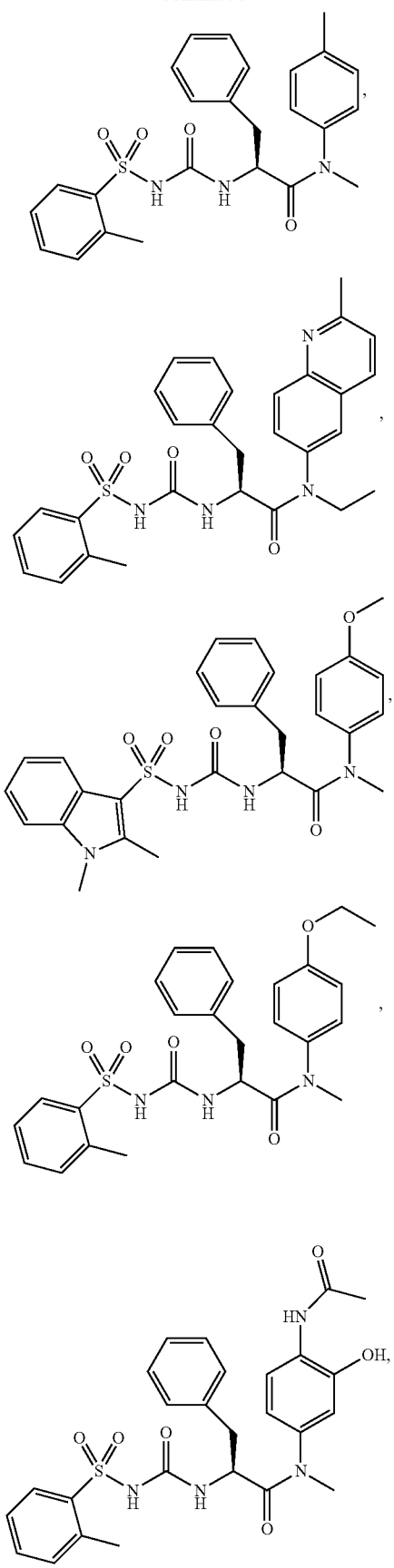
58
-continued
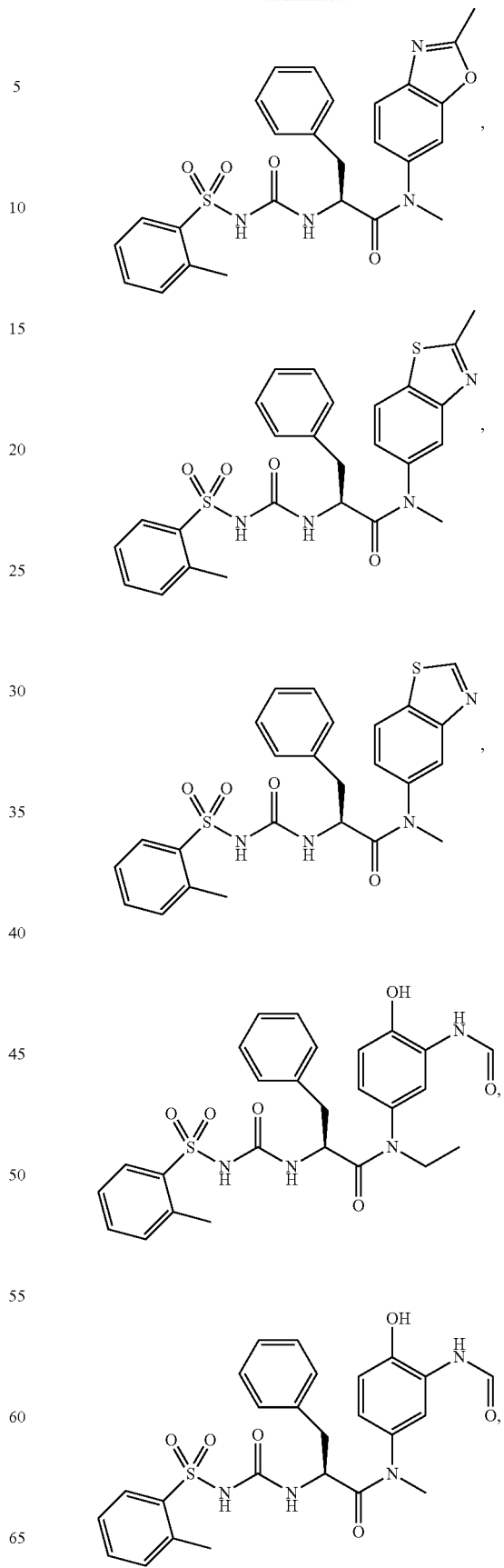

-continued
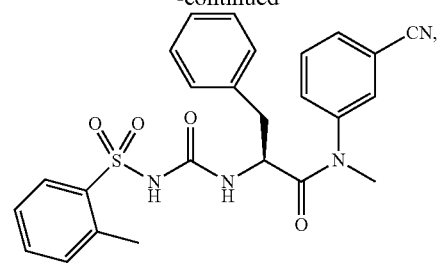
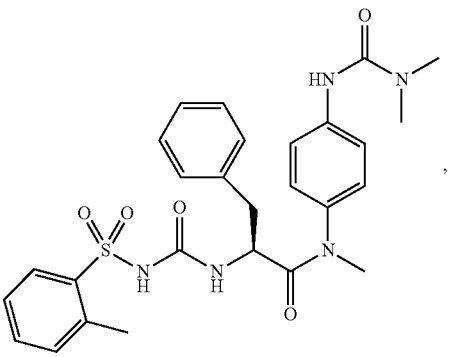
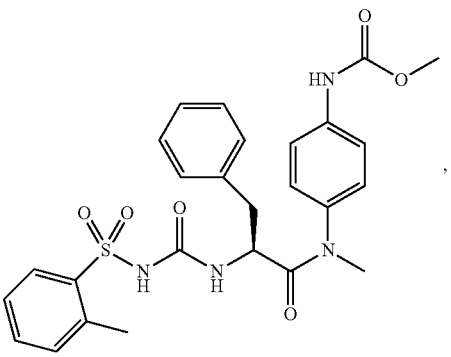
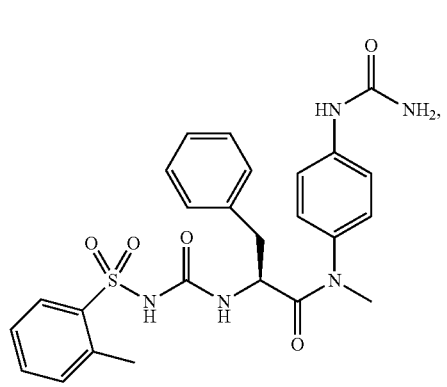
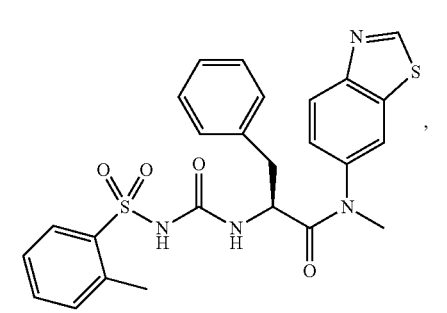
-continued
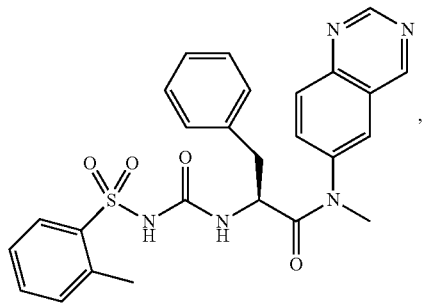
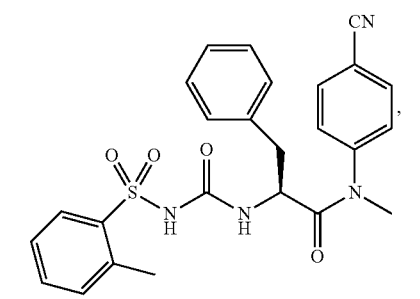
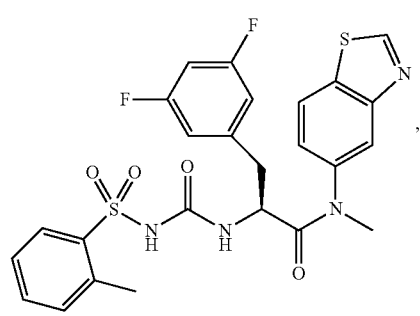
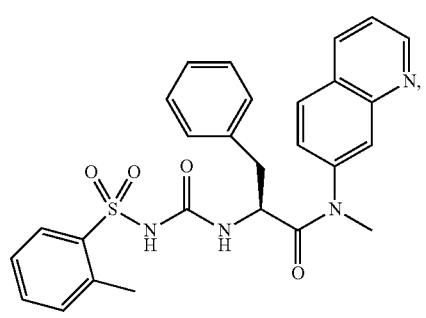
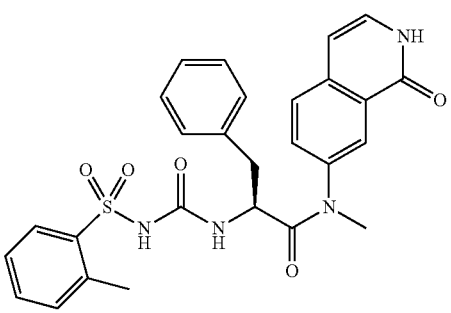

-continued
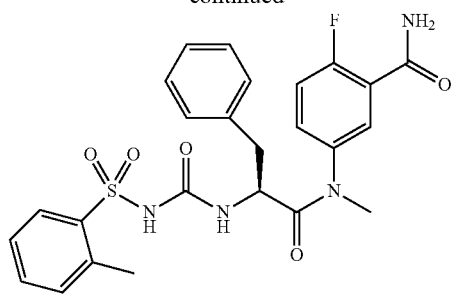
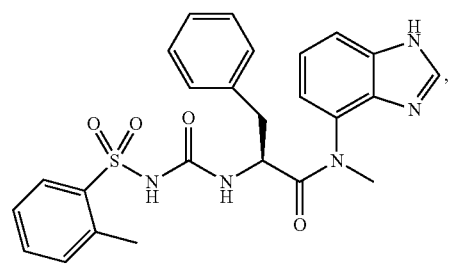
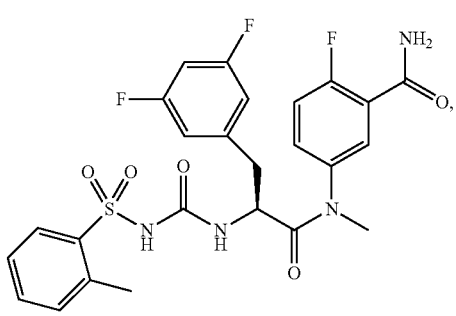
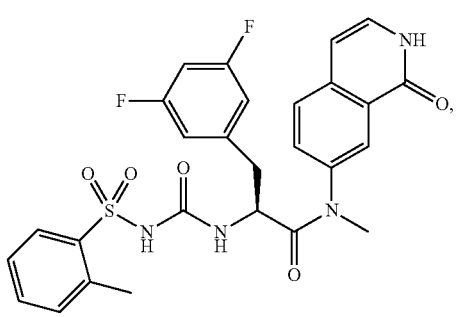
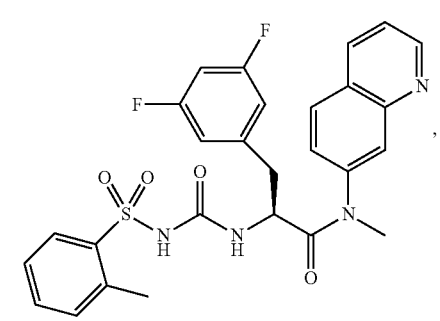
-continued
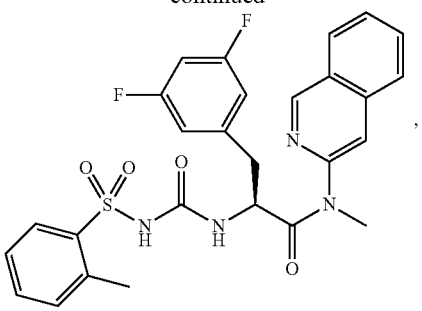
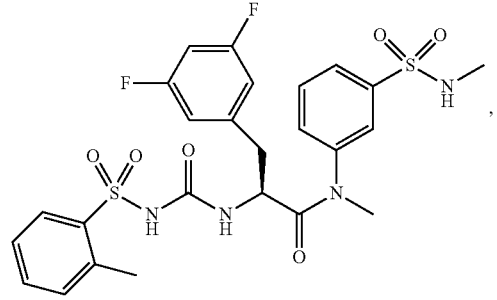
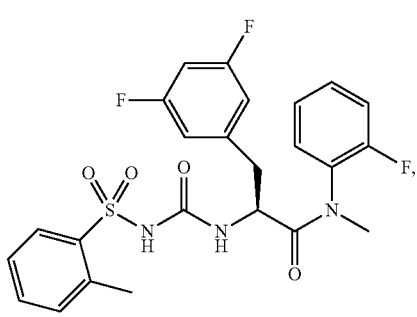
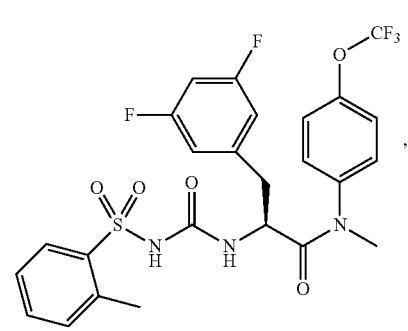
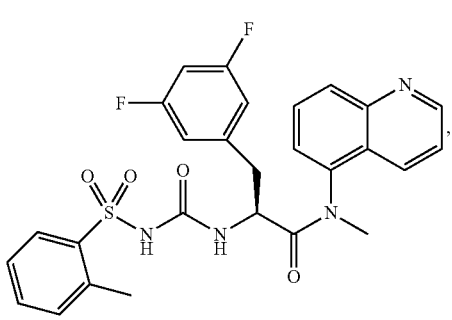

63
-continued
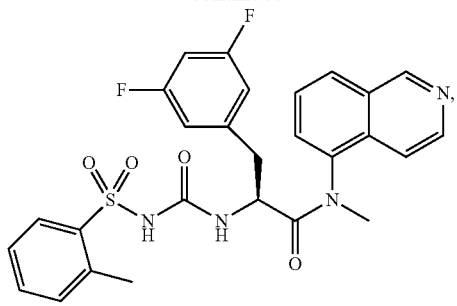
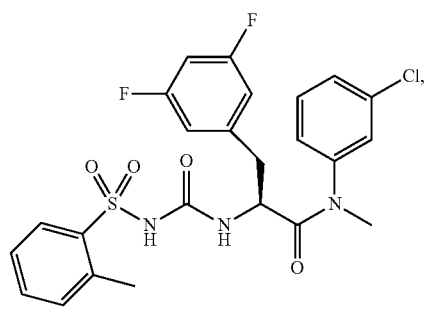
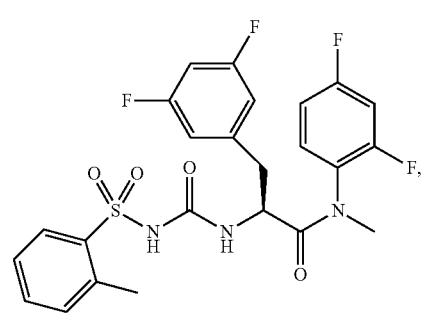
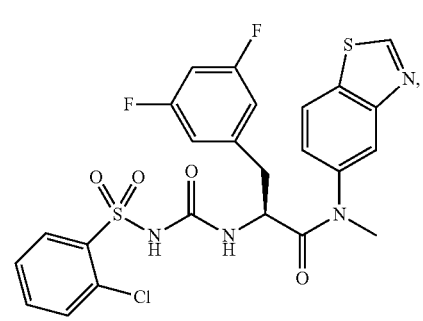
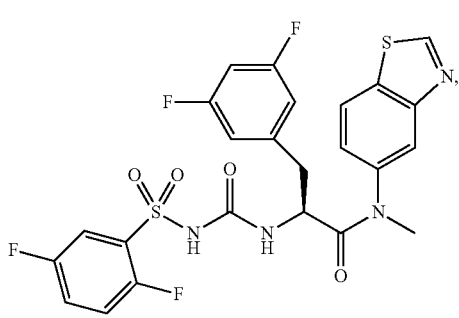
64
-continued
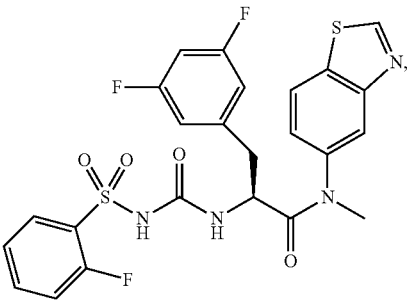
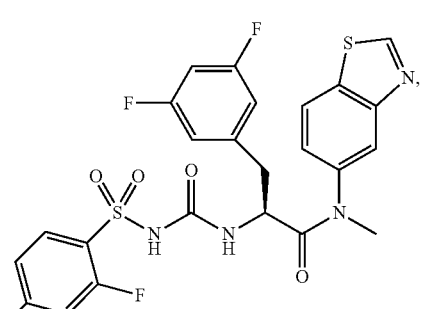
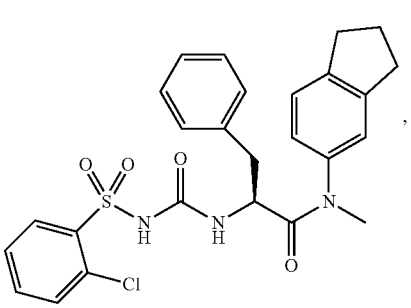
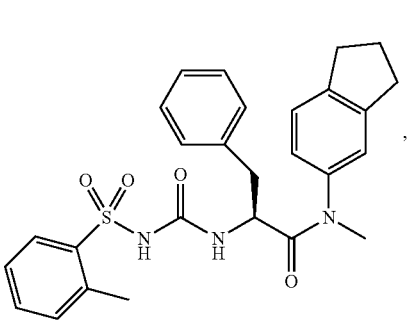
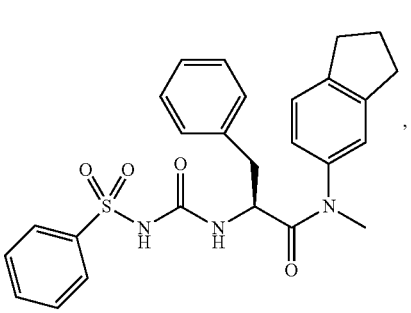

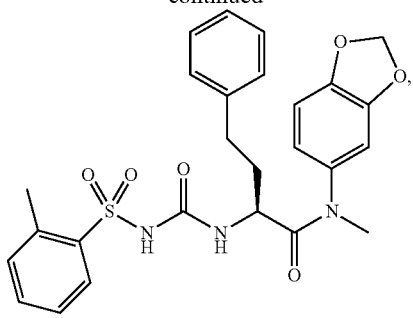
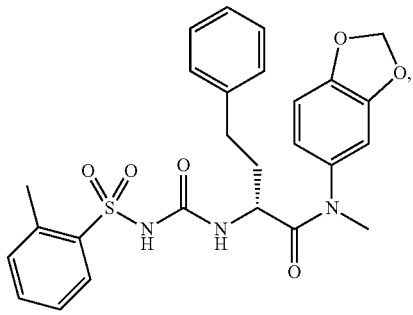
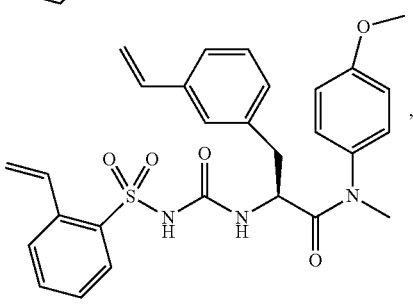
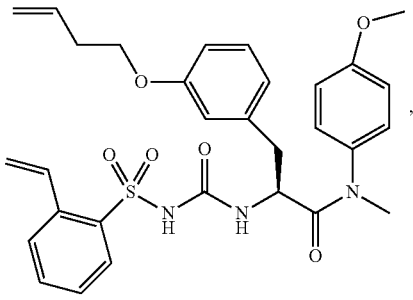
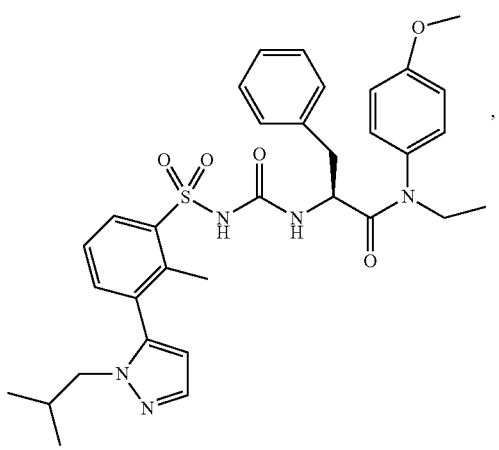
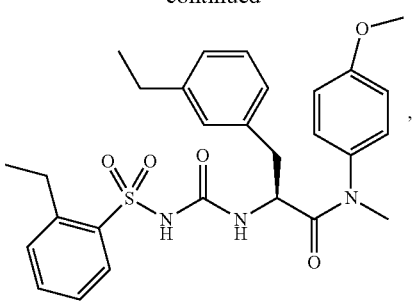
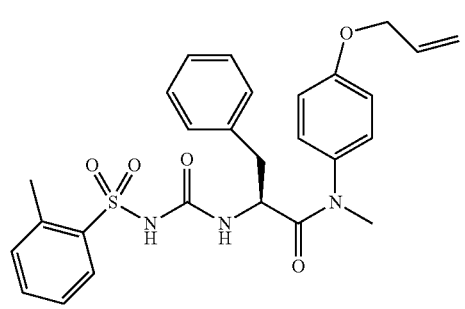
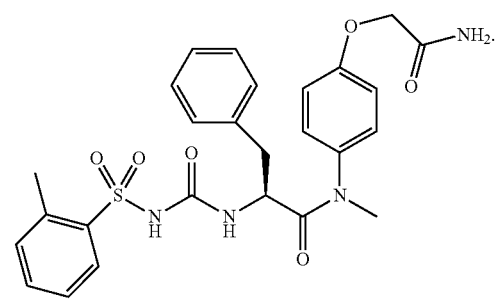
Other preferred compounds, including pharmaceutically acceptable salts thereof, are selected from the group of:
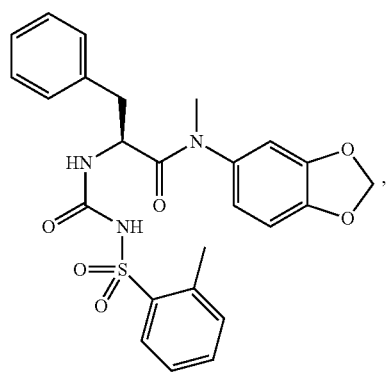

67
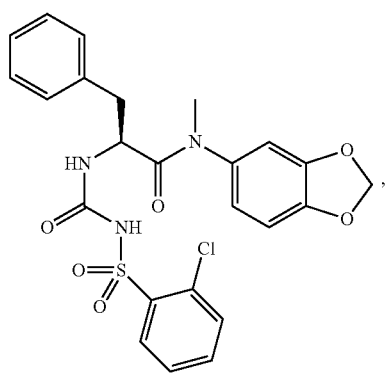,
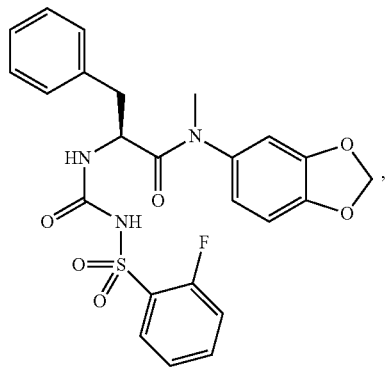,
,
,
68
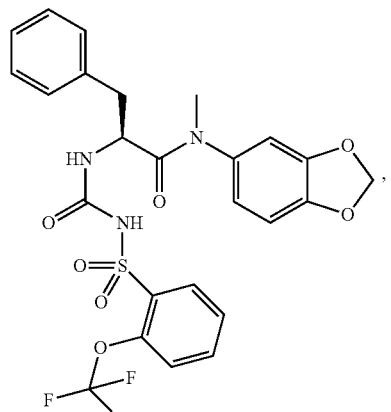,
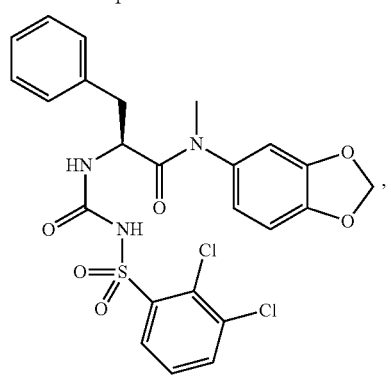,
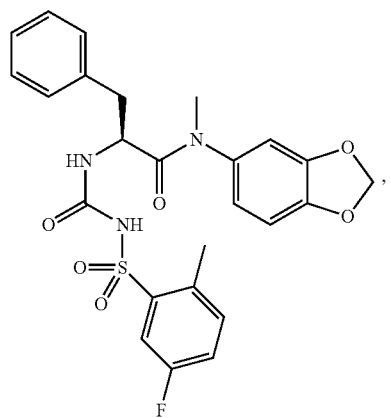,
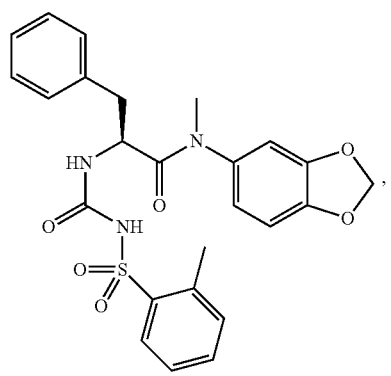,

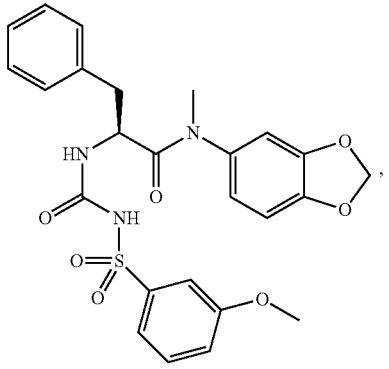
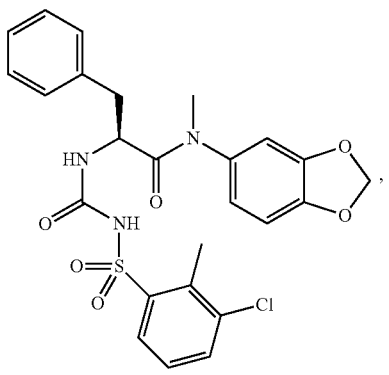
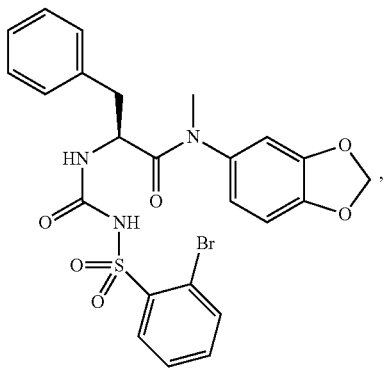
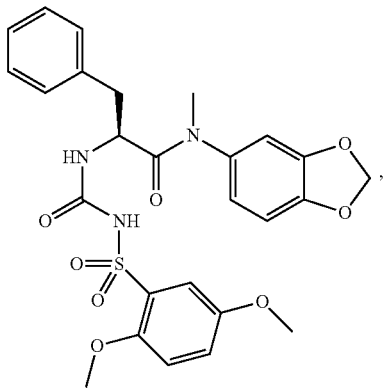
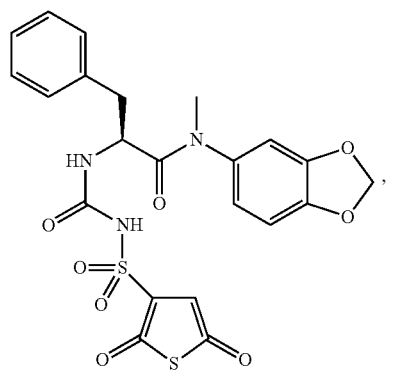
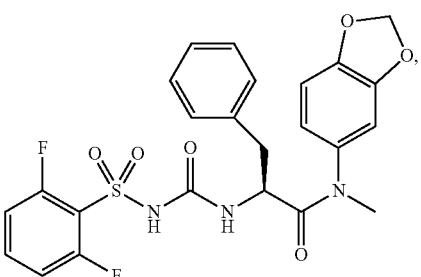
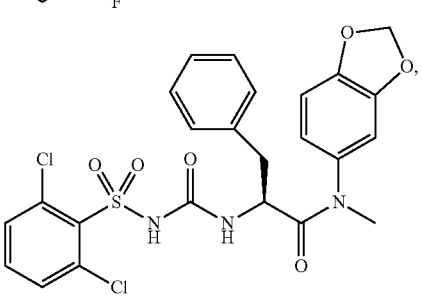
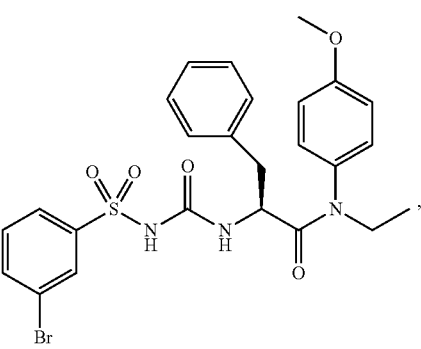
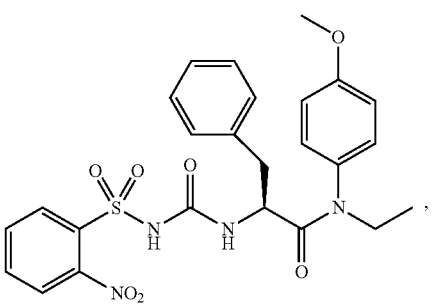

71
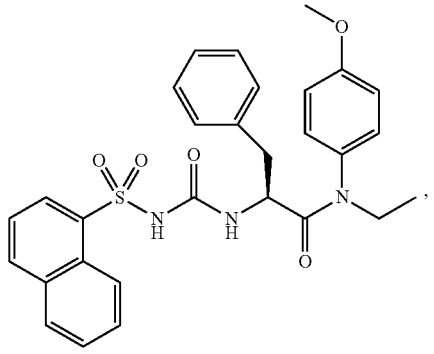
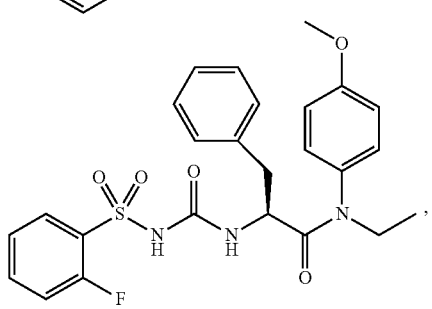
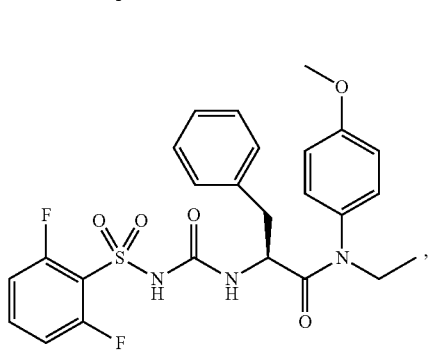
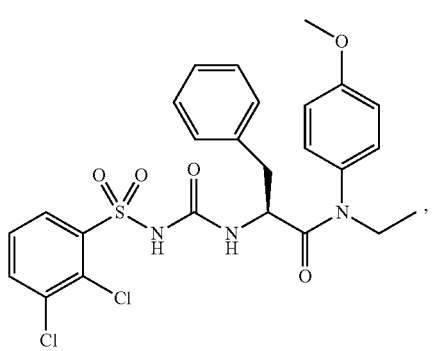
72
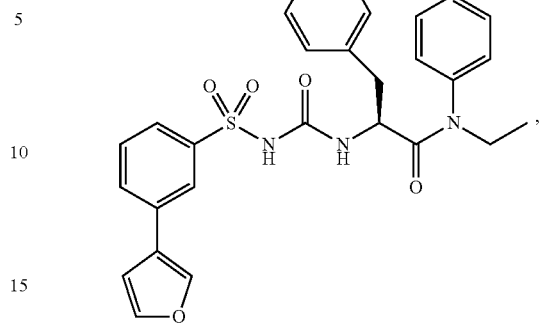
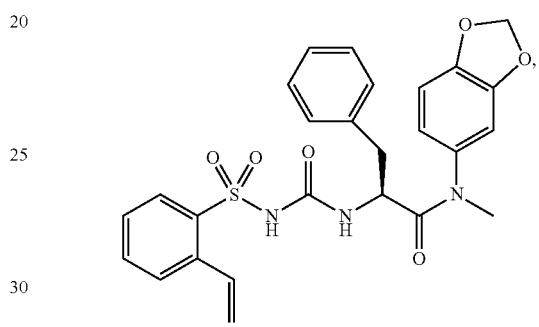
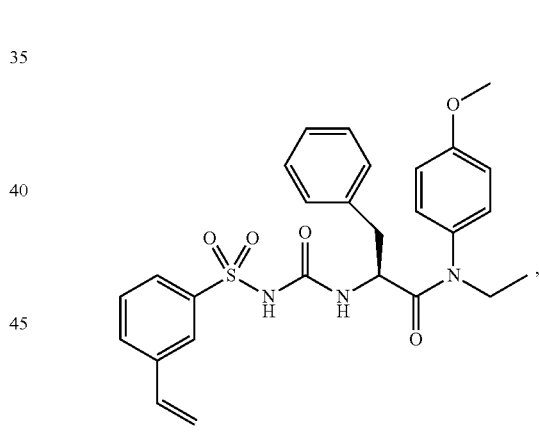
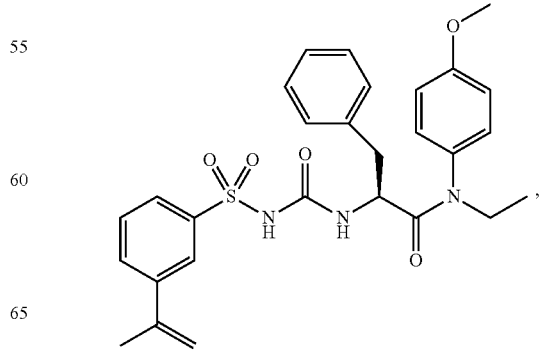

73
-continued
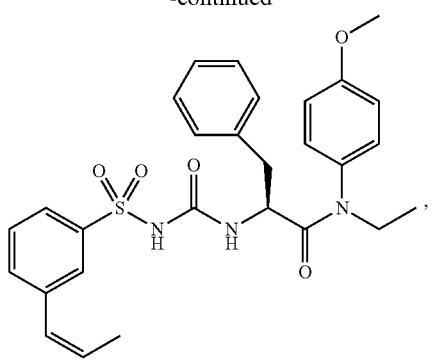
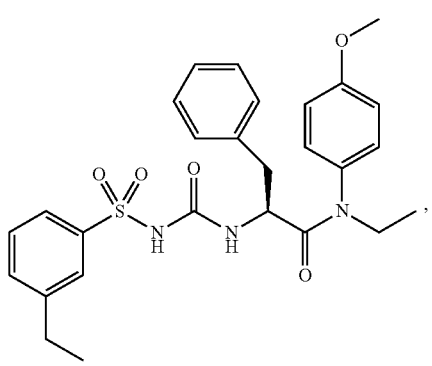
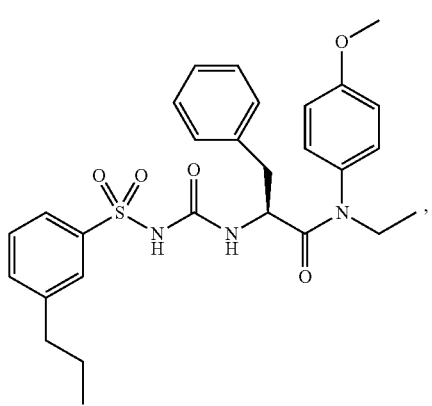
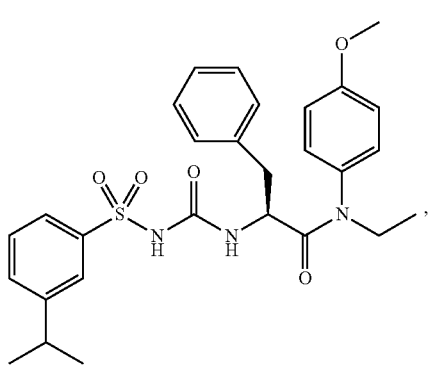
74
-continued
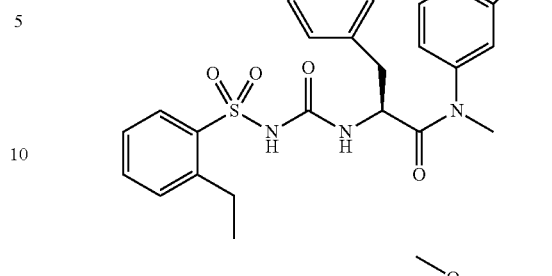
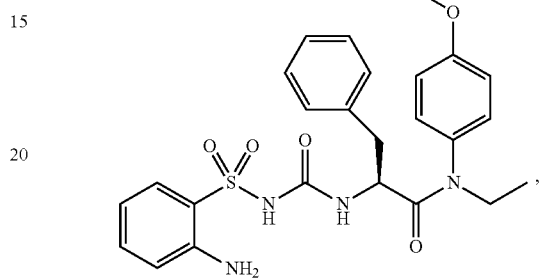
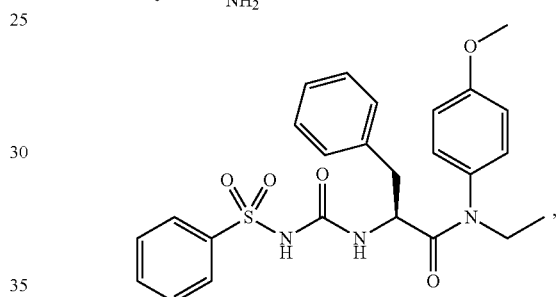
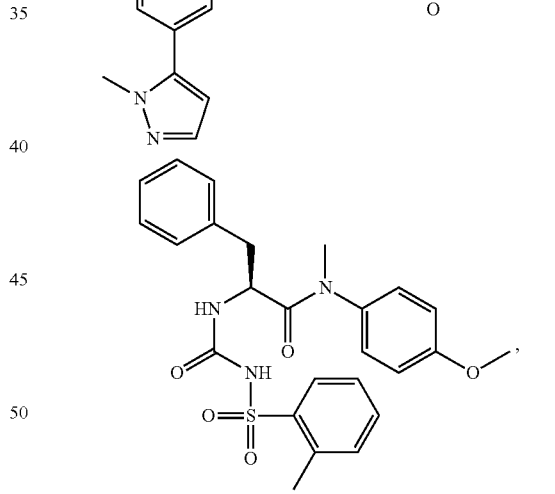
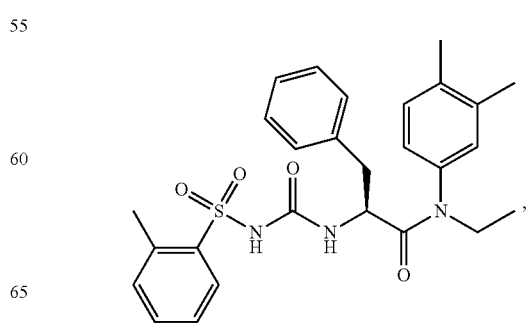

75
-continued
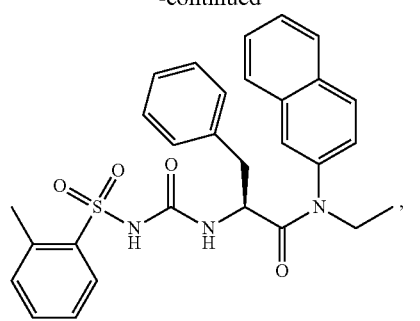
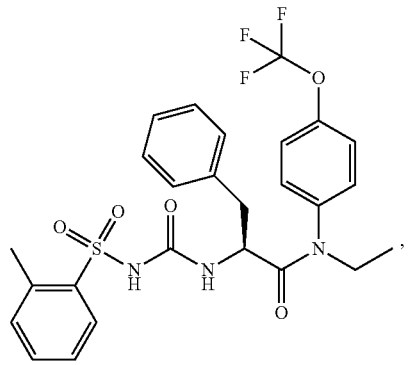
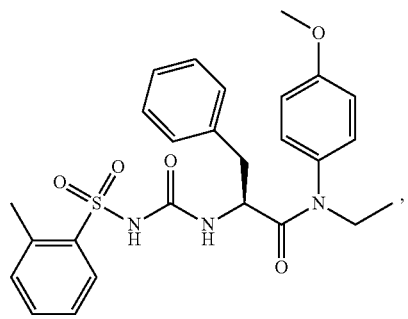
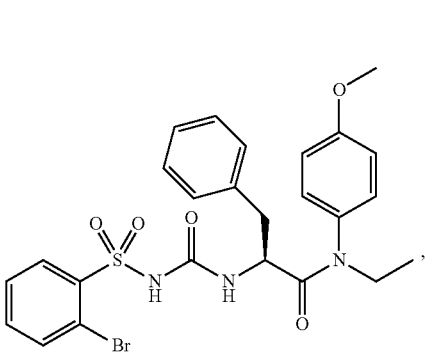
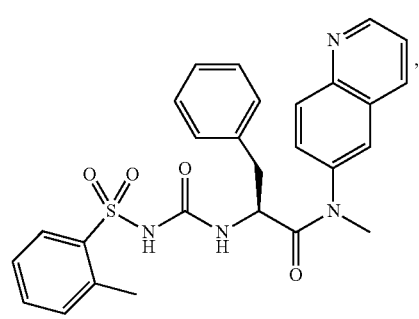
76
-continued
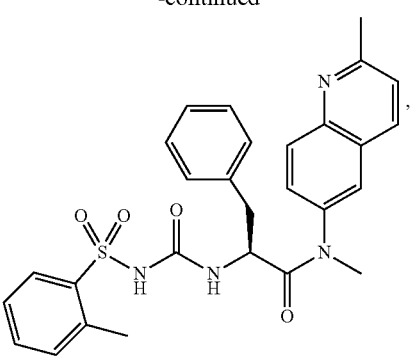
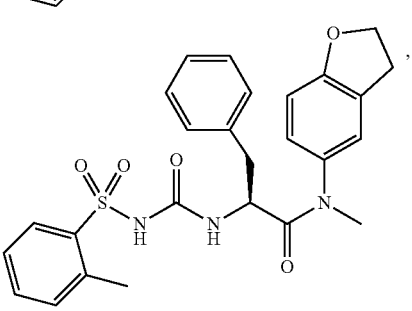
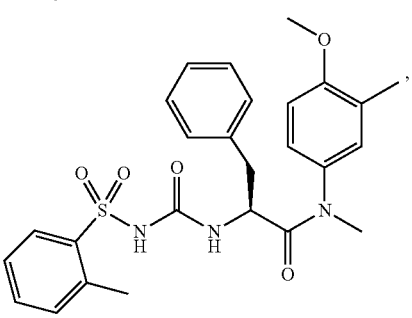
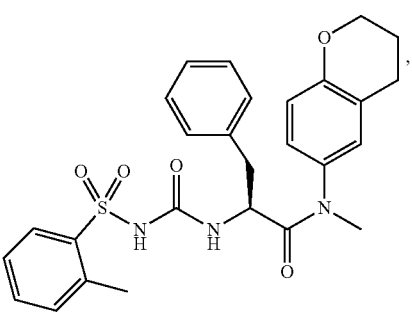
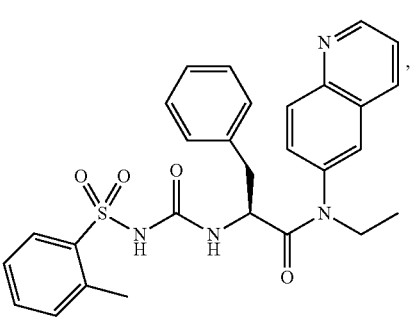

77
-continued
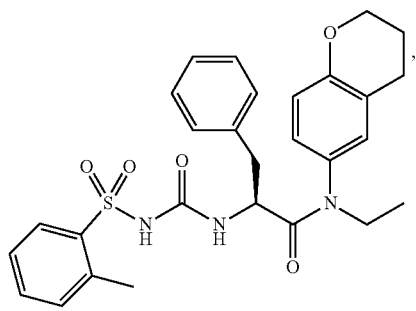
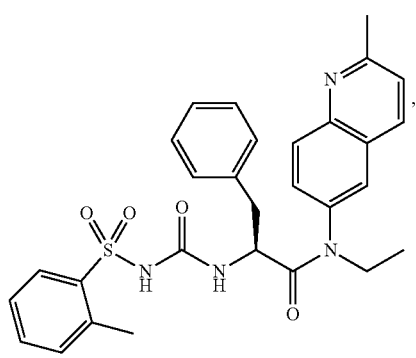
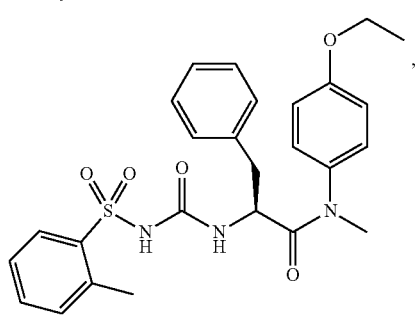
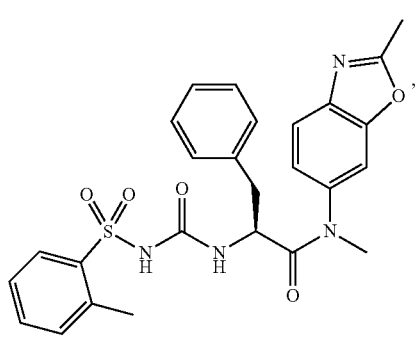
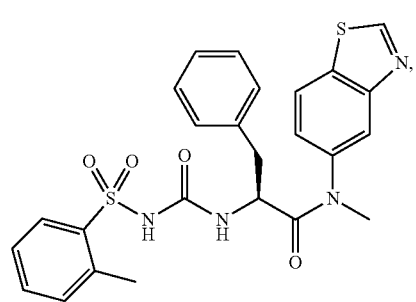
78
-continued
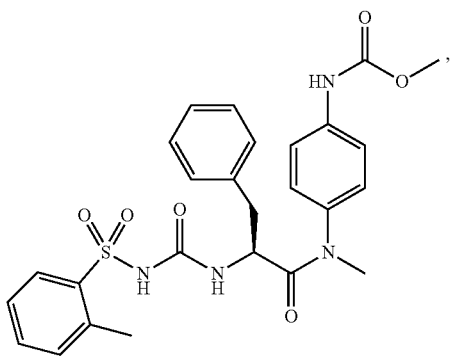
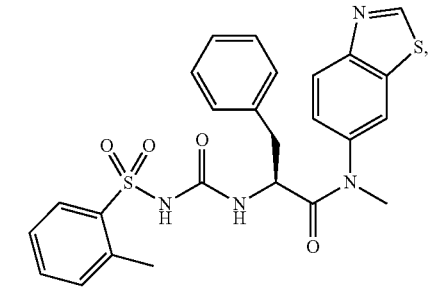
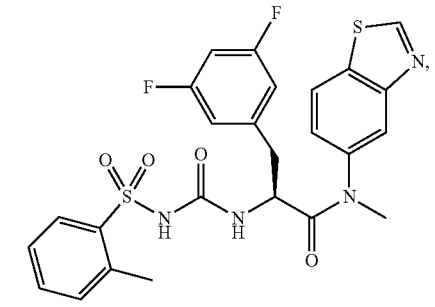
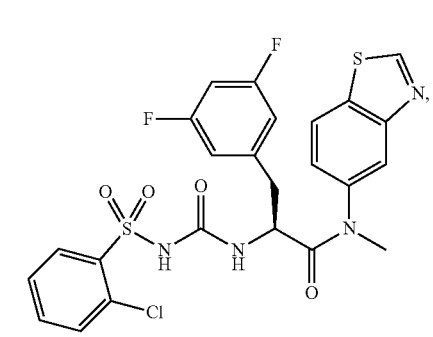
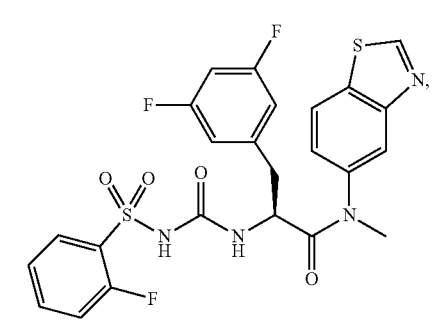

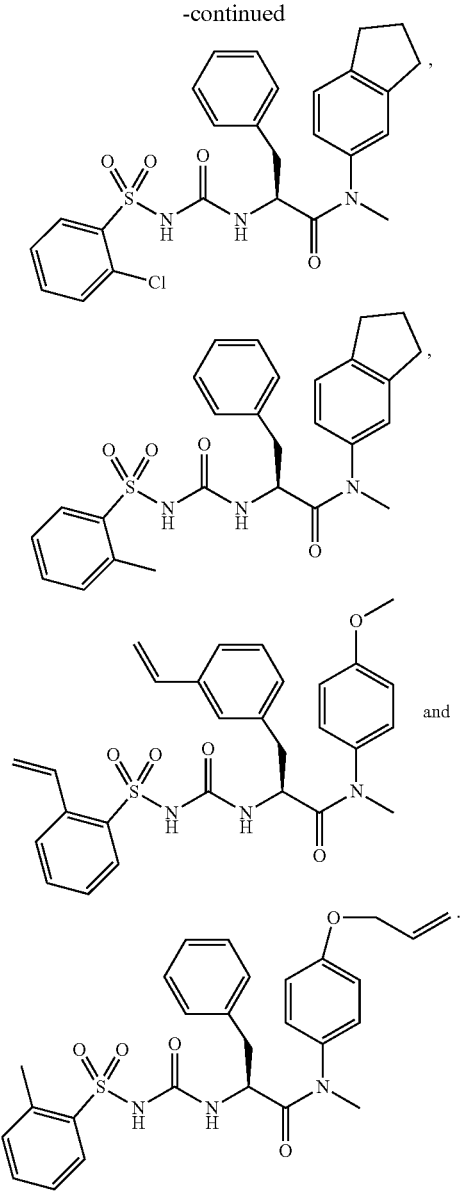

Pharmaceutical Compositions and Methods of Use

The compounds of the invention herein described and set forth are generally given as pharmaceutical compositions. These compositions are comprised of a therapeutically effective amount of a compound of Formula I or its pharmaceutically acceptable salt, and a pharmaceutically acceptable carrier and may contain one or more carriers, excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, lozenges, and powders as well as liquid suspensions, syrups, elixirs, and solutions. Compositions are made using available formulation techniques, and available excipients (such as binding and wetting agents) and vehicles (such as water and alcohols) are generally used for compositions. See, for example, *Remington's Pharmaceutical Sciences,* 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regimen, however, will be determined by a physician using sound medical judgment.

The compounds of this invention have activity against HIV. Accordingly, another aspect of the invention is a method for treating HIV infection in a human patient comprising administering a therapeutically effective amount of a compound of Formula I, including a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regimen, however, will be determined by a physician using sound medical judgment.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

| Drug Name | Manufacturer | Indication |
|---|---|---|
| ANTIVIRALS | | |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |

| Drug Name | Manufacturer | Indication |
|---|---|---|
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDS in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDS in development |
| CMX-157 Lipid conjugate of nucleotide tenofovir | Chimerix | HIV infection AIDs |
| GSK1349572 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |

85

-continued

| Drug Name | Manufacturer | Indication |
|---|---|---|
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Synthetic Methods

The compounds of the invention can be made by various methods available in the art including those of the following scheme and in the specific embodiments section which follows. The structure numbering and variable numbering shown in the synthetic schemes are distinct from, and should not be confused with, the structure or variable numbering in the claims or the rest of the specification. The variables in the schemes are meant only to illustrate how to make some of the compounds of the invention.

Abbreviations used in the schemes generally follow conventions used in the art. Chemical abbreviations used in the specification and examples are defined as follows: "DMF" for N,N-dimethylformamide; "MeOH" for methanol; "Ar" for aryl; "TFA" for trifluoroacetic acid; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HATU" for (1-[Bis(dimethylamino)methylene]-1H-1,2,3-triazolo[4,5-b]pyridinium 3-oxid hexafluorophosphate) "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Scheme 1.

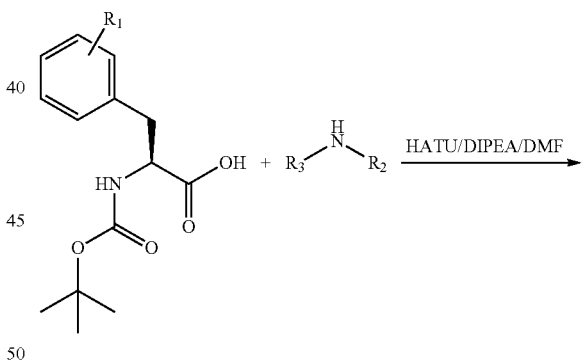

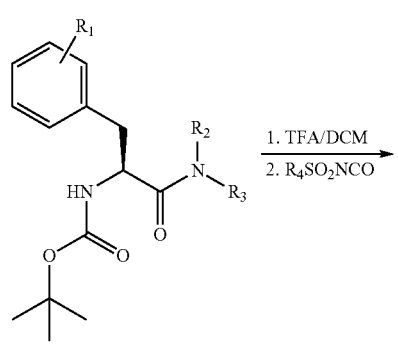

EXAMPLES

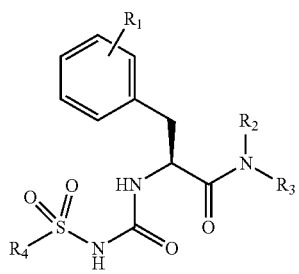

The following examples are provided by way of illustration only, and should not be construed as limiting the scope of the invention.

Intermediate 1

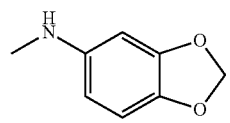

N-methylbenzo[d][1,3]dioxol-5-amine

Benzo[d][1,3]dioxol-5-amine (1.6 g, 12 mmol) was added to a solution of 25% wt. sodium methoxide (12.6 g, 58.3 mmol) in MeOH and paraformaldehyde (3.50 g, 117 mmol) in MeOH (50 mL). The reaction mixture was stirred at r.t. for 18 h and then sodium borohydride (1.32 g, 35.0 mmol) was added in portions and the reaction was heated at 40° C. for 3 h, cooled to r.t., and then concentrated. The residue was dissolved into EtOAc (~60 mL), washed with water (50 mL) and brine (50 mL) and then dried (MgSO$_4$), filtered and concentrated. The residue was purified using a Biotage Horizon (40 g SiO$_2$, 10-25% EtOAc/hexanes) to afford the title compound (1.43 g) as amber oil. $^1$H NMR (400 MHZ, CDCl$_3$) δ 6.69 (d, J=8.3 Hz, 1H), 6.26 (d, J=2.5 Hz, 1H), 6.06 (dd, J=8.3, 2.5 Hz, 1H), 5.87 (s, 2H), 2.80 (s, 3H).

| | |
|---|---|
| MS (M + H)$^+$ Calcd. | 152.1 |
| MS (M+ H)$^+$ Observ. | 152.2 |
| Retention Time | 0.298 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | acetonitrile:Water:TFA |
| Column | Phenomenex LUNA C18 30 × 2 mm, 3μ |

Intermediate 2

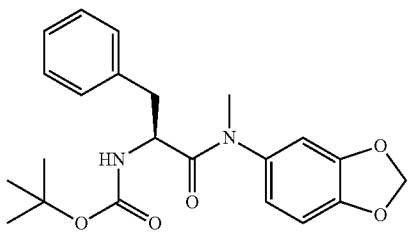

(S)-tert-butyl (1-(benzo[d][1,3]dioxol-5-yl(methyl)amino)-1-oxo-3-phenylpropan-2-yl)carbamate HATU (3.02 g, 7.94 mmol) was added to a stirred solution of (S)-2-((tert-butoxycarbonyl)amino)-3-phenylpropanoic acid (1.93 g, 7.28 mmol) and N-methylbenzo[d][1,3]dioxol-5-amine (1.0 g, 6.6 mmol) in diisopropylethylamine (2.3 mL, 13 mmol) and DMF (35 mL) and the reaction solution was stirred at r.t. for 18 h. The reaction was concentrated to dryness and partitioned between 1/2 sat. NaHCO$_3$ (aq) (50 mL) and EtOAc (100 mL). The organic layer was washed with brine (50 mL), dried (MgSO$_4$) filtered and concentrated. The residue was purified using a Biotage Horizon (80 g SiO$_2$, 10-40% EtOAc) to afford the title compound (2.15 g) as tan solidified foam. $^1$H NMR (400 MHZ, CDCl$_3$) δ 7.34-7.20 (m, 4H), 7.02 (br. s., 2H), 6.70 (d, J=7.5 Hz, 1H), 6.36-6.19 (m, 1H), 6.01 (s, 2H), 5.19 (d, J=7.0 Hz, 1H), 4.53 (d, J=7.0 Hz, 1H), 3.15 (s, 3H), 2.92-2.77 (m, 2H), 1.40 (s, 9H).

| | |
|---|---|
| MS (M + H)$^+$ Calcd. | 399.2 |
| MS (M + H)$^+$ Observ. | 399.3 |
| Retention Time | 1.68 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | acetonitrile:Water:TFA |
| Column | Phenomenex LUNA C18 30 × 2 mm, 3μ |

Intermediate 3

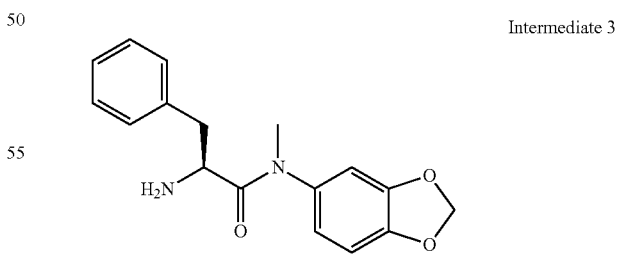

(S)-2-amino-N-(benzo[d][1,3]dioxol-5-yl)-N-methyl-3-phenylpropanamide

To (S)-tert-butyl (1-(benzo[d][1,3]dioxol-5-yl(methyl)amino)-1-oxo-3-phenylpropan-2-yl)carbamate (1070 mg, 2.69 mmol) was added 50% TFA in DCM (2 mL). The reaction mixture was stirred at r.t. for 1 hr. The solvent was evaporated to give the title compound (1090 mg) as a TFA salt.

| MS (M + H)+ Calcd. | 299.1 |
|---|---|
| MS (M + H)+ Observ. | 299.2 |
| Retention Time | 0.99 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | acetonitrile:Water:TFA |
| Column | Phenomenex Luna 30 × 2.0 MM 3 u |

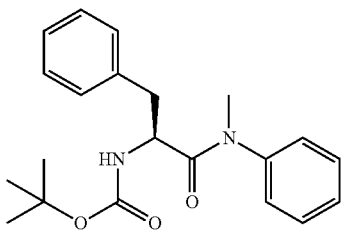

Intermediate 4

(S)-tert-butyl (1-(methyl(phenyl)amino)-1-oxo-3-phenylpropan-2-yl)carbamate

A solution of (S)-2-((tert-butoxycarbonyl)amino)-3-phenylpropanoic acid (26.5 mg, 0.100 mmol), N-methylaniline (11.77 mg, 0.110 mmol), HATU (38 mg, 0.100 mmol) and DIPEA (0.053 mL, 0.300 mmol) in DMF (1 mL) was stirred at room temperature for 18 h. The reaction mixture was partitioned between saturated aqueous sodium bicarbonate solution (10 mL) and ethyl acetate (20 mL). The organic component was washed with brine (10 mL), dried (MgSO4) filtered and concentrated. The residue was used without purification.

| MS (M + H)+ Calcd. | 355.2 |
|---|---|
| MS (M + H)+ Observ. | 355.3 |
| Retention Time | 1.88 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | acetonitrile:Water:TFA |
| Column | Phenomenex LUNA C18 30 × 2 mm, 3µ |

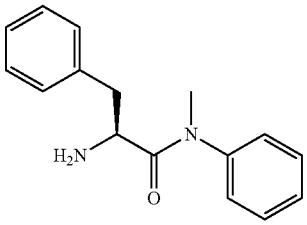

Intermediate 5

(S)-2-amino-N-methyl-N, 3-diphenylpropanamide

To (S)-tert-butyl (1-(methyl(phenyl)amino)-1-oxo-3-phenylpropan-2-yl)carbamate (20 mg, 0.056 mmol) was added 50% TFA in DCM (2 mL). The reaction mixture was stirred at r.t. for 1 hr. The solvent was evaporated to give the title compound (14.5 mg) as a TFA salt.

| MS (M + H)+ Calcd. | 255.1 |
|---|---|
| MS (M + H)+ Observ. | 255.2 |
| Retention Time | 1.19 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | acetonitrile:Water:TFA |
| Column | Phenomenex LUNA C18 30 × 2 mm, 3µ |

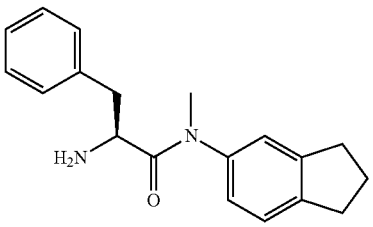

Intermediate 6

(S)-2-amino-N-(2,3-dihydro-1H-inden-5-yl)-N-methyl-3-phenylpropanamide

Intermediate 6 was prepared using the analogous procedures for the preparation of Intermediates 1-3 where the benzo[d][1,3]dioxol-5-amine used in the preparation of Intermediate 1 was replaced with 2,3-dihydro-1H-inden-5-amine and then carried through the subsequent steps. LC-MS retention time=1.17 min; m/z=295.3 [M+H]+. (Column: Phenonenex-Luna C18 2.0×30 mm 3 µm. Solvent A=90% Water: 10% Acetonitrile: 0.1% TFA. Solvent B=10% Water: 90% Acetonitrile: 0.1% TFA. Flow Rate=1.0 mL/min. Start % B=0. Final % B=100. Gradient Time=2 min. Wavelength=220).

Intermediate 7

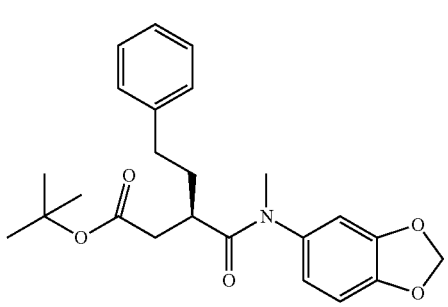

(S)-tert-butyl (1-(benzo[d][1,3]dioxol-5-yl(methyl)amino)-1-oxo-4-phenylbutan-2-yl)carbamate Intermediate 7 was prepared using the analogous procedure for the preparation of Intermediates 2 where the (S)-2-((tert-butoxycarbonyl)amino)-3-phenylpropanoic acid was replaced with (S)-2-((tert-butoxycarbonyl)amino)-4-phenylbutanoic acid. LC-MS retention time=1.68 min; m/z=413.3 [M+H]$^+$. (Column: Phenonenex-Luna C18 2.0× 30 mm 3 µm. Solvent A=90% Water: 10% Acetonitrile: 0.1% TFA. Solvent B=10% Water: 90% Acetonitrile: 0.1% TFA. Flow Rate=1.0 mL/min. Start % B=0. Final % B=100. Gradient Time=2 min. Wavelength=220).

Intermediate 8

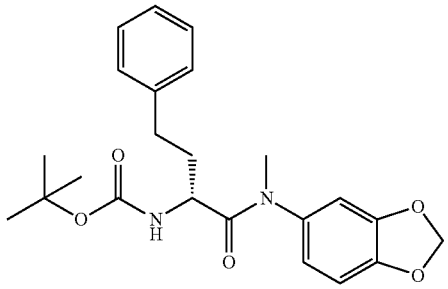

(R)-tert-butyl (1-(benzo[d][1,3]dioxol-5-yl(methyl)amino)-1-oxo-4-phenylbutan-2-yl)carbamate Intermediate 8 was prepared using the analogous procedure for the preparation of Intermediates 2 where the (S)-2-((tert-butoxycarbonyl)amino)-3-phenylpropanoic acid was replaced with (R)-2-((tert-butoxycarbonyl)amino)-4-phenylbutanoic acid. LC-MS retention time=1.67 min; m/z=413.3 [M+H]$^+$. (Column: Phenonenex-Luna C18 2.0× 30 mm 3 µm. Solvent A=90% Water: 10% Acetonitrile: 0.1% TFA. Solvent B=10% Water: 90% Acetonitrile: 0.1% TFA. Flow Rate=1.0 mL/min. Start % B=0. Final % B=100. Gradient Time=2 min. Wavelength=220).

Intermediate 9

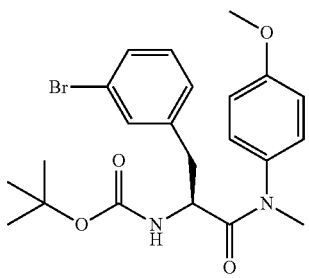

(S)-tert-butyl (3-(3-bromophenyl)-1-((4-methoxyphenyl)(methyl)amino)-1-oxopropan-2-yl)carbamate HATU (2.00 g, 5.26 mmol) was added to a stirred solution of 4-methoxy-N-methylaniline (0.601 g, 4.38 mmol), (S)-3-(3-bromophenyl)-2-((tert-butoxycarbonyl)amino)propanoic acid (1.508 g, 4.38 mmol) and DIPEA (2.3 mL, 13 mmol) in DMF (15 mL) and the reaction mixture was stirred at RT overnight. The reaction was diluted with water (50 mL), extracted by EtOAc (2×40 mL) and the combined organic component was concentrated to dryness to yield the title compound (1.9 g) which was used without further purification. LC-MS retention time=2.40 min; m/z=363.1 [M+H-Boc]$^+$. (Column: Phenonenex-Luna C18 2.0×30 mm 3 µm. Solvent A=95% Water: 5% Acetonitrile: 10 µM ammonium acetate. Solvent B=5% Water: 95% Acetonitrile: 10 µM ammonium acetate. Flow Rate=1.0 mL/min. Start % B=0. Final % B=100. Gradient Time=3 min. Wavelength=220).

Intermediate 10

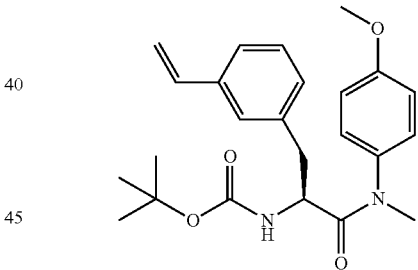

(S)-tert-butyl (1-((4-methoxyphenyl)(methyl)amino)-1-oxo-3-(3-vinylphenyl)propan-2-yl)carbamate A solution of (S)-tert-butyl (3-(3-bromophenyl)-1-((4-methoxyphenyl)(methyl)amino)-1-oxopropan-2-yl)carbamate (0.740 g, 1.56 mmol), 4,4,5,5-tetramethyl-2-vinyl-1,3,2-dioxaborolane (0.295 g, 1.92 mmol), 3M aqueous Na$_2$CO$_3$ (2.66 mL, 7.99 mmol) and PdCl$_2$(dppf) (0.117 g, 0.160 mmol) in DMF (2 mL) was degassed and heated at 110° C. for 2 h. The reaction mixture was allowed to cool, diluted with water (150 mL) and extracted with EtOAc (2×150 mL). The combined organic component was purified by silica gel chromatography (TLC (50% EtAOc/Hexanes, Rf0.66)) to yield the title compound (0.43 g). LC-MS retention time=2.38 min; m/z=411.3 [M+H]$^+$. (Column: Phenonenex-Luna C18 2.0×30 mm 3 µm. Solvent A=95% Water: 5% Acetonitrile: 10 µM ammonium acetate. Solvent B=5%

Water: 95% Acetonitrile: 10 μM ammonium acetate. Flow Rate=1.0 mL/min. Start % B=0. Final % B=100. Gradient Time=3 min. Wavelength=220). ¹H NMR (400 MHz, CHLOROFORM-d) δ 7.23-7.15 (m, 1H), 7.01-6.55 (m, 7H), 5.68 (d, J=17.6 Hz, 1H), 5.23 (d, J=11.0 Hz, 2H), 4.52 (d, J=7.6 Hz, 1H), 3.81 (s, 3H), 3.16 (s, 3H), 2.94-2.82 (m, 1H), 2.72 (dd, J=12.6, 6.7 Hz, 1H), 1.57 (s, 9H).

Intermediate 11

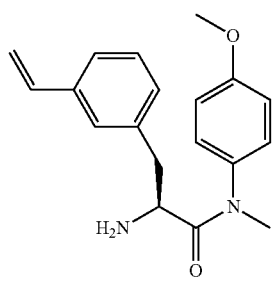

(S)-2-amino-N-(4-methoxyphenyl)-N-methyl-3-(3-vinylphenyl)propanamide

A solution of (S)-tert-butyl (1-((4-methoxyphenyl)(methyl)amino)-1-oxo-3-(3-vinylphenyl)propan-2-yl)carbamate (0.430 g, 1.047 mmol) and TFA (3 mL, 38.9 mmol) in DCM (6 mL) was stirred at RT for 1 h. Solvent was evaporated to yield a TFA salt of the title compound (0.445 g) which was used without further purification. LC-MS retention time=1.77 min; m/z=311.2 [M+H]⁺. (Column: Phenonenex-Luna C18 2.0×30 mm 3 μm. Solvent A=95% Water: 5% Acetonitrile: 10 μM ammonium acetate. Solvent B=5% Water: 95% Acetonitrile: 10 μM ammonium acetate. Flow Rate=1.0 mL/min. Start % B=0. Final % B=100. Gradient Time=3 min. Wavelength=220).

Intermediate 12

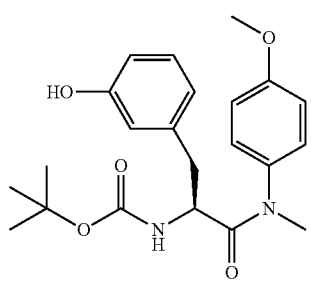

(S)-tert-butyl (3-(3-hydroxyphenyl)-1-((4-methoxyphenyl)(methyl)amino)-1-oxopropan-2-yl)carbamate HATU (0.800 g, 2.10 mmol) was added to a stirred solution of 4-methoxy-N-methylaniline (0.240 g, 1.75 mmol), (S)-2-((tert-butoxycarbonyl)amino)-3-(3-hydroxyphenyl)propanoic acid (0.493 g, 1.75 mmol) and DIPEA (0.92 mL, 5.3 mmol) in DMF (5 mL) and the reaction mixture was stirred at RT overnight. The reaction was diluted with water (50 mL), extracted with EtOAc (2×40 mL) and the combined organic component was concentrated to dryness and purified (40 g SiO₂, 0-30% EtOAc/DCM) to yield the title compound (0.58 g). LC-MS retention time=1.99 min; m/z=399.3 [M−H]⁻. (Column: Phenonenex-Luna C18 2.0×30 mm 3 μm. Solvent A=95% Water: 5% Acetonitrile: 10 μM ammonium acetate. Solvent B=5% Water: 95% Acetonitrile: 10 μM ammonium acetate. Flow Rate=1.0 mL/min. Start % B=0. Final % B=100. Gradient Time=3 min. Wavelength=220). ¹H NMR (400 MHz, CHLOROFORM-d) δ 7.10 (t, J=7.8 Hz, 1H), 6.91-6.66 (m, 5H), 6.52 (d, J=7.6 Hz, 1H), 6.46 (s, 1H), 5.57 (br. s., 1H), 5.20 (d, J=7.6 Hz, 1H), 4.52 (d, J=7.8 Hz, 1H), 3.81 (s, 3H), 3.19 (s, 3H), 2.84 (dd, J=13.0, 7.8 Hz, 1H), 2.68 (dd, J=12.8, 6.2 Hz, 1H), 1.40 (br. s., 9H).

Intermediate 13

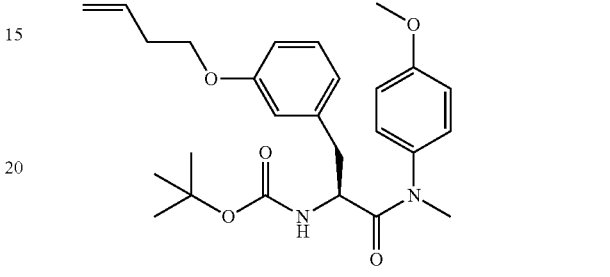

(S)-tert-butyl (3-(3-(but-3-en-1-yloxy)phenyl)-1-((4-methoxyphenyl)(methyl)amino)-1-oxopropan-2-yl)carbamate The reaction mixture of (S)-tert-butyl (3-(3-hydroxyphenyl)-1-((4-methoxyphenyl)(methyl)amino)-1-oxopropan-2-yl)carbamate (0.52 g, 1.3 mmol), 4-bromo-2-butene (0.26 mL, 2.6 mmol) and Cs₂CO₃ (0.465 g, 1.43 mmol) in THF (8 mL), EtOH (8 mL) and H₂O (8 mL) was stirred at 85° C. for 22 h. The reaction was diluted with water (80 mL), extracted with EtOAc (2×100 mL) and the combined organic component was concentrated to dryness and purified (24 g SiO₂, 0-40% EtOAc/DCM) to yield the title compound (0.28 g). LC-MS retention time=2.51 min; m/z=355.1 [M+H-Boc]⁺. (Column: Phenonenex-Luna C18 2.0×30 mm 3 μm. Solvent A=95% Water: 5% Acetonitrile: 10 μM ammonium acetate. Solvent B=5% Water: 95% Acetonitrile: 10 μM ammonium acetate. Flow Rate=1.0 mL/min. Start % B=0. Final % B=100. Gradient Time=3 min. Wavelength=220). ¹H NMR (400 MHz, CHLOROFORM-d) δ 7.12 (t, J=7.8 Hz, 1H), 6.93-6.67 (m, 5H), 6.55 (d, J=7.3 Hz, 1H), 6.44 (br. s., 1H), 5.91 (ddt, J=17.1, 10.4, 6.7 Hz, 1H), 5.22-5.09 (m, 3H), 4.52 (d, J=8.1 Hz, 1H), 3.90 (td, J=6.7, 3.4 Hz, 2H), 3.82 (s, 3H), 3.18 (s, 3H), 2.89-2.80 (m, 1H), 2.68 (dd, J=12.6, 6.0 Hz, 1H), 2.52 (q, J=6.6 Hz, 2H), 1.55 (s, 9H).

Intermediate 14

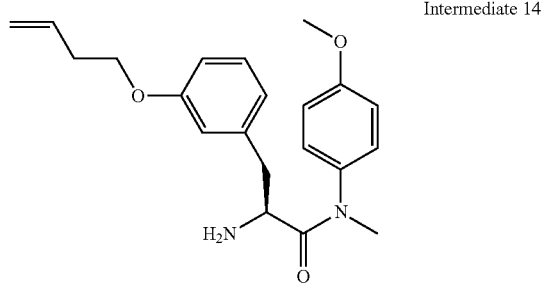 [SMILES: C=CCCOc1cccc(C[C@H](N)C(=O)N(C)c2ccc(OC)cc2)c1]

(S)-2-amino-3-(3-(but-3-en-1-yloxy)phenyl)-N-(4-methoxyphenyl)-N-methylpropanamide A solution of (S)-tert-butyl (3-(3-(but-3-en-1-yloxy)phenyl)-1-((4-methoxyphenyl)(methyl)amino)-1-oxopropan-2-yl)carbamate (0.280 g, 0.616 mmol) in TFA (1.0 mL, 13 mmol) and DCM (2 mL) was stirred at RT for 1 h. The solvent was removed to yield a TFA salt of the title compound (0.445 g) which was used without further purification. LC-MS retention time=1.87 min; m/z=355.1 [M+H]$^+$. (Column: Phenonenex-Luna C18 2.0×30 mm 3 μm. Solvent A=95% Water: 5% Acetonitrile: 10 μM ammonium acetate. Solvent B=5% Water: 95% Acetonitrile: 10 μM ammonium acetate. Flow Rate=1.0 mL/min. Start % B=0. Final % B=100. Gradient Time=3 min. Wavelength=220).

Intermediate 15

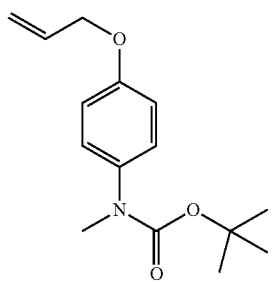

tert-butyl (4-(allyloxy)phenyl)(methyl) carbamate

A mixture of tert-butyl (4-hydroxyphenyl)(methyl)carbamate (1.00 g, 4.48 mmol), allyl bromide (0.58 mL, 6.7 mmol) and Cs$_2$CO$_3$ (2.92 g, 8.96 mmol) in acetone (40 mL) was sealed and heated to gentle reflux for 4 h. The reaction mixture was allowed to cool to rt, filtered and concentrated. The residue was taken up into EtOAc, washed with 5% citric acid and then brine, dried over MgSO$_4$, filtered, and concentrated. The residue was taken up into DCM and purified by flash column chromatography. $^1$H NMR (400 MHz, CHLOROFORM-d) δ 7.14 (d, J=8.3 Hz, 1H), 6.91-6.85 (m, 1H), 6.08 (ddt, J=17.3, 10.6, 5.3 Hz, 1H), 5.44 (dq, J=17.2, 1.6 Hz, 1H), 5.34-5.28 (m, 1H), 4.54 (dt, J=5.3, 1.5 Hz, 2H), 3.24 (s, 3H), 1.45 (s, 9H).

Intermediate 16

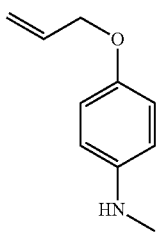

4-(allyloxy)-N-methylaniline

A solution of 2 M HCl in ether (0.949 mL, 1.899 mmol) was added to tert-butyl (4-(allyloxy)phenyl)-(methyl)carbamate (50 mg, 0.190 mmol) and stirred at RT overnight. The reaction was concentrated under a stream of nitrogen to yield the title compound which was used without further purification. LC-MS retention time=0.73 min; m/z=164.2 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220).

Intermediate 17

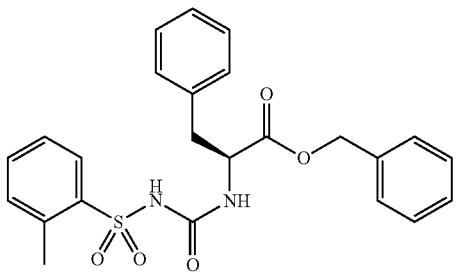

(S)-benzyl 3-phenyl-2-(3-(o-tolylsulfonyl)ureido)propanoate

2-Methylbenzenesulfonyl isocyanate (0.52 mL, 3.4 mmol) was added dropwise to an ice bath cooled mixture of (S)-benzyl 2-amino-3-phenylpropanoate, HCl (1.00 g, 3.43 mmol) and DIPEA (2.4 mL, 14 mmol) in acetonitrile (20 mL) and the resulting solution was stirred at RT for 2 h. The reaction mixture was concentrated and the residual oil was taken into EtOAc (100 mL) and washed with 5% citric acid and brine, dried over MgSO$_4$, filtered and concentrated. The residual oil was purified by flash column chromatography (80 g silica gel cartridge, eluted with gradient 30%~70% acetone-hexanes) to afford the title compound (1.20 g) as a white solid. LC-MS retention time=1.28 min; m/z=453.3 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220).

Intermediate 18

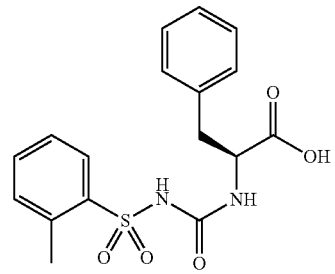

(S)-3-phenyl-2-(3-(o-tolylsulfonyl)ureido)propanoic acid

A mixture of (S)-benzyl 3-phenyl-2-(3-(o-tolylsulfonyl)ureido)propanoate (1.00 g, 2.21 mmol) and 10% Pd—C (0.118 g, 0.110 mmol) in EtOAc (15 mL) and MeOH (15 mL) was placed under a balloon of hydrogen and stirred at RT for 2 h. The reaction was filtered through celite and concentrated to dryness to yield the title compound (750 mg)

as a white solid. LC-MS retention time=0.99 min; m/z=363.0 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220).

Intermediate 19

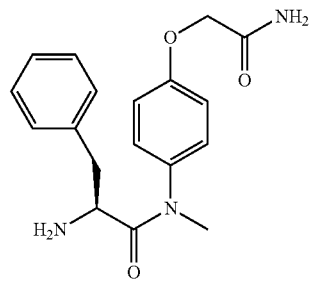

(S)-2-amino-N-(4-(2-amino-2-oxoethoxy)phenyl)-N-methyl-3-phenylpropanamide

Intermediate 19 was prepared using the chemical procedures displayed in the following scheme:

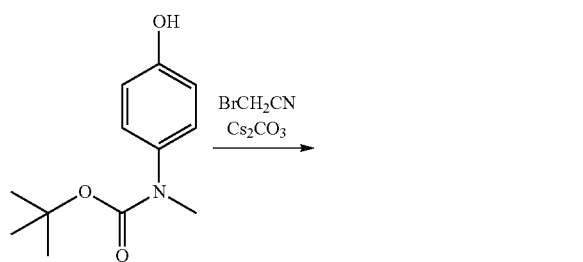

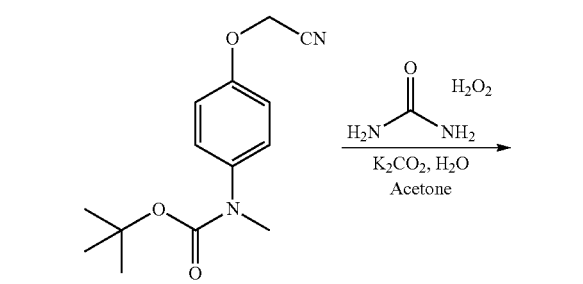

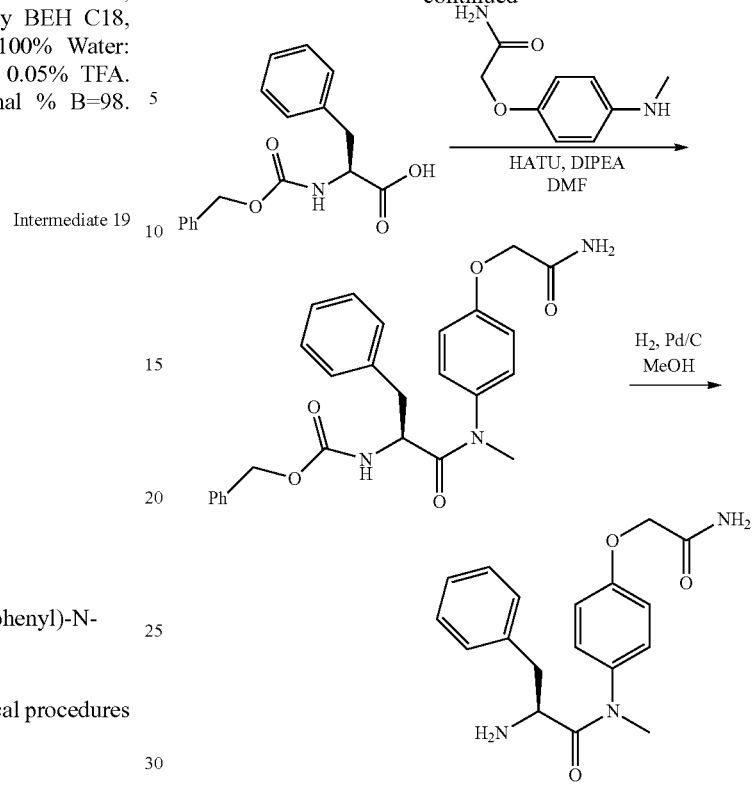

LC-MS retention time=0.73 min; m/z=328.2 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220).

Intermediate JB-1

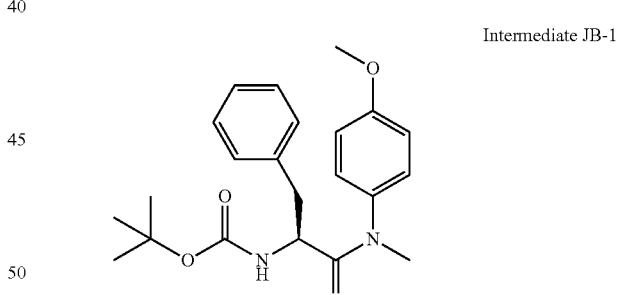

(S)-tert-butyl (1-((4-methoxyphenyl)(methyl)amino)-1-oxo-3-phenylpropan-2-yl)carbamate HATU (1.5 g, 4.0 mmol) was added to a stirred solution of 4-methoxy-N-methylaniline (500 mg, 3.64 mmol) and (S)-2-((tert-butoxycarbonyl)amino)-3-phenylpropanoic acid (1.06 g, 4.0 mmol) in DMF (20 mL) and DIPEA (1.3 mL, 7.3 mmol) and the reaction mixture was stirred at RT for 4 h. The reaction was concentrated and the residual crude oil was partitioned between EtOAc (~60 mL) and 1/2 sat. NaHCO$_3$ (aq) (~60 mL). The organic component was washed with brine (~40 mL), dried (MgSO$_4$), filtered, concentrated and purified using a Biotage Horizon (80 g SiO$_2$, 10-40%

EtOAc/hexanes) to yield (S)-tert-butyl (1-((4-methoxyphenyl)(methyl)amino)-1-oxo-3-phenylpropan-2-yl)carbamate (1.34 g) as a clear amber viscous oil. LC-MS retention time=3.17 min; m/z=385.3 [M+H]+. (Column: Phenonenex-Luna C18 2.0×50 mm 3 μm. Solvent A=95% Water: 5% Acetonitrile: 10 mM NH4OAc. Solvent B=5% Water: 95% Acetonitrile: 10 mM NH4OAc. Flow Rate=0.8 mL/min. Start % B=0. Final % B=100. Gradient Time=4 min. Wavelength=220). $^1$H NMR (400 MHz, CDCl$_3$) δ 7.25-7.20 (m, 3H), 7.03-6.64 (m, 6H), 5.20 (d, J=8.8 Hz, 1H), 4.53 (q, J=7.4 Hz, 1H), 3.83 (s, 3H), 3.18 (s, 3H), 2.89 (dd, J=13.1, 7.5 Hz, 1H), 2.71 (dd, J=13.1, 6.5 Hz, 1H), 1.39 (s, 9H).

Intermediate JB-2

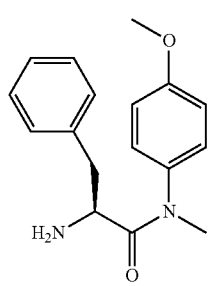

(S)-2-amino-N-(4-methoxyphenyl)-N-methyl-3-phenylpropanamide

A 4M HCl (15 mL, 60.0 mmol) in dioxanes solution was added to a stirred solution of (S)-tert-butyl (1-((4-methoxyphenyl)(methyl)amino)-1-oxo-3-phenylpropan-2-yl)carbamate (Intermediate JB-1) (1.34 g, 3.49 mmol) in THF (10 mL) and the reaction mixture was stirred at RT for 5 h. The reaction mixture was concentrated to dryness under vacuum to yield an HCl salt of (S)-2-amino-N-(4-methoxyphenyl)-N-methyl-3-phenylpropanamide (1.11 g) as a solidified foam which was used without additional purification. LC-MS retention time=2.33 min; m/z=285.2 [M+H]+. (Column: Phenonenex-Luna C18 2.0×50 mm 3 μm. Solvent A=95% Water: 5% Acetonitrile: 10 mM NH4OAc. Solvent B=5% Water: 95% Acetonitrile: 10 mM NH4OAc. Flow Rate=0.8 mL/min. Start % B=0. Final % B=100. Gradient Time=4 min. Wavelength=220).

Intermediate JB-7

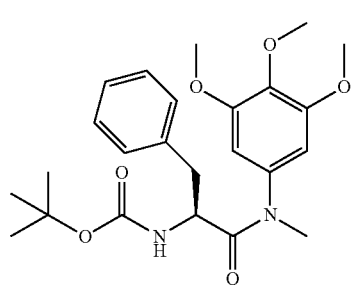

(S)-tert-butyl (1-(methyl(3,4,5-trimethoxyphenyl)amino)-1-oxo-3-phenylpropan-2-yl)carbamate HATU (776 mg, 2.04 mmol) was added to a stirred solution of 3,4,5-trimethoxy-N-methylaniline (350 mg, 1.78 mmol) and (S)-2-((tert-butoxycarbonyl)amino)-3-phenylpropanoic acid (518 mg, 1.95 mmol) in DMF (10 mL) and DIPEA (0.62 mL, 3.6 mmol) and stirred at RT ON. The reaction mixture was concentrated and the crude oil was partitioned between EtOAc (~40 mL) and 1/2 sat NaHCO$_3$ (aq) (~40 mL). The organic component was washed with brine (~30 mL), dried (MgSO$_4$), filtered and concentrated. The crude residue was then purified using a Biotage Horizon (80 g SiO$_2$, 10-40% EtOAc/hexanes) to yield (S)-tert-butyl (1-(methyl(3,4,5-trimethoxyphenyl)amino)-1-oxo-3-phenylpropan-2-yl)carbamate (474 mg) as a clear colorless solidified oil. Used without further purification. LC-MS retention time=1.60 min; m/z=385.3 [M+H]+. (Column: Phenonenex-Luna C18 2.0×50 mm 3 μm. Solvent A=90% Water: 10% Acetonitrile: 0.1% TFA. Solvent B=10% Water: 90% Acetonitrile: 0.1% TFA. Flow Rate=1.0 mL/min. Start % B=0. Final % B=100. Gradient Time=2 min. Wavelength=220). $^1$H NMR (400 MHz, CHLOROFORM-d) δ 7.27-7.17 (m, 3H), 7.01 (d, J=6.3 Hz, 2H), 6.11 (br. s., 2H), 5.21 (d, J=9.0 Hz, 1H), 4.76-4.64 (m, 1H), 3.86 (s, 3H), 3.77 (br. s., 6H), 3.17 (s, 3H), 3.01-2.87 (m, 1H), 2.77 (dd, J=12.8, 6.3 Hz, 1H), 1.40 (s, 9H).

Intermediate ZY-1

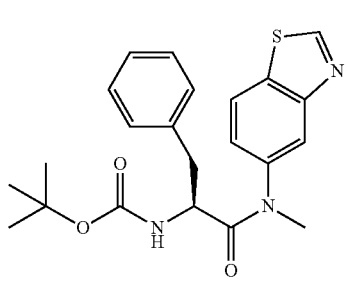

N-methylbenzo[d]thiazol-5-amine

Paraformaldehyde (80 mg, 2.7 mmol) was added to a stirred solution of benzo[d]thiazol-5-amine (200 mg, 1.332 mmol) in MeOH (5 mL) The resulting suspension was then treated with 25% w/w NaOMe in MeOH (1.5 mL, 6.7 mmol) and the clear reaction mixture was stirred at 60° C. for 16 h. The reaction was allowed to cool to RT and then treated with NaBH$_4$ (126 mg, 3.33 mmol) and stirred at RT for 16 h. The reaction mixture was diluted with water (10 mL) and extracted with CHCl$_3$ (3×20 mL). The combined organic component was concentrated and purified using a Biotage Horizon (12 g SiO$_2$, 0-50% EtOAc/hexanes) to yield N-methylbenzo[d]thiazol-5-amine (217 mg) as yellow gum. LC-MS retention time=0.67 min; m/z=165.05 [M+H]+. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^1$H NMR (400 MHz, CHLOROFORM-d) δ 8.92 (s, 1H), 7.69 (d, J=8.5 Hz, 1H), 7.31 (d, J=2.3 Hz, 1H), 6.82 (dd, J=8.8, 2.3 Hz, 1H), 3.93 (br. s., 1H), 2.94 (s, 3H).

Intermediate ZY-2

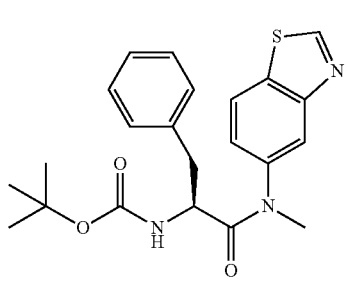

(S)-tert-butyl (1-(benzo[d]thiazol-5-yl(methyl)amino)-1-oxo-3-phenylpropan-2-yl)carbamate HATU (1.90 g, 5.01 mmol) was added to a solution of N-methylbenzo[d]thiazol-5-amine (Intermediate ZY-1) (685 mg, 4.17 mmol) and (S)-2-((tert-butoxycarbonyl)amino)-3-phenylpropanoic acid (1.33 g, 5.01 mmol) in DMF (20 mL) and DIPEA (2.18 mL, 12.5 mmol) and the reaction mixture was stirred at RT for 6 h. The crude reaction mixture was diluted with sat. aq. NaHCO$_3$ (20 mL) and extracted with EtOAc (3×50 mL). The combined organic component was washed with brine (~60 mL), dried (Na$_2$SO$_4$), filtered and concentrated. The crude material was then purified using a Biotage Horizon (12 g SiO$_2$, 0-40%-50% EtOAc/hexanes) to yield (S)-tert-butyl (1-(benzo[d]thiazol-5-yl(methyl)amino)-1-oxo-3-phenylpropan-2-yl)carbamate (1.7 g) as a white solid. LC-MS retention time=1.19 min; m/z=412.0 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^1$H NMR (400 MHz, CHLOROFORM-d) δ 9.07 (s, 1H), 7.90 (d, J=8.3 Hz, 1H), 7.38 (d, J=7.5 Hz, 1H), 7.27-7.19 (m, 3H), 6.94 (d, J=6.8 Hz, 3H), 5.22 (d, J=8.8 Hz, 1H), 4.58-4.48 (m, 1H), 3.26 (s, 3H), 2.93 (dd, J=12.9, 8.4 Hz, 1H), 2.78 (dd, J=12.4, 5.9 Hz, 1H), 1.40 (s, 9H).

Intermediate ZY-3

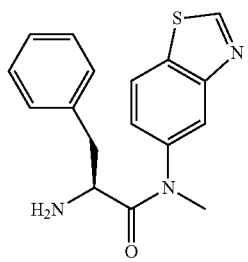

(S)-2-amino-N-(benzo[d]thiazol-5-yl)-N-methyl-3-phenylpropanamide

A solution of 4M HCl (10 mL, 40.0 mmol) in dioxanes was added to a stirred solution of (S)-tert-butyl (1-(benzo[d]thiazol-5-yl(methyl)amino)-1-oxo-3-phenylpropan-2-yl)carbamate (Intermediate ZY-2) (1.7 g, 4.13 mmol) in THF (10 mL) and the reaction mixture was stirred at RT for 16 h. The reaction mixture was concentrated, redissolved in EtOH/toluene, and then reconcentrated (3×) to yield an HCl salt of (S)-2-amino-N-(benzo[d]thiazol-5-yl)-N-methyl-3-phenylpropanamide (1.7 g, 4.42 mmol, 107% yield) as a pink sticky solid. LC-MS retention time=0.83 min; m/z=312.0 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^1$H NMR (400 MHz, METHANOL-d$_4$) δ 9.42 (s, 1H), 8.10 (d, J=8.3 Hz, 1H), 7.39-7.08 (m, 6H), 6.91 (d, J=7.0 Hz, 2H), 4.10 (dd, J=8.0, 6.5 Hz, 1H), 3.63-3.56 (m, 2H), 3.11 (dd, J=13.4, 8.2 Hz, 1H), 2.92 (dd, J=13.3, 6.5 Hz, 1H), 2.87 (s, 3H).

Intermediate ZY-4

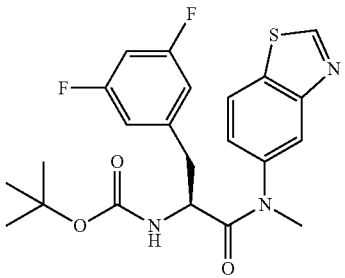

(S)-tert-butyl (1-(benzo[d]thiazol-5-yl(methyl)amino)-3-(3,5-difluorophenyl)-1-oxopropan-2-yl)carbamate HATU (592 mg, 1.556 mmol) was added to a stirred solution of N-methylbenzo[d]thiazol-5-amine (Intermediate ZY-1) (213 mg, 1.30 mmol) and (S)-2-((tert-butoxycarbonyl)amino)-3-(3,5-difluorophenyl)propanoic acid (469 mg, 1.56 mmol) in DMF (7 mL) and DIPEA (0.45 mL, 2.6 mmol) and the reaction mixture was stirred at RT for 16 h. The crude reaction mixture was diluted with sat. aq. NaHCO$_3$ (20 mL) and extracted with EtOAc (3×50 mL). The combined organic component was washed with brine (~60 mL), dried (Na$_2$SO$_4$), filtered and concentrated. The crude material was then purified using a Biotage Horizon (24 g SiO$_2$, 0-50% EtOAc/hexanes) yield (S)-tert-butyl (1-(benzo[d]thiazol-5-yl(methyl)amino)-3-(3,5-difluorophenyl)-1-oxopropan-2-yl)carbamate (581 mg) as a white solid. LC-MS retention time=1.23 min; m/z=448.0 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^1$H NMR (400 MHz, CHLOROFORM-d) δ 9.10 (s, 1H), 7.98 (d, J=8.3 Hz, 1H), 7.68 (br. s., 1H), 7.05 (br. s., 1H), 6.68 (t, J=8.9 Hz, 1H), 6.44 (d, J=6.3 Hz, 2H), 5.25 (d, J=9.0 Hz, 1H), 4.54 (q, J=7.3 Hz, 1H), 2.94-2.86 (m, 1H), 2.81 (s, 3H), 2.72 (dd, J=13.1, 6.5 Hz, 1H), 1.39 (s, 9H).

Intermediate ZY-5

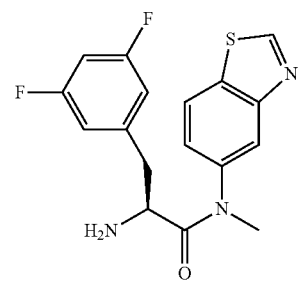

(S)-2-amino-N-(benzo[d]thiazol-5-yl)-3-(3,5-difluorophenyl)-N-methylpropanamide TFA (1.0 mL, 13 mmol) was added to a stirred solution of (S)-tert-butyl (1-(benzo[d]thiazol-5-yl(methyl)amino)-3-(3,5-difluorophenyl)-1-oxopropan-2-yl)carbamate (Intermediate ZY-4) (0.58 g, 1.23 mmol) in DCM (2 mL) and the reaction mixture was stirred at RT for 16 h. The crude reaction mixture was concentrated and the residue was dissolved in MeOH/DCM and 4 M HCl in dioxane (2 mL) and reconcentrated. The residue was redissolved in EtOH/toluene, and then reconcentrated (3×) to yield an HCl salt of (S)-2-amino-N-(benzo[d]thiazol-5-yl)-3-(3,5-difluorophenyl)-N-methylpropanamide (0.55 g) as a white solid. LC-MS retention time=0.83 min; m/z=348.1[M+H]+. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220).

Intermediate ZY-6

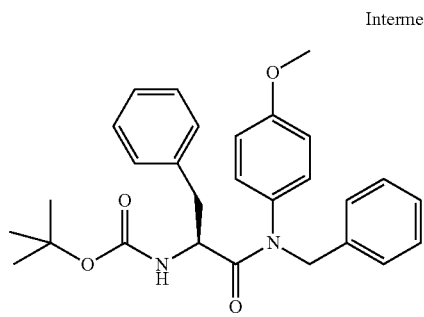

(S)-tert-butyl (1-(benzyl(4-methoxyphenyl)amino)-1-oxo-3-phenylpropan-2-yl)carbamate BOP-Cl (131 mg, 0.516 mmol) was added to a stirred solution of (S)-2-((tert-butoxycarbonyl)amino)-3-phenylpropanoic acid (124 mg, 0.469 mmol) and N-benzyl-4-methoxyaniline (100 mg, 0.469 mmol) in DCM (3 mL), and DIPEA (0.25 mL, 1.4 mmol) and the reaction mixture was stirred at RT for 16 h. The crude reaction mixture was concentrated and the residue was purified using a Biotage Horizon (12 g SiO2, 0-50% Et2O/hexanes) to yield the title compound (125 mg). LC-MS retention time=1.43 min; m/z=461.4 [M+H]+. (Column: Waters Aquity BEH C18 2.1×50 mm 1.7 U. Solvent A=100% Water/0.05% TFA. Solvent B=100% Acetonitrile/0.05% TFA. Flow Rate=0.8 mL/min. Start % B=2. Final % B=98. Gradient Time=1.5 min. Wavelength=220).

Intermediate ZY-7

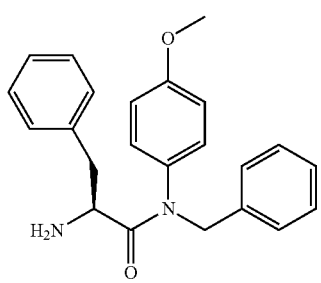

(S)-2-amino-N-benzyl-N-(4-methoxyphenyl)-3-phenylpropanamide

A 4M solution of HCl (1.3 mL, 5.2 mmol) in dioxane was added to a stirred solution of (S)-tert-butyl (1-(benzyl(4-methoxyphenyl)amino)-1-oxo-3-phenylpropan-2-yl)carbamate (Intermediate ZY-6) (120 mg, 0.261 mmol) in THF (1.3 mL) and the reaction mixture was stirred at RT for 2 h. The reaction mixture concentrated to yield an HCl salt of the title compound (117 mg). LC-MS retention time=0.99 min; m/z=361.2 [M+H]+. (Column: Waters Aquity BEH C18 2.1×50 mm 1.7 U. Solvent A=100% Water/0.05% TFA. Solvent B=100% Acetonitrile/0.05% TFA. Flow Rate=0.8 mL/min. Start % B=2. Final % B=98. Gradient Time=1.5 min. Wavelength=220).

Intermediate ZY-8

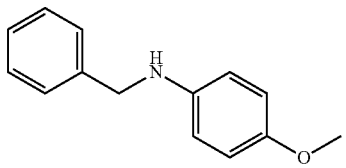

N-benzyl-4-methoxyaniline

Diethyl 2,6-dimethyl-1,4-dihydropyridine-3,5-dicarboxylate (0.617 g, 2.44 mmol) was added to a stirred solution of scandium trifluoromethanesulfonate (0.024 g, 0.049 mmol), benzaldehyde (0.248 mL, 2.44 mmol) and 4-methoxyaniline (0.300 g, 2.44 mmol) in DCM (10 mL) and the reaction mixture was stirred at RT for 16 h. The reaction was then concentrated and the residue was purified by silica gel chromatography (0-20% Et2O/hexanes) to yield the title compound (503 mg) as yellow oil.

| | |
|---|---|
| MS (M + H)+ Calcd. | 214.1 |
| MS (M + H)+ Observ. | 214.1 |
| Retention Time | 0.824 min |
| | LC Condition |
| Solvent A | 100% Water:0.05% TFA |
| Solvent B | 100% acetonitrile:0.05% TFA |
| Start % B | 2 |
| Final % B | 98 |
| Gradient Time | 1.5 min |
| Flow Rate | 0.8 mL/min |
| Wavelength | 220 |
| Solvent Pair | acetonitrile:Water:TFA |
| Column | Waters Aquity BEH C18 2.1 × 50 mm 1.7U |

Intermediate ZY-9

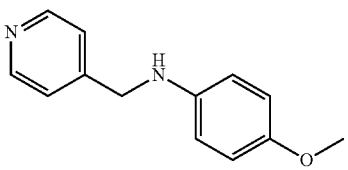

4-methoxy-N-(pyridin-4-ylmethyl)aniline

Diethyl 2,6-dimethyl-1,4-dihydropyridine-3,5-dicarboxylate (0.617 g, 2.44 mmol) was added to a stirred solution of scandium trifluoromethanesulfonate (0.024 g, 0.049 mmol), isonicotinaldehyde (0.229 mL, 2.44 mmol) and 4-methoxyaniline (0.300 g, 2.44 mmol) in DCM (10 mL) and the reaction mixture was stirred at RT for 16 h. The reaction was then concentrated and the residue was purified by silica gel chromatography (24 g SiO2, 0-100% Et2O/hexanes) to yield the title compound (447 mg) as yellow solid.

| | |
|---|---|
| MS (M + H)+ Calcd. | 215.1 |
| MS (M + H)+ Observ. | 215.1 |
| Retention Time | 0.719 min |
| | LC Condition |
| Solvent A | 100% Water:0.05% TFA |
| Solvent B | 100% acetonitrile:0.05% TFA |
| Start % B | 2 |
| Final % B | 98 |
| Gradient Time | 1.5 min |
| Flow Rate | 0.8 mL/min |
| Wavelength | 220 |
| Solvent Pair | acetonitrile:Water:TFA |
| Column | Waters Aquity BEH C18 2.1 × 50 mm 1.7U |

Intermediate ZY-10

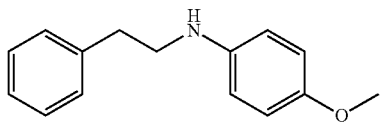

4-methoxy-N-phenethylaniline

Diethyl 2,6-dimethyl-1,4-dihydropyridine-3,5-dicarboxylate (1.03 g, 4.06 mmol) was added to a stirred solution of scandium trifluoromethanesulfonate (0.040 g, 0.081 mmol), 2-phenylacetaldehyde (0.488 g, 4.06 mmol) and 4-methoxyaniline (0.500 g, 4.06 mmol) in DCM (10 mL) and the reaction mixture was stirred at RT for 16 h and then heated at 50° C. for 2 h. Additional 2-phenylacetaldehyde (0.488 g, 4.06 mmol), and diethyl 2,6-dimethyl-1,4-dihydropyridine-3,5-dicarboxylate (1.03 g, 4.06 mmol) were added and heating at 50° C. was continued for 1 h. The reaction was then concentrated and the residue was purified by silica gel chromatography (24 g SiO$_2$, 0-20% Et$_2$O/hexanes) to yield the title compound (2.25 g) contaminated with and impurity, but used without additional purification, as red/orange oil.

| | |
|---|---|
| MS (M + H)+ Calcd. | 228.1 |
| MS (M + H)+ Observ. | 228.1 |
| Retention Time | 0.867 min |
| | LC Condition |
| Solvent A | 100% Water:0.05% TFA |
| Solvent B | 100% acetonitrile:0.05% TFA |
| Start % B | 2 |
| Final % B | 98 |
| Gradient Time | 1.5 min |
| Flow Rate | 0.8 mL/min |
| Wavelength | 220 |
| Solvent Pair | acetonitrile:Water:TFA |
| Column | Waters Aquity BEH C18 2.1 × 50 mm 1.7 U |

Intermediate ZY-11

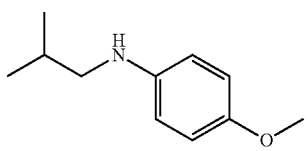

N-isobutyl-4-methoxyaniline

Diethyl 2,6-dimethyl-1,4-dihydropyridine-3,5-dicarboxylate (2.06 g, 8.12 mmol) was added to a stirred solution of scandium trifluoromethanesulfonate (0.080 g, 0.16 mmol), isobutyraldehyde (0.74 mL, 8.1 mmol) and 4-methoxyaniline (0.300 g, 2.44 mmol) in DCM (10 mL) and the reaction mixture was stirred at RT for 16 h. The reaction was then concentrated and the residue was purified by silica gel chromatography (40 g SiO$_2$, 0-20% Et$_2$O/hexanes) to yield the title compound (1.02 g) as clear colorless oil.

| | |
|---|---|
| MS (M + H)+ Calcd. | 180.1 |
| MS (M + H)+ Observ. | 180.1 |
| Retention Time | 0.774 min |
| | LC Condition |
| Solvent A | 100% Water:0.05% TFA |
| Solvent B | 100% acetonitrile:0.05% TFA |
| Start % B | 2 |
| Final % B | 98 |
| Gradient Time | 1.5 min |
| Flow Rate | 0.8 mL/min |
| Wavelength | 220 |
| Solvent Pair | acetonitrile:Water:TFA |
| Column | Waters Aquity BEH C18 2.1 × 50 mm 1.7 U |

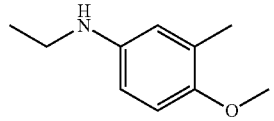

N-ethyl-4-methoxy-3-methylaniline

Acetic acid (0.042 mL, 0.73 mmol) was added to a stirred solution of 4-methoxy-3-methylaniline (100 mg, 0.729 mmol) and acetaldehyde (0.054 mL, 0.948 mmol) in DCM (3 mL) and the reaction mixture was stirred at RT for 5 min. Sodium triacetoxyborohydride (232 mg, 1.09 mmol) was then added to the reaction mixture and the reaction was stirred at RT for 16 h. The reaction was quenched with 1N aq. NaOH (4 mL), extracted with chloroform (3×10 mL) and the combined organic component was concentrated and purified by preparative HPLC (H$_2$O-MeOH with 0.1% TFA buffer) to yield a TFA salt of the title compound (27 mg) as dark pink oil.

| | |
|---|---|
| MS (M + H)+ Calcd. | 166.1 |
| MS (M + H)+ Observ. | 166.1 |
| Retention Time | 0.787 min |
| | LC Condition |
| Solvent A | 100% Water:0.05% TFA |
| Solvent B | 100% acetonitrile:0.05% TFA |
| Start % B | 2 |
| Final % B | 98 |
| Gradient Time | 1.5 min |
| Flow Rate | 0.8 mL/min |
| Wavelength | 220 |
| Solvent Pair | acetonitrile:Water:TFA |
| Column | Waters Aquity BEH C18 2.1 × 50 mm 1.7 U |

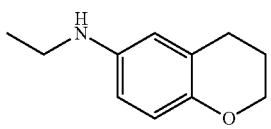

Intermediate ZY-13

N-ethylchroman-6-amine

Prepared using the procedure outlined for Intermediate ZY-12 where 4-methoxy-3-methylaniline was replaced with chroman-6-amine.

| | |
|---|---|
| MS (M + H)+ Calcd. | 178.1 |
| MS (M + H)+ Observ. | 178.1 |
| Retention Time | 0.774 min |
| LC Condition | |
| Solvent A | 100% Water:0.05% TFA |
| Solvent B | 100% acetonitrile:0.05% TFA |
| Start % B | 2 |
| Final % B | 98 |
| Gradient Time | 1.5 min |
| Flow Rate | 0.8 mL/min |
| Wavelength | 220 |
| Solvent Pair | acetonitrile:Water:TFA |
| Column | Waters Aquity BEH C18 2.1 × 50 mm 1.7 U |

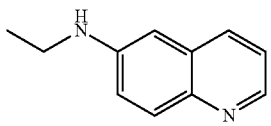

Intermediate ZY-14

N-ethylquinolin-6-amine

Prepared using the procedure outlined for Intermediate ZY-12 where 4-methoxy-3-methylaniline was replaced with quinoline-6-amine.

| | |
|---|---|
| MS (M + H)+ Calcd. | 173.1 |
| MS (M + H)+ Observ. | 173.1 |
| Retention Time | 0.775 min |
| LC Condition | |
| Solvent A | 100% Water:0.05% TFA |
| Solvent B | 100% acetonitrile:0.05% TFA |
| Start % B | 2 |
| Final % B | 98 |
| Gradient Time | 1.5 min |
| Flow Rate | 0.8 mL/min |
| Wavelength | 220 |
| Solvent Pair | acetonitrile:Water:TFA |
| Column | Waters Aquity BEH C18 2.1 × 50 mm 1.7 U |

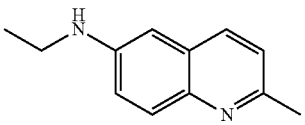

Intermediate ZY-15

N-ethyl-2-methylquinolin-6-amine

10% Pd—C (0.135 g, 0.126 mmol) was added to a mixture of 2-methylquinolin-6-amine (0.200 g, 1.26 mmol) in MeOH (10 mL) and MeCN (6.6 mL). The reaction mixture was vacuum flushed with $N_2$ (3×) followed by $H_2$ (3×) and then shaken at RT under 20 psi $H_2$ for 4 h. The reaction mixture was filtered through celite, concentrated and purified by flash silica chromatography (12 g $SiO_2$, 0-35% EtOAc/hexanes) to yield N-ethyl-2-methylquinolin-6-amine (192 mg) as brown solid.

| | |
|---|---|
| MS (M + H)+ Calcd. | 187.1 |
| MS (M + H)+ Observ. | 187.1 |
| Retention Time | 0.809 min |
| LC Condition | |
| Solvent A | 100% Water:0.05% TFA |
| Solvent B | 100% acetonitrile:0.05% TFA |
| Start % B | 2 |
| Final % B | 98 |
| Gradient Time | 1.5 min |
| Flow Rate | 0.8 mL/min |
| Wavelength | 220 |
| Solvent Pair | acetonitrile:Water:TFA |
| Column | Waters Aquity BEH C18 2.1 × 50 mm 1.7 U |

Example 1

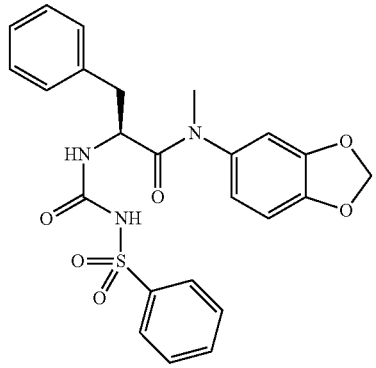 [SMILES: CN(C(=O)[C@H](Cc1ccccc1)NC(=O)NS(=O)(=O)c1ccccc1)c1ccc2c(c1)OCO2]

(S)—N-(benzo[d][1,3]dioxol-5-yl)-N-methyl-3-phenyl-2-(3-(phenylsulfonyl)ureido)propanamide 2M HCl (0.5 mL, 1 mmol) in dioxane was added to (S)-tert-butyl (1-(benzo[d][1,3]dioxol-5-yl(methyl)amino)-1-oxo-3-phenylpropan-2-yl)carbamate (49 mg, 0.12 mmol) and the reaction was stirred 3 h at r.t and then concentrated. The residue was dissolved into acetonitrile (0.5 mL) and treated with diisopropylethylamine (0.054 mL, 0.31 mmol) and then benzenesulfonyl isocyanate (33.8 mg, 0.184 mmol) (exothermic reaction observed). The reaction was stirred 3 h, diluted with MeOH (0.5 mL) and then concentrated. The residue was partitioned between water (1.5 mL) and EtOAc (3×1 mL). The combined organic component was concentrated, dissolved into MeOH, filtered and purified by preparative HPLC to afford the title compound (45.9 mg). $^1$H NMR (600 MHZ, DMSO-$d_6$) δ 7.79 (d, J=7.7 Hz, 2H), 7.71-7.62 (m, 1H), 7.61-7.52 (m, 2H), 7.20-1.14 (m, 3H), 6.90 (d, J=8.1 Hz, 1H), 6.80 (d, J=3.3 Hz, 2H), 6.69 (d, J=8.1

Hz, 2H), 6.59 (d, J=7.7 Hz, 1H), 6.08 (s, 2H), 4.31 (d, J=6.2 Hz, 1H), 3.07 (s, 3H), 2.83-2.77 (m, 1H), 2.58-2.52 (m, 1H).

| MS (M + H)+ Calcd. | 482.1 |
| MS (M + H)+ Observ. | 482.2 |
| Retention Time | 1.30 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-µ particles |

Example 2

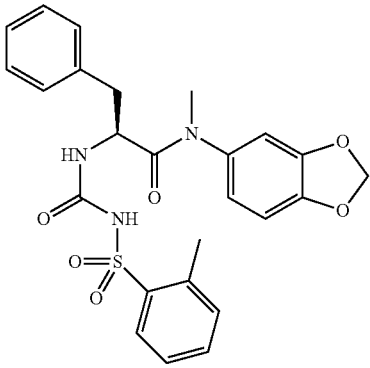

(S)—N-(benzo[d][1,3]dioxol-5-yl)-N-methyl-3-phenyl-2-(3-(o-tolylsulfonyl)ureido)propanamide To a solution of (S)-2-amino-N-(benzo[d][1,3]dioxol-5-yl)-N-methyl-3-phenylpropanamide, TFA (40 mg, 0.097 mmol) in dichloromethane (2 mL) was added diisopropylethylamine (0.051 mL, 0.291 mmol) followed by a solution of 2-methylbenzenesulfonyl isocyanate (28.7 mg, 0.146 mmol) in dichloromethane (2 mL). The reaction mixture was stirred at r.t. for 1 hr. The solvent was evaporated and the residue was purified by preparative HPLC to afford) of the title compound (34.4 mg. $^1$H NMR (500 MHZ, DMSO-$d_6$) δ 7.74 (d, J=7.6 Hz, 1H), 7.48-7.01 (m, 7H), 6.87-6.81 (m, 3H), 6.73-6.17 (m, 2H), 6.06 (s, 2H), 4.26 (br. s., 1H), 3.05 (s, 3H), 2.94-2.62 (m, 2H), 2.51 (s, 3H).

| MS (M + H)+ Calcd. | 496.2 |
| MS (M + H)+ Observ. | 496.3 |
| Retention Time | 1.46 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-µm particles |

Example 3

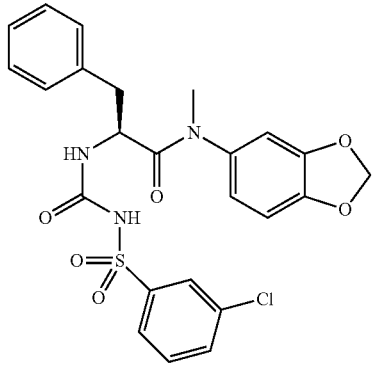 [SMILES: CN(C(=O)[C@H](Cc1ccccc1)NC(=O)NS(=O)(=O)c1cccc(Cl)c1)c1ccc2c(c1)OCO2]

(S)—N-(benzo[d][1,3]dioxol-5-yl)-2-(3-((3-chlorophenyl)sulfonyl)ureido)-N-methyl-3-phenylpropanamide To a solution of 3-chlorobenzenesulfonamide (100 mg, 0.522 mmol) in toluene (1 mL) was added 1-isocyanatobutane (5.05 mg, 0.051 mmol) followed by triphosgene (52.9 mg, 0.178 mmol). The reaction mixture was stirred at 110° C. for 24 hrs. The reaction mixture was allowed to cool and the solvent was evaporated to afford 3-chlorobenzenesulfonyl isocyanate which was used in the subsequent step without further purification. To a solution of (S)-2-amino-N-(benzo[d][1,3]dioxol-5-yl)-N-methyl-3-phenylpropanamide, TFA (30 mg, 0.073 mmol) in dichloromethane (0.5 mL) was added diisopropylethylamine (0.04 mL, 0.22 mmol) followed by 3-chlorobenzenesulfonyl isocyanate (23.8 mg, 0.11 mmol) in dichloromethane (0.5 mL). The reaction mixture was stirred at r.t. for 1 hr. The solvent was evaporated and the residue was purified by preparative HPLC to afford the title compound (15.2 mg). $^1$H NMR (600 MHZ, DMSO-$d_6$) δ 7.68 (br. s., 1H), 7.60 (d, J=7.3 Hz, 1H), 7.51-7.35 (m, 2H), 7.17-7.15 (m, 3H), 6.90-6.81 (m, 3H), 6.71-6.50 (m, 2H), 6.06-6.01 (m, 3H), 4.26 (br. s., 1H), 3.05 (s, 3H), 2.73-2.52 (m, 2H).

| MS (M + H)+ Calcd. | 516.1 |
| MS (M + H)+ Observ. | 516.4 |
| Retention Time | 1.36 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |

Example 4

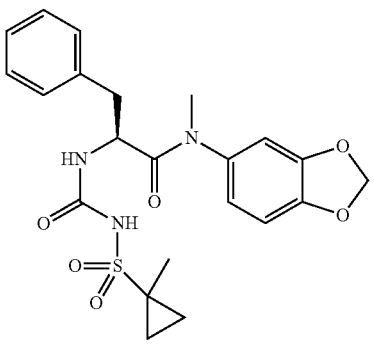 [SMILES: CN(C(=O)[C@H](Cc1ccccc1)NC(=O)NS(=O)(=O)C1(C)CC1)c1ccc2c(c1)OCO2]

(S)—N-(benzo[d][1,3]dioxol-5-yl)-N-methyl-2-(3-((1-methylcyclopropyl)sulfonyl) ureido)-3-phenyl-propanamide To a solution of 1-methylcyclopropane-1-sulfonamide (49.2 mg, 0.36 mmol) in toluene (1 mL) was added 1-isocyanatobutane (5.05 mg, 0.051 mmol) followed by triphosgene (34.5 mg, 0.12 mmol). The reaction mixture was stirred at 110° C. for 20 hrs. The reaction mixture (0.2 mL) was allowed to cool and then added to a solution of (S)-2-amino-N-(benzo[d][1,3]dioxol-5-yl)-N-methyl-3-phenylpropanamide, TFA (30 mg, 0.073 mmol) and diisopropylethylamine (0.04 mL, 0.22 mmol) in toluene (0.5 mL). The reaction mixture was stirred at r.t. for 1 hr. The solvent was evaporated and the residue was purified by preparative HPLC to afford the title compound (22.4 mg). $^1$H NMR (500 MHZ, DMSO-d$_6$) δ 7.35-7.13 (m, 3H), 7.05-6.86 (m, 3H), 6.82-6.60 (m, 3H), 6.11 (d, J=5.5 Hz, 2H), 4.45 (d, J=5.5 Hz, 1H), 3.11 (s, 3H), 2.96-2.55 (m, 2H), 1.34 (s, 3H), 1.27-1.11 (m, 2H), 0.91-0.69 (m, 2H).

| | |
|---|---|
| MS (M + H)$^+$ Calcd. | 460.2 |
| MS (M + H)$^+$ Observ. | 460.3 |
| Retention Time | 1.43 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

Examples 5-7 were synthesized using the procedure described above for Example 2.

Example 5

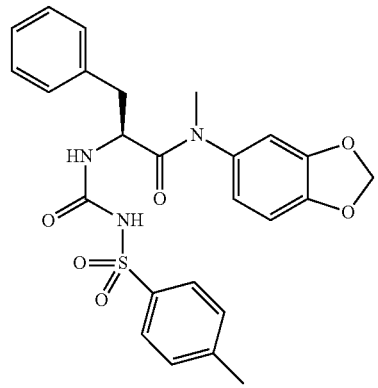 [SMILES: Cc1ccc(S(=O)(=O)NC(=O)N[C@@H](Cc2ccccc2)C(=O)N(C)c2ccc3c(c2)OCO3)cc1]

(S)—N-(benzo[d][1,3]dioxol-5-yl)-N-methyl-3-phenyl-2-(3-tosylureido)propanamide

| | |
|---|---|
| MS (M + H)$^+$ Calcd. | 496.2 |
| MS (M + H)$^+$ Observ. | 496.2 |
| Retention Time | 1.65 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (600 MHZ, DMSO-d$_6$) δ 7.65 (d, J=7.7 Hz, 2H), 7.33 (d, J=7.3 Hz, 2H), 7.18-7.16 (m, 3H), 6.89 (d, J=8.1 Hz, 1H), 6.81 (br. s., 2H), 6.73-6.50 (m, 3H), 6.08 (s, 2H), 4.30 (d, J=5.5 Hz, 1H), 3.07 (s, 3H), 2.84-2.52 (m, 2H), 2.37 (s, 3H).

Example 6

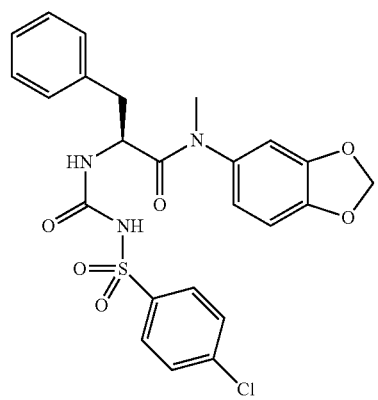

(S)—N-(benzo[d][1,3]dioxol-5-yl)-2-(3-((4-chlorophenyl)sulfonyl) ureido)-N-methyl-3-phenylpropanamide

| | |
|---|---|
| MS (M + H)+ Calcd. | 516.1 |
| MS (M + H)+ Observ. | 516.2 |
| Retention Time | 1.62 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (600 MHZ, DMSO-$d_6$) δ 7.79 (d, J=8.1 Hz, 2H), 7.63 (d, J=8.1 Hz, 2H), 7.16-7.15 (m, 3H), 6.91 (d, J=8.1 Hz, 1H), 6.85-6.53 (m, 5H), 6.08 (s, 2H), 4.31 (d, J=5.5 Hz, 1H), 3.08 (s, 3H), 2.85-2.53 (m, 2H).

Example 7

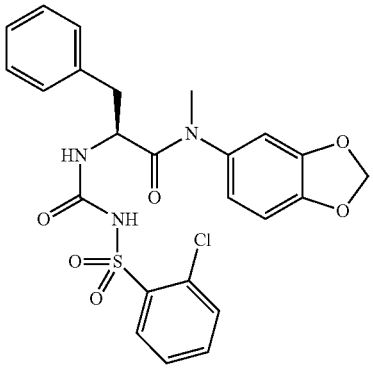

(S)—N-(benzo[d][1,3]dioxol-5-yl)-2-(3-((2-chlorophenyl)sulfonyl)ureido)-N-methyl-3-phenylpropanamide

| | |
|---|---|
| MS (M + H)+ Calcd. | 516.1 |
| MS (M + H)+ Observ. | 516.5 |
| Retention Time | 1.27 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (600 MHZ, DMSO-$d_6$) δ 7.95 (d, J=4.4 Hz, 1H), 7.66 (br. s., 2H), 7.51 (br. s., 1H), 7.23-7.09 (m, 3H), 6.88 (d, J=8.1 Hz, 1H), 6.82 (d, J=6.6 Hz, 2H), 6.76-6.54 (m, 3H), 6.06 (s, 2H), 4.29 (d, J=5.5 Hz, 1H), 3.08 (s, 3H), 2.83-2.52 (m, 2H).

Examples 8-35 were synthesized using the procedure described above for Example 3.

Example 8

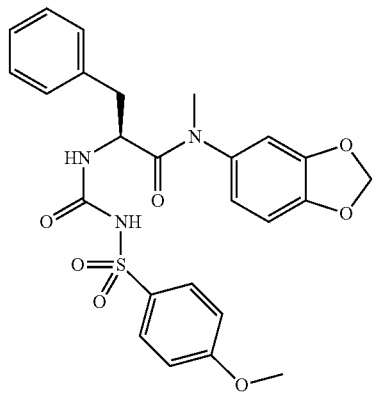

(S)—N-(benzo[d][1,3]dioxol-5-yl)-2-(3-((4-methoxyphenyl)sulfonyl)ureido)-N-methyl-3-phenylpropanamide

| | |
|---|---|
| MS (M + H)+ Calcd. | 512.1 |
| MS (M + H)+ Observ. | 512.2 |
| Retention Time | 1.57 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | acetonitrile:Water:TFA |
| Column | Phenomenex Luna 30 × 2.0 MM 3 u |

$^1$H NMR (400 MHZ, MeOH-$d_4$) δ 7.79 (d, J=9.0 Hz, 2H), 7.26-7.18 (m, 3H), 7.04 (d, J=9.0 Hz, 2H), 6.92 (d, J=3.0 Hz, 2H), 6.74 (d, J=8.3 Hz, 1H), 6.37 (br.s., 2H), 6.00 (d, J=3.3 Hz, 2H), 4.55-4.44 (m, 1H), 3.88 (s, 3H), 3.13 (s, 3H), 2.97-2.62 (m, 2H).

Example 9

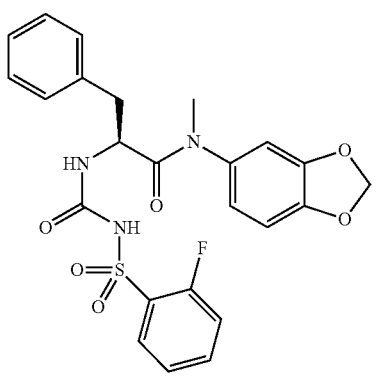

(S)—N-(benzo[d][1,3]dioxol-5-yl)-2-(3-((2-fluorophenyl)sulfonyl)ureido)-N-methyl-3-phenylpropanamide

| | |
|---|---|
| MS (M + H)+ Calcd. | 500.1 |
| MS (M + H)+ Observ. | 500.2 |
| Retention Time | 1.48 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.95 (s, 1H), 7.81-7.55 (m, 2H), 7.46-7.02 (m, 5H), 6.94-6.74 (m, 3H), 6.72-6.37 (m, 3H), 6.06 (s, 2H), 4.28 (d, J=4.6 Hz, 1H), 3.06 (s, 3H), 2.82-2.51 (m, 2H).

Example 10

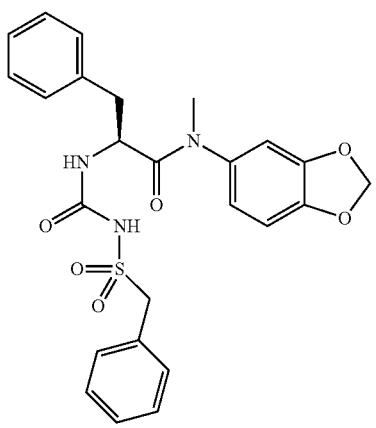 [SMILES: CN(C(=O)[C@H](Cc1ccccc1)NC(=O)NS(=O)(=O)Cc1ccccc1)c1ccc2c(c1)OCO2]

(S)—N-(benzo[d][1,3]dioxol-5-yl)-2-(3-(benzylsulfonyl)ureido)-N-methyl-3-phenylpropanamide

| | |
|---|---|
| MS (M + H)+ Calcd. | 496.2 |
| MS (M + H)+ Observ. | 496.3 |
| Retention Time | 1.78 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.35-7.31 (m, 3H), 7.26-7.22 (m, 3H), 7.16 (d, J=6.7 Hz, 2H), 6.98-6.92 (m, 1H), 6.87 (d, J=6.7 Hz, 2H), 6.78-6.61 (m, 2H), 6.58-6.51 (m, 1H), 6.06 (d, J=7.6 Hz, 2H), 4.49-4.44 (m, 3H), 3.10 (s, 3H), 2.90-2.54 (m, 2H).

Example 11

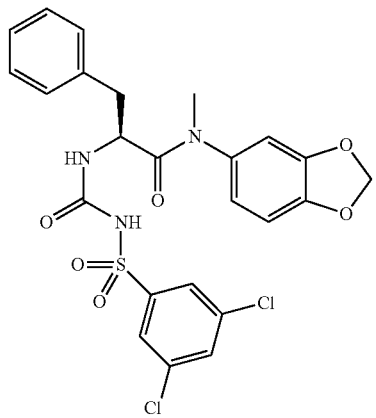 [SMILES: CN(C(=O)[C@H](Cc1ccccc1)NC(=O)NS(=O)(=O)c1cc(Cl)cc(Cl)c1)c1ccc2c(c1)OCO2]

(S)—N-(benzo[d][1,3]dioxol-5-yl)-2-(3-((3,5-dichlorophenyl)sulfonyl) ureido)-N-methyl-3-phenylpropanamide

| | |
|---|---|
| MS (M + H)+ Calcd. | 550.1 |
| MS (M + H)+ Observ. | 550.2 |
| Retention Time | 1.82 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |

117
-continued

| Column | Waters BEH C18, 2.0 × 50 mm, 1.7-μm particles |

$^1$H NMR (500 MHZ, DMSO-d$_6$) δ 7.95 (s, 1H), 7.80-7.53 (m, 3H), 7.21-7.06 (m, 3H), 6.95-6.76 (m, 3H), 6.73-6.15 (m, 2H), 6.07 (s, 2H), 4.25 (d, J=5.2 Hz, 1H), 3.05 (s, 3H), 2.93-2.53 (m, 2H).

Example 12

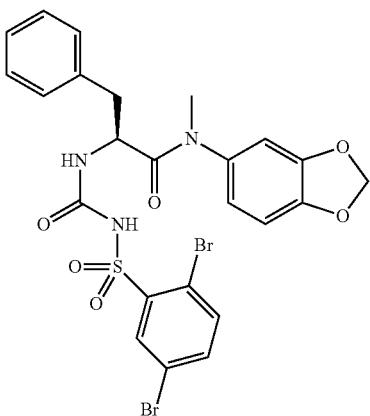 [SMILES: CN(C(=O)[C@H](Cc1ccccc1)NC(=O)NS(=O)(=O)c1cc(Br)ccc1Br)c1ccc2c(c1)OCO2]

(S)—N-(benzo[d][1,3]dioxol-5-yl)-2-(3-((2,5-dibromophenyl)sulfonyl) ureido)-N-methyl-3-phenylpropanamide

| | |
|---|---|
| MS (M + H)$^+$ Calcd. | 638.0 |
| MS (M + H)$^+$ Observ. | 638.1 |
| Retention Time | 1.88 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 8.00 (s, 1H), 7.73-7.55 (m, 2H), 7.16 (d, J=7.3 Hz, 3H), 6.91-6.82 (m, 3H), 6.72-6.48 (m, 2H), 6.39-6.13 (m, 1H), 6.06 (s, 2H), 4.27 (br. s., 1H), 3.06 (s, 3H), 2.96-2.53 (m, 2H).

118

Example 13

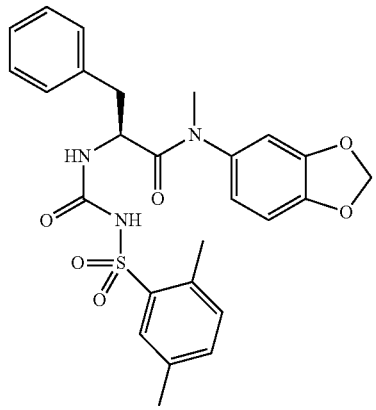 [SMILES: Cc1ccc(C)c(S(=O)(=O)NC(=O)N[C@@H](Cc2ccccc2)C(=O)N(C)c2ccc3c(c2)OCO3)c1]

(S)—N-(benzo[d][1,3]dioxol-5-yl)-2-(3-((2,5-dimethylphenyl)sulfonyl)ureido)-N-methyl-3-phenylpropanamide

| | |
|---|---|
| MS (M + H)$^+$ Calcd. | 510.2 |
| MS (M + H)$^+$ Observ. | 510.3 |
| Retention Time | 1.75 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.62 (s, 1H), 7.38-7.07 (m, 5H), 6.93-6.74 (m, 3H), 6.71-6.48 (m, 3H), 6.06 (s, 2H), 4.28 (d, J=5.2 Hz, 1H), 3.07 (s, 3H), 2.81-2.47 (m, 2H), 2.45 (s, 3H), 2.31 (s, 3H).

Example 14

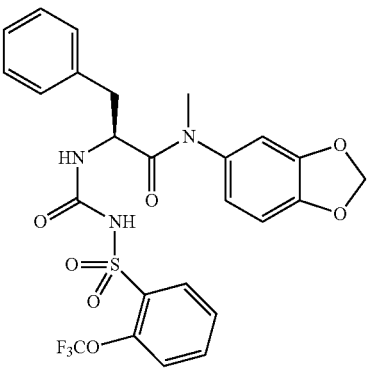 [SMILES: CN(C(=O)[C@H](Cc1ccccc1)NC(=O)NS(=O)(=O)c1ccccc1OC(F)(F)F)c1ccc2c(c1)OCO2]

(S)—N-(benzo[d][1,3]dioxol-5-yl)-N-methyl-3-phenyl-2-(3-((2-(trifluoromethoxy)phenyl)sulfonyl)ureido)propanamide

| | |
|---|---|
| MS (M + H)⁺ Calcd. | 566.1 |
| MS (M + H)⁺ Observ. | 566.2 |
| Retention Time | 1.78 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.91 (d, J=7.9 Hz, 1H), 7.82 (br. s., 1H), 7.66-7.48 (m, 2H), 7.17 (br. s., 3H), 6.89 (d, J=8.2 Hz, 1H), 6.85-6.63 (m, 4H), 6.60 (d, J=7.3 Hz, 1H), 6.07 (s, 2H), 4.30 (d, J=5.8 Hz, 1H), 3.08 (s, 3H), 2.81-2.49 (m, 2H).

Example 15

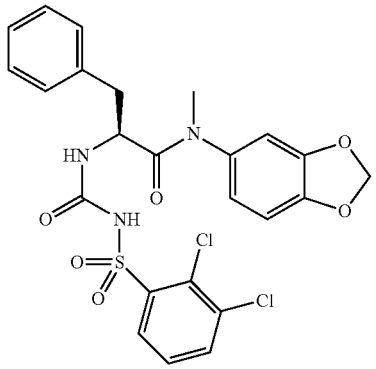 [SMILES: CN(C(=O)[C@H](Cc1ccccc1)NC(=O)NS(=O)(=O)c1cccc(Cl)c1Cl)c1ccc2c(c1)OCO2]

(S)—N-(benzo[d][1,3]dioxol-5-yl)-2-(3-((2,3-dichlorophenyl)sulfonyl) ureido)-N-methyl-3-phenylpropanamide

| | |
|---|---|
| MS (M + H)⁺ Calcd. | 550.1 |
| MS (M + H)⁺ Observ. | 550.2 |
| Retention Time | 1.41 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.92-7.79 (m, 2H), 7.46 (br. s., 1H), 7.20-7.06 (m, 3H), 6.88 (d, J=7.9 Hz, 1H), 6.82 (d, J=6.4 Hz, 2H), 6.76-6.39 (m, 3H), 6.06 (s, 2H), 4.28 (br. s., 1H), 3.08 (s, 3H), 2.82-2.53 (m, 2H).

Example 16

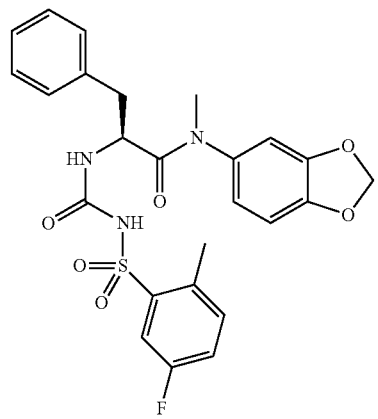 [SMILES: Cc1ccc(F)cc1S(=O)(=O)NC(=O)N[C@@H](Cc1ccccc1)C(=O)N(C)c1ccc2c(c1)OCO2]

(S)—N-(benzo[d][1,3]dioxol-5-yl)-2-(3-((5-fluoro-2-methylphenyl)sulfonyl)ureido)-N-methyl-3-phenylpropanamide

| | |
|---|---|
| MS (M + H)⁺ Calcd. | 514.1 |
| MS (M + H)⁺ Observ. | 514.3 |
| Retention Time | 1.57 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.50 (d, J=7.6 Hz, 1H), 7.41-7.25 (m, 2H), 7.22-7.06 (m, 3H), 6.88 (d, J=8.2 Hz, 1H), 6.83-6.27 (m, 5H), 6.06 (s, 2H), 4.28 (br. s., 1H), 3.06 (s, 3H), 2.78-2.48 (m, 2H), 2.46 (s, 3H).

Example 17

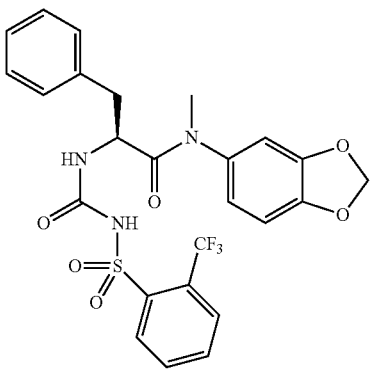

(S)—N-(benzo[d][1,3]dioxol-5-yl)-N-methyl-3-phenyl-2-(3-((2-(trifluoromethyl)phenyl)sulfonyl) ureido)propanamide

| | |
|---|---|
| MS (M + H)+ Calcd. | 550.1 |
| MS (M + H)+ Observ. | 550.3 |
| Retention Time | 1.61 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-µm particles |

$^1$H NMR (500 MHZ, DMSO-d$_6$) δ 8.06 (br. s., 1H), 7.93-7.68 (m, 3H), 7.12 (br. s., 3H), 6.88 (d, J=8.2 Hz, 1H), 6.83-6.40 (m, 5H), 6.06 (s, 2H), 4.29 (d, J=5.5 Hz, 1H), 3.06 (s, 3H), 2.77-2.48 (m, 2H).

Example 18

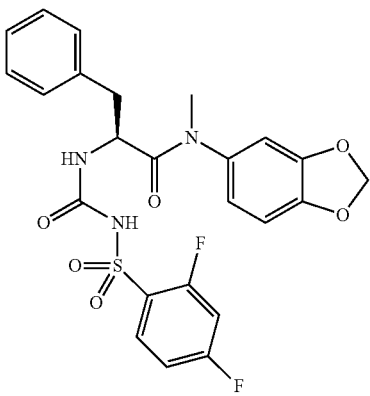

(S)—N-(benzo[d][1,3]dioxol-5-yl)-2-(3-((2,4-difluorophenyl)sulfonyl)ureido)-N-methyl-3-phenylpropanamide

| | |
|---|---|
| MS (M + H)+ Calcd. | 518.1 |
| MS (M + H)+ Observ. | 518.2 |
| Retention Time | 1.54 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-µm particles |

$^1$H NMR (500 MHZ, DMSO-d$_6$) δ 7.71 (br. s., 1H), 7.42-6.99 (m, 6H), 6.92-6.77 (m, 3H), 6.73-6.39 (m, 2H), 6.06 (s, 2H), 4.26 (br. s., 1H), 3.06 (s, 3H), 2.74-2.48 (m, 2H).

Example 19

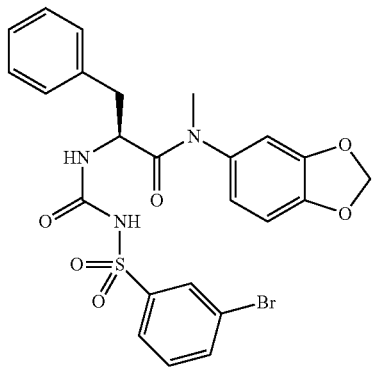 [SMILES: CN(C(=O)[C@H](Cc1ccccc1)NC(=O)NS(=O)(=O)c1cccc(Br)c1)c1ccc2c(c1)OCO2]

(S)—N-(benzo[d][1,3]dioxol-5-yl)-2-(3-((3-bromophenyl)sulfonyl)ureido)-N-methyl-3-phenylpropanamide

| | |
|---|---|
| MS (M + H)+ Calcd. | 560.0 |
| MS (M + H)+ Observ. | 560.1 |
| Retention Time | 1.63 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |

-continued

| | |
|---|---|
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.87 (br. s., 1H), 7.71 (d, J=8.2 Hz, 2H), 7.44 (br. s., 1H), 7.21-7.09 (m, 3H), 6.93-6.78 (m, 3H), 6.74-6.26 (m, 3H), 6.07 (s, 2H), 4.27 (d, J=6.4 Hz, 1H), 3.06 (s, 3H), 2.75-2.53 (m, 2H).

Example 20

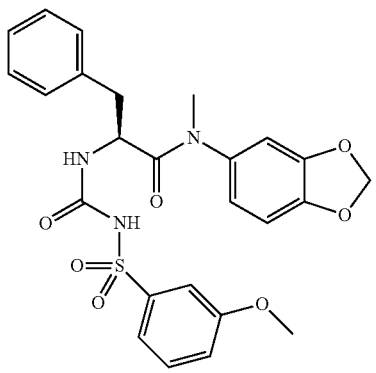 [SMILES: COc1cccc(S(=O)(=O)NC(=O)N[C@@H](Cc2ccccc2)C(=O)N(C)c2ccc3c(c2)OCO3)c1]

(S)—N-(benzo[d][1,3]dioxol-5-yl)-2-(3-((3-methoxyphenyl)sulfonyl)ureido)-N-methyl-3-phenylpropanamide

| | |
|---|---|
| MS (M + H)$^+$ Calcd. | 512.1 |
| MS (M + H)$^+$ Observ. | 512.2 |
| Retention Time | 1.61 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.41 (d, J=8.1 Hz, 1H), 7.36-7.25 (m, 2H), 7.16 (m, 5H), 6.92-6.78 (m, 3H), 6.72-6.46 (m, 2H), 6.08 (s, 2H), 4.30 (d, J=5.9 Hz, 1H), 3.80 (s, 3H), 3.07 (s, 3H), 2.77-2.53 (m, 2H).

Example 21

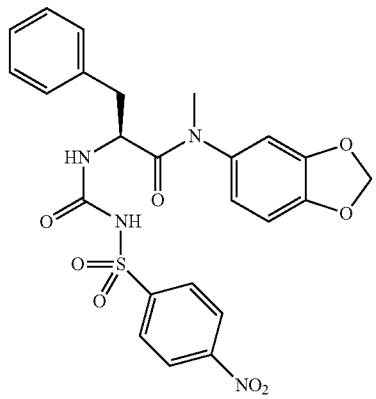 [SMILES: CN(C(=O)[C@H](Cc1ccccc1)NC(=O)NS(=O)(=O)c1ccc([N+](=O)[O-])cc1)c1ccc2c(c1)OCO2]

(S)—N-(benzo[d][1,3]dioxol-5-yl)-N-methyl-2-(3-((4-nitrophenyl)sulfonyl)ureido)-3-phenylpropanamide

| | |
|---|---|
| MS (M + H)$^+$ Calcd. | 527.1 |
| MS (M + H)$^+$ Observ. | 527.2 |
| Retention Time | 1.61 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 8.22 (d, J=7.6 Hz, 2H), 7.90 (d, J=7.9 Hz, 2H), 7.22-7.05 (m, 3H), 6.95-6.75 (m, 3H), 6.74-6.50 (m, 2H), 6.11 (br. s., 1H), 6.05 (s, 2H), 4.24 (br. s., 1H), 3.04 (s, 3H), 2.70-2.52 (m, 2H).

Example 22

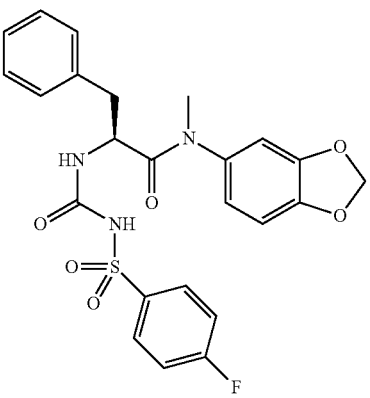

(S)—N-(benzo[d][1,3]dioxol-5-yl)-2-(3-((4-fluorophenyl)sulfonyl)ureido)-N-methyl-3-phenylpropanamide

| MS (M + H)⁺ Calcd. | 500.1 |
|---|---|
| MS (M + H)⁺ Observ. | 500.3 |
| Retention Time | 1.32 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (400 MHZ, MeOH-d$_4$) δ 7.89 (dd, J=8.6, 5.1 Hz, 2H), 7.33-7.11 (m, 6H), 6.91 (br. s., 2H), 6.73 (d, J=8.3 Hz, 1H), 6.59-6.17 (m, 2H), 5.99 (d, J=2.7 Hz, 2H), 4.57-4.40 (m, 1H), 3.11 (s, 3H), 2.93-2.64 (m, 2H).

Example 23

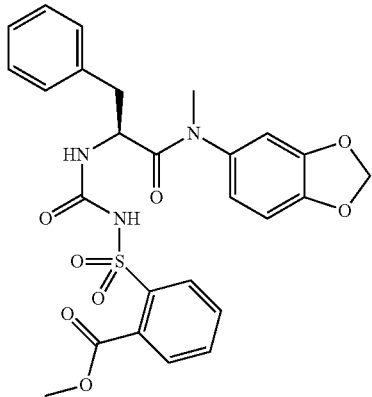 [SMILES: COC(=O)c1ccccc1S(=O)(=O)NC(=O)N[C@@H](Cc1ccccc1)C(=O)N(C)c1ccc2c(c1)OCO2]

(S)-methyl 2-(N-((1-(benzo[d][1,3]dioxol-5-yl(methyl)amino)-1-oxo-3-phenylpropan-2-yl)carbamoyl)sulfamoyl)benzoate

| MS (M + H)⁺ Calcd. | 540.1 |
|---|---|
| MS (M + H)⁺ Observ. | 540.4 |
| Retention Time | 1.32 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.85 (d, J=7.7 Hz, 1H), 7.69-7.42 (m, 3H), 7.36-7.08 (m, 3H), 6.99-6.80 (m, 3H), 6.64-6.41 (m, 3H), 6.06 (s, 2H), 4.30 (br. s., 1H), 3.78 (s, 3H), 3.06 (s, 3H), 2.81-2.52 (m, 2H).

Example 24

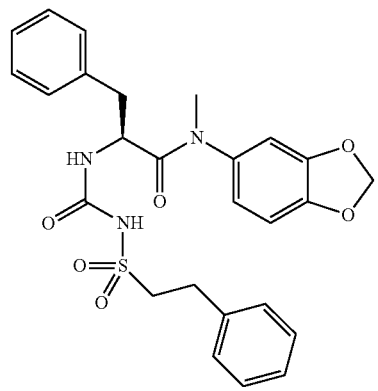 [SMILES: CN(C(=O)[C@H](Cc1ccccc1)NC(=O)NS(=O)(=O)CCc1ccccc1)c1ccc2c(c1)OCO2]

(S)—N-(benzo[d][1,3]dioxol-5-yl)-N-methyl-2-(3-(phenethylsulfonyl)ureido)-3-phenylpropanamide

| MS (M + H)⁺ Calcd. | 510.2 |
|---|---|
| MS (M + H)⁺ Observ. | 510.3 |
| Retention Time | 1.57 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.40-7.08 (m, 9H), 7.00-6.84 (m, 3H), 6.81-6.31 (m, 2H), 6.09 (s, 2H), 4.39 (br. s., 1H), 3.10 (s, 3H), 2.88-2.82 (m, 4H), 2.61-2.52 (m, 2H).

Example 25

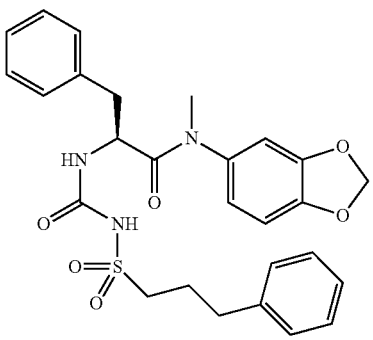 [SMILES: CN(C(=O)[C@H](Cc1ccccc1)NC(=O)NS(=O)(=O)CCCc1ccccc1)c1ccc2c(c1)OCO2]

(S)—N-(benzo[d][1,3]dioxol-5-yl)-N-methyl-3-phenyl-2-(3-((3-phenylpropyl)sulfonyl) ureido)propanamide

| | |
|---|---|
| MS (M + H)+ Calcd. | 524.2 |
| MS (M + H)+ Observ. | 524.3 |
| Retention Time | 1.68 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.33-7.25 (m, 3H), 7.24-7.14 (m, 6H), 6.96 (d, J=8.1 Hz, 1H), 6.90 (d, J=6.6 Hz, 2H), 6.80-6.60 (m, 2H), 6.11 (s, 2H), 4.41 (d, J=5.5 Hz, 1H), 3.23-3.15 (m, 2H), 3.11 (s, 3H), 2.87 (dd, J=13.6, 4.8 Hz, 1H), 2.68-2.54 (m, 3H), 1.91-1.79 (m, 2H).

Example 26

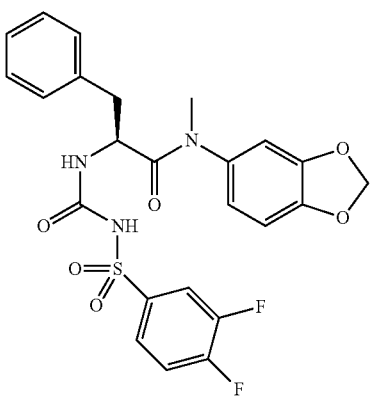 [SMILES: CN(C(=O)[C@H](Cc1ccccc1)NC(=O)NS(=O)(=O)c1ccc(F)c(F)c1)c1ccc2c(c1)OCO2]

(S)—N-(benzo[d][1,3]dioxol-5-yl)-2-(3-((3,4-difluorophenyl)sulfonyl)ureido)-N-methyl-3-phenylpropanamide

| | |
|---|---|
| MS (M + H)+ Calcd. | 518.1 |
| MS (M + H)+ Observ. | 518.2 |
| Retention Time | 1.37 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.78-7.42 (m, 3H), 7.22-7.11 (m, 3H), 6.90 (d, J=7.7 Hz, 1H), 6.83 (d, J=5.1 Hz, 2H), 6.76-6.17 (m, 2H), 6.08 (s, 2H), 4.27 (d, J=5.1 Hz, 1H), 3.07 (s, 3H), 2.80-2.52 (m, 2H).

Example 27

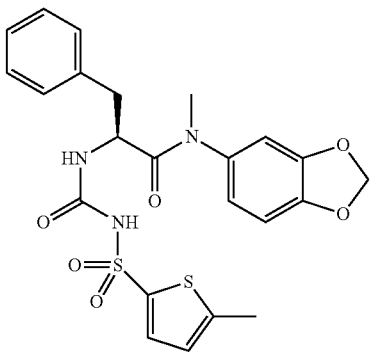 [SMILES: Cc1ccc(S(=O)(=O)NC(=O)N[C@@H](Cc2ccccc2)C(=O)N(C)c2ccc3c(c2)OCO3)s1]

(S)—N-(benzo[d][1,3]dioxol-5-yl)-N-methyl-2-(3-((5-methylthiophen-2-yl)sulfonyl)ureido)-3-phenylpropanamide

| | |
|---|---|
| MS (M + H)+ Calcd. | 502.1 |
| MS (M + H)+ Observ. | 502.3 |
| Retention Time | 1.35 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.17 (br. s., 4H), 6.97-6.80 (m, 3H), 6.76-6.53 (m, 3H), 6.22 (br. s., 1H), 6.08 (s, 2H), 4.32 (d, J=4.8 Hz, 1H), 3.07 (s, 3H), 2.82-2.53 (m, 2H), 2.43 (s, 3H).

Example 28

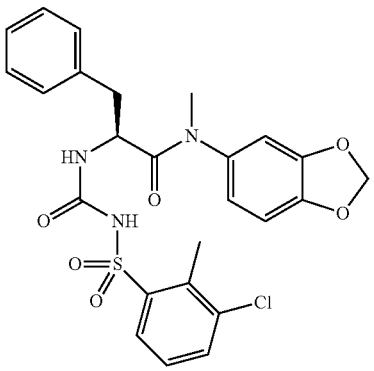 [SMILES: Cc1c(Cl)cccc1S(=O)(=O)NC(=O)N[C@@H](Cc1ccccc1)C(=O)N(C)c1ccc2c(c1)OCO2]

(S)—N-(benzo[d][1,3]dioxol-5-yl)-2-(3-((3-chloro-2-methylphenyl)sulfonyl)ureido)-N-methyl-3-phenylpropanamide

| MS (M + H)⁺ Calcd. | 530.1 |
|---|---|
| MS (M + H)⁺ Observ. | 530.4 |
| Retention Time | 1.53 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.76 (d, J=8.1 Hz, 1H), 7.62 (d, J=7.7 Hz, 1H), 7.30 (br. s., 1H), 7.20-7.03 (m, 4H), 6.88 (d, J=8.1 Hz, 1H), 6.79 (d, J=6.6 Hz, 2H), 6.73-6.31 (m, 2H), 6.06 (s, 2H), 4.26 (br. s., 1H), 3.06 (s, 3H), 2.80-2.55 (m, 2H), 2.53 (s, 3H).

Example 29

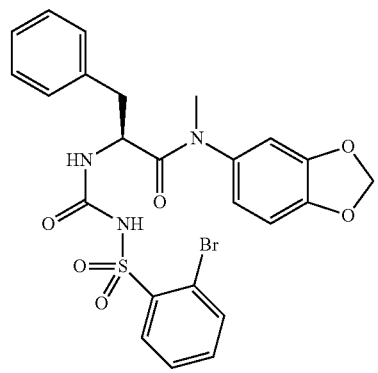

(S)—N-(benzo[d][1,3]dioxol-5-yl)-2-(3-((2-bromophenyl)sulfonyl) ureido)-N-methyl-3-phenylpropanamide

| MS (M + H)⁺ Calcd. | 560.0 |
|---|---|
| MS (M + H)⁺ Observ. | 560.3 |
| Retention Time | 1.35 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.94 (d, J=7.7 Hz, 1H), 7.77 (d, J=6.2 Hz, 1H), 7.48 (br. s., 2H), 7.34-7.09 (m, 3H), 6.85 (dd, J=13.0, 7.5 Hz, 3H), 6.72-6.46 (m, 3H), 6.06 (s, 2H), 4.28 (d, J=4.8 Hz, 1H), 3.07 (s, 3H), 2.81-2.52 (m, 2H).

Example 30

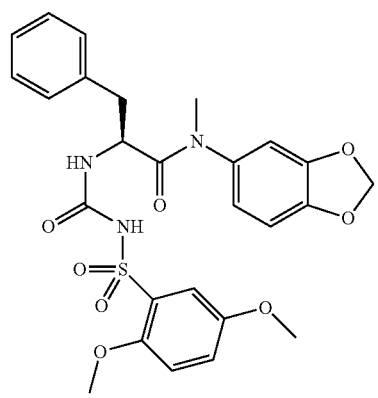 [SMILES: COc1ccc(OC)c(S(=O)(=O)NC(=O)N[C@@H](Cc2ccccc2)C(=O)N(C)c2ccc3c(c2)OCO3)c1]

(S)—N-(benzo[d][1,3]dioxol-5-yl)-2-(3-((2,5-dimethoxyphenyl)sulfonyl)ureido)-N-methyl-3-phenylpropanamide

| | |
|---|---|
| MS (M + H)+ Calcd. | 542.2 |
| MS (M + H)+ Observ. | 542.5 |
| Retention Time | 1.50 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.30-7.10 (m, 7H), 6.92-6.77 (m, 3H), 6.75-6.47 (m, 3H), 6.07 (s, 2H), 4.29 (d, J=4.8 Hz, 1H), 3.77 (s, 3H), 3.75 (s, 3H), 3.06 (s, 3H), 2.85-2.52 (m, 2H).

Example 31

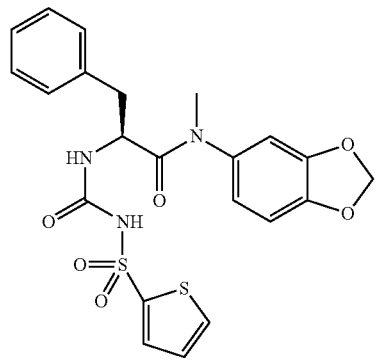 [SMILES: CN(C(=O)[C@H](Cc1ccccc1)NC(=O)NS(=O)(=O)c1cccs1)c1ccc2c(c1)OCO2]

(S)—N-(benzo[d][1,3]dioxol-5-yl)-N-methyl-3-phenyl-2-(3-(thiophen-2-ylsulfonyl) ureido)propanamide

| | |
|---|---|
| MS (M + H)+ Calcd. | 488.1 |
| MS (M + H)+ Observ. | 488.2 |
| Retention Time | 1.19 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.85 (br. s., 1H), 7.52 (br. s., 1H), 7.31-7.00 (m, 4H), 6.97-6.77 (m, 3H), 6.74-6.41 (m, 3H), 6.08 (s, 2H), 4.35 (d, J=6.1 Hz, 1H), 3.08 (s, 3H), 2.84-2.53 (m, 2H).

Example 32

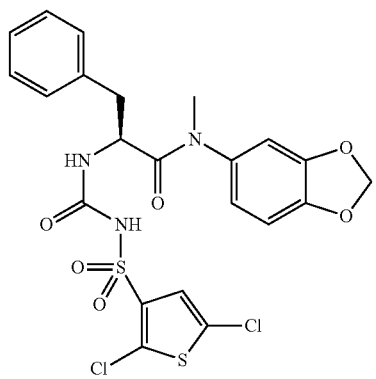 [SMILES: CN(C(=O)[C@H](Cc1ccccc1)NC(=O)NS(=O)(=O)c1cc(Cl)sc1Cl)c1ccc2c(c1)OCO2]

(S)—N-(benzo[d][1,3]dioxol-5-yl)-2-(3-((2,5-dichlorothiophen-3-yl)sulfonyl) ureido)-N-methyl-3-phenylpropanamide

| | |
|---|---|
| MS (M + H)+ Calcd. | 556.0 |
| MS (M + H)+ Observ. | 556.2 |
| Retention Time | 1.42 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.25-7.08 (m, 4H), 6.91 (d, J=7.9 Hz, 1H), 6.85 (d, J=6.7 Hz, 2H), 6.77-6.41 (m, 2H), 6.08 (s, 2H), 4.32 (d, J=5.2 Hz, 1H), 3.08 (s, 3H), 2.84-2.52 (m, 2H).

Example 33

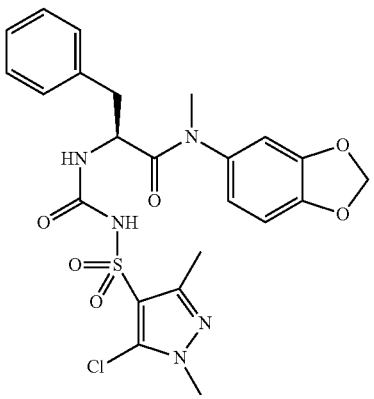 [SMILES: Cc1nn(C)c(Cl)c1S(=O)(=O)NC(=O)N[C@@H](Cc1ccccc1)C(=O)N(C)c1ccc2c(c1)OCO2]

(S)—N-(benzo[d][1,3]dioxol-5-yl)-2-(3-((5-chloro-1,3-dimethyl-1H-pyrazol-4-yl)sulfonyl) ureido)-N-methyl-3-phenylpropanamide

| | |
|---|---|
| MS (M + H)+ Calcd. | 534.1 |
| MS (M + H)+ Observ. | 534.3 |
| Retention Time | 1.18 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.18 (br. s., 3H), 6.91 (d, J=7.9 Hz, 1H), 6.84 (d, J=5.2 Hz, 2H), 6.77-6.38 (m, 3H), 6.08 (s, 2H), 4.31 (d, J=5.8 Hz, 1H), 3.74 (s, 3H), 3.08 (s, 3H), 2.84-2.53 (m, 2H), 2.24 (s, 3H).

Example 34

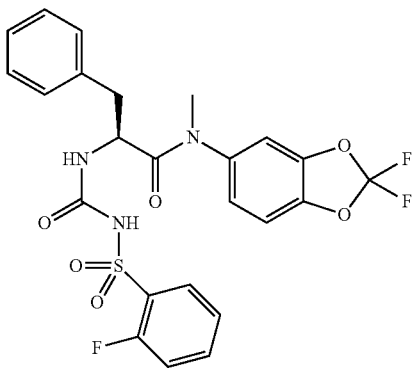

(S)—N-(2,2-difluorobenzo[d][1,3]dioxol-5-yl)-2-(3-((2-fluorophenyl)sulfonyl) ureido)-N-methyl-3-phenylpropanamide

| | |
|---|---|
| MS (M + H)+ Calcd. | 536.1 |
| MS (M + H)+ Observ. | 536.2 |
| Retention Time | 2.54 min |
| | LC Condition |
| Solvent A | 5% Methanol:95% Water:10 mM Ammonium Acetate |
| Solvent B | 95% Methanol:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | Methanol:Water:Ammonium Acetate |
| Column | Waters BEH C18, 2.0 × 50 mm, 1.7-μm particles |

$^1$H NMR (500 MHZ, DMSO-d$_6$) δ 7.69 (br. s., 1H), 7.51 (br. s., 1H), 7.36 (d, J=8.1 Hz, 1H), 7.30-7.00 (m, 6H), 6.95-6.77 (m, 2H), 6.30 (br. s., 1H), 4.20 (br. s., 1H), 3.08 (s, 3H), 2.77-2.53 (m, 2H).

Example 35

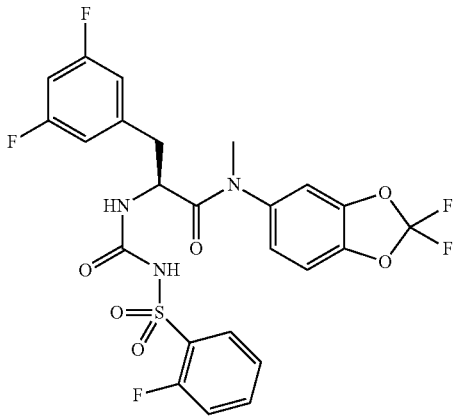 [SMILES: CN(C(=O)[C@H](Cc1cc(F)cc(F)c1)NC(=O)NS(=O)(=O)c1ccccc1F)c1ccc2c(c1)OC(F)(F)O2]

(S)—N-(2,2-difluorobenzo[d][1,3]dioxol-5-yl)-3-(3,5-difluorophenyl)-2-(3-((2-fluorophenyl)sulfonyl) ureido)-N-methylpropanamide

| | |
|---|---|
| MS (M + H)+ Calcd. | 572.1 |
| MS (M + H)+ Observ. | 572.4 |
| Retention Time | 1.61 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |

-continued

| Column | Waters BEH C18, 2.0 × 50 mm, 1.7-μm particles |

¹H NMR (500 MHZ, DMSO-d₆) δ 7.69 (br. s., 1H), 7.55 (br. s., 1H), 7.41 (d, J=8.4 Hz, 1H), 7.36 (br. s., 1H), 7.24 (d, J=7.7 Hz, 2H), 7.10 (br. s., 1H), 6.99 (br. s., 1H), 6.58-6.29 (m, 3H), 4.23 (d, J=5.5 Hz, 1H), 3.11 (s, 3H), 2.83-2.56 (m, 2H).

Examples 36-41 were synthesized using the procedure described above for Example 2.

Example 36

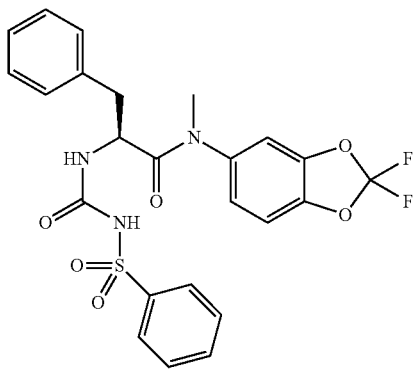

(S)—N-(2,2-difluorobenzo[d][1,3]dioxol-5-yl)-N-methyl-3-phenyl-2-(3-(phenylsulfonyl)ureido)propanamide

| MS (M + H)⁺ Calcd. | 518.1 |
| MS (M + H)⁺ Observ. | 518.3 |
| Retention Time | 1.65 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.80 (d, J=7.3 Hz, 2H), 7.67-7.50 (m, 3H), 7.41 (d, J=8.4 Hz, 1H), 7.28-7.01 (m, 4H), 6.99-6.63 (m, 4H), 4.23 (d, J=7.3 Hz, 1H), 3.09 (s, 3H), 2.84-2.53 (m, 2H).

Example 37

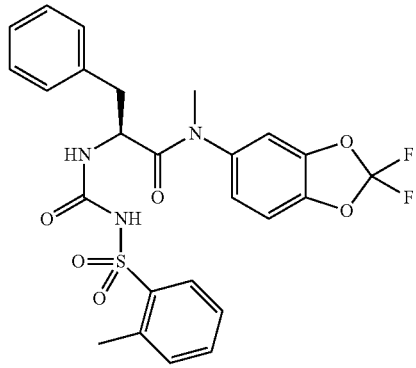

(S)—N-(2,2-difluorobenzo[d][1,3]dioxol-5-yl)-N-methyl-3-phenyl-2-(3-(o-tolylsulfonyl) ureido)propanamide

| MS (M + H)⁺ Calcd. | 532.1 |
| MS (M + H)⁺ Observ. | 532.4 |
| Retention Time | 1.68 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.81 (d, J=7.7 Hz, 1H), 7.60-7.48 (m, 1H), 7.44-7.31 (m, 3H), 7.24-7.06 (m, 4H), 6.95 (d, J=8.1 Hz, 1H), 6.81 (d, J=3.7 Hz, 2H), 6.68 (d, J=7.7 Hz, 1H), 4.23 (d, J=6.6 Hz, 1H), 3.10 (s, 3H), 2.85-2.55 (m, 2H), 2.53 (s, 3H).

Example 38

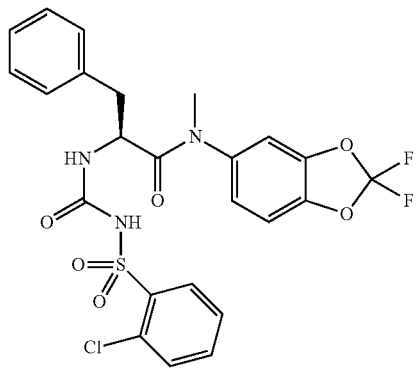

(S)-2-(3-((2-chlorophenyl)sulfonyl)ureido)-N-(2,2-difluorobenzo[d][1,3]dioxol-5-yl)-N-methyl-3-phenylpropanamide

| | |
|---|---|
| MS (M + H)+ Calcd. | 552.1 |
| MS (M + H)+ Observ. | 552.4 |
| Retention Time | 1.59 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d$_6$) δ 7.89 (d, J=6.6 Hz, 1H), 7.50 (br. s., 2H), 7.43-7.00 (m, 8H), 6.96-6.77 (m, 2H), 6.48-6.22 (m, 1H), 4.20 (br. s., 1H), 3.08 (s, 3H), 2.79-2.53 (m, 2H).

Example 39

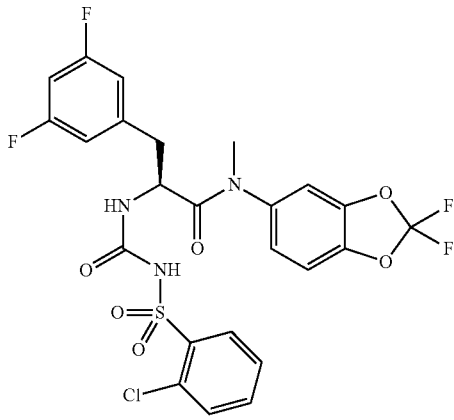

(S)-2-(3-((2-chlorophenyl)sulfonyl)ureido)-N-(2,2-difluorobenzo[d][1,3]dioxol-5-yl)-3-(3,5-difluorophenyl)-N-methylpropanamide

| | |
|---|---|
| MS (M + H)+ Calcd. | 588.1 |
| MS (M + H)+ Observ. | 588.4 |
| Retention Time | 1.61 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d$_6$) δ 7.88 (d, J=7.0 Hz, 1H), 7.58-7.18 (m, 5H), 7.16-6.89 (m, 2H), 6.51 (br. s., 3H), 4.25 (br. s., 1H), 3.12 (s, 3H), 2.83-2.57 (m, 2H).

Example 40

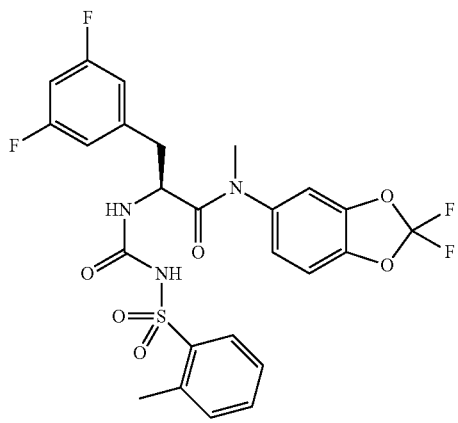

(S)—N-(2,2-difluorobenzo[d][1,3]dioxol-5-yl)-3-(3,5-difluorophenyl)-N-methyl-2-(3-(o-tolylsulfonyl)ureido)propanamide

| | |
|---|---|
| MS (M + H)+ Calcd. | 568.1 |
| MS (M + H)+ Observ. | 568.4 |
| Retention Time | 1.71 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d$_6$) δ 7.76 (d, J=7.0 Hz, 1H), 7.49-7.34 (m, 3H), 7.29 (d, J=5.9 Hz, 2H), 7.17-6.90 (m, 2H), 6.64-6.38 (m, 3H), 4.24 (br. s., 1H), 3.12 (s, 3H), 2.85-2.55 (m, 2H), 2.51 (s, 3H).

Example 41

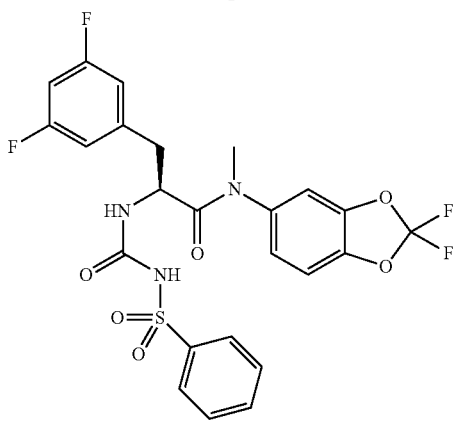

(S)—N-(2,2-difluorobenzo[d][1,3]dioxol-5-yl)-3-(3,5-difluorophenyl)-N-methyl-2-(3-(phenylsulfonyl)ureido)propanamide

| | |
|---|---|
| MS (M + H)+ Calcd. | 554.1 |
| MS (M + H)+ Observ. | 554.3 |
| Retention Time | 1.62 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.80 (d, J=7.7 Hz, 2H), 7.70-7.62 (m, 1H), 7.60-7.51 (m, 2H), 7.45 (d, J=8.4 Hz, 1H), 7.39 (br. s., 1H), 7.11 (d, J=8.4 Hz, 1H), 7.01 (t, J=8.8 Hz, 1H), 6.81 (d, J=7.7 Hz, 1H), 6.51 (d, J=7.0 Hz, 2H), 4.28 (d, J=5.5 Hz, 1H), 3.13 (s, 3H), 2.87-2.58 (m, 2H).

Examples 42-46 were synthesized using the procedure described above for Example 4.

Example 42

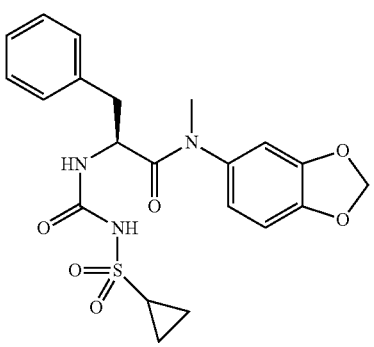 [SMILES: CN(C(=O)[C@H](Cc1ccccc1)NC(=O)NS(=O)(=O)C1CC1)c1ccc2c(c1)OCO2]

(S)—N-(benzo[d][1,3]dioxol-5-yl)-2-(3-(cyclopropylsulfonyl)ureido)-N-methyl-3-phenylpropanamide

| | |
|---|---|
| MS (M + H)+ Calcd. | 446.1 |
| MS (M + H)+ Observ. | 446.2 |
| Retention Time | 1.71 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.29-7.14 (m, 3H), 6.96 (d, J=8.2 Hz, 1H), 6.90 (d, J=7.0 Hz, 2H), 6.80-6.59 (m, 3H), 6.10 (d, J=3.4 Hz, 2H), 4.42 (d, J=5.8 Hz, 1H), 3.10 (s, 3H), 2.87-2.54 (m, 3H), 1.04-0.89 (m, 4H).

Example 43

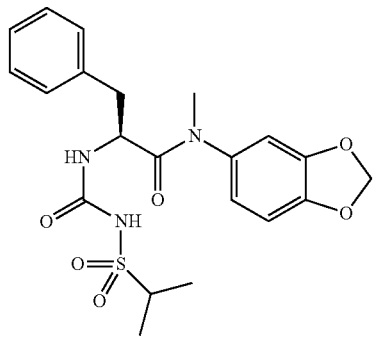 [SMILES: CC(C)S(=O)(=O)NC(=O)N[C@@H](Cc1ccccc1)C(=O)N(C)c1ccc2c(c1)OCO2]

(S)—N-(benzo[d][1,3]dioxol-5-yl)-2-(3-(isopropylsulfonyl) ureido)-N-methyl-3-phenylpropanamide

| | |
|---|---|
| MS (M + H)+ Calcd. | 448.2 |
| MS (M + H)+ Observ. | 448.2 |
| Retention Time | 1.72 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.25-7.20 (m, 3H), 6.97 (d, J=8.2 Hz, 1H), 6.90 (d, J=7.0 Hz, 2H), 6.83-6.58 (m,

3H), 6.11 (s, 2H), 4.43 (d, J=5.5 Hz, 1H), 3.11 (s, 3H), 2.88-2.55 (m, 3H), 1.27-1.07 (m, 6H).

Example 44

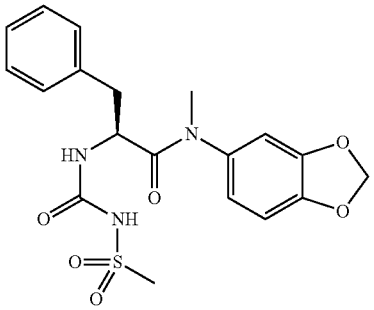 [SMILES: CN(C(=O)[C@H](Cc1ccccc1)NC(=O)NS(C)(=O)=O)c1ccc2c(c1)OCO2]

(S)—N-(benzo[d][1,3]dioxol-5-yl)-N-methyl-2-(3-(methylsulfonyl) ureido)-3-phenylpropanamide

| MS (M + H)+ Calcd. | 420.1 |
| MS (M + H)+ Observ. | 420.2 |
| Retention Time | 1.42 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.31-7.15 (m, 3H), 6.97 (d, J=8.2 Hz, 1H), 6.91 (d, J=7.0 Hz, 2H), 6.81-6.56 (m, 3H), 6.11 (d, J=2.1 Hz, 2H), 4.42 (d, J=5.8 Hz, 1H), 3.11 (s, 3H), 3.08 (s, 3H), 2.89-2.55 (m, 2H).

Example 45

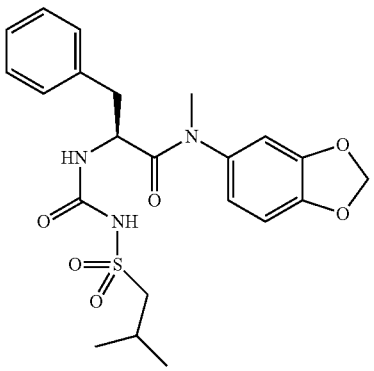 [SMILES: CC(C)CS(=O)(=O)NC(=O)N[C@@H](Cc1ccccc1)C(=O)N(C)c1ccc2c(c1)OCO2]

(S)—N-(benzo[d][1,3]dioxol-5-yl)-2-(3-(isobutylsulfonyl) ureido)-N-methyl-3-phenylpropanamide

| MS (M + H)+ Calcd. | 462.2 |
| MS (M + H)+ Observ. | 462.3 |
| Retention Time | 1.45 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.72 (s, 1H), 7.01-6.96 (m, 3H), 6.73 (d, J=7.9 Hz, 1H), 6.66 (d, J=7.0 Hz, 2H), 6.58-6.31 (m, 3H), 5.87 (d, J=4.0 Hz, 2H), 4.19 (d, J=4.9 Hz, 1H), 2.87 (s, 3H), 2.70-2.30 (m, 4H), 1.74 (dt, J=13.0, 6.4 Hz, 1H), 0.71 (dd, J=17.5, 6.6 Hz, 6H).

Example 46

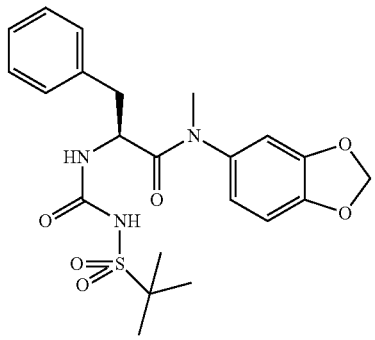 [SMILES: CN(C(=O)[C@H](Cc1ccccc1)NC(=O)NS(=O)(=O)C(C)(C)C)c1ccc2c(c1)OCO2]

(S)—N-(benzo[d][1,3]dioxol-5-yl)-2-(3-(tert-butylsulfonyl)ureido)-N-methyl-3-phenylpropanamide

| MS (M + H)+ Calcd. | 462.2 |
| MS (M + H)+ Observ. | 462.3 |
| Retention Time | 1.52 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.34-7.13 (m, 3H), 6.95 (d, J=7.9 Hz, 1H), 6.91-6.81 (m, 3H), 6.77-6.60 (m,

2H), 6.10 (d, J=4.9 Hz, 2H), 4.44 (d, J=5.5 Hz, 1H), 3.09 (s, 3H), 2.94-2.54 (m, 2H), 1.21 (s, 9H).

Example 47

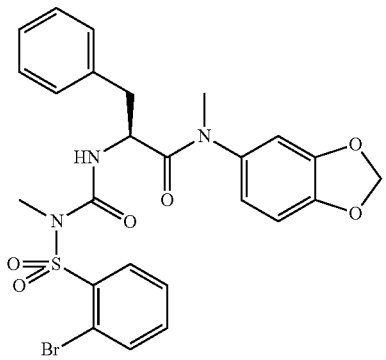 [SMILES: CN(C(=O)[C@H](Cc1ccccc1)NC(=O)N(C)S(=O)(=O)c1ccccc1Br)c1ccc2c(c1)OCO2]

(S)—N-(benzo[d][1,3]dioxol-5-yl)-2-(3-((2-bromophenyl)sulfonyl)-3-methylureido)-N-methyl-3-phenylpropanamid To a solution of (S)—N-(benzo[d][1,3]dioxol-5-yl)-2-(3-((2-bromophenyl)sulfonyl)ureido)-N-methyl-3-phenylpropanamide (30 mg, 0.054 mmol) in acetonitrile (1 mL) was added $K_2CO_3$ (74.0 mg, 0.535 mmol) followed by iodomethane (76 mg, 0.535 mmol). The reaction mixture was stirred at r.t. for 20 hrs. The solvent was filtered and evaporated and the residue was purified by preparative HPLC to afford the title compound (15.7 mg). $^1$H NMR (500 MHZ, DMSO-$d_6$) δ 8.05-7.95 (m, 1H), 7.86 (d, J=8.4 Hz, 1H), 7.66-7.56 (m, 2H), 7.53 (d, J=7.3 Hz, 1H), 7.27-7.12 (m, 3H), 6.92 (d, J=8.1 Hz, 1H), 6.83 (d, J=6.2 Hz, 2H), 6.73-6.66 (m, 1H), 6.63 (d, J=8.1 Hz, 1H), 6.08 (s, 2H), 4.35 (d, J=3.7 Hz, 1H), 3.16 (s, 3H), 3.09 (s, 3H), 2.94-2.66 (m, 2H).

| | |
|---|---|
| MS (M + H)$^+$ Calcd. | 574.1 |
| MS (M + H)$^+$ Observ. | 574.5 |
| Retention Time | 1.98 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-µm particles |

Example 48

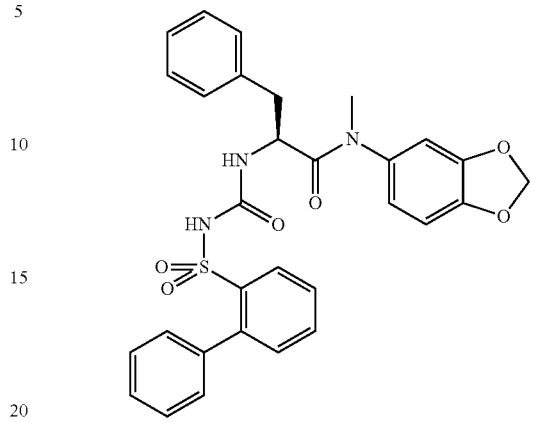

(S)-2-(3-([1,1'-biphenyl]-2-ylsulfonyl)ureido)-N-(benzo[d][1,3]dioxol-5-yl)-N-methyl-3-phenylpropanamide To a 0.5-2 mL microwave tube was added (S)—N-(benzo[d][1,3]dioxol-5-yl)-2-(3-((2-bromophenyl)sulfonyl)ureido)-N-methyl-3-phenylpropanamide (17 mg, 0.030 mmol), phenylboronic acid (7.40 mg, 0.061 mmol), Pd(PPh$_3$)$_4$ (3.51 mg, 3.03 µmol) and DMF (1 mL), followed by 2M aq. Na$_2$CO$_3$ (50 µl). The reaction mixture was heated in a microwave reactor at 125° C. for 15 min. The reaction mixture was filtered and the filtrate was purified by preparative HPLC to afford of the title compound (8.8 mg). $^1$H NMR (500 MHZ, DMSO-$d_6$) δ 7.91 (d, J=7.0 Hz, 1H), 7.56-7.10 (m, 12H), 6.87 (d, J=6.2 Hz, 3H), 6.70-6.49 (m, 2H), 6.20-6.11 (m, 1H), 6.07 (s, 2H), 4.29 (br. s., 1H), 3.06 (s, 3H), 2.80-2.53 (m, 2H).

| | |
|---|---|
| MS (M + H)$^+$ Calcd. | 558.2 |
| MS (M + H)$^+$ Observ. | 558.3 |
| Retention Time | 1.74 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-µm particles |

Examples 49-50 were synthesized using the procedure described above for Example 48.

Example 49

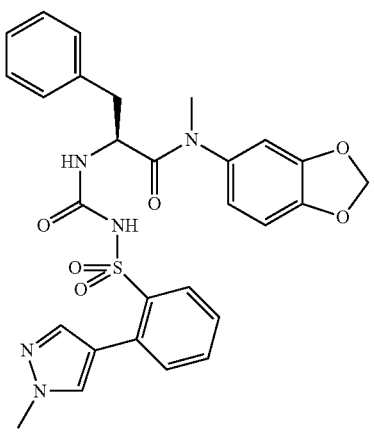 [SMILES: CN(C(=O)[C@H](Cc1ccccc1)NC(=O)NS(=O)(=O)c1ccccc1-c1cnn(C)c1)c1ccc2c(c1)OCO2]

(S)—N-(benzo[d][1,3]dioxol-5-yl)-N-methyl-2-(3-((2-(1-methyl-1H-pyrazol-4-yl)phenyl)sulfonyl)ureido)-3-phenylpropanamide

| | |
|---|---|
| MS (M + H)+ Calcd. | 562.2 |
| MS (M + H)+ Observ. | 562.3 |
| Retention Time | 1.43 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 8.00 (br. s., 1H), 7.89 (d, J=7.7 Hz, 1H), 7.62 (br. s., 1H), 7.52 (br. s., 1H), 7.38 (d, J=7.7 Hz, 2H), 7.17 (br. s., 3H), 6.92-6.78 (m, 3H), 6.69-6.29 (m, 3H), 6.06 (s, 2H), 4.27 (br. s., 1H), 3.88 (s, 3H), 3.06 (s, 3H), 2.73-2.47 (m, 2H).

Example 50

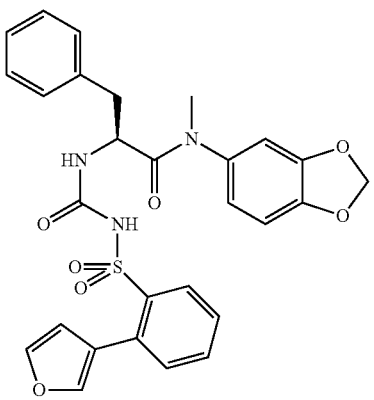 [SMILES: CN(C(=O)[C@H](Cc1ccccc1)NC(=O)NS(=O)(=O)c1ccccc1-c1ccoc1)c1ccc2c(c1)OCO2]

(S)—N-(benzo[d][1,3]dioxol-5-yl)-2-(3-((2-(furan-3-yl)phenyl)sulfonyl)ureido)-N-methyl-3-phenylpropanamide

| | |
|---|---|
| MS (M + H)+ Calcd. | 548.1 |
| MS (M + H)+ Observ. | 548.3 |
| Retention Time | 1.58 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.93 (d, J=7.7 Hz, 1H), 7.81-7.61 (m, 3H), 7.52 (t, J=7.3 Hz, 1H), 7.42 (d, J=7.3 Hz, 1H), 7.27-7.11 (m, 3H), 6.90 (d, J=8.1 Hz, 1H), 6.83 (d, J=5.5 Hz, 2H), 6.69-6.48 (m, 4H), 6.07 (s, 2H), 4.28 (d, J=5.9 Hz, 1H), 3.07 (s, 3H), 2.84-2.43 (m, 2H).

Examples 51-85 were synthesized using the procedure described above for Example 2.

Example 51

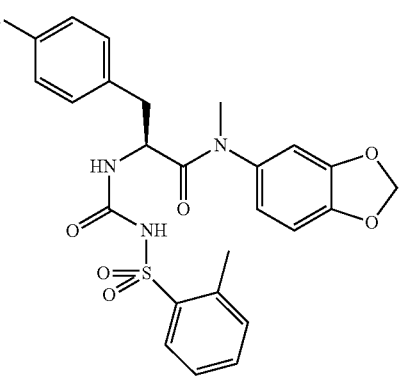

(S)—N-(benzo[d][1,3]dioxol-5-yl)-3-(4-chlorophenyl)-N-methyl-2-(3-(o-tolylsulfonyl) ureido)propanamide

| | |
|---|---|
| MS (M + H)+ Calcd. | 530.1 |
| MS (M + H)+ Observ. | 530.3 |
| Retention Time | 1.60 min |
| | LC Condition |
| Solvent A | 5% acetonitrile:95% Water:10mM Ammonium Acetate |
| Solvent B | 95% acetonitrile:5% Water:10mM Ammonium Acetate |
| Start % B | 0 |
| Final % B | 100 |
| Gradient Time | 3 min |
| Flow Rate | 1 mL/min |

-continued

| | |
|---|---|
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.74 (d, J=7.7 Hz, 1H), 7.54-7.08 (m, 5H), 6.98-6.59 (m, 5H), 6.52-6.31 (m, 1H), 6.07 (s, 2H), 4.27 (br. s., 1H), 3.07 (s, 3H), 2.73-2.54 (m, 2H), 2.51 (s, 3H).

Example 52

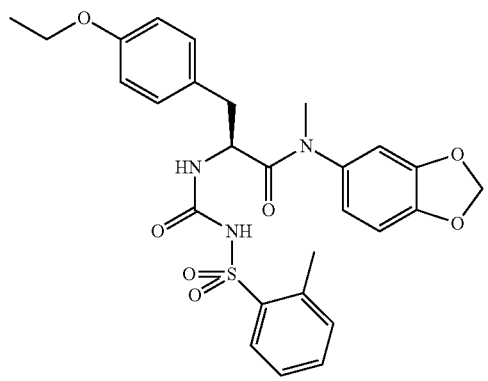 [SMILES: CCOc1ccc(C[C@H](NC(=O)NS(=O)(=O)c2ccccc2C)C(=O)N(C)c2ccc3c(c2)OCO3)cc1]

(S)—N-(benzo[d][1,3]dioxol-5-yl)-3-(4-ethoxyphenyl)-N-methyl-2-(3-(o-tolylsulfonyl) ureido)propanamide

| | |
|---|---|
| MS (M + H)$^+$ Calcd. | 540.2 |
| MS (M + H)$^+$ Observ. | 540.3 |
| Retention Time | 1.55 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.76 (d, J=8.1 Hz, 1H), 7.42 (br. s., 1H), 7.29 (br. s., 2H), 6.87 (d, J=8.1 Hz, 1H), 6.76-6.26 (m, 6H), 6.07 (s, 2H), 4.22 (br. s., 1H), 3.96 (q, J=6.7 Hz, 2H), 3.06 (s, 3H), 2.72-2.35 (m, 5H), 1.31 (t, J=6.6 Hz, 3H).

Example 53

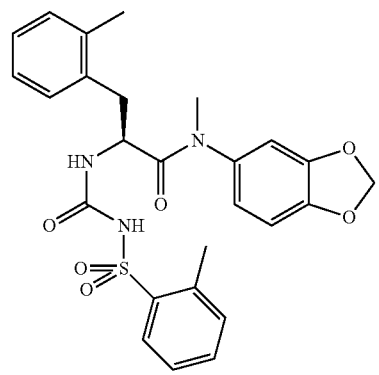 [SMILES: Cc1ccccc1C[C@H](NC(=O)NS(=O)(=O)c1ccccc1C)C(=O)N(C)c1ccc2c(c1)OCO2]

(S)—N-(benzo[d][1,3]dioxol-5-yl)-N-methyl-3-(o-tolyl)-2-(3-(o-tolylsulfonyl) ureido)propanamide

| | |
|---|---|
| MS (M + H)$^+$ Calcd. | 510.2 |
| MS (M + H)$^+$ Observ. | 510.3 |
| Retention Time | 1.65 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.74 (d, J=7.7 Hz, 1H), 7.43 (br. s., 1H), 7.29 (d, J=7.0 Hz, 2H), 7.10-7.04 (m, 1H), 7.03-6.96 (m, 2H), 6.80 (t, J=8.4 Hz, 2H), 6.40 (br. s., 2H), 6.04 (d, J=5.5 Hz, 2H), 4.38 (d, J=6.6 Hz, 1H), 3.02 (s, 3H), 2.77-2.48 (m, 5H), 1.82 (s, 3H).

Example 54

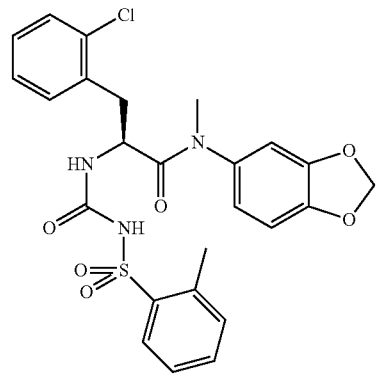 [SMILES: Cc1ccccc1S(=O)(=O)NC(=O)N[C@@H](Cc1ccccc1Cl)C(=O)N(C)c1ccc2c(c1)OCO2]

(S)—N-(benzo[d][1,3]dioxol-5-yl)-3-(2-chlorophenyl)-N-methyl-2-(3-(o-tolylsulfonyl) ureido)propanamide

| | |
|---|---|
| MS (M + H)+ Calcd. | 530.1 |
| MS (M + H)+ Observ. | 530.3 |
| Retention Time | 1.59 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.72 (d, J=7.7 Hz, 1H), 7.40 (br. s., 1H), 7.32-7.08 (m, 6H), 7.01 (br. s., 1H), 6.84 (d, J=7.3 Hz, 1H), 6.73-6.27 (m, 2H), 6.04 (d, J=7.0 Hz, 2H), 4.51 (br. s., 1H), 3.06 (s, 3H), 2.89-2.60 (m, 2H), 2.50 (s, 3H).

Example 55

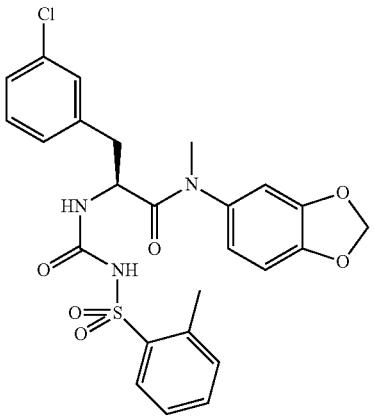 [SMILES: Cc1ccccc1S(=O)(=O)NC(=O)N[C@@H](Cc1cccc(Cl)c1)C(=O)N(C)c1ccc2c(c1)OCO2]

(S)—N-(benzo[d][1,3]dioxol-5-yl)-3-(3-chlorophenyl)-N-methyl-2-(3-(o-tolylsulfonyl)ureido)propanamide

| | |
|---|---|
| MS (M + H)+ Calcd. | 530.1 |
| MS (M + H)+ Observ. | 530.2 |
| Retention Time | 1.64 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.74 (d, J=7.0 Hz, 1H), 7.44-7.32 (m, 1H), 7.31-7.12 (m, 4H), 6.89 (d, J=8.4 Hz, 1H), 6.85-6.25 (m, 4H), 6.07 (d, J=5.9 Hz, 2H), 4.32-4.17 (m, 1H), 3.07 (s, 3H), 2.75-2.48 (m, 5H).

Example 56

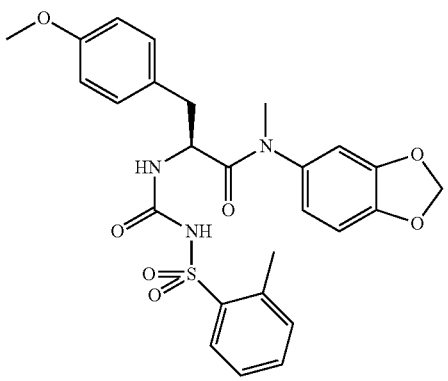 [SMILES: COc1ccc(C[C@H](NC(=O)NS(=O)(=O)c2ccccc2C)C(=O)N(C)c2ccc3c(c2)OCO3)cc1]

(S)—N-(benzo[d][1,3]dioxol-5-yl)-3-(4-methoxyphenyl)-N-methyl-2-(3-(o-tolylsulfonyl) ureido)propanamide

| | |
|---|---|
| MS (M + H)+ Calcd. | 526.2 |
| MS (M + H)+ Observ. | 526.3 |
| Retention Time | 1.51 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.77-7.69 (m, 1H), 7.45-7.17 (m, 3H), 6.90-6.83 (m, 1H), 6.71 (s, 4H), 6.66-6.31 (m, 2H), 6.04 (s, 2H), 4.29-4.12 (m, 1H), 3.69 (s, 3H), 3.04 (s, 3H), 2.71-2.35 (m, 5H).

Example 57

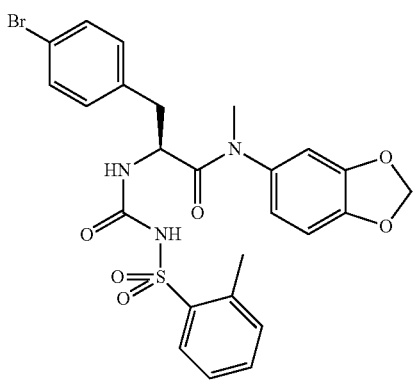 [SMILES: Cc1ccccc1S(=O)(=O)NC(=O)N[C@@H](Cc1ccc(Br)cc1)C(=O)N(C)c1ccc2c(c1)OCO2]

(S)—N-(benzo[d][1,3]dioxol-5-yl)-3-(4-bromophenyl)-N-methyl-2-(3-(o-tolylsulfonyl) ureido)propanamide

| | |
|---|---|
| MS (M + H)+ Calcd. | 574.1 |
| MS (M + H)+ Observ. | 574.3 |
| Retention Time | 1.64 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.72 (d, J=7.7 Hz, 1H), 7.49-7.07 (m, 5H), 6.87 (d, J=7.7 Hz, 1H), 6.80-6.34 (m, 4H), 6.06 (s, 2H), 4.26 (br. s., 1H), 3.06 (s, 3H), 2.79-2.34 (m, 5H).

Example 58

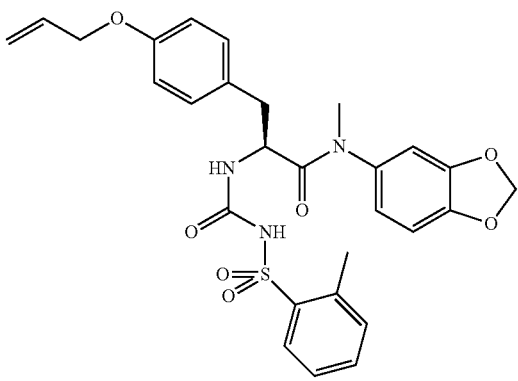 [SMILES: C=CCOc1ccc(C[C@H](NC(=O)NS(=O)(=O)c2ccccc2C)C(=O)N(C)c2ccc3c(c2)OCO3)cc1]

(S)-3-(4-(allyloxy)phenyl)-N-(benzo[d][1,3]dioxol-5-yl)-N-methyl-2-(3-(o-tolylsulfonyl) ureido)propanamide

| | |
|---|---|
| MS (M + H)+ Calcd. | 552.2 |
| MS (M + H)+ Observ. | 552.4 |
| Retention Time | 1.64 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.78 (d, J=7.3 Hz, 1H), 7.54-7.25 (m, 3H), 6.89 (d, J=8.4 Hz, 1H), 6.78-6.66 (m, 5H), 6.63-6.45 (m, 2H), 6.13-5.96 (m, 3H), 5.45-5.17 (m, 2H), 4.51 (d, J=5.1 Hz, 2H), 4.24 (d, J=5.1 Hz, 1H), 3.07 (s, 3H), 2.78-2.38 (m, 5H).

Example 59

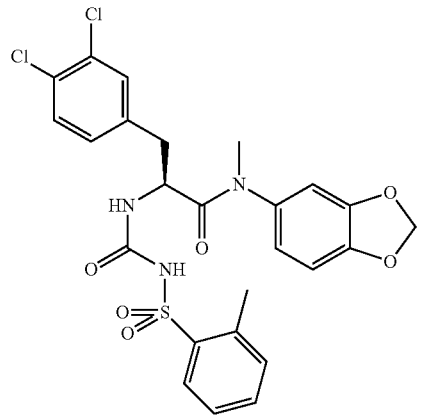 [SMILES: Cc1ccccc1S(=O)(=O)NC(=O)N[C@@H](Cc1ccc(Cl)c(Cl)c1)C(=O)N(C)c1ccc2c(c1)OCO2]

(S)—N-(benzo[d][1,3]dioxol-5-yl)-3-(3,4-dichlorophenyl)-N-methyl-2-(3-(o-tolylsulfonyl) ureido) propanamide

| | |
|---|---|
| MS (M + H)+ Calcd. | 564.1 |
| MS (M + H)+ Observ. | 564.2 |
| Retention Time | 1.69 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.73 (d, J=7.7 Hz, 1H), 7.51-7.06 (m, 5H), 7.00 (br. s., 1H), 6.90 (d, J=8.1 Hz, 1H), 6.85-6.66 (m, 3H), 6.42 (br. s., 1H), 6.08 (d, J=7.7 Hz, 2H), 4.29 (br. s., 1H), 3.08 (s, 3H), 2.79-2.46 (m, 5H).

Example 60

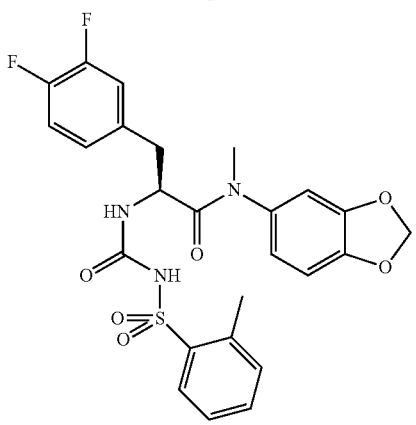 [SMILES: Cc1ccccc1S(=O)(=O)NC(=O)N[C@@H](Cc1ccc(F)c(F)c1)C(=O)N(C)c1ccc2c(c1)OCO2]

(S)—N-(benzo[d][1,3]dioxol-5-yl)-3-(3,4-difluorophenyl)-N-methyl-2-(3-(o-tolylsulfonyl) ureido) propanamide

| | |
|---|---|
| MS (M + H)+ Calcd. | 532.1 |
| MS (M + H)+ Observ. | 532.2 |
| Retention Time | 1.71 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-µm particles |

$^1$H NMR (500 MHZ, DMSO-d$_6$) δ 7.78 (d, J=8.1 Hz, 1H), 7.51 (t, J=7.2 Hz, 1H), 7.40-7.29 (m, 2H), 7.24-7.13 (m, 1H), 6.93 (d, J=8.1 Hz, 1H), 6.86 (s, 1H), 6.82-6.47 (m, 4H), 6.08 (d, J=7.3 Hz, 2H), 4.31 (d, J=4.0 Hz, 1H), 3.09 (s, 3H), 2.84-2.45 (m, 5H).

Example 61

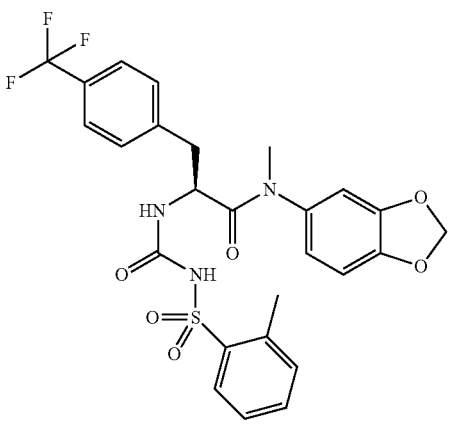 [SMILES: Cc1ccccc1S(=O)(=O)NC(=O)N[C@@H](Cc1ccc(C(F)(F)F)cc1)C(=O)N(C)c1ccc2c(c1)OCO2]

(S)—N-(benzo[d][1,3]dioxol-5-yl)-N-methyl-2-(3-(o-tolylsulfonyl)ureido)-3-(4-(trifluoromethyl)phenyl)propanamide

| | |
|---|---|
| MS (M + H)+ Calcd. | 564.1 |
| MS (M + H)+ Observ. | 564.2 |
| Retention Time | 1.69 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-µm particles |

$^1$H NMR (500 MHZ, DMSO-d$_6$) δ 7.77 (d, J=7.3 Hz, 1H), 7.55-7.42 (m, 3H), 7.38-7.26 (m, 2H), 7.00 (d, J=7.7 Hz, 2H), 6.90 (d, J=8.1 Hz, 1H), 6.83-6.55 (m, 3H), 6.08 (d, J=2.6 Hz, 2H), 4.34 (d, J=4.8 Hz, 1H), 3.09 (s, 3H), 2.92-2.57 (m, 2H), 2.50 (s, 3H).

Example 62

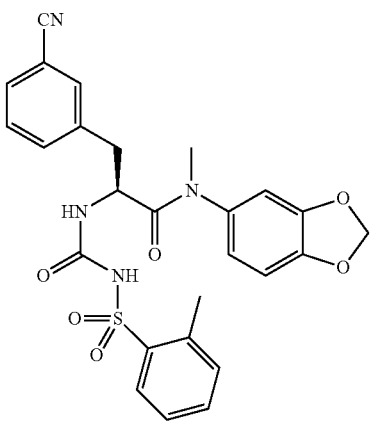

(S)—N-(benzo[d][1,3]dioxol-5-yl)-3-(3-cyanophenyl)-N-methyl-2-(3-(o-tolylsulfonyl) ureido)propanamide

| | |
|---|---|
| MS (M + H)+ Calcd. | 521.1 |
| MS (M + H)+ Observ. | 521.3 |
| Retention Time | 1.35 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |

| | |
|---|---|
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.71 (d, J=7.7 Hz, 1H), 7.60 (d, J=7.7 Hz, 1H), 7.45-7.04 (m, 6H), 6.89 (d, J=8.1 Hz, 1H), 6.79-6.28 (m, 2H), 6.06 (d, J=8.1 Hz, 2H), 4.28 (br. s., 1H), 3.06 (br. s., 3H), 2.83-2.55 (m, 2H), 2.48 (s, 3H).

Example 63

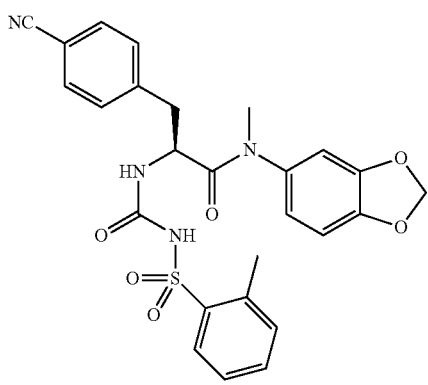

(S)—N-(benzo[d][1,3]dioxol-5-yl)-3-(4-cyanophenyl)-N-methyl-2-(3-(o-tolylsulfonyl) ureido)propanamide

| | |
|---|---|
| MS (M + H)$^+$ Calcd. | 521.1 |
| MS (M + H)$^+$ Observ. | 521.3 |
| Retention Time | 1.60 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.75-7.51 (m, 3H), 7.41-7.07 (m, 3H), 6.98 (d, J=5.1 Hz, 2H), 6.88 (d, J=8.1 Hz, 1H), 6.78-6.17 (m, 2H), 6.06 (br. s., 2H), 4.29 (br. s., 1H), 3.06 (s, 3H), 2.84-2.56 (m, 2H), 2.48 (s, 3H).

Example 64

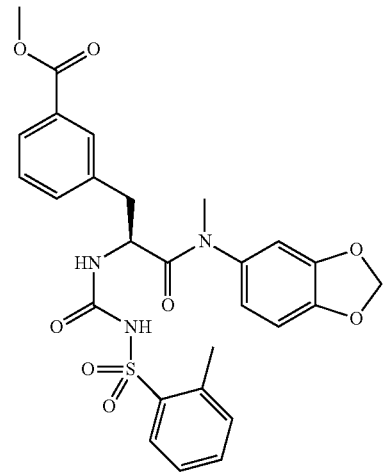 [SMILES: COC(=O)c1cccc(C[C@H](NC(=O)NS(=O)(=O)c2ccccc2C)C(=O)N(C)c2ccc3c(c2)OCO3)c1]

(S)-methyl 3-(3-(benzo[d][1,3]dioxol-5-yl(methyl)amino)-3-oxo-2-(3-(o-tolylsulfonyl)ureido)propyl)benzoate

| | |
|---|---|
| MS (M + H)$^+$ Calcd. | 554.2 |
| MS (M + H)$^+$ Observ. | 554.3 |
| Retention Time | 1.48 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.72 (dd, J=19.6, 7.5 Hz, 2H), 7.42-7.04 (m, 6H), 6.91-6.24 (m, 3H), 6.05 (d, J=10.6 Hz, 2H), 4.27 (br. s., 1H), 3.83 (s, 3H), 3.05 (s, 3H), 2.85-2.54 (m, 2H), 2.47 (s, 3H).

Example 65

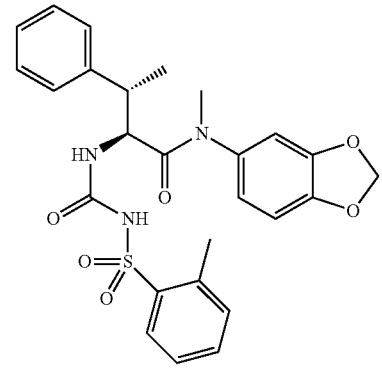 [SMILES: Cc1ccccc1S(=O)(=O)NC(=O)N[C@H](C(=O)N(C)c1ccc2c(c1)OCO2)[C@@H](C)c1ccccc1]

(2S,3S)-N-(benzo[d][1,3]dioxol-5-yl)-N-methyl-3-phenyl-2-(3-(o-tolylsulfonyl) ureido)butanamide

| | |
|---|---|
| MS (M + H)+ Calcd. | 510.2 |
| MS (M + H)+ Observ. | 510.3 |
| Retention Time | 1.48 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.71 (d, J=8.1 Hz, 1H), 7.41 (br. s., 1H), 7.33-7.10 (m, 6H), 6.94 (d, J=6.6 Hz, 2H), 6.90-6.57 (m, 3H), 6.08 (s, 2H), 4.45 (br. s., 1H), 3.08 (s, 3H), 2.85 (t, J=7.0 Hz, 1H), 2.51 (s, 3H), 0.94 (d, J=7.0 Hz, 3H).

Example 66

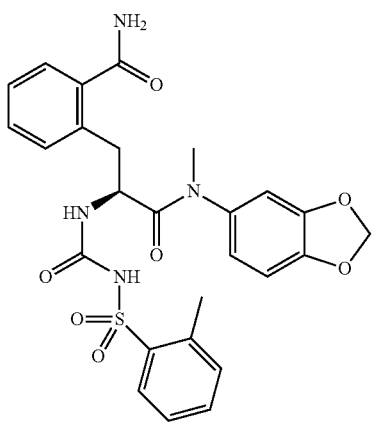 [SMILES: Cc1ccccc1S(=O)(=O)NC(=O)N[C@@H](Cc1ccccc1C(N)=O)C(=O)N(C)c1ccc2c(c1)OCO2]

(S)-2-(3-(benzo[d][1,3]dioxol-5-yl(methyl)amino)-3-oxo-2-(3-(o-tolylsulfonyl) ureido)propyl)benzamide

| | |
|---|---|
| MS (M + H)+ Calcd. | 539.2 |
| MS (M + H)+ Observ. | 539.3 |
| Retention Time | 1.41 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.71 (br. s., 2H), 7.54-7.03 (m, 7H), 6.99-6.78 (m, 1H), 6.64 (br. s., 2H), 6.07 (s, 2H), 4.33 (br. s., 1H), 3.08 (s, 3H), 2.90-2.62 (m, 2H), 2.48 (s, 3H).

Example 67

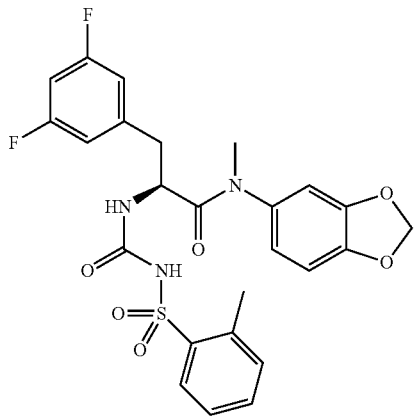 [SMILES: Cc1ccccc1S(=O)(=O)NC(=O)N[C@@H](Cc1cc(F)cc(F)c1)C(=O)N(C)c1ccc2c(c1)OCO2]

(S)-N-(benzo[d][1,3]dioxol-5-yl)-3-(3,5-difluorophenyl)-N-methyl-2-(3-(o-tolylsulfonyl) ureido)propanamide

| | |
|---|---|
| MS (M + H)+ Calcd. | 532.1 |
| MS (M + H)+ Observ. | 532.2 |
| Retention Time | 1.52 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-d$_6$) δ 7.73 (d, J=7.7 Hz, 1H), 7.37 (br. s., 1H), 7.23 (br. s., 2H), 7.04-6.80 (m, 3H), 6.78-6.65 (m, 1H), 6.48 (d, J=7.0 Hz, 2H), 6.36 (br. s., 1H), 6.07 (d, J=6.6 Hz, 2H), 4.29 (br. s., 1H), 3.08 (s, 3H), 2.82-2.54 (m, 2H), 2.49 (s, 3H).

Example 68

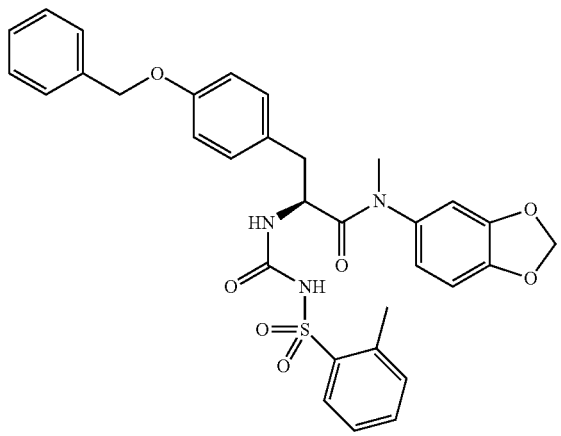 [SMILES: Cc1ccccc1S(=O)(=O)NC(=O)N[C@@H](Cc1ccc(OCc2ccccc2)cc1)C(=O)N(C)c1ccc2c(c1)OCO2]

(S)—N-(benzo[d][1,3]dioxol-5-yl)-3-(4-(benzyloxy)phenyl)-N-methyl-2-(3-(o-tolylsulfonyl) ureido)propanamide

| | |
|---|---|
| MS (M + H)+ Calcd. | 602.2 |
| MS (M + H)+ Observ. | 602.3 |
| Retention Time | 1.81 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-$d_6$) δ 7.78 (d, J=7.3 Hz, 1H), 7.53-7.22 (m, 8H), 6.90-6.77 (m, 3H), 6.71 (d, J=8.4 Hz, 3H), 6.62-6.39 (m, 2H), 6.07 (s, 2H), 5.05 (s, 2H), 4.24 (br. s., 1H), 3.06 (s, 3H), 2.75-2.35 (m, 5H).

Example 69

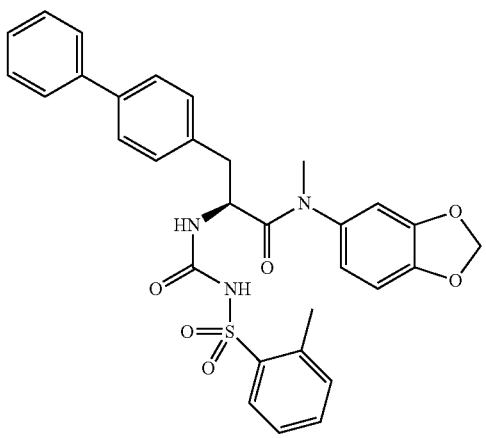 [SMILES: Cc1ccccc1S(=O)(=O)NC(=O)N[C@@H](Cc1ccc(-c2ccccc2)cc1)C(=O)N(C)c1ccc2c(c1)OCO2]

(S)-3-([1,1'-biphenyl]-4-yl)-N-(benzo[d][1,3]dioxol-5-yl)-N-methyl-2-(3-(o-tolylsulfonyl) ureido)propanamide

| | |
|---|---|
| MS (M + H)+ Calcd. | 572.2 |
| MS (M + H)+ Observ. | 572.4 |
| Retention Time | 1.81 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile: Water: Ammonium Acetate |
| Column | Waters BEH C18, 2.0 × 50 mm, 1.7-μm particles |

$^1$H NMR (500 MHZ, DMSO-$d_6$) δ 7.77 (d, J=6.6 Hz, 1H), 7.62 (d, J=7.3 Hz, 2H), 7.46 (d, J=7.3 Hz, 4H), 7.41-7.18 (m, 4H), 6.90 (d, J=7.0 Hz, 3H), 6.79-6.38 (m, 3H), 6.08 (s, 2H), 4.32 (br. s., 1H), 3.09 (s, 3H), 2.86-2.42 (m, 5H).

Example 70

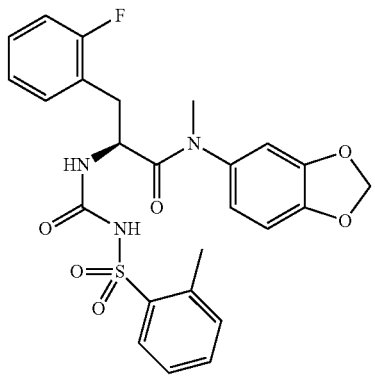 [SMILES: Cc1ccccc1S(=O)(=O)NC(=O)N[C@@H](Cc1ccccc1F)C(=O)N(C)c1ccc2c(c1)OCO2]

(S)—N-(benzo[d][1,3]dioxol-5-yl)-3-(2-fluorophenyl)-N-methyl-2-(3-(o-tolylsulfonyl) ureido)propanamide

| | |
|---|---|
| MS (M + H)+ Calcd. | 514.1 |
| MS (M + H)+ Observ. | 514.3 |
| Retention Time | 1.49 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.73 (d, J=7.7 Hz, 1H), 7.41 (br. s., 1H), 7.33-7.16 (m, 3H), 7.05-6.95 (m, 2H), 6.94-6.81 (m, 2H), 6.77-6.25 (m, 3H), 6.07 (s, 2H), 4.37 (br. s., 1H), 3.06 (s, 3H), 2.80-2.54 (m, 2H), 2.51 (s, 3H).

Example 71

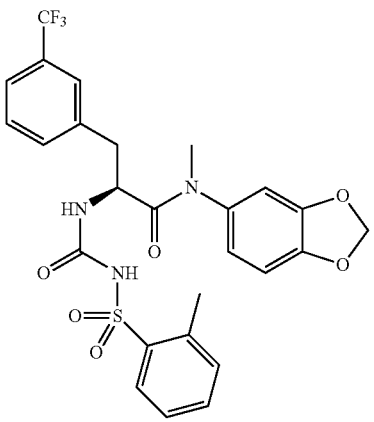 [SMILES: Cc1ccccc1S(=O)(=O)NC(=O)N[C@@H](Cc1cccc(C(F)(F)F)c1)C(=O)N(C)c1ccc2c(c1)OCO2]

(S)—N-(benzo[d][1,3]dioxol-5-yl)-N-methyl-2-(3-(o-tolylsulfonyl) ureido)-3-(3-(trifluoromethyl)phenyl)propanamide

| | |
|---|---|
| MS (M + H)$^+$ Calcd. | 564.1 |
| MS (M + H)$^+$ Observ. | 564.3 |
| Retention Time | 1.64 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.72 (d, J=7.7 Hz, 1H), 7.50 (br. s., 1H), 7.39 (t, J=7.7 Hz, 1H), 7.34 (br. s., 1H), 7.27-7.02 (m, 5H), 6.86 (d, J=8.1 Hz, 1H), 6.78-6.24 (m, 2H), 6.13-5.94 (m, 2H), 4.34-4.18 (m, 1H), 3.06 (s, 3H), 2.85-2.59 (m, 2H), 2.49 (s, 3H).

Example 72

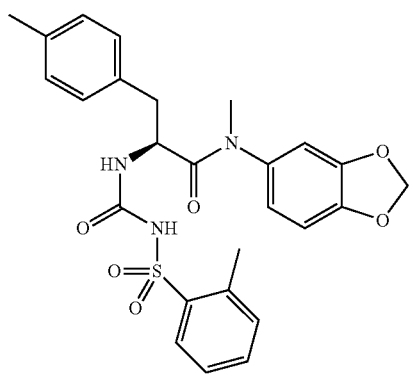 [SMILES: Cc1ccc(C[C@H](NC(=O)NS(=O)(=O)c2ccccc2C)C(=O)N(C)c2ccc3c(c2)OCO3)cc1]

(S)—N-(benzo[d][1,3]dioxol-5-yl)-N-methyl-3-(p-tolyl)-2-(3-(o-tolylsulfonyl) ureido)propanamide

| | |
|---|---|
| MS (M + H)$^+$ Calcd. | 510.2 |
| MS (M + H)$^+$ Observ. | 510.3 |
| Retention Time | 1.58 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.77 (d, J=7.7 Hz, 1H), 7.46 (d, J=7.0 Hz, 1H), 7.37-7.24 (m, 2H), 6.96 (d, J=7.7 Hz, 2H), 6.88 (d, J=8.1 Hz, 1H), 6.74-6.39 (m, 5H), 6.07 (s, 2H), 4.25 (d, J=5.9 Hz, 1H), 3.06 (s, 3H), 2.77-2.39 (m, 5H), 2.23 (s, 3H).

Example 73

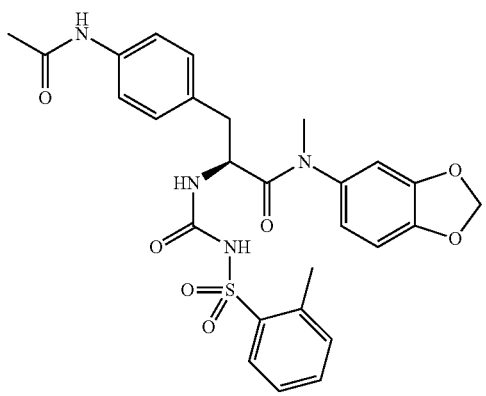 [SMILES: CC(=O)Nc1ccc(C[C@H](NC(=O)NS(=O)(=O)c2ccccc2C)C(=O)N(C)c2ccc3c(c2)OCO3)cc1]

(S)-3-(4-acetamidophenyl)-N-(benzo[d][1,3]dioxol-5-yl)-N-methyl-2-(3-(o-tolylsulfonyl) ureido)propanamide

| | |
|---|---|
| MS (M + H)+ Calcd. | 553.2 |
| MS (M + H)+ Observ. | 553.3 |
| Retention Time | 1.33 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 9.86 (br. s., 1H), 7.71 (d, J=7.7 Hz, 1H), 7.38-7.34 (m, 3H), 7.21 (br. s., 2H), 6.84 (d, J=8.1 Hz, 1H), 6.77-6.15 (m, 4H), 6.03 (s, 2H), 4.21 (br. s., 1H), 3.03 (s, 3H), 2.65-2.41 (m, 5H), 2.01 (s, 3H).

Example 74

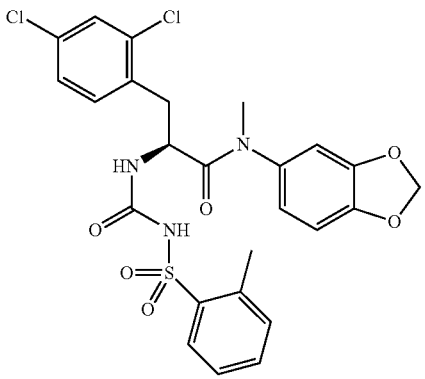 [SMILES: Cc1ccccc1S(=O)(=O)NC(=O)N[C@@H](Cc1ccc(Cl)cc1Cl)C(=O)N(C)c1ccc2c(c1)OCO2]

(S)—N-(benzo[d][1,3]dioxol-5-yl)-3-(2,4-dichlorophenyl)-N-methyl-2-(3-(o-tolylsulfonyl) ureido) propanamide

| | |
|---|---|
| MS (M + H)+ Calcd. | 564.1 |
| MS (M + H)+ Observ. | 564.3 |
| Retention Time | 1.71 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.72 (d, J=7.7 Hz, 1H), 7.49 (t, J=7.2 Hz, 1H), 7.39-7.26 (m, 3H), 7.18 (d, J=8.1 Hz, 1H), 6.96 (d, J=8.1 Hz, 1H), 6.90 (d, J=8.1 Hz, 1H), 6.83-6.52 (m, 3H), 6.06 (d, J=8.8 Hz, 2H), 4.53 (d, J=4.4 Hz, 1H), 3.10 (s, 3H), 2.92-2.56 (m, 2H), 2.51 (s, 3H).

Example 75

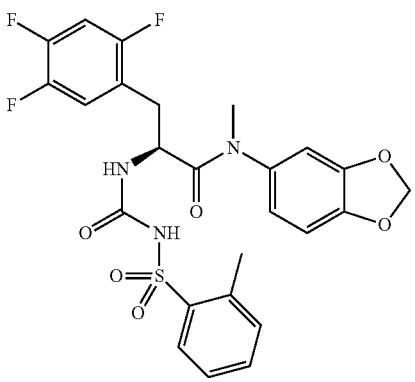 [SMILES: Cc1ccccc1S(=O)(=O)NC(=O)N[C@@H](Cc1cc(F)c(F)cc1F)C(=O)N(C)c1ccc2c(c1)OCO2]

(S)—N-(benzo[d][1,3]dioxol-5-yl)-N-methyl-2-(3-(o-tolylsulfonyl)ureido)-3-(2,4,5-trifluorophenyl) propanamide

| | |
|---|---|
| MS (M + H)+ Calcd. | 550.1 |
| MS (M + H)+ Observ. | 550.3 |
| Retention Time | 1.56 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.73 (d, J=7.7 Hz, 1H), 7.54-7.43 (m, 1H), 7.38-7.17 (m, 3H), 7.03-6.46 (m, 5H), 6.08 (d, J=7.0 Hz, 2H), 4.41 (d, J=4.0 Hz, 1H), 3.11 (s, 3H), 2.87-2.52 (m, 2H), 2.49 (s, 3H).

Example 76

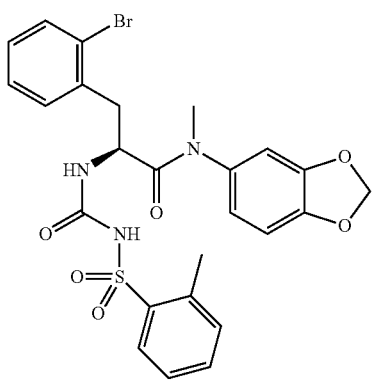 [SMILES: Cc1ccccc1S(=O)(=O)NC(=O)N[C@@H](Cc1ccccc1Br)C(=O)N(C)c1ccc2c(c1)OCO2]

(S)—N-(benzo[d][1,3]dioxol-5-yl)-3-(2-bromophenyl)-N-methyl-2-(3-(o-tolylsulfonyl) ureido)propanamide

| MS (M + H)+ Calcd. | 574.1 |
| --- | --- |
| MS (M + H)+ Observ. | 574.2 |
| Retention Time | 1.72 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.70 (d, J=7.3 Hz, 1H), 7.41 (d, J=7.7 Hz, 1H), 7.38-7.29 (m, 1H), 7.20 (br. s., 3H), 7.12 (d, J=7.3 Hz, 1H), 6.77 (br. s., 4H), 6.01 (d, J=8.8 Hz, 2H), 4.54-4.38 (m, 1H), 3.02 (s, 3H), 2.81-2.66 (m, 2H), 2.49 (br. s., 3H).

Example 77

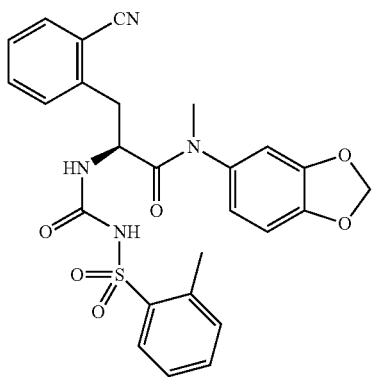 [SMILES: Cc1ccccc1S(=O)(=O)NC(=O)N[C@@H](Cc1ccccc1C#N)C(=O)N(C)c1ccc2c(c1)OCO2]

(S)—N-(benzo[d][1,3]dioxol-5-yl)-3-(2-cyanophenyl)-N-methyl-2-(3-(o-tolylsulfonyl) ureido)propanamide

| MS (M + H)+ Calcd. | 521.1 |
| --- | --- |
| MS (M + H)+ Observ. | 521.3 |
| Retention Time | 1.42 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.74-7.59 (m, 2H), 7.53-7.30 (m, 3H), 7.28-7.13 (m, 2H), 7.00-6.78 (m, 2H), 6.71 (br. s., 2H), 6.21-6.09 (m, 1H), 6.04 (d, J=8.4 Hz, 2H), 4.54-4.39 (m, 1H), 3.05 (s, 3H), 2.93-2.74 (m, 2H), 2.49 (s, 3H).

Example 78

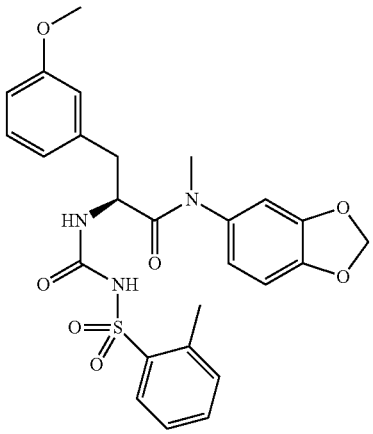 [SMILES: COc1cccc(C[C@H](NC(=O)NS(=O)(=O)c2ccccc2C)C(=O)N(C)c2ccc3c(c2)OCO3)c1]

(S)—N-(benzo[d][1,3]dioxol-5-yl)-3-(3-methoxyphenyl)-N-methyl-2-(3-(o-tolylsulfonyl) ureido) propanamide

| MS (M + H)+ Calcd. | 526.2 |
| --- | --- |
| MS (M + H)+ Observ. | 526.3 |
| Retention Time | 1.50 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |

| | |
|---|---|
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.72 (d, J=7.7 Hz, 1H), 7.48-7.01 (m, 4H), 6.86 (d, J=8.1 Hz, 1H), 6.77-6.53 (m, 2H), 6.42 (d, J=7.3 Hz, 1H), 6.32 (br. s., 2H), 6.03 (s, 2H), 4.24 (br. s., 1H), 3.63 (s, 3H), 3.05 (s, 3H), 2.78-2.34 (m, 5H).

Example 79

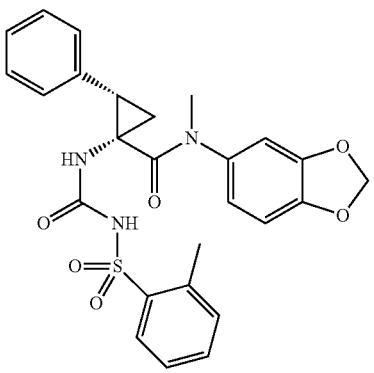 [SMILES: Cc1ccccc1S(=O)(=O)NC(=O)N[C@@]1(C(=O)N(C)c2ccc3c(c2)OCO3)C[C@H]1c1ccccc1]

(1S,2S)—N-(benzo[d][1,3]dioxol-5-yl)-N-methyl-2-phenyl-1-(3-(o-tolylsulfonyl)ureido)cyclopropan-ecarboxamide

| | |
|---|---|
| MS (M + H)$^+$ Calcd. | 508.2 |
| MS (M + H)$^+$ Observ. | 508.3 |
| Retention Time | 1.42 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.65 (d, J=7.7 Hz, 1H), 7.48-7.33 (m, 1H), 7.30-7.15 (m, 5H), 7.07 (br. s., 2H), 6.79-6.48 (m, 3H), 5.98 (d, J=17.2 Hz, 2H), 3.01 (s, 3H), 2.81-2.62 (m, 1H), 2.37 (s, 3H), 1.99-1.92 (m, 1H), 1.19-1.07 (m, 1H).

Example 80

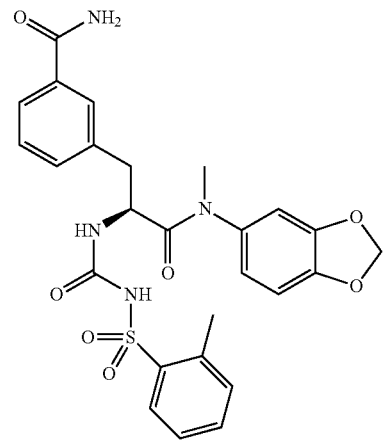 [SMILES: Cc1ccccc1S(=O)(=O)NC(=O)N[C@@H](Cc1cccc(C(N)=O)c1)C(=O)N(C)c1ccc2c(c1)OCO2]

(S)-3-(3-(benzo[d][1,3]dioxol-5-yl(methyl)amino)-3-oxo-2-(3-(o-tolylsulfonyl) ureido)propyl)benzamide

| | |
|---|---|
| MS (M + H)$^+$ Calcd. | 539.2 |
| MS (M + H)$^+$ Observ. | 539.3 |
| Retention Time | 1.30 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.93-7.55 (m, 3H), 7.47-7.04 (m, 6H), 6.93 (d, J=7.3 Hz, 1H), 6.80 (d, J=8.1 Hz, 1H), 6.67-6.18 (m, 2H), 6.04 (d, J=9.9 Hz, 2H), 4.28 (br. s., 1H), 3.04 (s, 3H), 2.83-2.37 (m, 5H).

Example 81

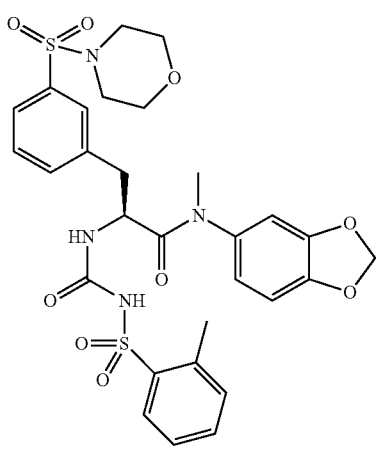 [SMILES: Cc1ccccc1S(=O)(=O)NC(=O)N[C@@H](Cc1cccc(S(=O)(=O)N2CCOCC2)c1)C(=O)N(C)c1ccc2c(c1)OCO2]

(S)—N-(benzo[d][1,3]dioxol-5-yl)-N-methyl-3-(3-(morpholinosulfonyl)phenyl)-2-(3-(o-tolylsulfonyl)ureido)propanamide

| | |
|---|---|
| MS (M + H)+ Calcd. | 645.2 |
| MS (M + H)+ Observ. | 645.3 |
| Retention Time | 1.37 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.75-7.66 (m, 1H), 7.47 (s, 8H), 6.91-6.82 (m, 1H), 6.81-6.30 (m, 2H), 6.05 (d, J=6.6 Hz, 2H), 3.62 (br. s., 4H), 3.07 (br. s., 3H), 2.87-2.61 (m, 6H), 2.50-2.35 (m, 4H).

Example 82

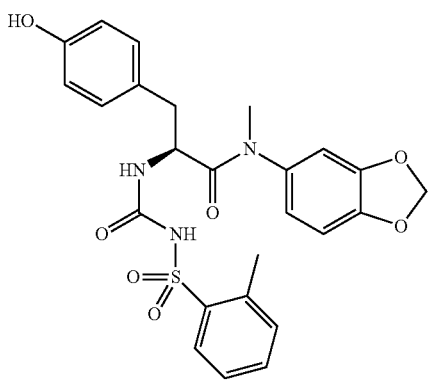 [SMILES: Cc1ccccc1S(=O)(=O)NC(=O)N[C@@H](Cc1ccc(O)cc1)C(=O)N(C)c1ccc2c(c1)OCO2]

(S)—N-(benzo[d][1,3]dioxol-5-yl)-3-(4-hydroxyphenyl)-N-methyl-2-(3-(o-tolylsulfonyl) ureido)propanamide

| | |
|---|---|
| MS (M + H)+ Calcd. | 512.1 |
| MS (M + H)+ Observ. | 512.3 |
| Retention Time | 1.45 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.72 (d, J=7.7 Hz, 1H), 7.47-7.09 (m, 3H), 6.84 (d, J=8.1 Hz, 1H), 6.71-6.48 (m, 5H), 6.32-6.16 (m, 1H), 6.04 (s, 2H), 4.28-4.10 (m, 1H), 3.04 (s, 3H), 2.68-2.30 (m, 5H).

Example 83

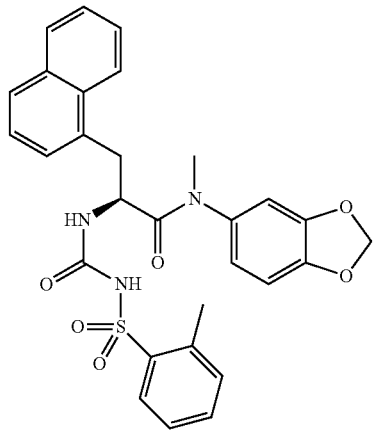 [SMILES: Cc1ccccc1S(=O)(=O)NC(=O)N[C@@H](Cc1cccc2ccccc12)C(=O)N(C)c1ccc2c(c1)OCO2]

(S)—N-(benzo[d][1,3]dioxol-5-yl)-N-methyl-3-(naphthalen-1-yl)-2-(3-(o-tolylsulfonyl) ureido)propanamide

| | |
|---|---|
| MS (M + H)+ Calcd. | 546.2 |
| MS (M + H)+ Observ. | 546.3 |
| Retention Time | 1.68 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |

-continued

| | |
|---|---|
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.84 (d, J=8.1 Hz, 1H), 7.76 (d, J=7.7 Hz, 1H), 7.67 (br. s., 1H), 7.48-7.08 (m, 8H), 6.75-6.20 (m, 3H), 6.07-5.89 (m, 2H), 4.57 (br. s., 1H), 3.00 (br. s., 4H), 2.48 (s, 3H), 2.37 (br. s., 1H).

Example 84

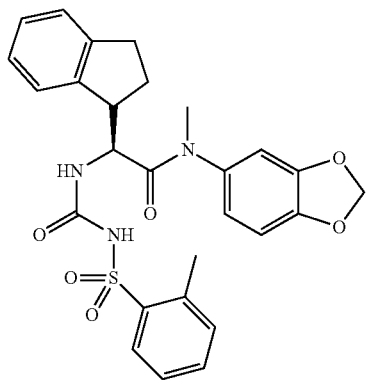 [SMILES: Cc1ccccc1S(=O)(=O)NC(=O)N[C@H](C(=O)N(C)c1ccc2c(c1)OCO2)C1CCc2ccccc21]

(S)—N-(benzo[d][1,3]dioxol-5-yl)-2-((S)-2,3-dihydro-1H-inden-1-yl)-N-methyl-2-(3-(o-tolylsulfonyl) ureido)acetamide

| | |
|---|---|
| MS (M + H)$^+$ Calcd. | 522.2 |
| MS (M + H)$^+$ Observ. | 522.3 |
| Retention Time | 1.87 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

Example 85

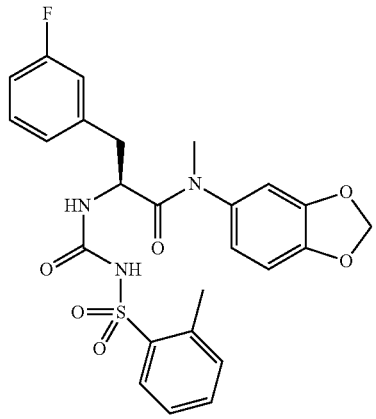

(S)—N-(benzo[d][1,3]dioxol-5-yl)-3-(3-fluorophenyl)-N-methyl-2-(3-(o-tolylsulfonyl) ureido)propanamide

| | |
|---|---|
| MS (M + H)$^+$ Calcd. | 514.1 |
| MS (M + H)$^+$ Observ. | 514.2 |
| Retention Time | 1.51 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (400 MHZ, MeOH-d$_4$) δ 7.95 (d, J=7.6 Hz, 1H), 7.54-7.41 (m, 1H), 7.39-7.27 (m, 2H), 7.25-7.12 (m, 1H), 6.92 (d, J=2.2 Hz, 1H), 6.73 (dd, J=13.1, 7.9 Hz, 2H), 6.63 (d, J=9.8 Hz, 1H), 6.50-6.23 (m, 2H), 6.00 (s, 2H), 4.57-4.43 (m, 1H), 3.13 (s, 3H), 2.95-2.57 (m, 5H).

Example 86 was synthesized using the procedure described above for Example 2 starting from (R)-tert-butyl (1-(benzo[d][1,3]dioxol-5-yl(methyl)amino)-1-oxo-3-phenylpropan-2-yl)carbamate.

Example 86

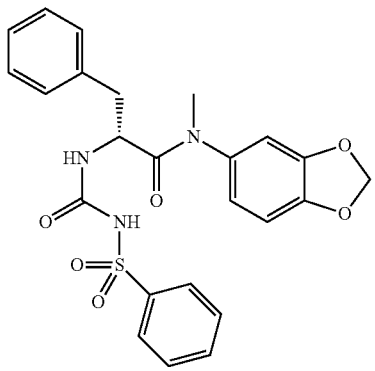 [SMILES: CN(C(=O)[C@@H](Cc1ccccc1)NC(=O)NS(=O)(=O)c1ccccc1)c1ccc2c(c1)OCO2]

(R)—N-(benzo[d][1,3]dioxol-5-yl)-N-methyl-3-phenyl2-(3phenylsulfonyl)ureido)propanamide

| | |
|---|---|
| MS (M + H)+ Calcd. | 482.1 |
| MS (M + H)+ Observ. | 482.2 |
| Retention Time | 1.67 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.66 (dd, J=7.8, 1.5 Hz, 2H), 7.36-7.31 (m, 3H), 7.23-7.10 (m, 4H), 6.93-6.76 (m, 4H), 6.64-6.56 (m, 2H), 6.06-5.98 (m, 2H), 4.27 (br. s., 1H), 3.05 (br. s., 3H), 2.76-2.51 (m, 2H)

Example 87

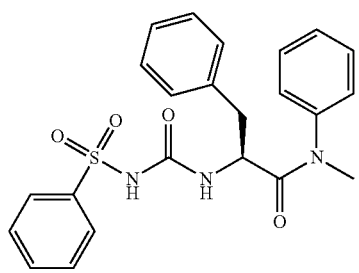 [SMILES: CN(C(=O)[C@H](Cc1ccccc1)NC(=O)NS(=O)(=O)c1ccccc1)c1ccccc1]

(S)—N-methyl-N, 3-diphenyl-2-(3-(phenylsulfonyl)ureido)propanamide

To a solution of (S)-tert-butyl (1 methyl(phenyl)amino)-1-oxo-3-phenylpropan-2-yl)carbamate, TFA (12.7 mg, 0.050 mmol) in dichloromethane (2 mL) was added diisopropylethylamine (0.026 mL, 0.15 mmol) followed by a solution of 2-methylbenzenesulfonyl isocyanate (13.7 mg, 0.075 mmol) in dichloromethane (2 mL). The reaction mixture was stirred at r.t. for 1 hr. The solvent was evaporated and the residue was purified by preparative HPLC to afford the title compound (16.9 mg).

$^1$H NMR (500 MHZ, DMSO-d$_6$) δ 7.76 (d, J=6.6 Hz, 2H), 7.64-7.33 (m, 6H), 7.14 (br. s., 5H), 6.72 (br. s., 2H), 6.58 (br. s., 1H), 4.29 (br. s., 1H), 3.13 (s, 3H), 2.73 (d, J=6.2 Hz, 2H).

| | |
|---|---|
| MS (M + H)+ Calcd. | 438.1 |
| MS (M + H)+ Observ. | 438.3 |
| Retention Time | 1.36 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm |

Examples 88-97 were synthesized using the procedure described above for Example 87.

Example 88

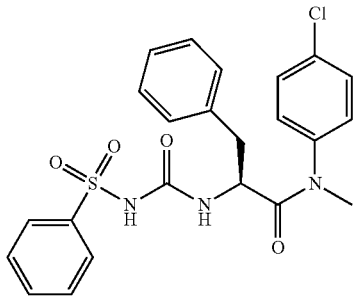

(S)—N-(4-chlorophenyl)-N-methyl-3-phenyl-2(3-phenylsulfonyl)ureido)propanamide

| | |
|---|---|
| MS (M + H)+ Calcd. | 472.1 |
| MS (M + H)+ Observ. | 472.2 |
| Retention Time | 1.56 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.77 (d, J=6.2 Hz, 2H), 7.60 (d, J=6.2 Hz, 1H), 7.54 (d, J=7.0 Hz, 2H), 7.43 (d, J=8.1 Hz, 2H), 7.23-7.05 (m, 5H), 6.79 (br. s., 2H), 6.63 (br. s., 1H), 4.24 (br. s., 1H), 3.09 (s, 3H), 2.81-2.64 (m, 2H).

Example 89

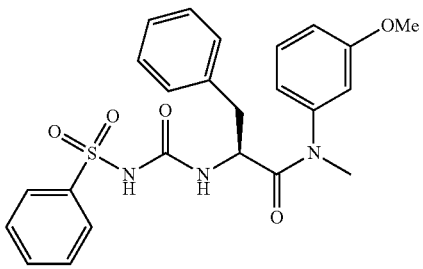 [SMILES: COc1cccc(N(C)C(=O)[C@H](Cc2ccccc2)NC(=O)NS(=O)(=O)c2ccccc2)c1]

(S)—N-(3-methoxyphenyl)-N-methyl-3-phenyl-2-(3-phenylsulfonyl)ureido)-propanamide

| MS (M + H)⁺ Calcd. | 468.2 |
| --- | --- |
| MS (M + H)⁺ Observ. | 468.3 |
| Retention Time | 1.44 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.76 (d, J=7.0 Hz, 2H), 7.62-7.43 (m, 3H), 7.28 (t, J=7.9 Hz, 1H), 7.15 (br. s., 3H), 6.92 (d, J=7.3 Hz, 1H), 6.77 (br. s., 3H), 6.66-6.46 (m, 2H), 4.34 (br. s., 1H), 3.70 (s, 3H), 3.11 (s, 3H), 2.81-2.68 (m, 2H).

Example 90

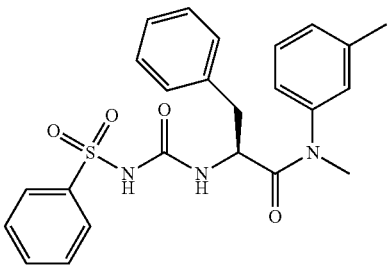 [SMILES: Cc1cccc(N(C)C(=O)[C@H](Cc2ccccc2)NC(=O)NS(=O)(=O)c2ccccc2)c1]

(S)—N-methyl-3-phenyl-2-(3-phenylsulfonyl)ureido)-N-(m-tolyl)propanamide

| MS (M + H)⁺ Calcd. | 452.2 |
| --- | --- |
| MS (M + H)⁺ Observ. | 452.3 |
| Retention Time | 1.50 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.79 (d, J=7.7 Hz, 2H), 7.70-7.47 (m, 3H), 7.32-7.23 (m, 1H), 7.17 (br. s., 4H), 6.91-6.72 (m, 4H), 6.66 (d, J=7.0 Hz, 1H), 4.27 (br. s., 4H), 3.09 (s, 3H), 2.81-2.68 (m, 2H), 2.51 (s, 3H).

Example 91

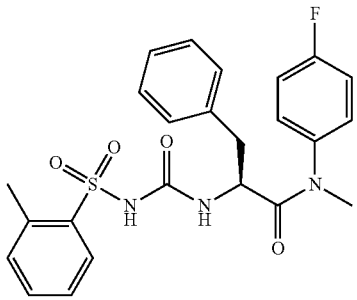 [SMILES: Cc1ccccc1S(=O)(=O)NC(=O)N[C@@H](Cc1ccccc1)C(=O)N(C)c1ccc(F)cc1]

(S)—N-(4-fluorophenyl)-N-methyl-3-phenyl-2(3-phenylsulfonyl)ureido)propanamide

| MS (M + H)⁺ Calcd. | 456.1 |
| --- | --- |
| MS (M + H)⁺ Observ. | 456.3 |
| Retention Time | 1.40 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.77 (d, J=7.7 Hz, 2H), 7.68-7.48 (m, 3H), 7.30-7.04 (m, 7H), 6.77 (br. s., 2H), 6.64 (d, J=6.6 Hz, 1H), 4.22 (d, J=5.5 Hz, 1H), 3.10 (s, 3H), 2.82-2.67 (m, 2H).

Example 92

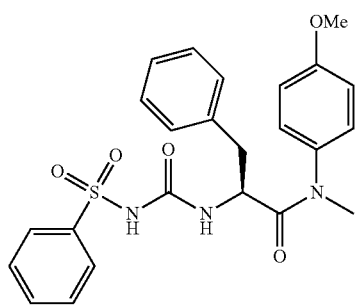 [SMILES: COc1ccc(N(C)C(=O)[C@H](Cc2ccccc2)NC(=O)NS(=O)(=O)c2ccccc2)cc1]

(S)—N-(4-methoxyphenyl)-N-methyl-3-phenyl-2(3-phenylsulfonyl)ureido)propanamide

| | |
|---|---|
| MS (M + H)+ Calcd. | 468.2 |
| MS (M + H)+ Observ. | 468.3 |
| Retention Time | 1.39 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.77 (d, J=7.7 Hz, 2H), 7.67-7.50 (m, 3H), 7.15 (d, J=2.9 Hz, 3H), 7.07-6.89 (m, 4H), 6.76 (br. s., 2H), 6.63 (d, J=7.7 Hz, 1H), 4.27 (br. s., 1H), 3.78 (s, 3H), 3.09 (s, 3H), 2.81-2.66 (m, 2H).

Example 93

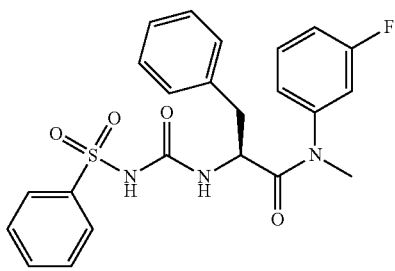 [SMILES: CN(C(=O)[C@H](Cc1ccccc1)NC(=O)NS(=O)(=O)c1ccccc1)c1cccc(F)c1]

(S)—N-(3-fluorophenyl)-N-methyl-3-phenyl-2(3-phenylsulfonyl) ureido)propanamide

| | |
|---|---|
| MS (M + H)+ Calcd. | 456.1 |
| MS (M + H)+ Observ. | 456.1 |
| Retention Time | 1.41 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (400 MHZ, MeOH-d$_4$) δ 7.88 (d, J=7.6 Hz, 2H), 7.65-7.46 (m, 3H), 7.39-7.29 (m, 1H), 7.26-7.17 (m, 3H), 7.09 (br. s., 1H), 6.90 (d, J=5.1 Hz, 2H), 6.81-6.74 (m, 1H), 6.59-6.46 (m, 1H), 4.47 (br. s., 1H), 3.16 (s, 3H), 2.96-2.63 (m, 2H).

Example 94

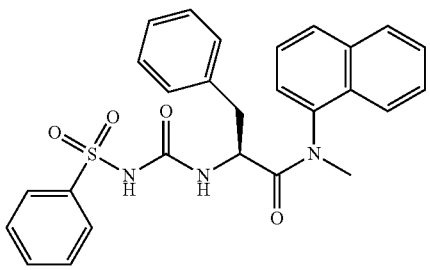 [SMILES: CN(C(=O)[C@H](Cc1ccccc1)NC(=O)NS(=O)(=O)c1ccccc1)c1cccc2ccccc12]

(S)—N-methyl-N-(naphthalen-1-yl)-3-phenyl-2-(3-(phenylsulfonyl)ureido)-propanamide

| | |
|---|---|
| MS (M + H)+ Calcd. | 488.2 |
| MS (M + H)+ Observ. | 488.2 |
| Retention Time | 1.47 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 8.09-7.76 (m, 3H), 7.68 (br. s., 3H), 7.58 (br. s., 2H), 7.50-7.35 (m, 3H), 7.32-7.18 (m, 2H), 7.14-7.03 (m, 2H), 6.61 (d, J=7.0 Hz, 1H), 6.51 (d, J=7.0 Hz, 1H), 4.19 (d, J=4.8 Hz, 1H), 3.23-3.08 (m, 3H), 2.86 (br. s., 2H).

Example 95

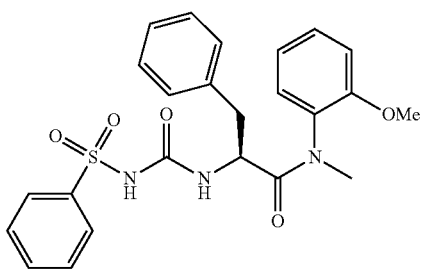 [SMILES: COc1ccccc1N(C)C(=O)[C@H](Cc1ccccc1)NC(=O)NS(=O)(=O)c1ccccc1]

(S)—N-(2-methoxyphenyl)-N-methyl-3-phenyl-2-(3 (phenylsulfonyl)ureido)-propanamide

| | |
|---|---|
| MS (M + H)+ Calcd. | 468.2 |
| MS (M + H)+ Observ. | 468.2 |
| Retention Time | 1.48 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

Example 96

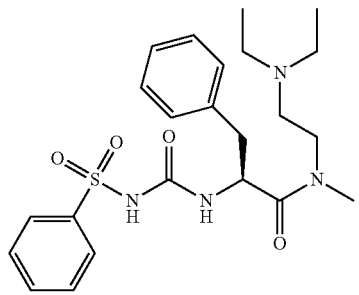 [SMILES: CCN(CC)CCN(C)C(=O)[C@H](Cc1ccccc1)NC(=O)NS(=O)(=O)c1ccccc1]

(S)—N-(2-(diethylamino)ethyl)-N-methyl-3-phenyl-2-(3-(phenylsulfonyl)ureido)propanamide

| | |
|---|---|
| MS (M + H)+ Calcd. | 461.2 |
| MS (M + H)+ Observ. | 461.4 |
| Retention Time | 1.84 min |
| | LC Condition |
| Solvent A | 5% Methanol:95% Water:10 mM Ammonium Acetate |
| Solvent B | 95% Methanol:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

Example 97

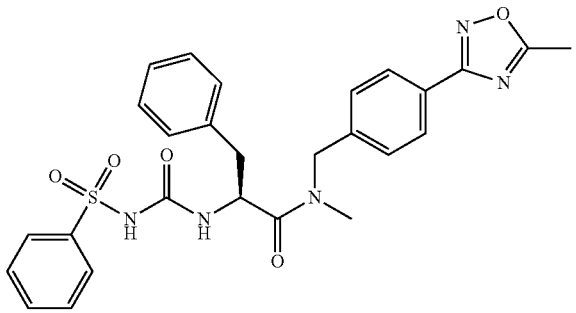 [SMILES: Cc1nc(-c2ccc(CN(C)C(=O)[C@H](Cc3ccccc3)NC(=O)NS(=O)(=O)c3ccccc3)cc2)no1]

(S)—N-methyl-N-(4-(5-methyl-1,2,4-oxadiazol-3-yl)benzyl)-3-phenyl-2-(3-(phenylsulfonyl)ureido)propanamide

| | |
|---|---|
| MS (M + H)+ Calcd. | 534.2 |
| MS (M + H)+ Observ. | 534.3 |
| Retention Time | 2.37 min |
| | LC Condition |
| Solvent A | 5% Methanol:95% Water:10 mM Ammonium Acetate |
| Solvent B | 95% Methanol:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (400 MHZ, MeOH-d$_4$) δ 8.07-7.88 (m, 4H), 7.63-7.43 (m, 3H), 7.31-6.92 (m, 7H), 4.60-4.31 (m, 3H), 3.22-2.90 (m, 2H), 2.80 (s, 3H), 2.67 (s, 3H).

Examples 98-120 were synthesized using the procedure described above for Example 3.

Example 98

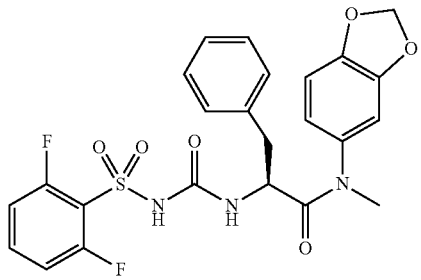 [SMILES: CN(C(=O)[C@H](Cc1ccccc1)NC(=O)NS(=O)(=O)c1c(F)cccc1F)c1ccc2c(c1)OCO2]

(S)—N-(benzo[d][1,3]dioxol-5-yl)-2-(3-((2,6-difluorophenyl)sulfonyl)ureido)-N-methyl-3-phenylpropanamide

| | |
|---|---|
| MS (M + H)+ Calcd. | 518.1 |
| MS (M + H)+ Observ. | 518.4 |
| Retention Time | 1.65 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.41 (br. s., 1H), 7.31-7.09 (m, 4H), 7.07-6.78 (m, 5H), 6.73-6.42 (m, 2H), 6.05 (s, 2H), 4.27 (br. s., 1H), 3.18 (s, 3H), 2.73-2.52 (m, 2H).

Example 99

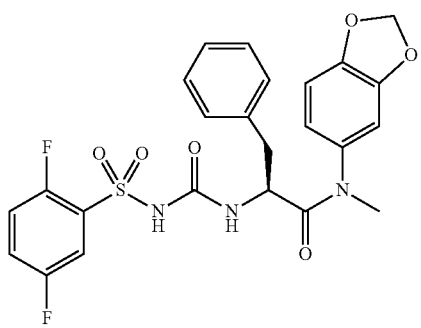 [SMILES: CN(C(=O)[C@H](Cc1ccccc1)NC(=O)NS(=O)(=O)c1cc(F)ccc1F)c1ccc2c(c1)OCO2]

(S)—N-(benzo[d][1,3]dioxol-5-yl)-2-(3-((2,5-difluorophenyl)sulfonyl)ureido)-N-methyl-3-phenylpropanamide

| | |
|---|---|
| MS (M + H)+ Calcd. | 518.1 |
| MS (M + H)+ Observ. | 518.3 |
| Retention Time | 1.48 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.49-7.09 (m, 7H), 6.92-6.78 (m, 3H), 6.73-6.52 (m, 2H), 6.06 (s, 2H), 4.26 (br. s., 1H), 3.06 (s, 3H), 2.79-2.53 (m, 2H).

Example 100

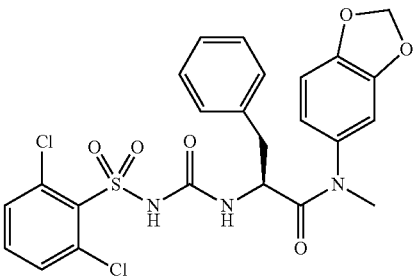 [SMILES: CN(C(=O)[C@H](Cc1ccccc1)NC(=O)NS(=O)(=O)c1c(Cl)cccc1Cl)c1ccc2c(c1)OCO2]

(S)—N-(benzo[d][1,3]dioxol-5-yl)-2-(3-((2,6-dichlorophenyl)sulfonyl) ureido)-N-methyl-3-phenylpropanamide

| | |
|---|---|
| MS (M + H)+ Calcd. | 550.1 |
| MS (M + H)+ Observ. | 550.4 |
| Retention Time | 1.55 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.68-7.41 (m, 3H), 7.17 (d, J=7.3 Hz, 4H), 6.96-6.79 (m, 3H), 6.75-6.47 (m, 2H), 6.07 (s, 2H), 4.30 (br. s., 1H), 3.08 (s, 3H), 2.79-2.53 (m, 2H).

Example 101

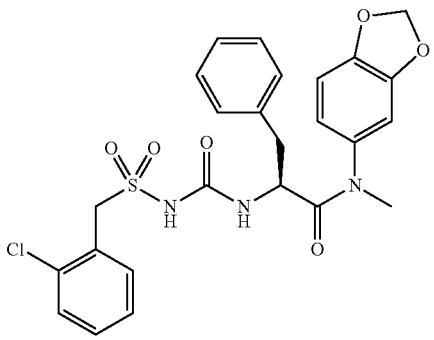 [SMILES: CN(C(=O)[C@H](Cc1ccccc1)NC(=O)NS(=O)(=O)Cc1ccccc1Cl)c1ccc2c(c1)OCO2]

(S)—N-(benzo[d][1,3]dioxol-5-yl)-2-(3-((2-chlorobenzyl)sulfonyl) ureido)-N-methyl-3-phenylpropanamide

| | |
|---|---|
| MS (M + H)+ Calcd. | 530.1 |
| MS (M + H)+ Observ. | 530.4 |
| Retention Time | 1.39 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.46 (d, J=8.4 Hz, 1H), 7.38-7.14 (m, 7H), 7.02-6.88 (m, 3H), 6.82-6.57 (m, 2H), 6.11 (s, 2H), 4.72-4.46 (m, 3H), 3.11 (s, 3H), 2.89-2.56 (m, 2H).

Example 102

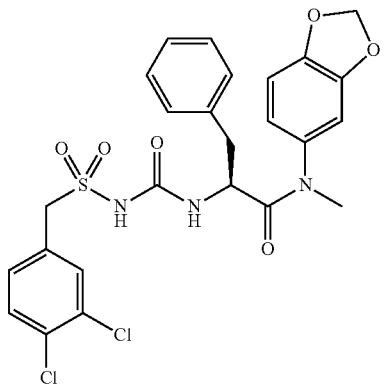 [SMILES: CN(C(=O)[C@H](Cc1ccccc1)NC(=O)NS(=O)(=O)Cc1ccc(Cl)c(Cl)c1)c1ccc2c(c1)OCO2]

(S)—N-(benzo[d][1,3]dioxol-5-yl)-2-(3-((3,4-dichlorobenzyl)sulfonyl) ureido)-N-methyl-3-phenylpropanamide

| | |
|---|---|
| MS (M + H)+ Calcd. | 564.1 |
| MS (M + H)+ Observ. | 564.4 |
| Retention Time | 1.53 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.60-7.42 (m, 2H), 7.32-7.11 (m, 4H), 7.03-6.85 (m, 3H), 6.83-6.58 (m, 2H), 6.10 (s, 2H), 4.51-4.26 (m, 3H), 3.11 (s, 3H), 2.85-2.55 (m, 2H).

Example 103

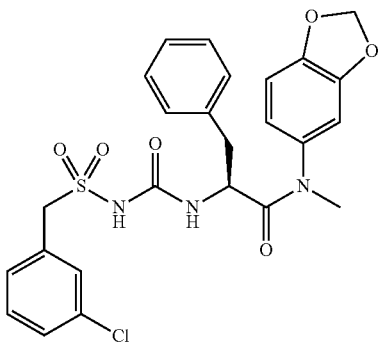 [SMILES: CN(C(=O)[C@H](Cc1ccccc1)NC(=O)NS(=O)(=O)Cc1cccc(Cl)c1)c1ccc2c(c1)OCO2]

(S)—N-(benzo[d][1,3]dioxol-5-yl)-2-(3-((3-chlorobenzyl)sulfonyl)ureido)-N-methyl-3-phenylpropanamide

| | |
|---|---|
| MS (M + H)+ Calcd. | 530.1 |
| MS (M + H)+ Observ. | 530.2 |
| Retention Time | 1.55 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.49-7.07 (m, 7H), 7.02-6.84 (m, 3H), 6.68-6.26 (m, 3H), 6.11 (s, 2H), 4.48 (br. s., 3H), 3.11 (s, 3H), 2.88-2.56 (m, 2H).

Example 104

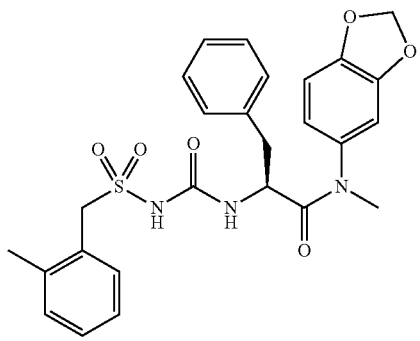 [SMILES: Cc1ccccc1CS(=O)(=O)NC(=O)N[C@@H](Cc1ccccc1)C(=O)N(C)c1ccc2c(c1)OCO2]

(S)—N-(benzo[d][1,3]dioxol-5-yl)-N-methyl-2-(3-((2-methylbenzyl)sulfonyl)ureido)-3-phenylpropanamide

| | |
|---|---|
| MS (M + H)⁺ Calcd. | 510.2 |
| MS (M + H)⁺ Observ. | 510.3 |
| Retention Time | 1.61 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.35-7.04 (m, 8H), 7.01-6.86 (m, 3H), 6.83-6.60 (m, 2H), 6.11 (s, 2H), 4.58-4.38 (m, 3H), 3.12 (s, 3H), 2.89-2.56 (m, 2H), 2.31 (s, 3H).

Example 105

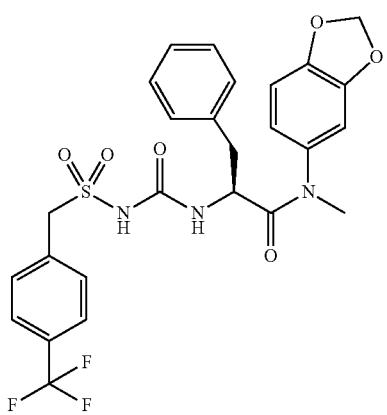 [SMILES: CN(C(=O)[C@H](Cc1ccccc1)NC(=O)NS(=O)(=O)Cc1ccc(C(F)(F)F)cc1)c1ccc2c(c1)OCO2]

(S)—N-(benzo[d][1,3]dioxol-5-yl)-N-methyl-3-phenyl-2-(3-((4-(trifluoromethyl)benzyl)sulfonyl) ureido)propanamide

| | |
|---|---|
| MS (M + H)⁺ Calcd. | 564.1 |
| MS (M + H)⁺ Observ. | 564.2 |
| Retention Time | 1.63 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.64 (d, J=6.6 Hz, 2H), 7.41 (d, J=7.7 Hz, 2H), 7.27-7.21 (m, 3H), 7.03-6.64 (m, 5H), 6.11 (br. s., 2H), 4.64-4.36 (m, 3H), 3.13 (s, 3H), 2.87-2.54 (m, 2H).

Example 106

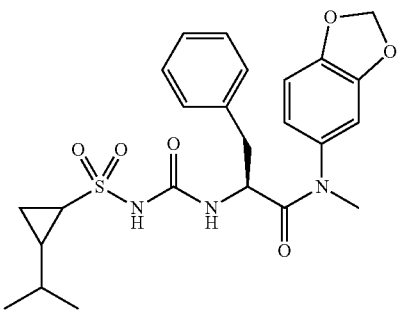 [SMILES: CC(C)C1CC1S(=O)(=O)NC(=O)N[C@@H](Cc1ccccc1)C(=O)N(C)c1ccc2c(c1)OCO2]

(2S)—N-(benzo[d][1,3]dioxol-5-yl)-2-(3-((2-isopropylcyclopropyl)sulfonyl) ureido)-N-methyl-3-phenylpropanamide

| | |
|---|---|
| MS (M + H)⁺ Calcd. | 488.2 |
| MS (M + H)⁺ Observ. | 488.5 |
| Retention Time | 1.60 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.31-7.16 (m, 3H), 7.00-6.83 (m, 3H), 6.80-6.52 (m, 3H), 6.10 (s, 2H), 4.43 (br. s., 1H), 3.09 (s, 3H), 2.89-2.56 (m, 2H), 1.28-1.00 (m, 3H), 0.96-0.74 (m, 8H).

Example 107

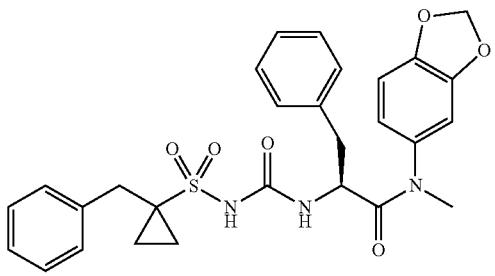 [SMILES: CN(C(=O)[C@H](Cc1ccccc1)NC(=O)NS(=O)(=O)C1(Cc2ccccc2)CC1)c1ccc2c(c1)OCO2]

(S)—N-(benzo[d][1,3]dioxol-5-yl)-2-(3-((1-benzyl-cyclopropyl)sulfonyl)ureido)-N-methyl-3-phenylpropanamide

| MS (M + H)$^+$ Calcd. | 536.2 |
| MS (M + H)$^+$ Observ. | 536.3 |
| Retention Time | 1.82 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.34-7.16 (m, 6H), 7.13 (d, J=7.0 Hz, 2H), 7.00-6.85 (m, 3H), 6.81-6.55 (m, 3H), 6.11 (d, J=4.8 Hz, 2H), 4.45 (d, J=5.9 Hz, 1H), 3.22-3.06 (m, 5H), 2.89-2.55 (m, 2H), 1.34-1.11 (m, 2H), 0.57 (br. s., 2H).

Example 108

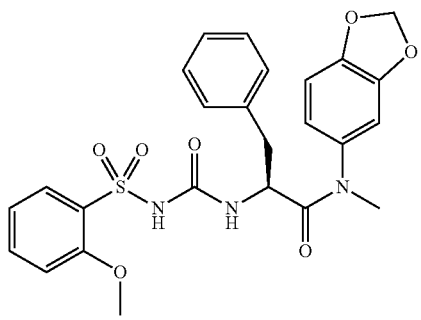 [SMILES: COc1ccccc1S(=O)(=O)NC(=O)N[C@@H](Cc1ccccc1)C(=O)N(C)c1ccc2c(c1)OCO2]

(S)—N-(benzo[d][1,3]dioxol-5-yl)-2-(3-((2-methoxyphenyl)sulfonyl)ureido)-N-methyl-3-phenylpropanamide

| MS (M + H)$^+$ Calcd. | 512.1 |
| MS (M + H)$^+$ Observ. | 512.2 |
| Retention Time | 1.51 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.69 (d, J=8.8 Hz, 1H), 7.62-7.52 (m, 1H), 7.18 (d, J=7.0 Hz, 4H), 7.04 (t, J=7.3 Hz, 1H), 6.91-6.77 (m, 3H), 6.70-6.45 (m, 3H), 6.06 (s, 2H), 4.28 (d, J=5.9 Hz, 1H), 3.81 (s, 3H), 3.06 (s, 3H), 2.85-2.45 (m, 2H).

Example 109

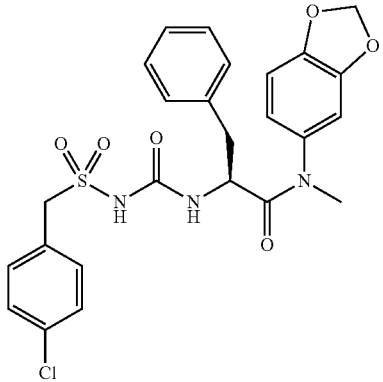 [SMILES: CN(C(=O)[C@H](Cc1ccccc1)NC(=O)NS(=O)(=O)Cc1ccc(Cl)cc1)c1ccc2c(c1)OCO2]

(S)—N-(benzo[d][1,3]dioxol-5-yl)-2-(3-((4-chlorobenzyl)sulfonyl)ureido)-N-methyl-3-phenylpropanamide

| MS (M + H)$^+$ Calcd. | 530.1 |
| MS (M + H)$^+$ Observ. | 530.2 |
| Retention Time | 1.56 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |

| Column | Waters BEH C18, 2.0 × 50 mm, 1.7-μm particles |

$^1$H NMR (500 MHZ, DMSO-d$_6$) δ 7.40 (d, J=8.4 Hz, 2H), 7.33-7.15 (m, 5H), 7.00 (d, J=8.1 Hz, 1H), 6.92 (d, J=7.0 Hz, 2H), 6.85-6.49 (m, 3H), 6.13 (d, J=5.1 Hz, 2H), 4.64-4.44 (m, 3H), 3.14 (s, 3H), 2.95-2.56 (m, 2H).

Example 110

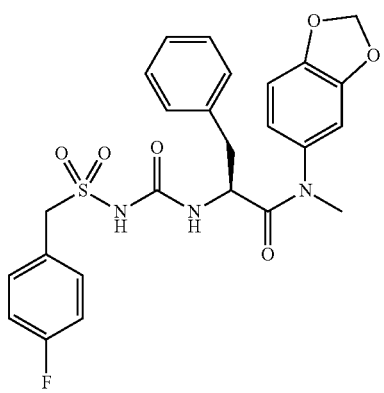

(S)—N-(benzo[d][1,3]dioxol-5-yl)-2-(3-((4-fluorobenzyl)sulfonyl) ureido)-N-methyl-3-phenylpropanamide

| MS (M + H)$^+$ Calcd. | 514.1 |
| MS (M + H)$^+$ Observ. | 514.2 |
| Retention Time | 1.49 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.23 (d, J=5.9 Hz, 6H), 7.10 (br. s., 2H), 7.01-6.87 (m, 3H), 6.85-6.61 (m, 2H), 6.11 (s, 2H), 4.52-4.26 (m, 3H), 3.12 (s, 3H), 2.87-2.55 (m, 2H).

Example 111

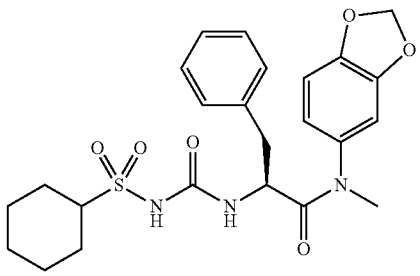

(S)—N-(benzo[d][1,3]dioxol-5-yl)-2-(3-(cyclohexylsulfonyl) ureido)-N-methyl-3-phenylpropanamide

| MS (M + H)$^+$ Calcd. | 488.2 |
| MS (M + H)$^+$ Observ. | 488.5 |
| Retention Time | 1.54 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (400 MHZ, MeOH-d$_4$) δ 7.31-7.20 (m, 3H), 6.97 (dd, J=7.3, 2.0 Hz, 2H), 6.84 (d, J=8.3 Hz, 1H), 6.59 (d, J=9.8 Hz, 2H), 6.04 (s, 2H), 4.61 (br. s., 1H), 3.33 (dt, J=3.2, 1.7 Hz, 1H), 3.19 (s, 3H), 2.73 (dd, J=13.4, 8.3 Hz, 2H), 2.09-1.17 (m, 10H).

Example 112

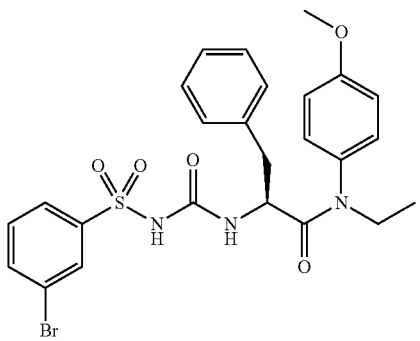 [SMILES: CCN(C(=O)[C@H](Cc1ccccc1)NC(=O)NS(=O)(=O)c1cccc(Br)c1)c1ccc(OC)cc1]

(S)-2-(3-(((3-bromophenyl)sulfonyl)ureido)-N-ethyl-N-(4-methoxyphenyl)-3-phenylpropanamide

| | |
|---|---|
| MS (M + H)+ Calcd. | 560.1 |
| MS (M + H)+ Observ. | 560.2 |
| Retention Time | 1.62 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.90 (br. s., 1H), 7.85-7.68 (m, 2H), 7.48 (t, J=8.3 Hz, 1H), 7.15 (d, J=2.2 Hz, 3H), 6.93 (br. s., 4H), 6.80 (br. s., 2H), 6.48 (br. s., 1H), 4.17 (d, J=6.6 Hz, 1H), 3.79 (s, 3H), 3.67-3.41 (m, 2H), 2.80-2.45 (m, 2H), 0.95 (t, J=7.0 Hz, 3H).

Example 113

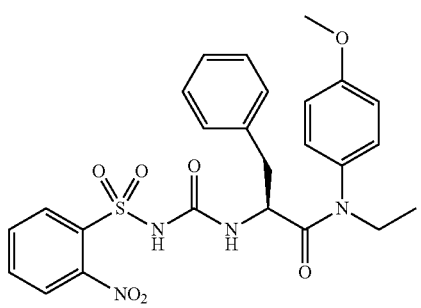 [SMILES: CCN(C(=O)[C@H](Cc1ccccc1)NC(=O)NS(=O)(=O)c1ccccc1[N+](=O)[O-])c1ccc(OC)cc1]

(S)—N-ethyl-N-(4-methoxyphenyl)-2-(3-((2-nitrophenyl)sulfonyl)ureido)-3-phenylpropanamide

| | |
|---|---|
| MS (M + H)+ Calcd. | 527.2 |
| MS (M + H)+ Observ. | 527.2 |
| Retention Time | 1.49 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 8.06-7.95 (m, 2H), 7.91 (t, J=7.2 Hz, 1H), 7.85-7.78 (m, 1H), 7.18-7.07 (m, 3H), 7.04-6.90 (m, 4H), 6.89-6.73 (m, 3H), 4.26-4.15 (m, 1H), 3.79 (s, 3H), 3.68-3.43 (m, 2H), 2.83-2.44 (m, 2H), 0.96 (t, J=7.2 Hz, 3H).

Example 114

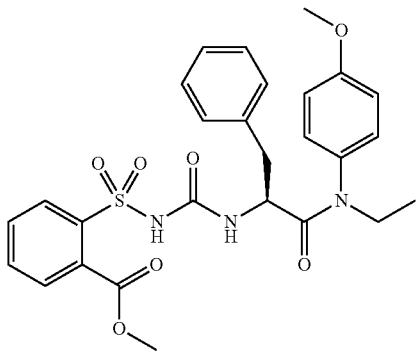 [SMILES: CCN(C(=O)[C@H](Cc1ccccc1)NC(=O)NS(=O)(=O)c1ccccc1C(=O)OC)c1ccc(OC)cc1]

(S)-methyl 2-(N-((1-(ethyl(4-methoxyphenyl)amino)-1-oxo-3-phenylpropan-2-yl)carbamoyl)sulfamoyl)benzoate

| | |
|---|---|
| MS (M + H)+ Calcd. | 540.2 |
| MS (M + H)+ Observ. | 540.2 |
| Retention Time | 1.50 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.93 (d, J=7.7 Hz, 1H), 7.80-7.73 (m, 1H), 7.69 (d, J=5.1 Hz, 2H), 7.17-7.09 (m, 3H), 7.03-6.85 (m, 5H), 6.80 (d, J=3.3 Hz, 2H), 4.24-4.13 (m, 1H), 3.86 (s, 3H), 3.78 (s, 3H), 3.67-3.44 (m, 2H), 2.82-2.43 (m, 2H), 0.96 (t, J=7.2 Hz, 3H).

Example 115

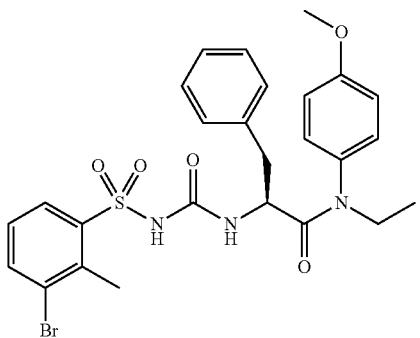 [SMILES: CCN(C(=O)[C@H](Cc1ccccc1)NC(=O)NS(=O)(=O)c1cccc(Br)c1C)c1ccc(OC)cc1]

(S)-2-(3-((3-bromo-2-methylphenyl)sulfonyl)ureido)-N-ethyl-N-(4-methoxyphenyl)-3-phenylpropanamide

| MS (M + H)⁺ Calcd. | 574.1 |
| --- | --- |
| MS (M + H)⁺ Observ. | 574.2 |
| Retention Time | 1.70 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.77 (d, J=7.3 Hz, 1H), 7.69 (br. s., 1H), 7.14 (br. s., 5H), 7.00-6.73 (m, 6H), 4.12 (d, J=5.9 Hz, 1H), 3.77 (s, 3H), 3.66-3.41 (m, 2H), 2.72-2.44 (m, 5H), 0.94 (br. s., 3H).

Example 116

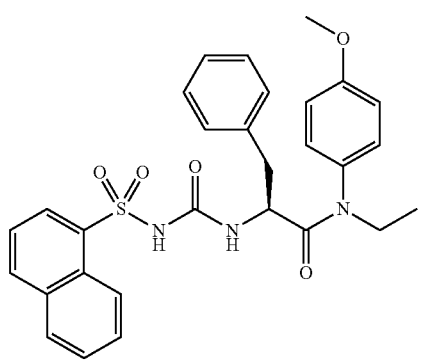 [SMILES: CCN(C(=O)[C@H](Cc1ccccc1)NC(=O)NS(=O)(=O)c1cccc2ccccc12)c1ccc(OC)cc1]

(S)—N-ethyl-N-(4-methoxyphenyl)-2-(3-(naphthalen-1-ylsulfonyl)ureido)-3-phenylpropanamide

| MS (M + H)⁺ Calcd. | 532.2 |
| --- | --- |
| MS (M + H)⁺ Observ. | 532.2 |
| Retention Time | 1.65 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 8.59 (d, J=7.7 Hz, 1H), 8.22 (d, J=8.1 Hz, 1H), 8.11 (d, J=7.0 Hz, 2H), 7.78-7.54 (m, 3H), 7.12-7.04 (m, 1H), 7.03-6.95 (m, 2H), 6.81 (br. s., 4H), 6.66 (d, J=7.3 Hz, 2H), 4.13-4.01 (m, 1H), 3.73 (s, 3H), 3.62-3.37 (m, 2H), 2.69-2.33 (m, 2H), 0.91 (t, J=7.0 Hz, 3H).

Example 117

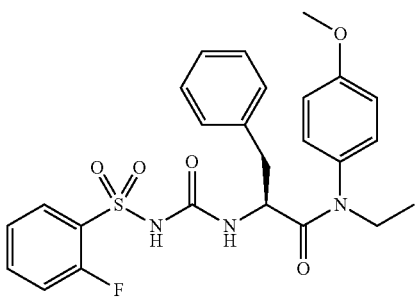 [SMILES: CCN(C(=O)[C@H](Cc1ccccc1)NC(=O)NS(=O)(=O)c1ccccc1F)c1ccc(OC)cc1]

(S)—N-ethyl-2-(3-((2-fluorophenyl)sulfonyl)ureido)-N-(4-methoxyphenyl)-3-phenylpropanamide

| MS (M + H)⁺ Calcd. | 500.2 |
| --- | --- |
| MS (M + H)⁺ Observ. | 500.1 |
| Retention Time | 1.40 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.63 (t, J=7.7 Hz, 1H), 7.42 (br. s., 1H), 7.22-7.08 (m, 6H), 6.93-6.78 (m, 6H), 4.15 (br. s., 1H), 3.77 (s, 3H), 3.66-3.25 (m, 2H), 2.72-2.52 (m, 2H), 0.94 (t, J=6.2 Hz, 3H).

Example 118

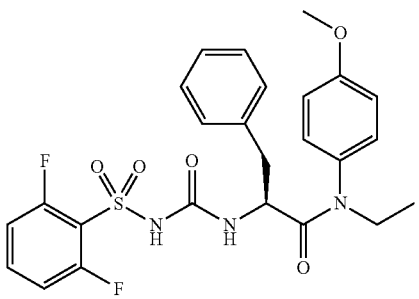 [SMILES: CCN(C(=O)[C@H](Cc1ccccc1)NC(=O)NS(=O)(=O)c1c(F)cccc1F)c1ccc(OC)cc1]

(S)-2-(3-((2,6-difluorophenyl)sulfonyl) ureido)-N-ethyl-N-(4-methoxyphenyl)-3-phenylpropanamide

| | |
|---|---|
| MS (M + H)+ Calcd. | 518.2 |
| MS (M + H)+ Observ. | 518.1 |
| Retention Time | 1.47 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.45 (br. s., 1H), 7.22-7.11 (m, 4H), 7.04 (br. s., 2H), 6.94-6.79 (m, 6H), 4.17 (br. s., 1H), 3.76 (s, 3H), 3.60-3.44 (m, 2H), 2.73-2.46 (m, 2H), 0.93 (t, J=5.9 Hz, 3H).

Example 119

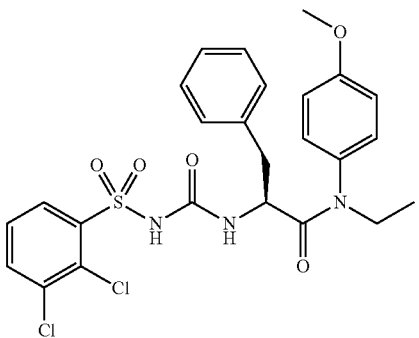 [SMILES: CCN(C(=O)[C@H](Cc1ccccc1)NC(=O)NS(=O)(=O)c1cccc(Cl)c1Cl)c1ccc(OC)cc1]

(S)-2-(3-((2,3-dichlorophenyl)sulfonyl) ureido)-N-ethyl-N-(4-methoxyphenyl)-3-phenylpropanamide

| | |
|---|---|
| MS (M + H)+ Calcd. | 550.1 |
| MS (M + H)+ Observ. | 550.2 |
| Retention Time | 1.62 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.84 (d, J=7.7 Hz, 1H), 7.74 (br. s., 1H), 7.38 (br. s., 1H), 7.19-7.11 (m, 3H), 6.98-6.76 (m, 6H), 4.19-4.09 (m, 1H), 3.76 (s, 3H), 3.69-3.40 (m, 2H), 2.76-2.45 (m, 2H), 0.95 (t, J=6.6 Hz, 3H).

Example 120

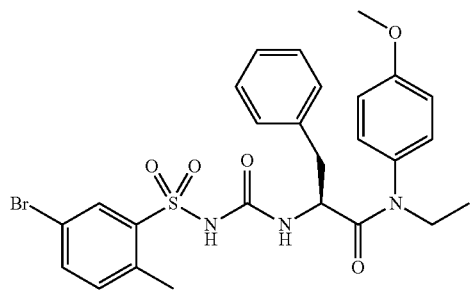

(S)-2-(3-((5-bromo-2-methylphenyl)sulfonyl) ureido)-N-ethyl-N-(4-methoxyphenyl)-3-phenylpropanamide

| | |
|---|---|
| MS (M + H)+ Calcd. | 574.1 |
| MS (M + H)+ Observ. | 574.2 |
| Retention Time | 1.76 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.87 (s, 1H), 7.71 (d, J=7.3 Hz, 1H), 7.34 (d, J=8.1 Hz, 1H), 7.15-7.14 (m, 3H), 6.93 (br. s., 4H), 6.77 (d, J=3.3 Hz, 2H), 6.50 (br. s., 1H), 4.16 (d, J=7.0 Hz, 1H), 3.78 (s, 3H), 3.67-3.43 (m, 2H), 2.79-2.38 (m, 5H), 0.95 (t, J=7.2 Hz, 3H).

Examples 121-133 were synthesized using the procedure described above for Example 48.

Example 121

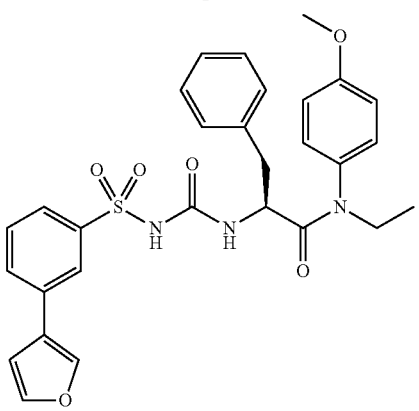 [SMILES: CCN(C(=O)[C@H](Cc1ccccc1)NC(=O)NS(=O)(=O)c1cccc(-c2ccoc2)c1)c1ccc(OC)cc1]

(S)—N-ethyl-2-(3-((3-(furan-3-yl)phenyl)sulfonyl)ureido)-N-(4-methoxyphenyl)-3-phenylpropanamide

| | |
|---|---|
| MS (M + H)+ Calcd. | 548.2 |
| MS (M + H)+ Observ. | 548.2 |
| Retention Time | 1.67 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 8.31 (s, 1H), 7.98 (br. s., 1H), 7.86 (d, J=6.6 Hz, 1H), 7.81 (s, 1H), 7.65 (d, J=7.3 Hz, 1H), 7.55 (t, J=7.7 Hz, 1H), 7.13 (br. s., 3H), 7.00 (s, 1H), 6.97-6.55 (m, 7H), 4.22-4.11 (m, 1H), 3.75 (s, 3H), 3.66-3.42 (m, 2H), 2.80-2.46 (m, 2H), 0.92 (t, J=7.0 Hz, 3H).

Example 122

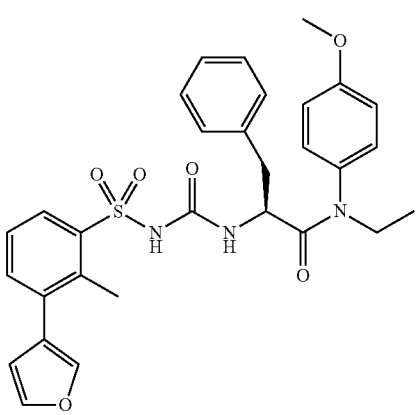 [SMILES: CCN(C(=O)[C@H](Cc1ccccc1)NC(=O)NS(=O)(=O)c1cccc(-c2ccoc2)c1C)c1ccc(OC)cc1]

(S)—N-ethyl-2-(3-((3-(furan-3-yl)-2-methylphenyl)sulfonyl)ureido)-N-(4-methoxyphenyl)-3-phenylpropanamide

| | |
|---|---|
| MS (M + H)+ Calcd. | 562.2 |
| MS (M + H)+ Observ. | 562.3 |
| Retention Time | 1.74 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.88 (s, 1H), 7.83-7.76 (m, 2H), 7.54 (d, J=7.3 Hz, 1H), 7.36 (t, J=7.9 Hz, 1H), 7.13 (d, J=2.6 Hz, 3H), 7.02-6.86 (m, 4H), 6.82-6.43 (m, 4H), 4.21-4.09 (m, 1H), 3.77 (s, 3H), 3.68-3.41 (m, 2H), 2.81-2.45 (m, 5H), 0.93 (t, J=7.0 Hz, 3H).

Example 123

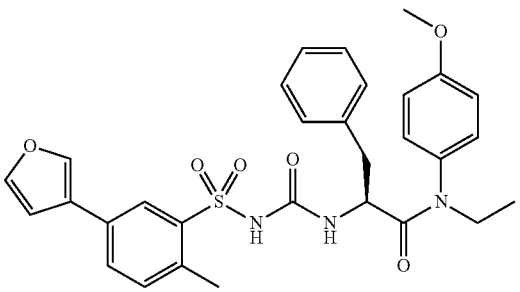 [SMILES: CCN(C(=O)[C@H](Cc1ccccc1)NC(=O)NS(=O)(=O)c1cc(-c2ccoc2)ccc1C)c1ccc(OC)cc1]

(S)—N-ethyl-2-(3-((5-(furan-3-yl)-2-methylphenyl)sulfonyl)ureido)-N-(4-methoxyphenyl)-3-phenylpropanamide

| | |
|---|---|
| MS (M + H)+ Calcd. | 562.2 |
| MS (M + H)+ Observ. | 562.3 |
| Retention Time | 1.87 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 8.26 (s, 1H), 7.98 (s, 1H), 7.83-7.74 (m, 2H), 7.43 (d, J=8.1 Hz, 1H), 7.21-7.09

(m, 3H), 7.00-6.83 (m, 5H), 6.76 (br. s., 2H), 6.70 (d, J=8.4 Hz, 1H), 4.22-4.07 (m, 1H), 3.73 (s, 3H), 3.67-3.41 (m, 2H), 2.80-2.42 (m, 5H), 0.93 (t, J=7.2 Hz, 3H).

Example 124

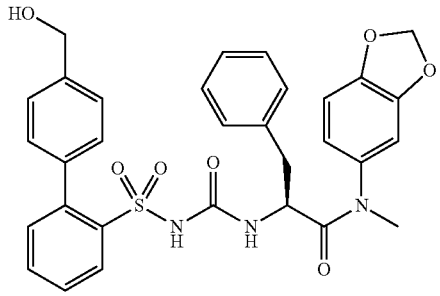 [SMILES: CN(C(=O)[C@H](Cc1ccccc1)NC(=O)NS(=O)(=O)c1ccccc1-c1ccc(CO)cc1)c1ccc2c(c1)OCO2]

(S)—N-(benzo[d][1,3]dioxol-5-yl)-2-(3-((4'-(hydroxymethyl)-[1,1'-biphenyl]-2-yl)sulfonyl) ureido)-N-methyl-3-phenylpropanamide

| | |
|---|---|
| MS (M + H)+ Calcd. | 588.2 |
| MS (M + H)+ Observ. | 588.2 |
| Retention Time | 1.57 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.92 (d, J=8.1 Hz, 1H), 7.70-7.59 (m, 1H), 7.53 (d, J=7.3 Hz, 1H), 7.36-7.08 (m, 9H), 6.91 (d, J=7.7 Hz, 1H), 6.86 (d, J=7.0 Hz, 2H), 6.71-6.48 (m, 3H), 6.08 (s, 2H), 4.58 (br. s., 2H), 4.31 (br. s., 1H), 3.08 (s, 3H), 2.98-2.77 (m, 2H).

Example 125

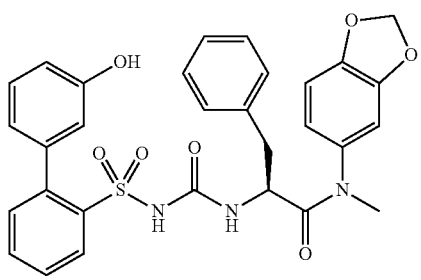 [SMILES: CN(C(=O)[C@H](Cc1ccccc1)NC(=O)NS(=O)(=O)c1ccccc1-c1cccc(O)c1)c1ccc2c(c1)OCO2]

(S)—N-(benzo[d][1,3]dioxol-5-yl)-2-(3-((3'-hydroxy-[1,1'-biphenyl]-2-yl)sulfonyl) ureido)-N-methyl-3-phenylpropanamide

| | |
|---|---|
| MS (M + H)+ Calcd. | 574.2 |
| MS (M + H)+ Observ. | 574.2 |
| Retention Time | 1.56 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.90 (d, J=7.3 Hz, 1H), 7.69-7.61 (m, 1H), 7.54 (t, J=7.9 Hz, 1H), 7.33-7.03 (m, 8H), 6.94-6.75 (m, 3H), 6.67 (br. s., 2H), 6.60-6.45 (m, 2H), 6.07 (s, 2H), 4.30 (d, J=6.6 Hz, 1H), 3.06 (s, 3H), 2.99-2.76 (m, 2H).

Example 126

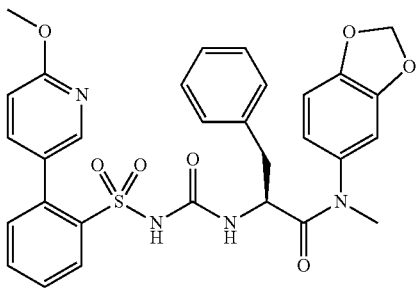 [SMILES: COc1ccc(-c2ccccc2S(=O)(=O)NC(=O)N[C@@H](Cc2ccccc2)C(=O)N(C)c2ccc3c(c2)OCO3)cn1]

(S)—N-(benzo[d][1,3]dioxol-5-yl)-2-(3-((2-(6-methoxypyridin-3-yl)phenyl)sulfonyl) ureido)-N-methyl-3-phenylpropanamide

| | |
|---|---|
| MS (M + H)+ Calcd. | 589.2 |
| MS (M + H)+ Observ. | 589.2 |
| Retention Time | 1.55 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 8.00-7.92 (m, 1H), 7.70 (s, 1H), 7.59 (s, 1H), 7.53-7.46 (m, 1H), 7.33 (d, J=7.3

Hz, 2H), 7.23-7.18 (m, 6H), 6.91 (d, J=8.4 Hz, 1H), 6.87-6.79 (m, 2H), 6.70-6.49 (m, 2H), 6.08 (s, 2H), 4.35-4.24 (m, 1H), 3.93 (s, 3H), 3.07 (s, 3H), 2.98-2.75 (m, 2H).

Example 127

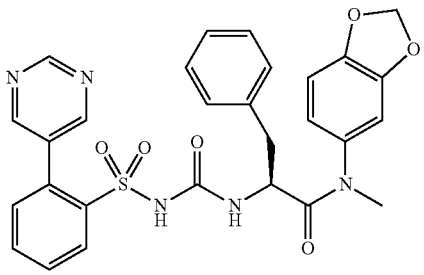

(S)—N-(benzo[d][1,3]dioxol-5-yl)-N-methyl-3-phenyl-2-(3-((2-(pyrimidin-5-yl)phenyl)sulfonyl)ureido)propanamide

| MS (M + H)⁺ Calcd. | 560.2 |
| --- | --- |
| MS (M + H)⁺ Observ. | 560.2 |
| Retention Time | 1.35 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 9.25 (s, 1H), 8.65 (br. s., 2H), 8.00 (d, J=8.1 Hz, 1H), 7.77 (s, 1H), 7.69 (d, J=8.1 Hz, 1H), 7.44 (d, J=7.3 Hz, 1H), 7.23-7.20 (m, 3H), 6.92 (d, J=8.1 Hz, 1H), 6.85 (d, J=7.0 Hz, 2H), 6.72-6.53 (m, 3H), 6.08 (s, 2H), 4.29 (d, J=6.6 Hz, 1H), 3.07 (s, 3H), 2.98-2.76 (m, 2H).

Example 128

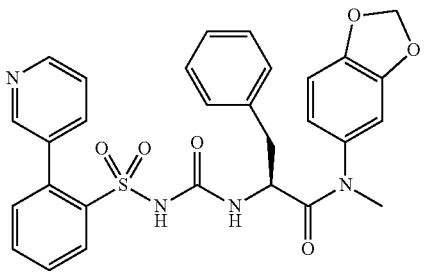 [SMILES: CN(C(=O)[C@H](Cc1ccccc1)NC(=O)NS(=O)(=O)c1ccccc1-c1cccnc1)c1ccc2c(c1)OCO2]

(S)—N-(benzo[d][1,3]dioxol-5-yl)-N-methyl-3-phenyl-2-(3-((2-(pyridin-3-yl)phenyl)sulfonyl)ureido)propanamide

| MS (M + H)⁺ Calcd. | 559.2 |
| --- | --- |
| MS (M + H)⁺ Observ. | 559.2 |
| Retention Time | 1.39 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 8.64 (d, J=3.7 Hz, 1H), 8.43 (s, 1H), 7.97 (d, J=8.1 Hz, 1H), 7.77-7.69 (m, 1H), 7.67-7.56 (m, 2H), 7.44 (dd, J=7.7, 5.1 Hz, 1H), 7.36 (d, J=7.7 Hz, 1H), 7.24-7.19 (m, 3H), 6.92 (d, J=8.1 Hz, 1H), 6.85 (d, J=6.6 Hz, 2H), 6.71-6.54 (m, 3H), 6.08 (s, 2H), 4.30 (d, J=5.5 Hz, 1H), 3.08 (s, 3H), 2.86-2.52 (m, 2H).

Example 129

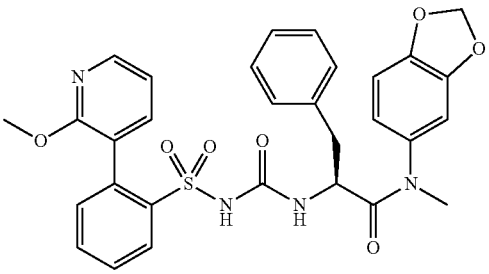 [SMILES: COc1ncccc1-c1ccccc1S(=O)(=O)NC(=O)N[C@@H](Cc1ccccc1)C(=O)N(C)c1ccc2c(c1)OCO2]

(S)—N-(benzo[d][1,3]dioxol-5-yl)-2-(3-((2-(2-methoxypyridin-3-yl)phenyl)sulfonyl) ureido)-N-methyl-3-phenylpropanamide

| MS (M + H)⁺ Calcd. | 589.2 |
| --- | --- |
| MS (M + H)⁺ Observ. | 589.2 |
| Retention Time | 1.63 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

Example 130

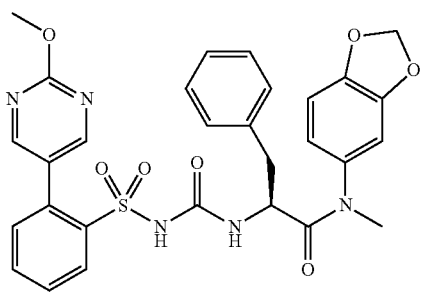 [SMILES: COc1ncc(-c2ccccc2S(=O)(=O)NC(=O)N[C@@H](Cc2ccccc2)C(=O)N(C)c2ccc3c(c2)OCO3)cn1]

(S)—N-(benzo[d][1,3]dioxol-5-yl)-2-(3-((2-(2-methoxypyrimidin-5-yl)phenyl)sulfonyl) ureido)-N-methyl-3-phenylpropanamide

| | |
|---|---|
| MS (M + H)+ Calcd. | 590.2 |
| MS (M + H)+ Observ. | 590.2 |
| Retention Time | 1.34 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 8.41 (s, 2H), 7.99 (d, J=8.1 Hz, 1H), 7.74 (d, J=7.0 Hz, 1H), 7.66 (d, J=8.1 Hz, 1H), 7.41 (d, J=7.3 Hz, 1H), 7.22-7.19 (m, 3H), 6.91 (d, J=8.1 Hz, 1H), 6.85 (d, J=6.6 Hz, 2H), 6.58 (d, J=7.3 Hz, 3H), 6.08 (s, 2H), 4.35-4.21 (m, 1H), 4.01 (s, 3H), 3.07 (s, 3H), 2.94-2.77 (m, 2H).

Example 131

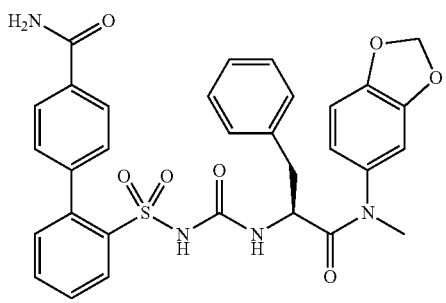 [SMILES: CN(C(=O)[C@H](Cc1ccccc1)NC(=O)NS(=O)(=O)c1ccccc1-c1ccc(C(N)=O)cc1)c1ccc2c(c1)OCO2]

(S)-2'-(N-((1-(benzo[d][1,3]dioxol-5-yl(methyl)amino)-1-oxo-3-phenylpropan-2-yl)carbamoyl)sulfamoyl)-[1,1'-biphenyl]-4-carboxamide

| | |
|---|---|
| MS (M + H)+ Calcd. | 601.2 |
| MS (M + H)+ Observ. | 601.3 |
| Retention Time | 1.36 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 8.08 (br. s., 1H), 7.95-7.88 (m, 2H), 7.74-7.67 (m, 1H), 7.62-7.56 (m, 1H), 7.45 (br. s., 1H), 7.32-7.18 (m, 6H), 6.92 (d, J=8.1 Hz, 1H), 6.86 (d, J=6.6 Hz, 2H), 6.69-6.55 (m, 3H), 6.08 (s, 2H), 4.32 (d, J=5.9 Hz, 1H), 3.08 (s, 3H), 2.86-2.52 (m, 2H).

Example 132

(S)—N-(benzo[d][1,3]dioxol-5-yl)-N-methyl-3-phenyl-2-(3-((2-(thiophen-3-yl)phenyl)sulfonyl)ureido)propanamide

| | |
|---|---|
| MS (M + H)+ Calcd. | 564.1 |
| MS (M + H)+ Observ. | 564.2 |
| Retention Time | 1.63 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.92 (d, J=7.7 Hz, 1H), 7.68-7.63 (m, 1H), 7.60-7.51 (m, 2H), 7.38-7.03 (m, 6H), 6.91 (d, J=8.1 Hz, 1H), 6.84 (d, J=5.9 Hz, 2H), 6.75-6.55 (m, J=8.1 Hz, 3H), 6.08 (s, 2H), 4.30 (d, J=8.4 Hz, 1H), 3.07 (s, 3H), 2.85-2.51 (m, 2H).

Example 133

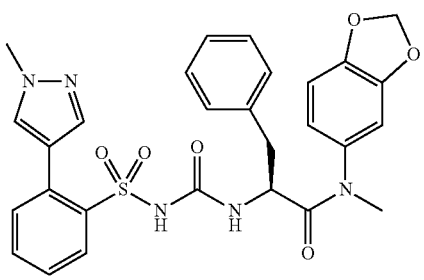 [SMILES: CN(C(=O)[C@H](Cc1ccccc1)NC(=O)NS(=O)(=O)c1ccccc1-c1cnn(C)c1)c1ccc2c(c1)OCO2]

(S)—N-(benzo[d][1,3]dioxol-5-yl)-N-methyl-2-(3-((2-(1-methyl-1H-pyrazol-4-yl)phenyl)sulfonyl)ureido)-3-phenylpropanamide

| | |
|---|---|
| MS (M + H)+ Calcd. | 562.2 |
| MS (M + H)+ Observ. | 562.1 |
| Retention Time | 1.38 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

Example 134

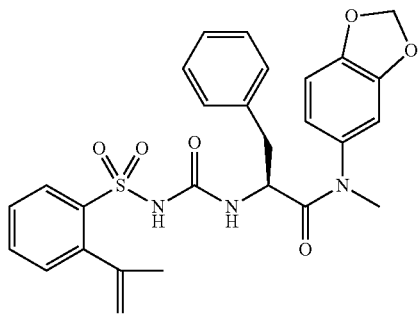 [SMILES: C=C(C)c1ccccc1S(=O)(=O)NC(=O)N[C@@H](Cc1ccccc1)C(=O)N(C)c1ccc2c(c1)OCO2]

(S)—N-(benzo[d][1,3]dioxol-5-yl)-N-methyl-3-phenyl-2-(3-((2-(prop-1-en-2-yl)phenyl)sulfonyl)ureido)propanamide To a 0.5-2 mL microwave tube was added (S)—N-(benzo[d][1,3]dioxol-5-yl)-2-(3-((2-bromophenyl)sulfonyl) ureido)-N-methyl-3-phenylpropanamide (30 mg, 0.054 mmol), 4,4,5,5-tetramethyl-2-(prop-1-en-2-yl)-1,3,2-dioxaborolane (0.1 mL, 0.080 mmol), Pd(PPh$_3$)$_4$ (6.19 mg, 5.35 μmol), DMF (1 mL), followed by 2M K$_2$CO$_3$ (60 μl, 0.120 mmol). The reaction mixture was heated in a microwave reactor at 125° C. for 15 min. The reaction mixture was filtered and the filtrate was purified by preparative HPLC to afford the title compound (13.4 mg).

$^1$H NMR (500 MHZ, DMSO-d$_6$) δ 7.81 (d, J=7.7 Hz, 1H), 7.50 (br. s., 1H), 7.36 (br. s., 1H), 7.16 (br. s., 4H), 6.88 (d, J=7.7 Hz, 1H), 6.82 (d, J=4.4 Hz, 2H), 6.69-6.39 (m, 3H), 6.06 (s, 2H), 5.12 (br. s., 1H), 4.67 (br. s., 1H), 4.27 (d, J=5.1 Hz, 1H), 3.06 (s, 3H), 2.82-2.43 (m, 2H), 1.99 (s, 3H).

| | |
|---|---|
| MS (M + H)+ Calcd. | 522.2 |
| MS (M + H)+ Observ. | 522.2 |
| Retention Time | 1.79 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

Example 135

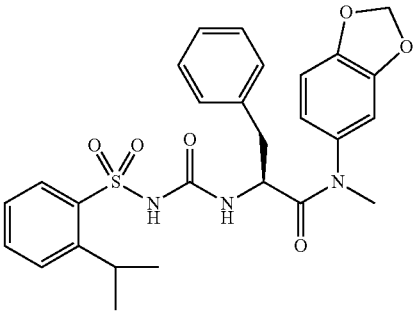 [SMILES: CC(C)c1ccccc1S(=O)(=O)NC(=O)N[C@@H](Cc1ccccc1)C(=O)N(C)c1ccc2c(c1)OCO2]

(S)—N-(benzo[d][1,3]dioxol-5-yl)-2-(3-((2-isopropylphenyl)sulfonyl)ureido)-N-methyl-3-phenylpropanamide A mixture of 10% palladium on carbon (1.0 mg, 0.94 mol) in methanol (1 mL) was stirred under H$_2$ balloon for 5 min. (S)—N-(benzo[d][1,3]dioxol-5-yl)-N-methyl-3-phenyl-2-(3-((2-(prop-1-en-2-yl)phenyl)sulfonyl)ureido)propanamide (15 mg, 0.029 mmol) in methanol (1 mL) was added. The reaction mixture was stirred under H$_2$ balloon for 16 hrs. The palladium catalyst was filtered off and the solvent was evaporated. The residue was purified by preparative HPLC to afford the title compound (8.2 mg). $^1$H NMR (500 MHZ, DMSO-d$_6$) δ 7.74 (d, J=7.3 Hz, 1H), 7.44 (br. s., 2H), 7.29-7.03 (m, 5H), 6.90-6.77 (m, 3H), 6.64-6.45 (m, 2H), 6.05 (br. s., 2H), 4.23 (d, J=5.9 Hz, 1H), 4.01-3.91 (m, 1H), 3.14-2.68 (m, 5H), 1.20-0.95 (m, 6H).

| | |
|---|---|
| MS (M + H)+ Calcd. | 524.2 |
| MS (M + H)+ Observ. | 524.3 |
| Retention Time | 1.72 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

Examples 136-140 were synthesized using the procedure described above for Example 134.

Example 136

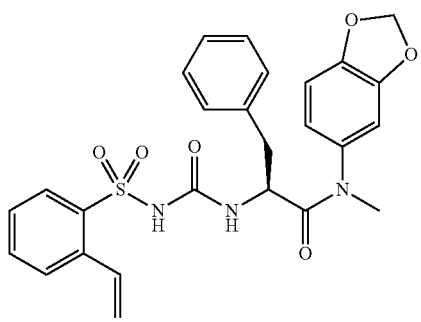

(S)—N-(benzo[d][1,3]dioxol-5-yl)-N-methyl-3-phenyl-2-(3-((2-vinylphenyl)sulfonyl)ureido)propanamide

| | |
|---|---|
| MS (M + H)+ Calcd. | 508.2 |
| MS (M + H)+ Observ. | 508.1 |
| Retention Time | 1.56 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.78 (d, J=7.7 Hz, 1H), 7.68 (br. s., 1H), 7.62-7.41 (m, 2H), 7.39-7.05 (m, 5H), 6.92-6.76 (m, 3H), 6.72-6.42 (m, 2H), 6.05 (s, 2H), 5.75 (d, J=15.4 Hz, 1H), 5.32 (d, J=11.4 Hz, 1H), 4.24 (br. s., 1H), 3.05 (s, 3H), 2.73-2.42 (m, 2H).

Example 137

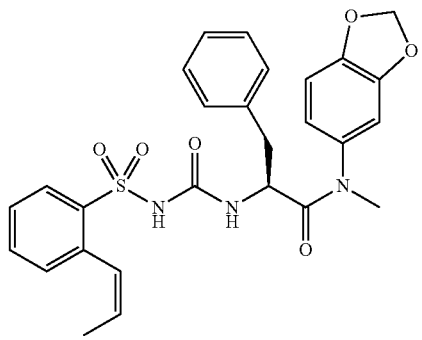 [SMILES: C/C=C\c1ccccc1S(=O)(=O)NC(=O)N[C@@H](Cc1ccccc1)C(=O)N(C)c1ccc2c(c1)OCO2]

(S,Z)—N-(benzo[d][1,3]dioxol-5-yl)-N-methyl-3-phenyl-2-(3-((2-(prop-1-en-1-yl)phenyl)sulfonyl)ureido)propanamide

| | |
|---|---|
| MS (M + H)+ Calcd. | 522.2 |
| MS (M + H)+ Observ. | 522.2 |
| Retention Time | 1.76 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.84 (d, J=7.3 Hz, 1H), 7.55 (br. s., 1H), 7.39 (br. s., 1H), 7.32 (d, J=7.0 Hz, 1H), 7.17 (br. s., 3H), 6.91-6.76 (m, 4H), 6.64-6.37 (m, 3H), 6.06 (s, 2H), 5.83 (dd, J=11.6, 7.9 Hz, 1H), 4.25 (br. s., 1H), 3.05 (s, 3H), 2.80-2.38 (m, 2H), 1.60 (d, J=6.6 Hz, 3H).

Example 138

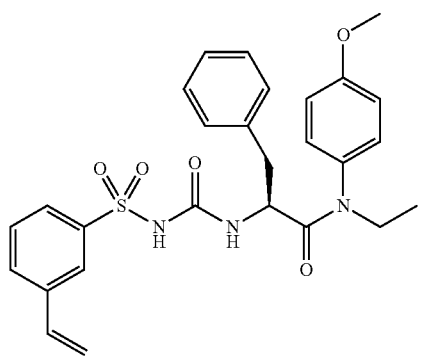

(S)—N-ethyl-N-(4-methoxyphenyl)-3-phenyl-2-(3-((3-vinylphenyl)sulfonyl)ureido)propanamide

| MS (M + H)+ Calcd. | 508.2 |
|---|---|
| MS (M + H)+ Observ. | 508.2 |
| Retention Time | 1.62 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.85 (s, 1H), 7.74 (d, J=7.3 Hz, 1H), 7.66 (d, J=7.0 Hz, 1H), 7.58-7.40 (m, 1H), 7.15 (d, J=2.9 Hz, 3H), 7.00-6.73 (m, 7H), 6.59 (br. s., 1H), 5.93 (d, J=17.6 Hz, 1H), 5.40 (d, J=11.0 Hz, 1H), 4.24-4.10 (m, J=5.9 Hz, 1H), 3.78 (s, 3H), 3.67-3.39 (m, 2H), 2.83-2.43 (m, 2H), 0.94 (t, J=7.0 Hz, 3H).

Example 139

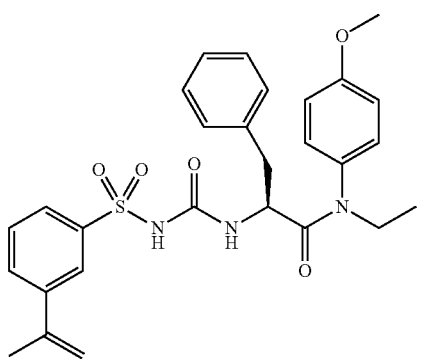 [SMILES: C=C(C)c1cccc(S(=O)(=O)NC(=O)N[C@@H](Cc2ccccc2)C(=O)N(CC)c2ccc(OC)cc2)c1]

(S)—N-ethyl-N-(4-methoxyphenyl)-3-phenyl-2-(3-((3-(prop-en-2-yl)phenyl)sulfonyl)ureido)propanamide

| MS (M + H)+ Calcd. | 522.2 |
|---|---|
| MS (M + H)+ Observ. | 522.2 |
| Retention Time | 1.68 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.91 (s, 1H), 7.82 (d, J=7.7 Hz, 1H), 7.72 (d, J=7.7 Hz, 1H), 7.62-7.50 (m, 1H), 7.20-7.08 (m, 3H), 6.92 (br. s., 4H), 6.83-6.66 (m, 3H), 5.52 (s, 1H), 5.26 (s, 1H), 4.24-4.12 (m, 1H), 3.78 (s, 3H), 3.66-3.41 (m, 2H), 2.86-2.44 (m, 2H), 2.14 (s, 3H), 0.94 (t, J=7.0 Hz, 3H).

Example 140

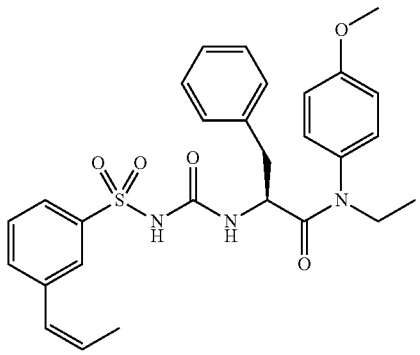 [SMILES: C/C=C\c1cccc(S(=O)(=O)NC(=O)N[C@@H](Cc2ccccc2)C(=O)N(CC)c2ccc(OC)cc2)c1]

(S,Z)—N-ethyl-N-(4-methoxyphenyl)-2-(3-((3-(prop-1-en-1-yl)phenyl)sulfonyl) ureido)propanamide

| MS (M + H)+ Calcd. | 522.2 |
|---|---|
| MS (M + H)+ Observ. | 522.2 |
| Retention Time | 1.70 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 7.76 (s, 1H), 7.67 (d, J=7.0 Hz, 1H), 7.63-7.54 (m, 2H), 7.15 (br. s., 3H), 6.93 (br. s., 4H), 6.82-6.64 (m, 3H), 6.51 (d, J=11.4 Hz, 1H), 5.93 (dd, J=11.6, 7.2 Hz, 1H), 4.18 (q, J=7.1 Hz, 1H), 3.78 (s, 3H), 3.68-3.42 (m, 2H), 2.82-2.45 (m, 2H), 1.86 (d, J=7.0 Hz, 3H), 0.94 (t, J=7.2 Hz, 3H).

Examples 141-146 were synthesized using the procedure described above for Example 135.

Example 141

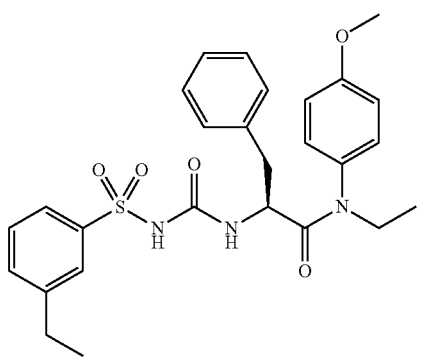 [SMILES: CCc1cccc(S(=O)(=O)NC(=O)N[C@@H](Cc2ccccc2)C(=O)N(CC)c2ccc(OC)cc2)c1]

(S)—N-ethyl-2-(3-((3-ethylphenyl)sulfonyl)ureido)-N-(4-methoxyphenyl)-3-phenylpropanamide

| | |
|---|---|
| MS (M + H)+ Calcd. | 510.2 |
| MS (M + H)+ Observ. | 510.2 |
| Retention Time | 1.81 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.66 (s, 1H), 7.61 (d, J=7.3 Hz, 1H), 7.56-7.45 (m, 2H), 7.21-7.11 (m, 3H), 6.93 (br. s., 4H), 6.82-6.66 (m, 3H), 4.23-4.14 (m, 1H), 3.78 (s, 3H), 3.67-3.42 (m, 2H), 2.81-2.46 (m, 4H), 1.19 (t, J=7.7 Hz, 3H), 0.95 (t, J=7.2 Hz, 3H).

Example 142

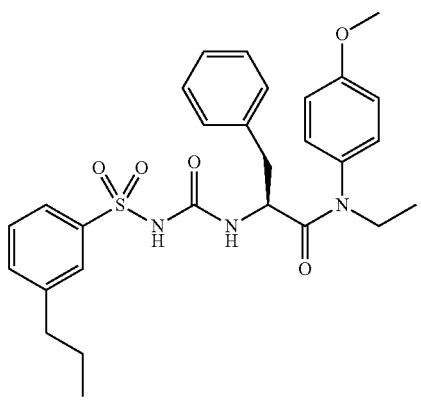 [SMILES: CCCc1cccc(S(=O)(=O)NC(=O)N[C@@H](Cc2ccccc2)C(=O)N(CC)c2ccc(OC)cc2)c1]

(S)—N-ethyl-N-(4-methoxyphenyl)-3-phenyl-2-(3-((3-propylphenyl)sulfonyl) ureido)propanamide

| | |
|---|---|
| MS (M + H)+ Calcd. | 524.2 |
| MS (M + H)+ Observ. | 524.3 |
| Retention Time | 1.91 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.66-7.57 (m, 2H), 7.54-7.45 (m, 2H), 7.16 (d, J=3.7 Hz, 3H), 6.93 (br. s., 4H), 6.77 (d, J=3.7 Hz, 2H), 6.72 (d, J=8.1 Hz, 1H), 4.22-4.14 (m, 1H), 3.78 (s, 3H), 3.65-3.46 (m, 2H), 2.81-2.42 (m, 4H), 1.65-1.52 (m, 2H), 0.94 (t, J=7.0 Hz, 3H), 0.88 (t, J=7.3 Hz, 3H).

Example 143

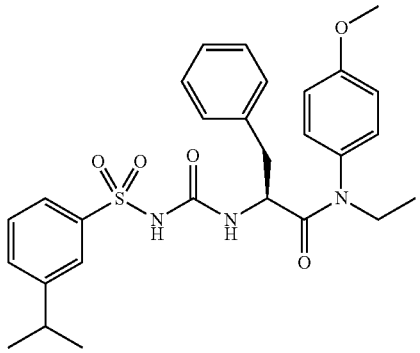 [SMILES: CCN(C(=O)[C@H](Cc1ccccc1)NC(=O)NS(=O)(=O)c1cccc(C(C)C)c1)c1ccc(OC)cc1]

(S)—N-ethyl-2-(3-((3-isopropylphenyl)sulfonyl)ureido)-N-(4-methoxyphenyl)-3-phenylpropanamide

| | |
|---|---|
| MS (M + H)+ Calcd. | 524.2 |
| MS (M + H)+ Observ. | 524.2 |
| Retention Time | 1.85 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (400 MHZ, MeOH-d₄) δ 7.81 (s, 1H), 7.71-7.65 (m, 1H), 7.53 (s, 1H), 7.47 (d, J=7.8 Hz, 1H), 7.24-7.15 (m, 3H), 6.93-6.83 (m, 6H), 4.41 (s, 1H), 3.82 (s, 3H), 3.75-3.45 (m, 2H), 3.02 (dt, J=13.9, 6.9 Hz, 1H), 2.94-2.60 (m, 2H), 1.30 (dd, J=6.8, 1.5 Hz, 6H), 1.04 (t, J=7.2 Hz, 3H).

Example 144

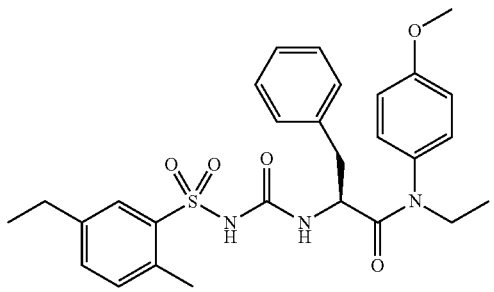 [SMILES: CCc1ccc(C)c(S(=O)(=O)NC(=O)N[C@@H](Cc2ccccc2)C(=O)N(CC)c2ccc(OC)cc2)c1]

(S)—N-ethyl-2-(3-((5-ethyl-2-methylphenyl)sulfonyl)ureido)-N-(4-methoxyphenyl)-3-phenylpropanamide

| MS (M + H)⁺ Calcd. | 524.2 |
| --- | --- |
| MS (M + H)⁺ Observ. | 524.3 |
| Retention Time | 1.89 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (400 MHZ, MeOH-d₄) δ 7.83 (d, J=1.5 Hz, 1H), 7.40-7.24 (m, 2H), 7.21-7.12 (m, 3H), 6.89-6.79 (m, 6H), 4.40 (t, J=6.7 Hz, 1H), 3.80 (s, 3H), 3.73-3.47 (m, 2H), 2.70 (d, J=7.8 Hz, 4H), 1.97 (s, 3H), 1.26 (t, J=7.6 Hz, 3H), 1.02 (t, J=7.2 Hz, 3H).

Example 145

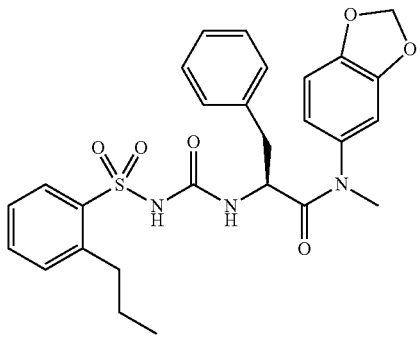 [SMILES: CCCc1ccccc1S(=O)(=O)NC(=O)N[C@@H](Cc1ccccc1)C(=O)N(C)c1ccc2c(c1)OCO2]

(S)—N-(benzo[d][1,3]dioxol-5-yl)-N-methyl-3-phenyl-2-(3-((2-propylphenyl)sulfonyl) ureido)propanamide

| MS (M + H)⁺ Calcd. | 524.2 |
| --- | --- |
| MS (M + H)⁺ Observ. | 524.3 |
| Retention Time | 1.88 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

¹H NMR (500 MHZ, DMSO-d₆) δ 7.76 (d, J=8.1 Hz, 1H), 7.55-7.08 (m, 7H), 6.91-6.78 (m, 3H), 6.70-6.40 (m, 2H), 6.06 (br. s., 2H), 4.27 (d, J=6.2 Hz, 1H), 3.06 (s, 3H), 2.94-2.69 (m, 2H), 2.58-2.41 (m, 2H), 1.62-1.42 (m, 2H), 0.94 (t, J=6.8 Hz, 3H).

Example 146

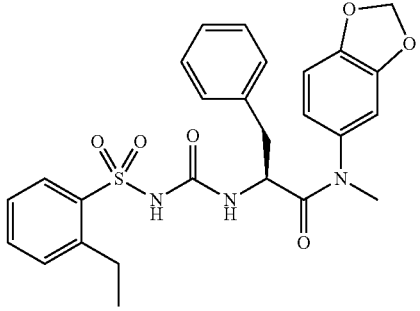

(S)—N-(benzo[d][1,3]dioxol-5-yl)-2-(3-((2-ethylphenyl)sulfonyl)ureido)-N-methyl-3-phenylpropanamide

| MS (M + H)⁺ Calcd. | 510.2 |
| --- | --- |
| MS (M + H)⁺ Observ. | 510.3 |
| Retention Time | 1.73 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-d$_6$) δ 7.77 (d, J=7.7 Hz, 1H), 7.56-7.07 (m, 7H), 6.88 (d, J=8.4 Hz, 1H), 6.80 (d, J=2.9 Hz, 2H), 6.71-6.35 (m, 2H), 6.06 (s, 2H), 4.27 (d, J=5.5 Hz, 1H), 3.06 (s, 3H), 2.94 (q, J=7.2 Hz, 2H), 2.82-2.45 (m, 2H), 1.14 (t, J=7.2 Hz, 3H).

Example 147

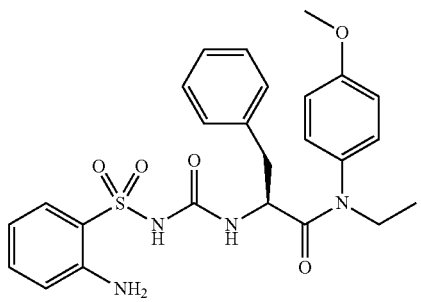

(S)-2-(3-((2-aminophenyl)sulfonyl) ureido)-N-ethyl-N-(4-methoxyphenyl)-3-phenylpropanamide A mixture of 10% palladium on carbon (4.0 mg, 3.8 µmol) in methanol (4 mL) was stirred under H$_2$ balloon for 5 min. (S)—N-ethyl-N-(4-methoxyphenyl)-2-(3-((2-nitrophenyl) sulfonyl)ureido)-3-phenylpropanamide (20 mg, 0.038 mmol) in methanol (1 mL) was added. The reaction mixture was stirred under a H$_2$ balloon for 3 hrs. The palladium catalyst was filtered off and the solvent was evaporated. The residue was purified by preparative HPLC to afford the title compound (14 mg).

$^1$H NMR (500 MHZ, DMSO-d$_6$) δ 7.47 (d, J=8.1 Hz, 1H), 7.28-7.12 (m, 4H), 6.90 (br. s., 4H), 6.83-6.72 (m, 3H), 6.63-6.48 (m, 2H), 4.21-4.11 (m, J=6.6 Hz, 1H), 3.77 (s, 3H), 3.67-3.43 (m, 2H), 2.79-2.46 (m, 2H), 0.95 (t, J=7.2 Hz, 3H).

| MS (M + H)$^+$ Calcd. | 497.2 |
|---|---|
| MS (M + H)$^+$ Observ. | 497.2 |
| Retention Time | 1.49 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-µm particles |

Example 148 was synthesized using the procedure described above for Example 48.

Example 148

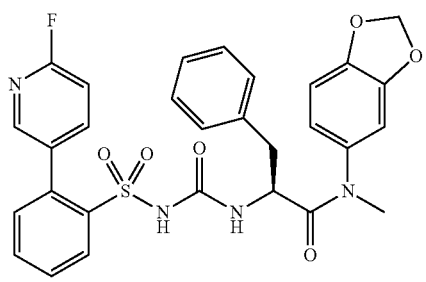 [SMILES: CN(C(=O)[C@H](Cc1ccccc1)NC(=O)NS(=O)(=O)c1ccccc1-c1ccc(F)nc1)c1ccc2c(c1)OCO2]

(S)—N-(benzo[d][1,3]dioxol-5-yl)-2-(3-((2-(6-fluo-ropyridin-3-yl)phenyl)sulfonyl) ureido)-N-methyl-3-phenylpropanamide

| MS (M + H)$^+$ Calcd. | 577.2 |
|---|---|
| MS (M + H)$^+$ Observ. | 577.2 |
| Retention Time | 1.54 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-µm particles |

$^1$H NMR (500 MHZ, DMSO-d$_6$) δ 8.08 (s, 1H), 7.96 (s, 1H), 7.85 (br. s., 1H), 7.68-7.51 (m, 2H), 7.34-7.08 (m, 6H), 6.95-6.80 (m, 3H), 6.71-6.48 (m, 2H), 6.07 (s, 2H), 4.29 (d, J=5.1 Hz, 1H), 3.06 (s, 3H), 2.83-2.52 (m, 2H).

Example 149

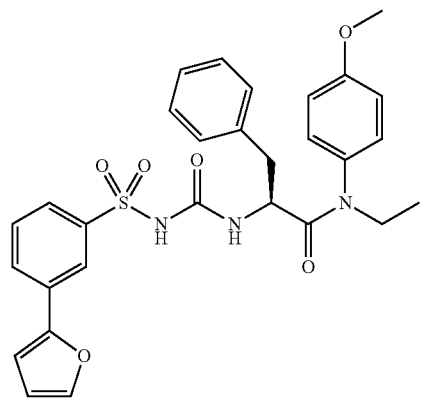 [SMILES: CCN(C(=O)[C@H](Cc1ccccc1)NC(=O)NS(=O)(=O)c1cccc(-c2ccco2)c1)c1ccc(OC)cc1]

(S)—N-ethyl-2-(3-(((3furan-2-phenyl)sulfonyl) ureido)-N-(4-methoxyphenyl)-3-phenylpropanamide To a 0.5-2 mL microwave tube was added (S)-2-(3-((3-bromophenyl)sulfonyl)ureido)-N-ethyl-N-(4-methoxyphenyl)-3-phenylpropanamide (18.5 mg, 0.033 mmol), 2-(furan-2-yl)-4,4,5,5-tetramethyl-1,3,2-dioxaborolane (11.6 mg, 0.060 mmol), 1,1'-bis(diphenylphosphino)ferrocene-palladium(II)chloride dichloromethane complex (1.23 mg, 1.05 μmol), 1,4-dioxane (1 mL), followed by 2M $K_3PO_4$ (100 μL). The reaction mixture was heated in a microwave reactor at 100° C. for 15 min. The reaction mixture was filtered and the filtrate was purified by preparative HPLC to afford the title compound (8.8 mg).

| | |
|---|---|
| MS (M + H)+ Calcd. | 548.1 |
| MS (M + H)+ Observ. | 548.1 |
| Retention Time | 1.73 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

Examples 150-154 were synthesized using the procedure described above for Example 149.

Example 150

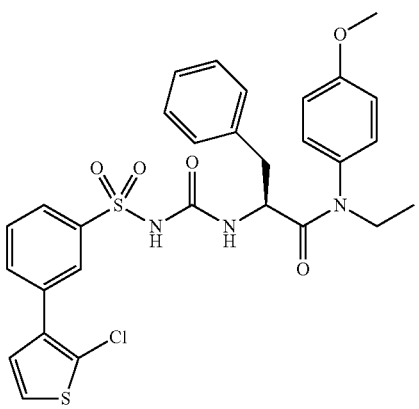 [SMILES: CCN(C(=O)[C@H](Cc1ccccc1)NC(=O)NS(=O)(=O)c1cccc(-c2ccsc2Cl)c1)c1ccc(OC)cc1]

(S)-2-(3-((3-(2-chlorothiophen-3-yl)phenyl)sulfonyl)ureido)-N-ethyl-N-ethyl-N-(4-methoxyphenyl)-3-phenylpropanamide

| | |
|---|---|
| MS (M + H)+ Calcd. | 598.1 |
| MS (M + H)+ Observ. | 598.1 |
| Retention Time | 1.82 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |

| | |
|---|---|
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHZ, DMSO-$d_6$) δ 8.02 (br. s., 1H), 7.89-7.78 (m, 2H), 7.72-7.57 (m, 3H), 7.28 (d, J=5.9 Hz, 2H), 7.12 (br. s., 3H), 6.90 (br. s., 4H), 6.78 (br. s., 2H), 4.18 (d, J=6.6 Hz, 1H), 3.77 (s, 3H), 3.66-3.45 (m, 2H), 2.80-2.51 (m, 2H), 2.51 (s, 3H), 0.93 (t, J=7.0 Hz, 4H).

Example 151

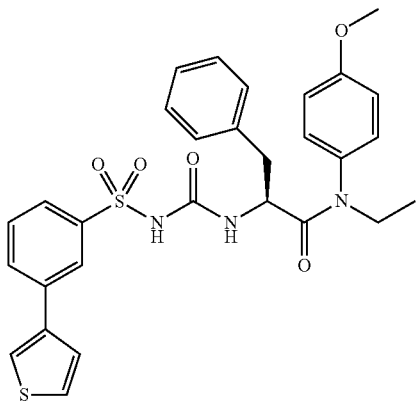 [SMILES: CCN(C(=O)[C@H](Cc1ccccc1)NC(=O)NS(=O)(=O)c1cccc(-c2ccsc2)c1)c1ccc(OC)cc1]

(S)—N-ethyl-N-(4-methoxyphenyl)-3-phenyl-2-(3-((3-(thiophen-3-yl)phenyl)sulfonyl)ureido)propanamide

| | |
|---|---|
| MS (M + H)+ Calcd. | 564.2 |
| MS (M + H)+ Observ. | 564.2 |
| Retention Time | 1.75 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 8.08 (br. s., 1H), 8.01-7.88 (m, 1H), 7.77-7.66 (m, 2H), 7.58 (d, J=5.5 Hz, 2H), 7.20-7.08 (m, 3H), 6.88 (br. s., 4H), 6.79 (br. s., 2H), 6.58 (br. s., 1H), 4.17 (d, J=6.2 Hz, 1H), 3.75 (s, 3H), 3.64-3.42 (m, 2H), 2.79-2.44 (m, 2H), 2.51 (s, 3H), 0.92 (t, J=6.8 Hz, 3H).

Example 152

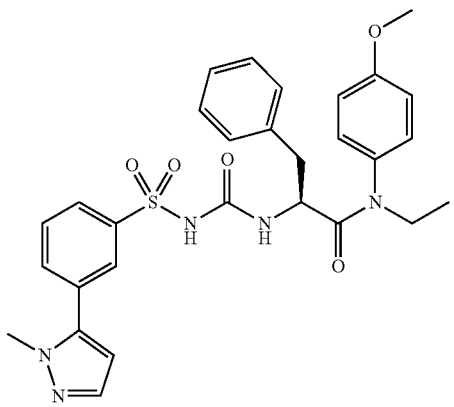 [SMILES: CCN(C(=O)[C@H](Cc1ccccc1)NC(=O)NS(=O)(=O)c1cccc(-c2ccnn2C)c1)c1ccc(OC)cc1]

(S)—N-ethyl-N-(4-methoxyphenyl)-2-(3-((3-(1-methyl-1H-pyrazol-5-yl)phenyl)sulfonyl)ureido)-3-phenylpropanamide

| | |
|---|---|
| MS (M + H)+ Calcd. | 562.4 |
| MS (M + H)+ Observ. | 562.4 |
| Retention Time | 1.59 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^{1}$H NMR (500 MHZ, DMSO-d$_{6}$) δ 7.90 (br. s., 1H), 7.83-7.74 (m, 2H), 7.71-7.61 (m, 1H), 7.52 (s, 1H), 7.21-7.09 (m, 3H), 6.91 (br. s., 4H), 6.78 (br. s., 2H), 6.58-6.41 (m, 2H), 4.17 (d, J=5.9 Hz, 1H), 3.88 (s, 3H), 3.72 (s, 3H), 3.64-3.44 (m, 2H), 2.79-2.38 (m, 2H), 0.93 (t, J=7.2 Hz, 3H).

Example 153

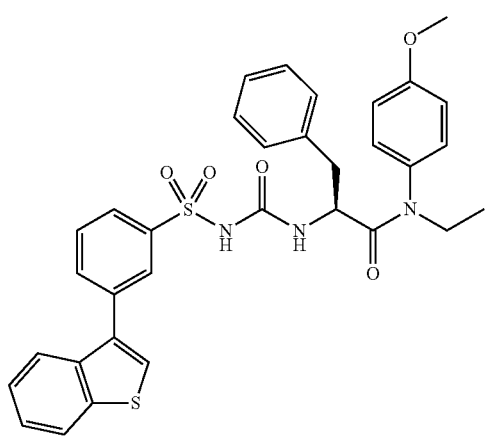 [SMILES: CCN(C(=O)[C@H](Cc1ccccc1)NC(=O)NS(=O)(=O)c1cccc(-c2csc3ccccc23)c1)c1ccc(OC)cc1]

(S)-2-(3-((3-(benzo[b]thiophen-3-yl)phenyl)sulfonyl) ureido)-N-ethyl-N-(4-methoxyphenyl)-3-phenylpropanamide

| | |
|---|---|
| MS (M + H)+ Calcd. | 614.2 |
| MS (M + H)+ Observ. | 614.2 |
| Retention Time | 1.94 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^{1}$H NMR (500 MHZ, DMSO-d$_{6}$) δ 8.12 (s, 1H), 8.05 (s, 1H), 7.93-7.82 (m, 3H), 7.78-7.66 (m, 1H), 7.53-7.34 (m, 2H), 7.06 (d, J=3.3 Hz, 3H), 6.95-6.83 (m, 4H), 6.76 (d, J=3.7 Hz, 2H), 6.67 (br. s., 1H), 4.26-4.13 (m, 1H), 3.73 (s, 3H), 3.61-3.36 (m, 2H), 2.81-2.45 (m, 2H), 0.90 (t, J=7.2 Hz, 3H).

Example 154

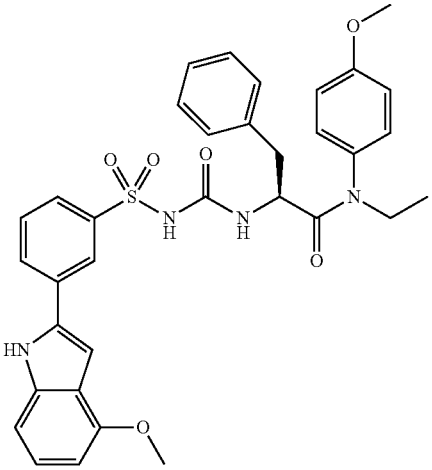 [SMILES: CCN(C(=O)[C@H](Cc1ccccc1)NC(=O)NS(=O)(=O)c1cccc(-c2cc3c(OC)cccc3[nH]2)c1)c1ccc(OC)cc1]

(S)—N-ethyl-2-(3-((3-(4-methoxy-1H-indol-2-yl)phenyl)sulfonyl)ureido)-N-(4-methoxyphenyl)-3-phenylpropanamide

| | |
|---|---|
| MS (M + H)+ Calcd. | 627.2 |
| MS (M + H)+ Observ. | 627.2 |
| Retention Time | 2.79 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |

| | |
|---|---|
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 11.75 (br. s., 1H), 8.25 (br. s., 1H), 8.03 (br. s., 1H), 7.70-7.45 (m, 3H), 7.11 (br. s., 2H), 7.06-7.03 (m, 2H), 6.98 (br. s., 1H), 6.86-6.78 (m, 4H), 6.52 (d, J=5.5 Hz, 1H), 4.18 (br. s., 1H), 3.89 (s, 3H), 3.69 (br. s., 3H), 3.62-3.37 (m, 2H), 2.82-2.45 (m, 2H), 0.90 (br. s., 3H).

Example 155

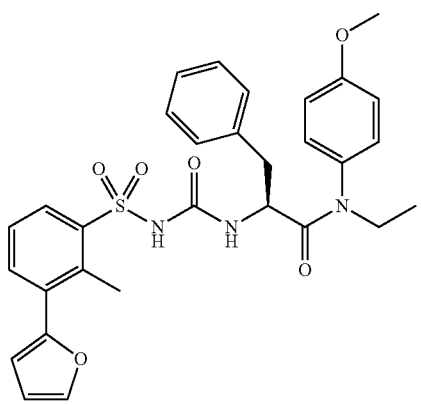 [SMILES: CCN(C(=O)[C@H](Cc1ccccc1)NC(=O)NS(=O)(=O)c1cccc(-c2ccco2)c1C)c1ccc(OC)cc1]

(S)—N-ethyl-2-(3-(((3furan-2-phenyl)sulfonyl) ureido)-N-(4-methoxyphenyl)-3-phenylpropanamide To a 0.5-2 mL microwave tube was added (S)-2-(3-((3-bromo-2-methylphenyl)sulfonyl)ureido)-N-ethyl-N-(4-methoxyphenyl)-3-phenylpropanamide (17.3 mg, 0.030 mmol), 2-(furan-2-yl)-4,4,5,5-tetramethyl-1,3,2-dioxaborolane (11.6 mg, 0.060 mmol), 1,1'-bis(diphenylphosphino)ferrocene-palladium(II)chloride dichloromethane complex (1.2 mg, 1.5 μmol), 1,4-dioxane (1 mL), followed by 2M $K_3PO_4$ (100 μL). The reaction mixture was heated in a microwave reactor at 100° C. for 15 min. The reaction mixture was filtered and the filtrate was purified by preparative HPLC to afford the title compound (5.5 mg).

| | |
|---|---|
| MS (M + H)$^+$ Calcd. | 562.2 |
| MS (M + H)$^+$ Observ. | 562.2 |
| Retention Time | 1.78 min |
| | LC condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.89-7.74 (m, 2H), 7.63 (br. s., 1H), 7.30 (br. s., 1H), 7.12 (d, J=4.0 Hz, 3H), 6.93-6.78 (m, 6H), 6.74-6.56 (m, 2H), 4.14 (br. s., 1H), 3.75 (br. s., 3H), 3.63-3.41 (m, 2H), 2.76-2.52 (m, 2H), 2.59 (s, 3H), 0.92 (br. s., 3H).

Examples 156-162 were synthesized using the procedure described above for Example 149.

Example 156

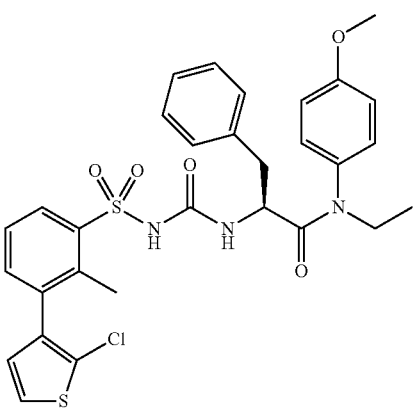 [SMILES: CCN(C(=O)[C@H](Cc1ccccc1)NC(=O)NS(=O)(=O)c1cccc(-c2ccsc2Cl)c1C)c1ccc(OC)cc1]

(S)-2-(3-((3-(2-chlorothiophen-3-yl)-2-methylphenyl)sulfonyl)ureido)-N-ethyl-N-(4-methoxyphenyl)-3-phenylpropanamide

| | |
|---|---|
| MS (M + H)$^+$ Calcd. | 612.1 |
| MS (M + H)$^+$ Observ. | 612.3 |
| Retention Time | 1.93 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 157

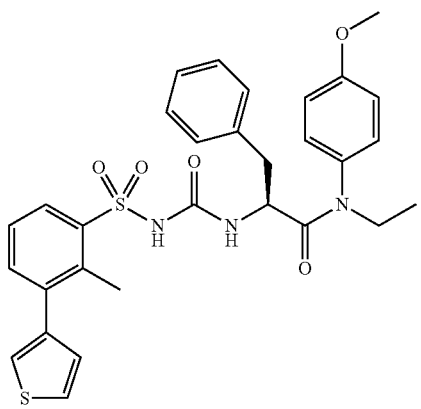 [SMILES: CCN(C(=O)[C@H](Cc1ccccc1)NC(=O)NS(=O)(=O)c1cccc(-c2ccsc2)c1C)c1ccc(OC)cc1]

(S)—N-ethyl-N-(4-methoxyphenyl)-2-(3-((2-methyl-3-(thiophen-3-yl)phenyl)sulfonyl)ureido)-3-phenyl-propanamide

| | |
|---|---|
| MS (M + H)+ Calcd. | 578.2 |
| MS (M + H)+ Observ. | 578.3 |
| Retention Time | 1.93 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.82 (d, J=8.1 Hz, 1H), 7.68 (br. s., 1H), 7.58-7.48 (m, 2H), 7.36 (br. s., 1H), 7.27-7.11 (m, 4H), 7.05-6.90 (m, 4H), 6.79 (br. s., 2H), 4.17 (br. s., 1H), 3.77 (s, 3H), 3.67-3.43 (m, 2H), 2.79-2.48 (m, 2H), 2.57 (s, 3H), 0.93 (t, J=7.0 Hz, 3H).

Example 158

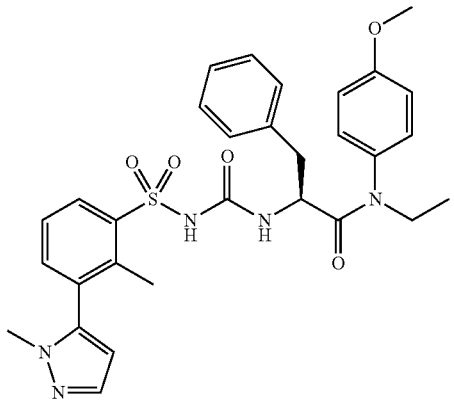 [SMILES: CCN(C(=O)[C@H](Cc1ccccc1)NC(=O)NS(=O)(=O)c1cccc(-c2ccnn2C)c1C)c1ccc(OC)cc1]

(S)—N-ethyl-N-(4-methoxyphenyl)-2-(3-((2-methyl-3-(1-methyl-1H-pyrazol-5-yl)phenyl)sulfonyl)ureido)-3-phenylpropanamide

| | |
|---|---|
| MS (M + H)+ Calcd. | 576.2 |
| MS (M + H)+ Observ. | 576.3 |
| Retention Time | 1.58 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.88 (d, J=8.8 Hz, 1H), 7.51 (s, 1H), 7.33 (br. s., 2H), 7.14 (br. s., 3H), 6.97-6.88 (m, 4H), 6.80 (br. s., 2H), 6.23 (br. s., 1H), 4.15 (br. s., 1H), 3.78 (s, 3H), 3.51 (s, 3H), 3.51-3.45 (m, 2H), 2.76-2.47 (m, 2H), 2.51 (s, 3H) 0.93 (t, J=7.0 Hz, 3H).

Example 159

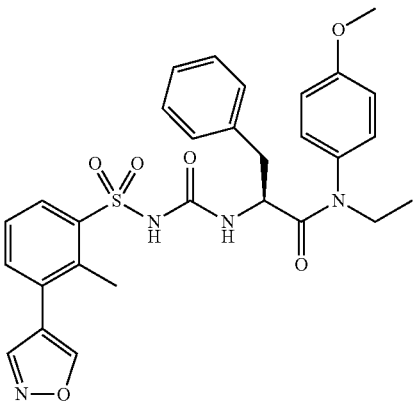 [SMILES: CCN(C(=O)[C@H](Cc1ccccc1)NC(=O)NS(=O)(=O)c1cccc(-c2cnoc2)c1C)c1ccc(OC)cc1]

(S)—N-ethyl-2-(3-((3-(isoxazol-4-yl)-2-methylphenyl)sulfonyl)ureido)-N-(4-methoxyphenyl)-3-phenylpropanamide

| | |
|---|---|
| MS (M + H)+ Calcd. | 563.2 |
| MS (M + H)+ Observ. | 563.3 |
| Retention Time | 1.63 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 160

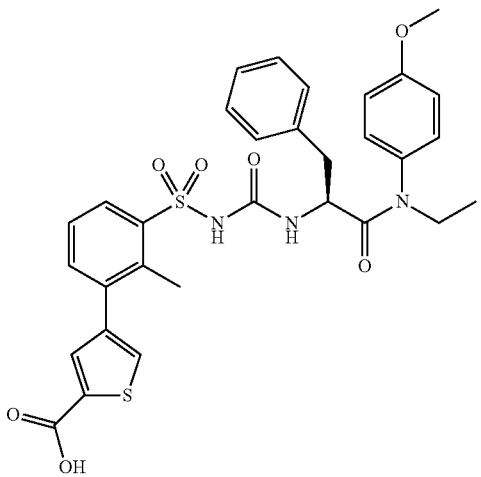 [SMILES: CCN(C(=O)[C@H](Cc1ccccc1)NC(=O)NS(=O)(=O)c1cccc(-c2csc(C(=O)O)c2)c1C)c1ccc(OC)cc1]

(S)-4-(3-(N-((1-(ethyl(4-methoxyphenylpropan-2-yl)carbamoyl)sulfamoyl)-2-methylphenyl)thiophene-2-carboxylic acid

| | |
|---|---|
| MS (M + H)+ Calcd. | 622.2 |
| MS (M + H)+ Observ. | 622.3 |
| Retention Time | 1.45 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-µm particles |

Example 161

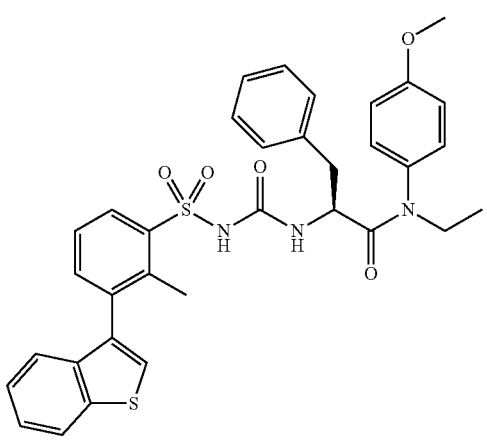 [SMILES: CCN(C(=O)[C@H](Cc1ccccc1)NC(=O)NS(=O)(=O)c1cccc(-c2csc3ccccc23)c1C)c1ccc(OC)cc1]

(S)-2-(3-((3-(benzo[b]thiophen-3-yl)-2-methylphenyl)sulfonyl) ureido)-N-ethyl-N-(4-methoxyphenyl)-3-phenylpropanamide

| | |
|---|---|
| MS (M + H)+ Calcd. | 628.3 |
| MS (M + H)+ Observ. | 628.3 |
| Retention Time | 2.05 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-µm particles |

$^1$H NMR (500 MHZ, DMSO-$d_6$) δ 8.10 (d, J=8.1 Hz, 1H), 7.76 (br. s., 1H), 7.59-7.53 (m, 1H), 7.49 (d, J=7.3 Hz, 1H), 7.46-7.40 (m, 1H), 7.26 (d, J=15.0 Hz, 2H), 7.14 (br. s., 3H), 6.95 (br. s., 4H), 6.81 (br. s., 2H), 6.60 (br. s., 1H), 4.22 (br. s., 1H), 3.78 (s, 3H), 3.69-3.46 (m, 2H), 2.82-2.53 (m, 2H), 2.31 (s, 3H), 0.94 (t, J=7.0 Hz, 3H).

Example 162

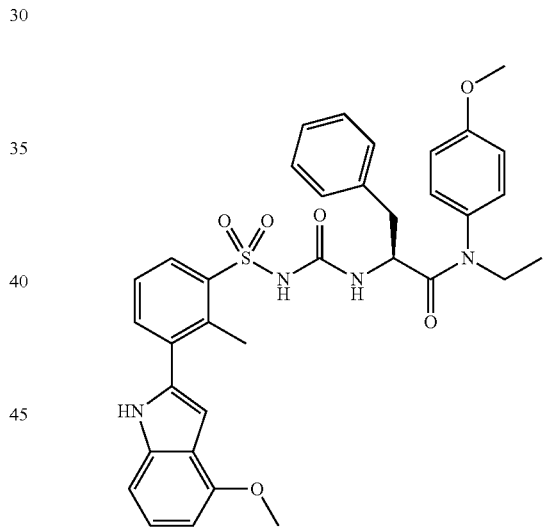

(S)—N-ethyl-2-(3-((3-(4-methoxy-1H-indol-2-yl)-2-methylphenyl)sulfonyl)ureido)-N-(4-methoxyphenyl)-3-phenylpropanamide

| | |
|---|---|
| MS (M + H)+ Calcd. | 641.2 |
| MS (M + H)+ Observ. | 641.3 |
| Retention Time | 1.88 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |

| | |
|---|---|
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 11.39 (br. s., 1H), 7.96 (s, 1H), 7.87 (d, J=7.7 Hz, 1H), 7.69 (d, J=8.4 Hz, 1H), 7.52-7.38 (m, 1H), 7.14 (br. s., 3H), 7.09-6.87 (m, 5H), 6.80 (d, J=3.7 Hz, 2H), 6.58-6.39 (m, 2H), 4.18 (br. s., 1H), 3.87 (s, 3H), 3.77 (s, 3H), 3.68-3.43 (m, 2H), 2.82-2.56 (m, 2H), 2.61 (s, 3H), 0.94 (t, J=7.2 Hz, 3H).

Examples 163-205 were synthesized using the procedure described above for Example 87.

Example 163

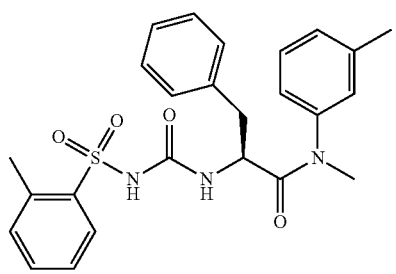 [SMILES: Cc1cccc(N(C)C(=O)[C@H](Cc2ccccc2)NC(=O)NS(=O)(=O)c2ccccc2C)c1]

(S)—N-methyl-3-phenyl-N-(m-tolyl)-2-(3-(o-tolylsulfonyl)ureido)propanamide

| | |
|---|---|
| MS (M + H)$^+$ Calcd. | 466.2 |
| MS (M + H)$^+$ Observ. | 466.2 |
| Retention Time | 1.47 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.79 (d, J=7.7 Hz, 2H), 7.63 (d, J=7.0 Hz, 1H), 7.60-7.51 (m, 2H), 7.32-7.23 (m, 1H), 7.17 (br. s., 5H), 6.88 (d, J=6.2 Hz, 1H), 6.76 (br. s., 1H), 6.66 (d, J=7.0 Hz, 1H), 4.27 (br. s., 1H), 3.09 (s, 3H), 2.51 (s, 3H), 2.81-2.42 (m, 2H), 2.24 (s, 3H).

Example 164

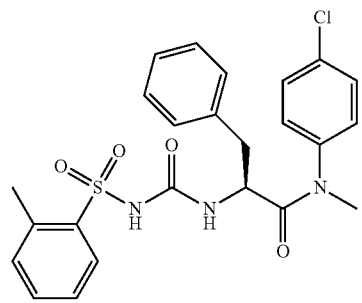 [SMILES: Cc1ccccc1S(=O)(=O)NC(=O)N[C@@H](Cc1ccccc1)C(=O)N(C)c1ccc(Cl)cc1]

(S)—N-(4-chlorophenyl)-N-methyl-3-phenyl-2-(3-(o-tolylsulfonyl) ureido)propanamide

| | |
|---|---|
| MS (M + H)$^+$ Calcd. | 486.1 |
| MS (M + H)$^+$ Observ. | 486.3 |
| Retention Time | 1.60 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.76 (d, J=5.9 Hz, 1H), 7.41 (d, J=7.7 Hz, 4H), 7.29 (br. s., 3H), 7.20-7.06 (m, 3H), 6.79 (br. s., 2H), 6.42 (br. s., 1H), 4.22 (br. s., 1H), 3.09 (br. s., 3H), 2.77-2.56 (m, 2H), 2.51 (s, 3H),

Example 165

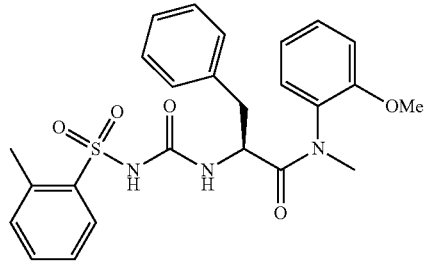 [SMILES: COc1ccccc1N(C)C(=O)[C@H](Cc1ccccc1)NC(=O)NS(=O)(=O)c1ccccc1C]

(S)—N-(2-methoxyphenyl)-N-methyl-3-phenyl-2-(3-(o-tolylsulfonyl) ureido)propanamide

| | |
|---|---|
| MS (M + H)$^+$ Calcd. | 482.5 |
| MS (M + H)$^+$ Observ. | 482.5 |
| Retention Time | 1.49 min |

-continued

| | LC Condition |
|---|---|
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.79 (dd, J=17.8, 7.9 Hz, 2H), 7.59-7.08 (m, 5H), 7.04-6.98 (m, 2H), 6.87 (t, J=7.5 Hz, 1H), 6.78-6.59 (m, 3H), 6.52 (br. s., 1H), 4.28 (br. s., 1H), 3.85 (s, 3H), 3.06 (s, 3H), 2.77-2.56 (m, 2H), 2.55 (s, 3H).

Example 166

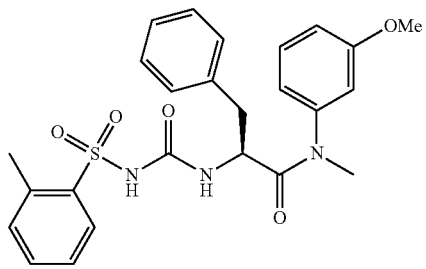 [SMILES: COc1cccc(N(C)C(=O)[C@H](Cc2ccccc2)NC(=O)NS(=O)(=O)c2ccccc2C)c1]

(S)—N-(3-methoxyphenyl)-N-methyl-3-phenyl-2-(3-(o-tolylsulfonyl) ureido)propanamide

| MS (M + H)$^+$ Calcd. | 482.2 |
|---|---|
| MS (M + H)$^+$ Observ. | 482.2 |
| Retention Time | 1.59 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.75 (d, J=7.3 Hz, 2H), 7.37 (br. s., 1H), 7.24 (d, J=7.7 Hz, 3H), 7.14 (br. s., 3H), 6.90 (br. s., 1H), 6.76 (br. s., 2H), 6.59 (br. s., 1H), 6.30 (br. s., 1H), 4.30 (br. s., 1H), 3.67 (br. s., 3H), 3.10 (br. s., 3H), 2.79-2.34 (m, 2H), 2.51 (br. s., 3H),

Example 167

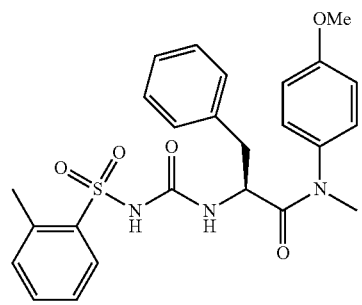 [SMILES: COc1ccc(N(C)C(=O)[C@H](Cc2ccccc2)NC(=O)NS(=O)(=O)c2ccccc2C)cc1]

(S)—N-(4-methoxyphenyl)-N-methyl-3-phenyl-2-(3-(o-tolylsulfonyl) ureido)propanamide

| MS (M + H)$^+$ Calcd. | 482.2 |
|---|---|
| MS (M + H)$^+$ Observ. | 482.5 |
| Retention Time | 1.34 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.78 (d, J=8.1 Hz, 1H), 7.50 (br. s., 1H), 7.40-7.28 (m, 2H), 7.15 (br. s., 3H), 7.05 (d, J=8.1 Hz, 2H), 6.93 (d, J=8.4 Hz, 2H), 6.75 (br. s., 2H), 6.55 (d, J=7.3 Hz, 1H), 4.26 (br. s., 1H), 3.77 (s, 3H), 3.09 (s, 3H), 2.79-2.34 (m, 2H), 2.51 (s, 3H).

Example 168

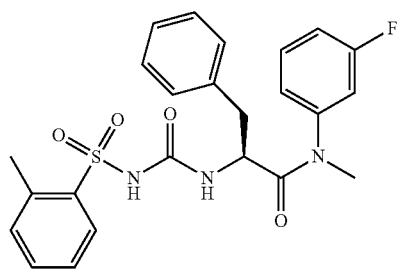 [SMILES: Cc1ccccc1S(=O)(=O)NC(=O)N[C@@H](Cc1ccccc1)C(=O)N(C)c1cccc(F)c1]

(S)—N-(3-fluorophenyl)-N-methyl-3-phenyl-2-(3-(o-tolylsulfonyl) ureido)propanamide

| | |
|---|---|
| MS (M + H)+ Calcd. | 470.2 |
| MS (M + H)+ Observ. | 470.2 |
| Retention Time | 1.58 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.79 (d, J=7.0 Hz, 1H), 7.52-7.38 (m, 3H), 7.36-7.29 (m, 2H), 7.26-7.10 (m, 4H), 7.03-6.92 (m, 2H), 6.77 (br. s., 2H), 6.54 (br. s., 1H), 4.27 (br. s., 1H), 3.12 (br. s., 3H), 2.51 (s, 3H), 2.76-2.41 (m, 2H).

Example 169

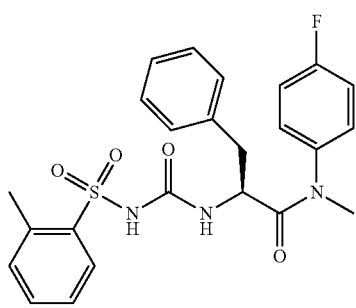 [SMILES: Cc1ccccc1S(=O)(=O)NC(=O)N[C@@H](Cc1ccccc1)C(=O)N(C)c1ccc(F)cc1]

(S)—N-(4-fluorophenyl)-N-methyl-3-phenyl-2-(3-(o-tolylsulfonyl) ureido)propanamide

| | |
|---|---|
| MS (M + H)+ Calcd. | 470.2 |
| MS (M + H)+ Observ. | 470.3 |
| Retention Time | 1.50 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.76 (d, J=7.7 Hz, 1H), 7.45 (br. s., 1H), 7.31 (br. s., 2H), 7.23-7.05 (m, 7H), 6.77 (br. s., 2H), 6.46 (br. s., 1H), 4.21 (br. s., 1H), 3.10 (s, 3H), 2.51 (s, 3H), 2.76-2.41 (m, 2H).

Example 170

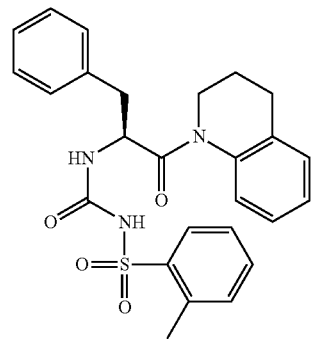 [SMILES: Cc1ccccc1S(=O)(=O)NC(=O)N[C@@H](Cc1ccccc1)C(=O)N1CCCc2ccccc21]

(S)—N-((1-(3,4-dihydroquinolin-1(2H)-yl)-1-oxo-3-phenylpropan-2-yl)carbamoyl)-2-methylbenzenesulfonamide

| | |
|---|---|
| MS (M + H)+ Calcd. | 478.2 |
| MS (M + H)+ Observ. | 478.4 |
| Retention Time | 1.51 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.77 (d, J=7.7 Hz, 1H), 7.32 (br. s., 2H), 7.21 (br. s., 2H), 7.09 (d, J=8.8 Hz, 5H), 6.77 (br. s., 1H), 6.31 (br. s., 1H), 4.93 (br. s., 1H), 3.91-3.81 (m, 2H), 3.39-3.27 (m, 2H), 2.61-2.35 (m, 2H), 2.54 (br. s., 3H), 1.72-1.48 (m, 2H).

Example 171

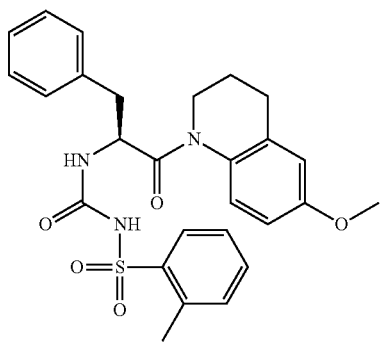 [SMILES: COc1ccc2c(c1)CCCN2C(=O)[C@H](Cc1ccccc1)NC(=O)NS(=O)(=O)c1ccccc1C]

(S)—N-((1-(6-methoxy-3,4-dihydroquinolin-1(2H)-yl)-1-oxo-3-phenylpropan-2-yl)carbamoyl)-2-methylbenzenesulfonamide

| MS (M + H)+ Calcd. | 508.5 |
| --- | --- |
| MS (M + H)+ Observ. | 508.5 |
| Retention Time | 1.48 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.84 (d, J=6.6 Hz, 1H), 7.52 (d, J=7.3 Hz, 1H), 7.45-7.34 (m, 2H), 7.27-6.98 (m, 4H), 6.81-6.51 (m, 4H), 4.92 (br. s., 1H), 3.95-3.83 (m, 2H), 3.73 (s, 3H), 3.41-3.29 (m, 2H), 2.70-2.35 (m, 2H), 2.55 (s, 3H), 1.80-1.44 (m, 2H).

Example 172

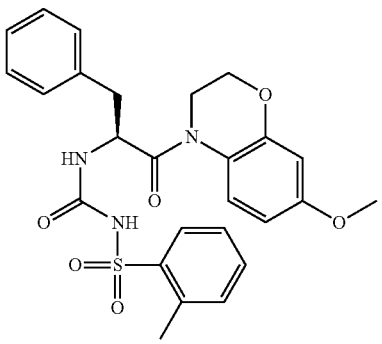 [SMILES: COc1ccc2c(c1)OCCN2C(=O)[C@H](Cc1ccccc1)NC(=O)NS(=O)(=O)c1ccccc1C]

(S)—N-((1-(7-methoxy-2H-benzo[b][1,4]oxazin-4(3H)-yl)-1-oxo-3-phenylpropan-2-yl)carbamoyl)-2-methylbenzenesulfonamide

| MS (M + H)+ Calcd. | 510.2 |
| --- | --- |
| MS (M + H)+ Observ. | 510.2 |
| Retention Time | 1.52 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.85 (br. s., 1H), 7.64 (br. s., 1H), 7.51 (d, J=6.6 Hz, 1H), 7.41-7.34 (m, 2H), 7.26-7.01 (m, 4H), 6.84 (br. s., 1H), 6.74 (br. s., 1H), 6.50-6.32 (m, 2H), 4.85 (br. s., 1H), 4.03 (br. s., 2H), 3.70 (br. s., 3H), 3.51-3.38 (m, 4H), 2.55 (s, 3H).

Example 173

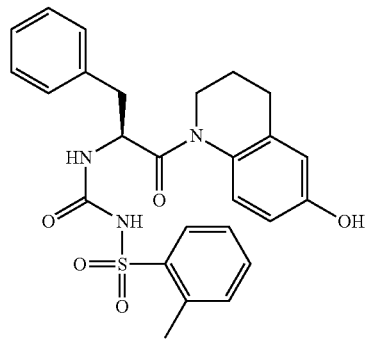 [SMILES: Cc1ccccc1S(=O)(=O)NC(=O)N[C@@H](Cc1ccccc1)C(=O)N1CCCc2cc(O)ccc21]

(S)—N-((1-(6-hydroxy-3,4-dihydroquinolin-1(2H)-yl)-1-oxo-3-phenylpropan-2-yl)carbamoyl)-2-methylbenzenesulfonamide

| MS (M + H)+ Calcd. | 494.2 |
| --- | --- |
| MS (M + H)+ Observ. | 494.5 |
| Retention Time | 1.20 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.82 (br. s., 1H), 7.47 (br. s., 1H), 7.33 (br. s., 3H), 7.25-7.08 (m, 2H), 6.94 (br. s., 1H), 6.75 (br. s., 1H), 6.60-6.29 (m, 3H), 4.92 (br. s., 1H), 3.91-3.36 (m, 2H), 2.54 (s, 3H), 2.70-2.35 (m, 2H), 2.45-2.29 (m, 2H), 1.74-1.48 (m, 2H).

Example 174

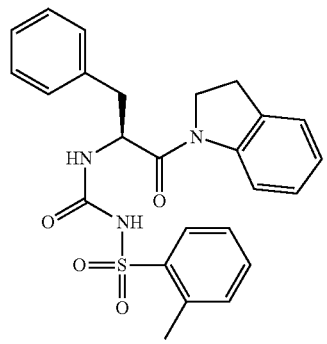 [SMILES: Cc1ccccc1S(=O)(=O)NC(=O)N[C@@H](Cc1ccccc1)C(=O)N1CCc2ccccc21]

(S)—N-((1-(indolin-1-yl)-1-oxo-3-phenylpropan-2-yl)carbamoyl)-2-methylbenzenesulfonamide

| MS (M + H)⁺ Calcd. | 464.2 |
| --- | --- |
| MS (M + H)⁺ Observ. | 464.4 |
| Retention Time | 1.43 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 8.05 (d, J=8.1 Hz, 1H), 7.81 (d, J=7.7 Hz, 1H), 7.53-7.29 (m, 2H), 7.25-7.09 (m, 7H), 7.02 (d, J=6.6 Hz, 1H), 6.68 (br. s., 1H), 4.58 (br. s., 1H), 4.21-3.76 (m, 2H), 3.42-2.68 (m, 4H), 2.58 (s, 3H).

Example 175

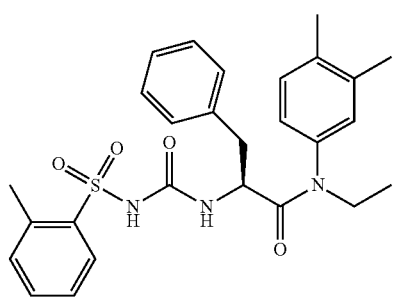 [SMILES: CCN(C(=O)[C@H](Cc1ccccc1)NC(=O)NS(=O)(=O)c1ccccc1C)c1ccc(C)c(C)c1]

(S)—N-(3,4-dimethylphenyl)-N-ethyl-3-phenyl-2-(3-(o-tolylsulfonyl) ureido)propanamide

| MS (M + H)⁺ Calcd. | 494.2 |
| --- | --- |
| MS (M + H)⁺ Observ. | 494.3 |
| Retention Time | 1.94 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.81 (d, J=8.1 Hz, 1H), 7.62-7.48 (m, 1H), 7.46-7.35 (m, 2H), 7.17 (d, J=3.3 Hz, 3H), 7.11 (d, J=8.1 Hz, 1H), 6.81-6.57 (m, 4H), 4.22-4.08 (m, 1H), 3.66-3.45 (m, 2H), 3.14-2.81 (m, 2H), 2.53 (s, 3H), 2.21 (s, 3H), 2.14 (s, 3H), 0.94 (t, J=7.2 Hz, 3H).

Example 176

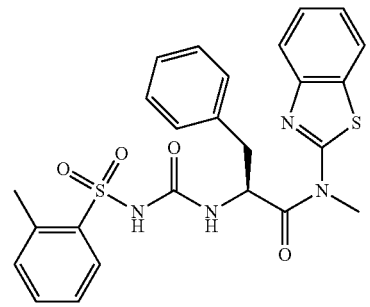 [SMILES: Cc1ccccc1S(=O)(=O)NC(=O)N[C@@H](Cc1ccccc1)C(=O)N(C)c1nc2ccccc2s1]

(S)—N-(benzo[d]thiazol-2-yl)-N-methyl-3-phenyl-2-(3-(o-tolylsulfonyl) ureido)propanamide

| MS (M + H)⁺ Calcd. | 509.1 |
| --- | --- |
| MS (M + H)⁺ Observ. | 509.3 |
| Retention Time | 1.71 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (400 MHZ, MeOH-$d_4$) δ 8.00 (d, J=1.0 Hz, 1H), 7.69 (d, J=7.8 Hz, 1H), 7.61 (d, J=7.6, Hz, 1H), 7.49 (d, J=8.1 Hz, 1H), 7.43-7.36 (m, 2H), 7.33 (d, J=7.6 Hz, 1H), 7.26-7.19 (m, 3H), 7.15 (t, J=7.5 Hz, 2H), 7.01 (d, J=7.3 Hz, 2H), 4.48 (s, 1H), 3.13 (s, 3H), 3.09-2.93 (m, 2H), 2.27 (s, 3H).

Example 177

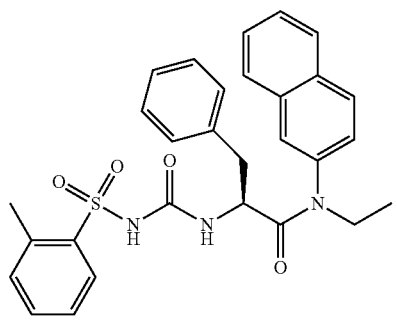 [SMILES: CCN(C(=O)[C@H](Cc1ccccc1)NC(=O)NS(=O)(=O)c1ccccc1C)c1ccc2ccccc2c1]

(S)—N-ethyl-N-(naphthalen-2-yl)-3-phenyl-2-(3-(o-tolylsulfonyl) ureido)propanamide

| MS (M + H)+ Calcd. | 516.2 |
| --- | --- |
| MS (M + H)+ Observ. | 516.3 |
| Retention Time | 1.82 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 8.66 (d, J=4.4 Hz, 1H), 7.77 (d, J=7.7 Hz, 1H), 7.61 (d, J=7.7 Hz, 1H), 7.52 (t, J=7.5 Hz, 1H), 7.44 (dd, J=7.7, 4.8 Hz, 1H), 7.37 (t, J=4.2 Hz, 2H), 7.34 (d, J=9.5 Hz, 2H), 7.13 (d, J=8.8 Hz, 1H), 7.08-7.02 (m, 3H), 6.93 (t, J=9.2 Hz, 1H), 6.33 (d, J=6.6 Hz, 2H), 4.7 (s, 1H), 3.81-3.6 (m, 2H), 3.01-2.70 (m, 2H), 2.51 (br s, 3H), 1.17 (t, J=7.3 Hz, 3H).

Example 178

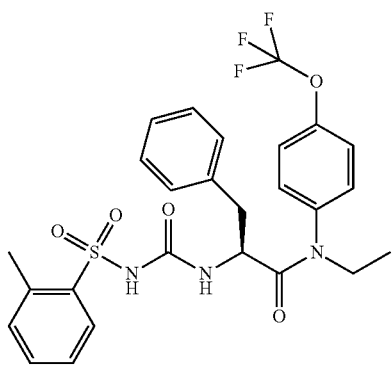 [SMILES: CCN(C(=O)[C@H](Cc1ccccc1)NC(=O)NS(=O)(=O)c1ccccc1C)c1ccc(OC(F)(F)F)cc1]

(S)—N-ethyl-3-phenyl-2-(3-(o-tolylsulfonyl)ureido)-N-(4-(trifluoromethoxy)phenyl)propanamide

| MS (M + H)+ Calcd. | 550.2 |
| --- | --- |
| MS (M + H)+ Observ. | 550.5 |
| Retention Time | 1.81 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.80 (d, J=7.7 Hz, 1H), 7.59-7.50 (m, 1H), 7.45-7.33 (m, 4H), 7.22 (d, J=8.1 Hz, 2H), 7.14 (d, J=7.0 Hz, 3H), 6.77-6.56 (m, 3H), 4.12 (d, J=4.8 Hz, 1H), 3.78-3.43 (m, 2H), 2.99-2.68 (m, 2H), 2.52 (br s., 3H), 0.96 (t, J=7.0 Hz, 3H).

Example 179

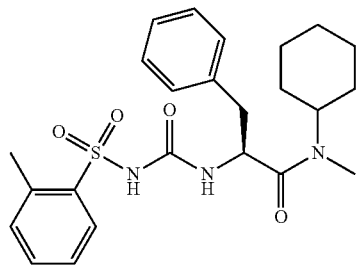 [SMILES: Cc1ccccc1S(=O)(=O)NC(=O)N[C@@H](Cc1ccccc1)C(=O)N(C)C1CCCCC1]

(S)—N-cyclohexyl-N-methyl-3-phenyl-2-(3-(o-tolylsulfonyl)ureido)propanamide

| MS (M + H)+ Calcd. | 458.2 |
| --- | --- |
| MS (M + H)+ Observ. | 458.5 |
| Retention Time | 1.54 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (400 MHZ, MeOH-d$_4$) δ 8.01 (dd, J=8.1, 2.0 Hz, 1H), 7.62-7.53 (m, 1H), 7.46-7.38 (m, 2H), 7.30-7.17 (m, 3H), 7.15-7.05 (m, 2H), 4.82 (t, J=7.1 Hz, 1H), 4.28-4.17 (m, 1H), 2.97-2.80 (m, 2H), 2.64 (s, 3H), 2.60 (s, 3H), 1.84-0.80 (m, 10H).

Example 180

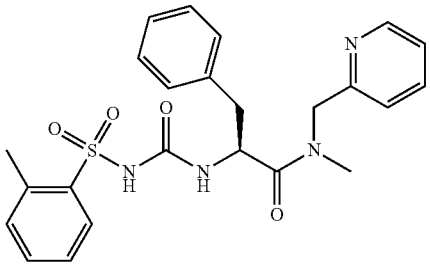 [SMILES: Cc1ccccc1S(=O)(=O)NC(=O)N[C@@H](Cc1ccccc1)C(=O)N(C)Cc1ccccn1]

(S)—N-methyl-3-phenyl-N-(pyridin-2-ylmethyl)-2-(3-(o-tolylsulfonyl) ureido)propanamide

| | |
|---|---|
| MS (M + H)+ Calcd. | 467.2 |
| MS (M + H)+ Observ. | 467.3 |
| Retention Time | 1.27 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 8.48 (d, J=4.8 Hz, 1H), 7.79 (d, J=7.7 Hz, 1H), 7.75-7.60 (m, 2H), 7.36 (br. s., 1H), 7.29-7.18 (m, 3H), 7.17-7.10 (m, 2H), 7.07 (br. s., 1H), 6.98 (br. s., 1H), 6.90 (d, J=8.1 Hz, 1H), 6.37 (br. s., 1H), 4.93-4.64 (m, 1H), 4.60-4.29 (m, 2H), 3.18 (s, 3H), 2.87 (br. s., 3H), 2.85-2.63 (m, 2H).

Example 181

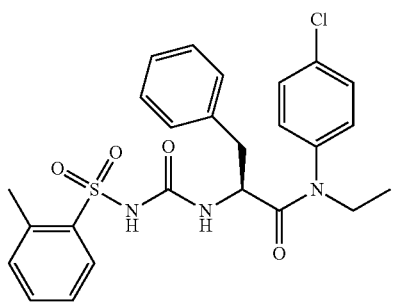 [SMILES: CCN(C(=O)[C@H](Cc1ccccc1)NC(=O)NS(=O)(=O)c1ccccc1C)c1ccc(Cl)cc1]

(S)—N-(4-chlorophenyl)-N-ethyl-3-phenyl-2-(3-(o-tolylsulfonyl) ureido)propanamide

| | |
|---|---|
| MS (M + H)+ Calcd. | 500.1 |
| MS (M + H)+ Observ. | 500.2 |
| Retention Time | 1.72 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.80 (d, J=8.1 Hz, 1H), 7.62-7.53 (m, 1H), 7.48-7.29 (m, 5H), 7.18 (br. s., 3H), 7.03 (d, J=7.3 Hz, 2H), 6.79 (br. s., 2H), 6.66 (d, J=7.0 Hz, 1H), 4.12 (d, J=7.0 Hz, 1H), 3.70-3.48 (m, 2H), 2.83-2.56 (m, 2H), 2.52 (s, 3H), 0.94 (t, J=7.0 Hz, 3H).

Example 182

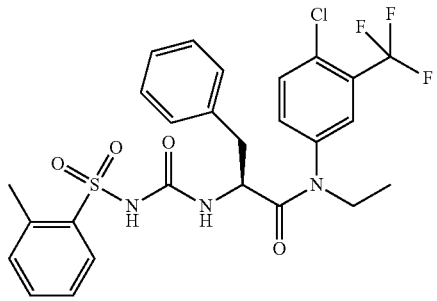 [SMILES: CCN(C(=O)[C@H](Cc1ccccc1)NC(=O)NS(=O)(=O)c1ccccc1C)c1ccc(Cl)c(C(F)(F)F)c1]

(S)—N-(4-chloro-3-(trifluoromethyl)phenyl)-N-ethyl-3-phenyl-2-(3-(o-tolylsulfonyl) ureido)propanamide

| | |
|---|---|
| MS (M + H)+ Calcd. | 568.1 |
| MS (M + H)+ Observ. | 568.5 |
| Retention Time | 1.87 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.84 (d, J=7.3 Hz, 1H), 7.68 (d, J=7.7 Hz, 1H), 7.60-7.50 (m, 1H), 7.45-7.33 (m, 3H), 7.20 (br. s., 4H), 6.84 (br. s., 2H), 6.75 (d, J=7.7 Hz, 1H), 4.03 (d, J=7.7 Hz, 1H), 3.69-3.45 (m, 2H), 2.83-2.56 (m, 2H), 2.53 (s, 3H), 0.91 (t, J=6.8 Hz, 3H).

Example 183

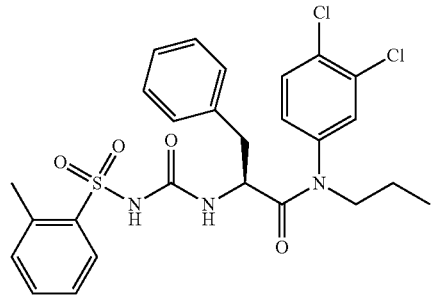 [SMILES: CCCN(C(=O)[C@H](Cc1ccccc1)NC(=O)NS(=O)(=O)c1ccccc1C)c1ccc(Cl)c(Cl)c1]

(S)—N-(3,4-dichlorophenyl)-3-phenyl-N-propyl-2-(3-(o-tolylsulfonyl) ureido)propanamide

| | |
|---|---|
| MS (M + H)+ Calcd. | 548.11 |
| MS (M + H)+ Observ. | 548.5 |
| Retention Time | 1.91 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.84 (d, J=7.3 Hz, 1H), 7.68 (d, J=7.7 Hz, 1H), 7.60-7.50 (m, 1H), 7.45-7.33 (m, 3H), 7.20 (br. s., 4H), 6.84 (br. s., 2H), 6.75 (d, J=7.7 Hz, 1H), 4.03 (d, J=7.7 Hz, 1H), 3.69-3.45 (m, 2H), 2.83-2.56 (m, 2H), 2.53 (s, 3H), 1.29 (m. 2H), 0.91 (t, J=6.8 Hz, 3H).

Example 184

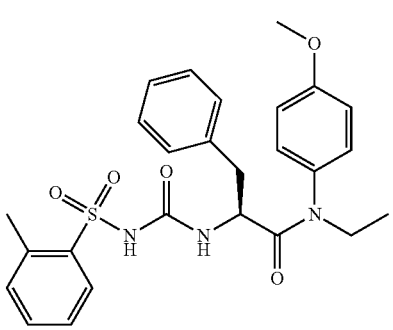 [SMILES: CCN(C(=O)[C@H](Cc1ccccc1)NC(=O)NS(=O)(=O)c1ccccc1C)c1ccc(OC)cc1]

(S)—N-ethyl-N-(4-methoxyphenyl)-3-phenyl-2-(3-(o-tolylsulfonyl) ureido)propanamide

| | |
|---|---|
| MS (M + H)+ Calcd. | 496.2 |
| MS (M + H)+ Observ. | 496.3 |
| Retention Time | 1.58 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.79 (d, J=7.7 Hz, 1H), 7.60-7.50 (m, 1H), 7.43-7.31 (m, 2H), 7.16-7.14 (m, 3H), 7.03-6.90 (m, 4H), 6.77-6.75 (m, 2H), 6.62 (d, J=8.8 Hz, 1H), 4.24 (br. s., 1H), 3.77 (s, 3H), 3.69-3.40 (m, 2H), 2.80-2.50 (m, 2H), 2.55 (s, 3H), 0.95 (t, J=7.0 Hz, 3H).

Example 185

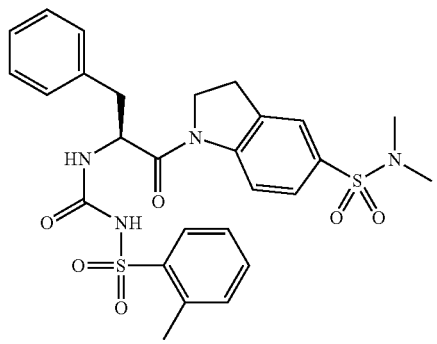 [SMILES: Cc1ccccc1S(=O)(=O)NC(=O)N[C@@H](Cc1ccccc1)C(=O)N1CCc2cc(S(=O)(=O)N(C)C)ccc21]

(S)—N,N-dimethyl-1-(3-phenyl-2-(3-(o-tolylsulfonyl) ureido)propanoyl)indoline-5-sulfonamide

| | |
|---|---|
| MS (M + H)+ Calcd. | 571.2 |
| MS (M + H)+ Observ. | 571.5 |
| Retention Time | 2.27 min |
| | LC Condition |
| Solvent A | 5% Methanol:95% Water:10 mM Ammonium Acetate |
| Solvent B | 95% Methanol:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (400 MHZ, MeOH-d$_4$) δ 8.52 (br. s., 1H), 8.29 (d, J=8.1 Hz, 2H), 7.95 (d, J=6.8 Hz, 2H), 7.64-7.53 (m, 2H), 7.47-7.37 (m, 3H), 7.29-7.26 (m, 3H), 4.75 (br. s., 1H), 4.20 (br. s., 1H), 3.63 (br. s., 1H), 3.16-2.87 (m, 4H), 2.70 (s, 3H), 2.67 (s, 3H), 2.64 (S, 3H).

Example 186

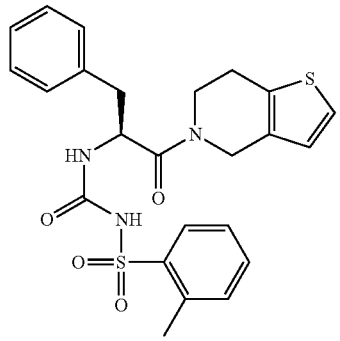 [SMILES: Cc1ccccc1S(=O)(=O)NC(=O)N[C@@H](Cc1ccccc1)C(=O)N1CCc2sccc2C1]

243

(S)—N-((1-(6,7-dihydrothieno[3,2-c]pyridin-5(4H)-yl)-1-oxo-3-phenylpropan-2-yl)carbamoyl)-2-methylbenzenesulfonamide

| | |
|---|---|
| MS (M + H)+ Calcd. | 484.1 |
| MS (M + H)+ Observ. | 484.2 |
| Retention Time | 1.73 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 187

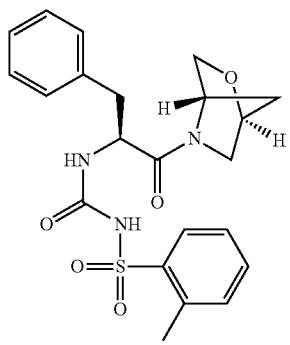 [SMILES: Cc1ccccc1S(=O)(=O)NC(=O)N[C@@H](Cc1ccccc1)C(=O)N1C[C@@H]2C[C@H]1CO2]

N—(((S)-1-((1S,4S)-2-oxa-5-azabicyclo[2.2.1]heptan-5-yl)-1-oxo-3-phenylpropan-2-yl) carbamoyl)-2-methylbenzenesulfonamide

| | |
|---|---|
| MS (M + H)+ Calcd. | 444.2 |
| MS (M + H)+ Observ. | 444.2 |
| Retention Time | 1.11 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

244

Example 188

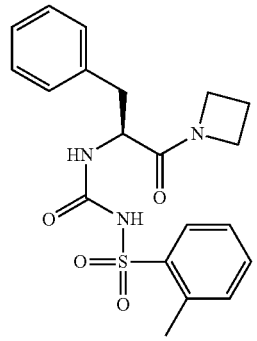 [SMILES: Cc1ccccc1S(=O)(=O)NC(=O)N[C@@H](Cc1ccccc1)C(=O)N1CCC1]

(S)—N-((1-(azetidin-1-yl)-1-oxo-3-phenylpropan-2-yl)carbamoyl)-2-methylbenzenesulfonamide

| | |
|---|---|
| MS (M + H)+ Calcd. | 402.1 |
| MS (M + H)+ Observ. | 402.2 |
| Retention Time | 1.14 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.83 (d, J=7.7 Hz, 1H), 7.48 (br. s., 1H), 7.35 (br. s., 1H), 7.24-7.26 (m, 4H), 7.08 (d, J=7.3 Hz, 2H), 6.47 (br. s., 1H), 4.17 (d, J=6.6 Hz, 1H), 3.85-3.68 (m, 2H), 3.66-3.54 (m, 2H), 2.82-2.63 (m, 2H), 2.51 (m, 3H), 2.16-1.90 (m, 2H).

Example 189

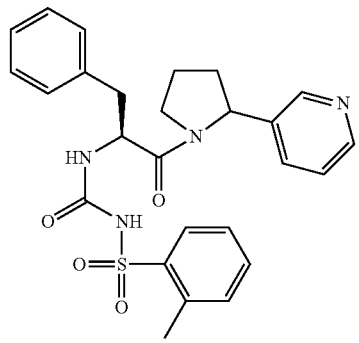 [SMILES: Cc1ccccc1S(=O)(=O)NC(=O)N[C@@H](Cc1ccccc1)C(=O)N1CCCC1c1cccnc1]

2-methyl-N-(((2S)-1-oxo-3-phenyl-1-(2-(pyridin-3-yl)pyrrolidin-1-yl)propan-2-yl)carbamoyl)benzenesulfonamide

| | |
|---|---|
| MS (M + H)+ Calcd. | 493.2 |
| MS (M + H)+ Observ. | 493.2 |
| Retention Time | 1.28 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 190

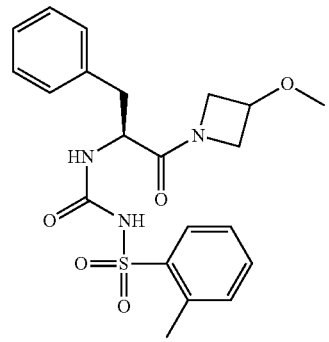 [SMILES: COC1CN(C(=O)[C@H](Cc2ccccc2)NC(=O)NS(=O)(=O)c2ccccc2C)C1]

(S)—N-((1-(3-methoxyazetidin-1-yl)-1-oxo-3-phenylpropan-2-yl)carbamoyl)-2-methylbenzenesulfonamide

| | |
|---|---|
| MS (M + H)+ Calcd. | 432.2 |
| MS (M + H)+ Observ. | 432.4 |
| Retention Time | 1.98 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.75 (d, J=7.3 Hz, 1H), 7.36-7.06 (m, 8H), 6.16 (br. s., 1H), 4.15 (br. s., 1H), 4.07-3.74 (m, 4H), 3.61-3.23 (m, 2H), 3.12 (s, 3H), 2.51 (s, 3H).

Example 191

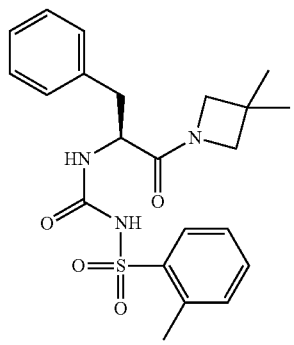 [SMILES: Cc1ccccc1S(=O)(=O)NC(=O)N[C@@H](Cc1ccccc1)C(=O)N1CC(C)(C)C1]

(S)—N-((1-(3,3-dimethylazetidin-1-yl)-1-oxo-3-phenylpropan-2-yl)carbamoyl)-2-methylbenzenesulfonamide

| | |
|---|---|
| MS (M + H)+ Calcd. | 430.2 |
| MS (M + H)+ Observ. | 430.3 |
| Retention Time | 1.36 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.77 (d, J=7.3 Hz, 1H), 7.36-7.03 (m, 8H), 6.12 (br. s., 1H), 4.12 (br. s., 1H), 3.67-3.00 (m, 6H), 2.51 (s, 3H), 1.07 (s, 3H), 0.91 (s, 3H).

Example 192

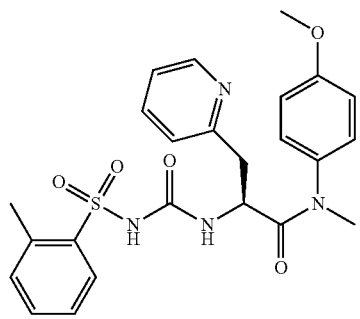 [SMILES: COc1ccc(N(C)C(=O)[C@H](Cc2ccccn2)NC(=O)NS(=O)(=O)c2ccccc2C)cc1]

(S)—N-(4-methoxyphenyl)-N-methyl-3-(pyridin-2-yl)-2-(3-(o-tolylsulfonyl) ureido)propanamide

| | |
|---|---|
| MS (M + H)+ Calcd. | 483.2 |
| MS (M + H)+ Observ. | 483.2 |
| Retention Time | 1.22 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 8.34 (d, J=4.0 Hz, 1H), 7.77 (d, J=8.1 Hz, 1H), 7.58 (t, J=7.3 Hz, 1H), 7.54-7.47 (m, 1H), 7.39-7.31 (m, 2H), 7.21-7.14 (m, 1H), 7.07 (d, J=8.1 Hz, 2H), 6.97-6.82 (m, 3H), 6.61 (br. s., 1H), 4.44 (br. s., 1H), 3.76 (s, 3H), 3.07 (s, 3H), 2.93-2.63 (m, 2H), 2.5 (s J=13.4, 3H).

Example 193

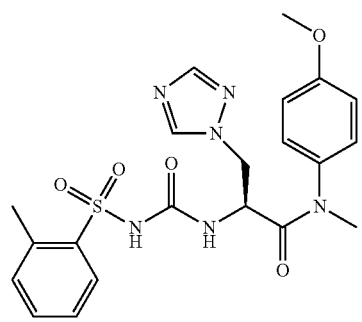 [SMILES: COc1ccc(N(C)C(=O)[C@H](Cn2cncn2)NC(=O)NS(=O)(=O)c2ccccc2C)cc1]

(S)—N-(4-methoxyphenyl)-N-methyl-2-(3-(o-tolylsulfonyl) ureido)-3-(1H-1,2,4-triazol-1-yl)propanamide

| | |
|---|---|
| MS (M + H)+ Calcd. | 473.2 |
| MS (M + H)+ Observ. | 473.1 |
| Retention Time | 1.85 min |
| | LC Condition |
| Solvent A | 5% Methanol:95% Water:10 mM Ammonium Acetate |
| Solvent B | 95% Methanol:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 8.24 (s, 1H), 7.87-7.74 (m, 2H), 7.53 (d, J=6.6 Hz, 1H), 7.44-7.33 (m, 2H), 7.15-7.11 (m, 3H), 6.92 (d, J=8.4 Hz, 2H), 6.83 (br. s., 1H), 4.46 (br. s., 1H), 4.31-4.02 (m, 2H), 3.76 (s, 3H), 3.09 (s, 3H), 2.54 (s, 3H).

Example 194

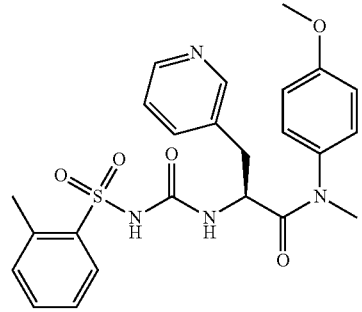

(S)—N-(4-methoxyphenyl)-N-methyl-3-(pyridin-3-yl)-2-(3-(o-tolylsulfonyl) ureido)propanamide

| | |
|---|---|
| MS (M + H)+ Calcd. | 483.2 |
| MS (M + H)+ Observ. | 483.2 |
| Retention Time | 1.15 |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 8.34 (br. s., 1H), 7.72 (d, J=7.7 Hz, 1H), 7.36 (br. s., 1H), 7.24 (br. s., 2H), 7.15-7.11 (m, 4H), 6.91-6.94 (m, 3H), 6.29 (br. s., 1H), 4.25 (br. s., 1H), 3.77 (br. s., 3H), 3.09 (s, 3H), 2.76-2.49 (m, 2H), 2.5 (s, 3H).

Example 195

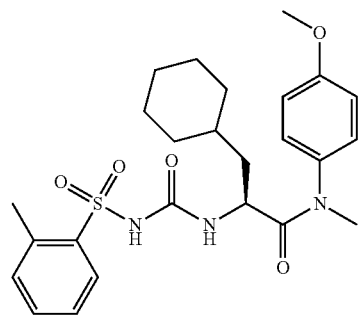 [SMILES: COc1ccc(N(C)C(=O)[C@H](CC2CCCCC2)NC(=O)NS(=O)(=O)c2ccccc2C)cc1]

(S)-3-cyclohexyl-N-(4-methoxyphenyl)-N-methyl-2-(3-(o-tolylsulfonyl) ureido)propanamide

| | |
|---|---|
| MS (M + H)+ Calcd. | 488.2 |
| MS (M + H)+ Observ. | 488.2 |
| Retention Time | 1.72 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.86 (d, J=7.7 Hz, 1H), 7.59-7.48 (m, 1H), 7.43-7.32 (m, 2H), 7.19 (d, J=8.4 Hz, 2H), 6.96 (d, J=8.4 Hz, 2H), 6.51 (br. s., 1H), 4.21 (t, J=7.7 Hz, 1H), 3.75 (s, 3H), 3.09 (s, 3H), 2.56 (s, 3H), 1.54-1.37 (m, 2H), 1.35-1.17 (m, 4H), 1.06-0.85 (m, 7H).

Example 196

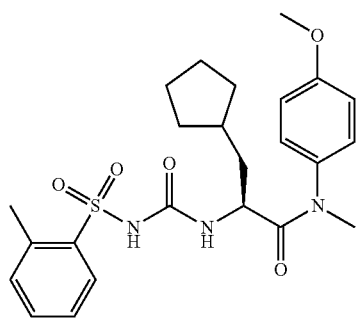 [SMILES: COc1ccc(N(C)C(=O)[C@H](CC2CCCC2)NC(=O)NS(=O)(=O)c2ccccc2C)cc1]

(S)-3-cyclopentyl-N-(4-methoxyphenyl)-N-methyl-2-(3-(o-tolylsulfonyl) ureido)propanamide

| | |
|---|---|
| MS (M + H)+ Calcd. | 474.2 |
| MS (M + H)+ Observ. | 474.2 |
| Retention Time | 1.61 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 197

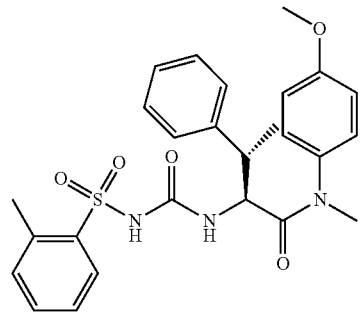 [SMILES: COc1ccc(N(C)C(=O)[C@@H](NC(=O)NS(=O)(=O)c2ccccc2C)[C@@H](C)c2ccccc2)cc1]

(2S,3S)—N-(4-methoxyphenyl)-N-methyl-3-phenyl-2-(3-(o-tolylsulfonyl) ureido)butanamide

| | |
|---|---|
| MS (M + H)+ Calcd. | 496.2 |
| MS (M + H)+ Observ. | 496.2 |
| Retention Time | 1.73 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.76 (d, J=7.7 Hz, 1H), 7.59-7.52 (m, 1H), 7.42-7.34 (m, 2H), 7.21-7.12 (m, 4H), 6.98-6.81 (m, 4H), 6.38 (br. s., 1H), 4.40-4.43 (m, 1H), 3.78 (s, 3H), 3.11 (s, 3H), 2.84-2.87 (m, 1H), 2.46 (s, 3H), 0.90 (d, J=7.3 Hz, 3H).

Example 198

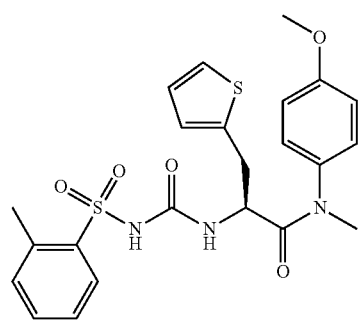 [SMILES: COc1ccc(N(C)C(=O)[C@H](Cc2cccs2)NC(=O)NS(=O)(=O)c2ccccc2C)cc1]

(S)—N-(4-methoxyphenyl)-N-methyl-3-(thiophen-2-yl)-2-(3-(o-tolylsulfonyl) ureido)propanamide

| | |
|---|---|
| MS (M + H)+ Calcd. | 488.1 |
| MS (M + H)+ Observ. | 488.1 |
| Retention Time | 1.4 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 7.81 (d, J=7.7 Hz, 1H), 7.51 (br. s., 1H), 7.42-7.32 (m, 2H), 7.25 (d, J=4.8 Hz, 1H), 7.07 (d, J=8.1 Hz, 2H), 6.93 (s, 1H), 6.87-6.81 (m, 1H), 6.66-6.49 (m, 2H), 4.24 (br. s., 1H), 3.76 (s, 3H), 3.09 (s, 3H), 2.99-2.67 (m, 2H), 2.55 (s, 3H).

Example 199

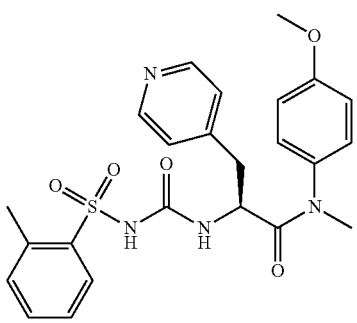 [SMILES: COc1ccc(N(C)C(=O)[C@H](Cc2ccncc2)NC(=O)NS(=O)(=O)c2ccccc2C)cc1]

(S)—N-(4-methoxyphenyl)-N-methyl-3-(pyridin-4-yl)-2-(3-(o-tolylsulfonyl) ureido)propanamide

| | |
|---|---|
| MS (M + H)+ Calcd. | 483.3 |
| MS (M + H)+ Observ. | 483.1 |
| Retention Time | 1.09 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-d$_6$) δ 8.31 (d, J=5.5 Hz, 1H), 7.73 (d, J=7.7 Hz, 1H), 7.43-7.22 (m, 3H), 7.13 (d, J=7.3 Hz, 2H), 6.94 (d, J=8.4 Hz, 2H), 6.75 (d, J=5.1 Hz, 2H), 6.36 (br. s., 1H), 4.29 (br. s., 1H), 3.78 (br. s., 3H), 3.10 (s, 3H), 2.74-2.54 (m, 2H), 2.5 (s, 3H).

Example 200

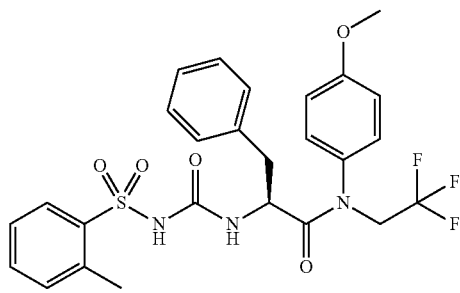 [SMILES: COc1ccc(N(CC(F)(F)F)C(=O)[C@H](Cc2ccccc2)NC(=O)NS(=O)(=O)c2ccccc2C)cc1]

(S)—N-(4-methoxyphenyl)-3-phenyl-2-(3-(o-tolylsulfonyl)ureido)-N-(2,2,2-trifluoroethyl)propanamide

| | |
|---|---|
| MS (M + H)+ Calcd. | 550.2 |
| MS (M + H)+ Observ. | 550.3 |
| Retention Time | 2.0 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 201

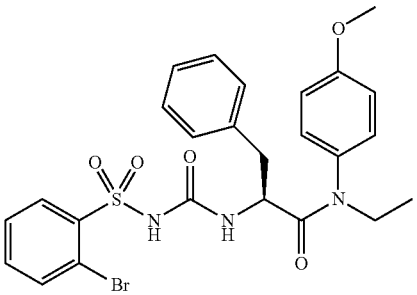 [SMILES: CCN(C(=O)[C@H](Cc1ccccc1)NC(=O)NS(=O)(=O)c1ccccc1Br)c1ccc(OC)cc1]

(S)-2-(3-((2-bromophenyl)sulfonyl)ureido)-N-ethyl-N-(4-methoxyphenyl)-3-phenylpropanamide

| | |
|---|---|
| MS (M + H)+ Calcd. | 560.1 |
| MS (M + H)+ Observ. | 560.1 |
| Retention Time | 1.61 min |

|  | LC Condition |
|---|---|
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.89 (d, J=7.7 Hz, 1H), 7.70 (d, J=7.3 Hz, 1H), 7.46-7.31 (m, 2H), 7.15 (br. s., 3H), 6.94-6.72 (m, 5H), 6.33 (br. s., 1H), 4.15 (br. s., 1H), 3.70 (s, 3H), 3.69-3.41 (m, 2H), 2.77-2.4 (m, 2H), 0.94 (t, J=7.0 Hz, 3H).

Example 203

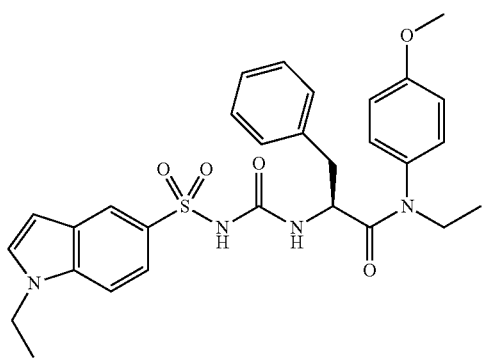 [SMILES: CCN(C(=O)[C@H](Cc1ccccc1)NC(=O)NS(=O)(=O)c1ccc2c(ccn2CC)c1)c1ccc(OC)cc1]

(S)—N-ethyl-2-(3-((1-ethyl-1H-indol-5-yl)sulfonyl) ureido)-N-(4-methoxyphenyl)-3-phenylpropanamide

| MS (M + H)$^+$ Calcd. | 549.2 |
|---|---|
| MS (M + H)$^+$ Observ. | 549.4 |
| Retention Time | 2.62 min |
|  | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 8.00 (br. s., 1H), 7.53 (br. s., 4H), 7.11 (br. s., 4H), 6.91-6.74 (m, 6H), 6.59 (br. s., 1H), 6.41 (br. s., 1H), 4.32-4.10 (m, 1H), 3.74 (br. s., 3H), 3.35 (br. s., 2H), 2.95-2.65 (m, 4H), 1.34 (br. s., 3H), 0.92 (br. s., 3H).

Example 204

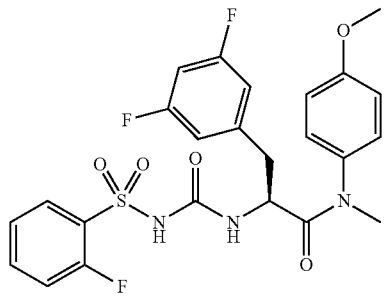 [SMILES: COc1ccc(N(C)C(=O)[C@H](Cc2cc(F)cc(F)c2)NC(=O)NS(=O)(=O)c2ccccc2F)cc1]

(S)-3-(3,5-difluorophenyl)-2-(3-((2-fluorophenyl) sulfonyl) ureido)-N-(4-methoxyphenyl)-N-methyl-propanamide

| MS (M + H)$^+$ Calcd. | 522.1 |
|---|---|
| MS (M + H)$^+$ Observ. | 522.2 |
| Retention Time | 1.61 min |
|  | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.74-7.50 (m, 2H), 7.32-7.15 (m, 4H), 6.96-6.97 (m, 3H), 6.41-6.43 (m, 3H), 4.28 (br. s., 1H), 3.78 (s, 3H), 3.10 (s, 3H), 2.77-2.52 (m, 2H).

Example 205

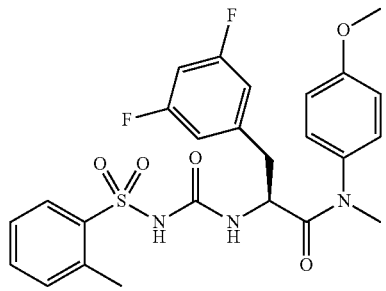 [SMILES: COc1ccc(N(C)C(=O)[C@H](Cc2cc(F)cc(F)c2)NC(=O)NS(=O)(=O)c2ccccc2C)cc1]

(S)-3-(3,5-difluorophenyl)-N-(4-methoxyphenyl)-N-methyl-2-(3-(o-tolylsulfonyl) ureido)propanamide

| MS (M + H)$^+$ Calcd. | 518.2 |
|---|---|
| MS (M + H)$^+$ Observ. | 518.2 |
| Retention Time | 1.73 min |

| | LC Condition |
|---|---|
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHZ, DMSO-$d_6$) δ 7.78 (d, J=8.1 Hz, 1H), 7.53 (t, J=7.2 Hz, 1H), 7.36 (d, J=7.7 Hz, 2H), 7.19 (d, J=8.8 Hz, 2H), 6.97-7.00 (m, 3H), 6.68 (d, J=8.1 Hz, 1H), 6.38 (d, J=6.6 Hz, 2H), 4.33-4.20 (m, 1H), 3.78 (s, 3H), 3.12 (s, 3H), 2.81-2.53 (m, 2H), 2.50 (s, 3H).

Intermediate JB-1

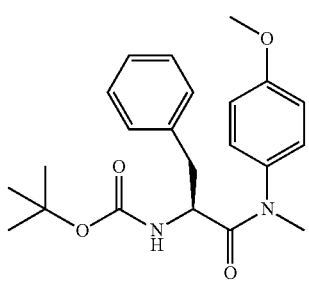 [SMILES: COc1ccc(N(C)C(=O)[C@H](Cc2ccccc2)NC(=O)OC(C)(C)C)cc1]

(S)-tert-butyl (1-((4-methoxyphenyl)(methyl)amino)-1-oxo-3-phenylpropan-2-yl)carbamate HATU (1.5 g, 4.0 mmol) was added to a stirred solution of 4-methoxy-N-methylaniline (500 mg, 3.64 mmol) and (S)-2-((tert-butoxycarbonyl)amino)-3-phenylpropanoic acid (1.06 g, 4.0 mmol) in DMF (20 mL) and DIPEA (1.3 mL, 7.3 mmol) and the reaction mixture was stirred at rt for 4 h. The reaction was concentrated and the residual crude oil was partitioned between EtOAc (~60 mL) and 1/2 sat. NaHCO$_3$ (aq) (~60 mL). The organic component was washed with brine (~40 mL), dried (MgSO$_4$), filtered, concentrated and purified using a Biotage Horizon (80 g SiO$_2$, 10-40% EtOAc/hexanes) to yield (S)-tert-butyl (1-((4-methoxyphenyl)(methyl)amino)-1-oxo-3-phenylpropan-2-yl)carbamate (1.34 g) as a clear amber viscous oil. LC-MS retention time=3.17 min; m/z=385.3 [M+H]$^+$. (Column: Phenonenex-Luna C18 2.0×50 mm 3 μm. Solvent A=95% Water: 5% Acetonitrile: 10 mM NH$_4$OAc. Solvent B=5% Water: 95% Acetonitrile: 10 mM NH$_4$OAc. Flow Rate=0.8 mL/min. Start % B=0. Final % B=100. Gradient Time=4 min. Wavelength=220). $^1$H NMR (400 MHZ, CDCl$_3$) δ 7.25-7.20 (m, 3H), 7.03-6.64 (m, 6H), 5.20 (d, J=8.8 Hz, 1H), 4.53 (q, J=7.4 Hz, 1H), 3.83 (s, 3H), 3.18 (s, 3H), 2.89 (dd, J=13.1, 7.5 Hz, 1H), 2.71 (dd, J=13.1, 6.5 Hz, 1H), 1.39 (s, 9H).

Intermediate JB-2

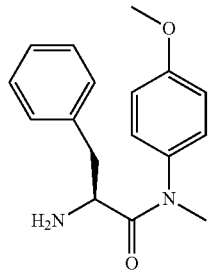 [SMILES: COc1ccc(N(C)C(=O)[C@@H](N)Cc2ccccc2)cc1]

(S)-2-amino-N-(4-methoxyphenyl)-N-methyl-3-phenylpropanamide

A 4M HCl (15 mL, 60.0 mmol) in dioxanes solution was added to a stirred solution of (S)-tert-butyl (1-((4-methoxyphenyl)(methyl)amino)-1-oxo-3-phenylpropan-2-yl)carbamate (Intermediate JB-1) (1.34 g, 3.49 mmol) in THF (10 mL) and the reaction mixture was stirred at rt for 5 h. The reaction mixture was concentrated to dryness under vacuum to yield an HCl salt of (S)-2-amino-N-(4-methoxyphenyl)-N-methyl-3-phenylpropanamide (1.11 g) as a solidified foam which was used without additional purification. LC-MS retention time=2.33 min; m/z=285.2 [M+H]$^+$. (Column: Phenonenex-Luna C18 2.0×50 mm 3 μm. Solvent A=95% Water: 5% Acetonitrile: 10 mM NH$_4$OAc. Solvent B=5% Water: 95% Acetonitrile: 10 mM NH$_4$OAc. Flow Rate=0.8 mL/min. Start % B=0. Final % B=100. Gradient Time=4 min. Wavelength=220).

Intermediate JB-7

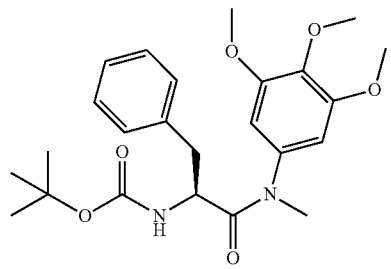 [SMILES: COc1cc(N(C)C(=O)[C@H](Cc2ccccc2)NC(=O)OC(C)(C)C)cc(OC)c1OC]

(S)-tert-butyl (1-(methyl(3,4,5-trimethoxyphenyl)amino)-1-oxo-3-phenylpropan-2-yl)carbamate HATU (776 mg, 2.04 mmol) was added to a stirred solution of 3,4,5-trimethoxy-N-methylaniline (350 mg, 1.78 mmol) and (S)-2-((tert-butoxycarbonyl)amino)-3-phenylpropanoic acid (518 mg, 1.95 mmol) in DMF (10 mL) and DIPEA (0.62 mL, 3.6 mmol) and stirred at rt ON. The reaction mixture was concentrated and the crude oil was partitioned between EtOAc (~40 mL) and 1/2 sat NaHCO$_3$ (aq) (~40 mL). The organic component was washed with brine (~30 mL), dried (MgSO$_4$), filtered and concentrated. The crude residue was then purified using a Biotage Horizon (80 g SiO$_2$, 10-40% EtOAc/hexanes) to yield(S)-tert-butyl (1-(methyl(3,4,5-trimethoxyphenyl)amino)-1-oxo-3-phenylpropan-2-yl)carbamate (474 mg) as a clear colorless solidified oil. Used without further purification. LC-MS retention time=1.60 min; m/z=385.3 [M+H]$^+$. (Column: Phenonenex-Luna C18 2.0×50 mm 3 μm. Solvent A=90% Water: 10% Acetonitrile: 0.1% TFA. Solvent B=10% Water: 90% Acetonitrile: 0.1% TFA. Flow Rate=1.0 mL/min. Start % B=0. Final % B=100. Gradient Time=2 min. Wavelength=220). $^1$H NMR (400 MHZ, CDCl$_3$) δ 7.27-7.17 (m, 3H), 7.01 (d, J=6.3 Hz, 2H), 6.11 (br. s., 2H), 5.21 (d, J=9.0 Hz, 1H), 4.76-4.64 (m, 1H), 3.86 (s, 3H), 3.77 (br. s., 6H), 3.17 (s, 3H), 3.01-2.87 (m, 1H), 2.77 (dd, J=12.8, 6.3 Hz, 1H), 1.40 (s, 9H).

Intermediate ZY-1

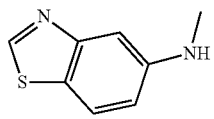

N-methylbenzo[d]thiazol-5-amine

Paraformaldehyde (80 mg, 2.7 mmol) was added to a stirred solution of benzo[d]thiazol-5-amine (200 mg, 1.332 mmol) in MeOH (5 mL) The resulting suspension was then treated with 25% w/w NaOMe in MeOH (1.5 mL, 6.7 mmol) and the clear reaction mixture was stirred at 60° C. for 16 h. The reaction was allowed to cool to rt and then treated with NaBH$_4$ (126 mg, 3.33 mmol) and stirred at rt for 16 h. The reaction mixture was diluted with water (10 mL) and extracted with CHCl$_3$ (3×20 mL). The combined organic component was concentrated and purified using a Biotage Horizon (12 g SiO$_2$, 0-50% EtOAc/hexanes) to yield N-methylbenzo[d]thiazol-5-amine (217 mg) as yellow gum. LC-MS retention time=0.67 min; m/z=165.05 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^1$H NMR (400 MHz, CDCl$_3$) δ 8.92 (s, 1H), 7.69 (d, J=8.5 Hz, 1H), 7.31 (d, J=2.3 Hz, 1H), 6.82 (dd, J=8.8, 2.3 Hz, 1H), 3.93 (br. s., 1H), 2.94 (s, 3H).

Intermediate ZY-2

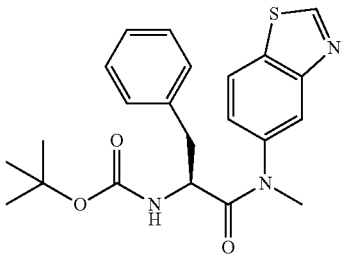 [SMILES: CN(C(=O)[C@H](Cc1ccccc1)NC(=O)OC(C)(C)C)c1ccc2scnc2c1]

(S)-tert-butyl (1-(benzo[d]thiazol-5-yl(methyl)amino)-1-oxo-3-phenylpropan-2-yl)carbamate HATU (1.90 g, 5.01 mmol) was added to a solution of N-methylbenzo[d]thiazol-5-amine (Intermediate ZY-1) (685 mg, 4.17 mmol) and (S)-2-((tert-butoxycarbonyl)amino)-3-phenylpropanoic acid (1.33 g, 5.01 mmol) in DMF (20 mL) and DIPEA (2.18 mL, 12.5 mmol) and the reaction mixture was stirred at rt for 6 h. The crude reaction mixture was diluted with sat. aq. NaHCO$_3$ (20 mL) and extracted with EtOAc (3×50 mL). The combined organic component was washed with brine (~60 mL), dried (Na$_2$SO$_4$), filtered and concentrated. The crude material was then purified using a Biotage Horizon (12 g SiO$_2$, 0-40%-50% EtOAc/hexanes) to yield (S)-tert-butyl (1-(benzo[d]thiazol-5-yl(methyl)amino)-1-oxo-3-phenylpropan-2-yl)carbamate (1.7 g) as a white solid. LC-MS retention time=1.19 min; m/z=412.0 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^1$H NMR (400 MHz, CDCl$_3$) δ 9.07 (s, 1H), 7.90 (d, J=8.3 Hz, 1H), 7.38 (d, J=7.5 Hz, 1H), 7.27-7.19 (m, 3H), 6.94 (d, J=6.8 Hz, 3H), 5.22 (d, J=8.8 Hz, 1H), 4.58-4.48 (m, 1H), 3.26 (s, 3H), 2.93 (dd, J=12.9, 8.4 Hz, 1H), 2.78 (dd, J=12.4, 5.9 Hz, 1H), 1.40 (s, 9H).

Intermediate ZY-3

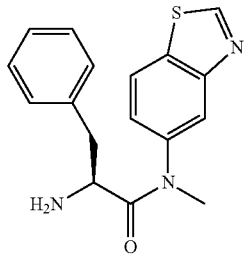 [SMILES: CN(C(=O)[C@@H](N)Cc1ccccc1)c1ccc2scnc2c1]

(S)-2-amino-N-(benzo[d]thiazol-5-yl)-N-methyl-3-phenylpropanamide

A solution of 4M HCl (10 mL, 40.0 mmol) in dioxanes was added to a stirred solution of (S)-tert-butyl (1-(benzo[d]thiazol-5-yl(methyl)amino)-1-oxo-3-phenylpropan-2-yl)carbamate (Intermediate ZY-2) (1.7 g, 4.13 mmol) in THF (10 mL) and the reaction mixture was stirred at rt for 16 h. The reaction mixture was concentrated, redissolved in EtOH/toluene, and then reconcentrated (3×) to yield an HCl salt of (S)-2-amino-N-(benzo[d]thiazol-5-yl)-N-methyl-3-phenylpropanamide (1.7 g, 4.42 mmol, 107% yield) as a pink sticky solid. LC-MS retention time=0.83 min; m/z=312.0 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^1$H NMR (400 MHZ, MeOH-d$_4$) δ 9.42 (s, 1H), 8.10 (d, J=8.3 Hz, 1H), 7.39-7.08 (m, 6H), 6.91 (d, J=7.0 Hz, 2H), 4.10 (dd, J=8.0, 6.5 Hz, 1H), 3.63-3.56 (m, 2H), 3.11 (dd, J=13.4, 8.2 Hz, 1H), 2.92 (dd, J=13.3, 6.5 Hz, 1H), 2.87 (s, 3H).

Intermediate ZY-4

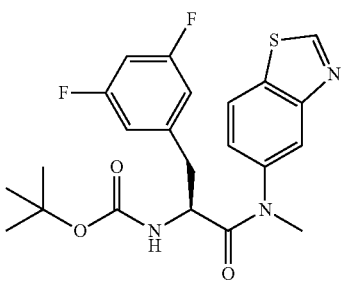 [SMILES: CN(C(=O)[C@H](Cc1cc(F)cc(F)c1)NC(=O)OC(C)(C)C)c1ccc2scnc2c1]

(S)-tert-butyl (1-(benzo[d]thiazol-5-yl(methyl)amino)-3-(3,5-difluorophenyl)-1-oxopropan-2-yl)carbamate HATU (592 mg, 1.556 mmol) was added to a stirred solution of N-methylbenzo[d]thiazol-5-amine (Intermediate ZY-1) (213 mg, 1.30 mmol) and (S)-2-((tert-butoxycarbonyl)amino)-3-(3,5-difluorophenyl)propanoic acid (469 mg, 1.56 mmol) in DMF (7 mL) and DIPEA (0.45 mL, 2.6 mmol) and the reaction mixture was stirred at rt for 16 h. The crude reaction mixture was diluted with sat. aq. NaHCO$_3$ (20 mL) and extracted with EtOAc (3×50 mL). The combined organic component was washed with brine (~60 mL), dried (Na$_2$SO$_4$), filtered and concentrated. The crude material was then purified using a Biotage Horizon (24 g SiO$_2$, 0-50% EtOAc/hexanes) yield (S)-tert-butyl (1-(benzo[d]thiazol-5-yl(methyl)amino)-3-(3,5-difluorophenyl)-1-oxopropan-2-yl)carbamate (581 mg) as a white solid. LC-MS retention time=1.23 min; m/z=448.0 [M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^1$H NMR (400 MHz, CDCl$_3$) δ 9.10 (s, 1H), 7.98 (d, J=8.3 Hz, 1H), 7.68 (br. s., 1H), 7.05 (br. s., 1H), 6.68 (t, J=8.9 Hz, 1H), 6.44 (d, J=6.3 Hz, 2H), 5.25 (d, J=9.0 Hz, 1H), 4.54 (q, J=7.3 Hz, 1H), 2.94-2.86 (m, 1H), 2.81 (s, 3H), 2.72 (dd, J=13.1, 6.5 Hz, 1H), 1.39 (s, 9H).

Intermediate ZY-5

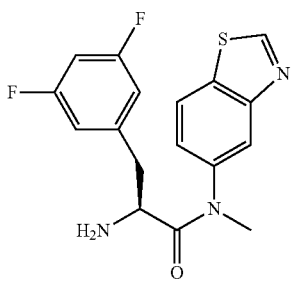

(S)-2-amino-N-(benzo[d]thiazol-5-yl)-3-(3,5-difluorophenyl)-N-methylpropanamide

TFA (1.0 mL, 13 mmol) was added to a stirred solution of (S)-tert-butyl (1-(benzo[d]thiazol-5-yl(methyl)amino)-3-(3, 5-difluorophenyl)-1-oxopropan-2-yl)carbamate (Intermediate ZY-4) (0.58 g, 1.23 mmol) in DCM (2 mL) and the reaction mixture was stirred at rt for 16 h. The crude reaction mixture was concentrated and the residue was dissolved in MeOH/DCM and 4 M HCl in dioxane (2 mL) and reconcentrated. The residue was redissolved in EtOH/toluene, and then reconcentrated (3×) to yield an HCl salt of (S)-2-amino-N-(benzo[d]thiazol-5-yl)-3-(3,5-difluorophenyl)-N-methylpropanamide (0.55 g) as a white solid. LC-MS retention time=0.83 min; m/z=348.1[M+H]$^+$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220).

Intermediate ZY-6

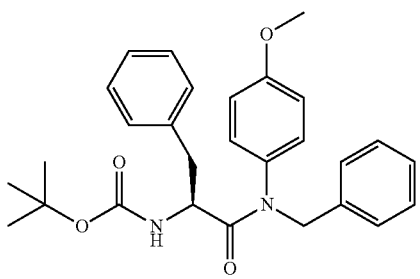 [SMILES: COc1ccc(N(Cc2ccccc2)C(=O)[C@H](Cc2ccccc2)NC(=O)OC(C)(C)C)cc1]

(S)-tert-butyl (1-(benzyl(4-methoxyphenyl)amino)-1-oxo-3-phenylpropan-2-yl)carbamate BOP-Cl (131 mg, 0.516 mmol) was added to a stirred solution of (S)-2-((tert-butoxycarbonyl)amino)-3-phenylpropanoic acid (124 mg, 0.469 mmol) and N-benzyl-4-methoxyaniline (100 mg, 0.469 mmol) in DCM (3 mL), and DIPEA (0.25 mL, 1.4 mmol) and the reaction mixture was stirred at rt for 16 h. The crude reaction mixture was concentrated and the residue was purified using a Biotage Horizon (12 g SiO$_2$, 0-50% Et$_2$O/hexanes) to yield the title compound (125 mg). LC-MS retention time=1.43 min; m/z=461.4 [M+H]$^+$. (Column: Waters Aquity BEH C18 2.1×50 mm 1.7 U. Solvent A=100% Water/0.05% TFA. Solvent B=100% Acetonitrile/0.05% TFA. Flow Rate=0.8 mL/min. Start % B=2. Final % B=98. Gradient Time=1.5 min. Wavelength=220).

Intermediate ZY-7

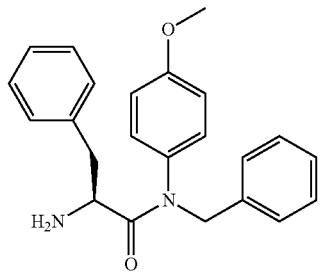 [SMILES: COc1ccc(N(Cc2ccccc2)C(=O)[C@@H](N)Cc2ccccc2)cc1]

(S)-2-amino-N-benzyl-N-(4-methoxyphenyl)-3-phenylpropanamide

A 4M solution of HCl (1.3 mL, 5.2 mmol) in dioxane was added to a stirred solution of (S)-tert-butyl (1-(benzyl(4-methoxyphenyl)amino)-1-oxo-3-phenylpropan-2-yl)carbamate (Intermediate ZY-6) (120 mg, 0.261 mmol) in THF (1.3 mL) and the reaction mixture was stirred at rt for 2 h. The reaction mixture concentrated to yield an HCl salt of the title compound (117 mg). LC-MS retention time=0.99 min; m/z=361.2 [M+H]$^+$. (Column: Waters Aquity BEH C18 2.1×50 mm 1.7 U. Solvent A=100% Water/0.05% TFA. Solvent B=100% Acetonitrile/0.05% TFA. Flow Rate=0.8 mL/min. Start % B=2. Final % B=98. Gradient Time=1.5 min. Wavelength=220).

Example JB-82

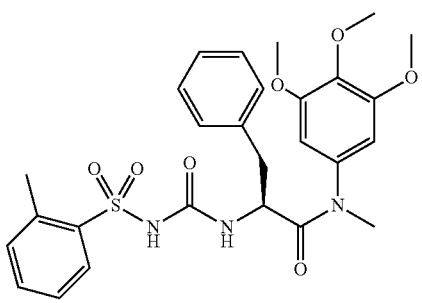 [SMILES: COc1cc(N(C)C(=O)[C@H](Cc2ccccc2)NC(=O)NS(=O)(=O)c2ccccc2C)cc(OC)c1OC]

(S)—N-methyl-3-phenyl-2-(3-(o-tolylsulfonyl)ureido)-N-(3,4,5-trimethoxyphenyl)propanamide A solution of 4M HCl (1 mL, 4.0 mmol) in dioxane was added to a stirred solution of Intermediate JB-7 (77 mg, 0.17 mmol) was dissolved into THF (1 mL) and the reaction was stirred at rt for 3 h. The reaction mixture was concentrated to dryness dissolved into CH$_3$CN (1 mL) and Hunig's Base (0.11 mL, 0.61 mmol) and then treated with 2-methylbenzenesulfonyl isocyanate (51 mg, 0.26 mmol) and stirred at rt for 3 h. The reaction mixture was quenched with MeOH (5 mL), stirred 5 min. and then concentrated to dryness. The residue was partitioned between EtOAc (10 mL) and water (5 mL) and the organic component was further washed with brine (5 mL) and concentrated. The residue was dissolved into MeOH, filtered and purified by preparative HPLC to yield the title compound (50.3 mg). LC-MS retention time=1.98 min; m/z=542.2 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Examples JB-83 and JB-84 were prepared using the procedure detailed for Example JB-82 where the 3,4,5-trimethoxy-N-methylaniline used in the preparation of Intermediate JB-7 was replaced with the appropriate amine.

Example JB-83

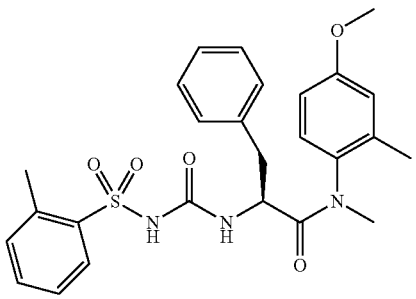 [SMILES: COc1ccc(N(C)C(=O)[C@H](Cc2ccccc2)NC(=O)NS(=O)(=O)c2ccccc2C)c(C)c1]

(S)—N-(4-methoxy-2-methylphenyl)-N-methyl-3-phenyl-2-(3-(o-tolylsulfonyl)ureido)propanamide LC-MS retention time=1.97 min; m/z=496.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-84

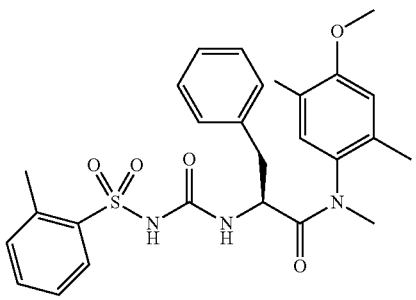 [SMILES: COc1cc(C)c(N(C)C(=O)[C@H](Cc2ccccc2)NC(=O)NS(=O)(=O)c2ccccc2C)cc1C]

(S)—N-(4-methoxy-2,5-dimethylphenyl)-N-methyl-3-phenyl-2-(3-(o-tolylsulfonyl)ureido)propanamide LC-MS retention time=2.03 min; m/z=510.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220.

Example JB-85

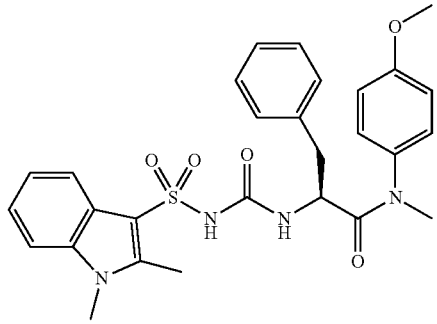 [SMILES: COc1ccc(N(C)C(=O)[C@H](Cc2ccccc2)NC(=O)NS(=O)(=O)c2c(C)n(C)c3ccccc23)cc1]

(S)-2-(3-((1,2-dimethyl-1H-indol-3-yl)sulfonyl)
ureido)-N-(4-methoxyphenyl)-N-methyl-3-phenyl-
propanamide A solution of sulfurisocyanatidic chloride (0.048 mL, 0.56 mmol) in DCM (1.5 mL) was added dropwise at 0° C. to a stirred solution of Intermediate JB-2 (140 mg, 0.37 mmol) in DCM (~1 mL) and the reaction mixture was stirred at 0° C. for 1 h. Then TEA (0.17 mL, 1.2 mmol) in DCM (0.6 mL) was added and reaction mixture was stirred at 0° C. for 3 min. A portion of this crude reaction mixture (~0.8 mL, 25%) was added to a stirred solution of 1,2-dimethyl-1H-indole (43.1 mg, 0.297 mmol) in DCM (1 mL) and stirred at rt for 2 h. The reaction was concentrated diluted with EtOAc (~2 mL) and washed with sat. aq. NaHCO$_3$ (aq) (1 mL) and brine (1 mL). The organic component was concentrated, dissolved into MeOH, filtered and purified by preparative HPLC to yield the title compound (10.8 mg). LC-MS retention time=1.74 min; m/z=535.4 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHZ, DMSO-d$_6$) δ 7.78 (d, J=8.1 Hz, 1H), 7.56 (d, J=8.1 Hz, 1H), 7.29-7.24 (m, 1H), 7.24-7.20 (m, 1H), 7.11-7.07 (m, 1H), 7.04-6.99 (m, 2H), 6.98-6.94 (m, 2H), 6.88 (d, J=8.8 Hz, 2H), 6.64 (d, J=7.3 Hz, 2H), 6.57 (d, J=8.1 Hz, 1H), 4.26-4.19 (m, 1H), 3.75 (s, 3H), 3.72 (s, 3H), 3.06 (s, 3H), 2.69 (dd, J=13.8, 5.3 Hz, 1H), 2.61 (s, 3H), 2.41 (dd, J=13.4, 7.5 Hz, 1H).

Example ZY-3

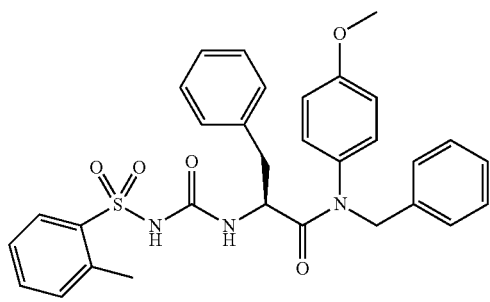 [SMILES: COc1ccc(N(Cc2ccccc2)C(=O)[C@H](Cc2ccccc2)NC(=O)NS(=O)(=O)c2ccccc2C)cc1]

(S)—N-benzyl-N-(4-methoxyphenyl)-3-phenyl-2-(3-
(o-tolylsulfonyl)ureido)propanamide To a stirred solution of Intermediate ZY-7 (32 mg, 0.081 mmol) in CH$_3$CN (1 mL) and DIPEA (0.042 mL, 0.242 mmol) was added 2-methylbenzenesulfonyl isocyanate (24 mg, 0.12 mmol) and the reaction mixture was stirred at rt for 16 h. The reaction mixture was concentrated, dissolved into MeOH, filtered and purified by preparative HPLC to yield the title compound (44.6 mg). LC-MS retention time=1.91 min; m/z=558.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHZ, DMSO-d$_6$) δ 7.80 (d, J=7.7 Hz, 1H), 7.49 (d, J=7.0 Hz, 1H), 7.38-7.31 (m, 2H), 7.27-7.12 (m, 7H), 7.06 (br. s., 2H), 6.79 (br. s., 6H), 4.87 (d, J=15.0 Hz, 1H), 4.63 (d, J=14.3 Hz, 1H), 4.23 (d, J=6.2 Hz, 1H), 3.71 (s, 3H), 2.81 (dd, J=13.6, 5.1 Hz, 1H), 2.59-2.53 (m, 4H).

Examples ZY-4 through ZY-6 were prepared using the procedure detailed for Example ZY-3 where the N-benzyl-4-methoxyaniline used in the preparation of Intermediate ZY-6 was replaced with the appropriate amine.

Example ZY-4

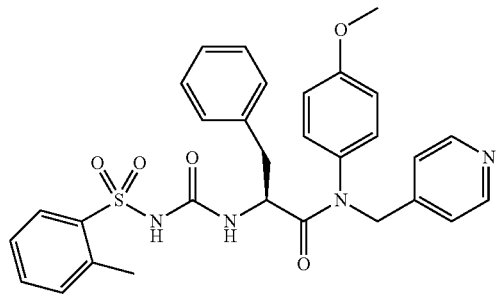 [SMILES: COc1ccc(N(Cc2ccncc2)C(=O)[C@H](Cc2ccccc2)NC(=O)NS(=O)(=O)c2ccccc2C)cc1]

(S)—N-(4-methoxyphenyl)-3-phenyl-N-(pyridin-4-
ylmethyl)-2-(3-(o-tolylsulfonyl)ureido)propanamide LC-MS retention time=1.48 min; m/z=559.2 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example ZY-5

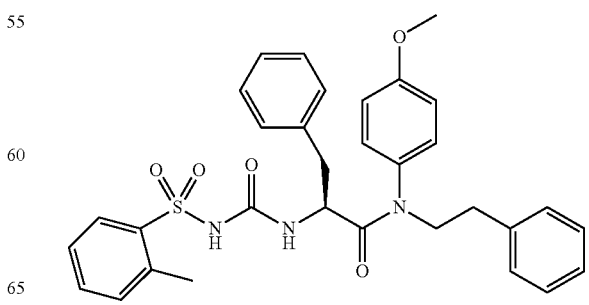

(S)—N-(4-methoxyphenyl)-N-phenethyl-3-phenyl-2-(3-(o-tolylsulfonyl)ureido)propanamide LC-MS retention time=1.87 min; m/z=572.3 [M+H]⁺. (Column: Waters BEH C18, 2.0×50 mm, 1.7-μm particles. Solvent A=95% Water: 5% Acetonitrile: 10 mM NH₄OAC. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example ZY-6

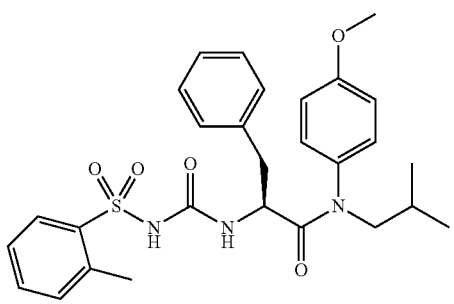 [SMILES: COc1ccc(N(CC(C)C)C(=O)[C@H](Cc2ccccc2)NC(=O)NS(=O)(=O)c2ccccc2C)cc1]

(S)—N-isobutyl-N-(4-methoxyphenyl)-3-phenyl-2-(3-(o-tolylsulfonyl)ureido)propanamide LC-MS retention time=1.84 min; m/z=524.4 [M+H]⁺. (Column: Waters BEH C18, 2.0×50 mm, 1.7-μm particles. Solvent A=95% Water: 5% Acetonitrile: 10 mM NH₄OAC. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220). ¹H NMR (600 MHZ, DMSO-d₆) δ 7.76 (d, J=7.7 Hz, 1H), 7.47 (d, J=6.6 Hz, 1H), 7.36-7.27 (m, 2H), 7.17-6.86 (m, 7H), 6.80-6.53 (m, 3H), 4.18 (d, J=5.9 Hz, 1H), 3.76 (s, 3H), 3.58-3.16 (m, 2H), 2.78-2.72 (m, 2H), 1.58-1.49 (m, 1H), 0.76 (dd, J=17.8, 6.4 Hz, 6H).

Example ZY-7

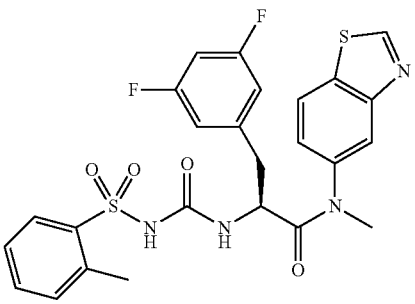

(S)—N-(benzo[d]thiazol-5-yl)-3-(3,5-difluorophenyl)-N-methyl-2-(3-(o-tolylsulfonyl)ureido)propanamide 2-Methylbenzenesulfonyl isocyanate (28.4 mg, 0.144 mmol) was added to a stirred solution of an HCl salt of Intermediate ZY-5 (55 mg, 0.131 mmol) in CH₃CN (1 mL) and DIPEA (0.11 mL, 0.65 mmol) and the reaction mixture was stirred at rt ON. Additional 2-methylbenzenesulfonyl isocyanate (20 mg) was added and the reaction mixture was stirred at rt for 2 h. The reaction mixture was concentrated, dissolved into MeOH, filtered and purified by preparative HPLC to yield the title compound (49.8 mg).

LC-MS retention time=2.33 min; m/z=545.1 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220). ¹H NMR (500 MHZ, DMSO-d₆) δ 9.49 (s, 1H), 8.23 (d, J=8.4 Hz, 1H), 8.04 (s, 1H), 7.78 (d, J=7.7 Hz, 1H), 7.54-7.48 (m, 1H), 7.41-7.30 (m, 3H), 6.95 (t, J=9.2 Hz, 1H), 6.74 (d, J=8.1 Hz, 1H), 6.35 (d, J=6.6 Hz, 2H), 4.31 (d, J=4.4 Hz, 1H), 3.23 (s, 3H), 2.90-2.80 (m, 1H), 2.60 (dd, J=13.6, 8.8 Hz, 1H), 2.50 (br. s., 3H).

For Examples CA-67 through CA-101, the following procedure was used:

A solution of POCl₃ (0.15 mmol) in pyridine (0.5 mL) was added to a solution of the appropriate aniline (0.11 mol) and (S)-2-((tert-butoxycarbonyl)amino)-3-phenylpropanoic acid (0.10 mmol) in pyridine (0.5 mL) at 0° C. The reaction mixture was allowed to warm to rt while being shaken ON. The reaction was cooled using ice bath, quenched with MeOH (0.5 mL) and concentrated to dryness. The crude residue was treated with DCM (0.5 mL) and TFA (0.5 mL) and the reaction mixture was shaken at rt for 4 h. The reaction mixture was concentrated to dryness and the crude residue was dissolved into DIPEA (0.3 mmol) in DCM (0.5 mL) and treated with a solution of 2-methylbenzenesulfonyl isocyanate (0.15 mmol) in DCM (0.5 mL). The reaction mixture was shaken at rt for 2 h, diluted with MeOH (0.5 mL) and concentrated to dryness. The crude residue was dissolved into DMF (1 mL), filtered and purified by preparative HPLC to yield the title compound.

Example CA-67

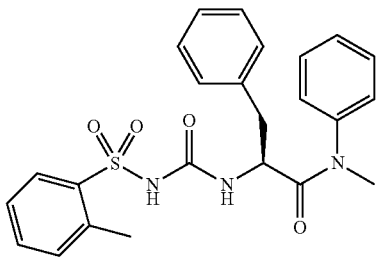 [SMILES: Cc1ccccc1S(=O)(=O)NC(=O)N[C@@H](Cc1ccccc1)C(=O)N(C)c1ccccc1]

(S)—N-methyl-N, 3-diphenyl-2-(3-(o-tolylsulfonyl)ureido)propanamide

LC-MS retention time=2.42 min; m/z=452.2 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-68

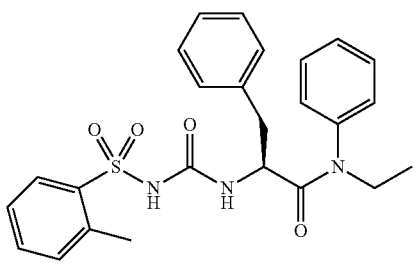 [SMILES: CCN(C(=O)[C@H](Cc1ccccc1)NC(=O)NS(=O)(=O)c1ccccc1C)c1ccccc1]

(S)—N-ethyl-N, 3-diphenyl-2-(3-(o-tolylsulfonyl) ureido)propanamide

LC-MS retention time=1.54 min; m/z=466.2 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-69

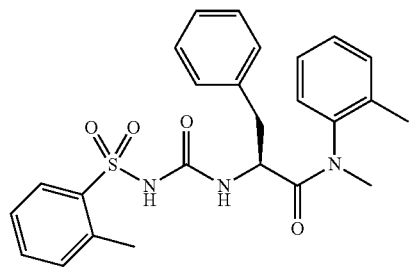 [SMILES: Cc1ccccc1N(C)C(=O)[C@H](Cc1ccccc1)NC(=O)NS(=O)(=O)c1ccccc1C]

(S)—N-methyl-3-phenyl-N-(o-tolyl)-2-(3-(o-tolylsulfonyl) ureido)propanamide

LC-MS retention time=1.52 min; m/z=466.2 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-70

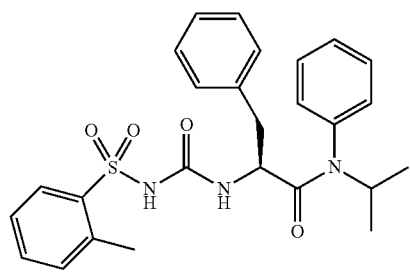 [SMILES: Cc1ccccc1S(=O)(=O)NC(=O)N[C@@H](Cc1ccccc1)C(=O)N(c1ccccc1)C(C)C]

(S)—N-isopropyl-N, 3-diphenyl-2-(3-(o-tolylsulfonyl)ureido)propanamide

LC-MS retention time=3.06 min; m/z=480.2 [M+H]+. (Column: Waters BEH C18, 2.0×50 mm, 1.7-μm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220).

Example CA-71

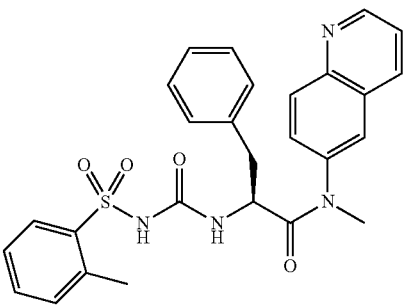 [SMILES: Cc1ccccc1S(=O)(=O)NC(=O)N[C@@H](Cc1ccccc1)C(=O)N(C)c1ccc2ncccc2c1]

(S)—N-methyl-3-phenyl-N-(quinolin-6-yl)-2-(3-(o-tolylsulfonyl) ureido)propanamide LC-MS retention time=2.22 min; m/z=503.1 [M+H]. (Column: Waters BEH C18, 2.0×50 mm, 1.7-μm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220).

Example CA-72

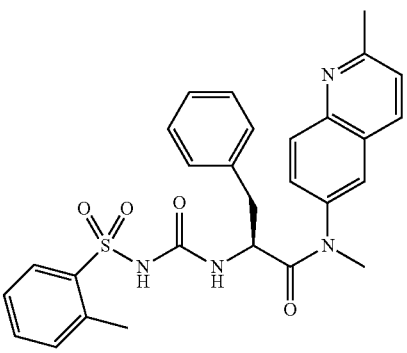 [SMILES: Cc1ccc2cc(N(C)C(=O)[C@H](Cc3ccccc3)NC(=O)NS(=O)(=O)c3ccccc3C)ccc2n1]

(S)—N-methyl-N-(2-methylquinolin-6-yl)-3-phenyl-2-(3-(o-tolylsulfonyl)ureido)propanamide LC-MS retention time=1.50 min; m/z=517.2 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc.

Example CA-73

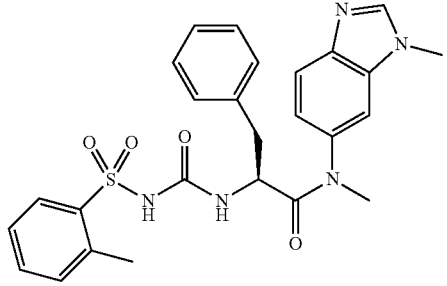 [SMILES: Cc1ccccc1S(=O)(=O)NC(=O)N[C@@H](Cc1ccccc1)C(=O)N(C)c1ccc2ncn(C)c2c1]

(S)—N-methyl-N-(1-methyl-H-benzo[d]imidazol-6-yl)-3-phenyl-2-(3-(o-tolylsulfonyl)ureido)propanamide LC-MS retention time=2.07 min; m/z=506.1 [M+H]$^+$. (Column: Waters BEH C18, 2.0×50 mm, 1.7-μm particles. Solvent A=95% Water: 5% MeOH: 10 mM NH$_4$OAc. Solvent % B=5% Water: 95% MeOH: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-74

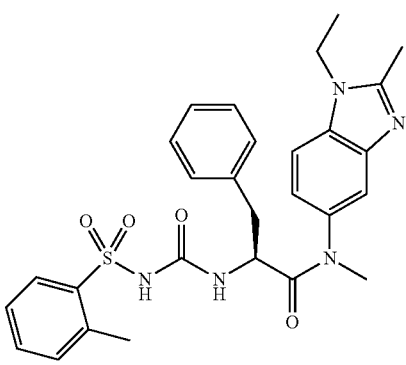 [SMILES: CCn1c(C)nc2cc(N(C)C(=O)[C@H](Cc3ccccc3)NC(=O)NS(=O)(=O)c3ccccc3C)ccc21]

(S)—N-(1-ethyl-2-methyl-1H-benzo[d]imidazol-5-yl)-N-methyl-3-phenyl-2-(3-(o-tolylsulfonyl)ureido)propanamide LC-MS retention time=2.23 min; m/z=534.2 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-75

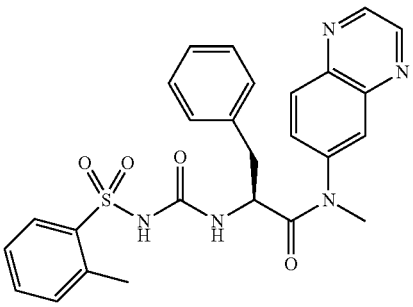

(S)—N-methyl-3-phenyl-N-(quinoxalin-6-yl)-2-(3-(o-tolylsulfonyl) ureido)propanamide LC-MS retention time=2.15 min; m/z=504.2 [M+H]$^+$. (Column: Waters BEH C18, 2.0×50 mm, 1.7-μm particles. Solvent A=95% Water: 5% MeOH: 10 mM NH$_4$OAc. Solvent % B=5% Water: 95% MeOH: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-76

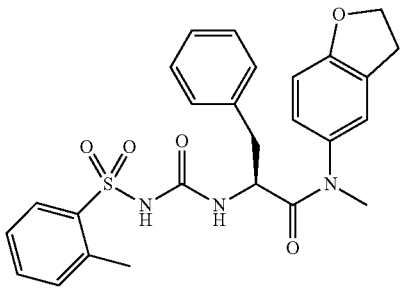 [SMILES: Cc1ccccc1S(=O)(=O)NC(=O)N[C@@H](Cc1ccccc1)C(=O)N(C)c1ccc2c(c1)CCO2]

(S)—N-(2,3-dihydrobenzofuran-5-yl)-N-methyl-3-phenyl-2-(3-(o-tolylsulfonyl)ureido)propanamide LC-MS retention time=2.38 min; m/z=494.2 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-77

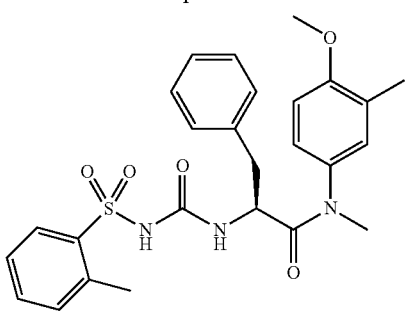

(S)—N-(4-methoxy-3-methylphenyl)-N-methyl-3-phenyl-2-(3-(o-tolylsulfonyl)ureido)propanamide LC-MS retention time=2.56 min; m/z=496.2 [M+H]$^+$. (Column: Waters BEH C18, 2.0×50 mm, 1.7-μm particles. Solvent A=95% Water: 5% MeOH: 10 mM NH$_4$OAc. Solvent % B=5% Water: 95% MeOH: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-78

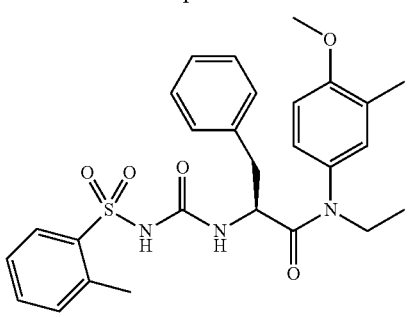

(S)—N-ethyl-N-(4-methoxy-3-methylphenyl)-3-phenyl-2-(3-(o-tolylsulfonyl)ureido)propanamide LC-MS retention time=2.67 min; m/z=510.2 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-79

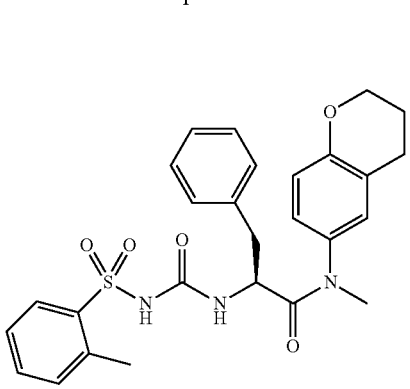

(S)—N-(chroman-6-yl)-N-methyl-3-phenyl-2-(3-(o-tolylsulfonyl)ureido)propanamide

LC-MS retention time=1.65 min; m/z=508.1 [M+H]$^+$. (Column: Waters BEH C18, 2.0×50 mm, 1.7-μm particles. Solvent A=95% Water: 5% Acetonitrile: 10 mM NH$_4$OAc. Solvent % B=5% Water: 95% Acetonitrile: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-80

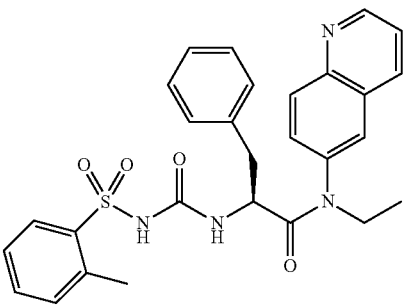 [SMILES: CCN(C(=O)[C@H](Cc1ccccc1)NC(=O)NS(=O)(=O)c1ccccc1C)c1ccc2ncccc2c1]

(S)—N-ethyl-3-phenyl-N-(quinolin-6-yl)-2-(3-(o-tolylsulfonyl)ureido)propanamide

LC-MS retention time=1.48 min; m/z=517.1 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-81

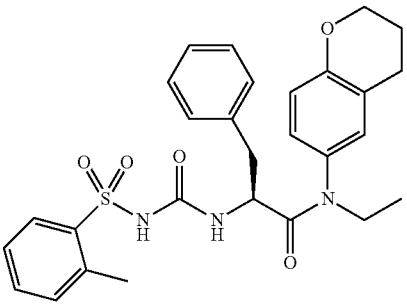 [SMILES: CCN(C(=O)[C@H](Cc1ccccc1)NC(=O)NS(=O)(=O)c1ccccc1C)c1ccc2c(c1)CCCO2]

(S)—N-(chroman-6-yl)-N-ethyl-3-phenyl-2-(3-(o-tolylsulfonyl) ureido)propanamide

LC-MS retention time=2.66 min; m/z=522.3 [M+H]$^+$. (Column: Waters BEH C18, 2.0×50 mm, 1.7-μm particles. Solvent A=95% Water: 5% MeOH: 10 mM NH$_4$OAc. Solvent % B=5% Water: 95% MeOH: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-82

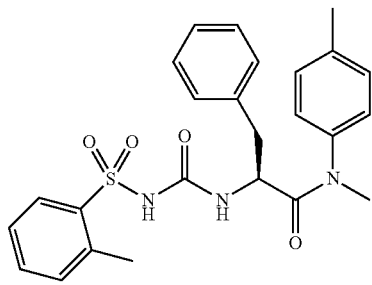 [SMILES: Cc1ccc(N(C)C(=O)[C@H](Cc2ccccc2)NC(=O)NS(=O)(=O)c2ccccc2C)cc1]

(S)—N-methyl-3-phenyl-N-(p-tolyl)-2-(3-(o-tolylsulfonyl) ureido)propanamide

LC-MS retention time=1.76 min; m/z=466.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-83

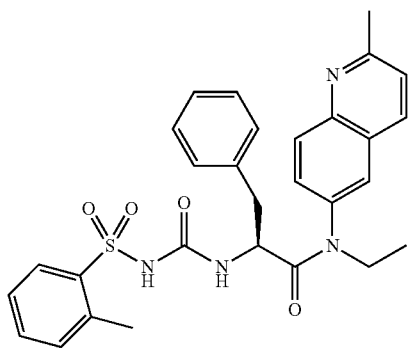 [SMILES: CCN(C(=O)[C@H](Cc1ccccc1)NC(=O)NS(=O)(=O)c1ccccc1C)c1ccc2nc(C)ccc2c1]

(S)—N-ethyl-N-(2-methylquinolin-6-yl)-3-phenyl-2-(3-(o-tolylsulfonyl)ureido)propanamide LC-MS retention time=1.66 min; m/z=531.2 [M+H]$^+$. (Column: Waters BEH C18, 2.0×50 mm, 1.7-μm particles. Solvent A=95% Water: 5% Acetonitrile: 10 mM NH$_4$OAc. Solvent % B=5% Water: 95% Acetonitrile: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-84

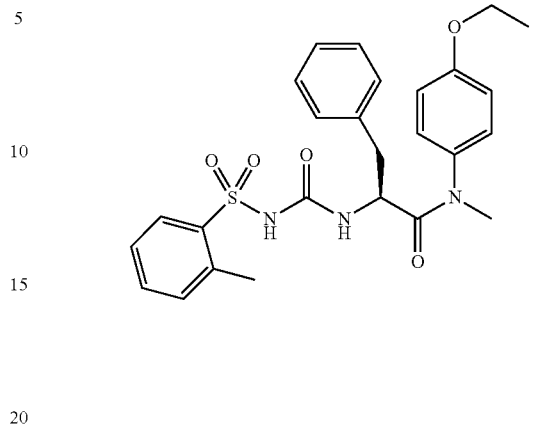

(S)-N-(4-ethoxyphenyl)-N-methyl-3-phenyl-2-(3-(o-tolylsulfonyl) ureido)propanamide LC-MS retention time=2.54 min; m/z=496.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-85

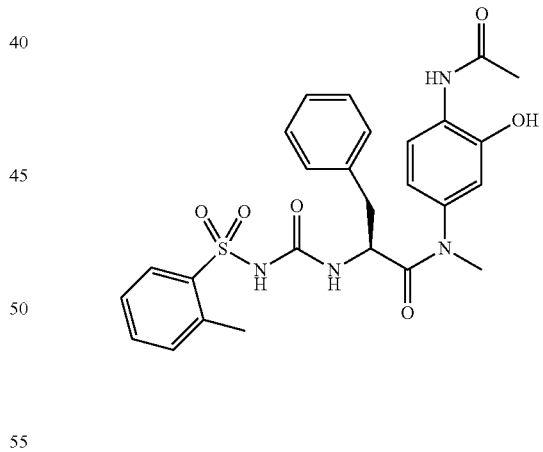

(S)—N-(4-acetamido-3-hydroxyphenyl)-N-methyl-3-phenyl-2-(3-(o-tolylsulfonyl)ureido)propanamide LC-MS retention time=2.43 min; m/z=525.2 [M+H]$^+$. (Column: Waters BEH C18, 2.0×50 mm, 1.7-μm particles. Solvent A=95% Water: 5% MeOH: 10 mM NH$_4$OAc. Solvent % B=5% Water: 95% MeOH: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-86

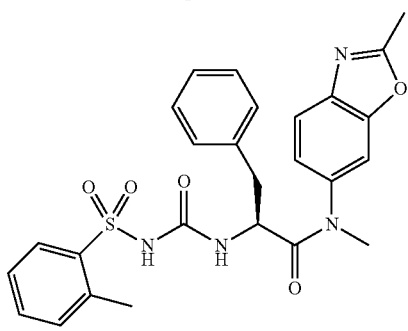 [SMILES: Cc1nc2ccc(N(C)C(=O)[C@H](Cc3ccccc3)NC(=O)NS(=O)(=O)c3ccccc3C)cc2o1]

(S)—N-methyl-N-(2-methylbenzo[d]oxazol-6-yl)-3-phenyl-2-(3-(o-tolylsulfonyl)ureido)propanamide LC-MS retention time=1.49 min; m/z=507.1 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-87

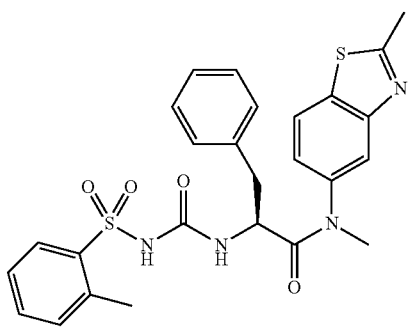 [SMILES: Cc1nc2cc(N(C)C(=O)[C@H](Cc3ccccc3)NC(=O)NS(=O)(=O)c3ccccc3C)ccc2s1]

(S)—N-methyl-N-(2-methylbenzo[d]thiazol-5-yl)-3-phenyl-2-(3-(o-tolylsulfonyl)ureido)propanamide LC-MS retention time=1.69 min; m/z=523.3 [M+H]$^+$. (Column: Waters BEH C18, 2.0×50 mm, 1.7-μm particles. Solvent A=95% Water: 5% Acetonitrile: 10 mM NH$_4$OAc. Solvent % B=5% Water: 95% Acetonitrile: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-88

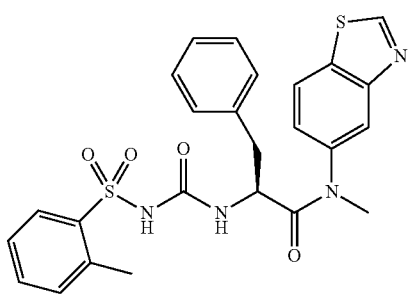 [SMILES: Cc1ccccc1S(=O)(=O)NC(=O)N[C@@H](Cc1ccccc1)C(=O)N(C)c1ccc2scnc2c1]

(S)—N-(benzo[d]thiazol-5-yl)-N-methyl-3-phenyl-2-(3-(o-tolylsulfonyl)ureido)propanamide LC-MS retention time=2.22 min; m/z=509.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-89

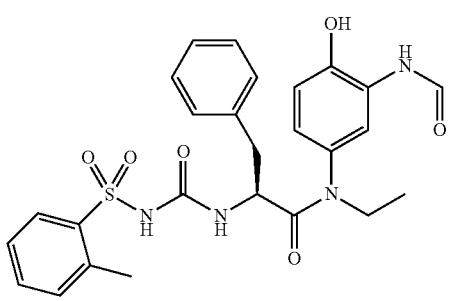 [SMILES: CCN(C(=O)[C@H](Cc1ccccc1)NC(=O)NS(=O)(=O)c1ccccc1C)c1ccc(O)c(NC=O)c1]

(S)—N-ethyl-N-(3-formamido-4-hydroxyphenyl)-3-phenyl-2-(3-(o-tolylsulfonyl)ureido)propanamide LC-MS retention time=1.31 min; m/z=525.1 [M+H]$^+$. (Column: Waters BEH C18, 2.0×50 mm, 1.7-μm particles. Solvent A=95% Water: 5% Acetonitrile: 10 mM NH$_4$OAc. Solvent % B=5% Water: 95% Acetonitrile: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-90

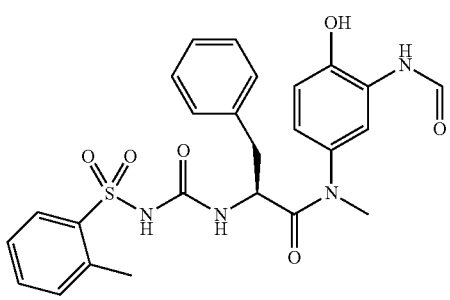 [SMILES: Cc1ccccc1S(=O)(=O)NC(=O)N[C@@H](Cc1ccccc1)C(=O)N(C)c1ccc(O)c(NC=O)c1]

(S)—N-(3-formamido-4-hydroxyphenyl)-N-methyl-3-phenyl-2-(3-(o-tolylsulfonyl)ureido)propanamide LC-MS retention time=1.96 min; m/z=511.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-91

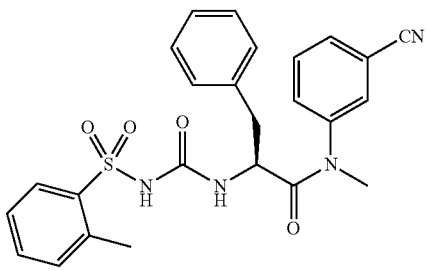 [SMILES: Cc1ccccc1S(=O)(=O)NC(=O)N[C@@H](Cc1ccccc1)C(=O)N(C)c1cccc(C#N)c1]

(S)—N-(3-cyanophenyl)-N-methyl-3-phenyl-2-(3-(o-tolylsulfonyl)ureido)propanamide LC-MS retention time=2.28 min; m/z=477.3 [M+H]$^+$. (Column: Waters BEH C18, 2.0×50 mm, 1.7-µm particles. Solvent A=95% Water: 5% MeOH: 10 mM NH$_4$OAc. Solvent % B=5% Water: 95% MeOH: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-92

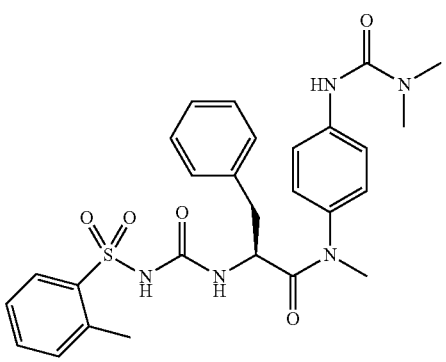 [SMILES: Cc1ccccc1S(=O)(=O)NC(=O)N[C@@H](Cc1ccccc1)C(=O)N(C)c1ccc(NC(=O)N(C)C)cc1]

(S)—N-(4-(3,3-dimethylureido)phenyl)-N-methyl-3-phenyl-2-(3-(o-tolylsulfonyl)ureido)propanamide LC-MS retention time=2.08 min; m/z=538.4 [M+H]$^+$. (Column: Waters BEH C18, 2.0×50 mm, 1.7-µm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHZ, DMSO-d$_6$) δ 8.41 (br. s., 1H), 7.76 (d, J=8.8 Hz, 1H), 7.47 (d, J=7.7 Hz, 3H), 7.30 (br. s., 2H), 7.15 (br. s., 3H), 6.92 (d, J=7.0 Hz, 2H), 6.78 (br. s., 2H), 6.45 (br. s., 1H), 4.29 (br. s., 1H), 3.08 (s, 3H), 2.93 (s, 6H), 2.73-2.69 (m, 1H), 2.55-2.46 (m, 4H).

Example CA-93

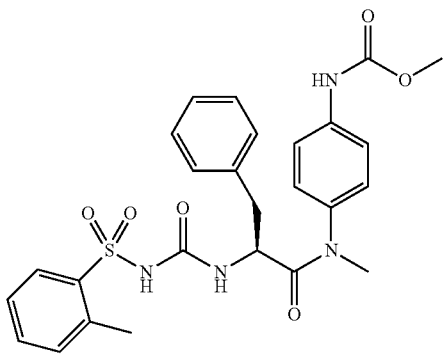

(S)-methyl (4-(N-methyl-3-phenyl-2-(3-(o-tolylsulfonyl) ureido)propanamido)phenyl)carbamate LC-MS retention time=2.73 min; m/z=525.1 [M+H]$^+$. (Column: Waters BEH C18, 2.0×50 mm, 1.7-µm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHZ, DMSO-d$_6$) δ 9.81 (s, 1H), 7.79 (d, J=7.7 Hz, 1H), 7.57-7.51 (m, 1H), 7.48-7.34 (m, 4H), 7.15 (d, J=4.0 Hz, 3H), 7.02 (d, J=8.4 Hz, 2H), 6.74 (d, J=4.0 Hz, 2H), 6.65 (d, J=8.1 Hz, 1H), 4.32-4.24 (m, 1H), 3.68 (s, 3H), 3.09 (s, 3H), 2.78-2.71 (m, 1H), 2.50 (s, 3H), 2.50-2.45 (m, 1H).

Example CA-94

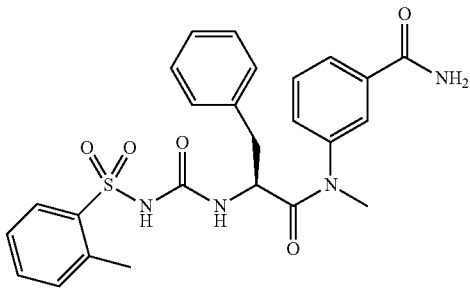 [SMILES: Cc1ccccc1S(=O)(=O)NC(=O)N[C@@H](Cc1ccccc1)C(=O)N(C)c1cccc(C(N)=O)c1]

(S)-3-(N-methyl-3-phenyl-2-(3-(o-tolylsulfonyl)ureido)propanamido)benzamide

LC-MS retention time=2.05 min; m/z=495.3 [M+H]$^+$. (Column: Waters BEH C18, 2.0×50 mm, 1.7-µm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-95

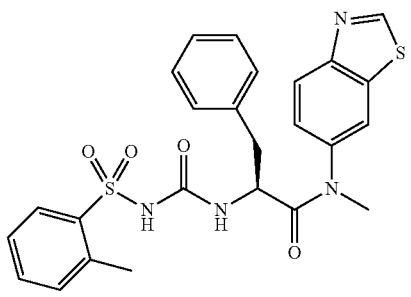 [SMILES: Cc1ccccc1S(=O)(=O)NC(=O)N[C@@H](Cc1ccccc1)C(=O)N(C)c1ccc2ncsc2c1]

(S)—N-(benzo[d]thiazol-6-yl)-N-methyl-3-phenyl-2-(3-(o-tolylsulfonyl)ureido)propanamide LC-MS retention time=2.19 min; m/z=509.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHZ, DMSO-d$_6$) δ 9.46 (s, 1H), 8.06 (d, J=8.8 Hz, 1H), 7.79 (d, J=7.7 Hz, 1H), 7.72 (br. s., 1H), 7.51 (d, J=6.6 Hz, 1H), 7.42-7.32 (m, 2H), 7.26 (d, J=7.7 Hz, 1H), 7.14 (d, J=7.0 Hz, 3H), 6.73 (d, J=6.6 Hz, 2H), 6.65 (br. s., 1H), 4.21 (d, J=5.5 Hz, 1H), 3.18 (s, 3H), 2.80 (d, J=7.3 Hz, 1H), 2.57-2.47 (m, 4H).

Example CA-96

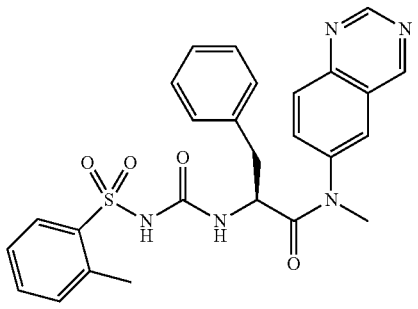 [SMILES: Cc1ccccc1S(=O)(=O)NC(=O)N[C@@H](Cc1ccccc1)C(=O)N(C)c1ccc2ncncc2c1]

(S)—N-methyl-3-phenyl-N-(quinazolin-6-yl)-2-(3-(o-tolylsulfonyl) ureido)propanamide LC-MS retention time=2.00 min; m/z=504.4 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-97

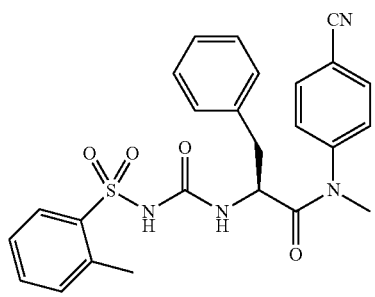 [SMILES: Cc1ccccc1S(=O)(=O)NC(=O)N[C@@H](Cc1ccccc1)C(=O)N(C)c1ccc(C#N)cc1]

(S)—N-(4-cyanophenyl)-N-methyl-3-phenyl-2-(3-(o-tolylsulfonyl)ureido)propanamide LC-MS retention time=2.61 min; m/z=476.9 [M+H]$^+$. (Column: Waters BEH C18, 2.0×50 mm, 1.7-μm particles. Solvent A=95% Water: 5% MeOH: 10 mM NH$_4$OAc. Solvent % B=5% Water: 95% MeOH: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-98

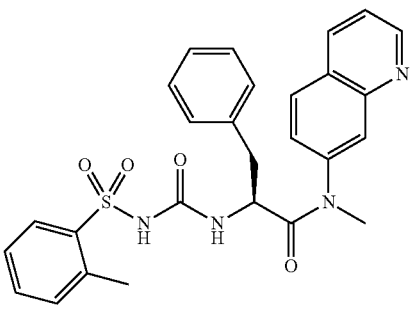 [SMILES: Cc1ccccc1S(=O)(=O)NC(=O)N[C@@H](Cc1ccccc1)C(=O)N(C)c1ccc2cccnc2c1]

(S)—N-methyl-3-phenyl-N-(quinolin-7-yl)-2-(3-(o-tolylsulfonyl)ureido)propanamide LC-MS retention time=2.22 min; m/z=503.1 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-99

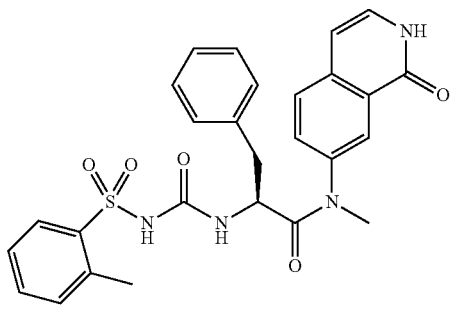 [SMILES: Cc1ccccc1S(=O)(=O)NC(=O)N[C@@H](Cc1ccccc1)C(=O)N(C)c1ccc2cc[nH]c(=O)c2c1]

(S)—N-methyl-N-(1-oxo-1,2-dihydroisoquinolin-7-yl)-3-phenyl-2-(3-(o-tolylsulfonyl)ureido)propanamide LC-MS retention time=2.48 min; m/z=519.0 [M+H]$^+$. (Column: Waters BEH C18, 2.0×50 mm, 1.7-μm particles. Solvent A=95% Water: 5% MeOH: 10 mM NH$_4$OAc. Solvent % B=5% Water: 95% MeOH: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-100

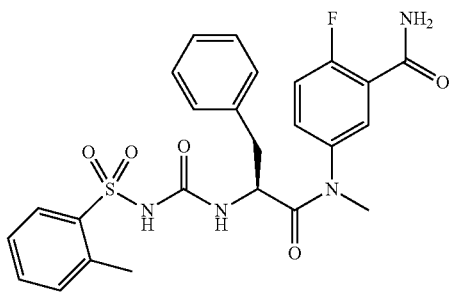 [SMILES: Cc1ccccc1S(=O)(=O)NC(=O)N[C@@H](Cc1ccccc1)C(=O)N(C)c1ccc(F)c(C(N)=O)c1]

(S)-2-fluoro-5-(N-methyl-3-phenyl-2-(3-(o-tolylsulfonyl)ureido)propanamido)benzamide LC-MS retention time=1.23 min; m/z=513.0 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-101

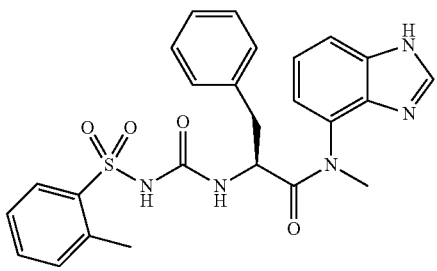 [SMILES: Cc1ccccc1S(=O)(=O)NC(=O)N[C@@H](Cc1ccccc1)C(=O)N(C)c1cccc2[nH]cnc12]

(S)—N-(1H-benzo[d]imidazol-4-yl)-N-methyl-3-phenyl-2-(3-(o-tolylsulfonyl)ureido)propanamide LC-MS retention time=1.26 min; m/z=492.0 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

For Examples CA-102 through CA-112, the following procedure was utilized:

A solution of POCl$_3$ (0.15 mmol) in pyridine (0.5 mL) was added to a solution of the appropriate aniline (0.11 mol) and (S)-2-((tert-butoxycarbonyl)amino)-3-(3,5-difluorophenyl)propanoic acid (0.10 mmol) in pyridine (0.5 mL) at 0° C. The reaction mixture was allowed to warm to rt while being shaken ON. The reaction was cooled using ice bath, quenched with MeOH (0.5 mL) and concentrated to dryness. The crude residue was treated with DCM (0.5 mL) and TFA (0.5 mL) and the reaction mixture was shaken at rt for 4 h. The reaction mixture was concentrated to dryness and the crude residue was dissolved into DIPEA (0.3 mmol) in DCM (0.5 mL) and treated with a solution of 2-methylbenzenesulfonyl isocyanate (0.15 mmol) in DCM (0.5 mL). The reaction mixture was shaken at rt for 2 h, diluted with MeOH (0.5 mL) and concentrated to dryness. The crude residue was dissolved into DMF (1 mL), filtered and purified by preparative HPLC to yield the title compound.

Example CA-102

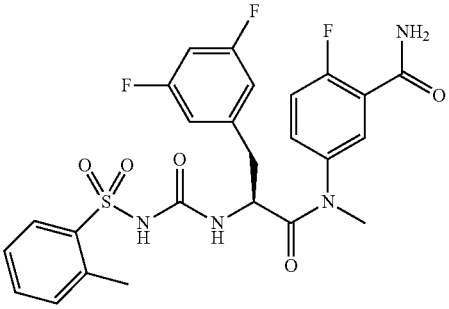 [SMILES: Cc1ccccc1S(=O)(=O)NC(=O)N[C@@H](Cc1cc(F)cc(F)c1)C(=O)N(C)c1ccc(F)c(C(N)=O)c1]

(S)-5-(3-(3,5-difluorophenyl)-N-methyl-2-(3-(o-tolylsulfonyl)ureido)propanamido)-2-fluorobenzamide A solution of (S)-2-((tert-butoxycarbonyl)amino)-3-(3,5-difluorophenyl)propanoic acid (30.1 mg, 100 μmol) and HATU (41.8 mg, 110 μmol) in DMF (0.5 mL) was added to a solution of 2-fluoro-5-(methylamino)benzamide (16.8 mg, 100 μmol) in DIPEA (0.044 mL, 250 μmol) and DMF (0.5 mL) and the reaction mixture was shaken at rt ON. The reaction mixture was concentrated to dryness, dissolved into DCM (0.5 mL) and TFA (0.5 mL) and the reaction mixture was shaken at rt for 4 h. The reaction mixture was concentrated to dryness. The crude residue was dissolved into DCM (1.0 mL) and treated with DIPEA (0.052 mL, 300 μmol) and 2-methylbenzenesulfonyl isocyanate (0.023 mL, 150 μmol), and then the reaction mixture was shaken at rt for 2 h and concentrated to dryness. The crude residue was dissolved into DMF (1 mL), filtered and purified by preparative HPLC to yield the title compound (19.4 mg). LC-MS retention time=1.14 min; m/z=549.2 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-103

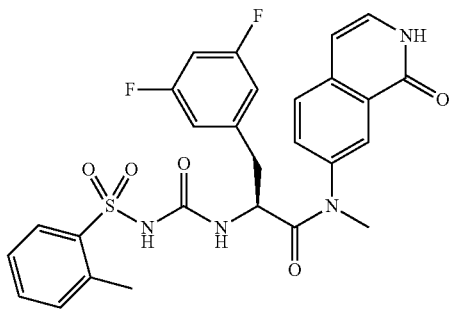 [SMILES: Cc1ccccc1S(=O)(=O)NC(=O)N[C@@H](Cc1cc(F)cc(F)c1)C(=O)N(C)c1ccc2cc[nH]c(=O)c2c1]

(S)-3-(3,5-difluorophenyl)-N-methyl-N-(1-oxo-1,2-dihydroisoquinolin-7-yl)-2-(3-(o-tolylsulfonyl)ureido)propanamide LC-MS retention time=2.11 min; m/z=555.4 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-104

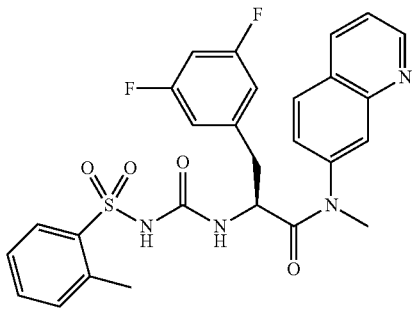 [SMILES: Cc1ccccc1S(=O)(=O)NC(=O)N[C@@H](Cc1cc(F)cc(F)c1)C(=O)N(C)c1ccc2cccnc2c1]

(S)-3-(3,5-difluorophenyl)-N-methyl-N-(quinolin-7-yl)-2-(3-(o-tolylsulfonyl)ureido)propanamide LC-MS retention time=1.32 min; m/z=539.2 [M+H]$^+$. (Column: Waters BEH C18, 2.0×50 mm, 1.7-μm particles. Solvent A=95% Water: 5% Acetonitrile: 10 mM NH$_4$OAc. Solvent % B=5% Water: 95% Acetonitrile: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-105

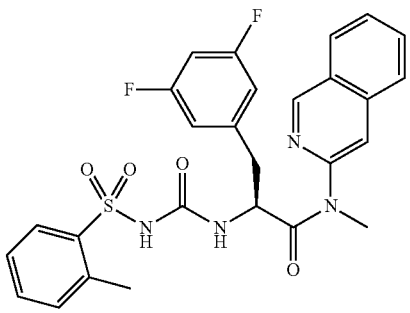

(S)-3-(3,5-difluorophenyl)-N-(isoquinolin-3-yl)-N-methyl-2-(3-(o-tolylsulfonyl)ureido)propanamide LC-MS retention time=1.46 min; m/z=539.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-106

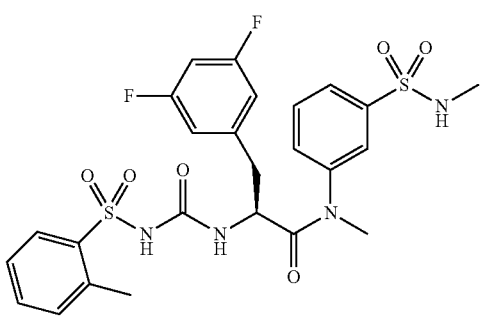 [SMILES: CNS(=O)(=O)c1cccc(N(C)C(=O)[C@H](Cc2cc(F)cc(F)c2)NC(=O)NS(=O)(=O)c2ccccc2C)c1]

(S)-3-(3,5-difluorophenyl)-N-methyl-N-(3-(N-methylsulfamoyl)phenyl)-2-(3-(o-tolylsulfonyl)ureido)propanamide LC-MS retention time=1.32 min; m/z=581.3 [M+H]$^+$. (Column: Waters BEH C18, 2.0×50 mm, 1.7-μm particles. Solvent A=95% Water: 5% Acetonitrile: 10 mM NH$_4$OAc. Solvent % B=5% Water: 95% Acetonitrile: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-107

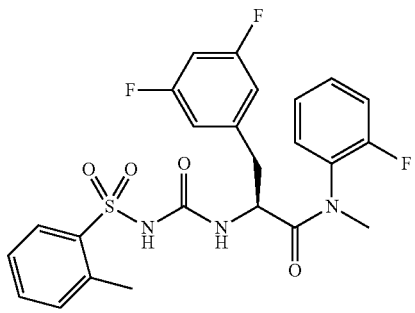 [SMILES: Cc1ccccc1S(=O)(=O)NC(=O)N[C@@H](Cc1cc(F)cc(F)c1)C(=O)N(C)c1ccccc1F]

(S)-3-(3,5-difluorophenyl)-N-(2-fluorophenyl)-N-methyl-2-(3-(o-tolylsulfonyl)ureido)propanamide LC-MS retention time=1.47 min; m/z=506.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-108

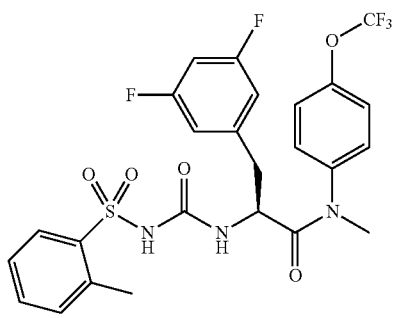 [SMILES: Cc1ccccc1S(=O)(=O)NC(=O)N[C@@H](Cc1cc(F)cc(F)c1)C(=O)N(C)c1ccc(OC(F)(F)F)cc1]

(S)-3-(3,5-difluorophenyl)-N-methyl-2-(3-(o-tolylsulfonyl) ureido)-N-(4-(trifluoromethoxy)phenyl)propanamide LC-MS retention time=1.83 min; m/z=572.1 [M+H]$^+$. (Column: Waters BEH C18, 2.0×50 mm, 1.7-μm particles. Solvent A=95% Water: 5% Acetonitrile: 10 mM NH$_4$OAc. Solvent % B=5% Water: 95% Acetonitrile: 10 mM NH$_4$OAc, Flow Rate=0.5 mL/min. Start % B=0. Final % B=100. Gradient Time=3 minutes, then a 0.5-minute hold at 100% B. Wavelength=220).

Example CA-109

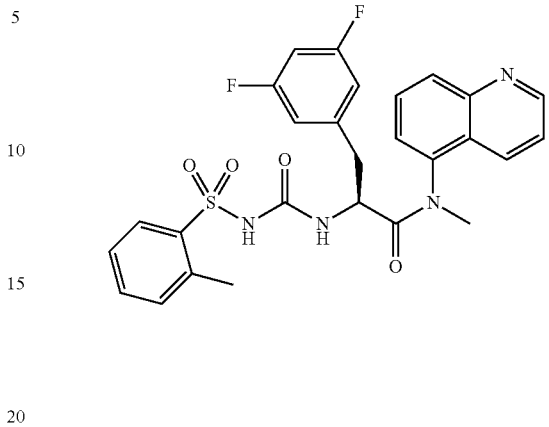

(S)-3-(3,5-difluorophenyl)-N-methyl-N-(quinolin-5-yl)-2-(3-(o-tolylsulfonyl)ureido)propanamide LC-MS retention time=2.36 min; m/z=539.1 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-110

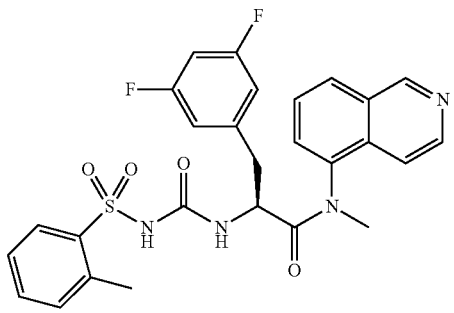 [SMILES: Cc1ccccc1S(=O)(=O)NC(=O)N[C@@H](Cc1cc(F)cc(F)c1)C(=O)N(C)c1cccc2cnccc12]

(S)-3-(3,5-difluorophenyl)-N-(isoquinolin-5-yl)-N-methyl-2-(3-(o-tolylsulfonyl)ureido)propanamide LC-MS retention time=2.34 min; m/z=539.2 [M+H]$^+$. (Column: Waters BEH C18, 2.0×50 mm, 1.7-μm particles. Solvent A=95% Water: 5% MeOH: 10 mM NH$_4$OAc. Solvent % B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-111

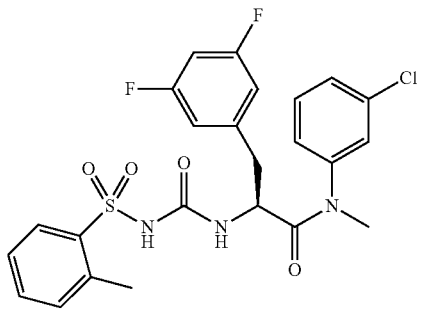 [SMILES: Cc1ccccc1S(=O)(=O)NC(=O)N[C@@H](Cc1cc(F)cc(F)c1)C(=O)N(C)c1cccc(Cl)c1]

(S)—N-(3-chlorophenyl)-3-(3,5-difluorophenyl)-N-methyl-2-(3-(o-tolylsulfonyl)ureido)propanamide LC-MS retention time=2.66 min; m/z=522.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-112

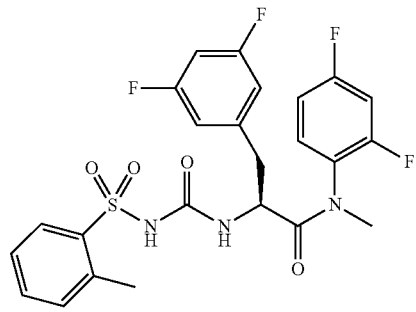 [SMILES: Cc1ccccc1S(=O)(=O)NC(=O)N[C@@H](Cc1cc(F)cc(F)c1)C(=O)N(C)c1ccc(F)cc1F]

(S)—N-(2,4-difluorophenyl)-3-(3,5-difluorophenyl)-N-methyl-2-(3-(o-tolylsulfonyl)ureido)propanamide LC-MS retention time=1.56 min; m/z=524.1 [M+H]$^+$. (Column: Waters BEH C18, 2.0×50 mm, 1.7-μm particles. Solvent A=95% Water: 5% Acetonitrile: 10 mM NH$_4$OAc. Solvent % B=5% Water: 95% Acetonitrile: 10 mM NH$_4$OAc, Flow Rate=0.5 mL/min. Start % B=0. Final % B=100. Gradient Time=3 minutes, then a 0.5-minute hold at 100% B. Wavelength=220).

Example ZY-13

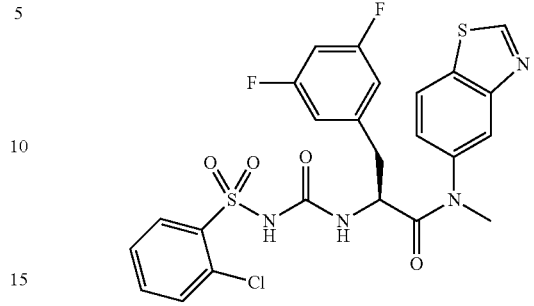

(S)—N-(benzo[d]thiazol-5-yl)-2-(3-((2-chlorophenyl)sulfonyl)ureido)-3-(3,5-difluorophenyl)-N-methylpropanamide Prepared using the procedure described for Example ZY-7 where 2-methylbenzenesulfonyl isocyanate was replaced by 2-chlorobenzenesulfonyl isocyanate. LC-MS retention time=2.23 min; m/z=565.1 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example ZY-14

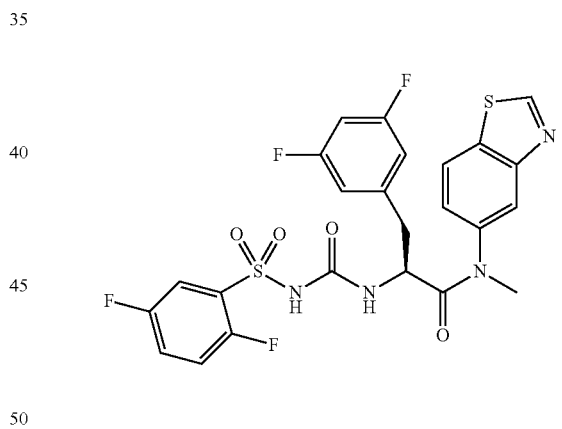

(S)—N-(benzo[d]thiazol-5-yl)-3-(3,5-difluorophenyl)-2-(3-((2,5-difluorophenyl)sulfonyl) ureido)-N-methylpropanamide Triphosgene (0.051 g, 0.17 mmol) was added to a stirred suspension of 2,5-difluorobenzenesulfonamide (0.10 g, 0.52 mmol) and 1-isocyanatobutane (5.8 μl, 0.052 mmol) in toluene (2 mL) and the reaction mixture was heated at 110° C. for 16 h. The reaction mixture was allowed to cool to rt, and ½ (1 mL) of the crude solution was added to a solution of an HCL salt of Intermediate ZY-5 (30 mg, 0.071 mmol) in CH$_3$CN (1 mL) and DIPEA (0.050 mL, 0.29 mmol) and stirred at rt for 2 h. The reaction mixture was concentrated, dissolved into MeOH, filtered and purified by preparative HPLC to yield the title compound (23.1 mg). LC-MS retention time=2.61 min; m/z=566.9 [M+H]$^+$. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example ZY-16

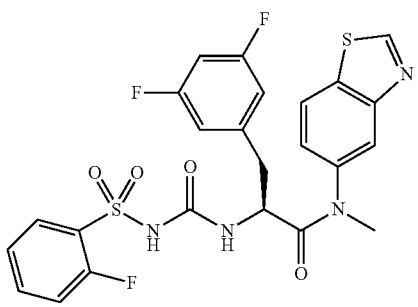 [SMILES: CN(C(=O)[C@H](Cc1cc(F)cc(F)c1)NC(=O)NS(=O)(=O)c1ccccc1F)c1ccc2scnc2c1]

(S)—N-(benzo[d]thiazol-5-yl)-3-(3,5-difluorophenyl)-2-(3-((2-fluorophenyl)sulfonyl)ureido)-N-methylpropanamide Prepared using the procedure described for Example ZY-14 where 2,5-difluorobenzenesulfonamide was replaced by 2-fluorobenzenesulfonamide. LC-MS retention time=1.28 min; m/z=549.1 [M+H]⁺. (Column: Waters BEH C18, 2.0× 50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example ZY-17

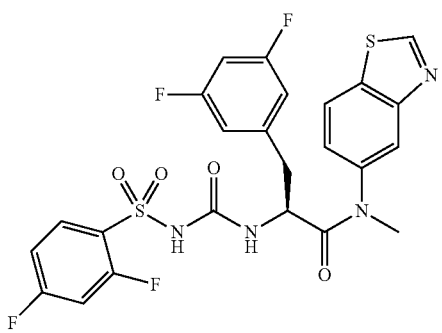 [SMILES: CN(C(=O)[C@H](Cc1cc(F)cc(F)c1)NC(=O)NS(=O)(=O)c1ccc(F)cc1F)c1ccc2scnc2c1]

(S)—N-(benzo[d]thiazol-5-yl)-3-(3,5-difluorophenyl)-2-(3-((2,4-difluorophenyl)sulfonyl) ureido)-N-methylpropanamide Prepared using the procedure described for Example ZY-14 where 2,5-difluorobenzenesulfonamide was replaced by 2,4-difluorobenzenesulfonamide. LC-MS retention time=2.23 min; m/z=567.1 [M+H]⁺. (Column: Waters BEH C18, 2.0× 50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example 206

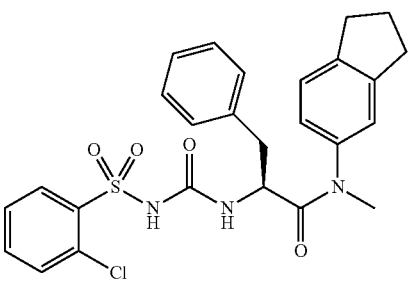 [SMILES: CN(C(=O)[C@H](Cc1ccccc1)NC(=O)NS(=O)(=O)c1ccccc1Cl)c1ccc2c(c1)CCC2]

(S)-2-(3-((2-chlorophenyl)sulfonyl)ureido)-N-(2,3-dihydro-1H-inden-5-yl)-N-methyl-3-phenylpropanamide A solution of 2-chlorobenzenesulfonyl isocyanate (21 mg, 0.098 mmol) in DCM (0.5 mL) was added dropwise to a stirred solution of a TFA salt of (S)-2-amino-N-(2,3-dihydro-1H-inden-5-yl)-N-methyl-3-phenylpropanamide (Intermediate 6) (40 mg, 0.098 mmol) and triethylamine (40 mg, 0.39 mmol) in DCM (1 mL) at RT and the reaction mixture was stirred at RT for 1 h. The reaction mixture was concentrated, dissolved into DMF, filtered and purified by preparative HPLC to yield the title compound (23.6 mg). LC-MS retention time=1.57 min; m/z=512.5 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example 207

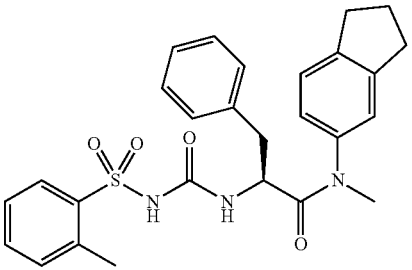 [SMILES: Cc1ccccc1S(=O)(=O)NC(=O)N[C@@H](Cc1ccccc1)C(=O)N(C)c1ccc2c(c1)CCC2]

(S)—N-(2,3-dihydro-1H-inden-5-yl)-N-methyl-3-phenyl-2-(3-(o-tolylsulfonyl)ureido)propanamide A solution of 2-methylbenzenesulfonyl isocyanate (19 mg, 0.098 mmol) in DCM (0.5 mL) was added dropwise to a stirred solution of a TFA salt of (S)-2-amino-N-(2,3-dihydro-1H-inden-5-yl)-N-methyl-3-phenylpropanamide (Intermediate 6) (40 mg, 0.098 mmol) and triethylamine (40 mg, 0.39 mmol) in DCM (1 mL) at RT and the reaction mixture was stirred at RT for 1 h. The reaction mixture was concentrated, dissolved into DMF, filtered and purified by preparative HPLC to yield the title compound (36.5 mg). LC-MS retention time=1.90 min; m/z=492.3 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example 208

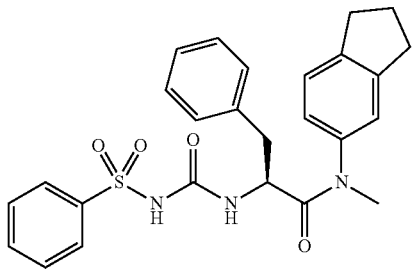 [SMILES: CN(C(=O)[C@H](Cc1ccccc1)NC(=O)NS(=O)(=O)c1ccccc1)c1ccc2c(c1)CCC2]

(S)—N-(2,3-dihydro-1H-inden-5-yl)-N-methyl-3-phenyl-2-(3-(phenylsulfonyl)ureido)propanamide A solution of benzenesulfonyl isocyanate (18 mg, 0.098 mmol) in DCM (0.5 mL) was added dropwise to a stirred solution of a TFA salt of (S)-2-amino-N-(2,3-dihydro-1H-inden-5-yl)-N-methyl-3-phenylpropanamide (Intermediate 6) (40 mg, 0.098 mmol) and triethylamine (40 mg, 0.39 mmol) in DCM (1 mL) at RT and the reaction mixture was stirred at RT for 1 h. The reaction mixture was concentrated, dissolved into DMF, filtered and purified by preparative HPLC to yield the title compound (34.4 mg). LC-MS retention time=1.81 min; m/z=478.3 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example 209

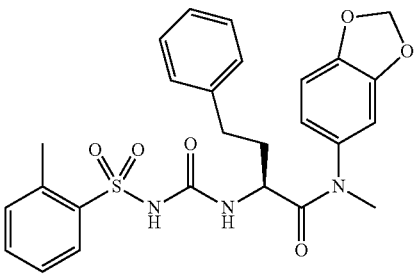 [SMILES: Cc1ccccc1S(=O)(=O)NC(=O)N[C@@H](CCc1ccccc1)C(=O)N(C)c1ccc2c(c1)OCO2]

(S)—N-(benzo[d][1,3]dioxol-5-yl)-N-methyl-4-phenyl-2-(3-(o-tolylsulfonyl) ureido)butanamide A solution of 4M HCl (0.67 mL, 2.7 mmol) in dioxane was added to a stirred solution of (S)-tert-butyl (1-(benzo[d][1,3]dioxol-5-yl(methyl)amino)-1-oxo-4-phenylbutan-2-yl)carbamate (Intermediate 7) (110 mg, 0.267 mmol) in dioxane (0.67 mL) and the reaction mixture was stirred at RT for 2 h. The crude reaction mixture was concentrated to dryness and the residue was dissolved into acetonitrile (1.1 mL) and DIPEA (0.116 mL, 0.667 mmol) and then treated with 2-methylbenzenesulfonyl isocyanate (79 mg, 0.40 mmol) and stirred at RT for 2.5 h. The reaction was quenched with MeOH (~5 mL), concentrated and the residue was partitioned between EtOAc (~8 mL) and water (~5 mL). The organic component was washed with brine (5 mL), concentrated, dissolved into MeOH, filtered and purified by preparative HPLC to yield the title compound (63.1 mg). LC-MS retention time=1.88 min; m/z=510.3 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example 210

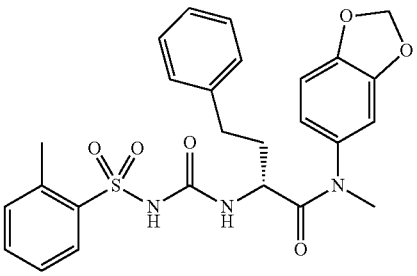 [SMILES: Cc1ccccc1S(=O)(=O)NC(=O)N[C@H](CCc1ccccc1)C(=O)N(C)c1ccc2c(c1)OCO2]

(R)—N-(benzo[d][1,3]dioxol-5-yl)-N-methyl-4-phenyl-2-(3-(o-tolylsulfonyl) ureido)butanamide A solution of 4M HCl (0.54 mL, 2.2 mmol) in dioxane was added to a stirred solution of (R)-tert-butyl (1-(benzo[d][1,3]dioxol-5-yl(methyl)amino)-1-oxo-4-phenylbutan-2-yl)carbamate (Intermediate 8) (89 mg, 0.22 mmol) in dioxane (0.54 mL) and the reaction mixture was stirred at RT for 2 h. The crude reaction mixture was concentrated to dryness and the residue was dissolved into acetonitrile (1 mL) and DIPEA (0.0.94 mL, 0.54 mmol) and then treated with 2-methylbenzenesulfonyl isocyanate (64 mg, 0.32 mmol) and stirred at RT for 2.5 h. The reaction was quenched with MeOH (~5 mL), concentrated and the residue was partitioned between EtOAc (~8 mL) and water (~5 mL). The organic component was washed with brine (5 mL), concentrated, dissolved into MeOH, filtered and purified by preparative HPLC to yield the title compound (58.7 mg). LC-MS retention time=2.44 min; m/z=510.2 [M+H]+. (Column: Waters BEH C18, 2.0×50 mm, 1.7-μm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220).

Example 212

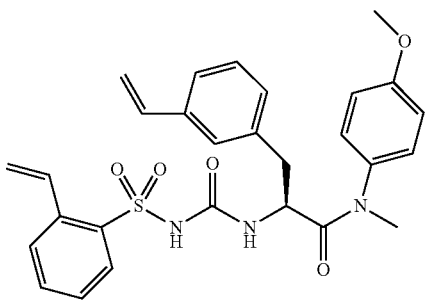 [SMILES: C=Cc1cccc(C[C@H](NC(=O)NS(=O)(=O)c2ccccc2C=C)C(=O)N(C)c2ccc(OC)cc2)c1]

(S)—N-(4-methoxyphenyl)-N-methyl-3-(3-vinylphenyl)-2-(3-((2-vinylphenyl)sulfonyl)ureido)propanamide A suspension of 2-vinylbenzenesulfonamide (77.4 mg, 0.422 mmol) in toluene (1 mL) in an 8-mL glass vial was treated with butyl isocyanate (4.2 mg, 0.042 mmol) and triphosgene (44 mg, 0.15 mmol). The vial was sealed and the reaction mixture was stirred at 115° C. overnight. The crude reaction mixture was concentrated to dryness, dissolved into DCM (1 mL) and added dropwise to a suspension of (S)-2-amino-N-(4-methoxyphenyl)-N-methyl-3-(3-vinylphenyl)propanamide, TFA (Intermediate 11) (179 mg, 0.422 mmol) in DIPEA (0.368 mL, 2.11 mmol) and DCM (5 mL) and the resulting reaction solution was stirred at RT for 1 h. The reaction was concentrated and purified by preparative HPLC (0.1% TFA, MeOH/H$_2$O) to yield the title compound (76 mg). LC-MS retention time=1.97 min; m/z=520.2 [M+H]$^+$. (Column: Phenonenex-Luna C18 2.0×30 mm 3 μm. Solvent A=95% Water: 5% Acetonitrile: 10 μM ammonium acetate. Solvent B=5% Water: 95% Acetonitrile: 10 μM ammonium acetate. Flow Rate=1.0 mL/min. Start % B=0. Final % B=100. Gradient Time=3 min. Wavelength=220). $^1$H NMR (400 MHz, DMSO-d$_6$) δ 10.66 (s, 1H), 7.82 (dd, J=7.8, 1.0 Hz, 1H), 7.76 (d, J=7.3 Hz, 1H), 7.64 (t, J=7.5 Hz, 1H), 7.49-7.43 (m, 1H), 7.35 (dd, J=17.4, 11.0 Hz, 1H), 7.24 (d, J=7.8 Hz, 1H), 7.12 (t, J=7.6 Hz, 1H), 7.01 (d, J=8.8 Hz, 2H), 6.91 (d, J=9.0 Hz, 2H), 6.75 (s, 1H), 6.71-6.54 (m, 3H), 5.83 (d, J=17.1 Hz, 1H), 5.67 (d, J=17.4 Hz, 1H), 5.45 (d, J=11.5 Hz, 1H), 5.22 (d, J=11.2 Hz, 1H), 4.23 (td, J=8.0, 5.3 Hz, 1H), 3.75 (s, 3H), 3.08 (s, 3H), 2.74 (dd, J=13.4, 5.1 Hz, 1H), 2.46 (d, J=8.1 Hz, 1H).

Example 213

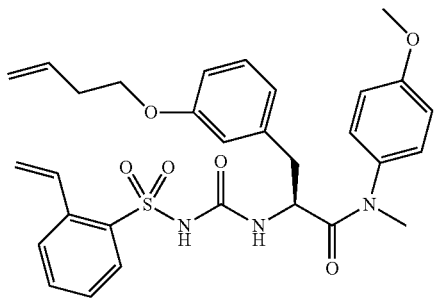 [SMILES: C=CCCOc1cccc(C[C@H](NC(=O)NS(=O)(=O)c2ccccc2C=C)C(=O)N(C)c2ccc(OC)cc2)c1]

(S)-3-(3-(but-3-en-1-yloxy)phenyl)-N-(4-methoxyphenyl)-N-methyl-2-(3-((2-vinylphenyl)sulfonyl)ureido)propanamide A suspension of 2-vinylbenzenesulfonamide (121 mg, 0.66 mmol) in toluene (1.4 mL) in an 8-mL glass vial was treated with butyl isocyanante (6.6 mg, 0.066 mmol) and triphosgene (69 mg, 0.23 mmol). The vial was sealed and the reaction mixture was stirred at 115° C. overnight. The crude reaction mixture was concentrated under a stream of nitrogen, dissolved into DCM (1 mL) and added dropwise to a suspension of (S)-2-amino-3-(3-(but-3-en-1-yloxy)phenyl)-N-(4-methoxyphenyl)-N-methylpropanamide, TFA (136 mg, 0.290 mmol) (Intermediate 14) in DIPEA (0.253 mL, 1.45 mmol) and DCM (5 mL) and the resulting reaction solution was stirred at RT for 1 h. The reaction was concentrated and purified by preparative HPLC (0.1% TFA, MeOH/H$_2$O) to yield the title compound (96 mg). LC-MS retention time=2.11 min; m/z=564.3 [M+H]$^+$. (Column: Phenonenex-Luna C18 2.0×30 mm 3 μm. Solvent A=95% Water: 5% Acetonitrile: 10 μM ammonium acetate. Solvent B=5% Water: 95% Acetonitrile: 10 μM ammonium acetate. Flow Rate=1.0 mL/min. Start % B=0. Final % B=100. Gradient Time=3 min. Wavelength=220). $^1$H NMR (400 MHz, DMSO-d$_6$) δ 10.56 (s, 1H), 7.88 (s, 1H), 7.81 (d, J=7.8 Hz, 1H), 7.70 (d, J=7.8 Hz, 1H), 7.60-7.53 (m, 1H), 7.08-7.01 (m, 3H), 6.94 (d, J=8.8 Hz, 2H), 6.90-6.68 (m, 3H), 6.37 (d, J=7.6 Hz, 1H), 6.24 (s, 1H), 6.00-5.80 (m, 2H), 5.43 (d, J=11.0 Hz, 1H), 5.22-5.05 (m, 2H), 4.28 (td, J=8.2, 5.1 Hz, 1H), 3.86 (t, J=6.5 Hz, 2H), 3.78 (s, 3H), 3.09 (s, 3H), 2.75 (dd, J=13.6, 5.0 Hz, 1H), 2.48-2.41 (m, 3H).

Example 214

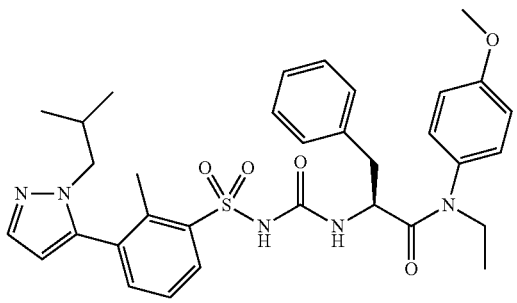 [SMILES: CCN(C(=O)[C@H](Cc1ccccc1)NC(=O)NS(=O)(=O)c1cccc(-c2ccnn2CC(C)C)c1C)c1ccc(OC)cc1]

(S)—N-ethyl-2-(3-((3-(1-isobutyl-1H-pyrazol-5-yl)-2-methylphenyl)sulfonyl)ureido)-N-(4-methoxyphenyl)-3-phenylpropanamide Example 214 was synthesized using the procedure described above for Example 149. LC-MS retention time=1.64 min; m/z=618.1 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example 215

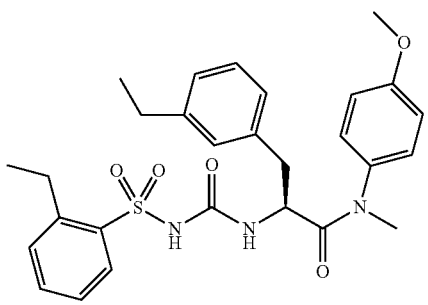 [SMILES: CCc1cccc(C[C@H](NC(=O)NS(=O)(=O)c2ccccc2CC)C(=O)N(C)c2ccc(OC)cc2)c1]

(S)-3-(3-ethylphenyl)-2-(3-((2-ethylphenyl)sulfonyl)ureido)-N-(4-methoxyphenyl)-N-methylpropanamide 10% Palladium on carbon (7.4 mg, 6.9 µmol) was added to a solution of (S)—N-(4-methoxyphenyl)-N-methyl-3-(3-vinylphenyl)-2-(3-((2-vinylphenyl)sulfonyl)ureido)propanamide (18 mg, 0.035 mmol) in MeOH (4 mL) and DCM (3 mL) and the reaction mixture was stirred under a balloon of hydrogen at RT for 1 h. The catalyst was removed by filtration and the reaction mixture was concentrated to dryness. The reaction mixture was concentrated, dissolved into MeOH, filtered and purified by preparative HPLC to yield the title compound (8.2 mg). LC-MS retention time=2.13 min; m/z=524.4 [M+H]$^+$. (Column: Waters BEH C18, 2.0×50 mm, 1.7-µm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example 216

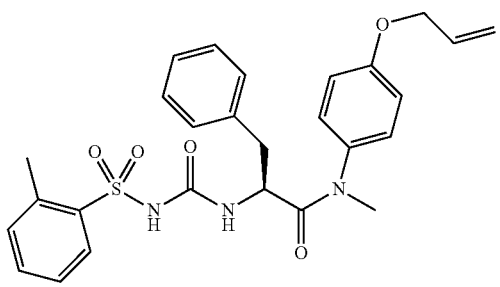 [SMILES: C=CCOc1ccc(N(C)C(=O)[C@H](Cc2ccccc2)NC(=O)NS(=O)(=O)c2ccccc2C)cc1]

(S)—N-(4-(allyloxy)phenyl)-N-methyl-3-phenyl-2-(3-(o-tolylsulfonyl)ureido)propanamide HATU (63.5 mg, 0.167 mmol) was added to a solution of 4-(allyloxy)-N-methylaniline, HCl (36.4 mg, 0.182 mmol), (S)-3-phenyl-2-(3-(o-tolylsulfonyl)ureido)propanoic acid (55 mg, 0.15 mmol) and DIPEA (0.11 mL, 0.61 mmol) in DMF (1.4 mL) and the reaction mixture was stirred at RT for 2 h. The reaction mixture was transferred into a microwave vial and heated in a microwave system at 65° C. for 2 h. The reaction mixture was filtered and purified by preparative HPLC to yield the title compound (8.3 mg). LC-MS retention time=1.48 min; m/z=508.4 [M+H]$^+$. (Column: Waters BEH C18, 2.0×50 mm, 1.7-µm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example 217

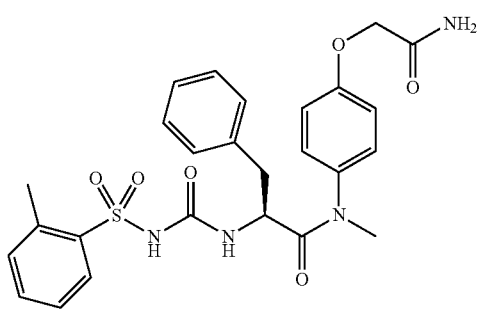 [SMILES: Cc1ccccc1S(=O)(=O)NC(=O)N[C@@H](Cc1ccccc1)C(=O)N(C)c1ccc(OCC(N)=O)cc1]

(S)—N-(4-(2-amino-2-oxoethoxy)phenyl)-N-methyl-3-phenyl-2-(3-(o-tolylsulfonyl)ureido)propanamide 2-Methylbenzenesulfonyl isocyanate (0.015 mL, 0.10 mmol) was added dropwise to an ice bath cooled stirred solution of (S)-2-amino-N-(4-(2-amino-2-oxoethoxy)phenyl)-N-methyl-3-phenylpropanamide (33 mg, 0.10 mmol) and DIPEA (0.070 mL, 0.40 mmol) in acetonitrile (1 mL) and the resulting reaction solution was stirred at RT overnight. The reaction mixture was concentrated, dissolved into MeOH, filtered and purified by preparative HPLC to yield the title compound (17.6 mg). LC-MS retention time=1.04 min; m/z=525.4 [M+H]$^+$. (Column: Waters BEH C18, 2.0×50 mm, 1.7-µm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Biological Methods

HIV cell culture assay—MT-2 cells, 293T cells and the proviral DNA clone of NL$_{4-3}$ virus were obtained from the NIH AIDS Research and Reference Reagent Program. MT-2 cells were propagated in RPMI 1640 media supplemented with 10% heat inactivated fetal bovine serum (FBS), 100 ug/ml penicillin G and up to 100 units/ml streptomycin. The 293T cells were propagated in DMEM media supplemented with 10% heat inactivated FBS, 100 ug/ml penicillin G and 100 ug/ml streptomycin. A recombinant NL$_{4-3}$ proviral clone, in which a section of the nef gene was replaced with the Renilla luciferase gene, was used to make the reference virus used in these studies. The recombinant virus was prepared through transfection of the recombinant NL$_{4-3}$ proviral clone into 293T cells using Transit-293 Transfection Reagent from Mirus Bio LLC (Madison, Wis.). Supernatent was harvested after 2-3 days after transfection, and the amount of virus present was titered in MT-2 cells using luciferase enzyme activity as a marker. Luciferase activity was quantitated using the EnduRen Live Cell Substrate from Promega (Madison, Wis.). Antiviral activities of compounds toward the recombinant virus were quantified by measuring luciferase activity in MT-2 cells infected for 4-5 days with the recombinant virus in the presence of serial dilutions of the compound.

The 50% effective concentration ($EC_{50}$) was calculated by using the exponential form of the median effect equation where (Fa)=1/[1+($ED_{50}$/drug conc.)$^m$](Johnson V A, Byington R T. Infectivity Assay. In *Techniques in HIV Research*. ed. Aldovini A, Walker B D. 71-76. New York: Stockton Press. 1990).

Compound cytotoxicity and the corresponding $CC_{50}$ values were determined using the same protocol as described in the antiviral assay except that uninfected cells were used. Cytotoxicity was assessed on day 4 in uninfected MT2 cells by using a XTT-based (2,3-bis[2-Methoxy-4-nitro-5-sulfophenyl]-2H-tetrazolium-5-carboxyanilide inner salt)-based colorimetric assay (Sigma-Aldrich, St Louis, Mo.).

Compounds demonstrated antiviral activity as depicted in the table below. Activity equal to A refers to a compound having an $EC_{50}$ value which is <0.1 μM, B is 0.1 to <1.0 μM, C is 1.0 to <10 μM, and D is 10 to <100 μM.

TABLE 1

| Example | Structure | Activity | $EC_{50}$ (μM) |
|---|---|---|---|
| 1 | 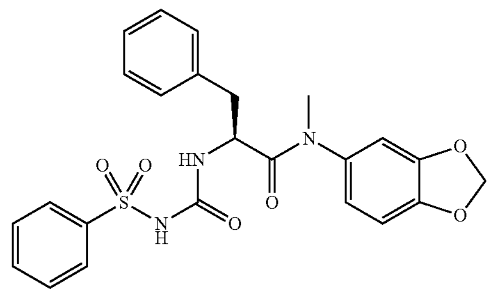 [SMILES: CN(C(=O)[C@H](Cc1ccccc1)NC(=O)NS(=O)(=O)c1ccccc1)c1ccc2c(c1)OCO2] | B | 0.26 |
| 2 | 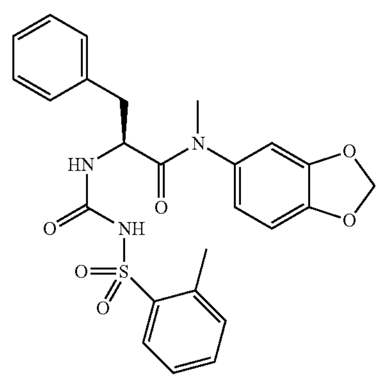 [SMILES: Cc1ccccc1S(=O)(=O)NC(=O)N[C@@H](Cc1ccccc1)C(=O)N(C)c1ccc2c(c1)OCO2] | A | 0.07 |
| 3 | 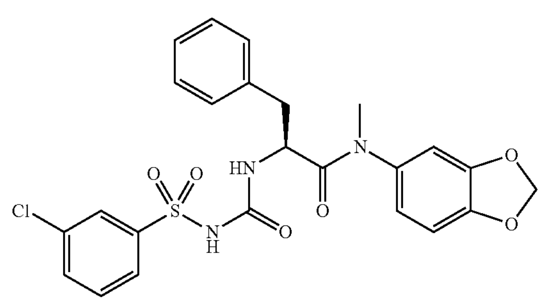 [SMILES: CN(C(=O)[C@H](Cc1ccccc1)NC(=O)NS(=O)(=O)c1cccc(Cl)c1)c1ccc2c(c1)OCO2] | B | |

TABLE 1-continued

| Example | Structure | Activity | EC$_{50}$ (μM) |
|---|---|---|---|
| 4 | 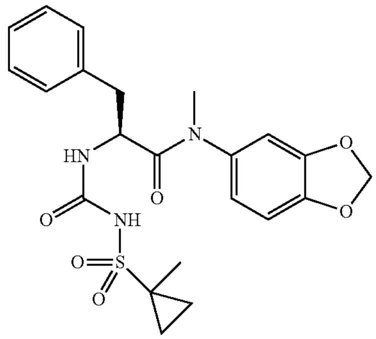 [SMILES: CN(C(=O)[C@H](Cc1ccccc1)NC(=O)NS(=O)(=O)C1(C)CC1)c1ccc2c(c1)OCO2] | C | 1.11 |
| 5 | 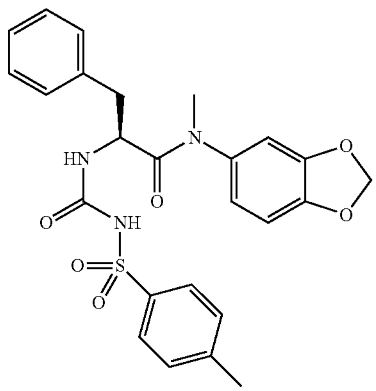 [SMILES: Cc1ccc(S(=O)(=O)NC(=O)N[C@@H](Cc2ccccc2)C(=O)N(C)c2ccc3c(c2)OCO3)cc1] | B | |
| 6 | 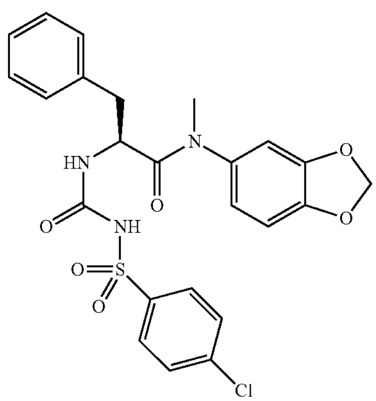 [SMILES: CN(C(=O)[C@H](Cc1ccccc1)NC(=O)NS(=O)(=O)c1ccc(Cl)cc1)c1ccc2c(c1)OCO2] | B | |
| 7 | 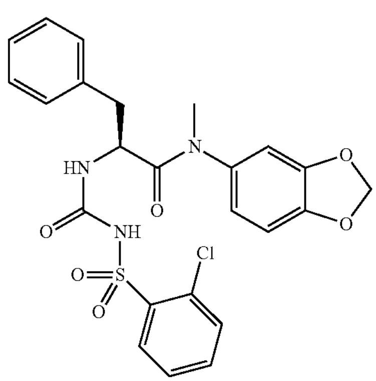 [SMILES: CN(C(=O)[C@H](Cc1ccccc1)NC(=O)NS(=O)(=O)c1ccccc1Cl)c1ccc2c(c1)OCO2] | A | |

TABLE 1-continued

| Example | Structure | Activity | EC$_{50}$ (μM) |
|---|---|---|---|
| 8 | 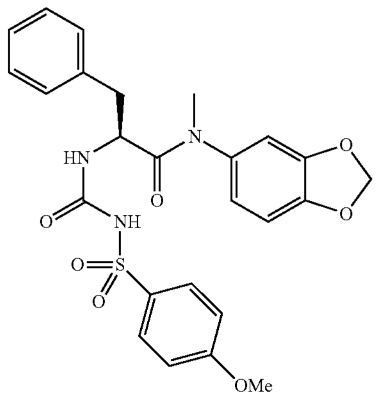 [SMILES: COc1ccc(S(=O)(=O)NC(=O)N[C@@H](Cc2ccccc2)C(=O)N(C)c2ccc3c(c2)OCO3)cc1] | B | 0.18 |
| 9 | 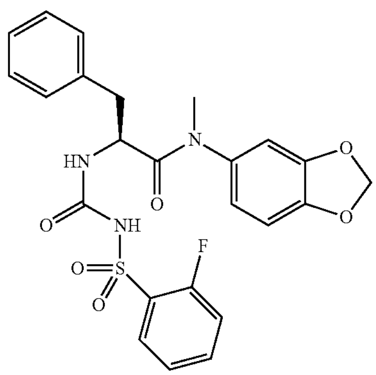 | A | |
| 10 | 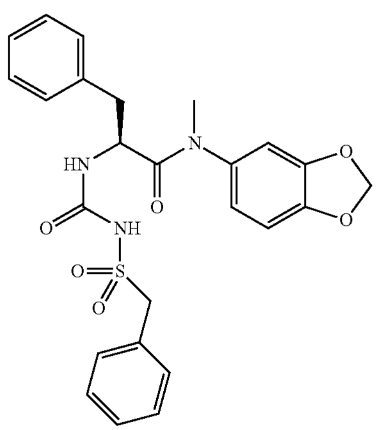 [SMILES: CN(C(=O)[C@H](Cc1ccccc1)NC(=O)NS(=O)(=O)Cc1ccccc1)c1ccc2c(c1)OCO2] | B | |
| 11 | 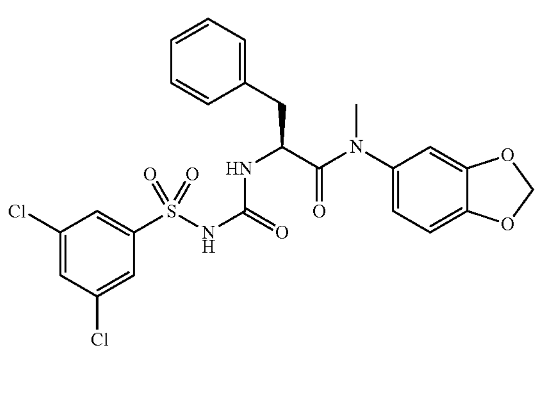 [SMILES: CN(C(=O)[C@H](Cc1ccccc1)NC(=O)NS(=O)(=O)c1cc(Cl)cc(Cl)c1)c1ccc2c(c1)OCO2] | B | |

TABLE 1-continued
| Example | Structure | Activity | EC$_{50}$ (μM) |
|---|---|---|---|
| 12 | 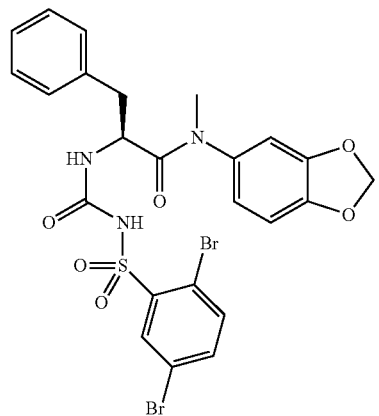 [SMILES: CN(C(=O)[C@H](Cc1ccccc1)NC(=O)NS(=O)(=O)c1cc(Br)ccc1Br)c1ccc2c(c1)OCO2] | A | |
| 13 | 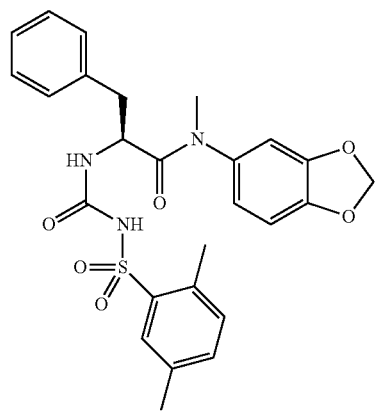 [SMILES: Cc1ccc(C)c(S(=O)(=O)NC(=O)N[C@@H](Cc2ccccc2)C(=O)N(C)c2ccc3c(c2)OCO3)c1] | A | 0.05 |
| 14 | 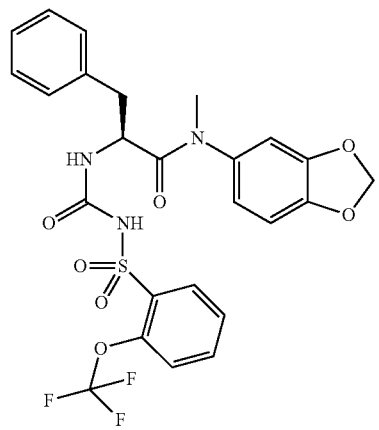 [SMILES: CN(C(=O)[C@H](Cc1ccccc1)NC(=O)NS(=O)(=O)c1ccccc1OC(F)(F)F)c1ccc2c(c1)OCO2] | A | |

TABLE 1-continued

| Example | Structure | Activity | EC$_{50}$ (μM) |
|---|---|---|---|
| 15 | 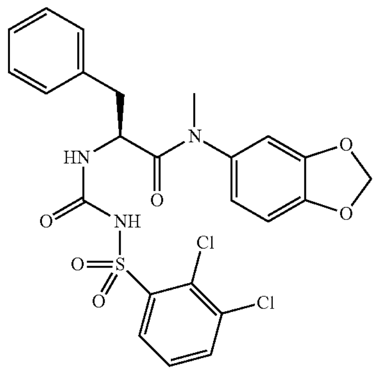 | A | |
| 16 | 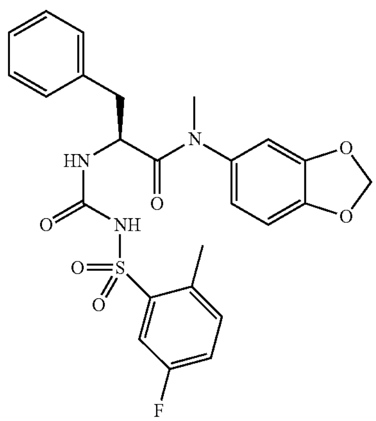 [SMILES: Cc1ccc(F)cc1S(=O)(=O)NC(=O)N[C@@H](Cc1ccccc1)C(=O)N(C)c1ccc2c(c1)OCO2] | A | |
| 17 | 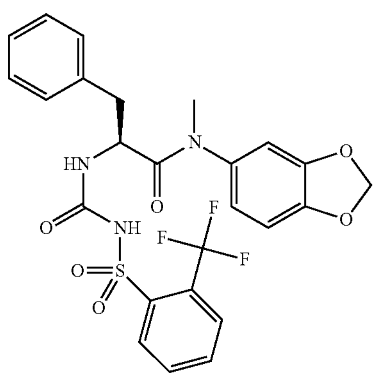 [SMILES: CN(C(=O)[C@H](Cc1ccccc1)NC(=O)NS(=O)(=O)c1ccccc1C(F)(F)F)c1ccc2c(c1)OCO2] | B | |
| 18 | 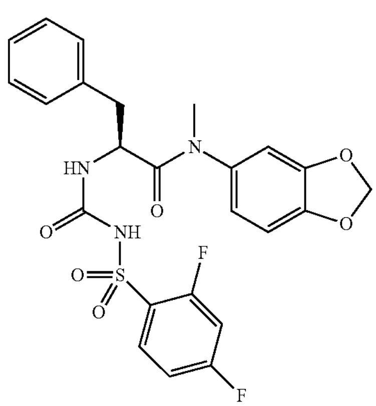 [SMILES: CN(C(=O)[C@H](Cc1ccccc1)NC(=O)NS(=O)(=O)c1ccc(F)cc1F)c1ccc2c(c1)OCO2] | B | 0.20 |

TABLE 1-continued

| Example | Structure | Activity | EC$_{50}$ (μM) |
|---|---|---|---|
| 19 | 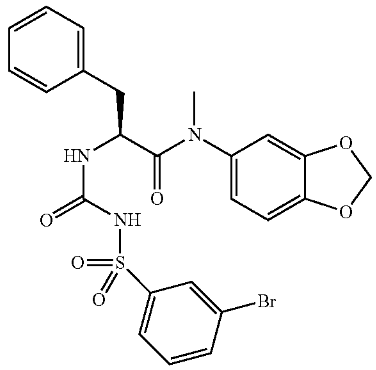 [SMILES: CN(C(=O)[C@H](Cc1ccccc1)NC(=O)NS(=O)(=O)c1cccc(Br)c1)c1ccc2c(c1)OCO2] | B | |
| 20 | 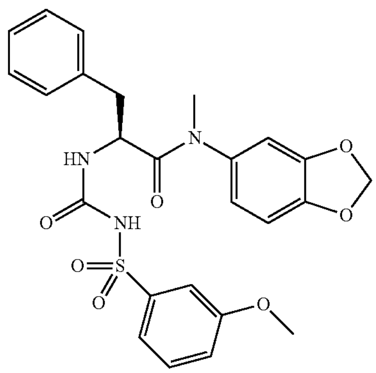 [SMILES: COc1cccc(S(=O)(=O)NC(=O)N[C@@H](Cc2ccccc2)C(=O)N(C)c2ccc3c(c2)OCO3)c1] | A | 0.09 |
| 21 | 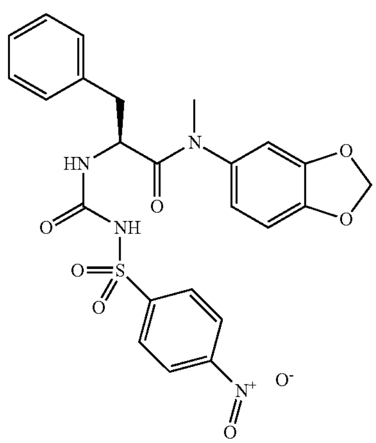 | C | |
| 22 | 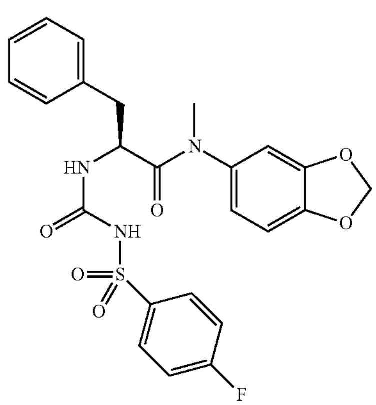 | B | |

TABLE 1-continued

| Example | Structure | Activity | EC$_{50}$ (μM) |
|---|---|---|---|
| 23 | 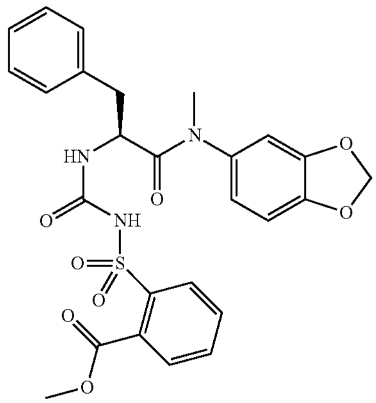 [SMILES: COC(=O)c1ccccc1S(=O)(=O)NC(=O)N[C@@H](Cc1ccccc1)C(=O)N(C)c1ccc2c(c1)OCO2] | C | |
| 24 | 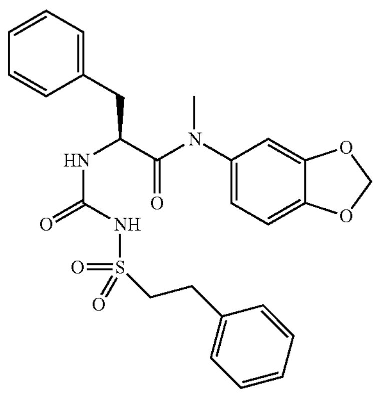 [SMILES: CN(C(=O)[C@H](Cc1ccccc1)NC(=O)NS(=O)(=O)CCc1ccccc1)c1ccc2c(c1)OCO2] | B | |
| 25 | 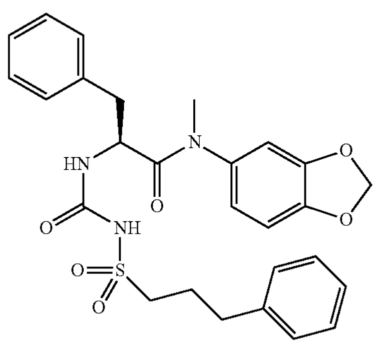 [SMILES: CN(C(=O)[C@H](Cc1ccccc1)NC(=O)NS(=O)(=O)CCCc1ccccc1)c1ccc2c(c1)OCO2] | B | 0.93 |
| 26 | 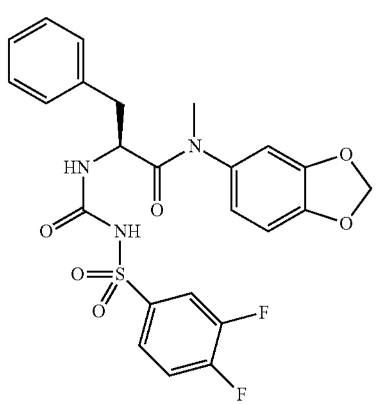 [SMILES: CN(C(=O)[C@H](Cc1ccccc1)NC(=O)NS(=O)(=O)c1ccc(F)c(F)c1)c1ccc2c(c1)OCO2] | B | |

TABLE 1-continued

| Example | Structure | Activity | EC$_{50}$ (μM) |
|---------|-----------|----------|----------------|
| 27 | 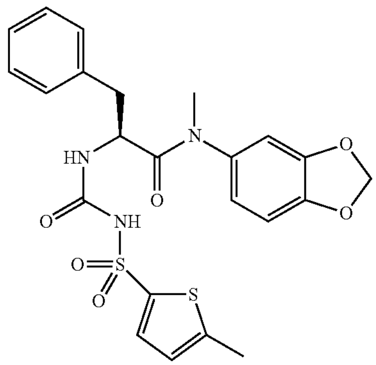 [SMILES: Cc1ccc(S(=O)(=O)NC(=O)N[C@@H](Cc2ccccc2)C(=O)N(C)c2ccc3c(c2)OCO3)s1] | B | |
| 28 | 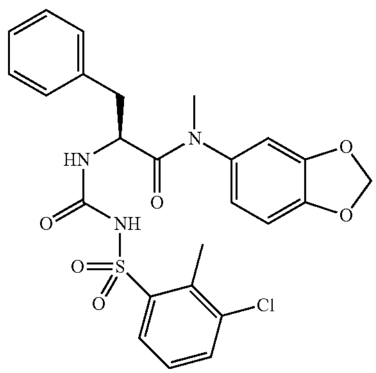 [SMILES: Cc1c(Cl)cccc1S(=O)(=O)NC(=O)N[C@@H](Cc1ccccc1)C(=O)N(C)c1ccc2c(c1)OCO2] | A | |
| 29 | 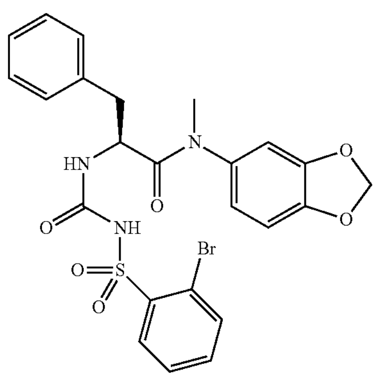 | A | |
| 30 | 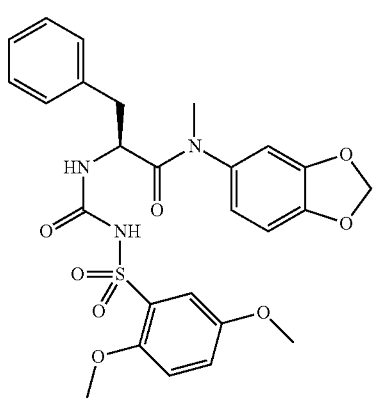 [SMILES: COc1ccc(OC)c(S(=O)(=O)NC(=O)N[C@@H](Cc2ccccc2)C(=O)N(C)c2ccc3c(c2)OCO3)c1] | A | |

TABLE 1-continued

| Example | Structure | Activity | EC$_{50}$ (µM) |
|---|---|---|---|
| 31 | 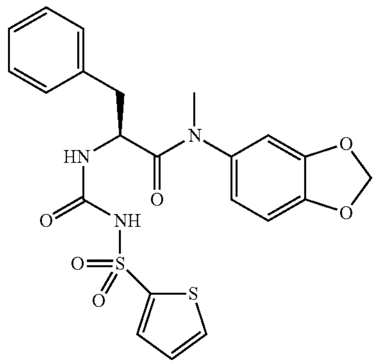 [SMILES: CN(C(=O)[C@H](Cc1ccccc1)NC(=O)NS(=O)(=O)c1cccs1)c1ccc2c(c1)OCO2] | B | |
| 32 | 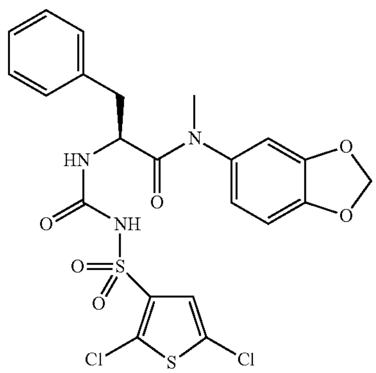 [SMILES: CN(C(=O)[C@H](Cc1ccccc1)NC(=O)NS(=O)(=O)c1cc(Cl)sc1Cl)c1ccc2c(c1)OCO2] | A | 0.07 |
| 33 | 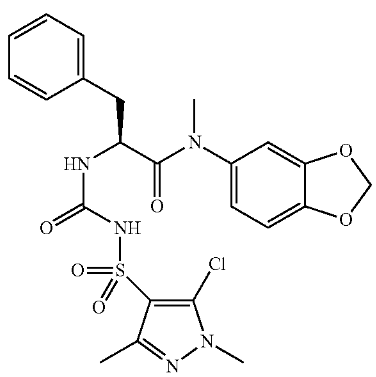 [SMILES: Cc1nn(C)c(Cl)c1S(=O)(=O)NC(=O)N[C@@H](Cc1ccccc1)C(=O)N(C)c1ccc2c(c1)OCO2] | B | 0.21 |
| 34 | 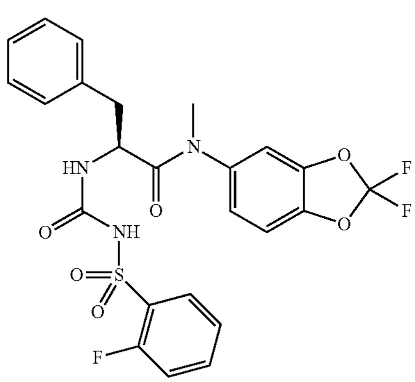 | B | |

TABLE 1-continued

| Example | Structure | Activity | EC$_{50}$ (µM) |
|---|---|---|---|
| 35 | 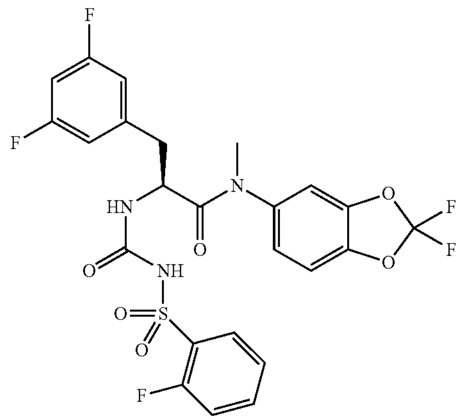 [SMILES: CN(C(=O)[C@H](Cc1cc(F)cc(F)c1)NC(=O)NS(=O)(=O)c1ccccc1F)c1ccc2c(c1)OC(F)(F)O2] | B | |
| 36 | 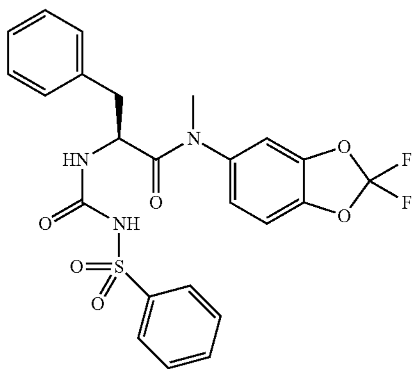 [SMILES: CN(C(=O)[C@H](Cc1ccccc1)NC(=O)NS(=O)(=O)c1ccccc1)c1ccc2c(c1)OC(F)(F)O2] | C | |
| 37 | 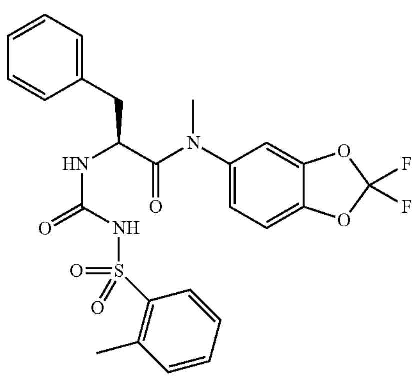 [SMILES: Cc1ccccc1S(=O)(=O)NC(=O)N[C@@H](Cc1ccccc1)C(=O)N(C)c1ccc2c(c1)OC(F)(F)O2] | B | |
| 38 | 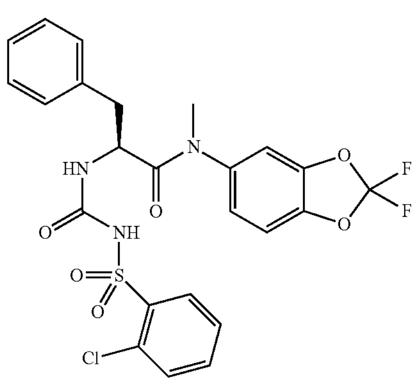 [SMILES: CN(C(=O)[C@H](Cc1ccccc1)NC(=O)NS(=O)(=O)c1ccccc1Cl)c1ccc2c(c1)OC(F)(F)O2] | B | 0.31 |

TABLE 1-continued

| Example | Structure | Activity | EC$_{50}$ (μM) |
|---|---|---|---|
| 39 | 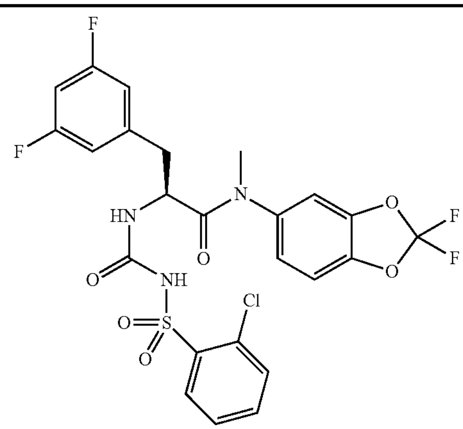 | B | |
| 40 | 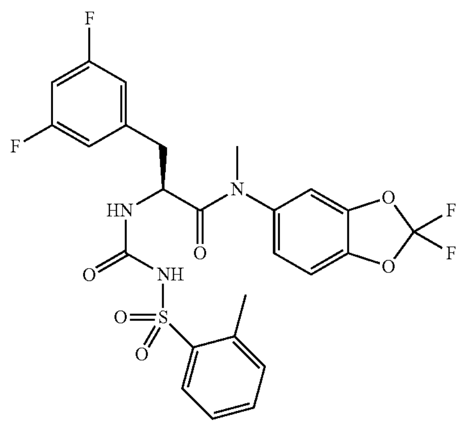 [SMILES: Cc1ccccc1S(=O)(=O)NC(=O)N[C@@H](Cc1cc(F)cc(F)c1)C(=O)N(C)c1ccc2c(c1)OC(F)(F)O2] | B | |
| 41 | 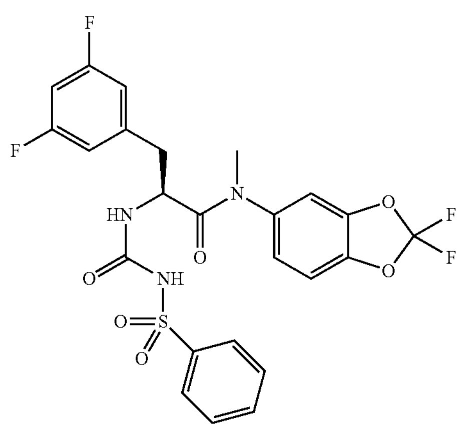 [SMILES: CN(C(=O)[C@H](Cc1cc(F)cc(F)c1)NC(=O)NS(=O)(=O)c1ccccc1)c1ccc2c(c1)OC(F)(F)O2] | B | |
| 42 | 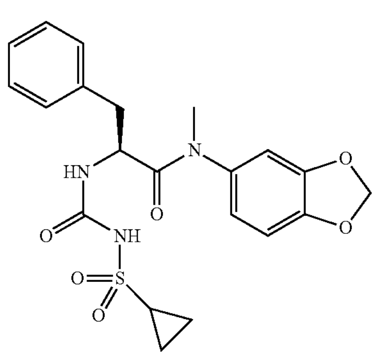 [SMILES: CN(C(=O)[C@H](Cc1ccccc1)NC(=O)NS(=O)(=O)C1CC1)c1ccc2c(c1)OCO2] | B | 0.48 |

TABLE 1-continued

| Example | Structure | Activity | EC$_{50}$ (µM) |
|---------|-----------|----------|----------------|
| 43 | 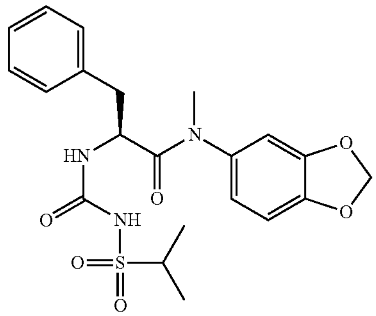 [SMILES: CC(C)S(=O)(=O)NC(=O)N[C@@H](Cc1ccccc1)C(=O)N(C)c1ccc2c(c1)OCO2] | B | |
| 44 | 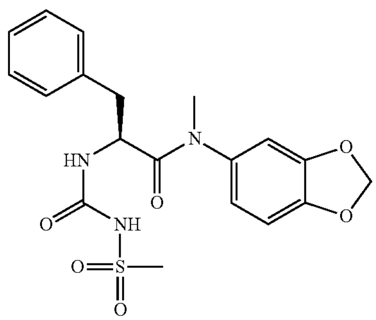 [SMILES: CN(C(=O)[C@H](Cc1ccccc1)NC(=O)NS(C)(=O)=O)c1ccc2c(c1)OCO2] | C | 2.48 |
| 45 | 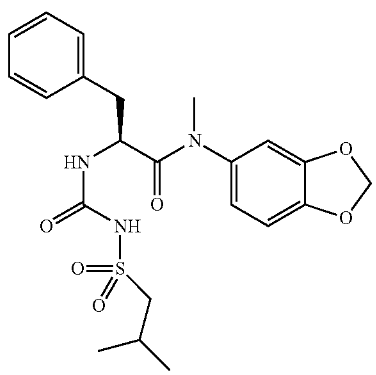 [SMILES: CC(C)CS(=O)(=O)NC(=O)N[C@@H](Cc1ccccc1)C(=O)N(C)c1ccc2c(c1)OCO2] | B | |
| 46 | 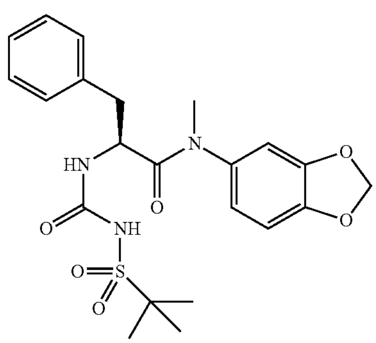 [SMILES: CN(C(=O)[C@H](Cc1ccccc1)NC(=O)NS(=O)(=O)C(C)(C)C)c1ccc2c(c1)OCO2] | C | |

TABLE 1-continued

| Example | Structure | Activity | EC$_{50}$ (μM) |
|---|---|---|---|
| 47 | 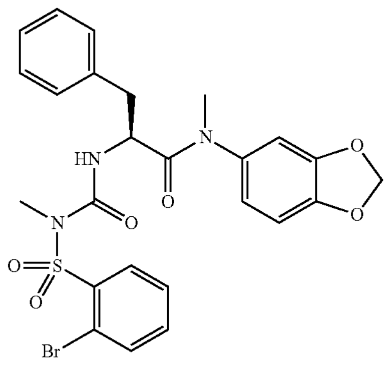 [SMILES: CN(C(=O)[C@H](Cc1ccccc1)NC(=O)N(C)S(=O)(=O)c1ccccc1Br)c1ccc2c(c1)OCO2] | C | |
| 48 | 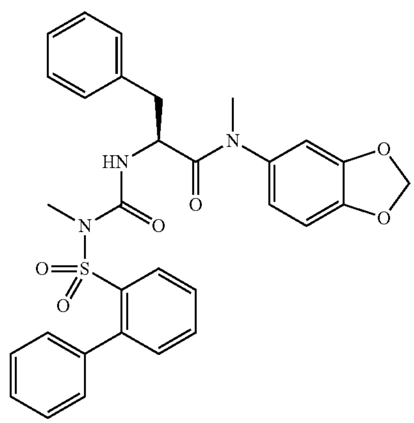 [SMILES: CN(C(=O)[C@H](Cc1ccccc1)NC(=O)N(C)S(=O)(=O)c1ccccc1-c1ccccc1)c1ccc2c(c1)OCO2] | C | |
| 49 | 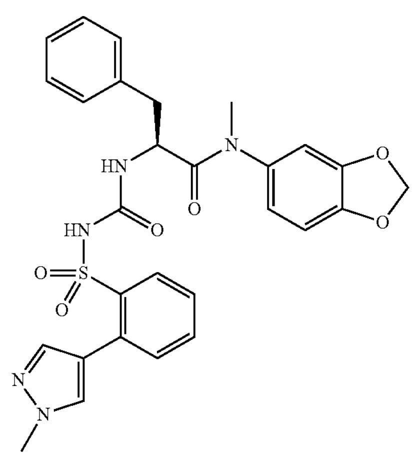 [SMILES: CN(C(=O)[C@H](Cc1ccccc1)NC(=O)NS(=O)(=O)c1ccccc1-c1cnn(C)c1)c1ccc2c(c1)OCO2] | C | 1.34 |

TABLE 1-continued

| Example | Structure | Activity | EC$_{50}$ (μM) |
|---|---|---|---|
| 50 | 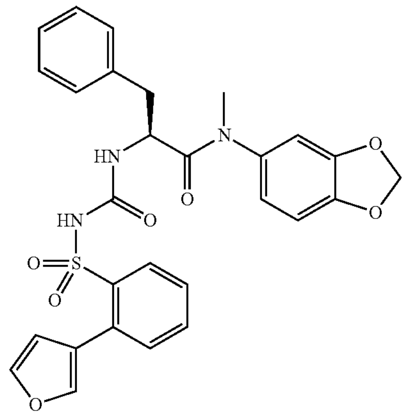 [SMILES: CN(C(=O)[C@H](Cc1ccccc1)NC(=O)NS(=O)(=O)c1ccccc1-c1ccoc1)c1ccc2c(c1)OCO2] | B | |
| 51 | 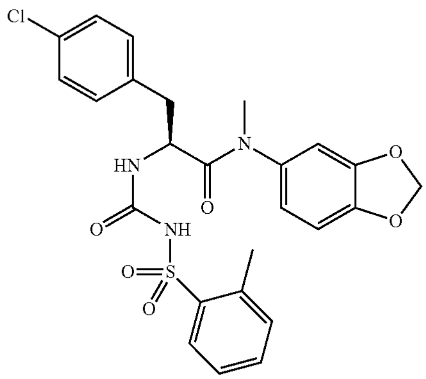 [SMILES: Cc1ccccc1S(=O)(=O)NC(=O)N[C@@H](Cc1ccc(Cl)cc1)C(=O)N(C)c1ccc2c(c1)OCO2] | B | 0.49 |
| 52 | 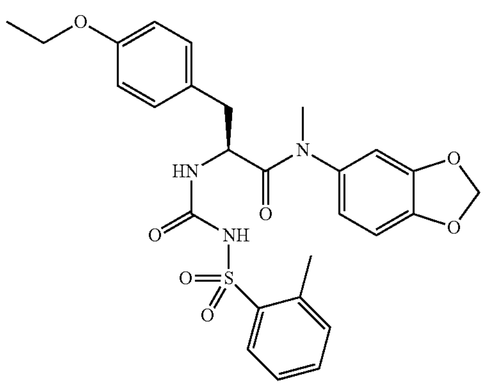 [SMILES: CCOc1ccc(C[C@H](NC(=O)NS(=O)(=O)c2ccccc2C)C(=O)N(C)c2ccc3c(c2)OCO3)cc1] | C | 6.23 |
| 53 | 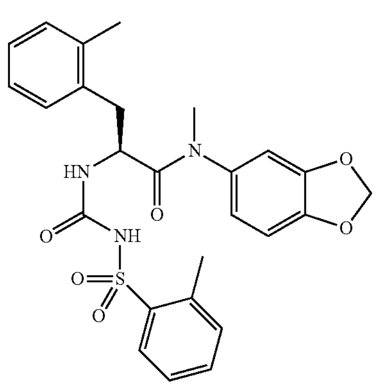 [SMILES: Cc1ccccc1C[C@H](NC(=O)NS(=O)(=O)c1ccccc1C)C(=O)N(C)c1ccc2c(c1)OCO2] | B | |

TABLE 1-continued

| Example | Structure | Activity | EC$_{50}$ (μM) |
|---|---|---|---|
| 54 | *(structure)* | B | |
| 55 | *(structure)* | B | |
| 56 | *(structure)* | C | |
| 57 | *(structure)* | C | |

TABLE 1-continued
| Example | Structure | Activity | EC$_{50}$ (μM) |
|---|---|---|---|
| 58 | 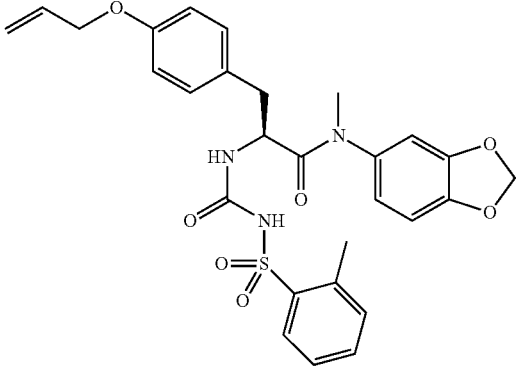 [SMILES: C=CCOc1ccc(C[C@H](NC(=O)NS(=O)(=O)c2ccccc2C)C(=O)N(C)c2ccc3c(c2)OCO3)cc1] | C | |
| 59 | 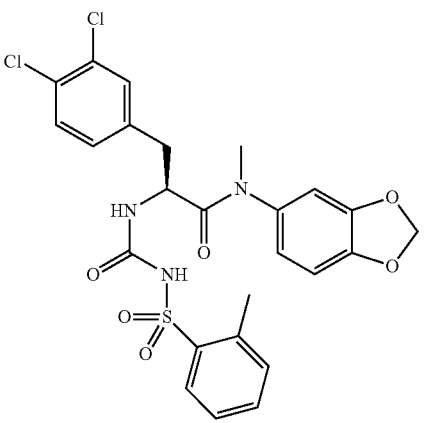 [SMILES: Cc1ccccc1S(=O)(=O)NC(=O)N[C@@H](Cc1ccc(Cl)c(Cl)c1)C(=O)N(C)c1ccc2c(c1)OCO2] | C | 1.04 |
| 60 | 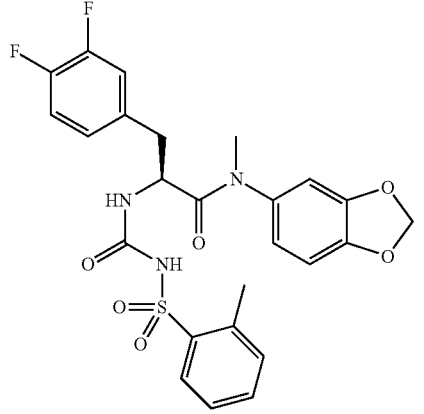 [SMILES: Cc1ccccc1S(=O)(=O)NC(=O)N[C@@H](Cc1ccc(F)c(F)c1)C(=O)N(C)c1ccc2c(c1)OCO2] | B | 0.23 |

TABLE 1-continued
| Example | Structure | Activity | EC$_{50}$ (μM) |
|---|---|---|---|
| 61 | 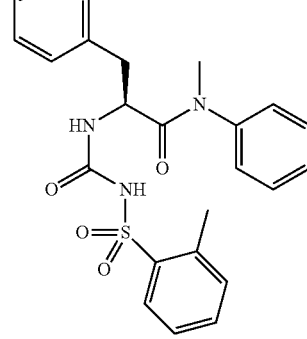 | C | 6.62 |
| 62 | 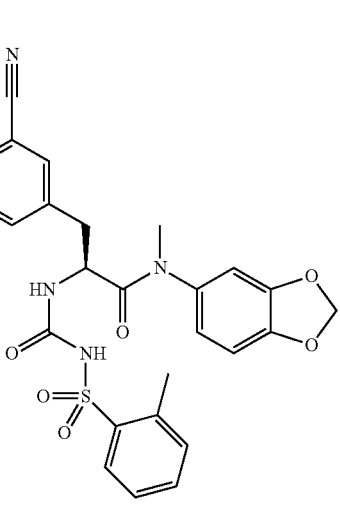 | C | |
| 63 | 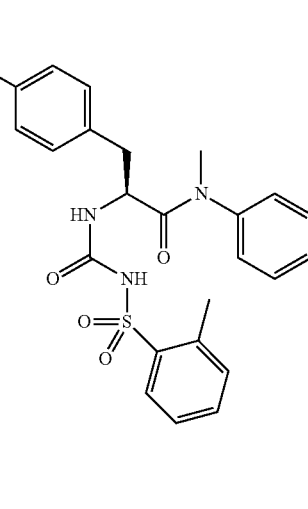 | C | |

TABLE 1-continued
| Example | Structure | Activity | EC$_{50}$ (μM) |
|---------|-----------|----------|----------------|
| 64 | 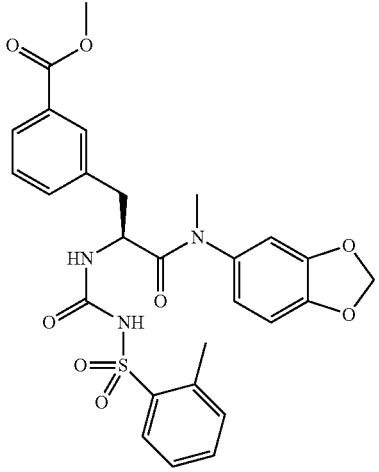 [SMILES: COC(=O)c1cccc(C[C@H](NC(=O)NS(=O)(=O)c2ccccc2C)C(=O)N(C)c2ccc3c(c2)OCO3)c1] | C | |
| 65 | 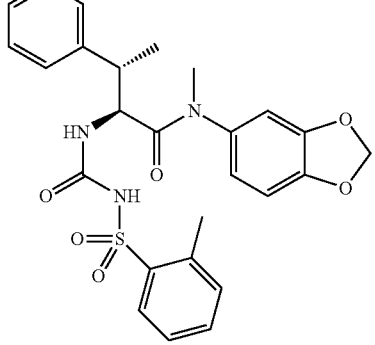 | C | 6.83 |
| 66 | 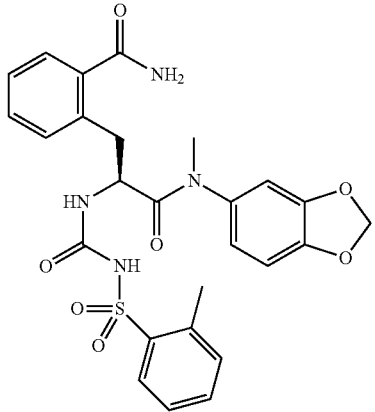 [SMILES: Cc1ccccc1S(=O)(=O)NC(=O)N[C@@H](Cc1ccccc1C(N)=O)C(=O)N(C)c1ccc2c(c1)OCO2] | | >100 |

TABLE 1-continued

| Example | Structure | Activity | EC$_{50}$ (μM) |
|---|---|---|---|
| 67 | 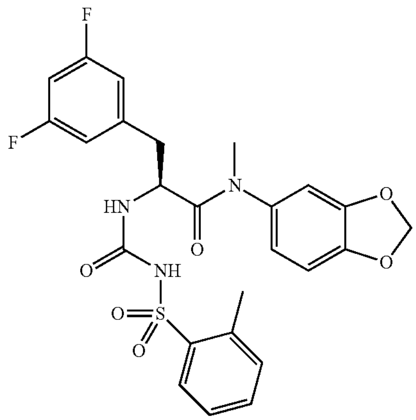 [SMILES: Cc1ccccc1S(=O)(=O)NC(=O)N[C@@H](Cc1cc(F)cc(F)c1)C(=O)N(C)c1ccc2c(c1)OCO2] | B | |
| 68 | 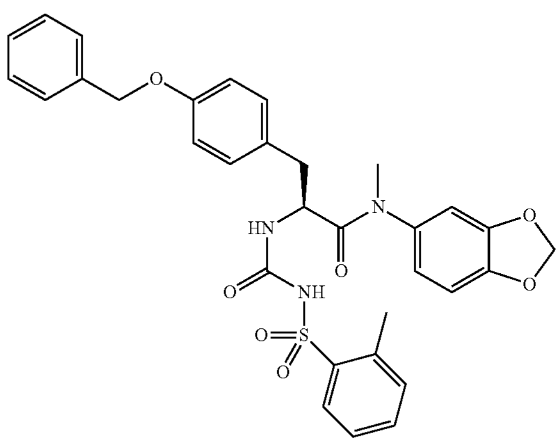 [SMILES: Cc1ccccc1S(=O)(=O)NC(=O)N[C@@H](Cc1ccc(OCc2ccccc2)cc1)C(=O)N(C)c1ccc2c(c1)OCO2] | D | 16.0 |
| 69 | 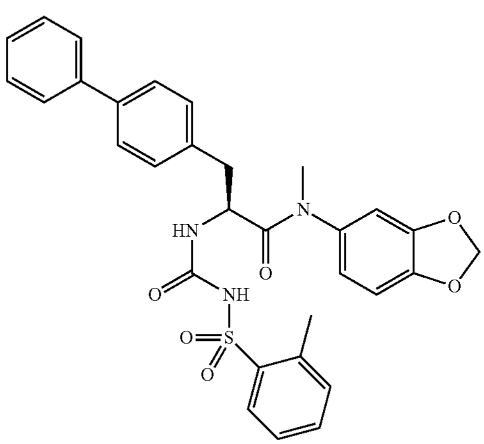 [SMILES: Cc1ccccc1S(=O)(=O)NC(=O)N[C@@H](Cc1ccc(-c2ccccc2)cc1)C(=O)N(C)c1ccc2c(c1)OCO2] | D | |

TABLE 1-continued
| Example | Structure | Activity | EC$_{50}$ (µM) |
|---|---|---|---|
| 70 | 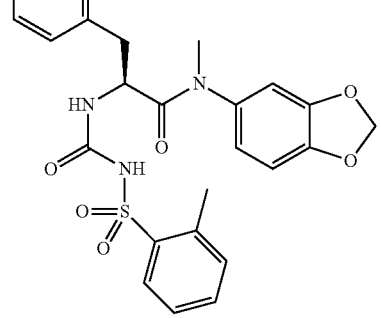 | B | |
| 71 | 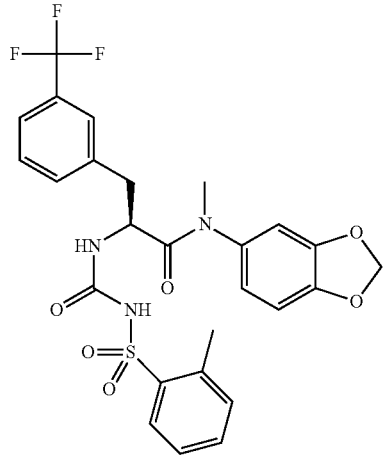 [SMILES: Cc1ccccc1S(=O)(=O)NC(=O)N[C@@H](Cc1cccc(C(F)(F)F)c1)C(=O)N(C)c1ccc2c(c1)OCO2] | B | |
| 72 | 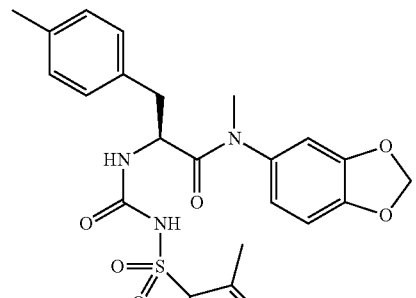 | B | 0.58 |

TABLE 1-continued

| Example | Structure | Activity | EC$_{50}$ (μM) |
|---------|-----------|----------|----------------|
| 73 | 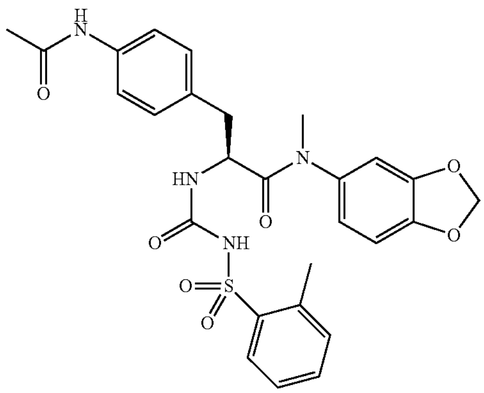 [SMILES: CC(=O)Nc1ccc(C[C@H](NC(=O)NS(=O)(=O)c2ccccc2C)C(=O)N(C)c2ccc3c(c2)OCO3)cc1] | | >100 |
| 74 | 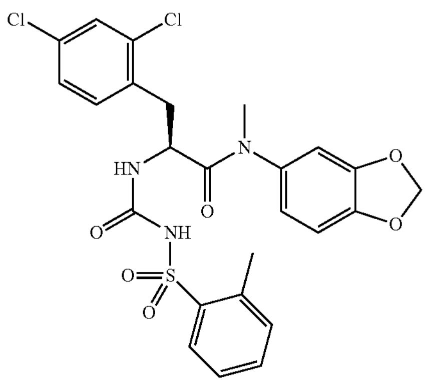 [SMILES: Cc1ccccc1S(=O)(=O)NC(=O)N[C@@H](Cc1ccc(Cl)cc1Cl)C(=O)N(C)c1ccc2c(c1)OCO2] | C | 3.88 |
| 75 | 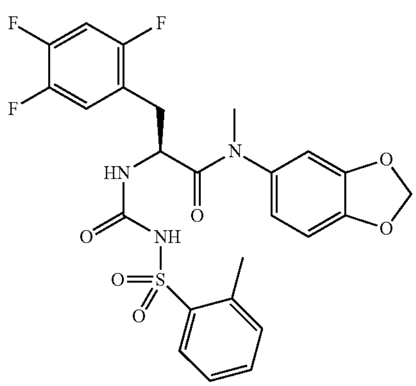 [SMILES: Cc1ccccc1S(=O)(=O)NC(=O)N[C@@H](Cc1cc(F)c(F)cc1F)C(=O)N(C)c1ccc2c(c1)OCO2] | B | 0.29 |
| 76 | 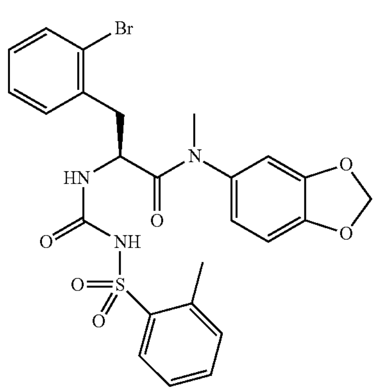 | C | |

TABLE 1-continued

| Example | Structure | Activity | EC$_{50}$ (μM) |
|---|---|---|---|
| 77 | 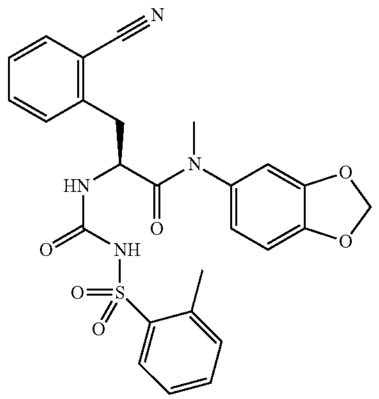 [SMILES: Cc1ccccc1S(=O)(=O)NC(=O)N[C@@H](Cc1ccccc1C#N)C(=O)N(C)c1ccc2c(c1)OCO2] | C | |
| 78 | 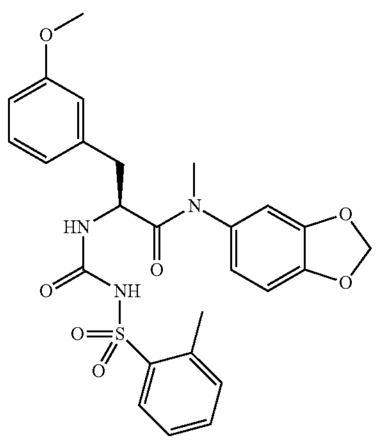 [SMILES: COc1cccc(C[C@H](NC(=O)NS(=O)(=O)c2ccccc2C)C(=O)N(C)c2ccc3c(c2)OCO3)c1] | B | |
| 79 | 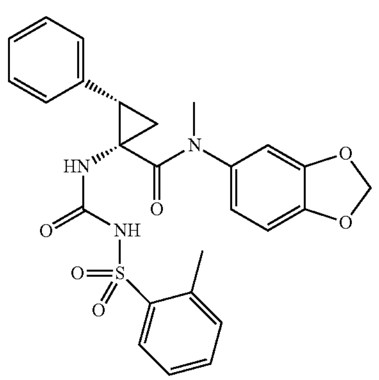 [SMILES: Cc1ccccc1S(=O)(=O)NC(=O)N[C@@]1(C(=O)N(C)c2ccc3c(c2)OCO3)C[C@H]1c1ccccc1] | D | |

TABLE 1-continued

| Example | Structure | Activity | EC$_{50}$ (μM) |
|---------|-----------|----------|----------------|
| 80 | 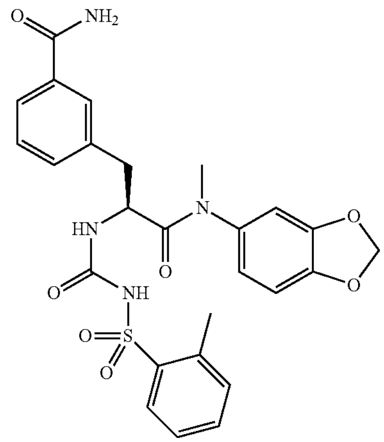 [SMILES: Cc1ccccc1S(=O)(=O)NC(=O)N[C@@H](Cc1cccc(C(N)=O)c1)C(=O)N(C)c1ccc2c(c1)OCO2] | | >100 |
| 81 | 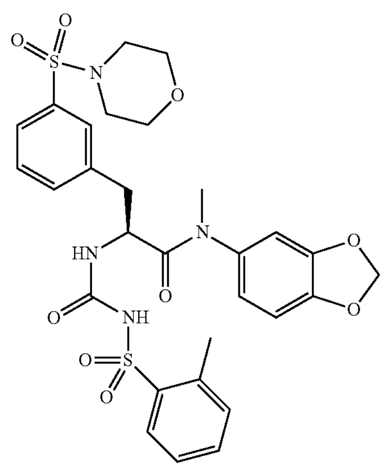 [SMILES: Cc1ccccc1S(=O)(=O)NC(=O)N[C@@H](Cc1cccc(S(=O)(=O)N2CCOCC2)c1)C(=O)N(C)c1ccc2c(c1)OCO2] | D | |
| 82 | 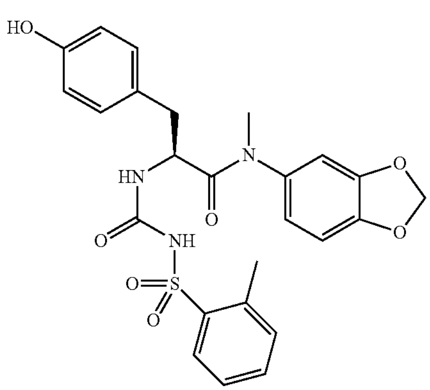 | C | |

TABLE 1-continued

| Example | Structure | Activity | EC$_{50}$ (μM) |
|---|---|---|---|
| 83 | 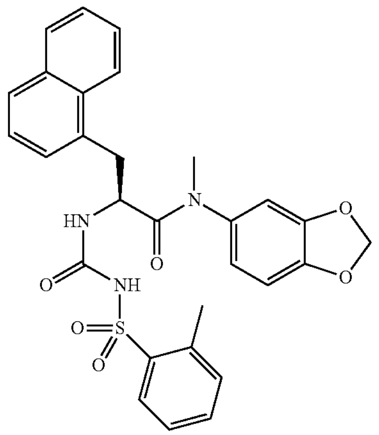 [SMILES: Cc1ccccc1S(=O)(=O)NC(=O)N[C@@H](Cc1cccc2ccccc12)C(=O)N(C)c1ccc2c(c1)OCO2] | C | 4.28 |
| 84 | 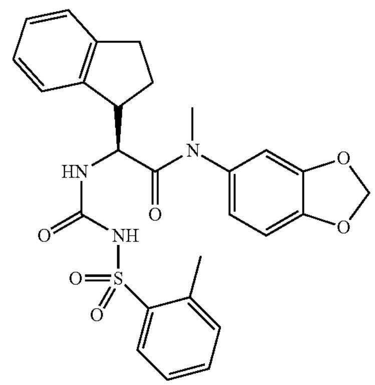 [SMILES: Cc1ccccc1S(=O)(=O)NC(=O)N[C@H](C(=O)N(C)c1ccc2c(c1)OCO2)C1CCc2ccccc21] | D | 22.1 |
| 85 | 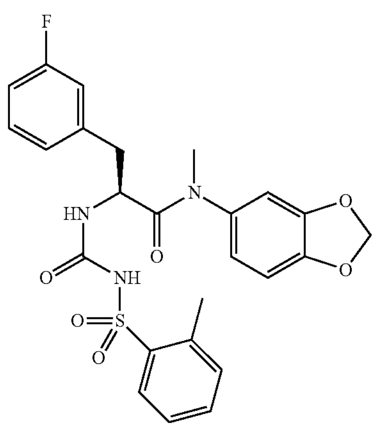 [SMILES: Cc1ccccc1S(=O)(=O)NC(=O)N[C@@H](Cc1cccc(F)c1)C(=O)N(C)c1ccc2c(c1)OCO2] | B | |
| 86 | 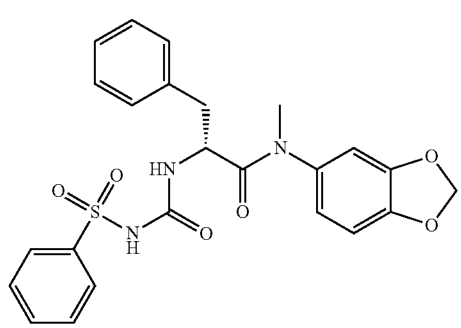 [SMILES: CN(C(=O)[C@@H](Cc1ccccc1)NC(=O)NS(=O)(=O)c1ccccc1)c1ccc2c(c1)OCO2] | D | |

TABLE 1-continued

| Example | Structure | Activity | EC$_{50}$ (μM) |
|---|---|---|---|
| 87 | 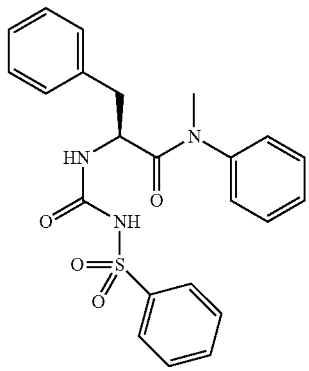 [SMILES: CN(C(=O)[C@H](Cc1ccccc1)NC(=O)NS(=O)(=O)c1ccccc1)c1ccccc1] | B | |
| 88 | 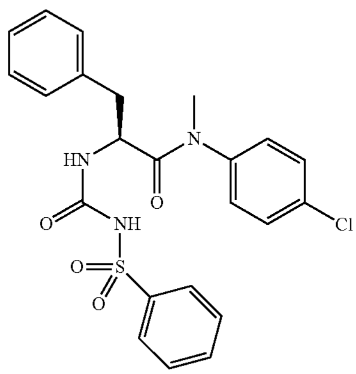 [SMILES: CN(C(=O)[C@H](Cc1ccccc1)NC(=O)NS(=O)(=O)c1ccccc1)c1ccc(Cl)cc1] | B | 0.45 |
| 89 | 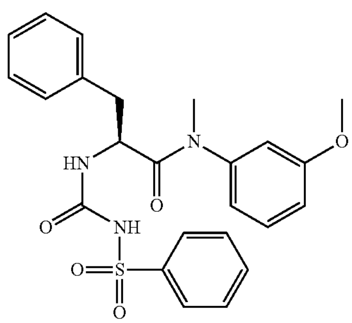 [SMILES: COc1cccc(N(C)C(=O)[C@H](Cc2ccccc2)NC(=O)NS(=O)(=O)c2ccccc2)c1] | B | |
| 90 | 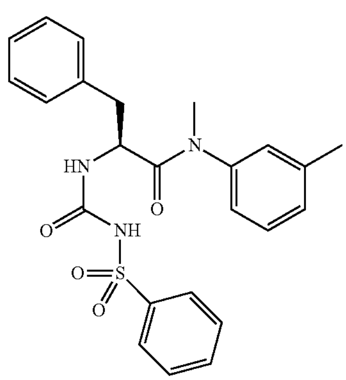 [SMILES: Cc1cccc(N(C)C(=O)[C@H](Cc2ccccc2)NC(=O)NS(=O)(=O)c2ccccc2)c1] | B | |

TABLE 1-continued

| Example | Structure | Activity | EC$_{50}$ (μM) |
|---------|-----------|----------|----------------|
| 91 | 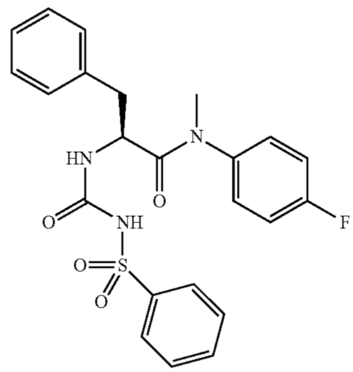 [SMILES: CN(C(=O)[C@H](Cc1ccccc1)NC(=O)NS(=O)(=O)c1ccccc1)c1ccc(F)cc1] | B | |
| 92 | 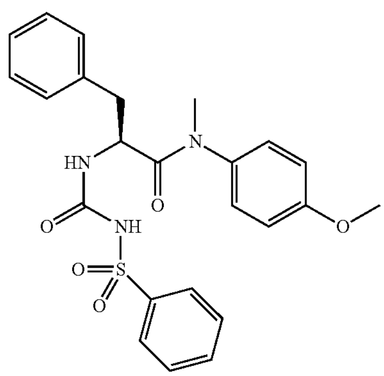 [SMILES: COc1ccc(N(C)C(=O)[C@H](Cc2ccccc2)NC(=O)NS(=O)(=O)c2ccccc2)cc1] | B | |
| 93 | 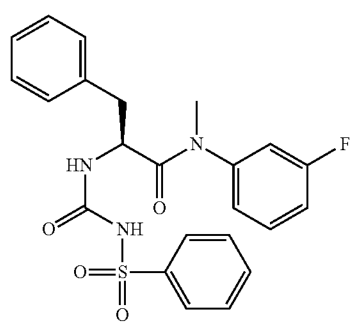 [SMILES: CN(C(=O)[C@H](Cc1ccccc1)NC(=O)NS(=O)(=O)c1ccccc1)c1cccc(F)c1] | C | 1.59 |
| 94 | 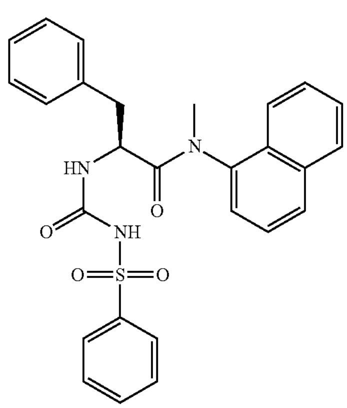 [SMILES: CN(C(=O)[C@H](Cc1ccccc1)NC(=O)NS(=O)(=O)c1ccccc1)c1cccc2ccccc12] | D | |

TABLE 1-continued

| Example | Structure | Activity | EC$_{50}$ (μM) |
|---|---|---|---|
| 95 | 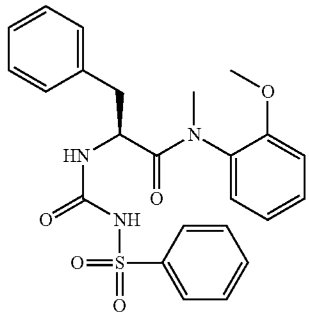 [SMILES: COc1ccccc1N(C)C(=O)[C@H](Cc1ccccc1)NC(=O)NS(=O)(=O)c1ccccc1] | C | |
| 96 | 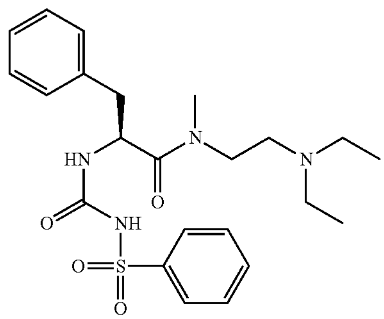 [SMILES: CCN(CC)CCN(C)C(=O)[C@H](Cc1ccccc1)NC(=O)NS(=O)(=O)c1ccccc1] | | >100 |
| 97 | 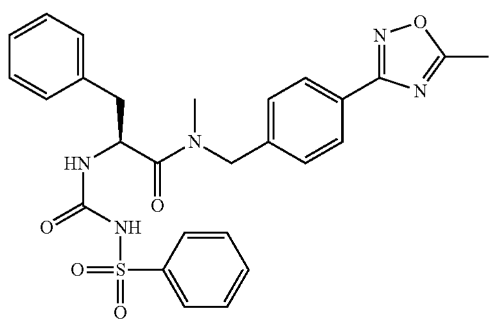 [SMILES: Cc1nc(-c2ccc(CN(C)C(=O)[C@H](Cc3ccccc3)NC(=O)NS(=O)(=O)c3ccccc3)cc2)no1] | C | |
| 98 | 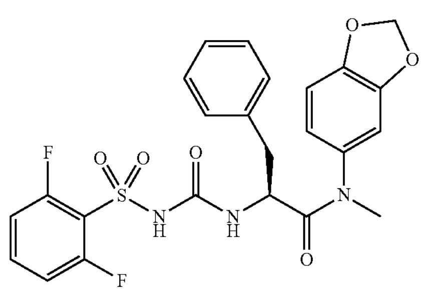 [SMILES: CN(C(=O)[C@H](Cc1ccccc1)NC(=O)NS(=O)(=O)c1c(F)cccc1F)c1ccc2c(c1)OCO2] | A | 0.09 |
| 99 | 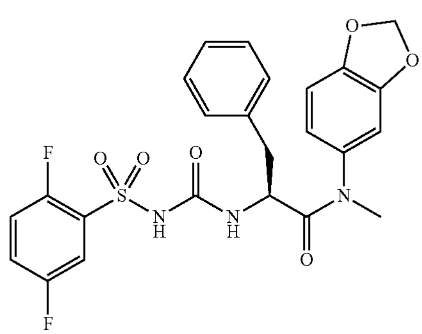 [SMILES: CN(C(=O)[C@H](Cc1ccccc1)NC(=O)NS(=O)(=O)c1cc(F)ccc1F)c1ccc2c(c1)OCO2] | B | 0.15 |

TABLE 1-continued

| Example | Structure | Activity | EC$_{50}$ (μM) |
|---------|-----------|----------|----------------|
| 100 | 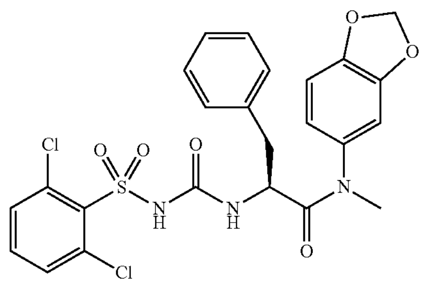 [SMILES: CN(C(=O)[C@H](Cc1ccccc1)NC(=O)NS(=O)(=O)c1c(Cl)cccc1Cl)c1ccc2c(c1)OCO2] | A | |
| 101 | 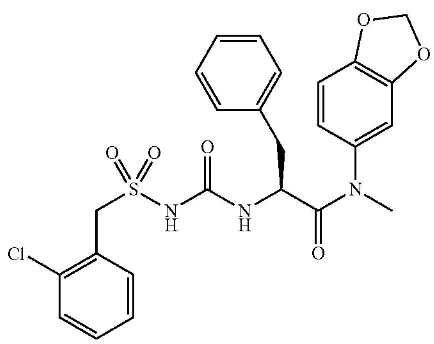 [SMILES: CN(C(=O)[C@H](Cc1ccccc1)NC(=O)NS(=O)(=O)Cc1ccccc1Cl)c1ccc2c(c1)OCO2] | B | |
| 102 | 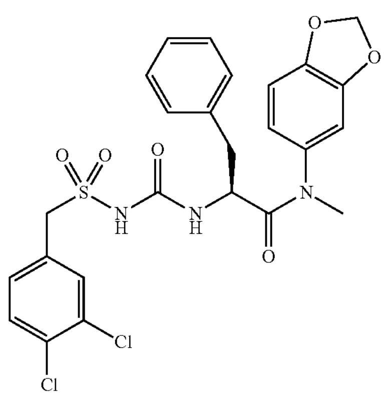 [SMILES: CN(C(=O)[C@H](Cc1ccccc1)NC(=O)NS(=O)(=O)Cc1ccc(Cl)c(Cl)c1)c1ccc2c(c1)OCO2] | B | |
| 103 | 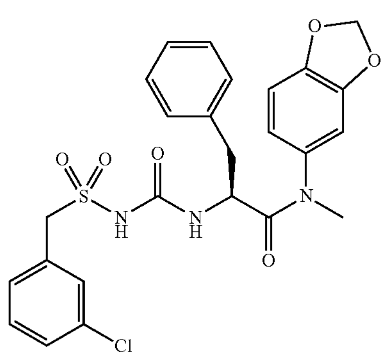 [SMILES: CN(C(=O)[C@H](Cc1ccccc1)NC(=O)NS(=O)(=O)Cc1cccc(Cl)c1)c1ccc2c(c1)OCO2] | B | |

TABLE 1-continued

| Example | Structure | Activity | EC$_{50}$ (μM) |
|---------|-----------|----------|----------------|
| 104 | 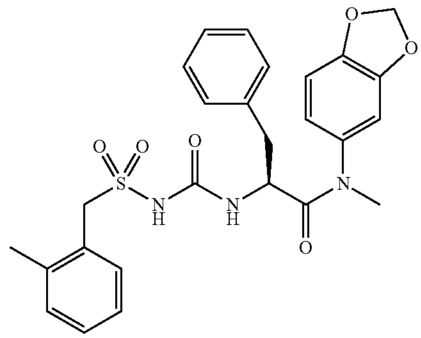 [SMILES: Cc1ccccc1CS(=O)(=O)NC(=O)N[C@@H](Cc1ccccc1)C(=O)N(C)c1ccc2c(c1)OCO2] | B | 0.62 |
| 105 | 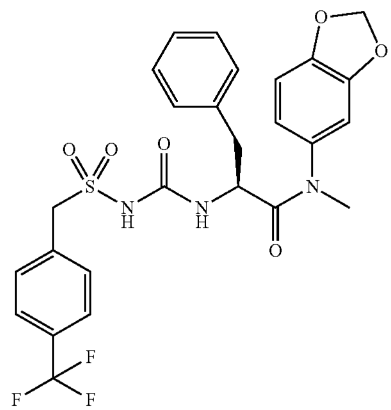 [SMILES: CN(C(=O)[C@H](Cc1ccccc1)NC(=O)NS(=O)(=O)Cc1ccc(C(F)(F)F)cc1)c1ccc2c(c1)OCO2] | B | |
| 106 | 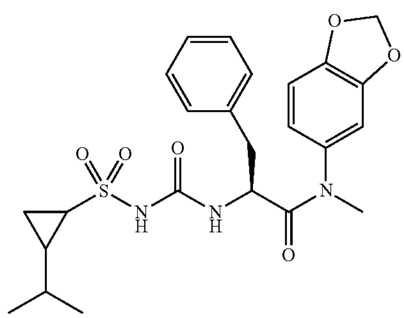 [SMILES: CC(C)C1CC1S(=O)(=O)NC(=O)N[C@@H](Cc1ccccc1)C(=O)N(C)c1ccc2c(c1)OCO2] | B | |
| 107 | 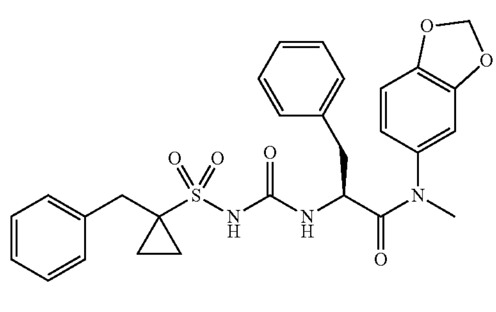 [SMILES: CN(C(=O)[C@H](Cc1ccccc1)NC(=O)NS(=O)(=O)C1(Cc2ccccc2)CC1)c1ccc2c(c1)OCO2] | C | |

TABLE 1-continued

| Example | Structure | Activity | EC₅₀ (μM) |
|---|---|---|---|
| 108 | 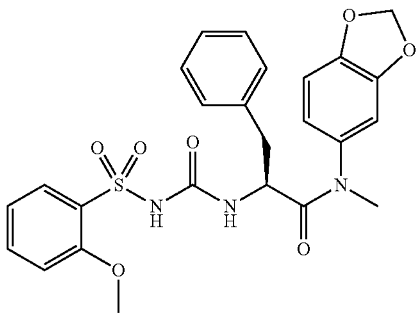 [SMILES: COc1ccccc1S(=O)(=O)NC(=O)N[C@@H](Cc1ccccc1)C(=O)N(C)c1ccc2c(c1)OCO2] | B | |
| 109 | 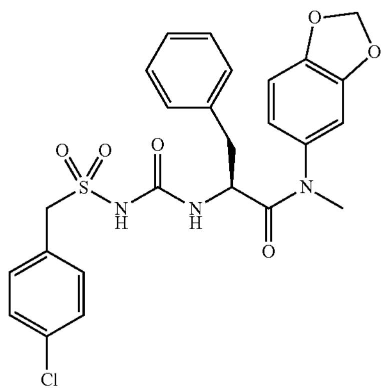 [SMILES: CN(C(=O)[C@H](Cc1ccccc1)NC(=O)NS(=O)(=O)Cc1ccc(Cl)cc1)c1ccc2c(c1)OCO2] | B | |
| 110 | 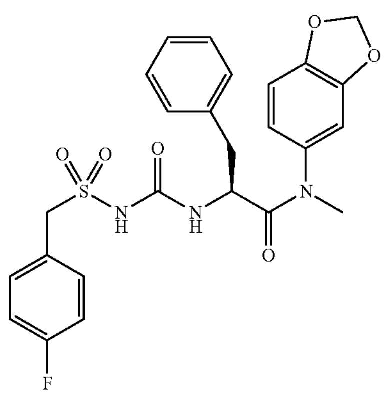 | B | 0.16 |
| 111 | 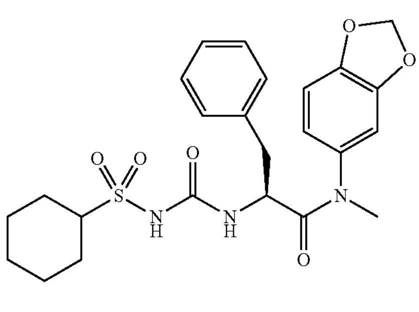 [SMILES: CN(C(=O)[C@H](Cc1ccccc1)NC(=O)NS(=O)(=O)C1CCCCC1)c1ccc2c(c1)OCO2] | B | |

TABLE 1-continued

| Example | Structure | Activity | EC$_{50}$ (μM) |
|---------|-----------|----------|----------------|
| 112 | 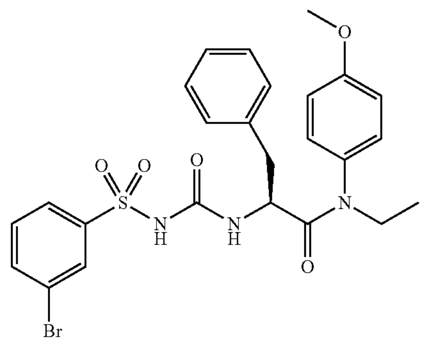 [SMILES: CCN(C(=O)[C@H](Cc1ccccc1)NC(=O)NS(=O)(=O)c1cccc(Br)c1)c1ccc(OC)cc1] | A | |
| 113 | 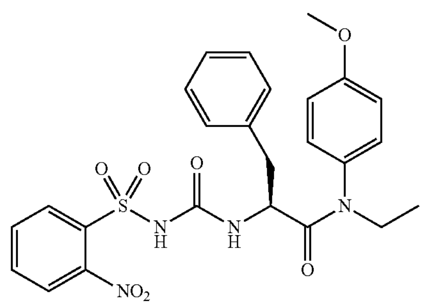 [SMILES: CCN(C(=O)[C@H](Cc1ccccc1)NC(=O)NS(=O)(=O)c1ccccc1[N+](=O)[O-])c1ccc(OC)cc1] | A | |
| 114 | 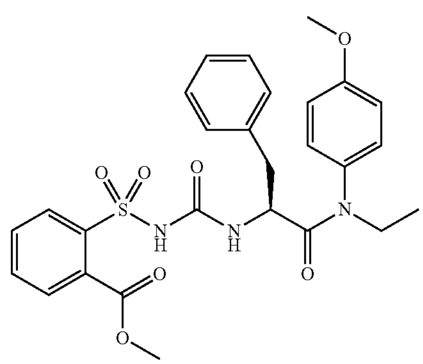 [SMILES: CCN(C(=O)[C@H](Cc1ccccc1)NC(=O)NS(=O)(=O)c1ccccc1C(=O)OC)c1ccc(OC)cc1] | C | 1.06 |
| 115 | 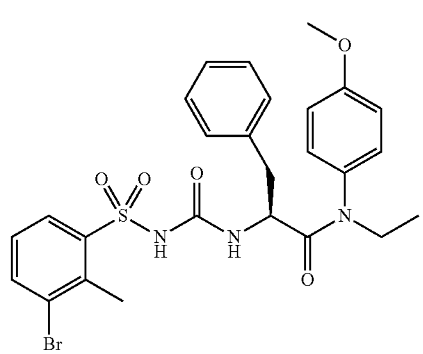 [SMILES: CCN(C(=O)[C@H](Cc1ccccc1)NC(=O)NS(=O)(=O)c1cccc(Br)c1C)c1ccc(OC)cc1] | A | |

TABLE 1-continued

| Example | Structure | Activity | EC$_{50}$ (μM) |
|---------|-----------|----------|----------------|
| 116 | 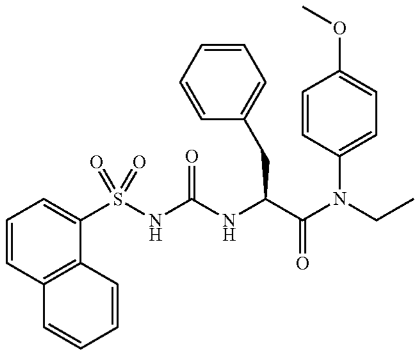 [SMILES: CCN(C(=O)[C@H](Cc1ccccc1)NC(=O)NS(=O)(=O)c1cccc2ccccc12)c1ccc(OC)cc1] | A | |
| 117 | 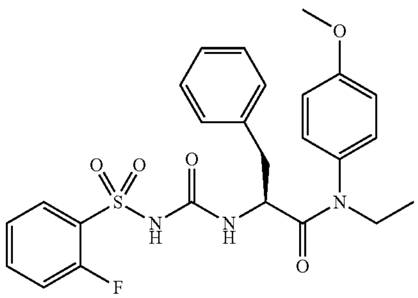 [SMILES: CCN(C(=O)[C@H](Cc1ccccc1)NC(=O)NS(=O)(=O)c1ccccc1F)c1ccc(OC)cc1] | A | |
| 118 | 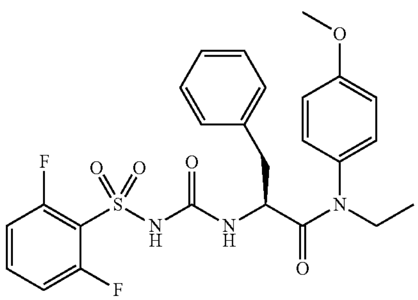 | A | 0.04 |
| 119 | 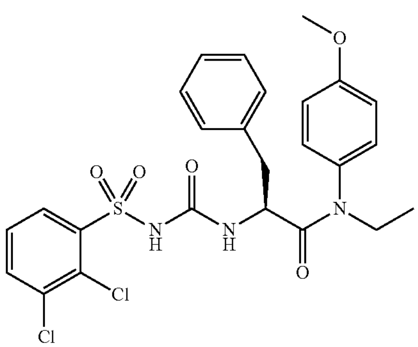 [SMILES: CCN(C(=O)[C@H](Cc1ccccc1)NC(=O)NS(=O)(=O)c1cccc(Cl)c1Cl)c1ccc(OC)cc1] | A | |
| 120 | 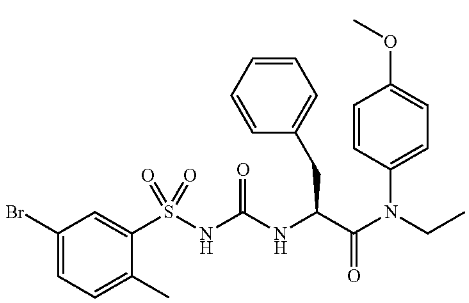 [SMILES: CCN(C(=O)[C@H](Cc1ccccc1)NC(=O)NS(=O)(=O)c1cc(Br)ccc1C)c1ccc(OC)cc1] | B | |

TABLE 1-continued

| Example | Structure | Activity | EC$_{50}$ (μM) |
|---------|-----------|----------|----------------|
| 121 | 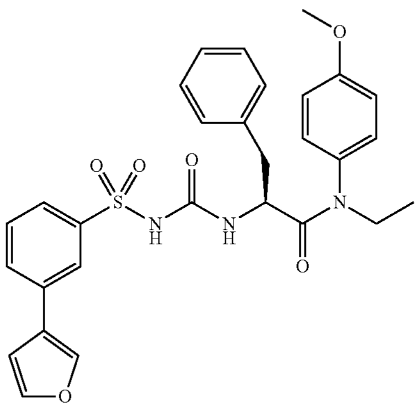 [SMILES: CCN(C(=O)[C@H](Cc1ccccc1)NC(=O)NS(=O)(=O)c1cccc(-c2ccoc2)c1)c1ccc(OC)cc1] | A | |
| 122 | 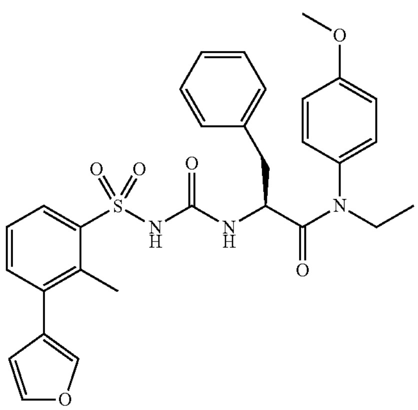 [SMILES: CCN(C(=O)[C@H](Cc1ccccc1)NC(=O)NS(=O)(=O)c1cccc(-c2ccoc2)c1C)c1ccc(OC)cc1] | B | |
| 123 | 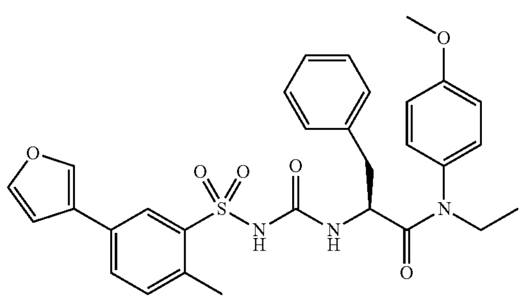 [SMILES: CCN(C(=O)[C@H](Cc1ccccc1)NC(=O)NS(=O)(=O)c1cc(-c2ccoc2)ccc1C)c1ccc(OC)cc1] | B | 0.66 |
| 124 | 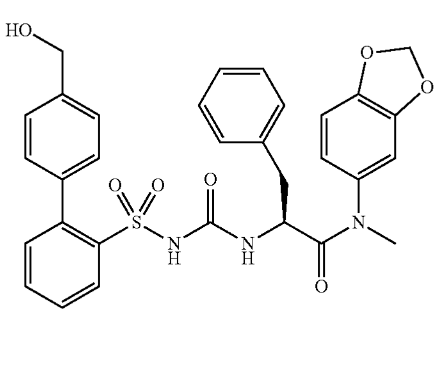 [SMILES: CN(C(=O)[C@H](Cc1ccccc1)NC(=O)NS(=O)(=O)c1ccccc1-c1ccc(CO)cc1)c1ccc2c(c1)OCO2] | C | |

TABLE 1-continued

| Example | Structure | Activity | EC$_{50}$ (μM) |
|---|---|---|---|
| 125 | 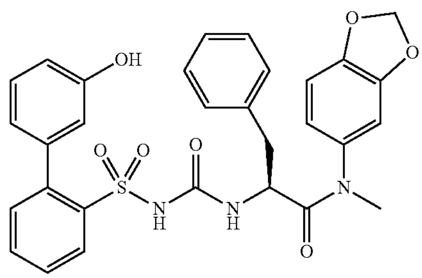 [SMILES: CN(C(=O)[C@H](Cc1ccccc1)NC(=O)NS(=O)(=O)c1ccccc1-c1cccc(O)c1)c1ccc2c(c1)OCO2] | C | |
| 126 | 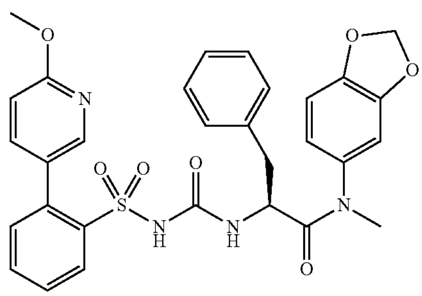 [SMILES: COc1ccc(-c2ccccc2S(=O)(=O)NC(=O)N[C@@H](Cc2ccccc2)C(=O)N(C)c2ccc3c(c2)OCO3)cn1] | D | |
| 127 | 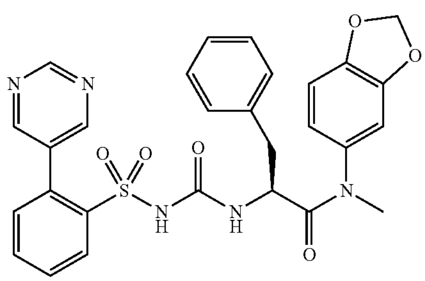 [SMILES: CN(C(=O)[C@H](Cc1ccccc1)NC(=O)NS(=O)(=O)c1ccccc1-c1cncnc1)c1ccc2c(c1)OCO2] | D | 21.74 |
| 128 | 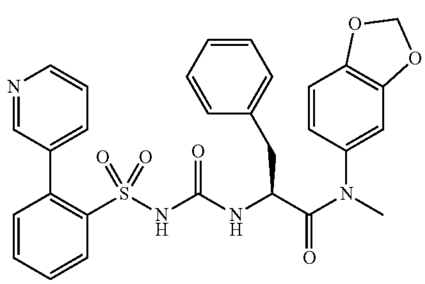 [SMILES: CN(C(=O)[C@H](Cc1ccccc1)NC(=O)NS(=O)(=O)c1ccccc1-c1cccnc1)c1ccc2c(c1)OCO2] | C | |
| 129 | 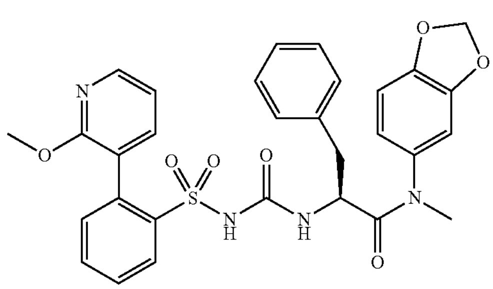 [SMILES: COc1ncccc1-c1ccccc1S(=O)(=O)NC(=O)N[C@@H](Cc1ccccc1)C(=O)N(C)c1ccc2c(c1)OCO2] | C | 5.52 |

TABLE 1-continued
| Example | Structure | Activity | EC$_{50}$ (µM) |
|---|---|---|---|
| 130 | 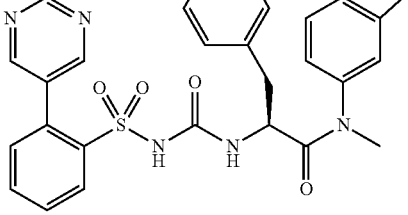 | C | |
| 131 | 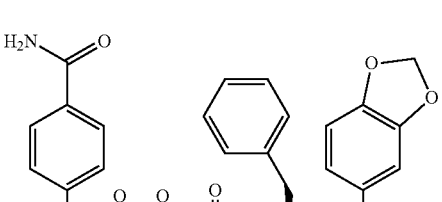 | D | |
| 132 | 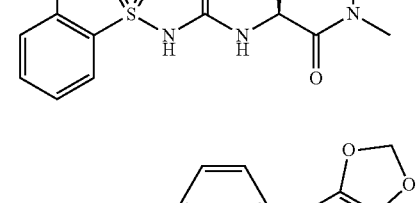 | D | |
| 133 | 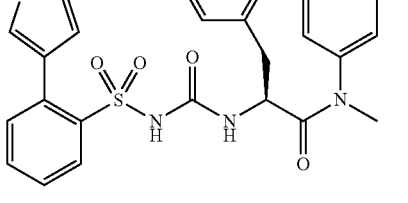 | B | |
| 134 | 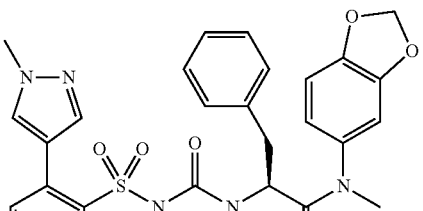 | C | |

TABLE 1-continued

| Example | Structure | Activity | EC$_{50}$ (μM) |
|---------|-----------|----------|----------------|
| 135 | 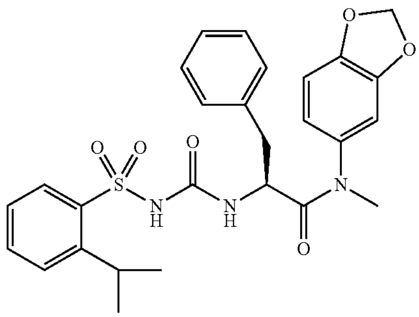 | B | |
| 136 | 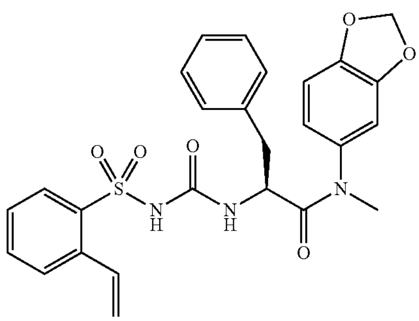 | A | |
| 137 | 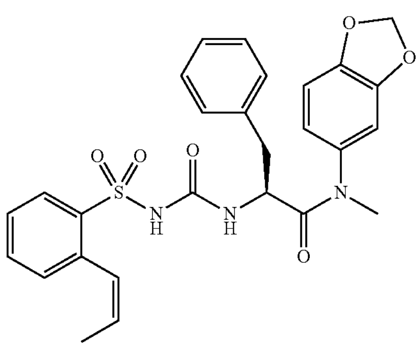 [SMILES: C/C=C\c1ccccc1S(=O)(=O)NC(=O)N[C@@H](Cc1ccccc1)C(=O)N(C)c1ccc2c(c1)OCO2] | B | |
| 138 | 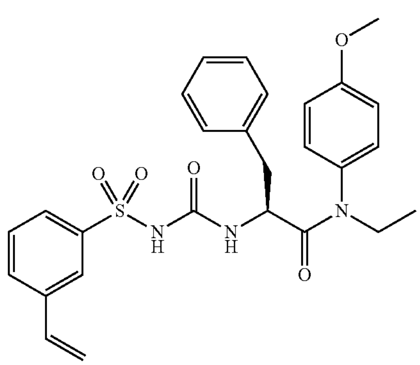 [SMILES: C=Cc1cccc(S(=O)(=O)NC(=O)N[C@@H](Cc2ccccc2)C(=O)N(CC)c2ccc(OC)cc2)c1] | A | 0.05 |

TABLE 1-continued

| Example | Structure | Activity | EC$_{50}$ (μM) |
|---|---|---|---|
| 139 | 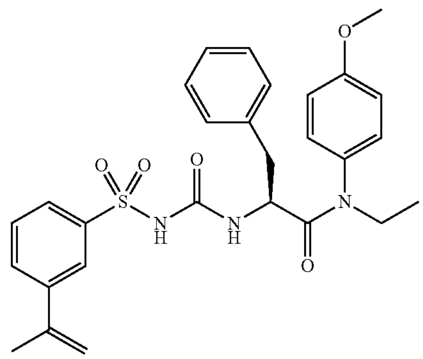 [SMILES: C=C(C)c1cccc(S(=O)(=O)NC(=O)N[C@@H](Cc2ccccc2)C(=O)N(CC)c2ccc(OC)cc2)c1] | A | |
| 140 | 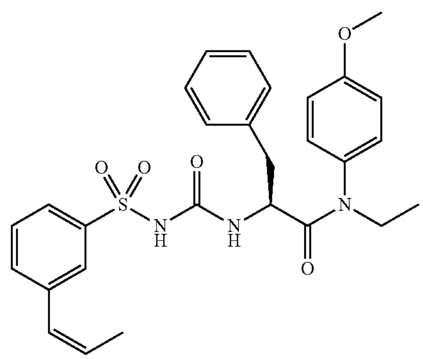 [SMILES: C/C=C\c1cccc(S(=O)(=O)NC(=O)N[C@@H](Cc2ccccc2)C(=O)N(CC)c2ccc(OC)cc2)c1] | A | |
| 141 | 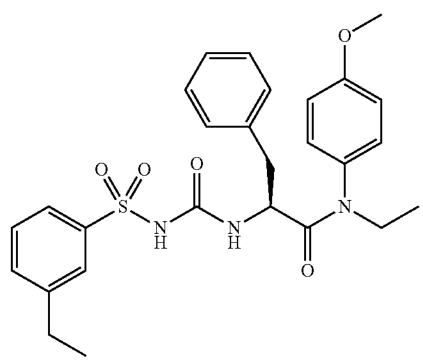 [SMILES: CCc1cccc(S(=O)(=O)NC(=O)N[C@@H](Cc2ccccc2)C(=O)N(CC)c2ccc(OC)cc2)c1] | A | |
| 142 | 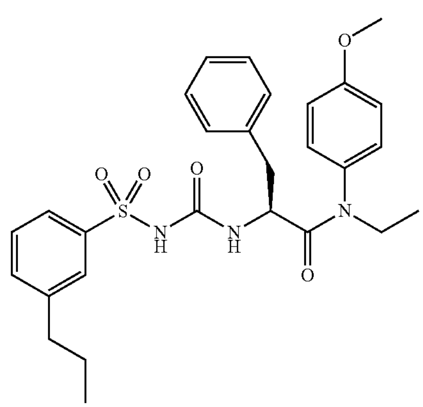 [SMILES: CCCc1cccc(S(=O)(=O)NC(=O)N[C@@H](Cc2ccccc2)C(=O)N(CC)c2ccc(OC)cc2)c1] | A | 0.06 |

TABLE 1-continued
| Example | Structure | Activity | EC$_{50}$ (µM) |
|---|---|---|---|
| 143 | 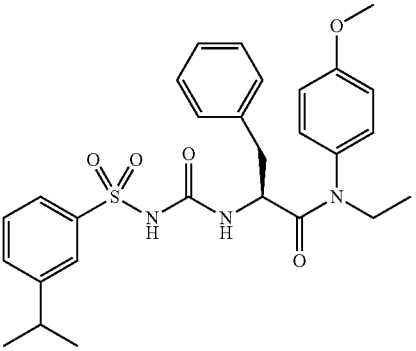 [SMILES: CCN(C(=O)[C@H](Cc1ccccc1)NC(=O)NS(=O)(=O)c1cccc(C(C)C)c1)c1ccc(OC)cc1] | A | |
| 144 | 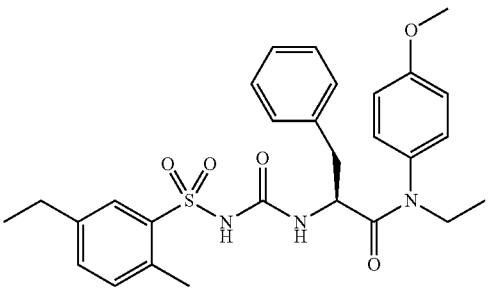 [SMILES: CCc1ccc(C)c(S(=O)(=O)NC(=O)N[C@@H](Cc2ccccc2)C(=O)N(CC)c2ccc(OC)cc2)c1] | B | 0.62 |
| 145 | 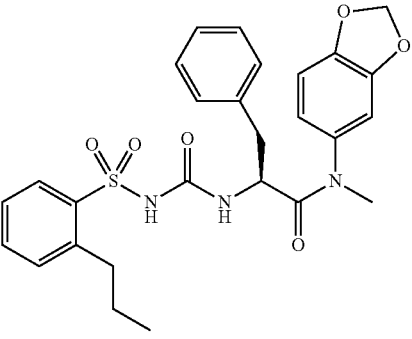 [SMILES: CCCc1ccccc1S(=O)(=O)NC(=O)N[C@@H](Cc1ccccc1)C(=O)N(C)c1ccc2c(c1)OCO2] | B | |
| 146 | 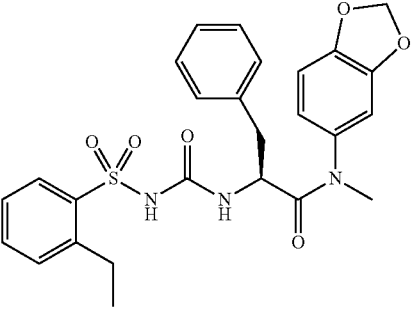 | A | |

TABLE 1-continued

| Example | Structure | Activity | EC$_{50}$ (μM) |
|---------|-----------|----------|----------------|
| 147 | 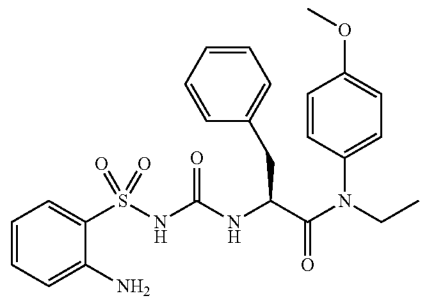 | A | |
| 148 | 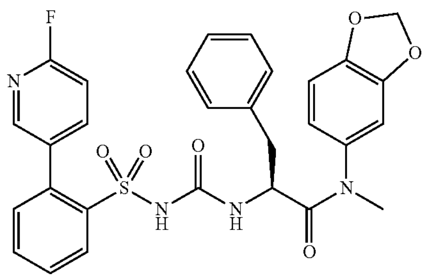 [SMILES: CN(C(=O)[C@H](Cc1ccccc1)NC(=O)NS(=O)(=O)c1ccccc1-c1ccc(F)nc1)c1ccc2c(c1)OCO2] | C | |
| 149 | 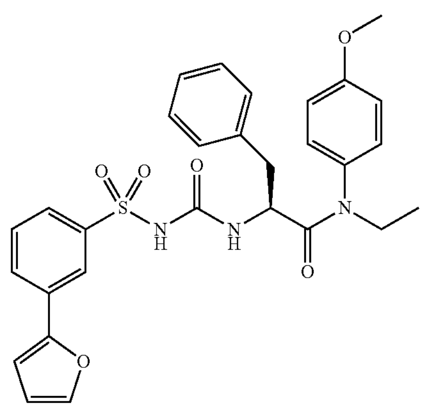 [SMILES: CCN(C(=O)[C@H](Cc1ccccc1)NC(=O)NS(=O)(=O)c1cccc(-c2ccco2)c1)c1ccc(OC)cc1] | B | |
| 150 | 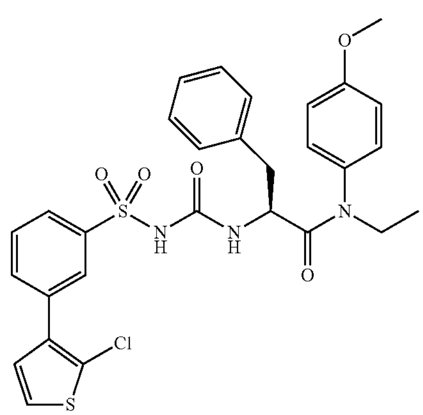 [SMILES: CCN(C(=O)[C@H](Cc1ccccc1)NC(=O)NS(=O)(=O)c1cccc(-c2ccsc2Cl)c1)c1ccc(OC)cc1] | B | |

TABLE 1-continued

| Example | Structure | Activity | EC$_{50}$ (μM) |
|---------|-----------|----------|----------------|
| 151 | 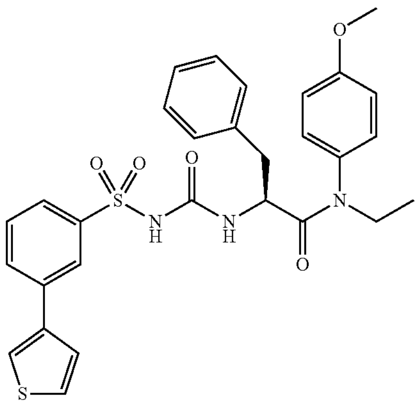 [SMILES: CCN(C(=O)[C@H](Cc1ccccc1)NC(=O)NS(=O)(=O)c1cccc(-c2ccsc2)c1)c1ccc(OC)cc1] | B | 0.11 |
| 152 | 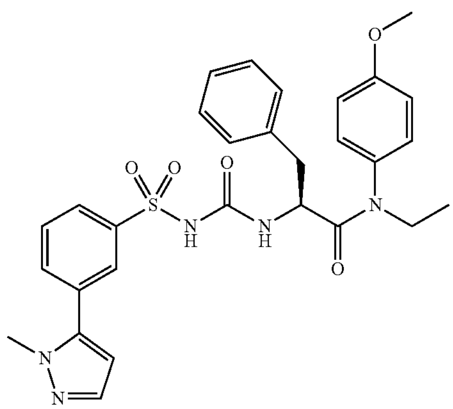 [SMILES: CCN(C(=O)[C@H](Cc1ccccc1)NC(=O)NS(=O)(=O)c1cccc(-c2ccnn2C)c1)c1ccc(OC)cc1] | A | 0.09 |
| 153 | 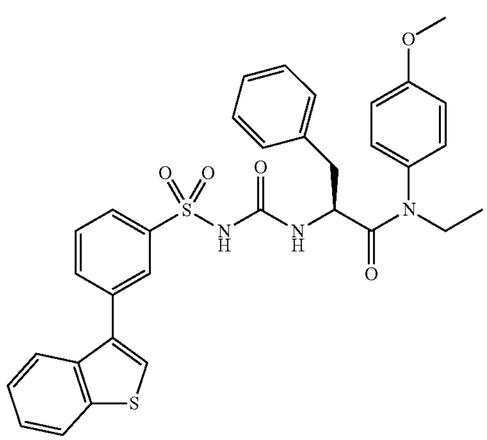 [SMILES: CCN(C(=O)[C@H](Cc1ccccc1)NC(=O)NS(=O)(=O)c1cccc(-c2csc3ccccc23)c1)c1ccc(OC)cc1] | B | |

TABLE 1-continued

| Example | Structure | Activity | EC$_{50}$ (μM) |
|---------|-----------|----------|----------------|
| 154 | 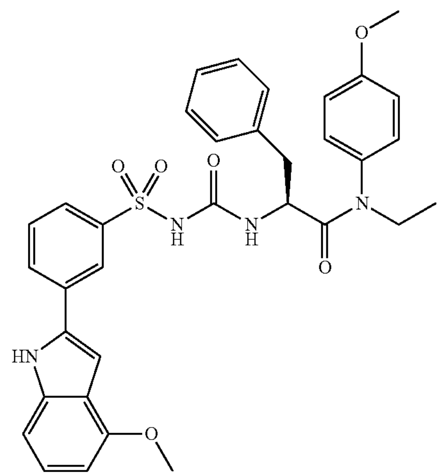 [SMILES: CCN(C(=O)[C@H](Cc1ccccc1)NC(=O)NS(=O)(=O)c1cccc(-c2cc3c(OC)cccc3[nH]2)c1)c1ccc(OC)cc1] | B | 0.67 |
| 155 | 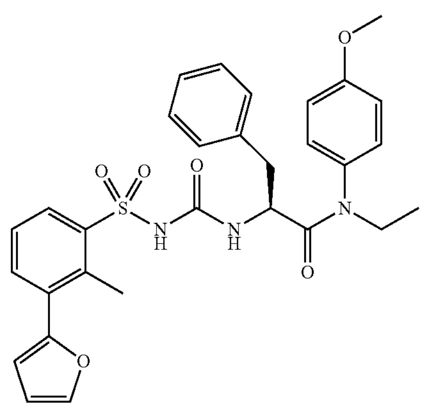 [SMILES: CCN(C(=O)[C@H](Cc1ccccc1)NC(=O)NS(=O)(=O)c1cccc(-c2ccco2)c1C)c1ccc(OC)cc1] | C | |
| 156 | 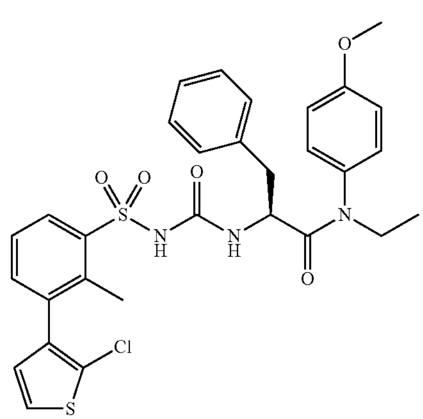 [SMILES: CCN(C(=O)[C@H](Cc1ccccc1)NC(=O)NS(=O)(=O)c1cccc(-c2ccsc2Cl)c1C)c1ccc(OC)cc1] | B | |

TABLE 1-continued

| Example | Structure | Activity | EC$_{50}$ (μM) |
|---------|-----------|----------|----------------|
| 157 | 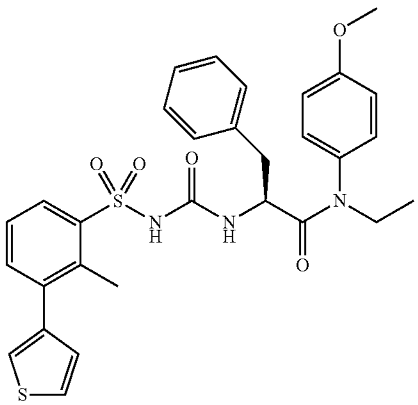 [SMILES: CCN(C(=O)[C@H](Cc1ccccc1)NC(=O)NS(=O)(=O)c1cccc(-c2ccsc2)c1C)c1ccc(OC)cc1] | B | |
| 158 | 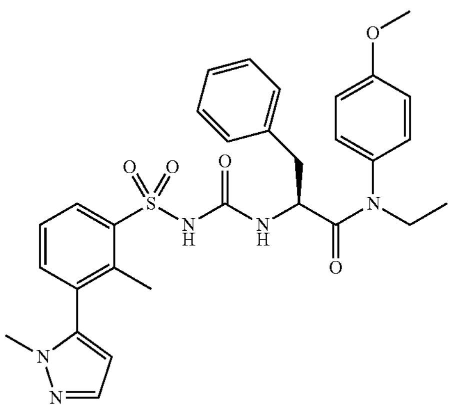 [SMILES: CCN(C(=O)[C@H](Cc1ccccc1)NC(=O)NS(=O)(=O)c1cccc(-c2ccnn2C)c1C)c1ccc(OC)cc1] | B | 0.23 |
| 159 | 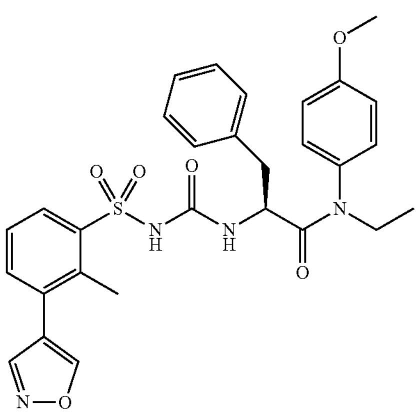 [SMILES: CCN(C(=O)[C@H](Cc1ccccc1)NC(=O)NS(=O)(=O)c1cccc(-c2cnoc2)c1C)c1ccc(OC)cc1] | B | |

TABLE 1-continued

| Example | Structure | Activity | EC$_{50}$ (μM) |
|---|---|---|---|
| 160 | 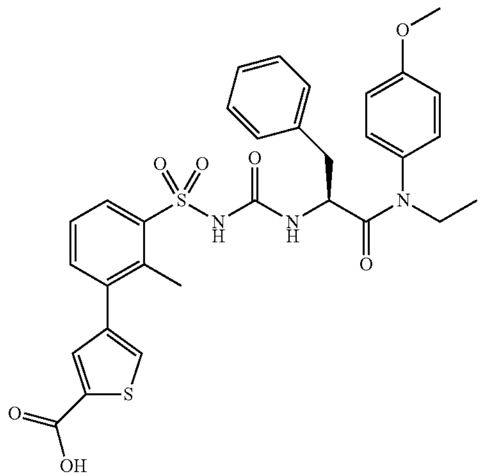 [SMILES: CCN(C(=O)[C@H](Cc1ccccc1)NC(=O)NS(=O)(=O)c1cccc(-c2csc(C(=O)O)c2)c1C)c1ccc(OC)cc1] | C | 5.64 |
| 161 | 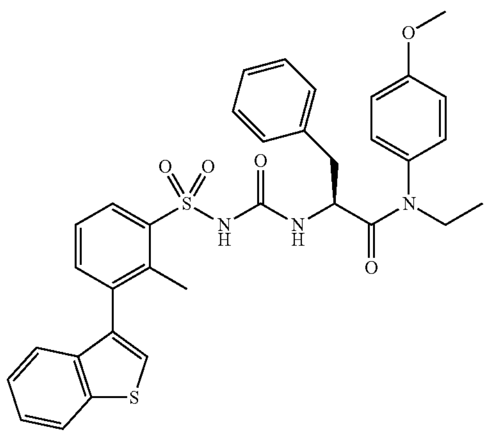 [SMILES: CCN(C(=O)[C@H](Cc1ccccc1)NC(=O)NS(=O)(=O)c1cccc(-c2csc3ccccc23)c1C)c1ccc(OC)cc1] | C | |
| 162 | 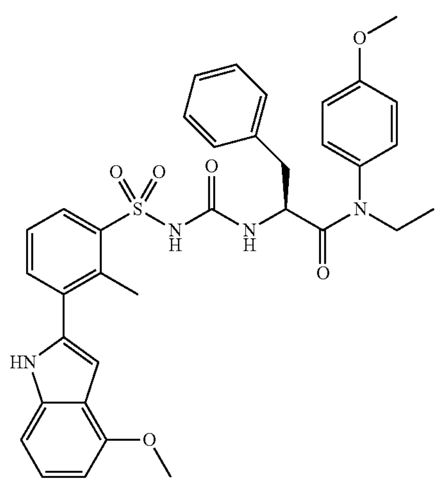 [SMILES: CCN(C(=O)[C@H](Cc1ccccc1)NC(=O)NS(=O)(=O)c1cccc(-c2cc3c(OC)cccc3[nH]2)c1C)c1ccc(OC)cc1] | C | |

TABLE 1-continued

| Example | Structure | Activity | EC$_{50}$ (μM) |
|---|---|---|---|
| 163 | 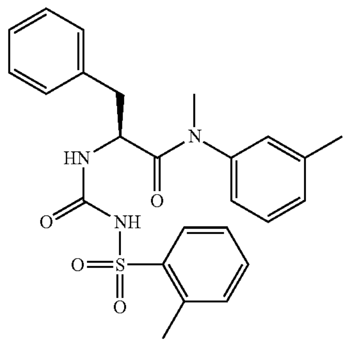 [SMILES: Cc1cccc(N(C)C(=O)[C@H](Cc2ccccc2)NC(=O)NS(=O)(=O)c2ccccc2C)c1] | B | |
| 164 | 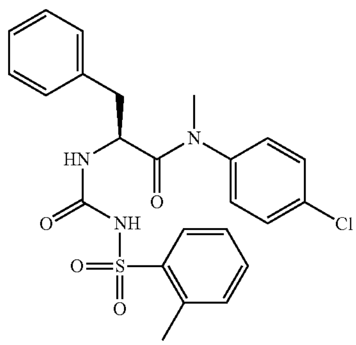 [SMILES: Cc1ccccc1S(=O)(=O)NC(=O)N[C@@H](Cc1ccccc1)C(=O)N(C)c1ccc(Cl)cc1] | B | |
| 165 | 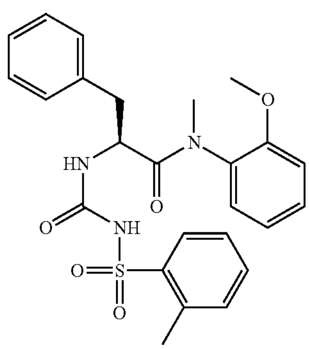 [SMILES: COc1ccccc1N(C)C(=O)[C@H](Cc1ccccc1)NC(=O)NS(=O)(=O)c1ccccc1C] | C | |
| 166 | 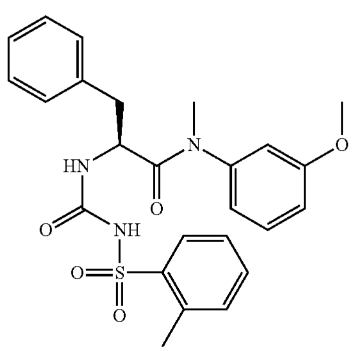 [SMILES: COc1cccc(N(C)C(=O)[C@H](Cc2ccccc2)NC(=O)NS(=O)(=O)c2ccccc2C)c1] | B | 0.24 |

TABLE 1-continued

| Example | Structure | Activity | EC$_{50}$ (μM) |
|---|---|---|---|
| 167 | 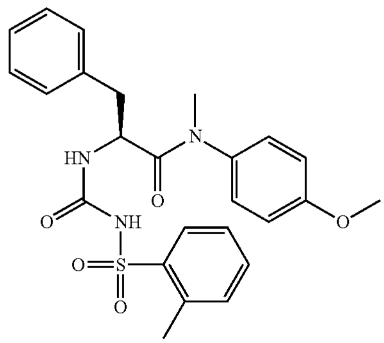 [SMILES: COc1ccc(N(C)C(=O)[C@H](Cc2ccccc2)NC(=O)NS(=O)(=O)c2ccccc2C)cc1] | A | |
| 168 | 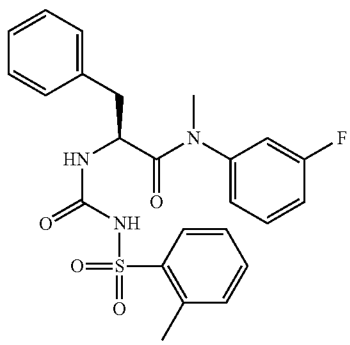 [SMILES: Cc1ccccc1S(=O)(=O)NC(=O)N[C@@H](Cc1ccccc1)C(=O)N(C)c1cccc(F)c1] | B | |
| 169 | 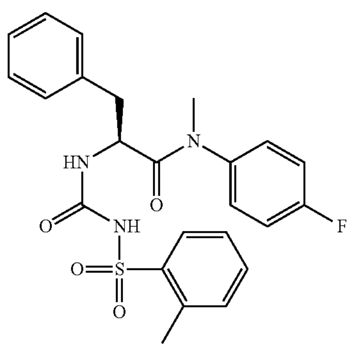 [SMILES: Cc1ccccc1S(=O)(=O)NC(=O)N[C@@H](Cc1ccccc1)C(=O)N(C)c1ccc(F)cc1] | B | |
| 170 | 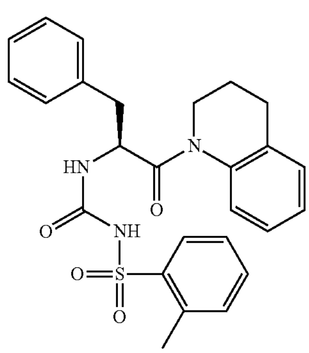 [SMILES: Cc1ccccc1S(=O)(=O)NC(=O)N[C@@H](Cc1ccccc1)C(=O)N1CCCc2ccccc21] | C | |

TABLE 1-continued

| Example | Structure | Activity | EC$_{50}$ (μM) |
|---|---|---|---|
| 171 | 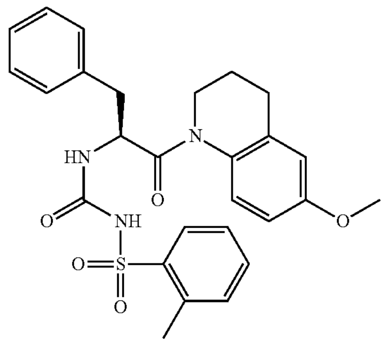 | B | |
| 172 | 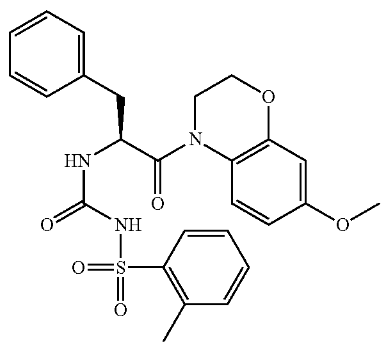 | B | 0.27 |
| 173 | 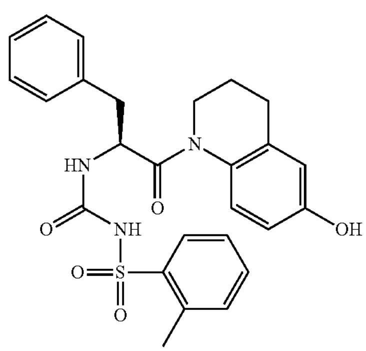 [SMILES: Cc1ccccc1S(=O)(=O)NC(=O)N[C@@H](Cc1ccccc1)C(=O)N1CCCc2cc(O)ccc21] | B | |
| 174 | 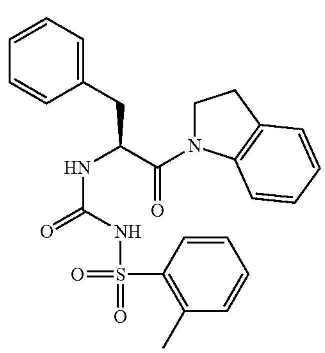 [SMILES: Cc1ccccc1S(=O)(=O)NC(=O)N[C@@H](Cc1ccccc1)C(=O)N1CCc2ccccc21] | C | 3.84 |

TABLE 1-continued

| Example | Structure | Activity | EC$_{50}$ (μM) |
|---|---|---|---|
| 175 | 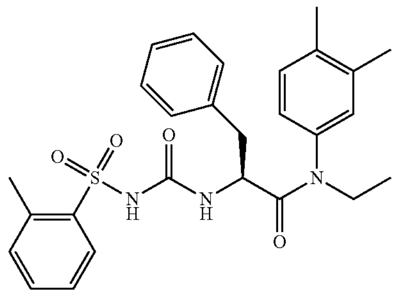 [SMILES: CCN(C(=O)[C@H](Cc1ccccc1)NC(=O)NS(=O)(=O)c1ccccc1C)c1ccc(C)c(C)c1] | A | |
| 176 | 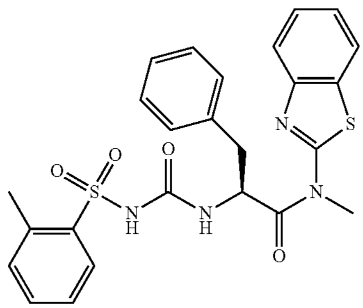 [SMILES: Cc1ccccc1S(=O)(=O)NC(=O)N[C@@H](Cc1ccccc1)C(=O)N(C)c1nc2ccccc2s1] | D | |
| 177 | 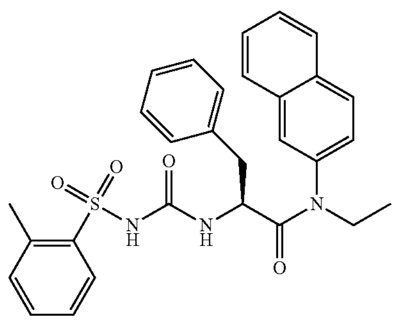 [SMILES: CCN(C(=O)[C@H](Cc1ccccc1)NC(=O)NS(=O)(=O)c1ccccc1C)c1ccc2ccccc2c1] | A | |
| 178 | 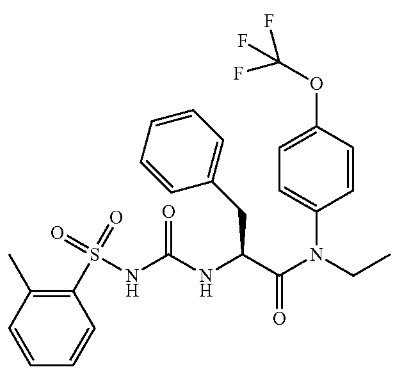 [SMILES: CCN(C(=O)[C@H](Cc1ccccc1)NC(=O)NS(=O)(=O)c1ccccc1C)c1ccc(OC(F)(F)F)cc1] | A | 0.08 |
| 179 | 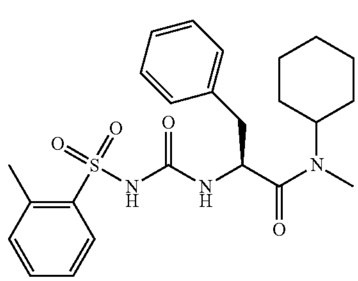 [SMILES: Cc1ccccc1S(=O)(=O)NC(=O)N[C@@H](Cc1ccccc1)C(=O)N(C)C1CCCCC1] | C | |

TABLE 1-continued
| Example | Structure | Activity | EC$_{50}$ (μM) |
|---|---|---|---|
| 180 | 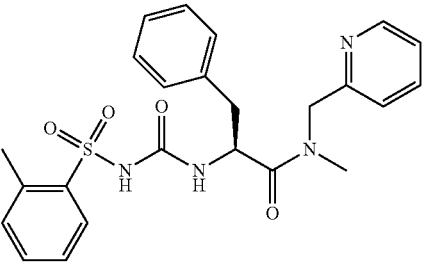 [SMILES: Cc1ccccc1S(=O)(=O)NC(=O)N[C@@H](Cc1ccccc1)C(=O)N(C)Cc1ccccn1] | C | |
| 181 | 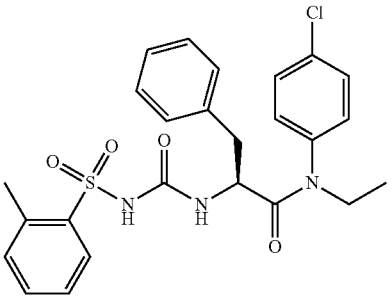 [SMILES: CCN(C(=O)[C@H](Cc1ccccc1)NC(=O)NS(=O)(=O)c1ccccc1C)c1ccc(Cl)cc1] | B | |
| 182 | 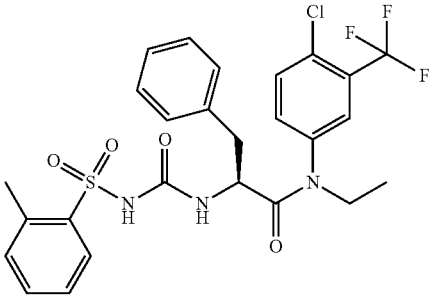 [SMILES: CCN(C(=O)[C@H](Cc1ccccc1)NC(=O)NS(=O)(=O)c1ccccc1C)c1ccc(Cl)c(C(F)(F)F)c1] | B | |
| 183 | 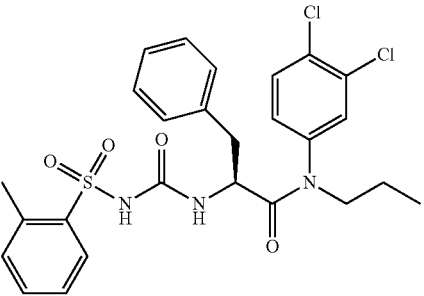 [SMILES: CCCN(C(=O)[C@H](Cc1ccccc1)NC(=O)NS(=O)(=O)c1ccccc1C)c1ccc(Cl)c(Cl)c1] | B | 0.31 |
| 184 | 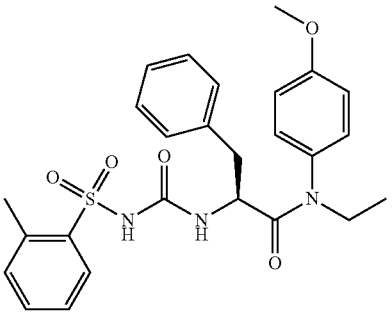 [SMILES: CCN(C(=O)[C@H](Cc1ccccc1)NC(=O)NS(=O)(=O)c1ccccc1C)c1ccc(OC)cc1] | A | |

TABLE 1-continued

| Example | Structure | Activity | EC$_{50}$ (μM) |
|---------|-----------|----------|----------------|
| 185 | 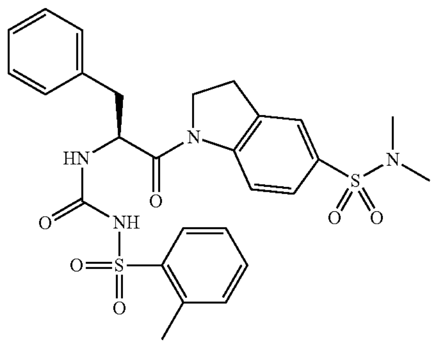 [SMILES: Cc1ccccc1S(=O)(=O)NC(=O)N[C@@H](Cc1ccccc1)C(=O)N1CCc2cc(S(=O)(=O)N(C)C)ccc21] | C | |
| 186 | 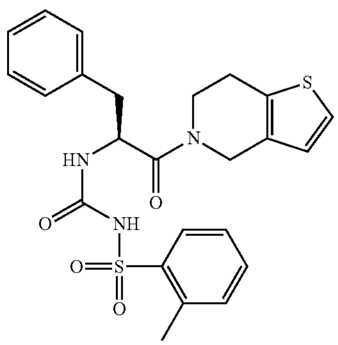 [SMILES: Cc1ccccc1S(=O)(=O)NC(=O)N[C@@H](Cc1ccccc1)C(=O)N1CCc2sccc2C1] | C | 3.59 |
| 187 | 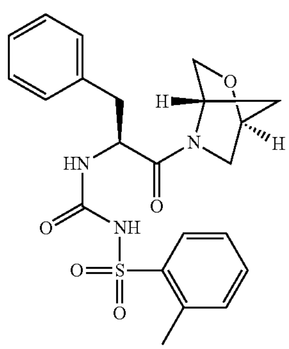 [SMILES: Cc1ccccc1S(=O)(=O)NC(=O)N[C@@H](Cc1ccccc1)C(=O)N1C[C@@H]2C[C@H]1CO2] | | >33.3 |
| 188 | 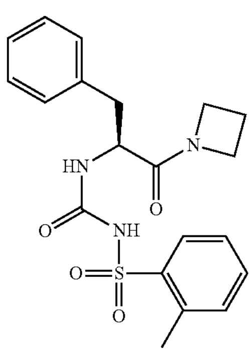 [SMILES: Cc1ccccc1S(=O)(=O)NC(=O)N[C@@H](Cc1ccccc1)C(=O)N1CCC1] | D | 27.5 |

TABLE 1-continued

| Example | Structure | Activity | EC$_{50}$ (μM) |
|---|---|---|---|
| 189 | 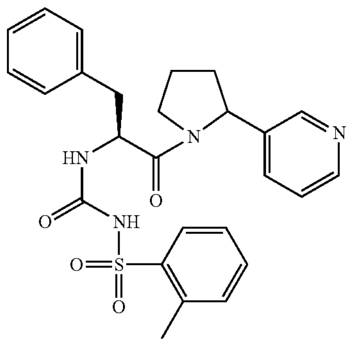 [SMILES: Cc1ccccc1S(=O)(=O)NC(=O)N[C@@H](Cc1ccccc1)C(=O)N1CCCC1c1cccnc1] | C | |
| 190 | 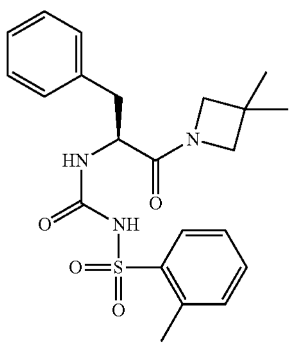 [SMILES: Cc1ccccc1S(=O)(=O)NC(=O)N[C@@H](Cc1ccccc1)C(=O)N1CC(C)(C)C1] | | >100 |
| 191 | 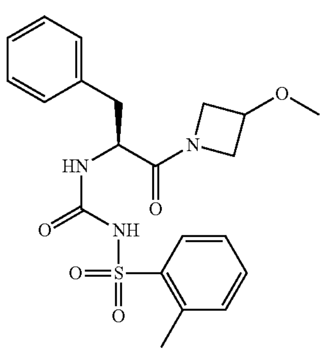 [SMILES: COC1CN(C(=O)[C@H](Cc2ccccc2)NC(=O)NS(=O)(=O)c2ccccc2C)C1] | | >100 |
| 192 | 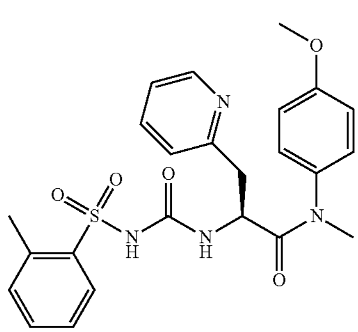 [SMILES: COc1ccc(N(C)C(=O)[C@H](Cc2ccccn2)NC(=O)NS(=O)(=O)c2ccccc2C)cc1] | D | |

TABLE 1-continued

| Example | Structure | Activity | EC$_{50}$ (μM) |
|---------|-----------|----------|----------------|
| 193 | 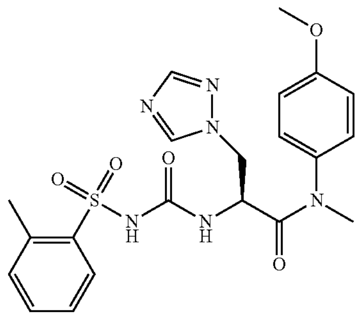 [SMILES: COc1ccc(N(C)C(=O)[C@H](Cn2cncn2)NC(=O)NS(=O)(=O)c2ccccc2C)cc1] | | >100 |
| 194 | 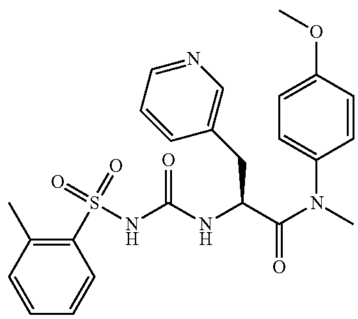 [SMILES: COc1ccc(N(C)C(=O)[C@H](Cc2cccnc2)NC(=O)NS(=O)(=O)c2ccccc2C)cc1] | D | |
| 195 | 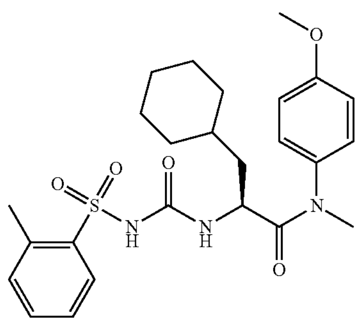 [SMILES: COc1ccc(N(C)C(=O)[C@H](CC2CCCCC2)NC(=O)NS(=O)(=O)c2ccccc2C)cc1] | C | |
| 196 | 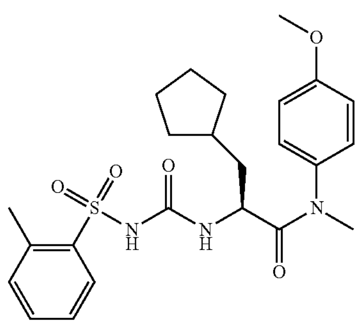 [SMILES: COc1ccc(N(C)C(=O)[C@H](CC2CCCC2)NC(=O)NS(=O)(=O)c2ccccc2C)cc1] | D | |
| 197 | 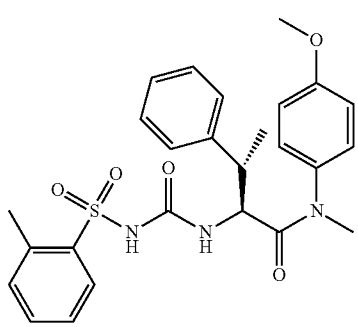 [SMILES: COc1ccc(N(C)C(=O)[C@@H](NC(=O)NS(=O)(=O)c2ccccc2C)[C@@H](C)c2ccccc2)cc1] | D | 11.5 |

TABLE 1-continued

| Example | Structure | Activity | EC$_{50}$ (µM) |
|---|---|---|---|
| 198 | 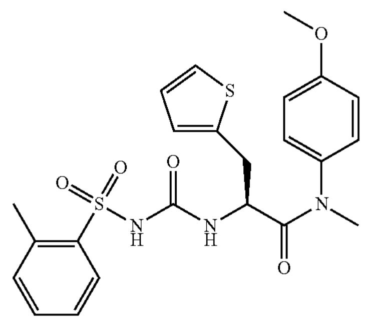 [SMILES: COc1ccc(N(C)C(=O)[C@H](Cc2cccs2)NC(=O)NS(=O)(=O)c2ccccc2C)cc1] | B | 0.27 |
| 199 | 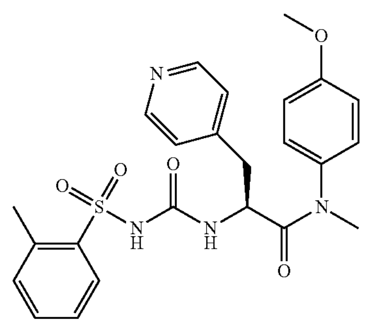 [SMILES: COc1ccc(N(C)C(=O)[C@H](Cc2ccncc2)NC(=O)NS(=O)(=O)c2ccccc2C)cc1] | D | |
| 200 | 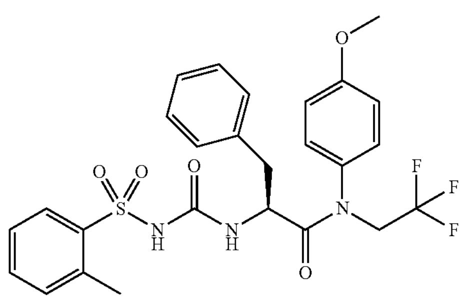 [SMILES: COc1ccc(N(CC(F)(F)F)C(=O)[C@H](Cc2ccccc2)NC(=O)NS(=O)(=O)c2ccccc2C)cc1] | B | |
| 201 | 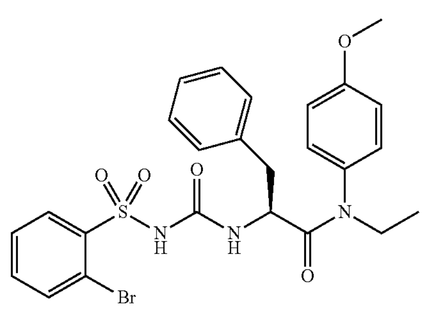 [SMILES: CCN(C(=O)[C@H](Cc1ccccc1)NC(=O)NS(=O)(=O)c1ccccc1Br)c1ccc(OC)cc1] | A | |

TABLE 1-continued

| Example | Structure | Activity | EC$_{50}$ ($\mu$M) |
|---|---|---|---|
| 203 | 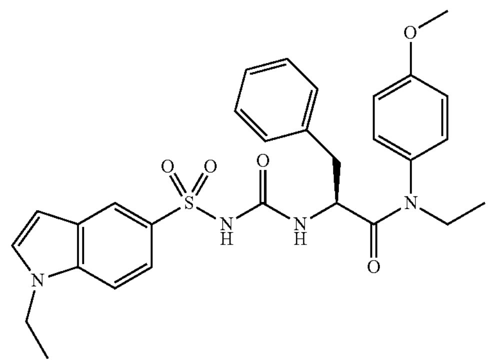 [SMILES: CCN(C(=O)[C@H](Cc1ccccc1)NC(=O)NS(=O)(=O)c1ccc2c(ccn2CC)c1)c1ccc(OC)cc1] | B | |
| 204 | 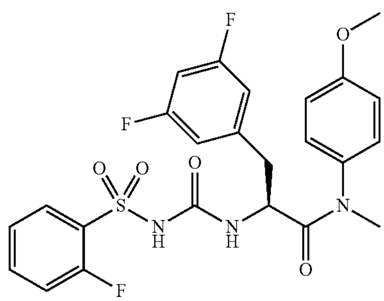 [SMILES: COc1ccc(N(C)C(=O)[C@H](Cc2cc(F)cc(F)c2)NC(=O)NS(=O)(=O)c2ccccc2F)cc1] | B | |
| 205 | 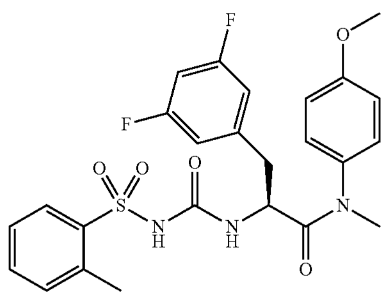 [SMILES: COc1ccc(N(C)C(=O)[C@H](Cc2cc(F)cc(F)c2)NC(=O)NS(=O)(=O)c2ccccc2C)cc1] | B | 0.11 |
| JB-82 | 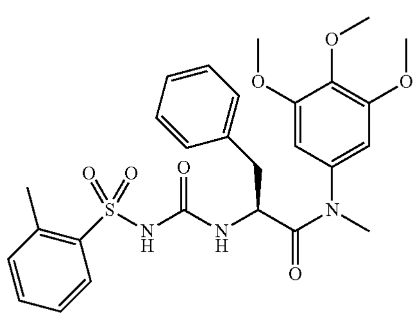 [SMILES: COc1cc(N(C)C(=O)[C@H](Cc2ccccc2)NC(=O)NS(=O)(=O)c2ccccc2C)cc(OC)c1OC] | C | |
| JB-83 | 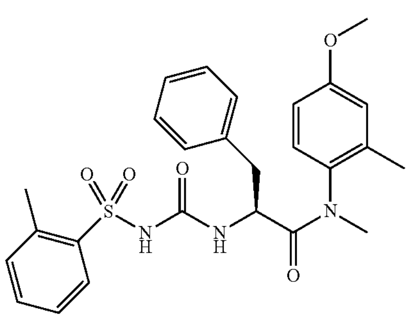 [SMILES: COc1ccc(N(C)C(=O)[C@H](Cc2ccccc2)NC(=O)NS(=O)(=O)c2ccccc2C)c(C)c1] | B | |

TABLE 1-continued

| Example | Structure | Activity | EC₅₀ (μM) |
|---|---|---|---|
| JB-84 | 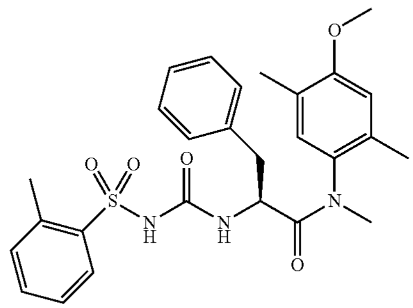 [SMILES: COc1cc(C)c(N(C)C(=O)[C@H](Cc2ccccc2)NC(=O)NS(=O)(=O)c2ccccc2C)cc1C] | B | |
| ZY-3 | 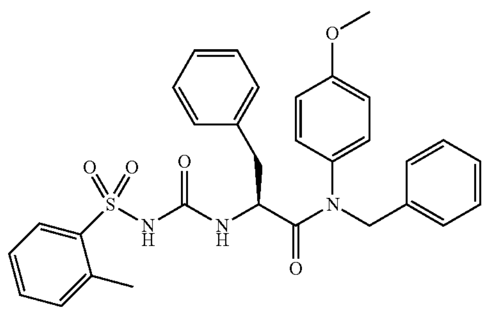 [SMILES: COc1ccc(N(Cc2ccccc2)C(=O)[C@H](Cc2ccccc2)NC(=O)NS(=O)(=O)c2ccccc2C)cc1] | C | 3.61 |
| ZY-4 | 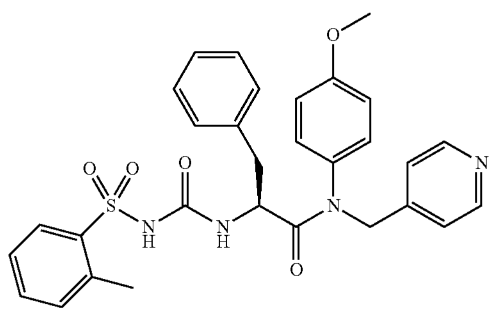 [SMILES: COc1ccc(N(Cc2ccncc2)C(=O)[C@H](Cc2ccccc2)NC(=O)NS(=O)(=O)c2ccccc2C)cc1] | C | |
| ZY-5 | 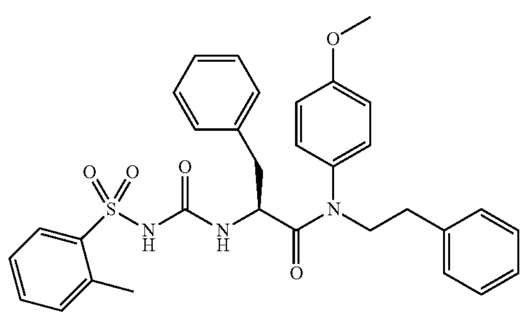 [SMILES: COc1ccc(N(CCc2ccccc2)C(=O)[C@H](Cc2ccccc2)NC(=O)NS(=O)(=O)c2ccccc2C)cc1] | D | 11.42 |
| ZY-6 | 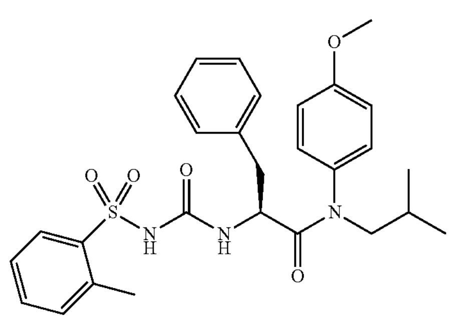 [SMILES: COc1ccc(N(CC(C)C)C(=O)[C@H](Cc2ccccc2)NC(=O)NS(=O)(=O)c2ccccc2C)cc1] | C | |

TABLE 1-continued

| Example | Structure | Activity | EC$_{50}$ (μM) |
|---------|-----------|----------|----------------|
| CA-67 | 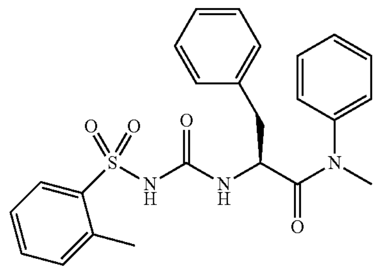 [SMILES: Cc1ccccc1S(=O)(=O)NC(=O)N[C@@H](Cc1ccccc1)C(=O)N(C)c1ccccc1] | B | 0.49 |
| CA-68 | 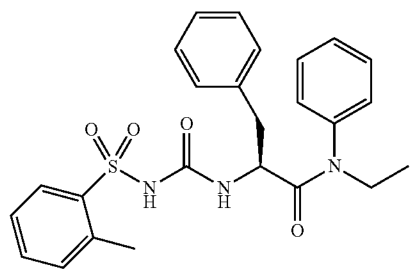 | B | |
| CA-69 | 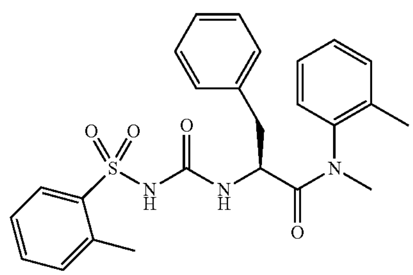 [SMILES: Cc1ccccc1N(C)C(=O)[C@H](Cc1ccccc1)NC(=O)NS(=O)(=O)c1ccccc1C] | C | |
| CA-70 | 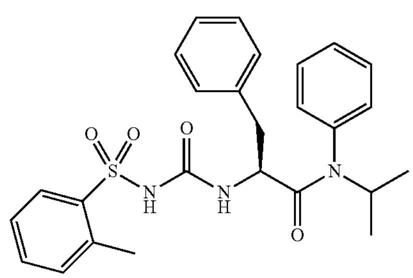 [SMILES: Cc1ccccc1S(=O)(=O)NC(=O)N[C@@H](Cc1ccccc1)C(=O)N(c1ccccc1)C(C)C] | B | |
| CA-71 | 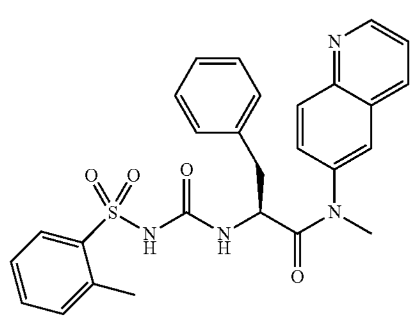 [SMILES: Cc1ccccc1S(=O)(=O)NC(=O)N[C@@H](Cc1ccccc1)C(=O)N(C)c1ccc2ncccc2c1] | A | |

TABLE 1-continued

| Example | Structure | Activity | EC$_{50}$ (μM) |
|---------|-----------|----------|----------------|
| CA-72 | 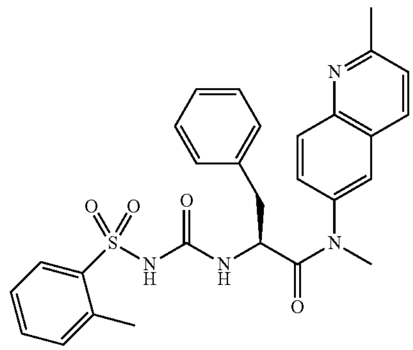 [SMILES: Cc1ccc2cc(N(C)C(=O)[C@H](Cc3ccccc3)NC(=O)NS(=O)(=O)c3ccccc3C)ccc2n1] | A | 0.03 |
| CA-73 | 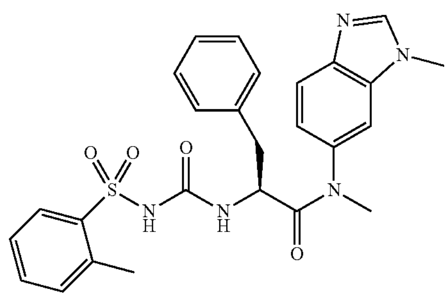 [SMILES: Cc1ccccc1S(=O)(=O)NC(=O)N[C@@H](Cc1ccccc1)C(=O)N(C)c1ccc2ncn(C)c2c1] | B | |
| CA-74 | 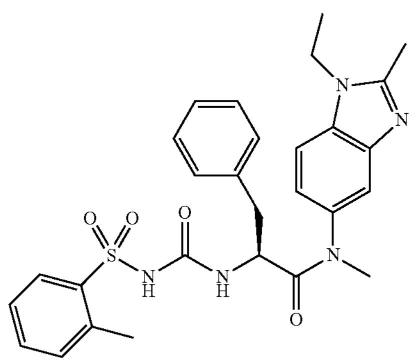 [SMILES: CCn1c(C)nc2cc(N(C)C(=O)[C@H](Cc3ccccc3)NC(=O)NS(=O)(=O)c3ccccc3C)ccc21] | C | 2.03 |
| CA-75 | 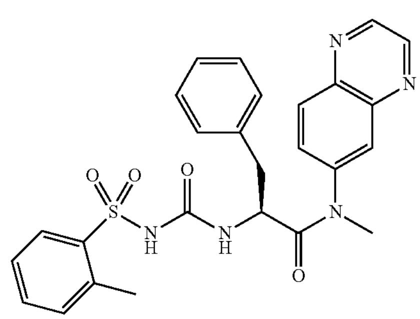 [SMILES: Cc1ccccc1S(=O)(=O)NC(=O)N[C@@H](Cc1ccccc1)C(=O)N(C)c1ccc2nccnc2c1] | B | |

TABLE 1-continued

| Example | Structure | Activity | EC$_{50}$ (μM) |
|---|---|---|---|
| CA-76 | 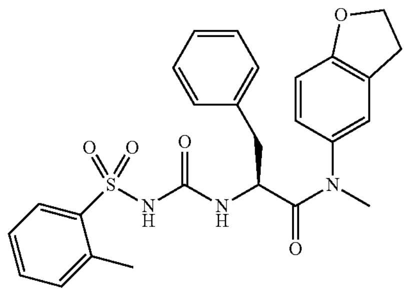 [SMILES: Cc1ccccc1S(=O)(=O)NC(=O)N[C@@H](Cc1ccccc1)C(=O)N(C)c1ccc2c(c1)CCO2] | A | |
| CA-77 | 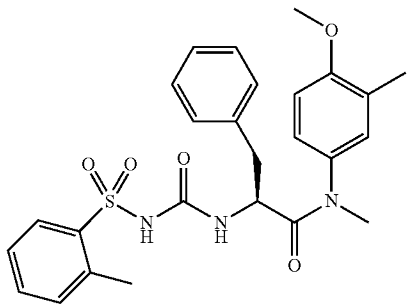 [SMILES: COc1ccc(N(C)C(=O)[C@H](Cc2ccccc2)NC(=O)NS(=O)(=O)c2ccccc2C)cc1C] | A | |
| CA-78 | 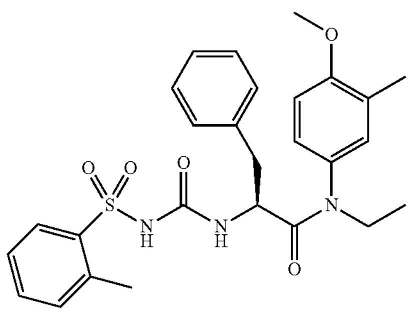 [SMILES: CCN(C(=O)[C@H](Cc1ccccc1)NC(=O)NS(=O)(=O)c1ccccc1C)c1ccc(OC)c(C)c1] | B | 0.12 |
| CA-79 | 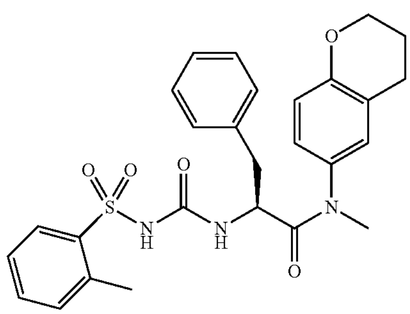 [SMILES: Cc1ccccc1S(=O)(=O)NC(=O)N[C@@H](Cc1ccccc1)C(=O)N(C)c1ccc2c(c1)CCCO2] | A | |
| CA-80 | 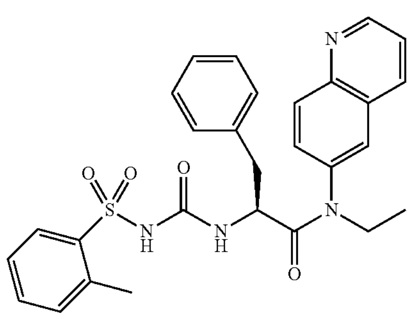 [SMILES: CCN(C(=O)[C@H](Cc1ccccc1)NC(=O)NS(=O)(=O)c1ccccc1C)c1ccc2ncccc2c1] | A | 0.03 |

TABLE 1-continued

| Example | Structure | Activity | EC$_{50}$ (μM) |
|---------|-----------|----------|----------------|
| CA-81 | 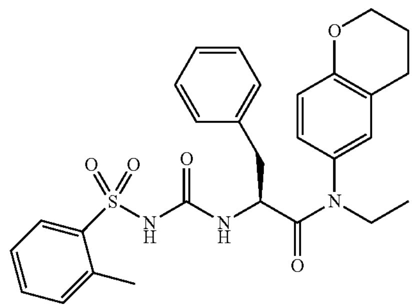 [SMILES: CCN(C(=O)[C@H](Cc1ccccc1)NC(=O)NS(=O)(=O)c1ccccc1C)c1ccc2c(c1)CCCO2] | A | 0.04 |
| CA-82 | 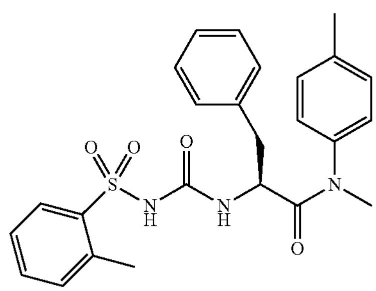 [SMILES: Cc1ccc(N(C)C(=O)[C@H](Cc2ccccc2)NC(=O)NS(=O)(=O)c2ccccc2C)cc1] | B | |
| CA-83 | 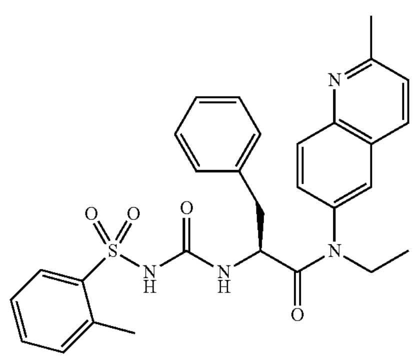 [SMILES: CCN(C(=O)[C@H](Cc1ccccc1)NC(=O)NS(=O)(=O)c1ccccc1C)c1ccc2nc(C)ccc2c1] | A | |
| JB-85 | 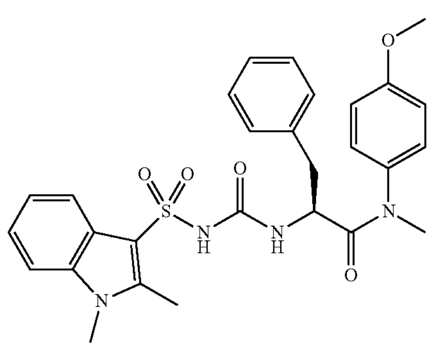 [SMILES: COc1ccc(N(C)C(=O)[C@H](Cc2ccccc2)NC(=O)NS(=O)(=O)c2c(C)n(C)c3ccccc23)cc1] | B | |

TABLE 1-continued
| Example | Structure | Activity | EC$_{50}$ (μM) |
|---|---|---|---|
| CA-84 | 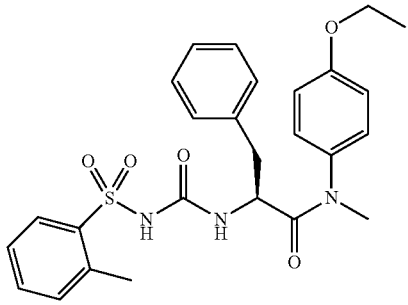 [SMILES: CCOc1ccc(N(C)C(=O)[C@H](Cc2ccccc2)NC(=O)NS(=O)(=O)c2ccccc2C)cc1] | A | |
| CA-85 | 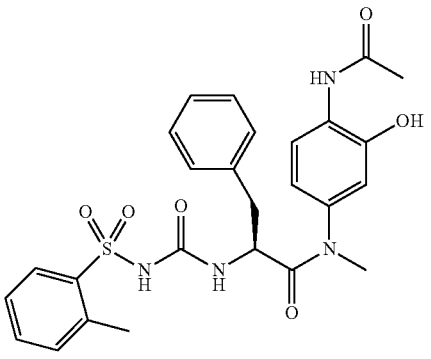 [SMILES: CC(=O)Nc1ccc(N(C)C(=O)[C@H](Cc2ccccc2)NC(=O)NS(=O)(=O)c2ccccc2C)cc1O] | C | |
| CA-86 | 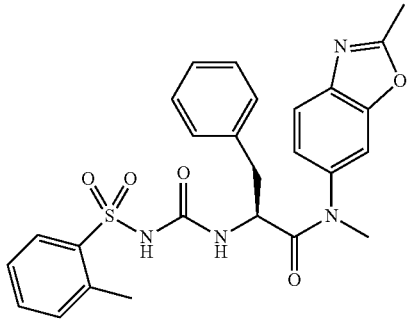 [SMILES: Cc1nc2ccc(N(C)C(=O)[C@H](Cc3ccccc3)NC(=O)NS(=O)(=O)c3ccccc3C)cc2o1] | A | |
| CA-87 | 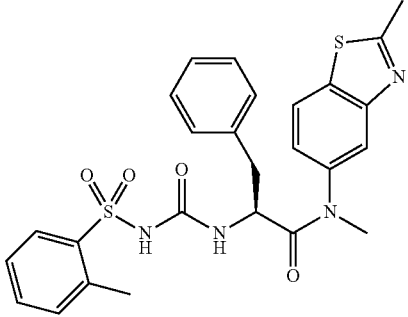 [SMILES: Cc1nc2cc(N(C)C(=O)[C@H](Cc3ccccc3)NC(=O)NS(=O)(=O)c3ccccc3C)ccc2s1] | B | |

TABLE 1-continued

| Example | Structure | Activity | EC$_{50}$ (μM) |
|---|---|---|---|
| CA-88 | 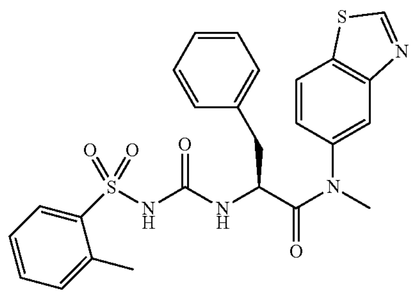 [SMILES: Cc1ccccc1S(=O)(=O)NC(=O)N[C@@H](Cc1ccccc1)C(=O)N(C)c1ccc2scnc2c1] | A | 0.06 |
| CA-89 | 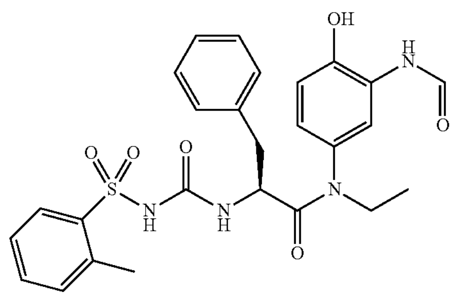 [SMILES: CCN(C(=O)[C@H](Cc1ccccc1)NC(=O)NS(=O)(=O)c1ccccc1C)c1ccc(O)c(NC=O)c1] | B | 0.60 |
| CA-90 | 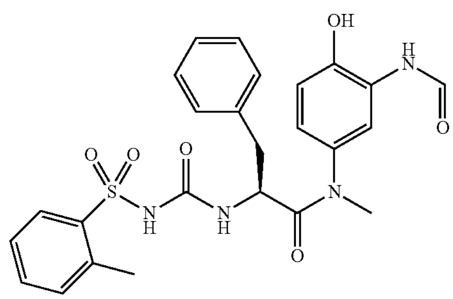 [SMILES: Cc1ccccc1S(=O)(=O)NC(=O)N[C@@H](Cc1ccccc1)C(=O)N(C)c1ccc(O)c(NC=O)c1] | C | |
| CA-91 | 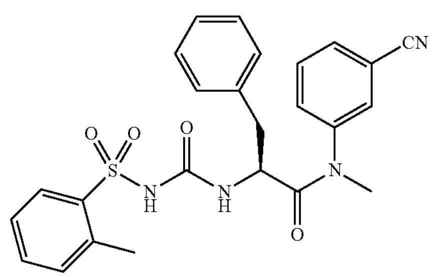 [SMILES: Cc1ccccc1S(=O)(=O)NC(=O)N[C@@H](Cc1ccccc1)C(=O)N(C)c1cccc(C#N)c1] | B | |
| CA-92 | 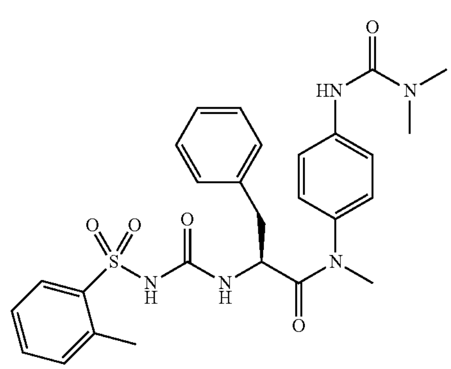 [SMILES: Cc1ccccc1S(=O)(=O)NC(=O)N[C@@H](Cc1ccccc1)C(=O)N(C)c1ccc(NC(=O)N(C)C)cc1] | C | |

TABLE 1-continued

| Example | Structure | Activity | EC$_{50}$ (µM) |
|---|---|---|---|
| CA-93 | 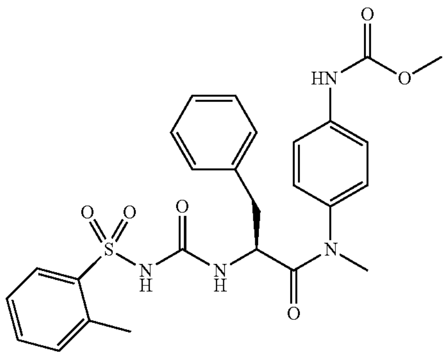 [SMILES: COC(=O)Nc1ccc(N(C)C(=O)[C@H](Cc2ccccc2)NC(=O)NS(=O)(=O)c2ccccc2C)cc1] | A | |
| CA-94 | 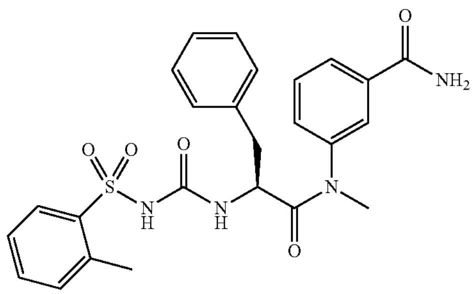 [SMILES: Cc1ccccc1S(=O)(=O)NC(=O)N[C@@H](Cc1ccccc1)C(=O)N(C)c1cccc(C(N)=O)c1] | C | 3.26 |
| CA-95 | 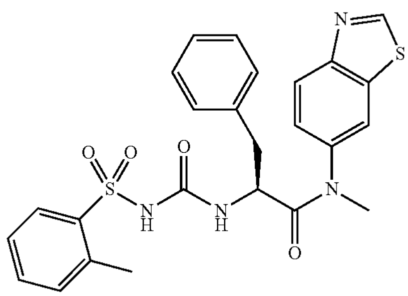 [SMILES: Cc1ccccc1S(=O)(=O)NC(=O)N[C@@H](Cc1ccccc1)C(=O)N(C)c1ccc2ncsc2c1] | A | |
| CA-96 | 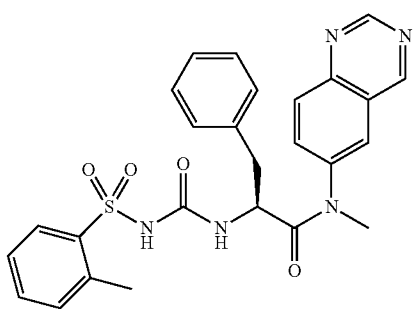 [SMILES: Cc1ccccc1S(=O)(=O)NC(=O)N[C@@H](Cc1ccccc1)C(=O)N(C)c1ccc2ncncc2c1] | B | |
| CA-97 | 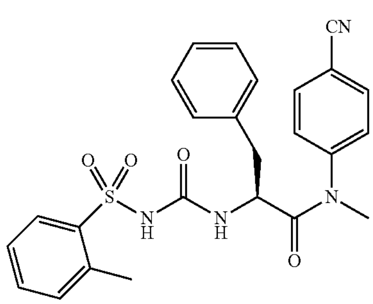 [SMILES: Cc1ccccc1S(=O)(=O)NC(=O)N[C@@H](Cc1ccccc1)C(=O)N(C)c1ccc(C#N)cc1] | B | |

TABLE 1-continued

| Example | Structure | Activity | EC$_{50}$ (µM) |
|---|---|---|---|
| ZY-7 | 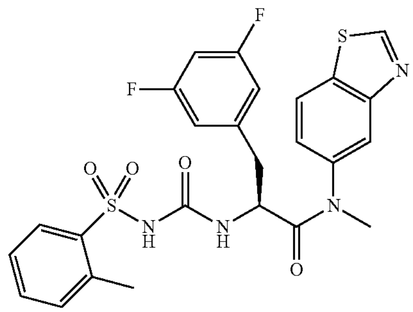 [SMILES: Cc1ccccc1S(=O)(=O)NC(=O)N[C@@H](Cc1cc(F)cc(F)c1)C(=O)N(C)c1ccc2scnc2c1] | A | |
| CA-98 | 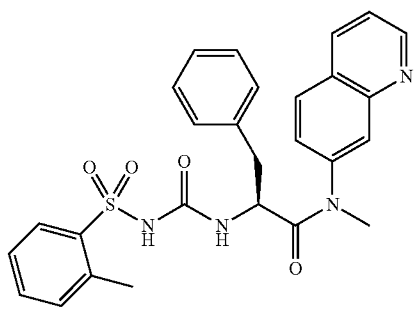 [SMILES: Cc1ccccc1S(=O)(=O)NC(=O)N[C@@H](Cc1ccccc1)C(=O)N(C)c1ccc2cccnc2c1] | B | 0.12 |
| CA-99 | 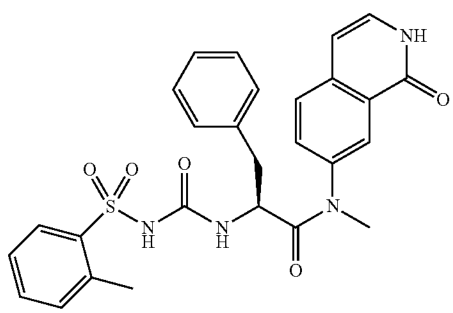 [SMILES: Cc1ccccc1S(=O)(=O)NC(=O)N[C@@H](Cc1ccccc1)C(=O)N(C)c1ccc2cc[nH]c(=O)c2c1] | C | |
| CA-100 | 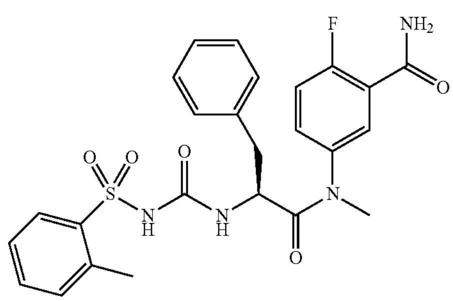 [SMILES: Cc1ccccc1S(=O)(=O)NC(=O)N[C@@H](Cc1ccccc1)C(=O)N(C)c1ccc(F)c(C(N)=O)c1] | C | |
| CA-101 | 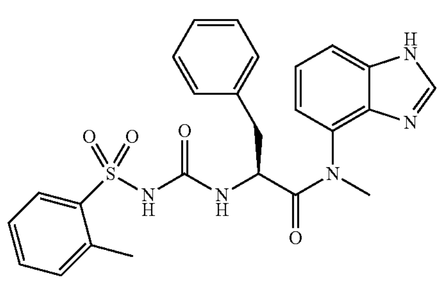 [SMILES: Cc1ccccc1S(=O)(=O)NC(=O)N[C@@H](Cc1ccccc1)C(=O)N(C)c1cccc2[nH]cnc12] | C | |

TABLE 1-continued

| Example | Structure | Activity | EC$_{50}$ (μM) |
|---|---|---|---|
| CA-102 | 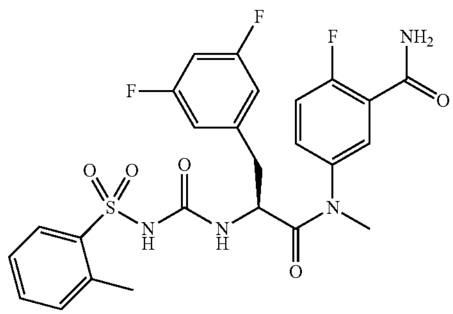 [SMILES: Cc1ccccc1S(=O)(=O)NC(=O)N[C@@H](Cc1cc(F)cc(F)c1)C(=O)N(C)c1ccc(F)c(C(N)=O)c1] | C | 2.58 |
| CA-103 | 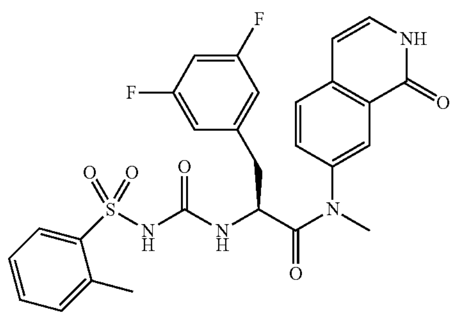 [SMILES: Cc1ccccc1S(=O)(=O)NC(=O)N[C@@H](Cc1cc(F)cc(F)c1)C(=O)N(C)c1ccc2cc[nH]c(=O)c2c1] | C | 1.33 |
| CA-104 | 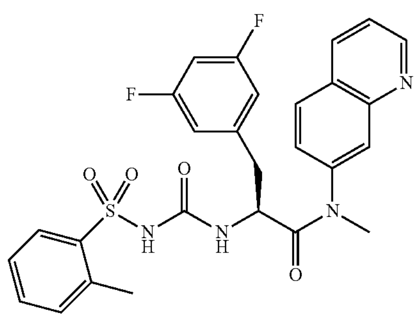 [SMILES: Cc1ccccc1S(=O)(=O)NC(=O)N[C@@H](Cc1cc(F)cc(F)c1)C(=O)N(C)c1ccc2cccnc2c1] | B | |
| CA-105 | 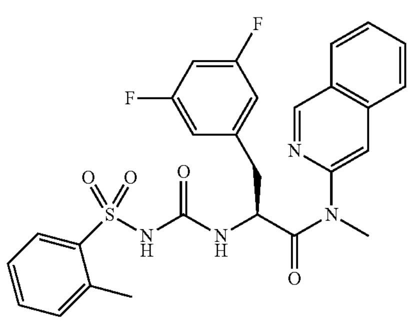 [SMILES: Cc1ccccc1S(=O)(=O)NC(=O)N[C@@H](Cc1cc(F)cc(F)c1)C(=O)N(C)c1cc2ccccc2cn1] | B | |
| CA-106 | 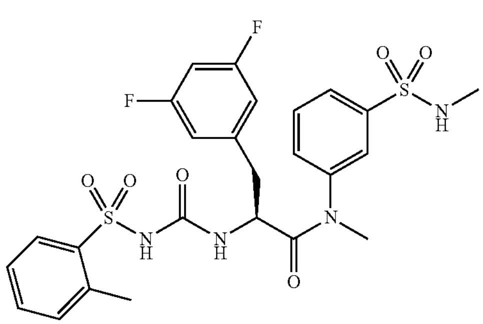 [SMILES: CNS(=O)(=O)c1cccc(N(C)C(=O)[C@H](Cc2cc(F)cc(F)c2)NC(=O)NS(=O)(=O)c2ccccc2C)c1] | C | |

TABLE 1-continued

| Example | Structure | Activity | EC$_{50}$ (μM) |
|---------|-----------|----------|----------------|
| CA-107 | 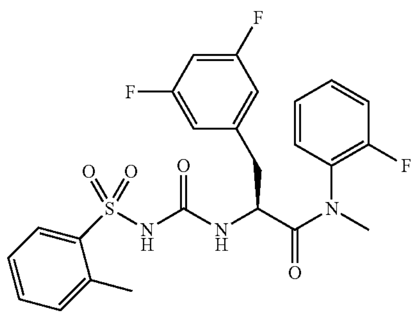 [SMILES: Cc1ccccc1S(=O)(=O)NC(=O)N[C@@H](Cc1cc(F)cc(F)c1)C(=O)N(C)c1ccccc1F] | C | |
| CA-108 | 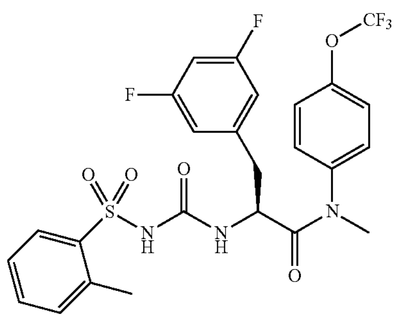 [SMILES: Cc1ccccc1S(=O)(=O)NC(=O)N[C@@H](Cc1cc(F)cc(F)c1)C(=O)N(C)c1ccc(OC(F)(F)F)cc1] | B | |
| CA-109 | 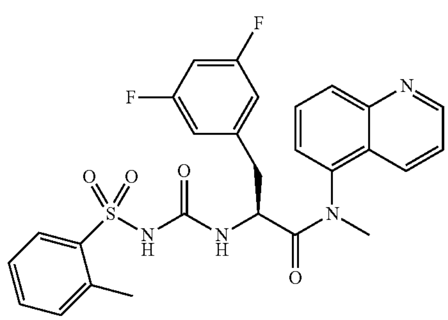 [SMILES: Cc1ccccc1S(=O)(=O)NC(=O)N[C@@H](Cc1cc(F)cc(F)c1)C(=O)N(C)c1cccc2ncccc12] | B | 0.37 |
| CA-110 | 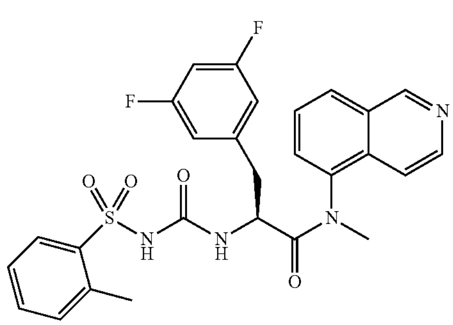 [SMILES: Cc1ccccc1S(=O)(=O)NC(=O)N[C@@H](Cc1cc(F)cc(F)c1)C(=O)N(C)c1cccc2cnccc12] | B | |

TABLE 1-continued

| Example | Structure | Activity | EC$_{50}$ (μM) |
|---------|-----------|----------|----------------|
| CA-111 | 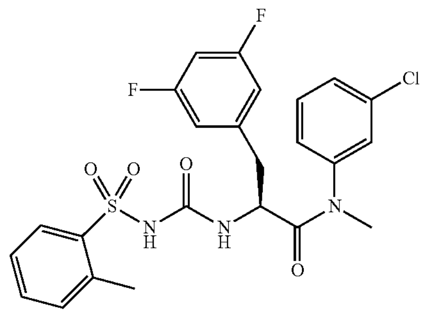 [SMILES: Cc1ccccc1S(=O)(=O)NC(=O)N[C@@H](Cc1cc(F)cc(F)c1)C(=O)N(C)c1cccc(Cl)c1] | C | |
| CA-112 | 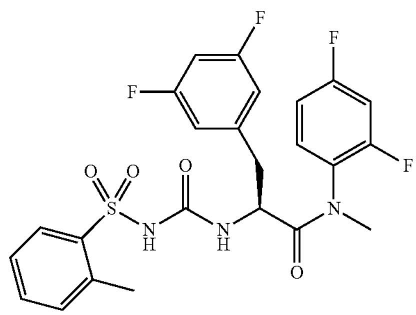 [SMILES: Cc1ccccc1S(=O)(=O)NC(=O)N[C@@H](Cc1cc(F)cc(F)c1)C(=O)N(C)c1ccc(F)cc1F] | C | 1.29 |
| ZY-13 | 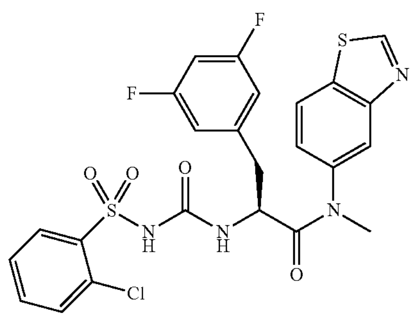 [SMILES: CN(C(=O)[C@H](Cc1cc(F)cc(F)c1)NC(=O)NS(=O)(=O)c1ccccc1Cl)c1ccc2scnc2c1] | A | 0.03 |
| ZY-14 | 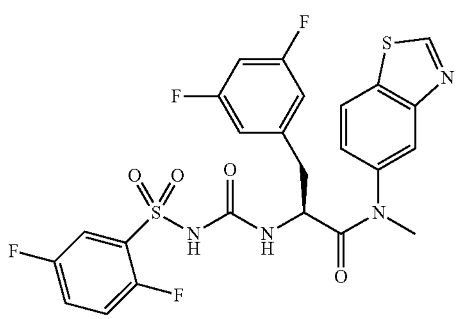 [SMILES: CN(C(=O)[C@H](Cc1cc(F)cc(F)c1)NC(=O)NS(=O)(=O)c1cc(F)ccc1F)c1ccc2scnc2c1] | B | |
| ZY-16 | 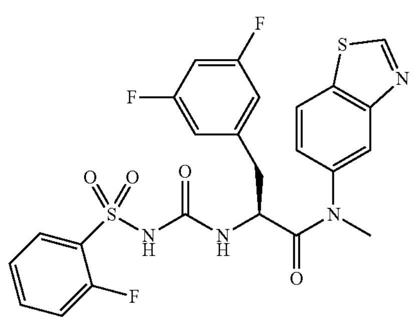 [SMILES: CN(C(=O)[C@H](Cc1cc(F)cc(F)c1)NC(=O)NS(=O)(=O)c1ccccc1F)c1ccc2scnc2c1] | A | |

TABLE 1-continued

| Example | Structure | Activity | EC$_{50}$ (μM) |
|---------|-----------|----------|----------------|
| ZY-17 | 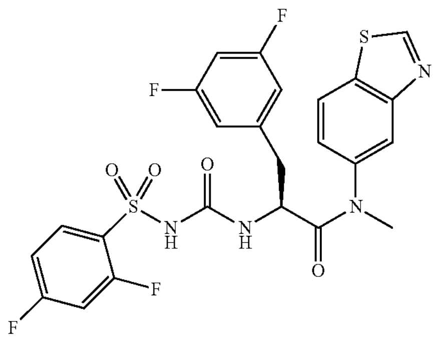 [SMILES: CN(C(=O)[C@H](Cc1cc(F)cc(F)c1)NC(=O)NS(=O)(=O)c1ccc(F)cc1F)c1ccc2scnc2c1] | B | |
| 206 | 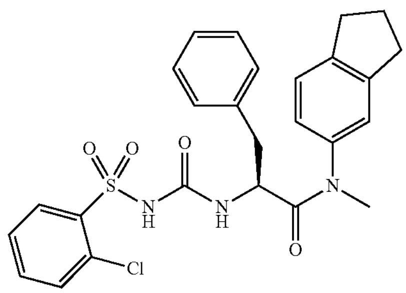 [SMILES: CN(C(=O)[C@H](Cc1ccccc1)NC(=O)NS(=O)(=O)c1ccccc1Cl)c1ccc2c(c1)CCC2] | A | |
| 207 | 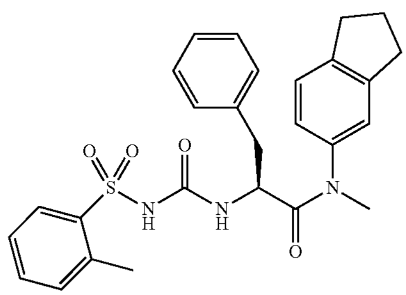 [SMILES: Cc1ccccc1S(=O)(=O)NC(=O)N[C@@H](Cc1ccccc1)C(=O)N(C)c1ccc2c(c1)CCC2] | A | |
| 208 | 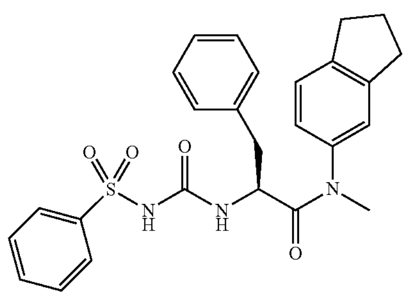 [SMILES: CN(C(=O)[C@H](Cc1ccccc1)NC(=O)NS(=O)(=O)c1ccccc1)c1ccc2c(c1)CCC2] | B | |
| 209 | 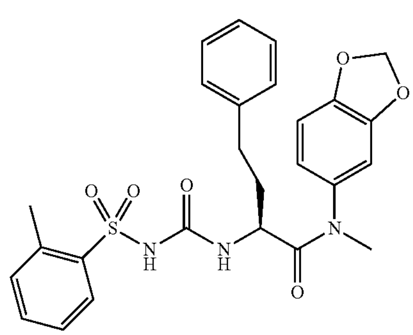 [SMILES: Cc1ccccc1S(=O)(=O)NC(=O)N[C@@H](CCc1ccccc1)C(=O)N(C)c1ccc2c(c1)OCO2] | D | |

TABLE 1-continued

| Example | Structure | Activity | EC$_{50}$ (μM) |
|---|---|---|---|
| 210 | 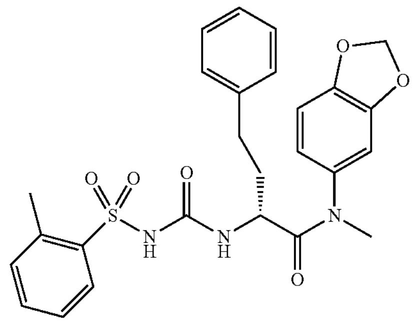 [SMILES: Cc1ccccc1S(=O)(=O)NC(=O)N[C@H](CCc1ccccc1)C(=O)N(C)c1ccc2c(c1)OCO2] | D | |
| 212 | 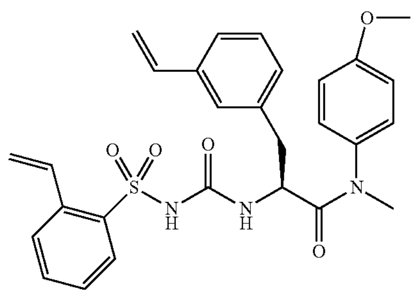 [SMILES: C=Cc1cccc(C[C@H](NC(=O)NS(=O)(=O)c2ccccc2C=C)C(=O)N(C)c2ccc(OC)cc2)c1] | A | 0.058 |
| 213 | 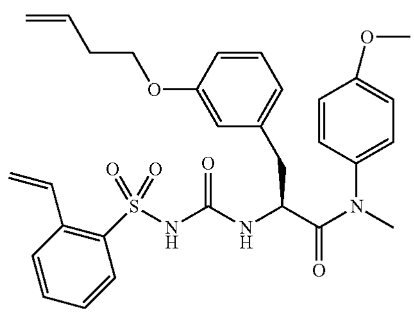 [SMILES: C=CCCOc1cccc(C[C@H](NC(=O)NS(=O)(=O)c2ccccc2C=C)C(=O)N(C)c2ccc(OC)cc2)c1] | C | 5.07 |
| 214 | 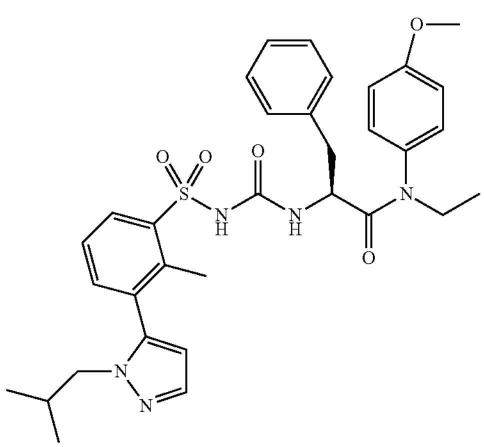 [SMILES: CCN(C(=O)[C@H](Cc1ccccc1)NC(=O)NS(=O)(=O)c1cccc(-c2ccnn2CC(C)C)c1C)c1ccc(OC)cc1] | B | 0.87 |

TABLE 1-continued

| Example | Structure | Activity | EC$_{50}$ (μM) |
|---|---|---|---|
| 215 | 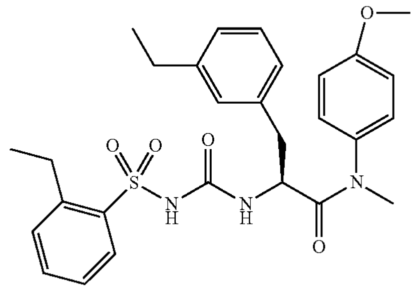 [SMILES: CCc1cccc(C[C@H](NC(=O)NS(=O)(=O)c2ccccc2CC)C(=O)N(C)c2ccc(OC)cc2)c1] | B | |
| 216 | 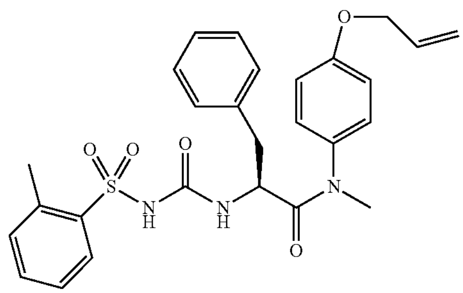 [SMILES: C=CCOc1ccc(N(C)C(=O)[C@H](Cc2ccccc2)NC(=O)NS(=O)(=O)c2ccccc2C)cc1] | A | |
| 217 | 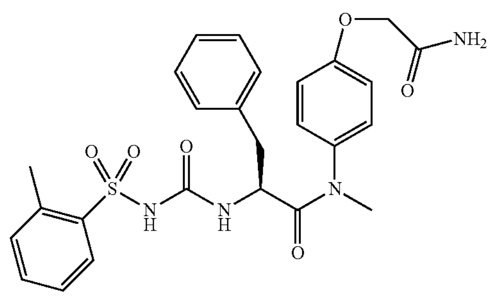 [SMILES: Cc1ccccc1S(=O)(=O)NC(=O)N[C@@H](Cc1ccccc1)C(=O)N(C)c1ccc(OCC(N)=O)cc1] | B | |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula I, or a pharmaceutically acceptable salt thereof:

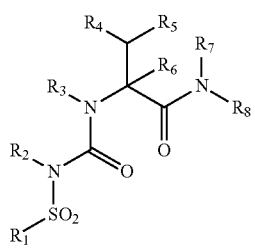

I wherein:

R$^1$ is alkyl, aryl, arylalkyl, cycloalkyl or heteroaryl; wherein said aryl, arylalkyl or heteroaryl moieties are linked to the parent molecule through their respective carbon atoms, and further wherein said aryl, arylalkyl or heteroaryl moieties are substituted with 0-4 groups independently selected from the group consisting of alkenyl, alkoxy, alkoxycarbonyl, alkoxycarbonylamino, alkyl, alkylsulphonyl, alkylthioxy, aminocarbonyl, alkynyl, carboxylic acid, cyano, halo, haloalkyl, haloalkoxy, hydroxy, hydroxyalkyl, thioxy, —SO$_2$alkyl, heteroaryl, and nitro;

R$^2$ is —H, C$_1$-C$_4$ alkyl or C$_3$-C$_4$ cycloalkyl;

or R$^1$ and R$^2$ together with the atoms to which they are attached form a heterocyclic ring optionally substituted with 0-2 alkyl groups;

R$^3$ is —H, C$_1$-C$_4$ alkyl or C$_3$-C$_4$ cycloalkyl;

R$^4$ is aryl which is substituted with 0-3 groups independently selected from the group consisting of alkenoxy, alkenyl, alkoxy, alkoxycarbonyl, alkyl, benzyloxy, carboamide, cyano, halo, haloalkyl, haloalkoxy, —NHCO(alkyl), —SO$_2$NH-heterocycle, —OH, nitro, and —CH$_2$OH;

R$^5$ and R$^6$ are independently selected from H or alkyl, or R$^5$ and R$^4$ together with the atom to which they are attached form an aryl group, or R⁵ and R⁶ together with the atoms to which they are attached form a $C_3$-$C_4$ cycloalkyl;

R⁷ is alkyl, aryl, heteroaryl, $C_3$-$C_7$ cycloalkyl or dialkylaminoalkyl, wherein said aryl or heteroaryl is substituted with 0-3 groups independently selected from the group consisting of —OH, —NHCOalkyl, —NHCON(alkyl)₂, —NHCO₂-alkyl, —CONH₂, —CN, —SO₂N(alkyl)₂, alkoxy, alkyl, halo, haloalkoxy, and haloalkyl; and R⁸ is alkyl containing 1-6 carbon atoms, or $C_3$-$C_4$ cycloalkyl;

or R⁷ and R⁸ together with the nitrogen atom to which they are attached form a heterocycle which is substituted with 0-3 groups independently selected from the group consisting of alkyl, alkoxy, halo, —OH, —CN, and —SO₂N(alkyl)₂.

2. A compound or salt of claim 1, wherein R¹ is aryl.

3. A compound or salt of claim 2, wherein R¹ is phenyl, biphenyl or naphthalenyl.

4. A compound of claim 1, wherein R¹ is heteroaryl.

5. A compound of claim 4, wherein R¹ is selected from the group of thiophene, pyrrazolophenyl, furanylphenyl, pyridinylphenyl, pyrimidinylphenyl, thiophenylphenyl, benzothiophene, oxadiazolephenyl, indole, and azaindole.

6. A compound of claim 1, wherein R¹ and R² together with the —N—SO₂ moiety to which they are attached form a heterocyclic ring.

7. A compound of claim 6, wherein said heterocyclic ring is isothiazolidine 1,1-dioxide.

8. A compound or salt of claim 1, wherein R⁴ is phenyl, naphthanenyl, or biaryl.

9. A compound of claim 1, wherein R⁷ is aryl.

10. A compound of claim 9, wherein R⁷ is phenyl or naphthalenyl.

11. A compound or salt of claim 1, wherein R⁷ is selected from the group of bezodioxolyl, dihalobezodioxolyl, benzothiazole, quinoline, benzothiazole, benzimidazole, quinazoline, quinoxaline, dihydrobenzofuran, chroman, benzoxazole, isoquinoline, and isoquinolinone.

12. A compound of claim 1, wherein R⁷ and R⁸ together form a heterocycle which is selected from the group of tetrahydroisoquinoline, dihydro-benzo[1,4]oxazine, dihydroindole, tetrahydrothieno[3,2-c]pyridine, 2-oxa-5-azabicyclo[2.2.1]heptanes, azetidine, and pyridinylpyrrolidine.

13. A compound selected from the group consisting of:

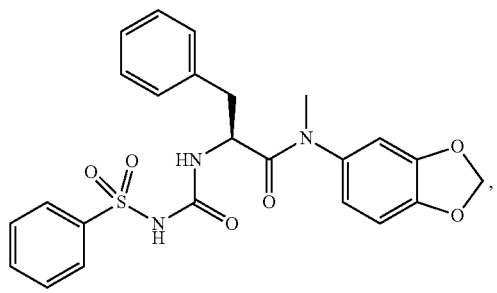

-continued

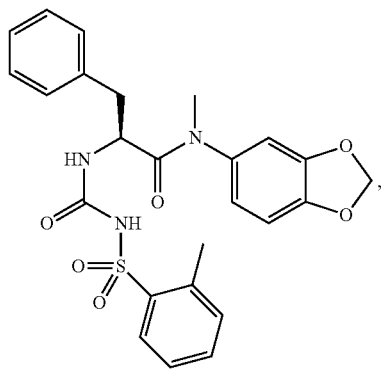

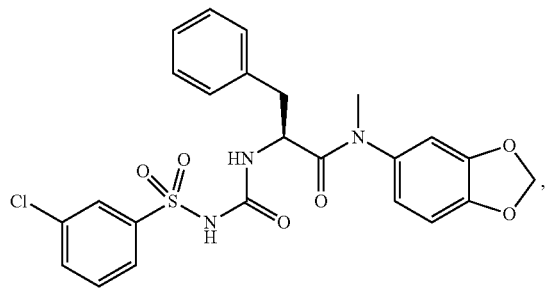

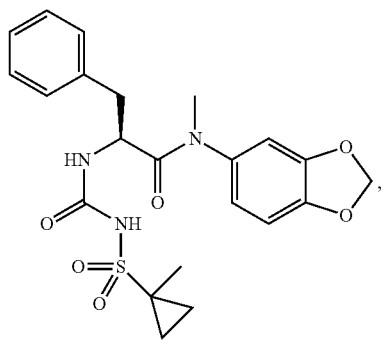

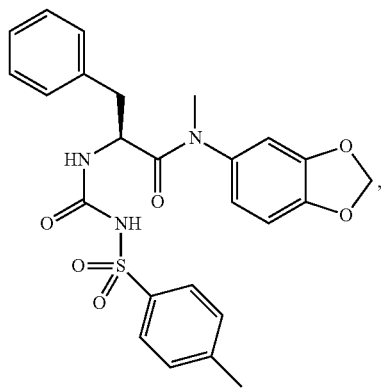

435
-continued
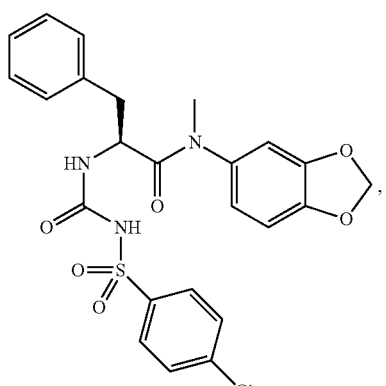
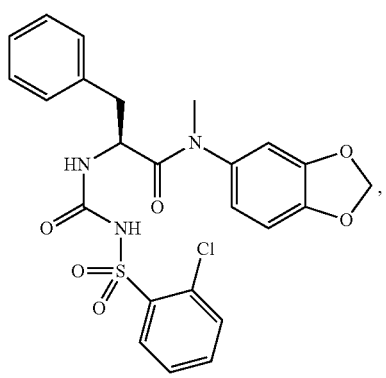
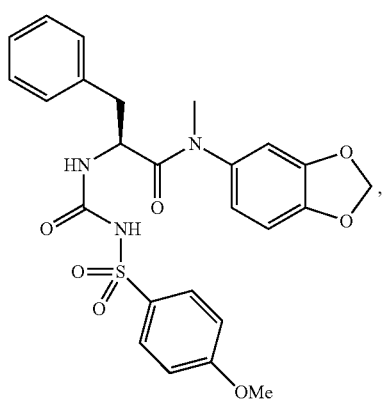
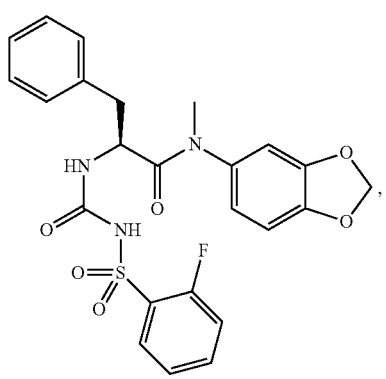
436
-continued
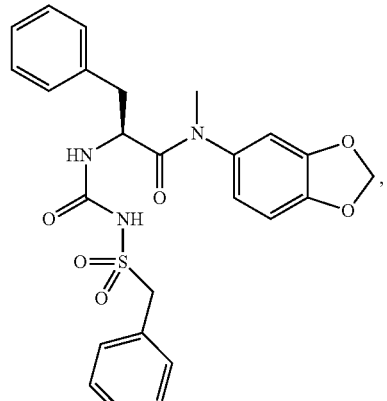
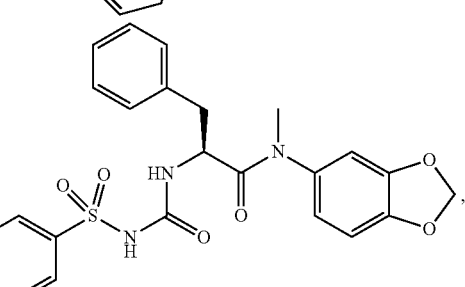
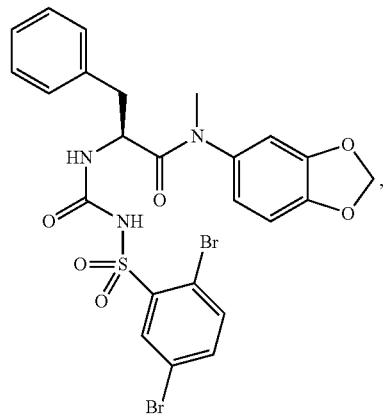
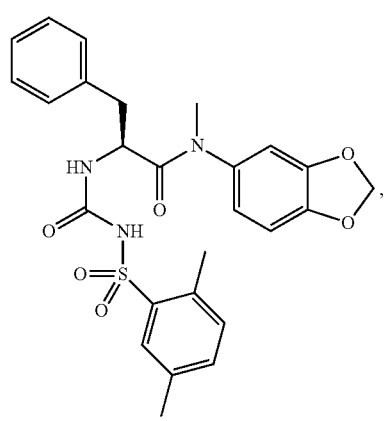

437
-continued
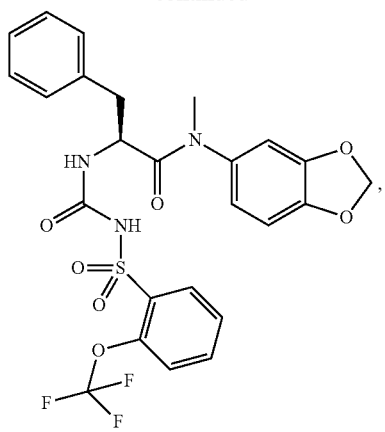
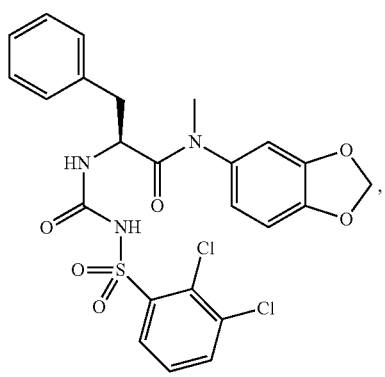
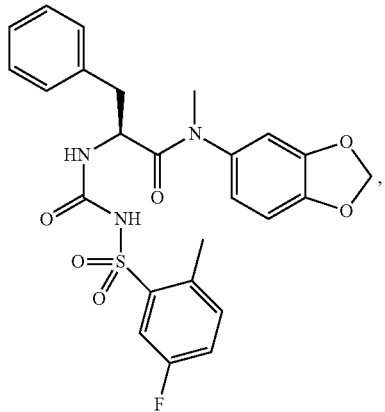
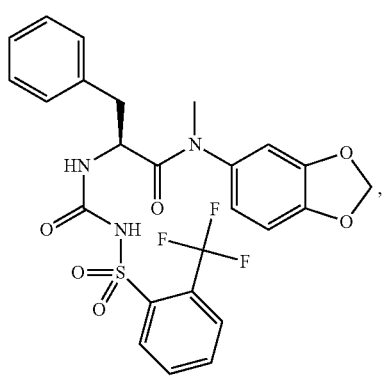
438
-continued
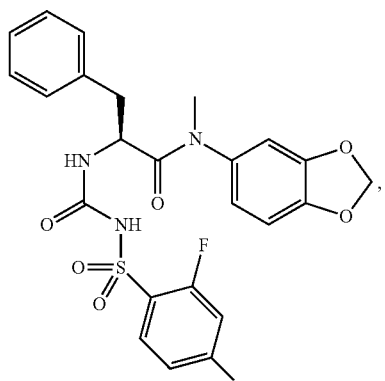
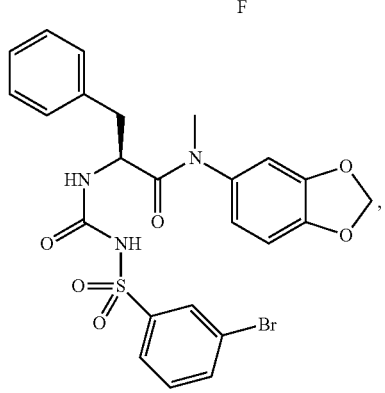
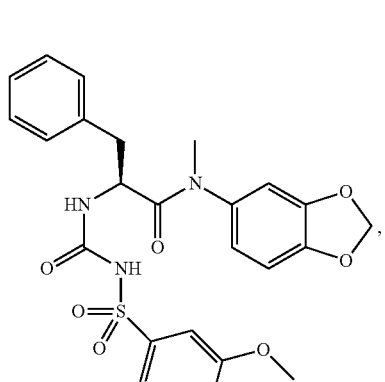
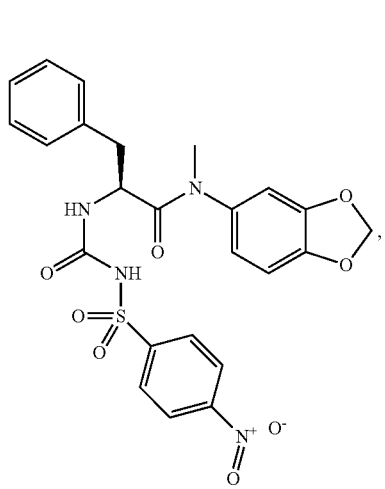

439
-continued
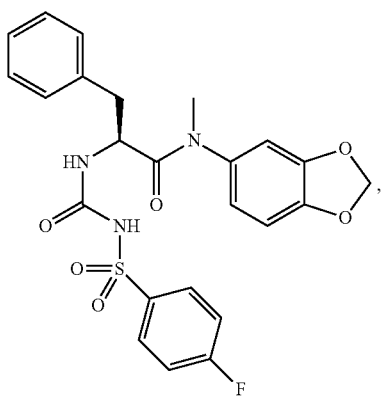
440
-continued
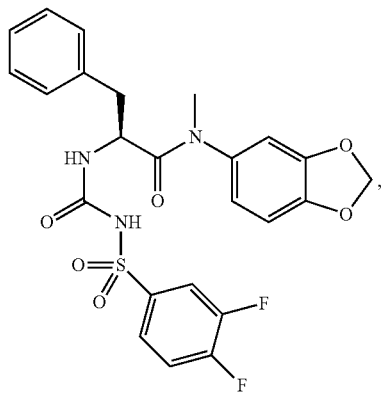
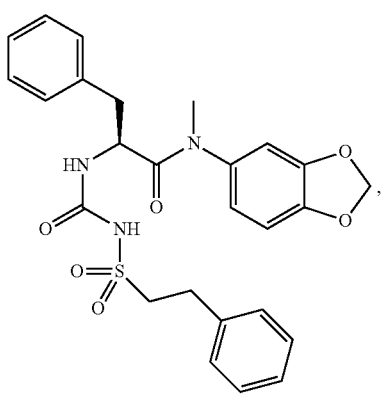
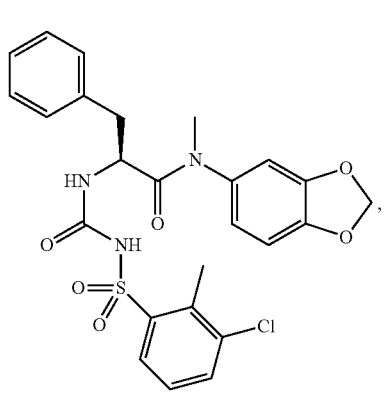
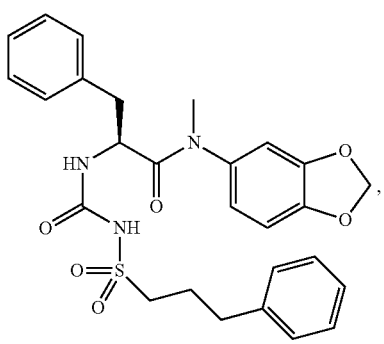
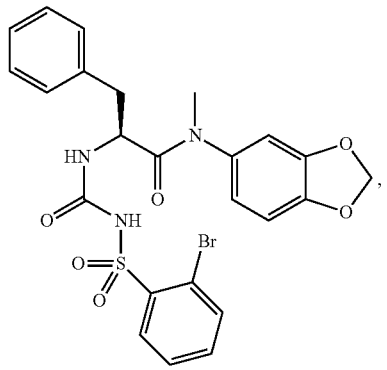

441
-continued
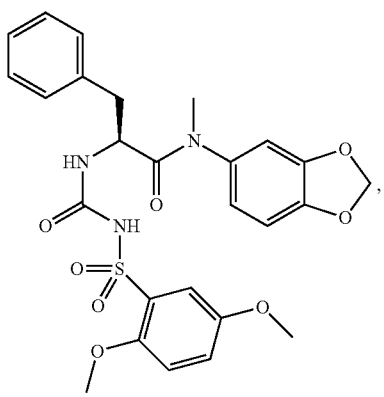
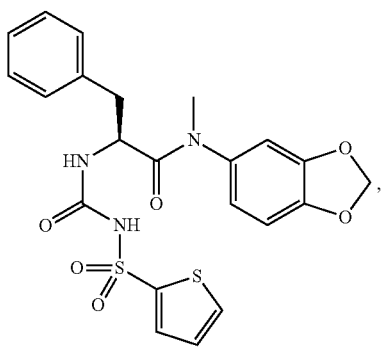
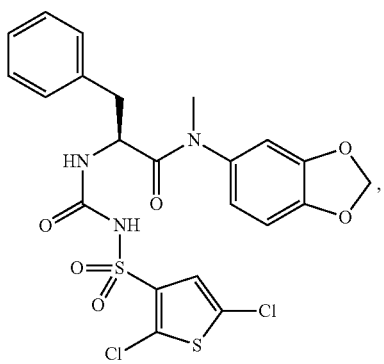
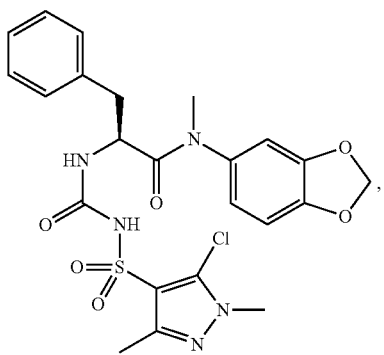
442
-continued
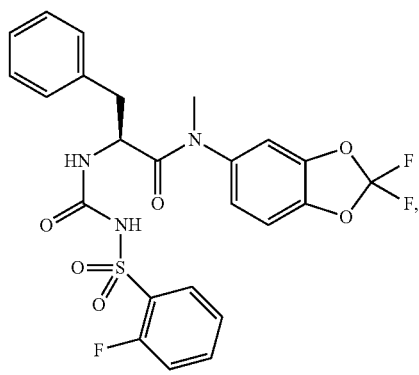
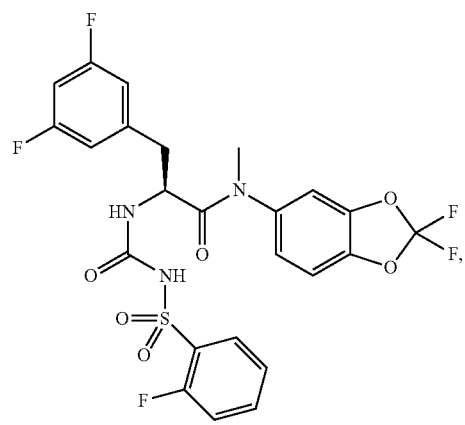
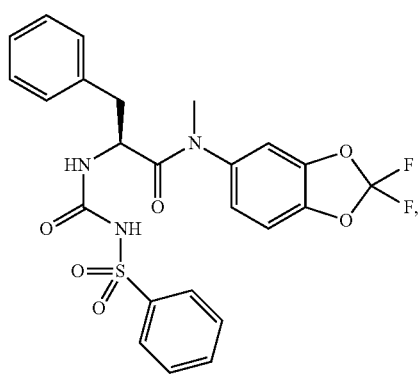
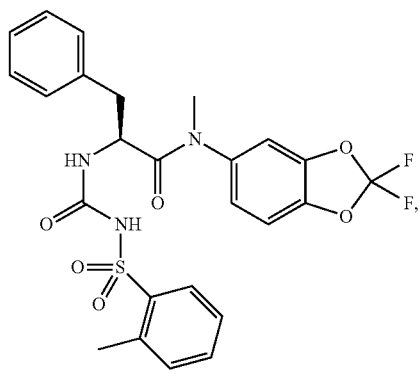

443
-continued
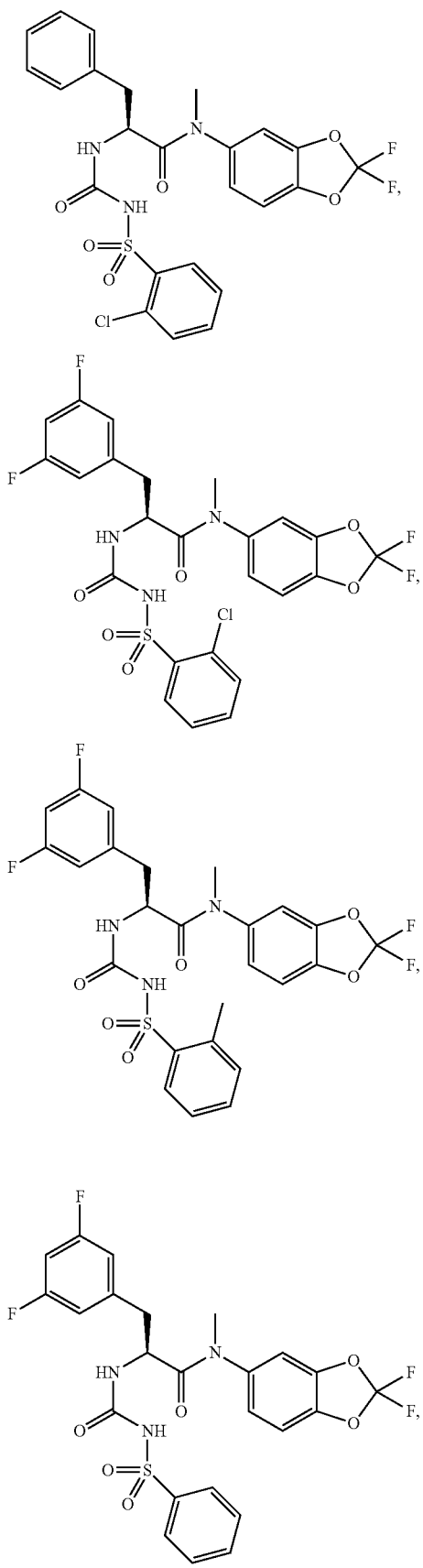
444
-continued
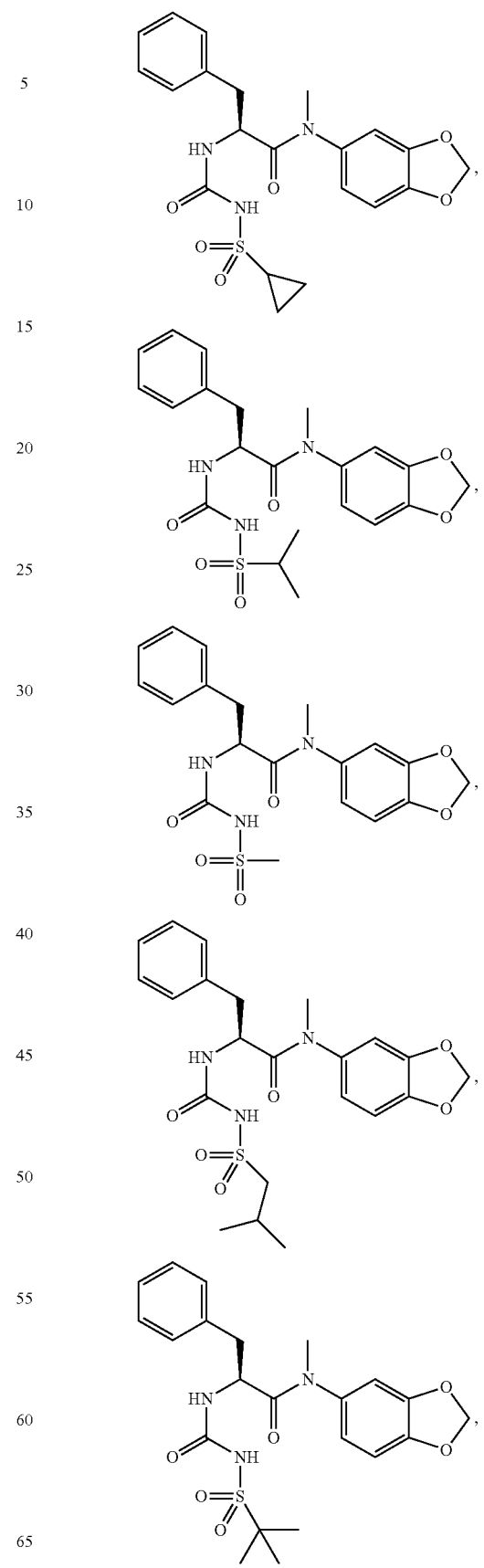

445
-continued
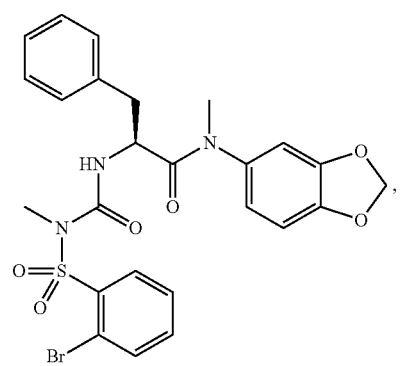
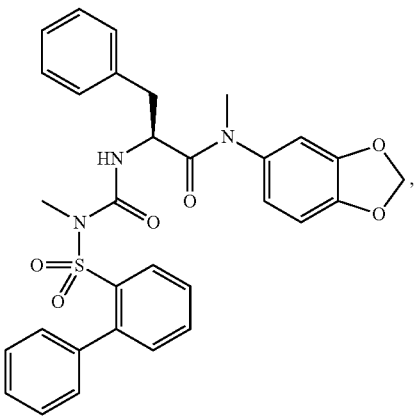
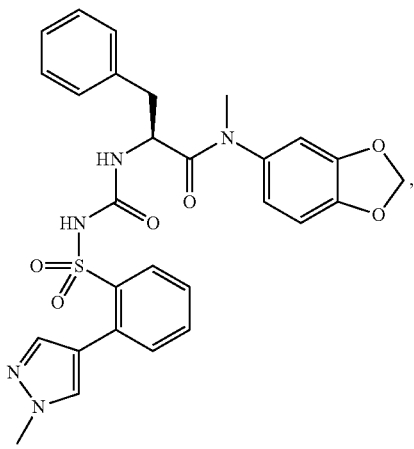
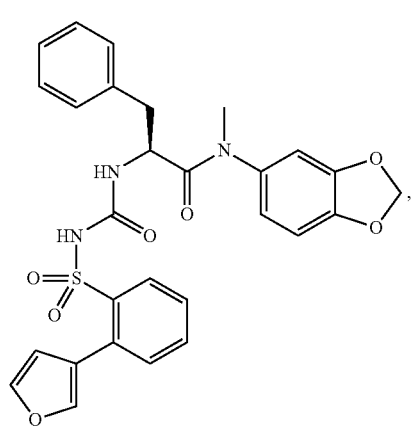
446
-continued
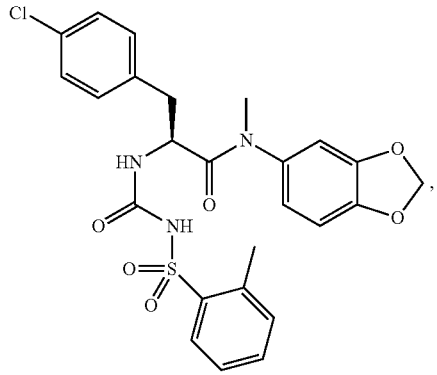
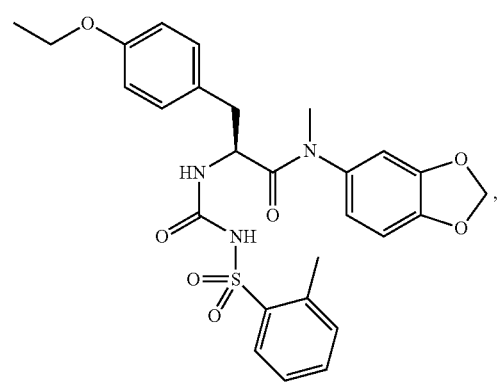
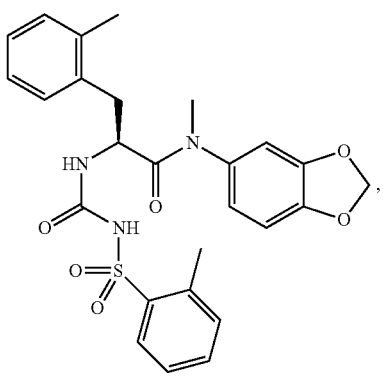
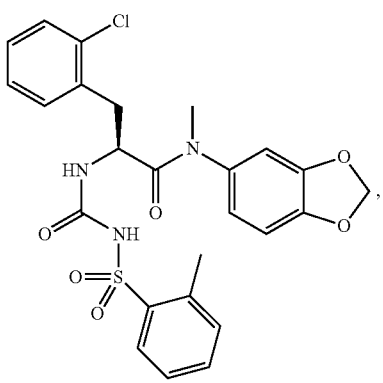

447
-continued
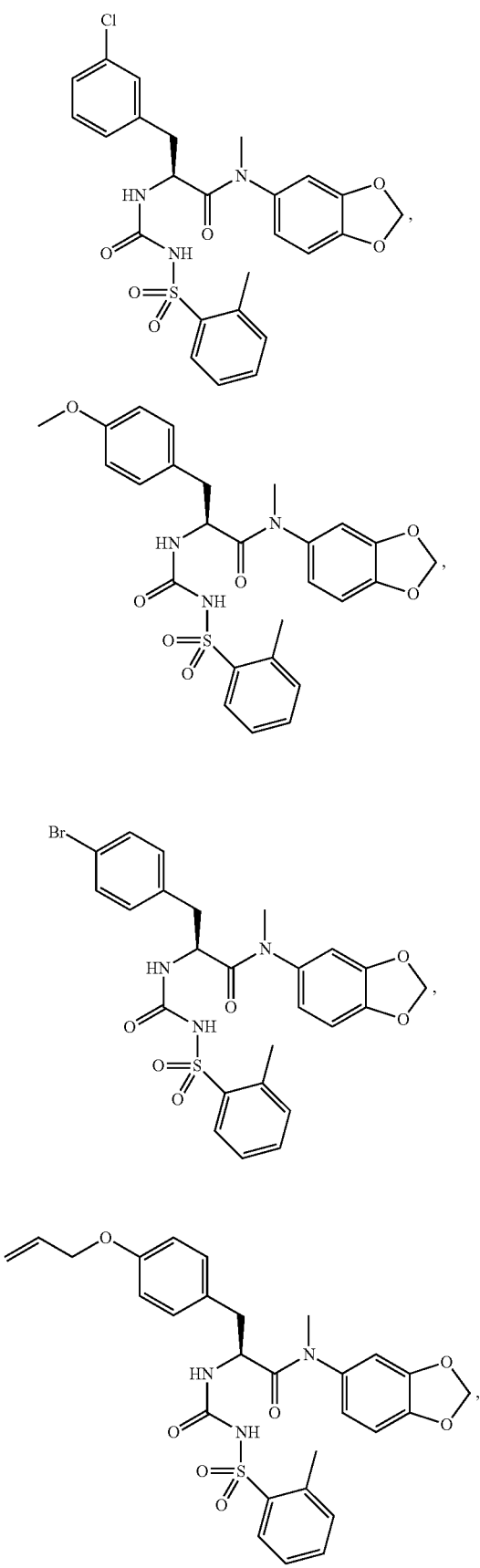
448
-continued
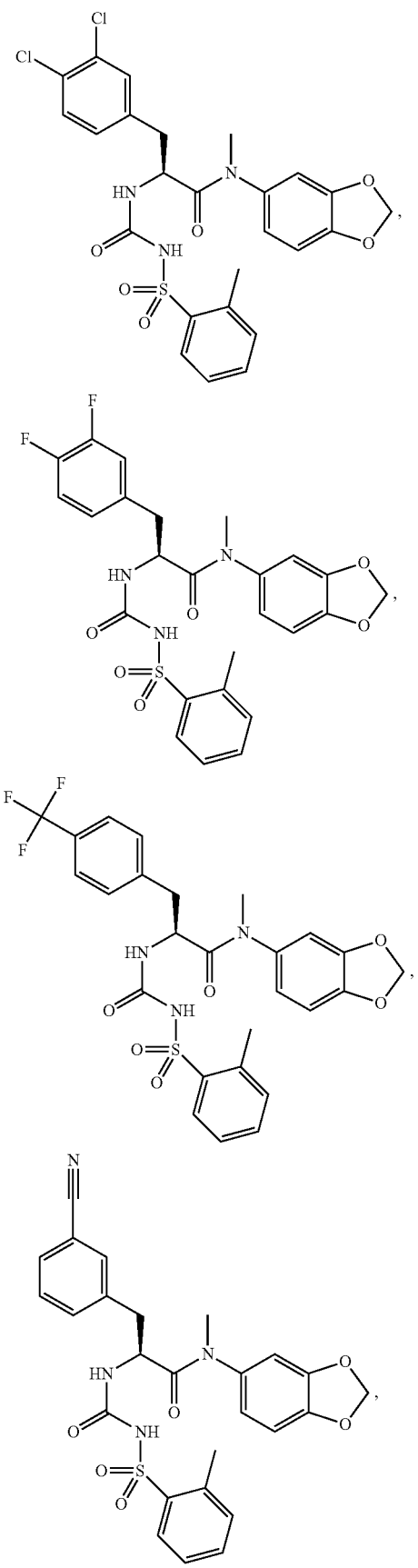

449
-continued
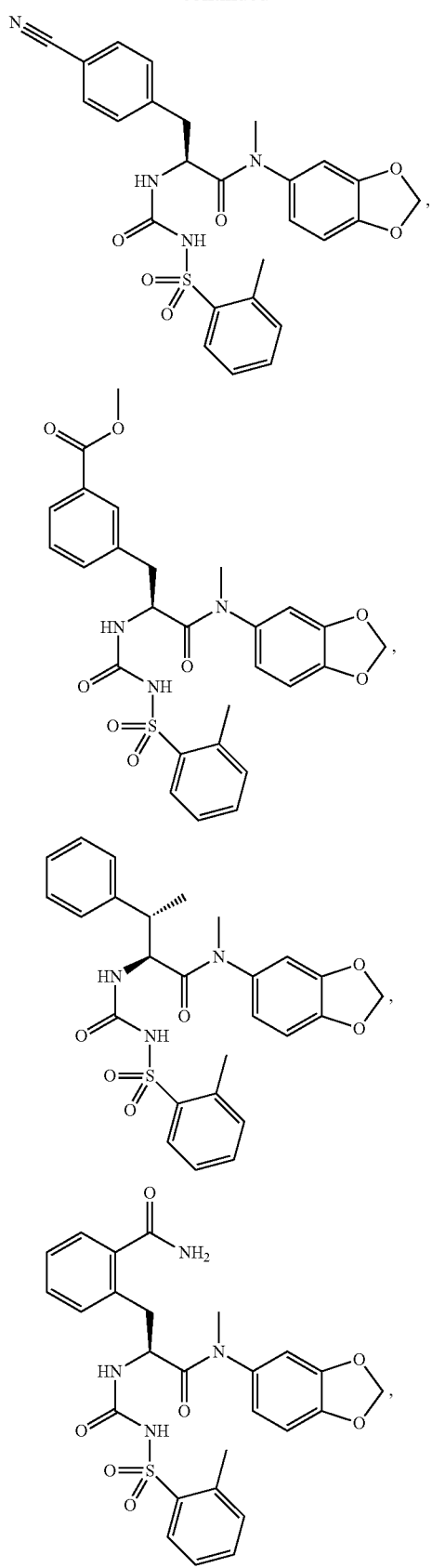 [SMILES: Cc1ccccc1S(=O)(=O)NC(=O)N[C@@H](Cc1ccc(C#N)cc1)C(=O)N(C)c1ccc2c(c1)OCO2 ; COC(=O)c1cccc(C[C@H](NC(=O)NS(=O)(=O)c2ccccc2C)C(=O)N(C)c2ccc3c(c2)OCO3)c1 ; Cc1ccccc1S(=O)(=O)NC(=O)N[C@H](C(=O)N(C)c1ccc2c(c1)OCO2)[C@@H](C)c1ccccc1 ; Cc1ccccc1S(=O)(=O)NC(=O)N[C@@H](Cc1ccccc1C(N)=O)C(=O)N(C)c1ccc2c(c1)OCO2]
450
-continued
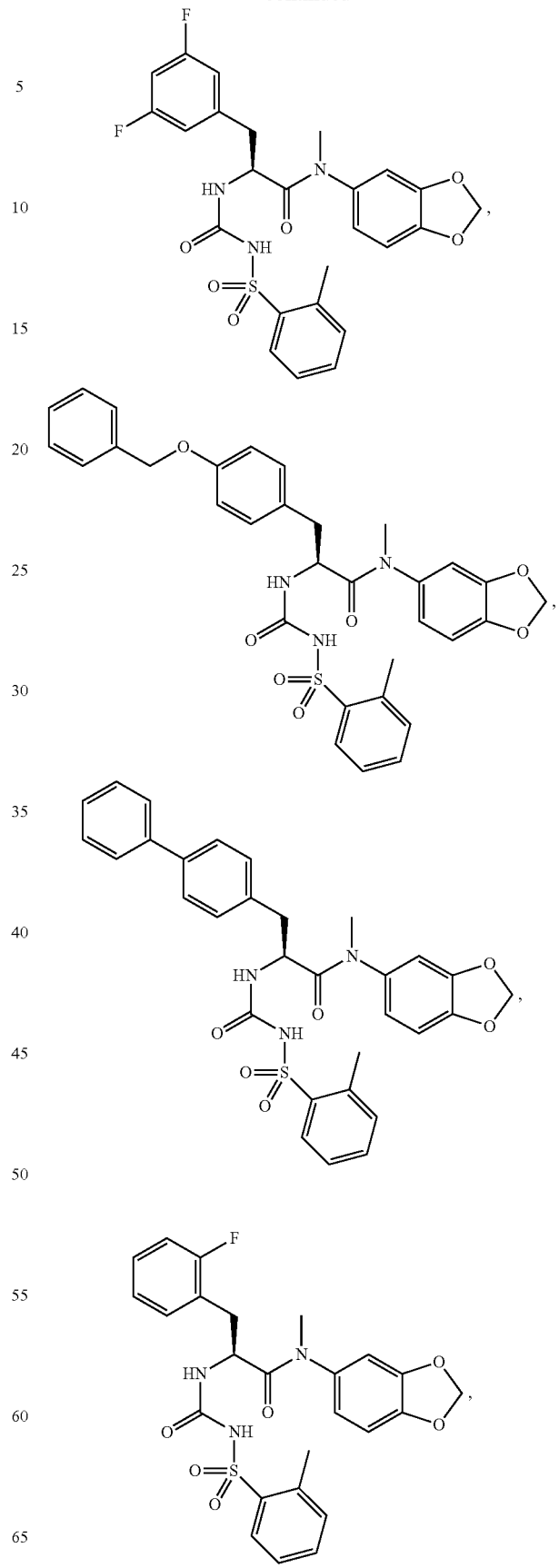

451
-continued
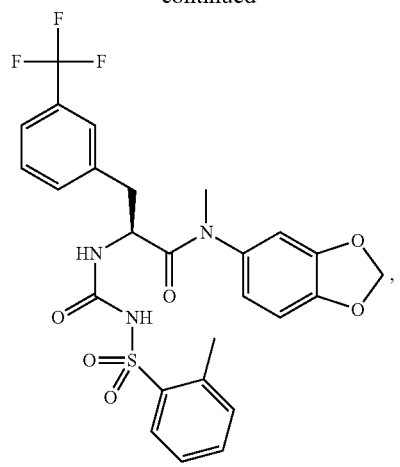
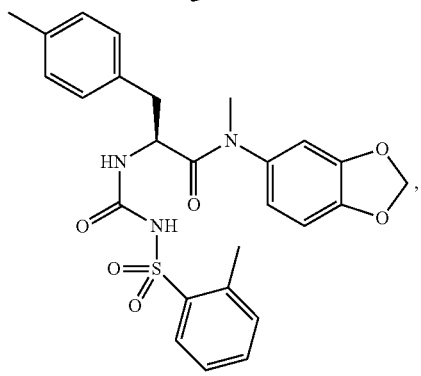
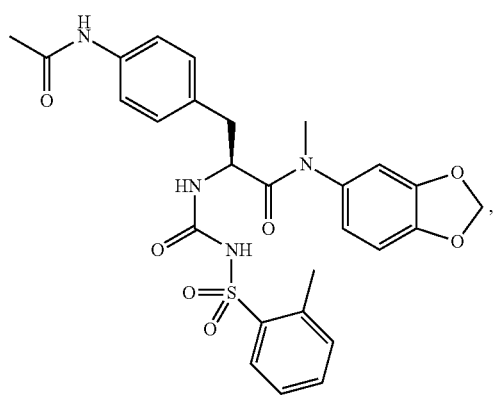
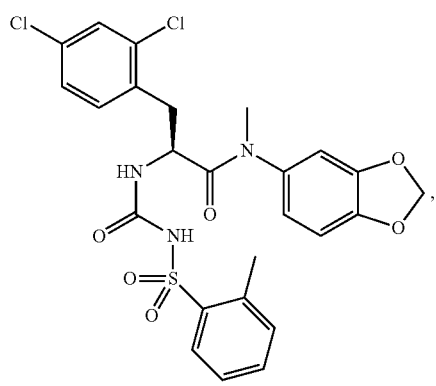
452
-continued
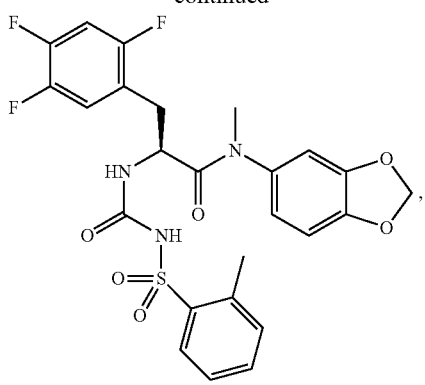
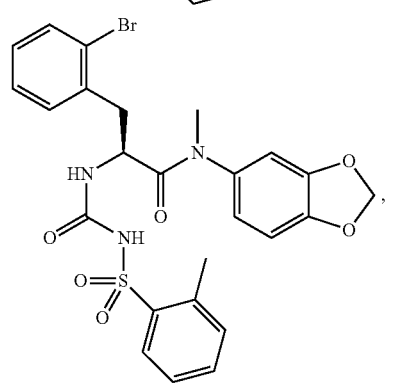
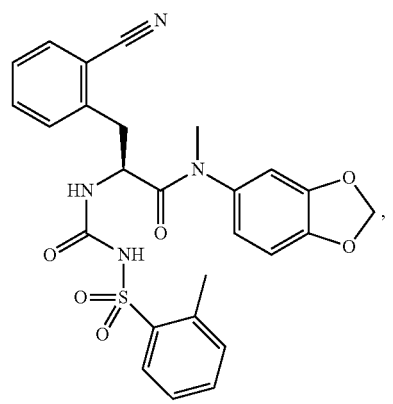
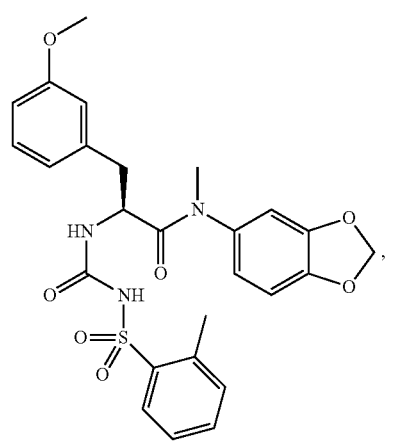

453
-continued
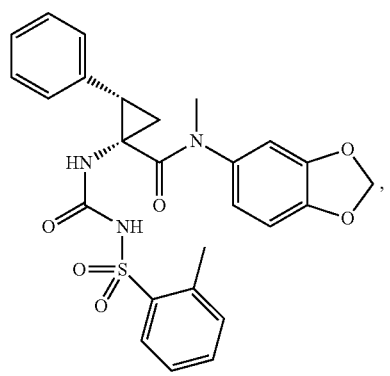
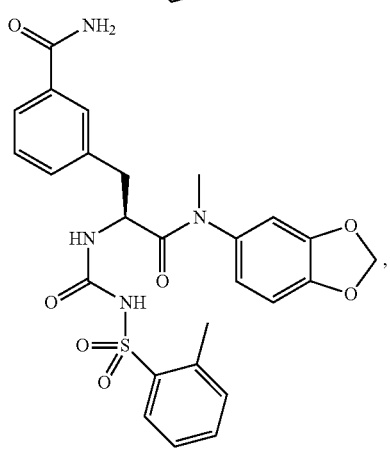
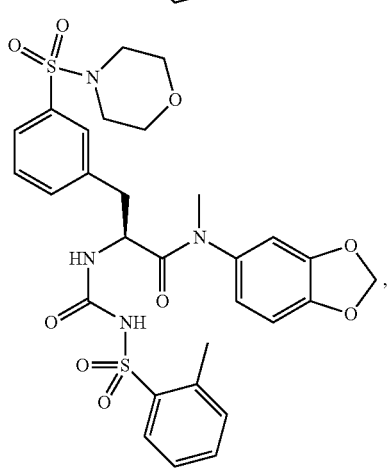
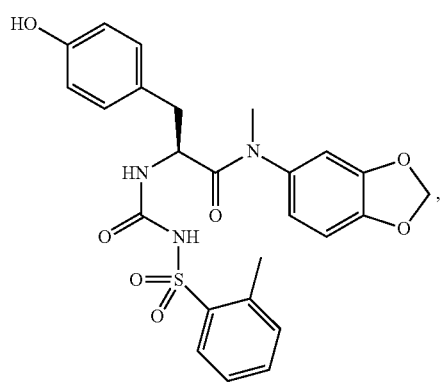
454
-continued
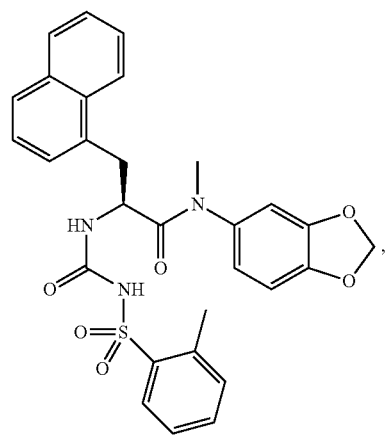
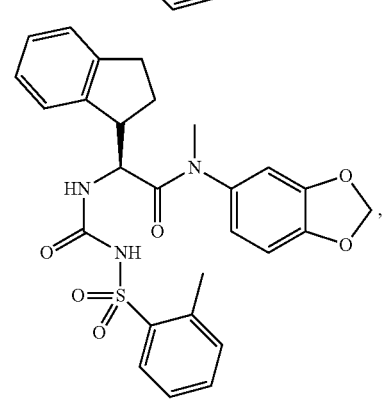
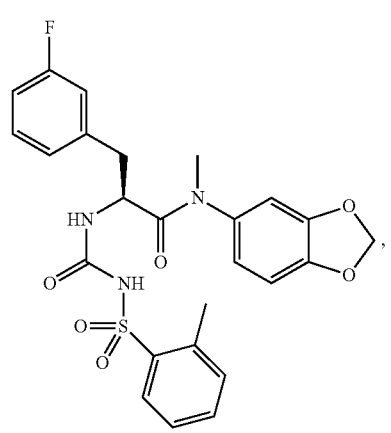
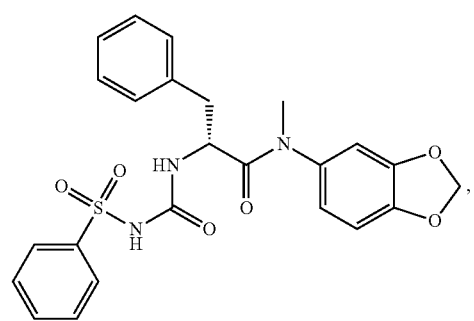

455
-continued
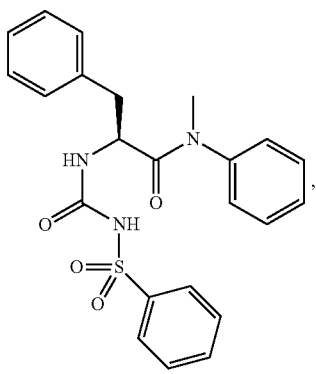
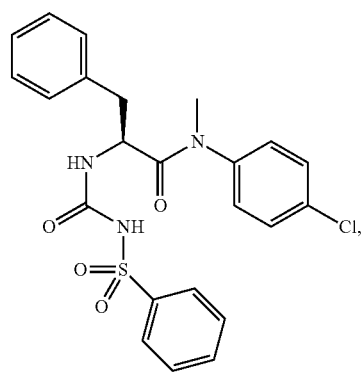
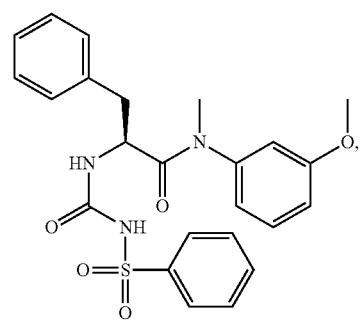
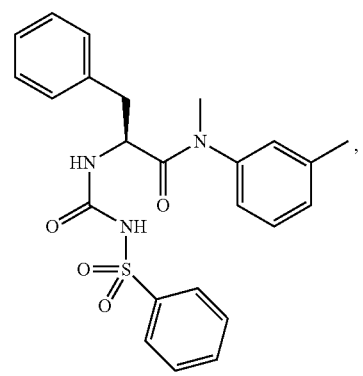
456
-continued
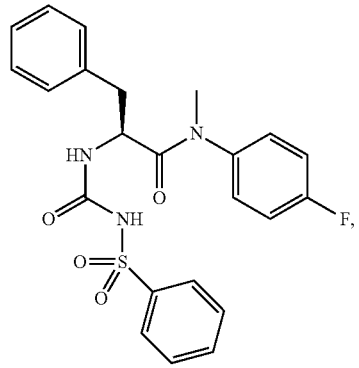
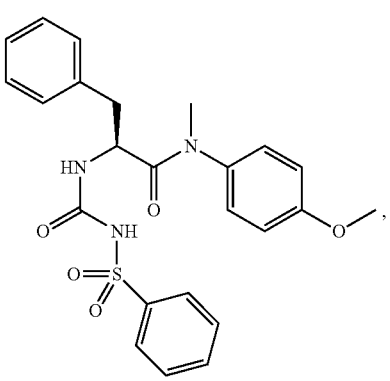
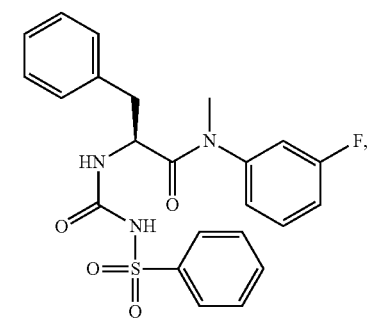
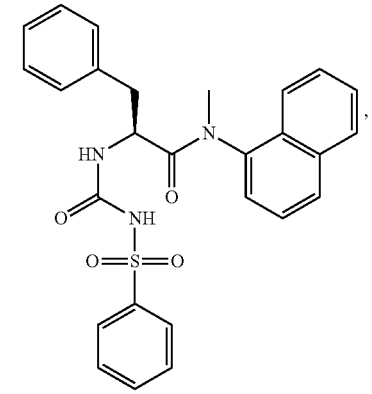

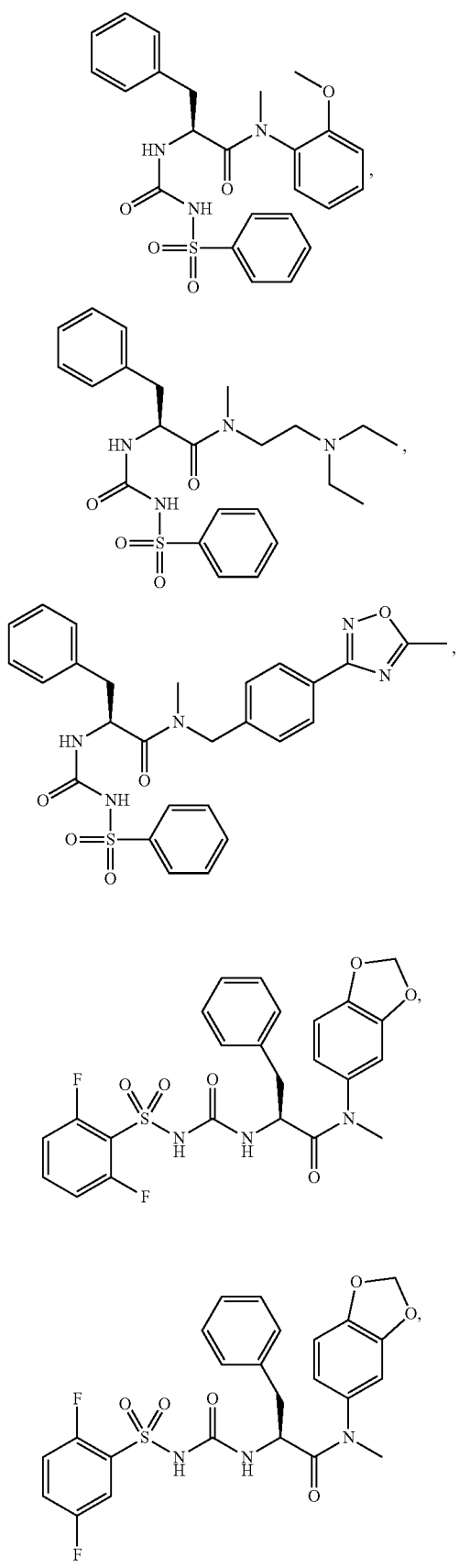
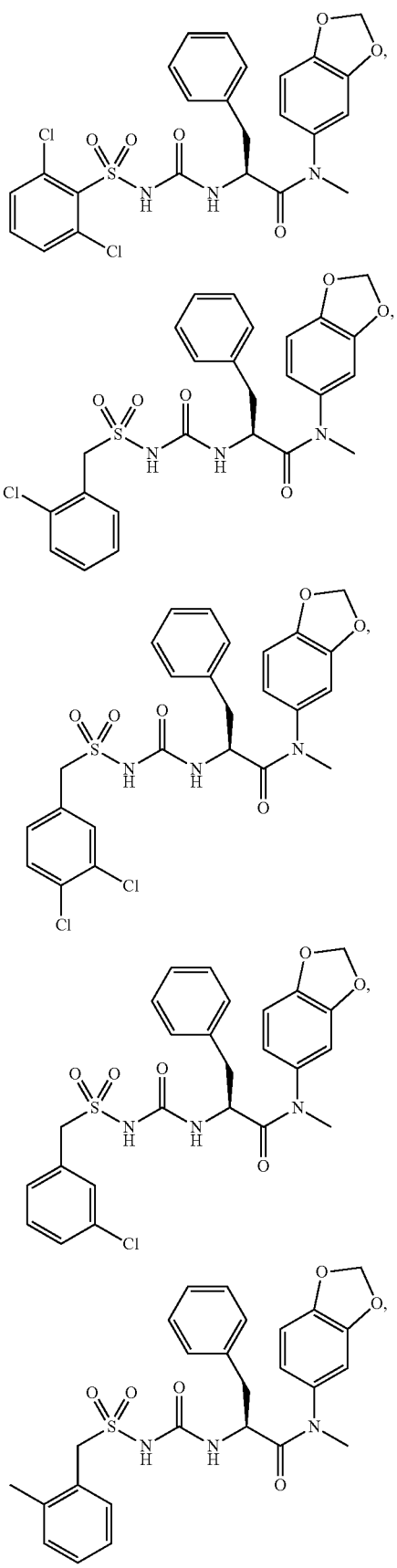 [SMILES: CN(C(=O)[C@H](Cc1ccccc1)NC(=O)NS(=O)(=O)c1c(Cl)cccc1Cl)c1ccc2c(c1)OCO2 ; CN(C(=O)[C@H](Cc1ccccc1)NC(=O)NS(=O)(=O)Cc1ccccc1Cl)c1ccc2c(c1)OCO2 ; CN(C(=O)[C@H](Cc1ccccc1)NC(=O)NS(=O)(=O)Cc1ccc(Cl)c(Cl)c1)c1ccc2c(c1)OCO2 ; CN(C(=O)[C@H](Cc1ccccc1)NC(=O)NS(=O)(=O)Cc1cccc(Cl)c1)c1ccc2c(c1)OCO2 ; Cc1ccccc1CS(=O)(=O)NC(=O)N[C@@H](Cc1ccccc1)C(=O)N(C)c1ccc2c(c1)OCO2]

459
-continued
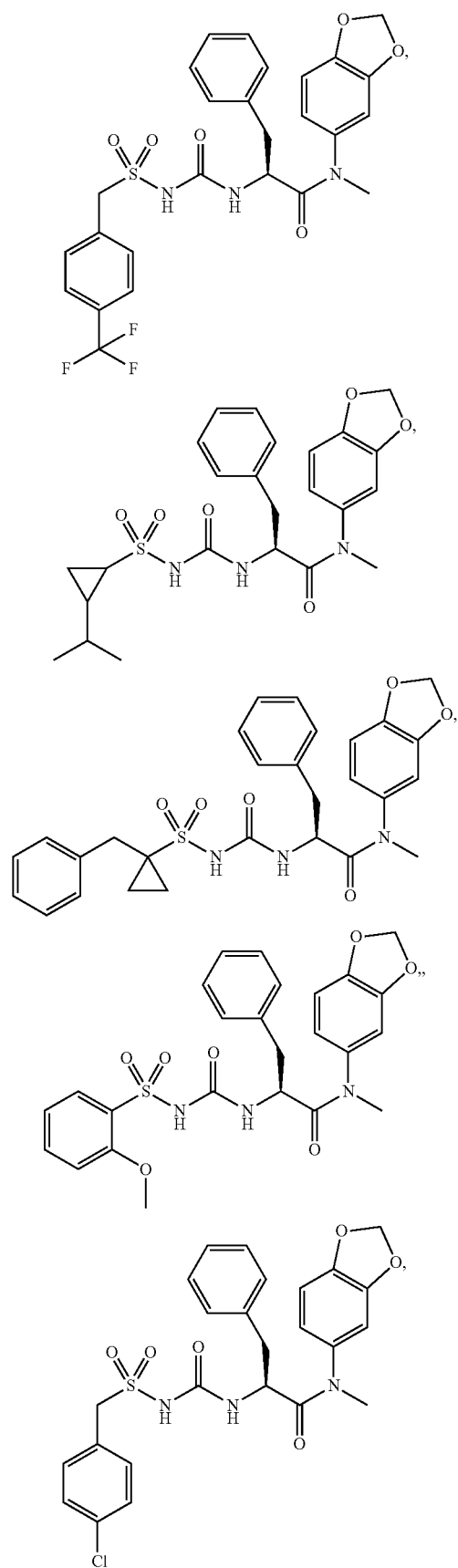
460
-continued
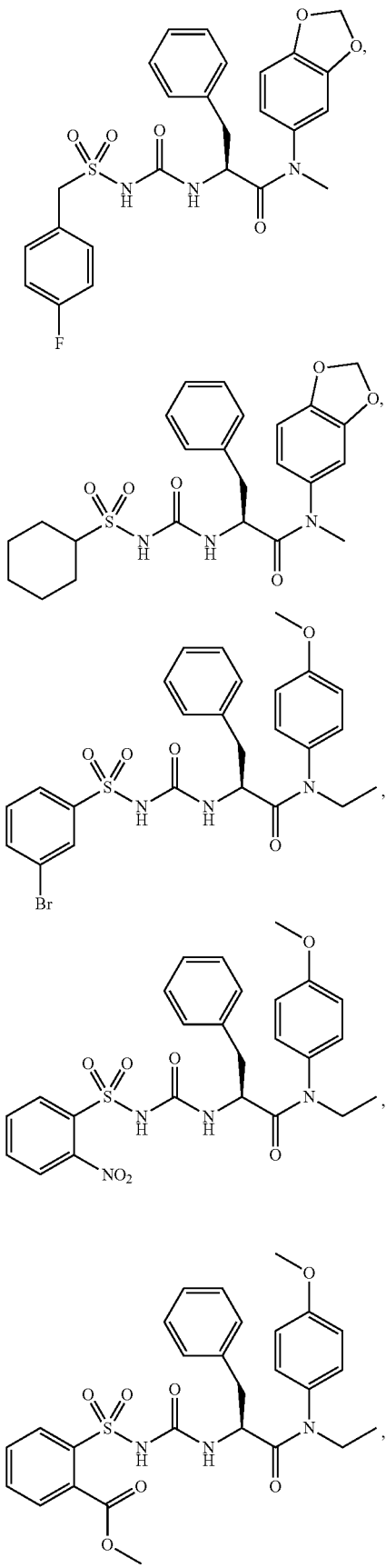

461
-continued
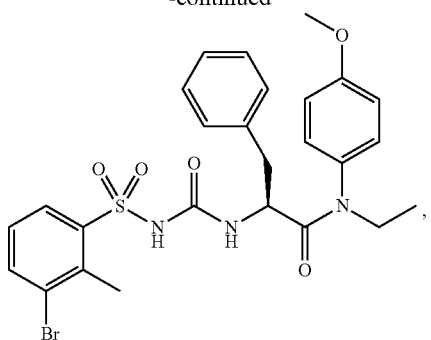
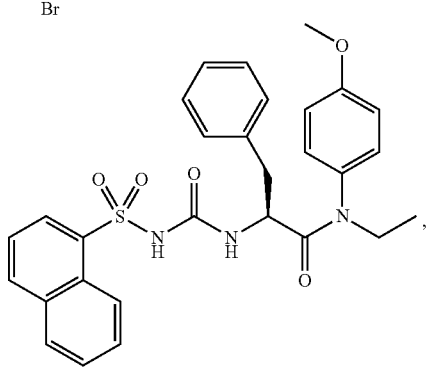
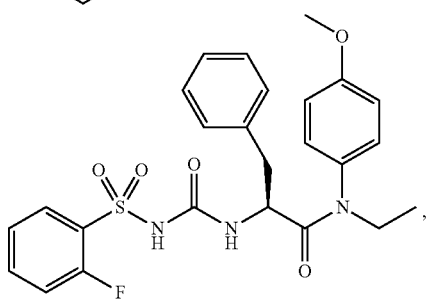
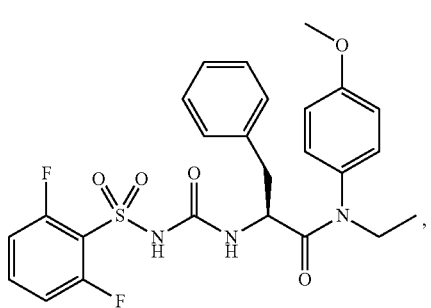
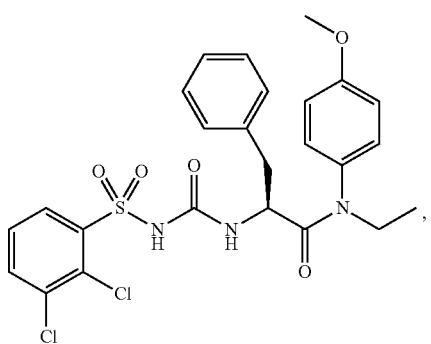
462
-continued
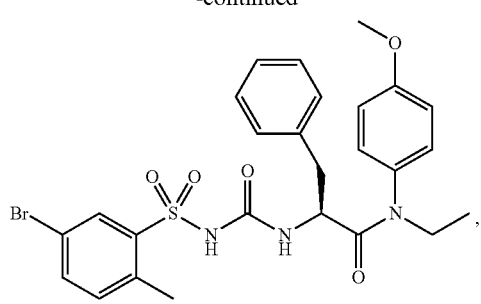
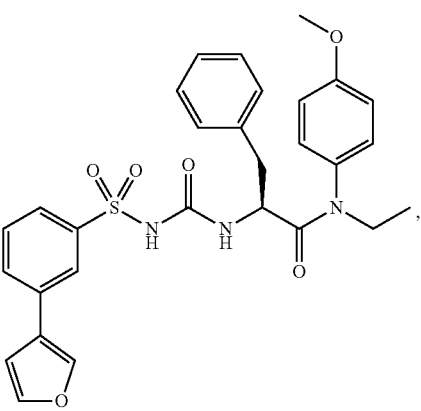
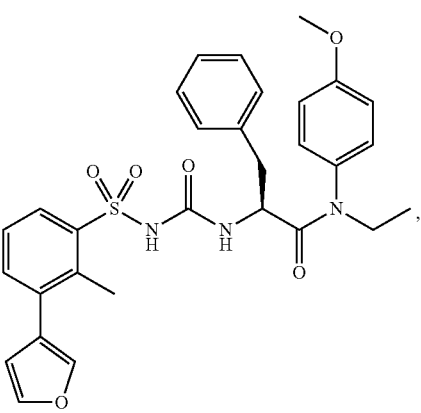
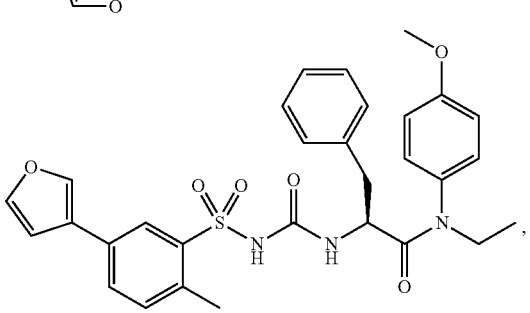

463
-continued
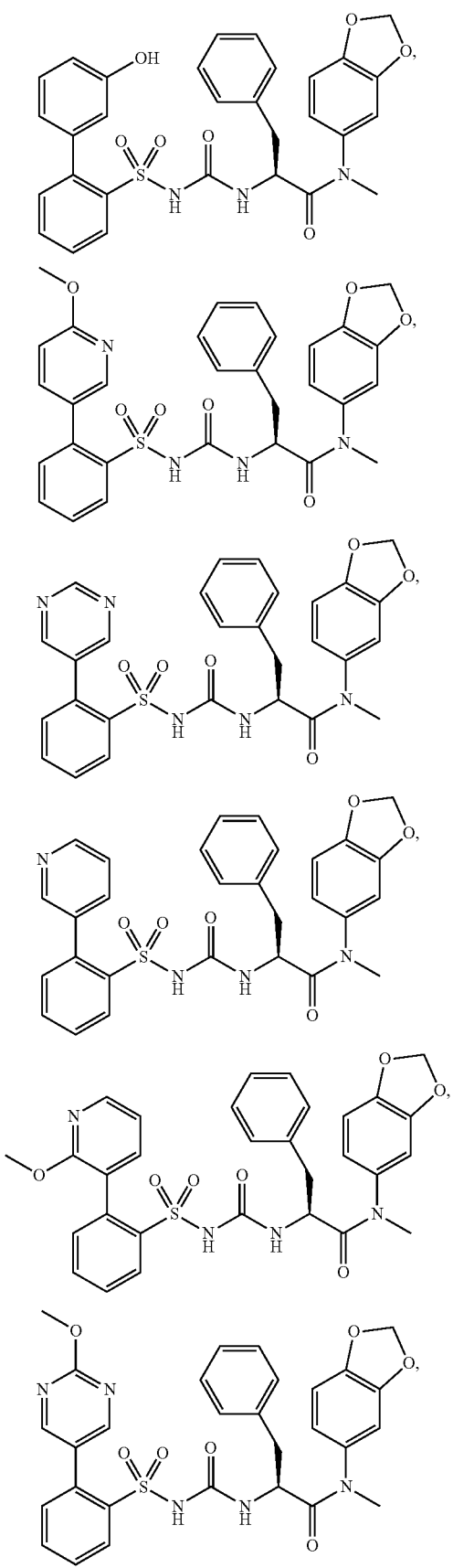
464
-continued
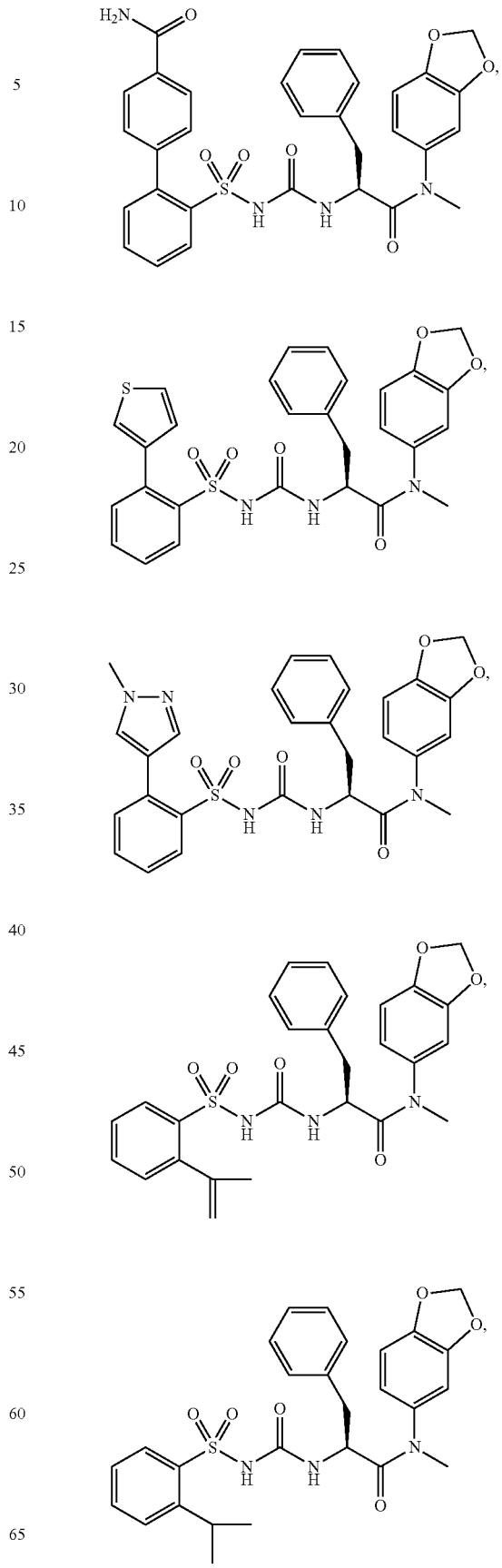

465
-continued
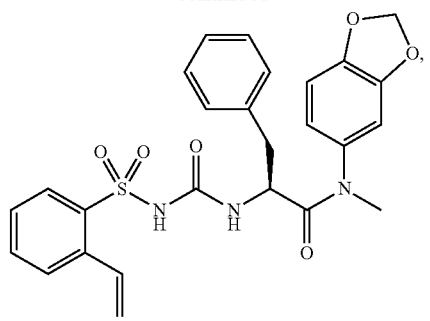
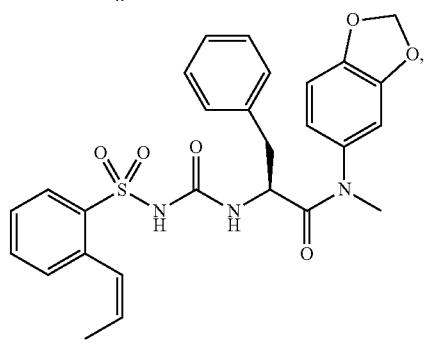
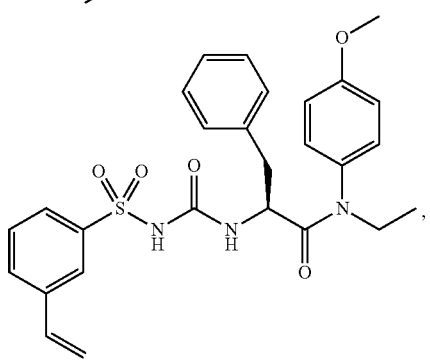
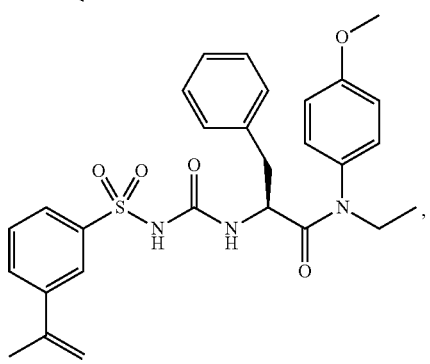
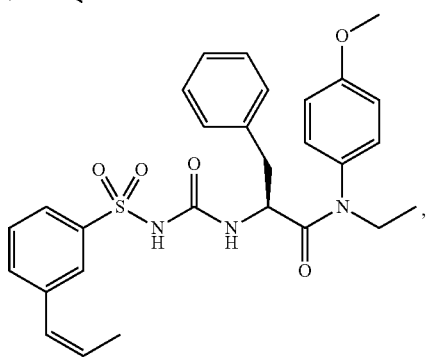
466
-continued
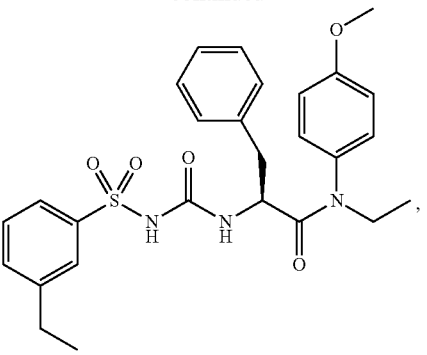
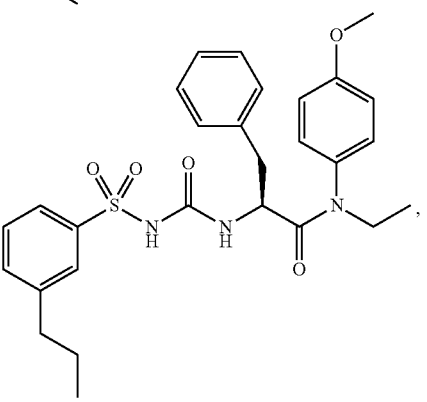
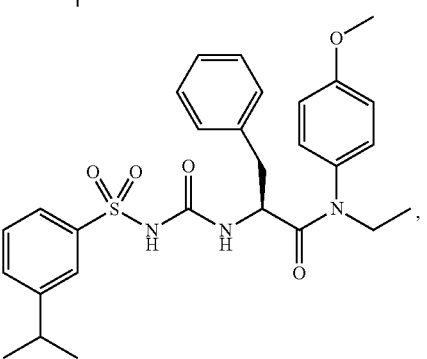
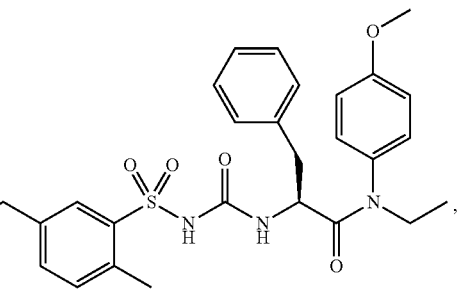
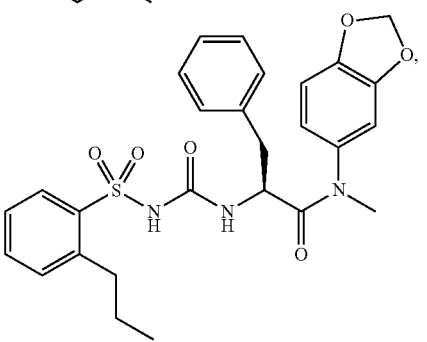

467
-continued
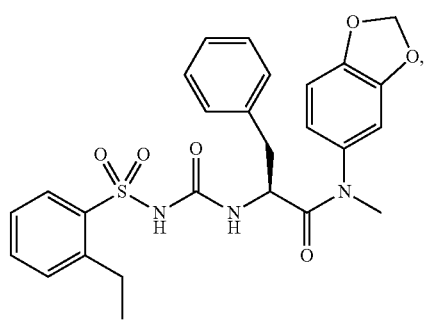
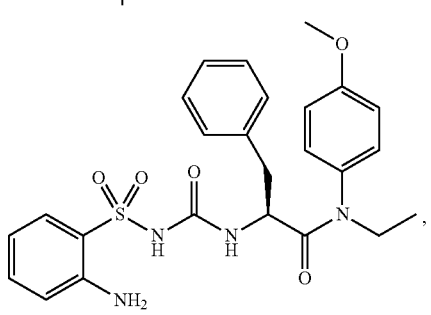
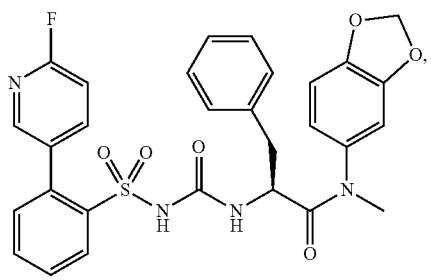
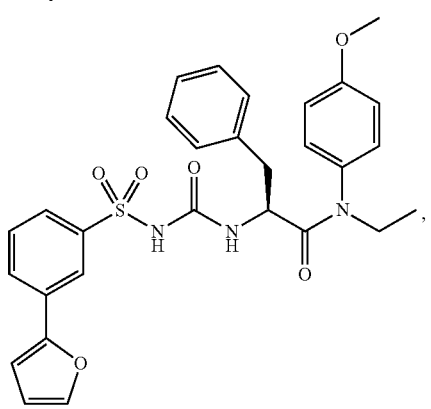
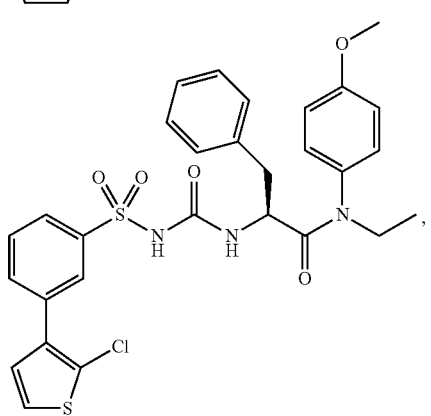
468
-continued
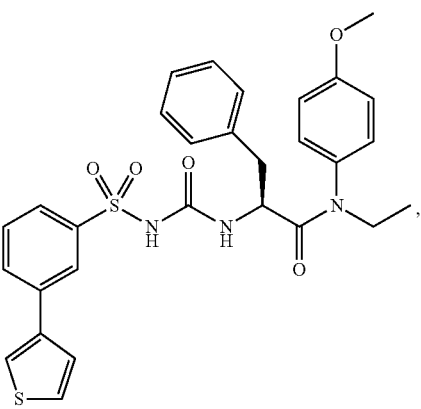
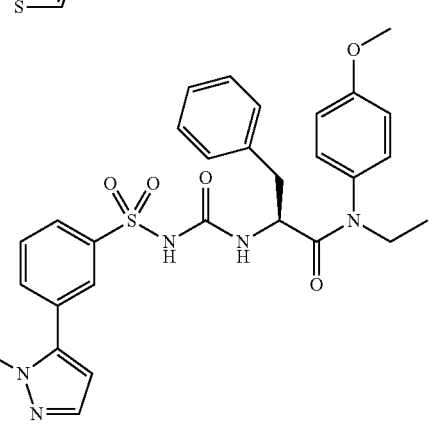
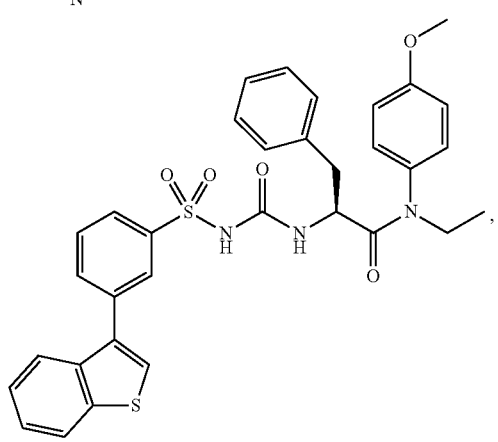
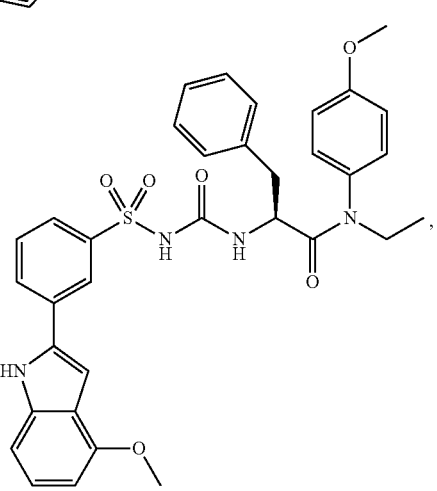

469
-continued
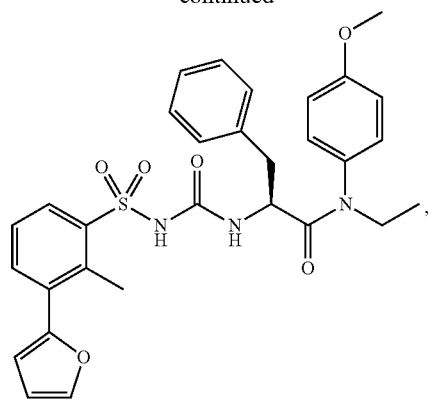
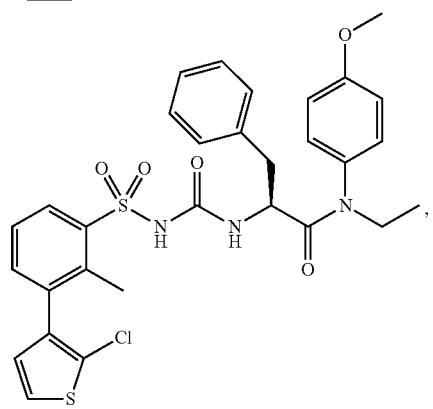
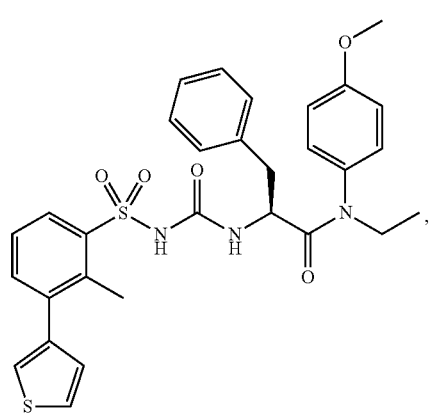
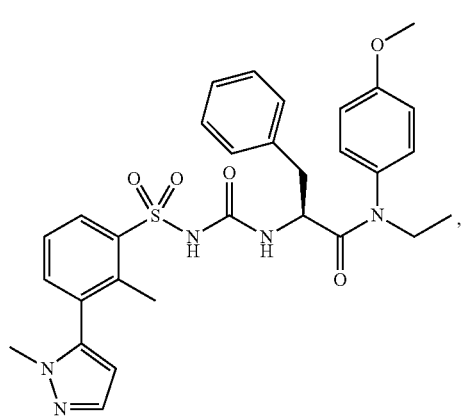
470
-continued
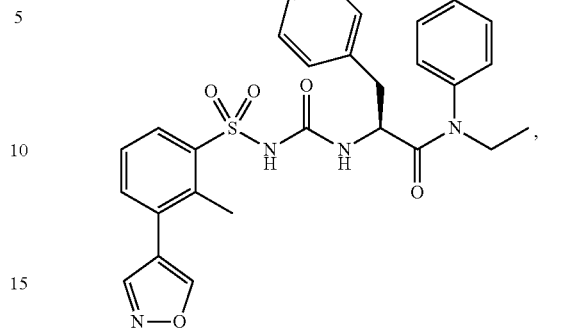
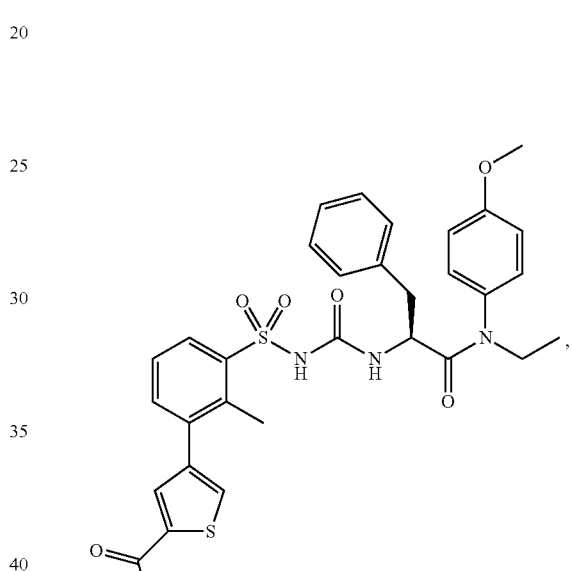
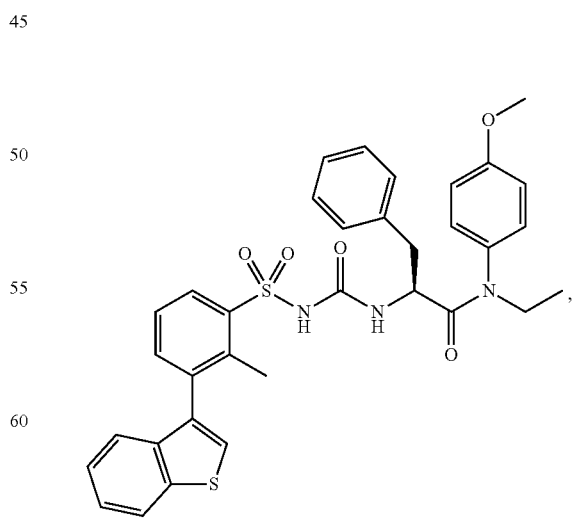

471
-continued
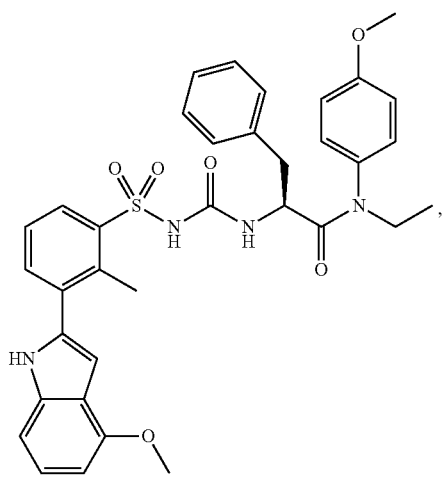
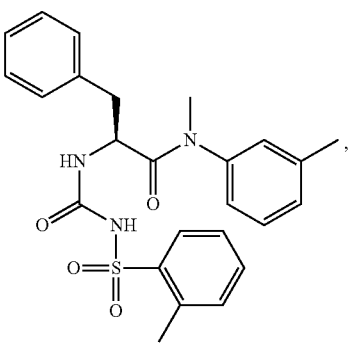
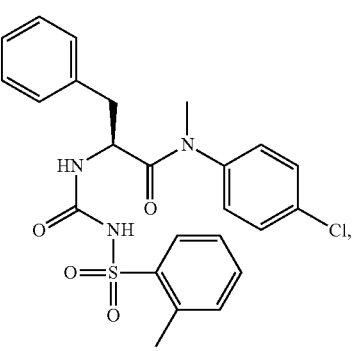
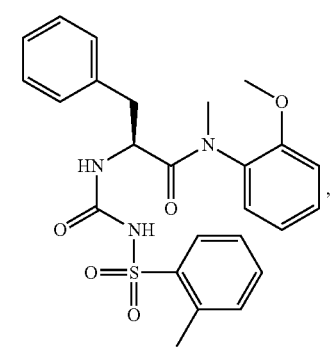
472
-continued
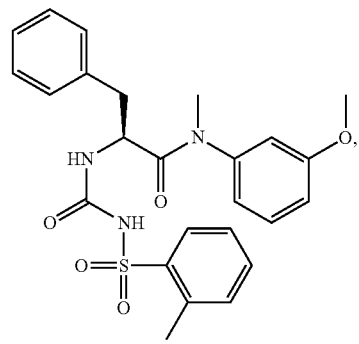
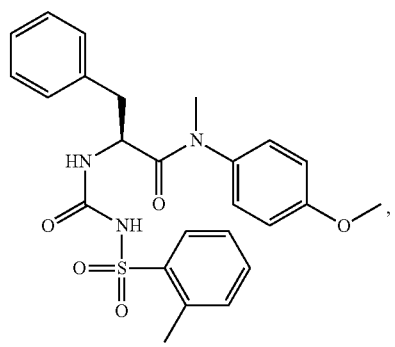
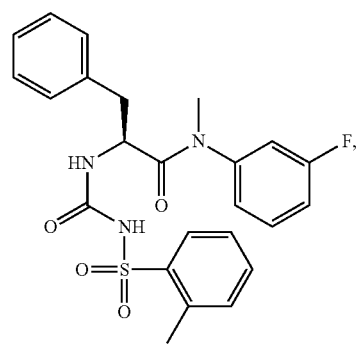
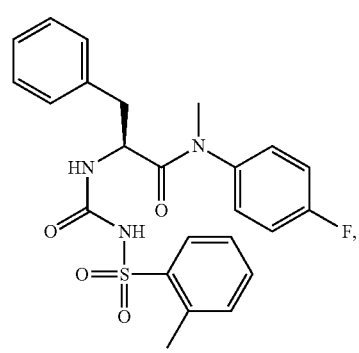
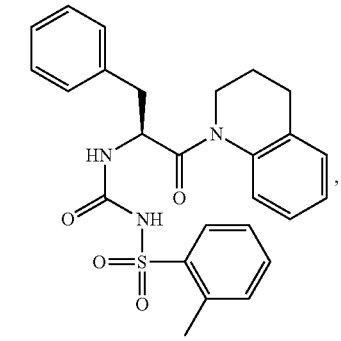

473
-continued
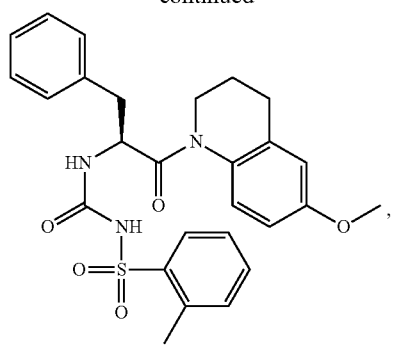
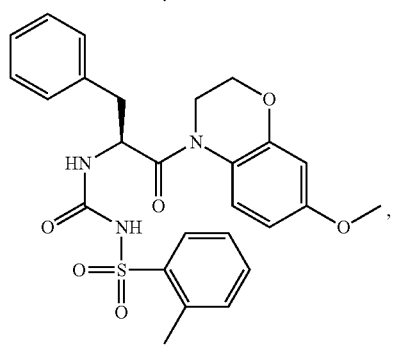
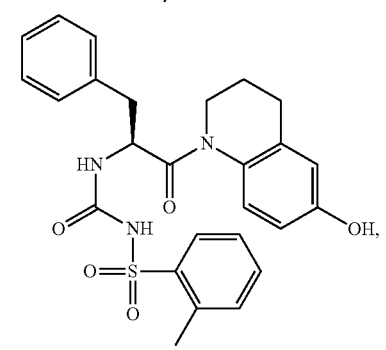
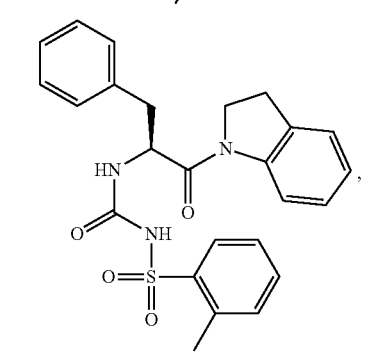
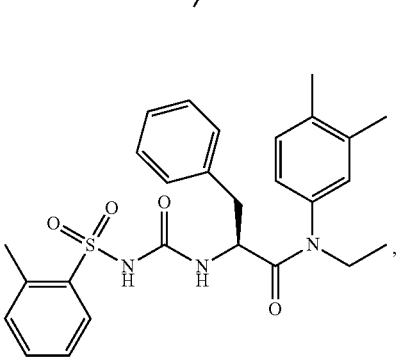
474
-continued
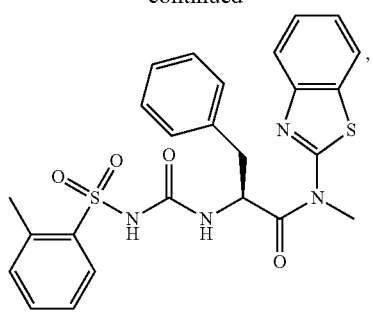
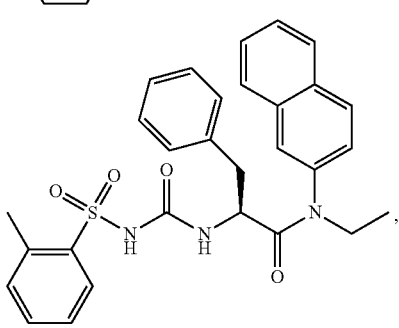
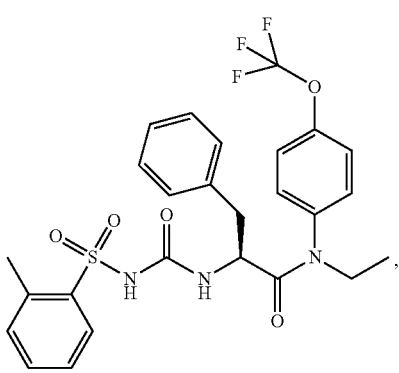
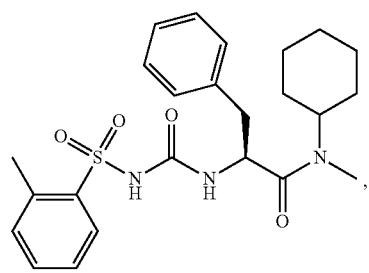
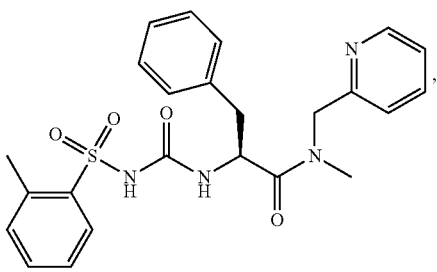

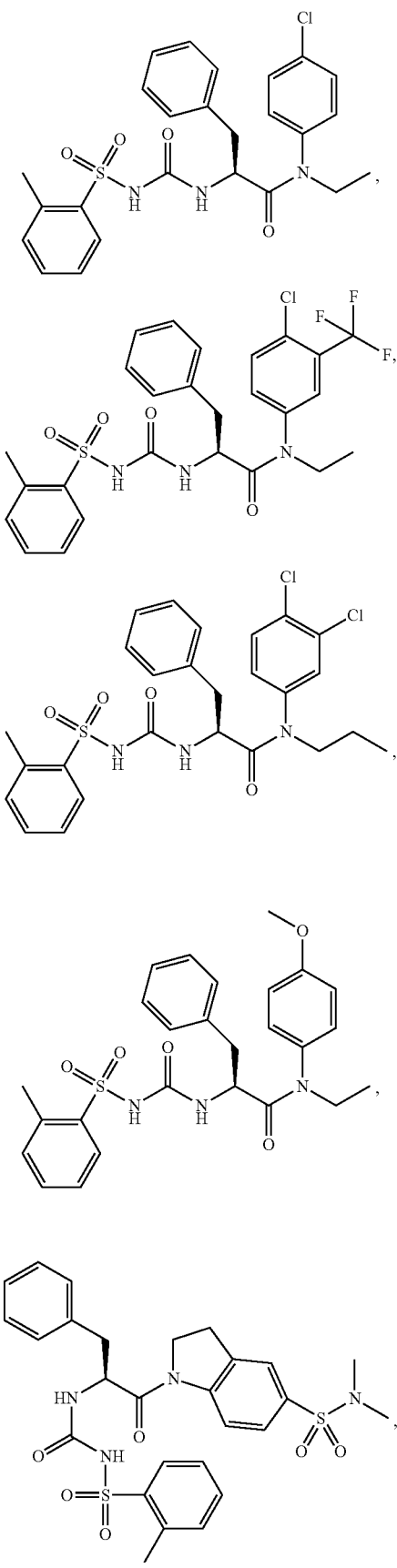
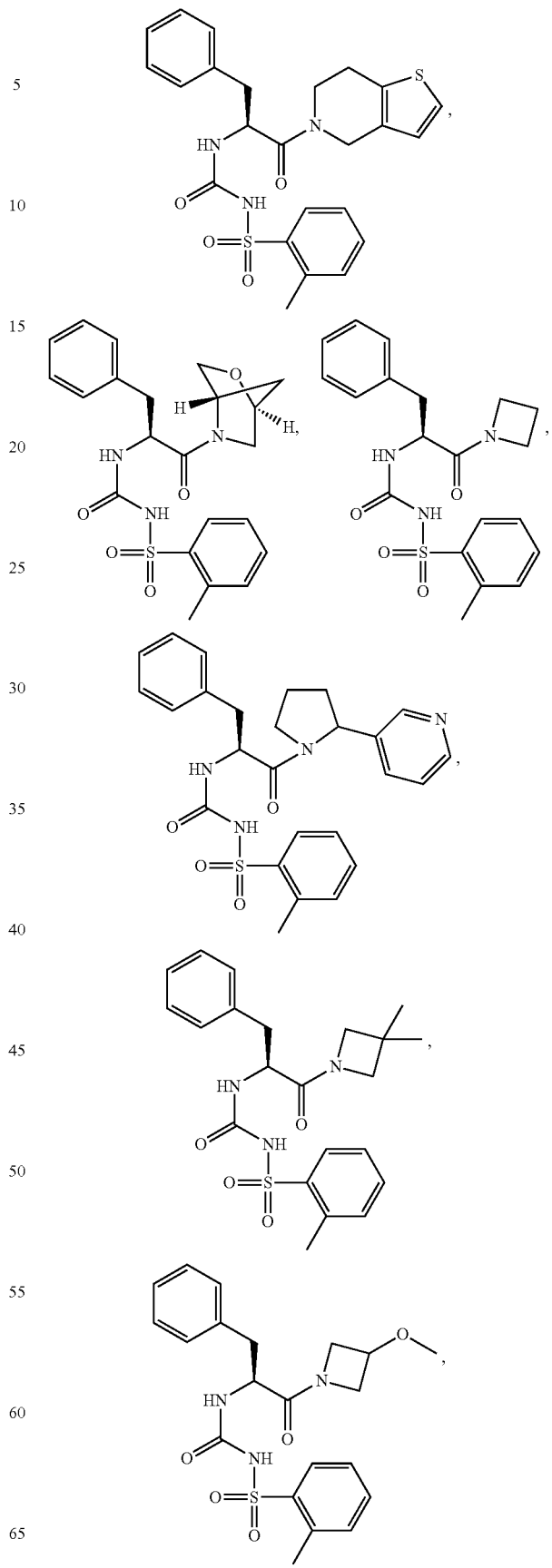

477
-continued
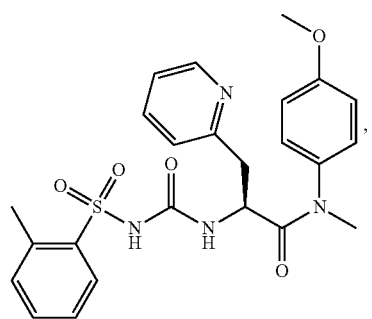
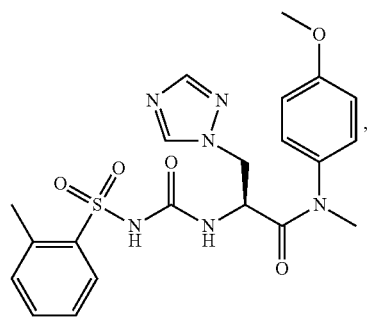
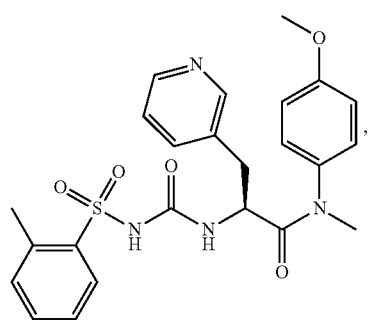
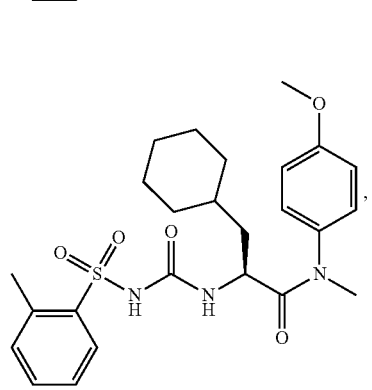
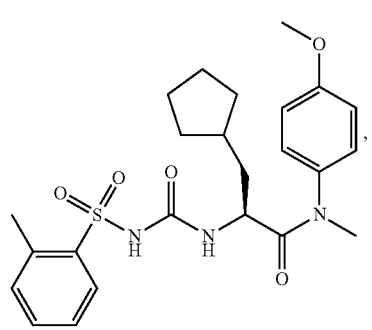
478
-continued
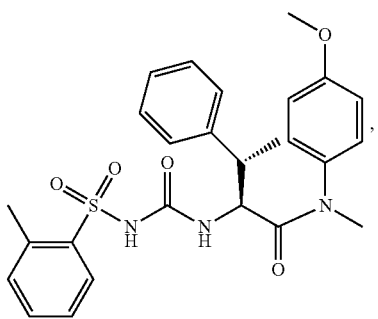
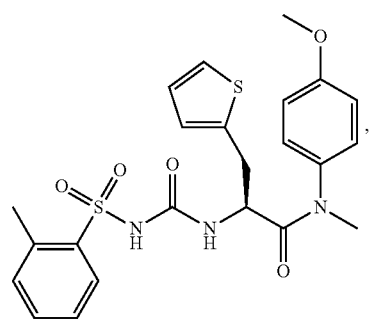
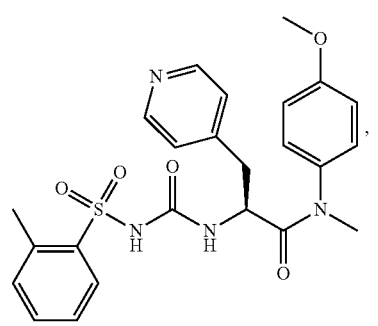
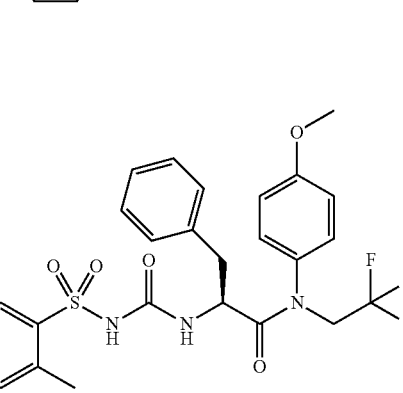
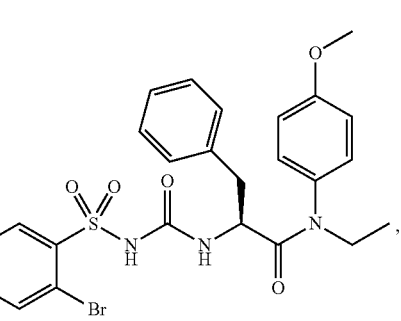

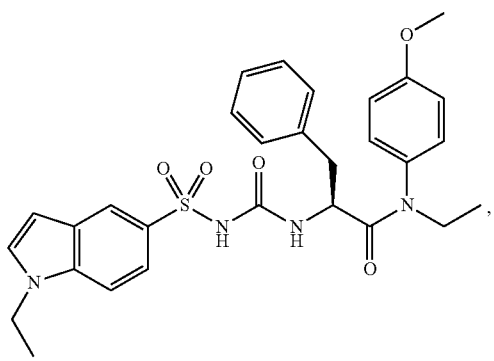
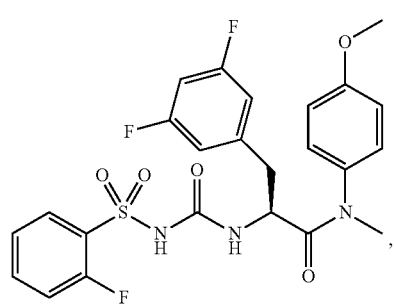
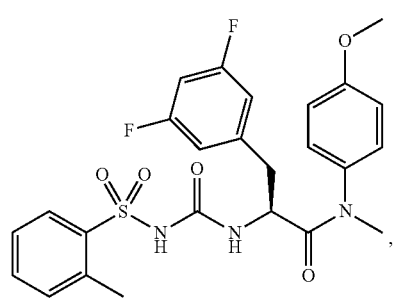
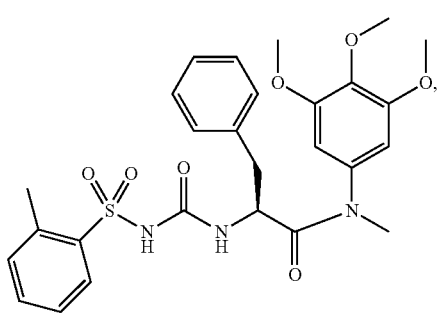
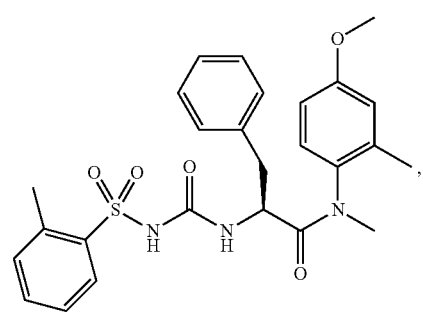
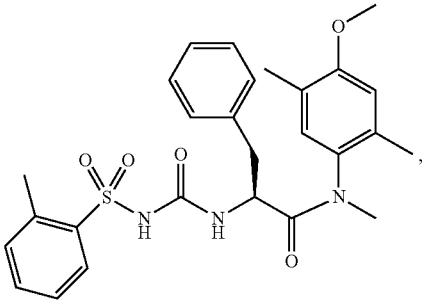
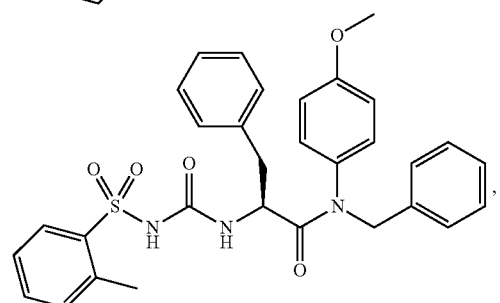
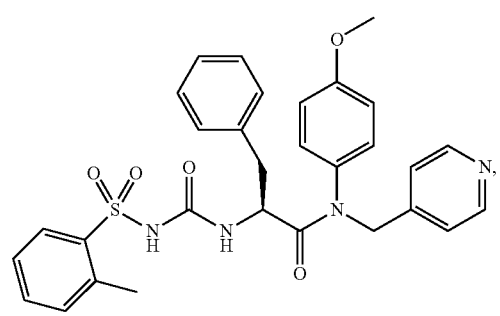
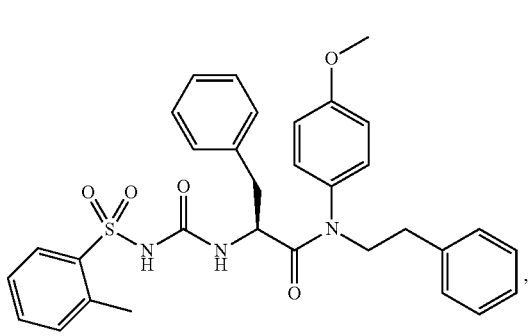
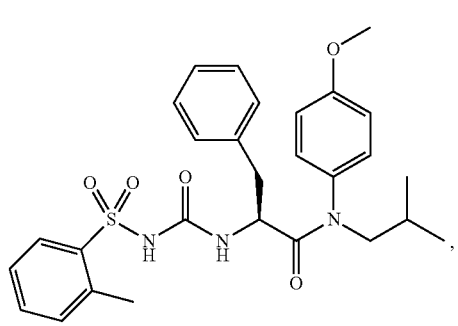

481
-continued
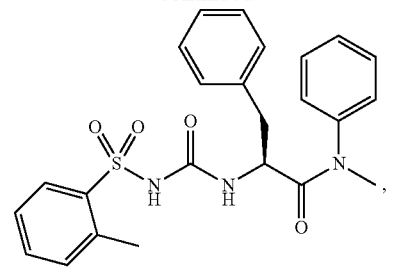
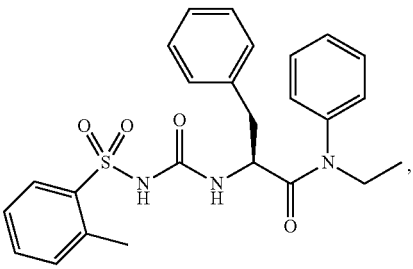
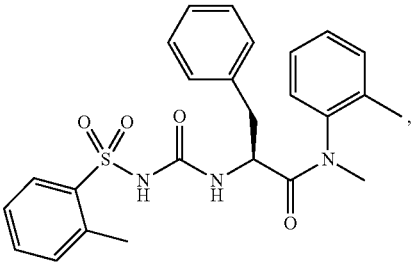
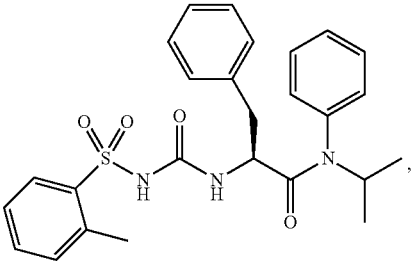
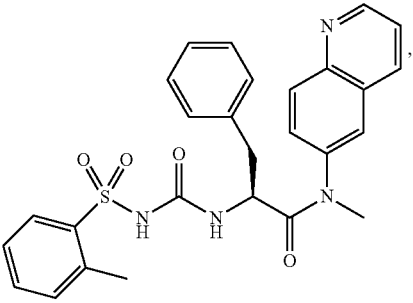
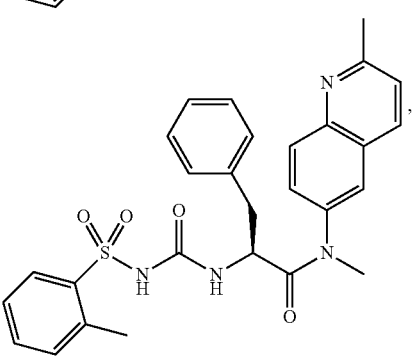
482
-continued
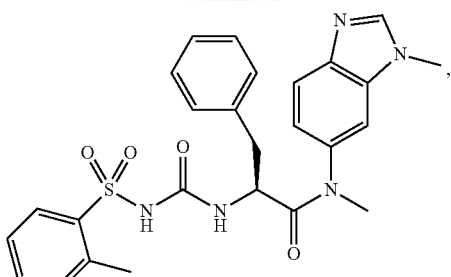
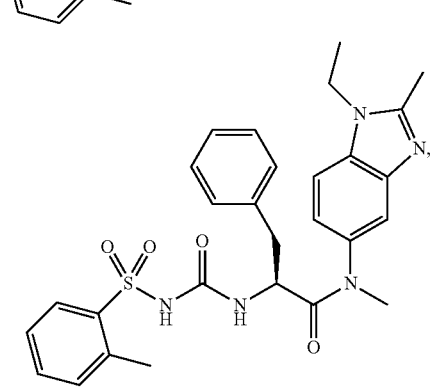
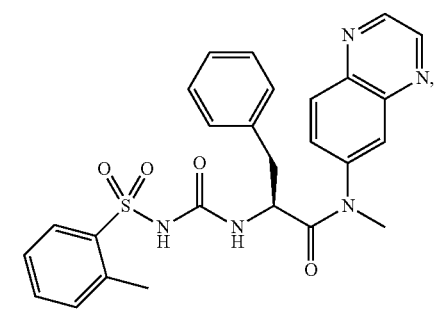
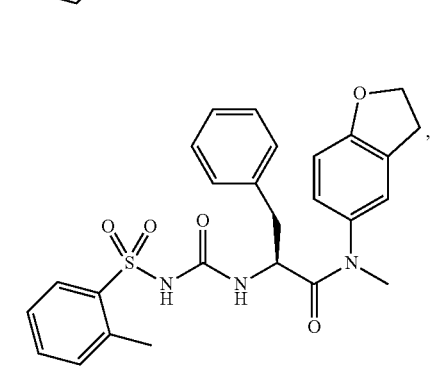
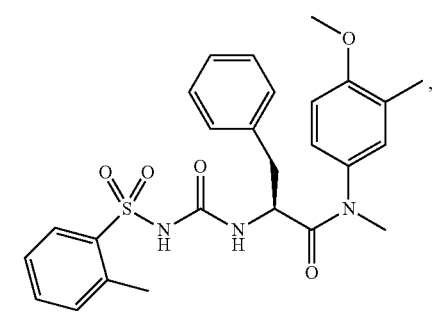

483
-continued
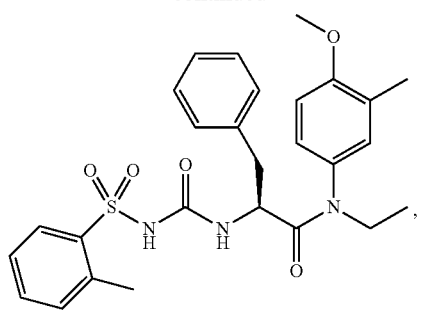
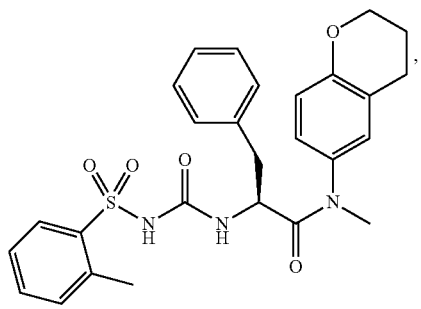
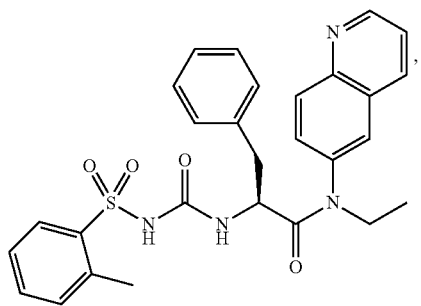
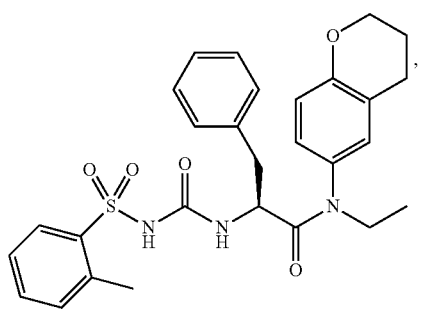
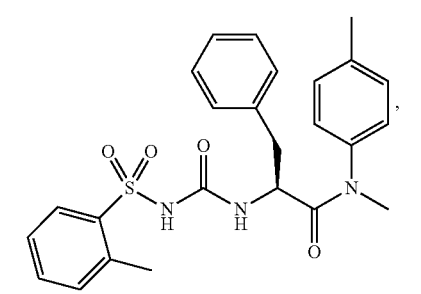
484
-continued
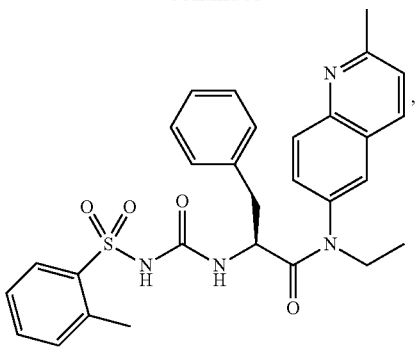
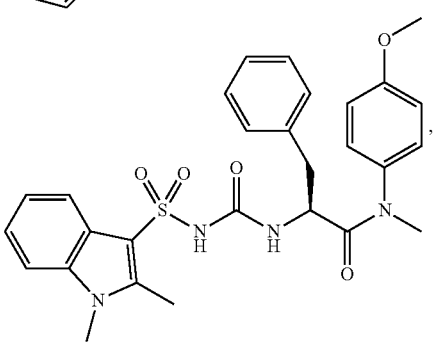
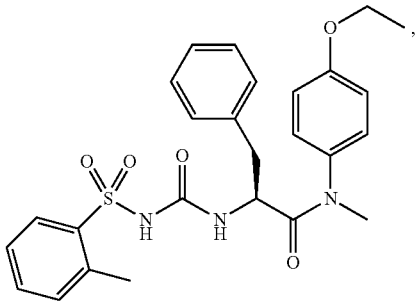
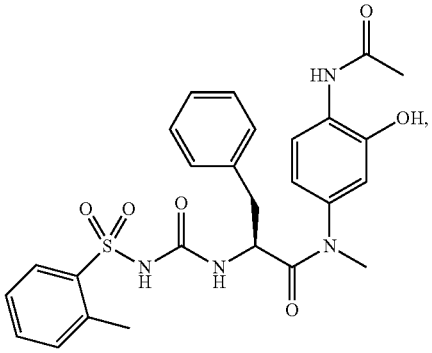
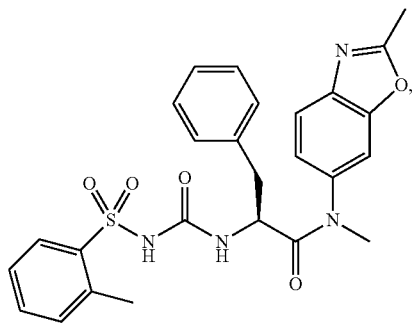

485
-continued
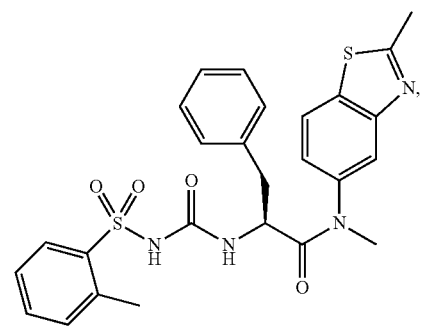
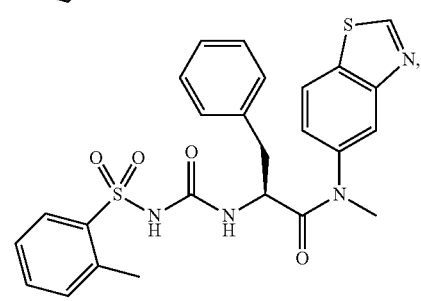
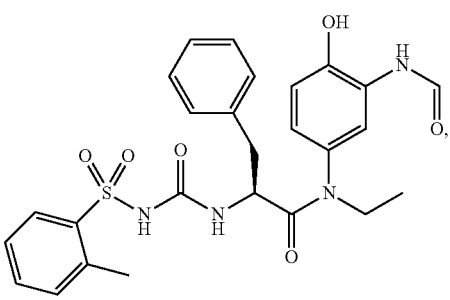
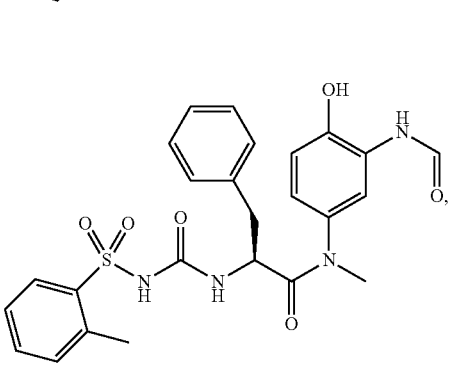
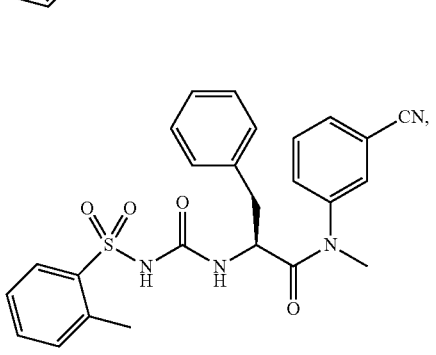
486
-continued
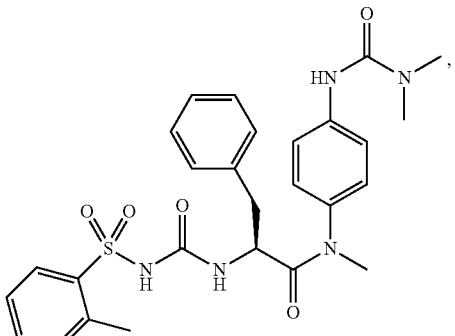
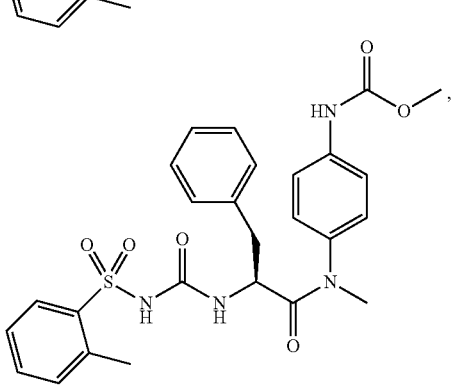
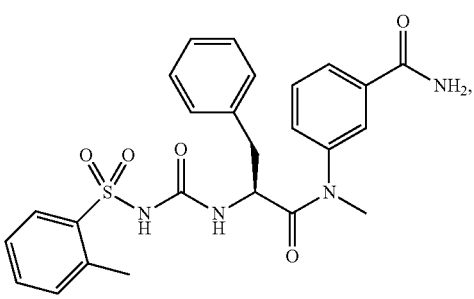
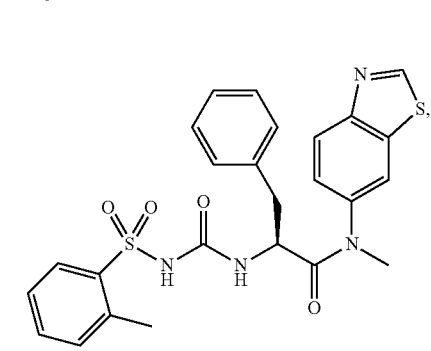
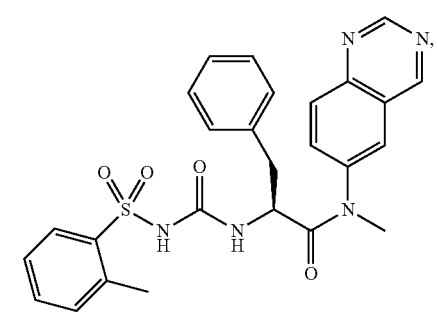

487
-continued
488
-continued
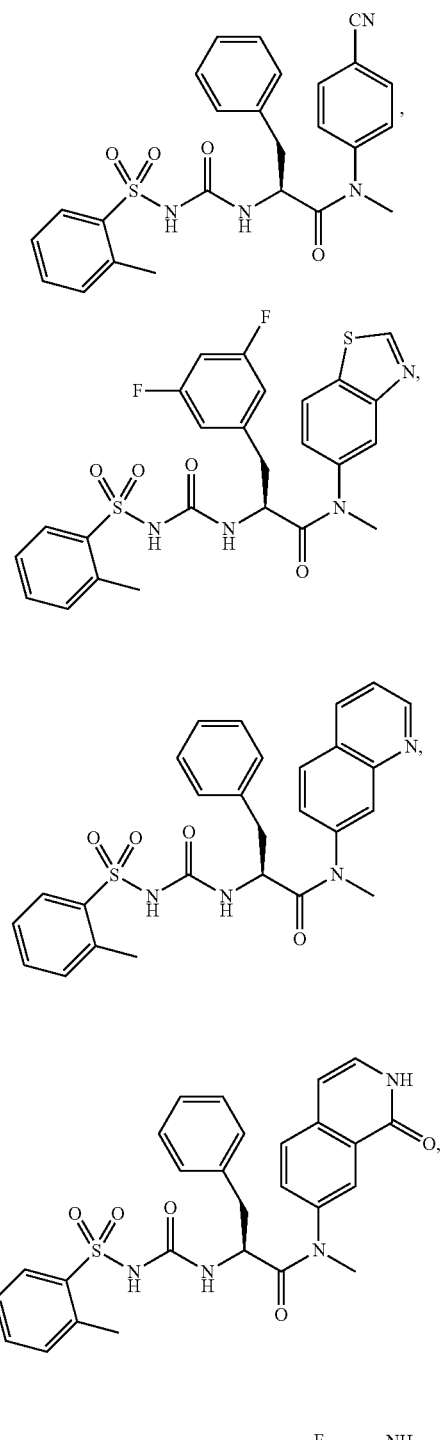
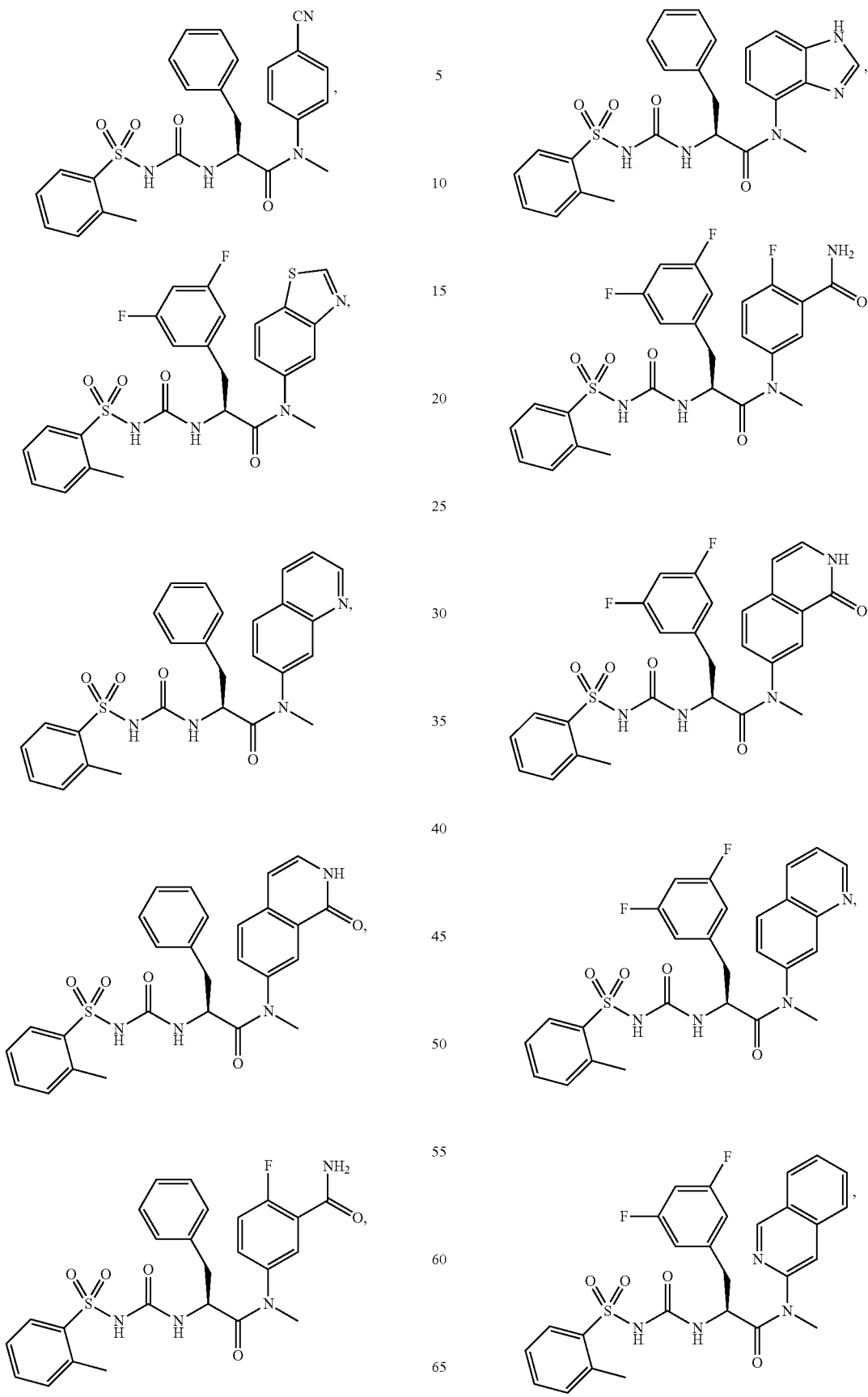

489
-continued
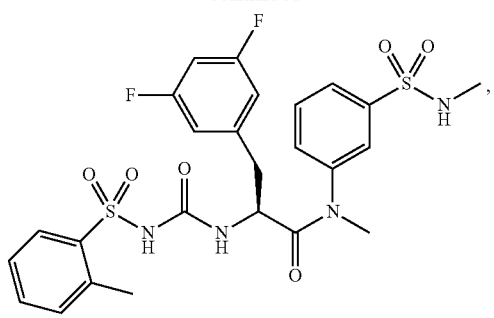
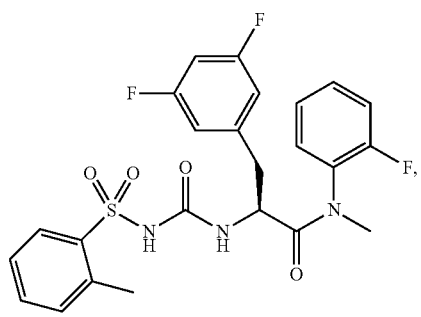
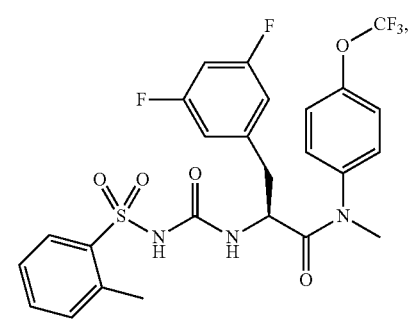
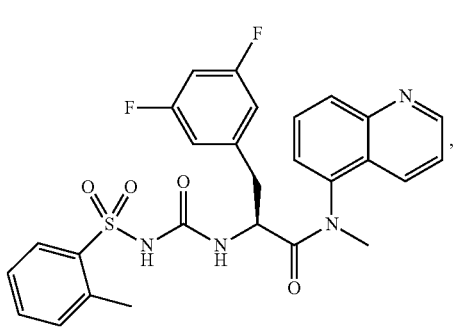
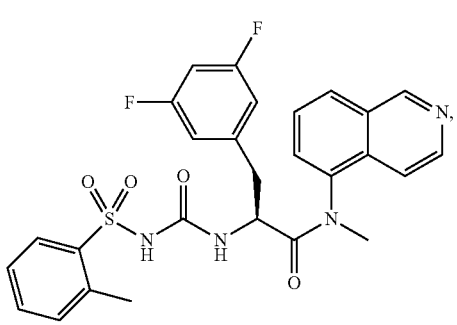
490
-continued
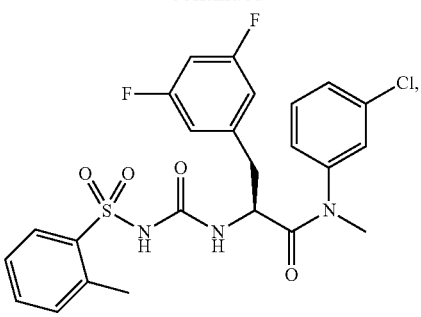
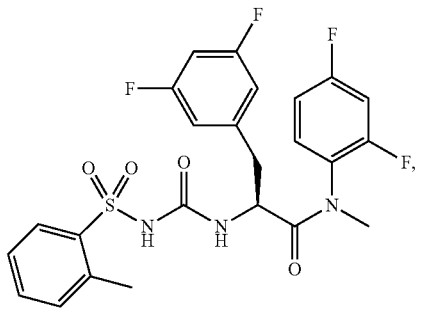
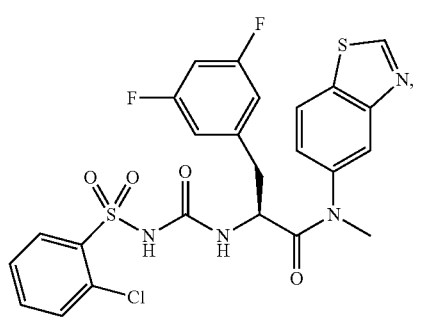
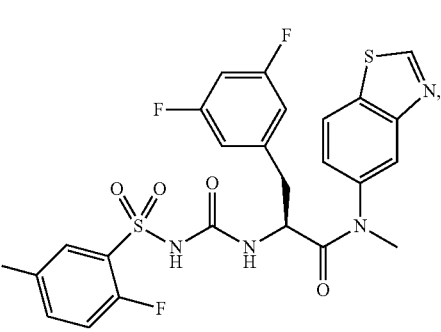
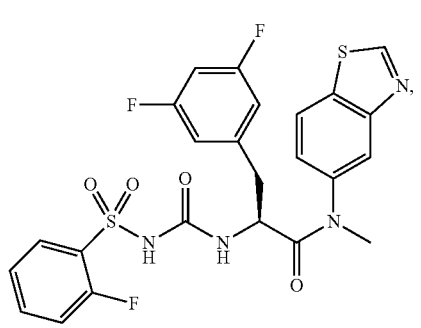

491
-continued
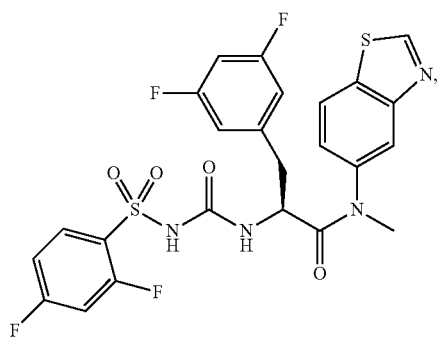
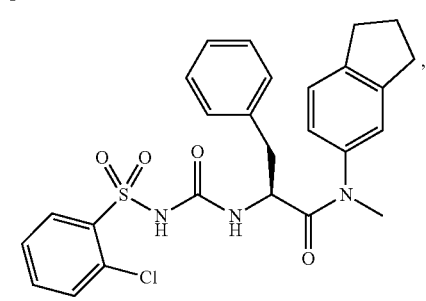
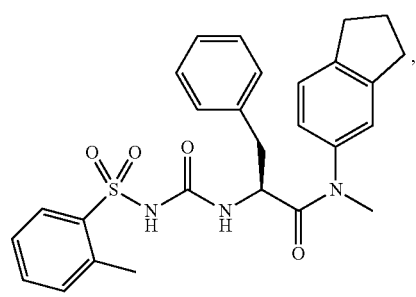
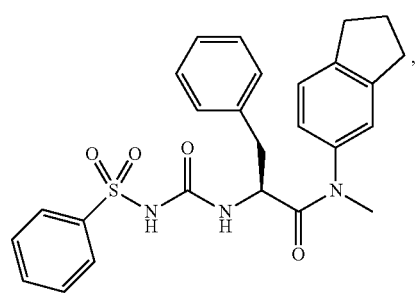
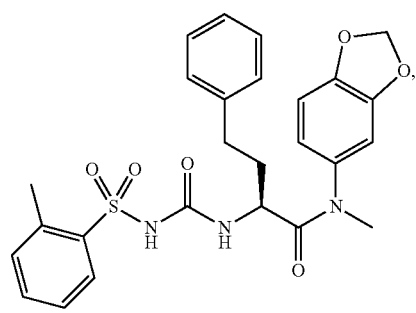
492
-continued
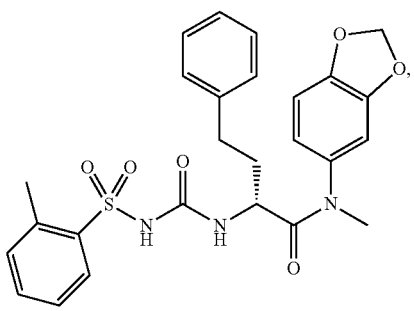
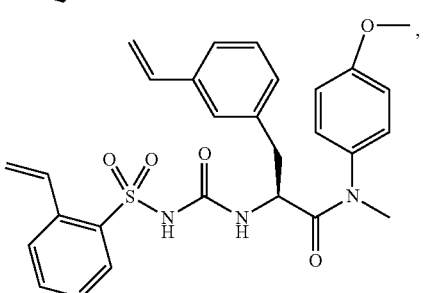
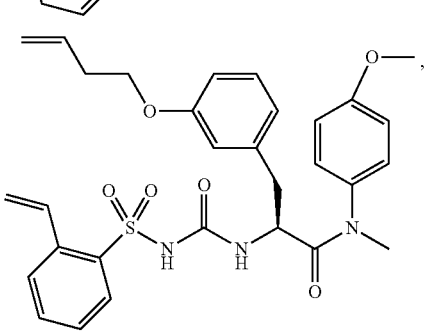
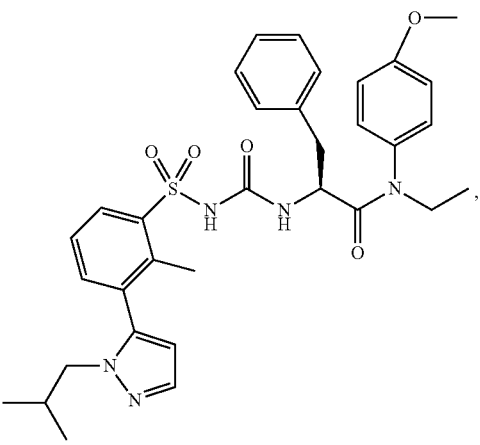
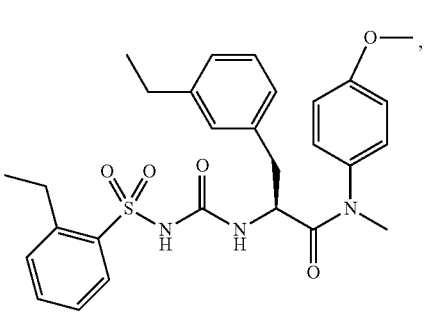

493
-continued
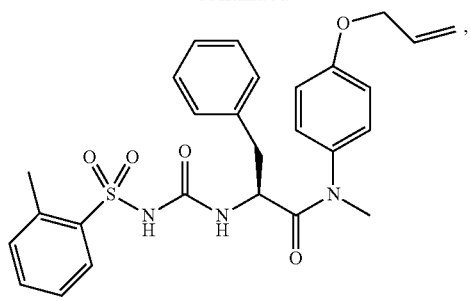
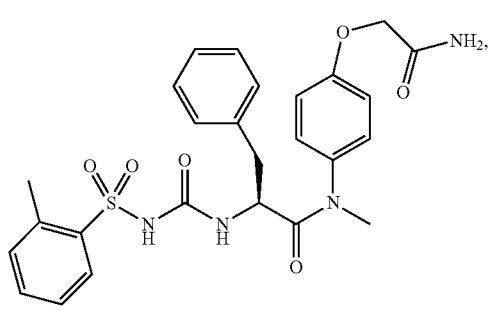
and pharmaceutically acceptable salts thereof.
14. A compound selected from the group consisting of:
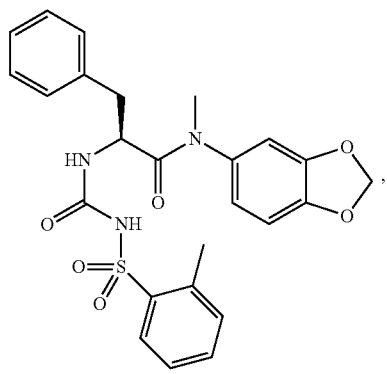
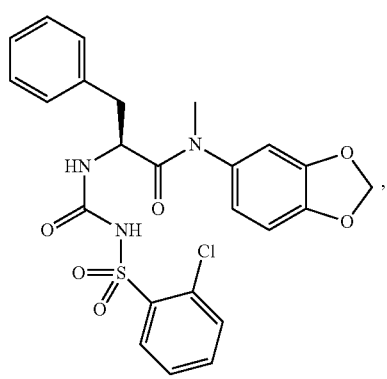
494
-continued
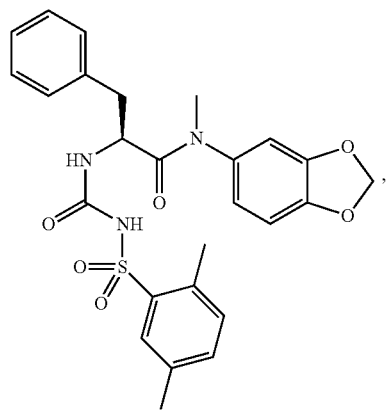
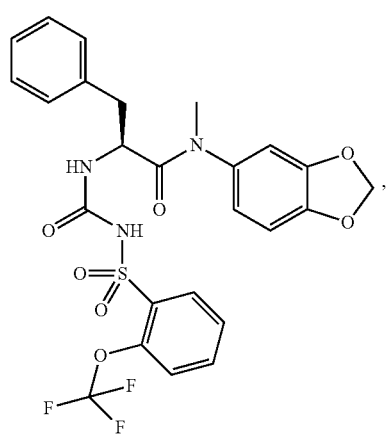

495
-continued
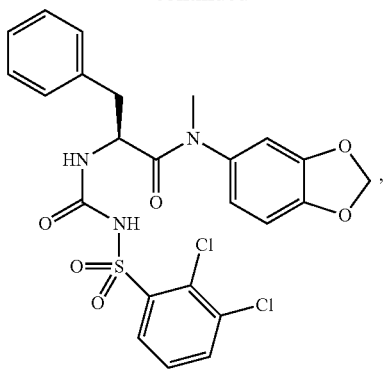
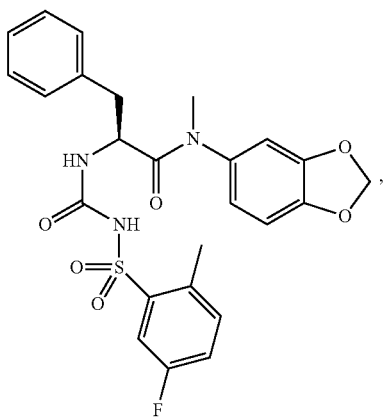
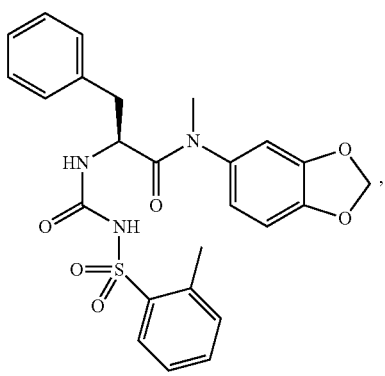
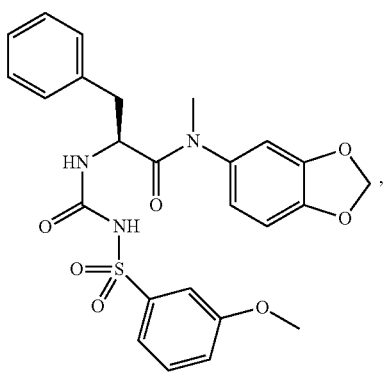
496
-continued
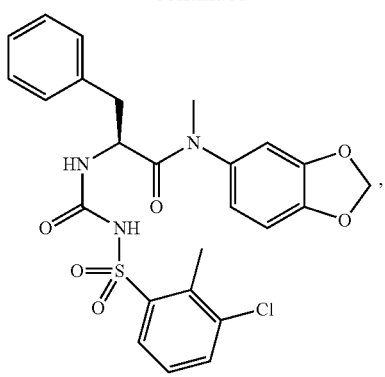
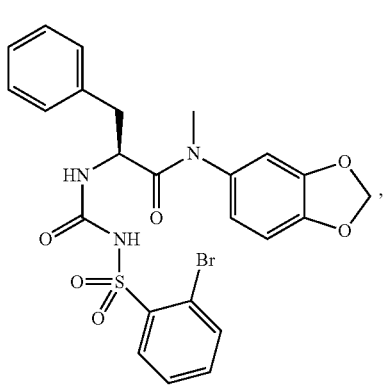
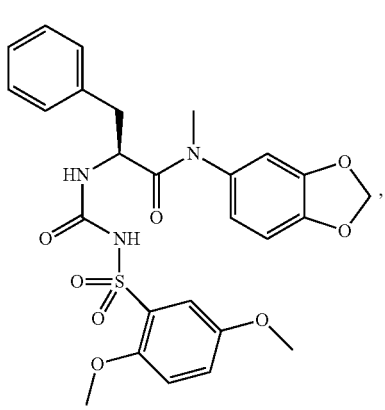
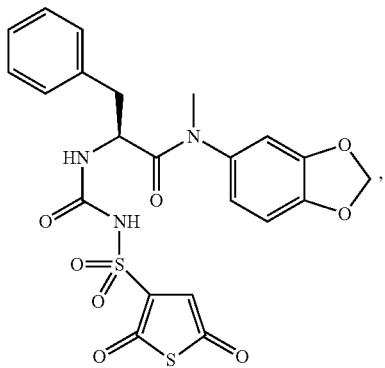

497
-continued
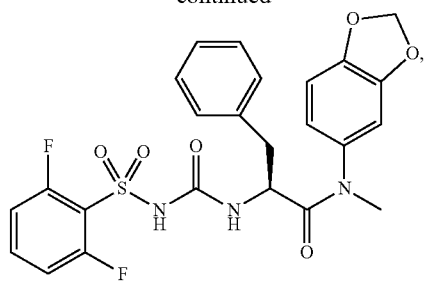
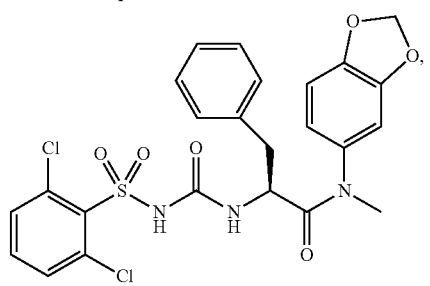
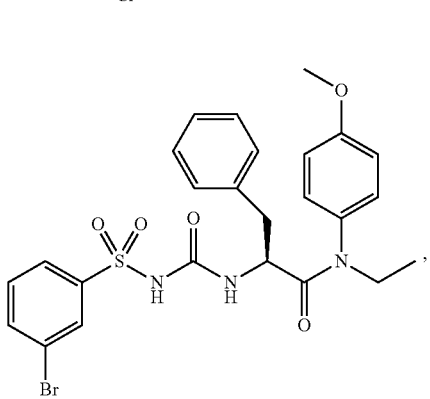
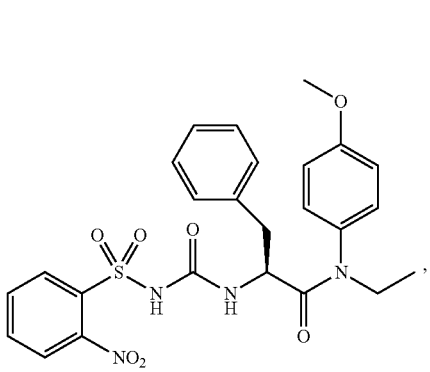
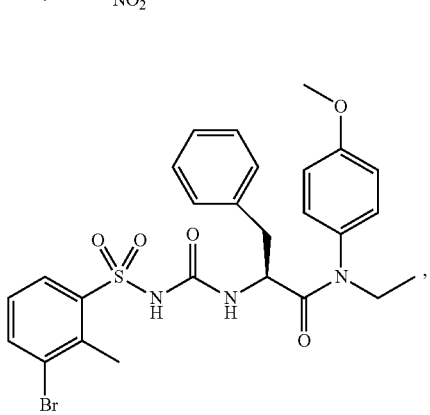
498
-continued
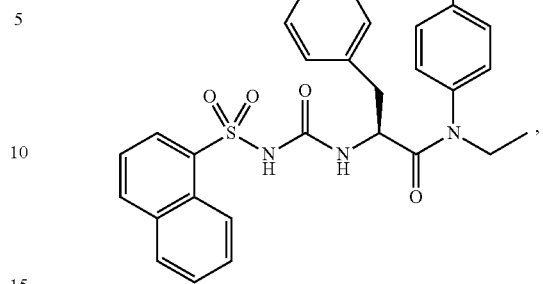
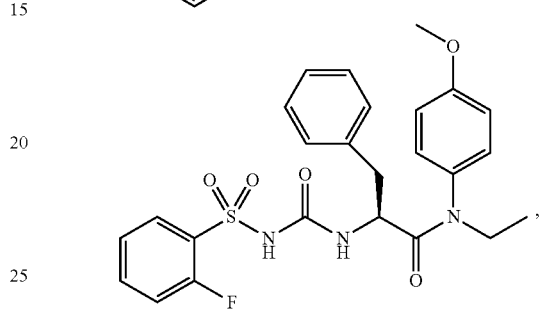
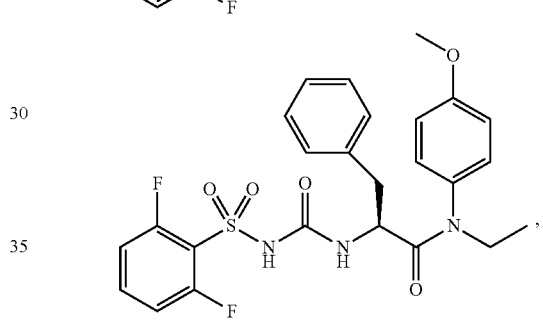
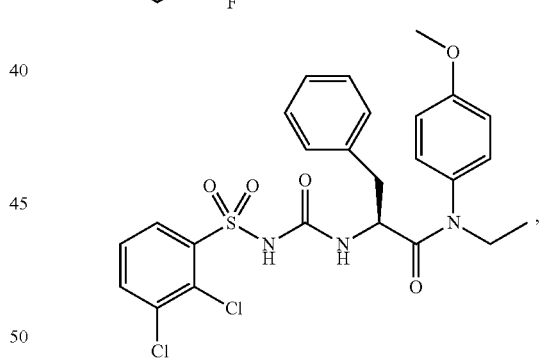
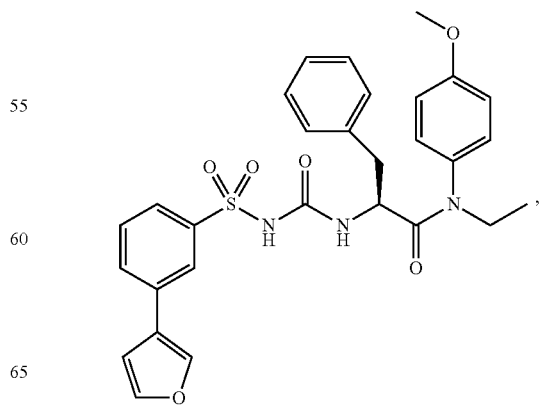

499
-continued
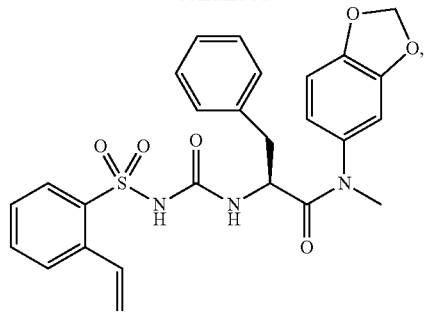
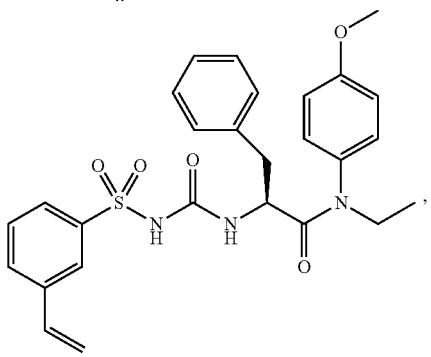
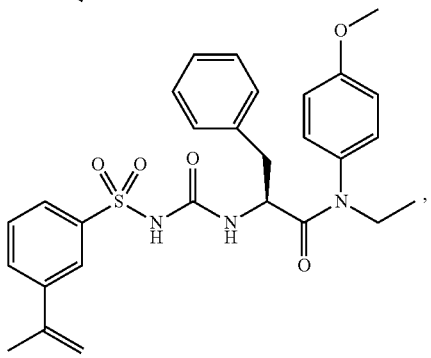
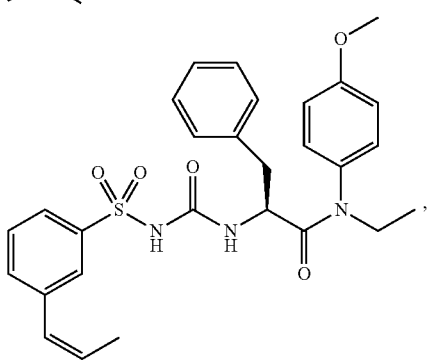
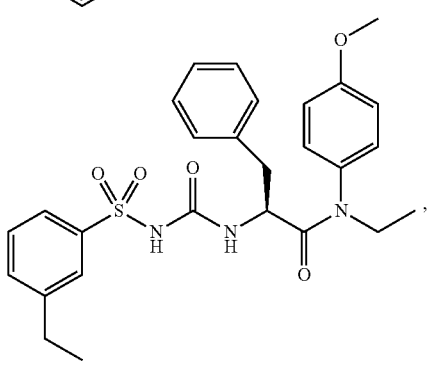
500
-continued
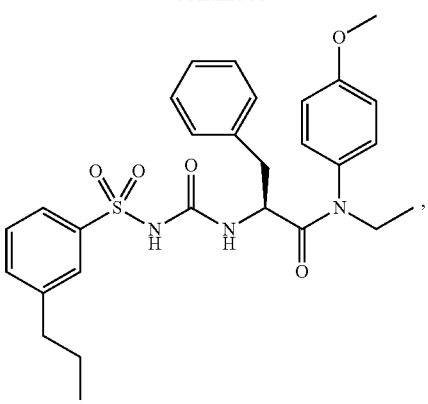
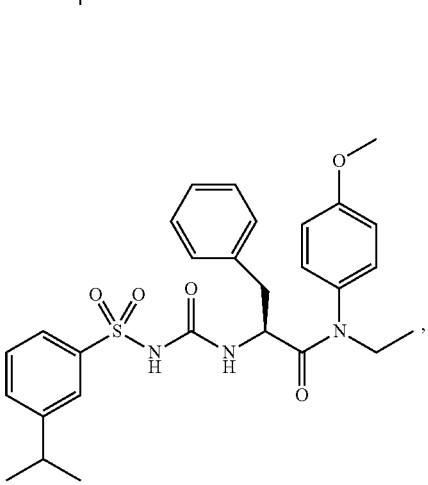
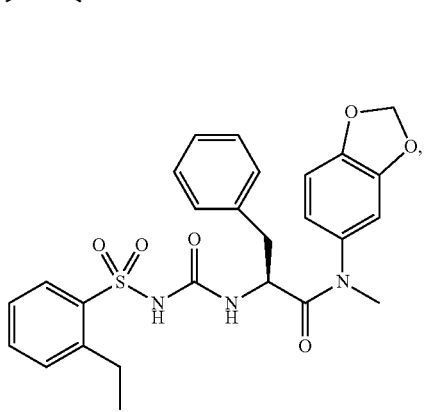
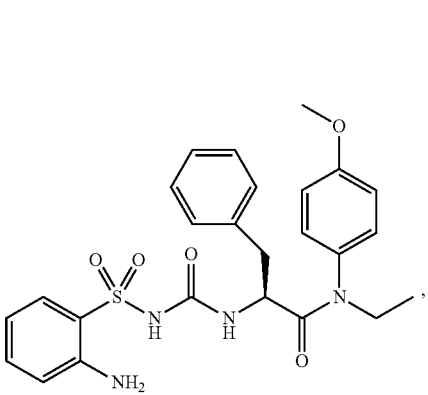

501
-continued
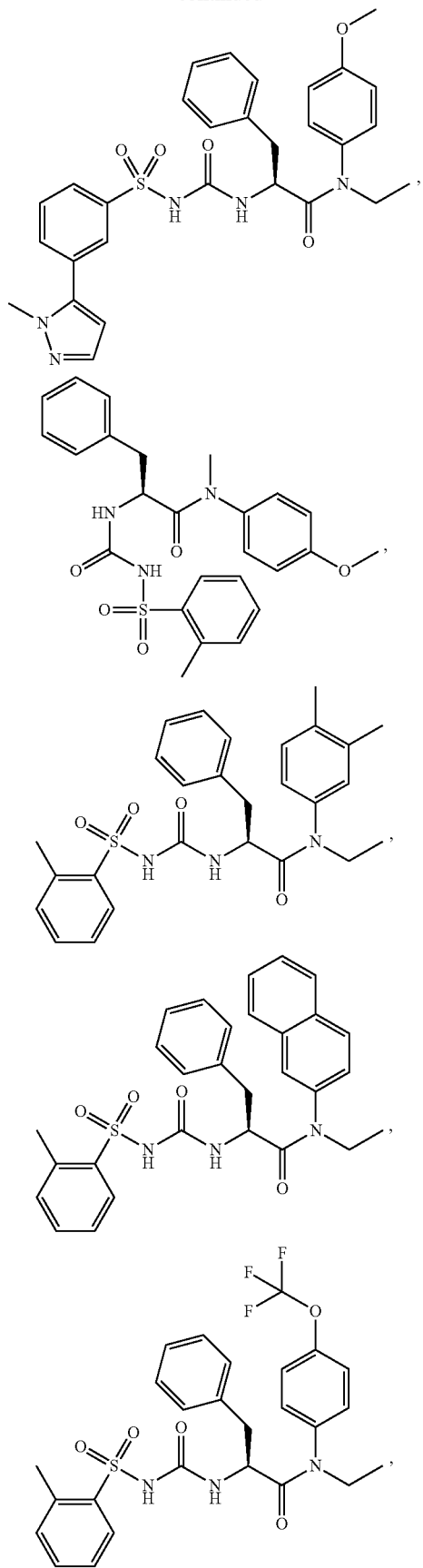
502
-continued
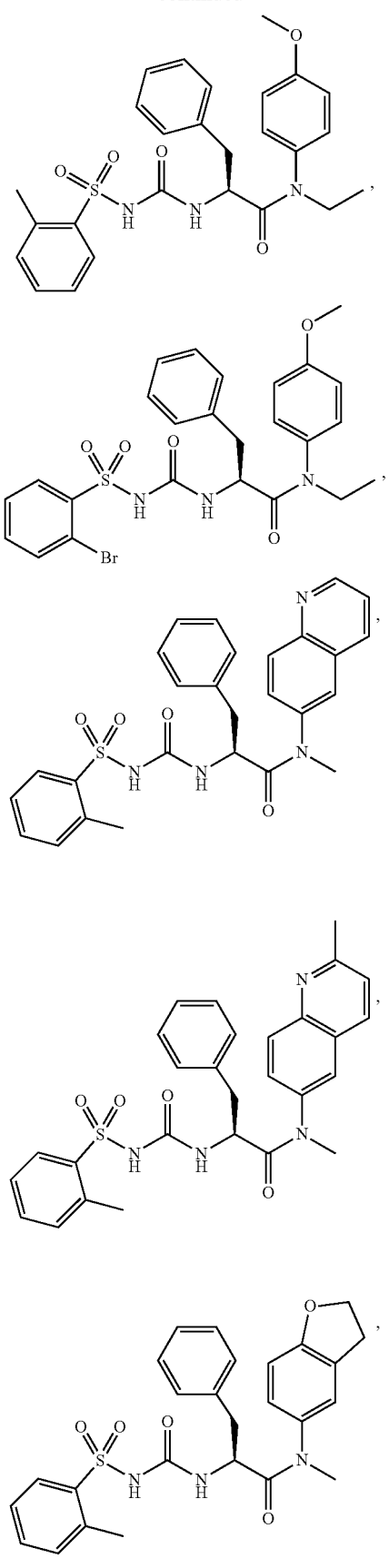

503
-continued
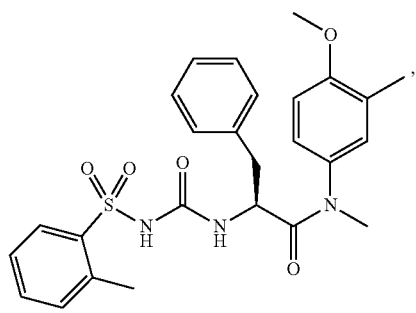
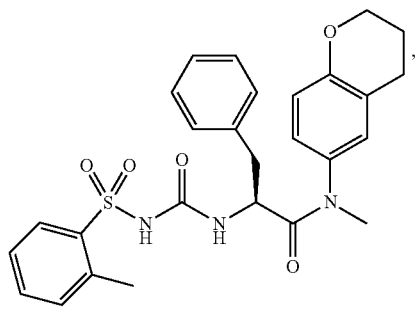
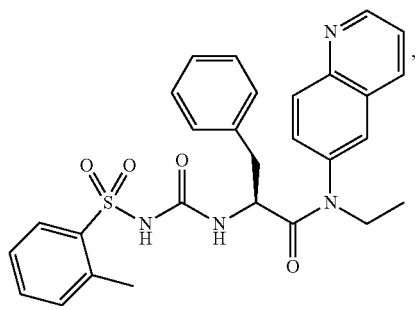
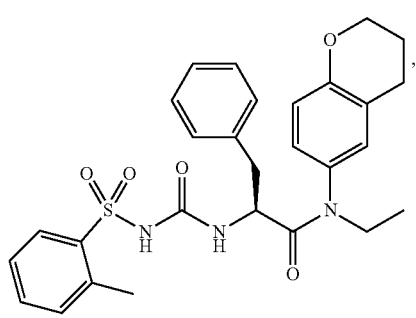
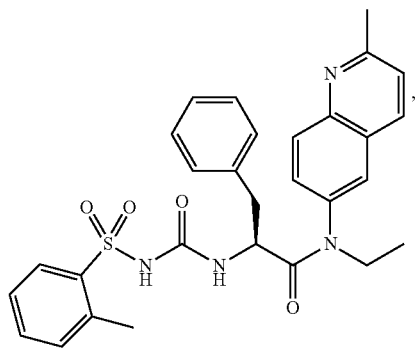
504
-continued
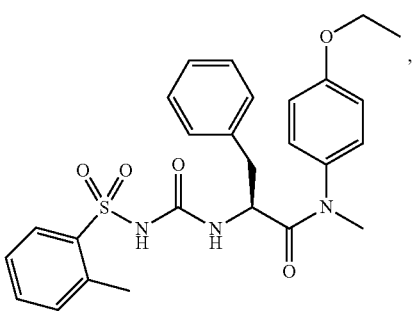
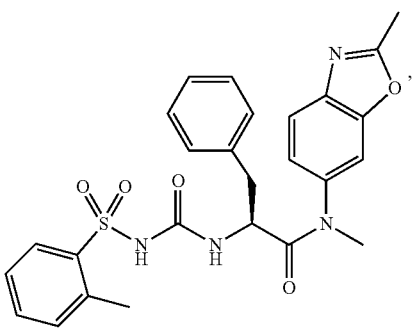
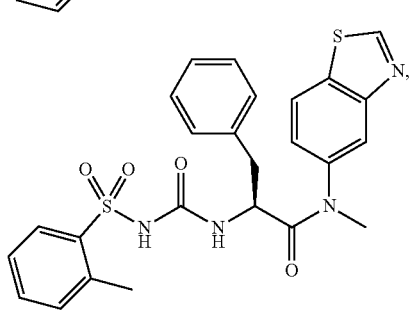
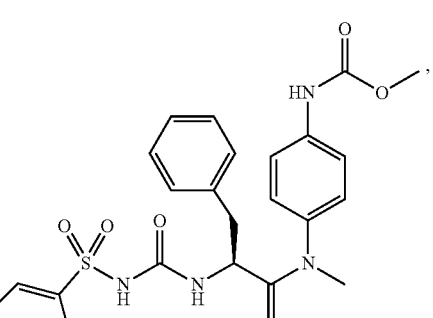
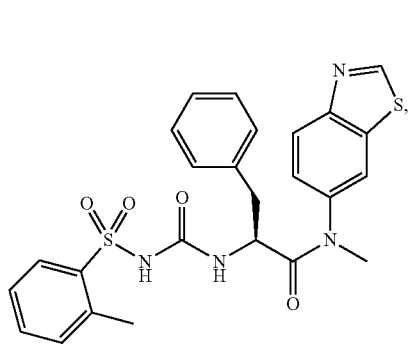

505

-continued

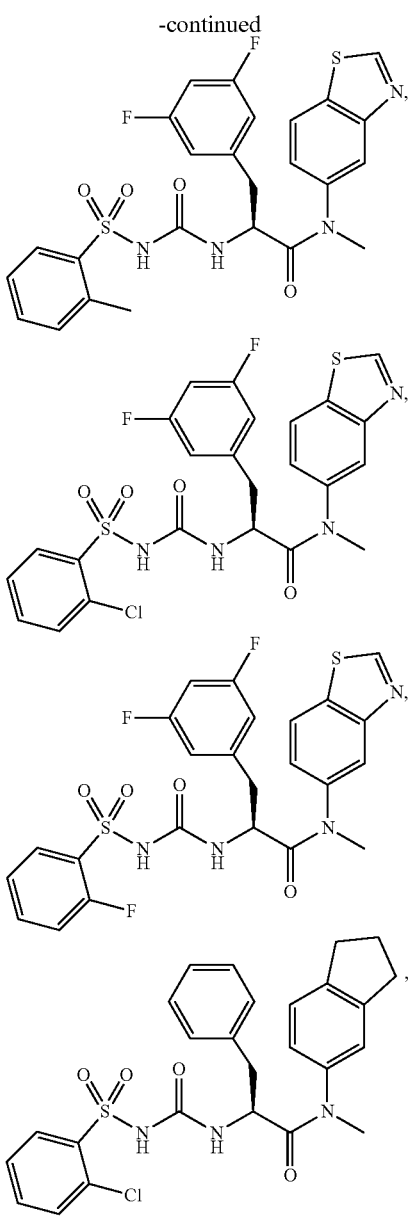

506

-continued

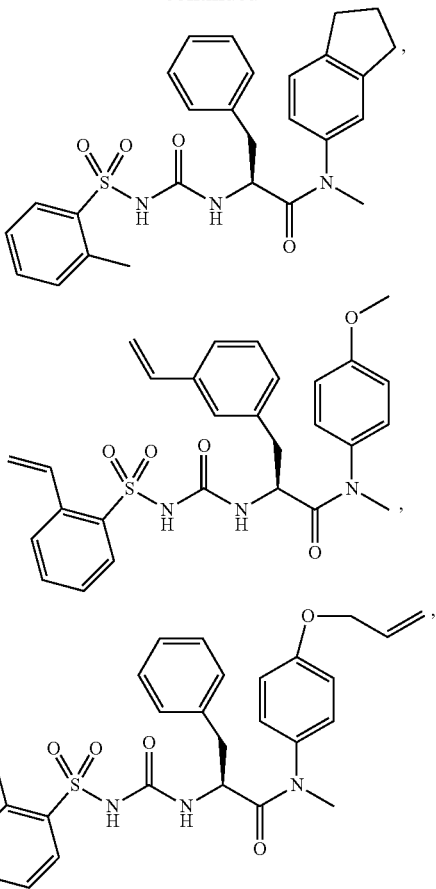

and pharmaceutically acceptable salts thereof.

15. A composition useful for treating HIV infection comprising a compound or salt of claim 1 and a pharmaceutically acceptable carrier, excipient and/or diluent.

16. A method for treating HIV infection comprising administering a therapeutically effective amount of a compound of claim 1, or a pharmaceutically acceptable salt thereof, to a patient in need thereof.

* * * * *